(12) United States Patent
Daily et al.

(10) Patent No.: US 11,623,051 B2
(45) Date of Patent: Apr. 11, 2023

(54) AUTOMATIC INJECTION DEVICE

(71) Applicant: ELCAM MEDICAL AGRICULTURAL COOPERATIVE ASSOCIATION LTD., Kibbutz Bar-Am (IL)

(72) Inventors: David Daily, Herzlia (IL); Lior Raday, D. N. Hof Ashkelon (IL)

(73) Assignee: E3D AGRICULTURAL COOPERATIVE ASSOCIATION LTD., Merom Hagalil (IL)

(*) Notice: Subject to any disclaimer, the term of this patent is extended or adjusted under 35 U.S.C. 154(b) by 613 days.

(21) Appl. No.: 16/271,622

(22) Filed: Feb. 8, 2019

(65) Prior Publication Data

US 2019/0255257 A1  Aug. 22, 2019

Related U.S. Application Data

(60) Continuation of application No. 13/611,899, filed on Sep. 12, 2012, now Pat. No. 10,238,810, which is a
(Continued)

(30) Foreign Application Priority Data

Sep. 17, 2003  (IL) .......................................... 157981

(51) Int. Cl.
*A61M 5/32* (2006.01)
*A61M 5/20* (2006.01)
(Continued)

(52) U.S. Cl.
CPC .......... *A61M 5/326* (2013.01); *A61M 5/2033* (2013.01); *A61M 5/24* (2013.01);
(Continued)

(58) Field of Classification Search
CPC .... A61M 5/326; A61M 5/165; A61M 5/2033; A61M 2005/206; A61M 5/24;
(Continued)

(56) References Cited

U.S. PATENT DOCUMENTS 4,333,447 A  6/1982 Lemrow
4,474,572 A  10/1984 McNaughton
(Continued)

FOREIGN PATENT DOCUMENTS

AU  2004269838 B2  2/2009
CN  100522268  8/2009
(Continued)

OTHER PUBLICATIONS

US 5,954,699 A, 09/1999, Jost (withdrawn)
(Continued)

*Primary Examiner* — Lauren P Farrar
*Assistant Examiner* — Hamza A Darb
(74) *Attorney, Agent, or Firm* — Fish & Richardson P.C.

(57) ABSTRACT

An automatic injection device including a housing element, at least one resilient element arranged to be located within the housing element, a syringe including at least one syringe piston, a needle guard adapted for selectable positioning with respect to the housing element and a selectable driving element adapted, when actuated, to be driven by the at least one resilient element for initially displacing the syringe relative to the housing element from a non-penetration position to a penetration position and thereafter displacing the at least one syringe piston in the syringe to effect drug delivery and displacing the needle guard into a needle guarding position.

20 Claims, 236 Drawing Sheets

Related U.S. Application Data division of application No. 10/572,214, filed as application No. PCT/IL2004/000851 on Sep. 15, 2004, now Pat. No. 8,376,998.

(51) Int. Cl.
*A61M 5/24* (2006.01)
*A61M 5/31* (2006.01)

(52) U.S. Cl.
CPC ......... *A61M 5/3134* (2013.01); *A61M 5/3202* (2013.01); *A61M 2005/206* (2013.01); *A61M 2005/208* (2013.01); *A61M 2005/2086* (2013.01); *A61M 2005/3109* (2013.01)

(58) Field of Classification Search
CPC .............. A61M 5/3134; A61M 5/3202; A61M 2005/208; A61M 2005/2086; A61M 2005/3109; A61M 5/321; A61M 5/3243
See application file for complete search history.

(56) References Cited

U.S. PATENT DOCUMENTS

| | | | |
|---|---|---|---|
| 4,475,906 A | 10/1984 | Holzner |
| 4,484,910 A | 11/1984 | Sarnoff |
| 4,487,602 A | 12/1984 | Christensen |
| 4,505,710 A | 3/1985 | Collins |
| 4,512,767 A | 4/1985 | Raymond |
| 4,515,590 A | 5/1985 | Daniel |
| 4,518,387 A | 5/1985 | Murphy |
| 4,529,401 A | 7/1985 | Leslie |
| 4,529,403 A | 7/1985 | Kamstra |
| 4,530,695 A | 7/1985 | Phillips |
| 4,534,759 A | 8/1985 | Trawoger |
| 4,547,189 A | 10/1985 | Moore, Jr. |
| 4,553,962 A | 11/1985 | Brunet |
| 4,573,970 A | 3/1986 | Wagner |
| 4,573,976 A | 3/1986 | Smith |
| 4,578,061 A | 3/1986 | Lemelson |
| 4,578,064 A | 3/1986 | Sarnoff |
| 4,580,561 A | 4/1986 | Williamson |
| 4,592,744 A | 6/1986 | Jagger |
| 4,594,073 A | 6/1986 | Stine |
| 4,596,558 A | 6/1986 | Smith |
| 4,597,753 A | 7/1986 | Turley |
| 4,600,403 A | 7/1986 | Wagner |
| 4,601,708 A | 7/1986 | Jordan |
| 4,613,328 A | 9/1986 | Boyd |
| 4,620,540 A | 11/1986 | Goodale |
| 4,620,847 A | 11/1986 | Shishov |
| 4,624,660 A | 11/1986 | Mijers |
| 4,650,468 A | 3/1987 | Jennings, Jr. |
| 4,658,830 A | 4/1987 | Sarnoff |
| 4,659,326 A | 4/1987 | Johnson |
| 4,664,651 A | 5/1987 | Weinshenker |
| 4,664,654 A | 5/1987 | Strauss |
| 4,666,436 A | 5/1987 | McDonald |
| 4,672,967 A | 6/1987 | Smith |
| 4,681,565 A | 7/1987 | Gourlandt |
| 4,687,465 A | 8/1987 | Prindle |
| 4,687,467 A | 8/1987 | Cygielski |
| 4,689,042 A | 8/1987 | Sarnoff |
| 4,699,614 A | 10/1987 | Glazier |
| 4,710,170 A | 12/1987 | Haber |
| 4,723,937 A | 2/1988 | Sarnoff |
| 4,735,618 A | 4/1988 | Hagen |
| 4,738,663 A | 4/1988 | Bogan |
| 4,743,234 A | 5/1988 | Leopoldi |
| 4,744,955 A | 5/1988 | Shapiro |
| 4,745,907 A | 5/1988 | Russel, Jr. |
| 4,747,829 A | 5/1988 | Jacob |
| 4,747,831 A | 5/1988 | Kulli |
| 4,753,636 A | 6/1988 | Free |
| 4,755,169 A | 7/1988 | Sarnoff |
| 4,758,227 A | 7/1988 | Lancaster, Jr. |
| 4,758,230 A | 7/1988 | Rycroft |
| 4,758,231 A | 7/1988 | Rycroft |
| 4,766,908 A | 8/1988 | Clement |
| 4,767,407 A | 8/1988 | Foran |
| 4,767,413 A | 8/1988 | Haber |
| 4,770,655 A | 9/1988 | Haber |
| 4,781,683 A | 11/1988 | Wozniak |
| 4,781,685 A | 11/1988 | Lehmann |
| 4,781,688 A | 11/1988 | Thoma |
| 4,784,640 A | 11/1988 | Johnson |
| 4,787,384 A | 11/1988 | Campbell |
| 4,787,893 A | 11/1988 | Villette |
| 4,790,823 A | 12/1988 | Pierre |
| 4,790,827 A | 12/1988 | Haber |
| 4,795,432 A | 1/1989 | Karczmer |
| 4,795,433 A | 1/1989 | Sarnoff |
| 4,798,587 A | 1/1989 | Willoughby |
| 4,799,921 A | 1/1989 | Johnson |
| 4,804,370 A | 2/1989 | Haber |
| 4,808,169 A | 2/1989 | Haber |
| 4,813,937 A | 3/1989 | Vaillancourt |
| 4,813,940 A | 3/1989 | Parry |
| 4,820,275 A | 4/1989 | Haber |
| 4,820,286 A | 4/1989 | Van der Wal |
| 4,826,484 A | 5/1989 | Haber |
| 4,826,489 A | 5/1989 | Haber |
| 4,826,490 A | 5/1989 | Byme |
| 4,828,548 A | 5/1989 | Walter |
| 4,832,682 A | 5/1989 | Sarnoff |
| 4,832,693 A | 5/1989 | Gloyer |
| 4,834,704 A | 5/1989 | Reinicke |
| 4,834,718 A | 5/1989 | McDonald |
| 4,842,598 A | 6/1989 | Tran |
| 4,846,811 A | 7/1989 | Vanderhoof |
| 4,850,961 A | 7/1989 | Wanderer |
| 4,850,968 A | 7/1989 | Romano |
| 4,850,971 A | 7/1989 | Colvin |
| 4,850,976 A | 7/1989 | Heinrich |
| 4,850,977 A | 7/1989 | Bayless |
| 4,850,994 A | 7/1989 | Zerbst |
| 4,861,338 A | 8/1989 | Mathiesen |
| 4,863,427 A | 9/1989 | Cocchi |
| 4,863,435 A | 9/1989 | Sturman |
| 4,863,436 A | 9/1989 | Glick |
| 4,865,592 A | 9/1989 | Rycroft |
| 4,874,372 A | 10/1989 | McArthur |
| 4,874,382 A | 10/1989 | Lindemann |
| 4,883,466 A | 11/1989 | Glazier |
| 4,883,472 A | 11/1989 | Michel |
| 4,886,499 A | 12/1989 | Cirelli |
| 4,887,998 A | 12/1989 | Martin |
| 4,892,107 A | 1/1990 | Haber |
| 4,892,523 A | 1/1990 | Haber |
| 4,894,054 A | 1/1990 | Miskinyar |
| 4,894,055 A | 1/1990 | Sudnak |
| 4,898,589 A | 2/1990 | Dolgin |
| 4,900,303 A | 2/1990 | Lemelson |
| 4,900,307 A | 2/1990 | Kulli |
| 4,900,311 A | 2/1990 | Lawrence |
| 4,902,279 A | 2/1990 | Schmidtz |
| 4,904,242 A | 2/1990 | Kulli |
| 4,906,236 A | 3/1990 | Alberts |
| 4,908,022 A | 3/1990 | Haber |
| 4,909,794 A | 3/1990 | Haber |
| 4,909,795 A | 3/1990 | Gelabert |
| 4,911,706 A | 3/1990 | Levitt |
| 4,913,702 A | 4/1990 | Yum |
| 4,915,702 A | 4/1990 | Haber |
| 4,917,672 A | 4/1990 | Temdmp |
| 4,919,146 A | 4/1990 | Rhinehart |
| 4,919,657 A | 4/1990 | Haber |
| 4,923,443 A | 5/1990 | Greenwood |
| 4,923,445 A | 5/1990 | Ryan |
| 4,923,447 A | 5/1990 | Morgan |
| 4,927,414 A | 5/1990 | Kulli |
| 4,929,237 A | 5/1990 | Medway |
| 4,929,241 A | 5/1990 | Kulli |
| 4,931,040 A | 6/1990 | Haber |

(56) References Cited

U.S. PATENT DOCUMENTS

| | | |
|---|---|---|
| 4,932,944 A | 6/1990 | Jagger |
| 4,932,946 A | 6/1990 | Shields |
| 4,932,947 A | 6/1990 | Cardwell |
| 4,935,013 A | 6/1990 | Haber |
| 4,935,014 A | 6/1990 | Haber |
| 4,936,830 A | 6/1990 | Verlier |
| 4,941,879 A | 7/1990 | Butler |
| 4,944,723 A | 7/1990 | Haber |
| 4,944,725 A | 7/1990 | McDonald |
| 4,946,441 A | 8/1990 | Laderoute |
| 4,950,240 A | 8/1990 | Greenwood |
| 4,950,241 A | 8/1990 | Ranford |
| 4,950,250 A | 8/1990 | Haber |
| 4,950,252 A | 8/1990 | Luther |
| 4,955,866 A | 9/1990 | Corey |
| 4,955,868 A | 9/1990 | Klein |
| 4,955,869 A | 9/1990 | Bin |
| 4,955,870 A | 9/1990 | Ridderheim |
| 4,961,728 A | 10/1990 | Kosinski |
| 4,966,589 A | 10/1990 | Kaufman |
| 4,966,592 A | 10/1990 | Burns |
| 4,966,593 A | 10/1990 | Lennox |
| 4,973,310 A | 11/1990 | Kosinski |
| 4,973,317 A | 11/1990 | Bobrove |
| 4,976,704 A | 12/1990 | McLees |
| 4,988,335 A | 1/1991 | Prindle |
| 4,988,339 A | 1/1991 | Vadher |
| 4,994,045 A | 2/1991 | Ranford |
| RE33,585 E | 3/1991 | Haber |
| 4,998,918 A | 3/1991 | Mimura |
| 4,998,921 A | 3/1991 | Vickroy |
| 4,998,922 A | 3/1991 | Kuracina |
| 5,000,736 A | 3/1991 | Kaufhold, Jr. |
| 5,000,737 A | 3/1991 | Free |
| 5,002,548 A | 3/1991 | Campbell |
| 5,007,903 A | 4/1991 | Ellard |
| 5,011,475 A | 4/1991 | Olson |
| 5,015,240 A | 5/1991 | Soproni |
| 5,017,187 A | 5/1991 | Sullivan |
| 5,019,043 A | 5/1991 | Segui Pastor |
| 5,019,044 A | 5/1991 | Tsao |
| 5,019,047 A | 5/1991 | Kriesel |
| 5,019,048 A | 5/1991 | Margolin |
| 5,021,059 A | 6/1991 | Kensey |
| 5,024,665 A | 6/1991 | Kaufman |
| 5,026,349 A | 6/1991 | Schmitz |
| 5,030,208 A | 7/1991 | Novacek |
| 5,034,003 A | 7/1991 | Raymond |
| 5,037,306 A | 8/1991 | Van Schoonhoven |
| 5,037,382 A | 8/1991 | Ingelise |
| 5,037,393 A | 8/1991 | Ellgass |
| 5,037,400 A | 8/1991 | Curry |
| 5,041,094 A | 8/1991 | Perego |
| 5,042,977 A | 8/1991 | Bechtold |
| 5,045,066 A | 9/1991 | Scheuble |
| 5,047,016 A | 9/1991 | Dolgin |
| 5,049,133 A | 9/1991 | Villen Pascual |
| 5,049,136 A | 9/1991 | Johnson |
| 5,053,010 A | 10/1991 | McGary |
| 5,053,018 A | 10/1991 | Talon |
| 5,055,102 A | 10/1991 | Sitnik |
| 5,057,086 A | 10/1991 | Dillard, III |
| 5,057,089 A | 10/1991 | Greco |
| 5,059,180 A | 10/1991 | McLees |
| 5,059,185 A | 10/1991 | Ryan |
| 5,061,249 A | 10/1991 | Campbell |
| 5,061,251 A | 10/1991 | Juhasz |
| 5,064,419 A | 11/1991 | Gaarde |
| 5,067,448 A | 11/1991 | Haber |
| 5,067,490 A | 11/1991 | Haber |
| 5,067,948 A | 11/1991 | Haber |
| 5,071,353 A | 12/1991 | Van der Wal |
| 5,080,104 A | 1/1992 | Marks |
| 5,084,027 A | 1/1992 | Bernard |
| 5,084,029 A | 1/1992 | Nacci nee Tagliaferri |
| 5,084,030 A | 1/1992 | Byme |
| 5,085,640 A | 2/1992 | Gibbs |
| 5,085,641 A | 2/1992 | Sarnoff |
| 5,085,642 A | 2/1992 | Sarnoff |
| 5,088,986 A | 2/1992 | Nusbaum |
| 5,088,988 A | 2/1992 | Talon |
| 5,092,842 A | 3/1992 | Bechtold |
| 5,092,843 A | 3/1992 | Monroe |
| 5,092,851 A | 3/1992 | Ragner |
| 5,092,852 A | 3/1992 | Poling |
| 5,092,853 A | 3/1992 | Couvertier, II |
| 5,098,382 A | 3/1992 | Haber |
| 5,098,400 A | 3/1992 | Crouse |
| 5,098,401 A | 3/1992 | De Lange |
| 5,102,393 A | 4/1992 | Sarnoff |
| 5,102,397 A | 4/1992 | Brunet |
| 5,104,378 A | 4/1992 | Haber |
| 5,104,380 A | 4/1992 | Holman |
| 5,104,384 A | 4/1992 | Parry |
| 5,104,385 A | 4/1992 | Huband |
| 5,106,370 A | 4/1992 | Stewart |
| 5,106,372 A | 4/1992 | Ranford |
| 5,106,379 A | 4/1992 | Leap |
| 5,108,378 A | 4/1992 | Firth |
| 5,108,379 A | 4/1992 | Dolgin |
| 5,112,307 A | 5/1992 | Haber |
| 5,112,316 A | 5/1992 | Venturini |
| 5,114,404 A | 5/1992 | Paxton |
| 5,120,309 A | 6/1992 | Watts |
| 5,120,310 A | 6/1992 | Shaw |
| 5,120,314 A | 6/1992 | Greenwood |
| 5,120,321 A | 6/1992 | Oksman |
| 5,122,118 A | 6/1992 | Haber |
| 5,122,124 A | 6/1992 | Novacek |
| 5,125,898 A | 6/1992 | Kaufhold, Jr. |
| 5,125,899 A | 6/1992 | Frignoli |
| 5,127,910 A | 7/1992 | Talonn |
| 5,135,507 A | 8/1992 | Haber |
| 5,135,510 A | 8/1992 | Maszkiewicz |
| 5,137,515 A | 8/1992 | Hogan |
| 5,137,516 A | 8/1992 | Rand |
| 5,141,496 A | 8/1992 | Tino |
| 5,143,411 A | 9/1992 | Watts |
| 5,143,414 A | 9/1992 | Rosellini |
| 5,147,311 A | 9/1992 | Pickhard |
| 5,147,314 A | 9/1992 | Rosellini |
| 5,147,326 A | 9/1992 | Talonn |
| 5,147,327 A | 9/1992 | Johnson |
| 5,149,323 A | 9/1992 | Colonnna |
| 5,163,917 A | 9/1992 | Norman |
| 5,152,751 A | 10/1992 | Kozlowski |
| 5,156,599 A | 10/1992 | Ranford |
| 5,160,326 A | 11/1992 | Talonn |
| 5,163,916 A | 11/1992 | Sunderland |
| 5,163,918 A | 11/1992 | Righi |
| 5,167,632 A | 12/1992 | Eid |
| 5,167,641 A | 12/1992 | Schmitz |
| 5,169,389 A | 12/1992 | Kriesel |
| 5,169,392 A | 12/1992 | Ranford |
| 5,176,641 A | 1/1993 | Idriss |
| 5,176,655 A | 1/1993 | Mccormick |
| 5,176,656 A | 1/1993 | Bayless |
| 5,176,657 A | 1/1993 | Shields |
| 5,183,468 A | 2/1993 | McLees |
| 5,183,469 A | 2/1993 | Capaccio |
| 5,188,614 A | 2/1993 | Hart |
| 5,190,526 A | 3/1993 | Murry |
| 5,193,552 A | 3/1993 | Columbus |
| 5,195,982 A | 3/1993 | Hoenig |
| 5,195,983 A | 3/1993 | Boese |
| 5,195,985 A | 3/1993 | Hall |
| 5,199,952 A | 4/1993 | Marshall, Sr. |
| 5,201,708 A | 4/1993 | Martin |
| 5,201,710 A | 4/1993 | Caselli |
| 5,205,826 A | 4/1993 | Chen |
| 5,205,827 A | 4/1993 | Novacek |
| 5,207,646 A | 5/1993 | Brunel |
| 5,207,699 A | 5/1993 | Coe |
| 5,209,739 A | 5/1993 | Talalay |

(56) References Cited

U.S. PATENT DOCUMENTS

| | | |
|---|---|---|
| 5,211,628 A | 5/1993 | Marshall |
| 5,211,629 A | 5/1993 | Pressly |
| 5,215,524 A | 6/1993 | Vallelunga |
| 5,215,533 A | 6/1993 | Robb |
| 5,215,534 A | 6/1993 | De Harde |
| 5,215,535 A | 6/1993 | Gettig |
| 5,215,536 A | 6/1993 | Lampropoulos |
| 5,217,437 A | 6/1993 | Talonn |
| 5,219,338 A | 6/1993 | Haworth |
| 5,221,262 A | 6/1993 | Kite |
| 5,222,943 A | 6/1993 | Mazzara |
| 5,222,947 A | 6/1993 | D'Amico |
| 5,222,974 A | 6/1993 | Kensey |
| 5,224,936 A | 7/1993 | Gallagher |
| 5,226,882 A | 7/1993 | Bates |
| 5,228,883 A | 7/1993 | Blakely |
| RE34,335 E | 8/1993 | Butler |
| 5,232,457 A | 8/1993 | Grim |
| 5,232,458 A | 8/1993 | Chen |
| 5,238,654 A | 8/1993 | Nohl |
| 5,242,388 A | 9/1993 | Marshall, Sr. |
| 5,242,401 A | 9/1993 | Colsky |
| 5,242,416 A | 9/1993 | Hutson |
| 5,242,420 A | 9/1993 | Martin |
| 5,246,428 A | 9/1993 | Falknor |
| 5,250,031 A | 10/1993 | Kaplan |
| 5,256,152 A | 10/1993 | Marks |
| 5,257,976 A | 11/1993 | Fenet |
| 5,261,894 A | 11/1993 | Smith |
| 5,263,933 A | 11/1993 | Novacek |
| 5,267,961 A | 12/1993 | Shaw |
| 5,267,962 A | 12/1993 | Jenson |
| 5,267,963 A | 12/1993 | Bachynsky |
| 5,269,761 A | 12/1993 | Stehrenberger |
| 5,269,762 A | 12/1993 | Armbruster |
| 5,269,763 A | 12/1993 | Boehmer |
| 5,269,766 A | 12/1993 | Haber |
| 5,273,532 A | 12/1993 | Niezink |
| 5,273,538 A | 12/1993 | Chen |
| 5,273,539 A | 12/1993 | Chen |
| 5,273,541 A | 12/1993 | Malenchek |
| 5,274,544 A | 12/1993 | Iida |
| 5,279,554 A | 1/1994 | Turley |
| 5,279,566 A | 1/1994 | Kline, Jr. |
| 5,279,577 A | 1/1994 | Collett |
| 5,279,579 A | 1/1994 | D'Amico |
| 5,279,581 A | 1/1994 | Firth |
| 5,279,582 A | 1/1994 | Davison |
| 5,279,583 A | 1/1994 | Shober, Jr. |
| 5,279,590 A | 1/1994 | Sinko |
| 5,282,793 A | 2/1994 | Larson |
| 5,282,822 A | 2/1994 | Macors |
| 5,282,827 A | 2/1994 | Kensey |
| 5,284,479 A | 2/1994 | De Jong |
| 5,290,233 A | 3/1994 | Campbell |
| 5,290,239 A | 3/1994 | Classey |
| 5,290,240 A | 3/1994 | Horres, Jr. |
| 5,290,254 A | 3/1994 | Vaillancourt |
| 5,292,314 A | 3/1994 | D'alessio |
| 5,295,963 A | 3/1994 | Decks |
| 5,295,965 A | 3/1994 | Wilmont |
| 5,295,972 A | 3/1994 | Mischenko |
| 5,295,973 A | 3/1994 | Chen |
| 5,295,974 A | 3/1994 | O'Laughlin |
| 5,295,975 A | 3/1994 | Lockwood, Jr. |
| 5,300,029 A | 4/1994 | Raymond |
| 5,300,030 A | 4/1994 | Crossman |
| 5,300,040 A | 4/1994 | Kershenstine |
| 5,300,045 A | 4/1994 | Plassche, Jr. |
| 5,304,137 A | 4/1994 | Fluke |
| 5,304,138 A | 4/1994 | Mercado |
| 5,306,251 A | 4/1994 | Alexander |
| 5,306,258 A | 4/1994 | De la Fuente |
| 5,308,332 A | 5/1994 | Dillard, III |
| 5,311,841 A | 5/1994 | Thaxton |
| 5,312,353 A | 5/1994 | Boggess |
| 5,312,366 A | 5/1994 | Vailancourt |
| 5,312,368 A | 5/1994 | Haynes |
| 5,312,370 A | 5/1994 | Talonn |
| 5,312,371 A | 5/1994 | Dombrowski |
| 5,312,372 A | 5/1994 | DeHarde |
| 5,314,503 A | 5/1994 | Bobrove |
| 5,318,538 A | 6/1994 | Martin |
| 5,320,609 A | 6/1994 | Haber |
| 5,322,517 A | 6/1994 | Sircom |
| 5,324,265 A | 6/1994 | Murry |
| 5,328,475 A | 7/1994 | Chen |
| 5,328,476 A | 7/1994 | Bidwell |
| 5,328,482 A | 7/1994 | Sircom |
| 5,328,484 A | 7/1994 | Somers |
| 5,330,430 A | 7/1994 | Sullivan |
| 5,334,149 A | 8/1994 | Nortman |
| 5,334,158 A | 8/1994 | McLees |
| 5,334,173 A | 8/1994 | Armstrong, Jr. |
| 5,336,180 A | 8/1994 | Kriesel |
| 5,336,187 A | 8/1994 | Terry |
| 5,336,199 A | 8/1994 | Castillo |
| 5,338,303 A | 8/1994 | King |
| 5,338,311 A | 8/1994 | Mahurkar |
| 5,342,310 A | 8/1994 | Ueyama |
| 5,342,320 A | 8/1994 | Cameron |
| 5,344,407 A | 9/1994 | Ryan |
| 5,344,408 A | 9/1994 | Partika |
| 5,346,475 A | 9/1994 | Gregorio |
| 5,346,480 A | 9/1994 | Hess |
| 5,346,481 A | 9/1994 | Bunin |
| 5,348,544 A | 9/1994 | Sweeney |
| 5,352,200 A | 10/1994 | Hammett |
| 5,352,202 A | 10/1994 | Hammett |
| 5,352,203 A | 10/1994 | Vallelunga |
| 5,354,287 A | 10/1994 | Wacks |
| 5,356,387 A | 10/1994 | Sirbola |
| 5,358,489 A | 10/1994 | Erika |
| 5,360,410 A | 11/1994 | Wacks |
| 5,364,362 A | 11/1994 | Schulz |
| 5,364,370 A | 11/1994 | Szerlip |
| 5,366,447 A | 11/1994 | Guriy |
| 5,368,568 A | 11/1994 | Pitts |
| 5,368,570 A | 11/1994 | Thompson |
| 5,368,571 A | 11/1994 | Horres, Jr. |
| 5,370,619 A | 12/1994 | Rossi |
| 5,370,626 A | 12/1994 | Farris |
| 5,370,628 A | 12/1994 | Allison |
| 5,374,250 A | 12/1994 | Dixon |
| 5,378,240 A | 1/1995 | Curie |
| 5,383,857 A | 1/1995 | Levitov |
| 5,385,550 A | 1/1995 | Su |
| 5,385,551 A | 1/1995 | Shaw |
| 5,385,557 A | 1/1995 | Thompson |
| 5,389,076 A | 2/1995 | Shaw |
| 5,389,085 A | 2/1995 | D'Alessio |
| 5,391,151 A | 2/1995 | Wilmot |
| 5,391,183 A | 2/1995 | Janzen |
| 5,395,317 A | 3/1995 | Kambin |
| 5,395,337 A | 3/1995 | Clems |
| 5,399,163 A | 3/1995 | Peterson |
| 5,401,246 A | 3/1995 | Mazur |
| 5,401,249 A | 3/1995 | Shields |
| 5,401,251 A | 3/1995 | Hui |
| 5,403,286 A | 4/1995 | Lockwood, Jr. |
| 5,403,287 A | 4/1995 | Talonn |
| 5,405,326 A | 4/1995 | Haber |
| 5,405,327 A | 4/1995 | Chen |
| 5,407,436 A | 4/1995 | Toft |
| 5,409,466 A | 4/1995 | Watson |
| RE34,936 E | 5/1995 | Campbell |
| 5,411,487 A | 5/1995 | Castagna |
| 5,415,638 A | 5/1995 | Novacek |
| 5,415,645 A | 5/1995 | Friend |
| 5,415,648 A | 5/1995 | Malay |
| 5,419,766 A | 5/1995 | Chang |
| 5,419,773 A | 5/1995 | Rupp |
| 5,423,746 A | 6/1995 | Burkett |
| 5,425,715 A | 6/1995 | Lawrence |

(56) References Cited

U.S. PATENT DOCUMENTS

| | | | |
|---|---|---|---|
| 5,425,722 A | 6/1995 | Whisson | |
| 5,429,611 A | 7/1995 | Rait | |
| 5,429,612 A | 7/1995 | Berthier | |
| 5,429,613 A | 7/1995 | D'Amico | |
| 5,431,631 A | 7/1995 | Lu | |
| 5,431,632 A | 7/1995 | Lu | |
| 5,433,712 A | 7/1995 | Stiles | |
| 5,445,618 A | 8/1995 | Adobbati | |
| 5,445,620 A | 8/1995 | Haber | |
| 5,451,210 A | 9/1995 | Kramer | |
| 5,458,576 A | 10/1995 | Haber | |
| 5,458,580 A | 10/1995 | Hajishoreh | |
| 5,460,611 A | 10/1995 | Alexander | |
| 5,462,531 A | 10/1995 | Novacek | |
| 5,466,223 A | 11/1995 | Bressler | |
| 5,468,227 A | 11/1995 | Haskell | |
| 5,474,687 A | 12/1995 | Van Vlasselaer | |
| 5,478,314 A | 12/1995 | Malenchek | |
| 5,478,316 A * | 12/1995 | Bitdinger | A61M 5/2033 604/135 |
| 5,478,328 A | 12/1995 | Silverman | |
| 5,480,385 A | 1/1996 | Thorne | |
| 5,480,387 A | 1/1996 | Gabriel | |
| 5,480,390 A | 1/1996 | Hajishoreh | |
| 5,482,039 A | 1/1996 | Place | |
| 5,484,414 A | 1/1996 | Pace | |
| 5,486,163 A | 1/1996 | Haynes | |
| 5,486,164 A | 1/1996 | Streck | |
| 5,487,732 A | 1/1996 | Jeffrey | |
| 5,487,733 A | 1/1996 | Caizza | |
| 5,487,734 A | 1/1996 | Thome | |
| 5,489,272 A | 2/1996 | Wirtz | |
| 5,492,536 A | 2/1996 | Mascia | |
| 5,496,278 A | 3/1996 | Buff | |
| 5,501,672 A | 3/1996 | Firth | |
| 5,512,048 A | 4/1996 | Slettenmark | |
| 5,512,050 A | 4/1996 | Caizza | |
| 5,514,097 A | 5/1996 | Knauer | |
| 5,514,107 A | 5/1996 | Haber | |
| 5,520,639 A | 5/1996 | Peterson | |
| 5,520,649 A | 5/1996 | Novacek | |
| 5,522,797 A | 6/1996 | Grimm | |
| 5,522,812 A | 6/1996 | Talon | |
| 5,527,283 A | 6/1996 | Kyler | |
| 5,527,284 A | 6/1996 | Ohnemus | |
| 5,527,287 A | 6/1996 | Miskinyar | |
| 5,527,307 A | 6/1996 | Srisathapat | |
| 5,529,189 A | 6/1996 | Feldschuh | |
| 5,531,691 A | 7/1996 | Shonfeld | |
| 5,531,692 A | 7/1996 | Rogers | |
| 5,531,694 A | 7/1996 | Clems | |
| 5,531,704 A | 7/1996 | Knotek | |
| 5,531,706 A | 7/1996 | De la Fuente | |
| 5,533,975 A | 7/1996 | Lu | |
| 5,533,984 A | 7/1996 | Parmigiani | |
| 5,536,243 A | 7/1996 | Jeyendran | |
| 5,536,253 A | 7/1996 | Haber | |
| 5,536,257 A | 7/1996 | Byme | |
| 5,538,506 A | 7/1996 | Farris | |
| 5,538,508 A | 7/1996 | Steyn | |
| 5,540,664 A | 7/1996 | Wyrick | |
| 5,540,666 A | 7/1996 | Barta | |
| 5,542,920 A | 8/1996 | Cherif Cheikh | |
| 5,542,927 A | 8/1996 | Thorne | |
| 5,549,558 A | 8/1996 | Martin | |
| 5,549,568 A | 8/1996 | Shields | |
| 5,549,570 A | 8/1996 | Rogalsky | |
| 5,549,572 A | 8/1996 | Byme | |
| 5,549,708 A | 8/1996 | Thorne | |
| 5,558,648 A | 9/1996 | Shields | |
| 5,562,623 A | 10/1996 | Shonfeld | |
| 5,562,624 A | 10/1996 | Righi | |
| 5,562,626 A | 10/1996 | Sanpietro | |
| 5,562,631 A | 10/1996 | Bogert | |
| 5,565,553 A | 10/1996 | Deitz | |
| 5,569,202 A | 10/1996 | Kovalic | |
| 5,569,203 A | 10/1996 | Chen | |
| 5,573,513 A | 11/1996 | Wozencroft | |
| 5,575,770 A | 11/1996 | Melsky | |
| 5,578,011 A | 11/1996 | Shaw | |
| 5,578,014 A | 11/1996 | Erez | |
| 5,578,015 A | 11/1996 | Robb | |
| 5,582,591 A | 12/1996 | Cheikh | |
| 5,584,815 A | 12/1996 | Pawelka | |
| 5,586,976 A | 12/1996 | Coutoumanos | |
| 5,591,133 A | 1/1997 | Feuerborn | |
| 5,591,134 A | 1/1997 | Shu | |
| 5,591,137 A | 1/1997 | Rupp | |
| 5,591,138 A | 1/1997 | Vaillancourt | |
| 5,593,388 A | 1/1997 | Phillips | |
| 5,593,390 A | 1/1997 | Castellano | |
| 5,599,309 A | 2/1997 | Marshall | |
| 5,599,313 A | 2/1997 | Gyure | |
| 5,599,316 A | 2/1997 | Blakely | |
| 5,599,318 A | 2/1997 | Sweeney | |
| 5,601,532 A | 2/1997 | Gaba | |
| 5,601,535 A | 2/1997 | Bryne | |
| 5,605,544 A | 2/1997 | Tsao | |
| 5,609,577 A | 3/1997 | Haber | |
| 5,611,781 A | 3/1997 | Sircom | |
| 5,611,782 A | 3/1997 | Haedt | |
| 5,613,500 A | 3/1997 | Bishop | |
| 5,613,951 A | 3/1997 | Meyer | |
| 5,613,952 A | 3/1997 | Pressly, Sr. | |
| 5,615,771 A | 4/1997 | Hollister | |
| 5,616,123 A | 4/1997 | Cheikh | |
| 5,616,128 A | 4/1997 | Meyer | |
| 5,616,132 A | 4/1997 | Newman | |
| 5,616,134 A | 4/1997 | Firth | |
| 5,616,135 A | 4/1997 | Thorne | |
| 5,620,422 A | 4/1997 | Halbich | |
| 5,620,425 A | 4/1997 | Heffernan | |
| 5,624,401 A | 4/1997 | Bo | |
| 5,624,405 A | 4/1997 | Futagawa | |
| 5,628,765 A | 5/1997 | Morita | |
| 5,630,803 A | 5/1997 | Tamaro | |
| 5,632,730 A | 5/1997 | Tamaro | |
| 5,632,733 A | 5/1997 | Shaw | |
| 5,634,906 A | 6/1997 | Haber | |
| 5,634,909 A | 6/1997 | Schmitz | |
| 5,634,937 A | 6/1997 | Mollenauer | |
| 5,637,094 A | 6/1997 | Stewart, Jr. | |
| 5,643,220 A | 7/1997 | Cosme | |
| 5,643,222 A | 7/1997 | Mahurkar | |
| 5,647,851 A | 7/1997 | Pokras | |
| 5,647,854 A | 7/1997 | Olsen | |
| 5,649,622 A | 7/1997 | Hollister | |
| 5,651,774 A | 7/1997 | Taranto | |
| 5,653,687 A | 8/1997 | Mills | |
| 5,653,688 A | 8/1997 | Mills | |
| 5,653,693 A | 8/1997 | Seiyaku | |
| 5,656,031 A | 8/1997 | Thorne | |
| 5,658,256 A | 8/1997 | Shields | |
| 5,658,257 A | 8/1997 | Ryles | |
| 5,658,258 A | 8/1997 | Kneer | |
| 5,658,259 A | 8/1997 | Pearson | |
| 5,662,610 A | 9/1997 | Sircom | |
| 5,662,617 A | 9/1997 | Odell | |
| 5,665,071 A | 9/1997 | Wyrick | |
| 5,665,075 A | 9/1997 | Gyure | |
| 5,669,889 A | 9/1997 | Gyure | |
| 5,672,155 A | 9/1997 | Riley | |
| 5,672,161 A | 9/1997 | Allen | |
| 5,681,295 A | 10/1997 | Gyure | |
| 5,681,291 A | 11/1997 | Galli | |
| 5,688,240 A | 11/1997 | Novacek | |
| 5,688,251 A | 11/1997 | Chanoch | |
| 5,693,016 A | 12/1997 | Gumaste | |
| 5,693,022 A | 12/1997 | Haynes | |
| 5,693,023 A | 12/1997 | Adams | |
| 5,695,472 A | 12/1997 | Wyrick | |
| 5,704,911 A | 1/1998 | Parsons | |
| 5,704,921 A | 1/1998 | Carilli | |
| 5,707,393 A | 1/1998 | Kensey | |

(56) References Cited

U.S. PATENT DOCUMENTS

| | | |
|---|---|---|
| 5,709,662 A | 1/1998 | Olive |
| 5,709,667 A | 1/1998 | Carilli |
| 5,709,668 A | 1/1998 | Wacks |
| 5,713,866 A | 2/1998 | Wilmot |
| 5,713,871 A | 2/1998 | Stock |
| 5,713,872 A | 2/1998 | Mark |
| 5,720,727 A | 2/1998 | Alexander |
| 5,725,498 A | 3/1998 | Janzen |
| 5,738,655 A | 4/1998 | Vallelunga |
| 5,741,223 A | 4/1998 | Janzen |
| 5,743,879 A | 4/1998 | Kriesel |
| 5,743,887 A | 4/1998 | Brattesani |
| 5,743,888 A | 4/1998 | Wilkes |
| 5,743,891 A | 4/1998 | Tolkoff |
| 5,746,718 A | 5/1998 | Steyn |
| 5,749,854 A | 5/1998 | Shen |
| 5,749,860 A | 5/1998 | Kyte |
| 5,755,692 A | 5/1998 | Manicom |
| 5,769,822 A | 6/1998 | McGary |
| 5,769,827 A | 6/1998 | Demichele |
| 5,779,675 A | 7/1998 | Reilly |
| 5,779,677 A | 7/1998 | Frezza |
| 5,779,684 A | 7/1998 | Tamaro |
| 5,788,677 A | 8/1998 | Botich |
| 5,788,713 A | 8/1998 | Dubach |
| 5,792,107 A | 8/1998 | Petrocelli |
| 5,792,121 A | 8/1998 | Tamaro |
| 5,792,122 A | 8/1998 | Brimhall |
| 5,795,336 A | 8/1998 | Romano |
| 5,797,885 A | 8/1998 | Rubin |
| 5,800,403 A | 9/1998 | Pressly, Sr. |
| 5,807,334 A | 9/1998 | Hodosh |
| 5,807,345 A | 9/1998 | Grabenkort |
| 5,807,352 A | 9/1998 | Tamaro |
| 5,810,775 A | 9/1998 | Shaw |
| 5,810,784 A | 9/1998 | Tamaro |
| 5,817,054 A | 10/1998 | Grimm |
| 5,817,070 A | 10/1998 | Tamaro |
| 5,820,602 A | 10/1998 | Kovelman |
| 5,823,997 A | 10/1998 | Thome |
| 5,823,998 A | 10/1998 | Yamagata |
| 5,827,293 A | 10/1998 | Elliott |
| 5,830,130 A | 11/1998 | Janzen |
| 5,836,911 A | 11/1998 | Marzynski |
| 5,836,920 A | 11/1998 | Robertson |
| 5,843,036 A | 12/1998 | Olive |
| 5,843,047 A | 12/1998 | Pyrozyk |
| 5,848,990 A | 12/1998 | Cirelli |
| 5,851,197 A | 12/1998 | Marano |
| 5,853,390 A | 12/1998 | Freschi |
| 5,853,393 A | 12/1998 | Bogert |
| 5,855,839 A | 1/1999 | Marc |
| 5,858,000 A | 1/1999 | Novacek |
| 5,865,227 A | 2/1999 | Carilli |
| 5,865,804 A | 2/1999 | Bachynsky |
| 5,868,711 A | 2/1999 | Kramer |
| 5,879,337 A | 3/1999 | Kuracina |
| 5,882,342 A | 3/1999 | Cooper |
| 5,885,257 A | 3/1999 | Badger |
| 5,891,052 A | 4/1999 | Simmons |
| 5,891,092 A | 4/1999 | Castellano |
| 5,891,097 A | 4/1999 | Saito |
| 5,891,105 A | 4/1999 | Mahurkar |
| 5,897,508 A | 4/1999 | Konrad |
| 5,899,885 A | 5/1999 | Reilly |
| 5,899,886 A | 5/1999 | Cosme |
| 5,908,404 A | 6/1999 | Elliott |
| 5,908,408 A | 6/1999 | McGary |
| 5,910,131 A | 6/1999 | McGary |
| 5,911,706 A | 6/1999 | Estabrook |
| 5,919,166 A | 7/1999 | McGary |
| 5,921,959 A | 7/1999 | McGary |
| 5,921,960 A | 7/1999 | McGary |
| 5,921,961 A | 7/1999 | McGary |
| 5,921,963 A | 7/1999 | Erez |
| 5,921,964 A | 7/1999 | Martin |
| 5,925,019 A | 7/1999 | Ljungquist |
| 5,928,188 A | 7/1999 | McGary |
| 5,928,194 A | 7/1999 | Maget |
| 5,928,205 A | 7/1999 | Marshall |
| 5,931,813 A | 8/1999 | Neng |
| 5,938,638 A | 8/1999 | Passariello |
| 5,938,639 A | 8/1999 | Reilly |
| 5,941,850 A | 8/1999 | Shah |
| 5,944,692 A | 8/1999 | McGary |
| 5,944,693 A | 8/1999 | Jacobs |
| 5,951,522 A | 9/1999 | Rosato |
| 5,957,892 A | 9/1999 | Thorne |
| 5,957,895 A | 9/1999 | Sage |
| 5,957,897 A | 9/1999 | Jeffrey |
| 5,960,797 A | 10/1999 | Kramer |
| 5,961,491 A | 10/1999 | McGary |
| 5,971,953 A | 10/1999 | Bachynsky |
| RE36,398 E | 11/1999 | Byme |
| 5,975,355 A | 11/1999 | Cecala |
| 5,976,111 A | 11/1999 | Hart |
| 5,980,487 A | 11/1999 | Jones |
| 5,980,488 A | 11/1999 | Thorne |
| 5,980,491 A | 11/1999 | Hansen |
| 5,980,494 A | 11/1999 | Malenchek |
| 5,984,899 A | 11/1999 | D'Alessio |
| 5,984,900 A | 11/1999 | Mikkelsen |
| 5,989,219 A | 11/1999 | Villas |
| 5,989,221 A | 11/1999 | Hjertman |
| 5,993,417 A | 11/1999 | Yerfino |
| 5,993,418 A | 11/1999 | Alexander |
| RE36,447 E | 12/1999 | Byme |
| 5,997,500 A | 12/1999 | Cook |
| 5,997,511 A | 12/1999 | Curie |
| 5,997,513 A | 12/1999 | Smith |
| 6,001,080 A | 12/1999 | Kuracina |
| 6,007,474 A | 12/1999 | Rydell |
| 6,010,486 A | 1/2000 | Carter |
| 6,010,487 A | 1/2000 | DeMichele |
| 6,015,396 A | 1/2000 | Buttgen |
| 6,015,438 A | 1/2000 | Shaw |
| 6,017,325 A | 1/2000 | Yerfino |
| 6,022,337 A | 2/2000 | Herbst |
| 6,033,386 A | 3/2000 | Novacek |
| 6,033,387 A | 3/2000 | Brunel |
| 6,036,674 A | 3/2000 | Caizza |
| 6,039,713 A | 3/2000 | Botich |
| 6,050,974 A | 4/2000 | Allard |
| 6,050,977 A | 4/2000 | Adams |
| 6,056,716 A | 5/2000 | D'Antonio |
| 6,056,724 A | 5/2000 | Lacroix |
| 6,056,734 A | 5/2000 | Jacobsen |
| 6,063,040 A | 5/2000 | Owen |
| 6,063,053 A | 5/2000 | Castellano |
| 6,066,115 A | 5/2000 | Chang Lai |
| 6,068,616 A | 5/2000 | Janus |
| 6,074,360 A | 6/2000 | Haar |
| 6,074,369 A | 6/2000 | Sage |
| 6,074,370 A | 6/2000 | Pressly |
| 6,077,245 A | 6/2000 | Heinrich |
| 6,080,135 A | 6/2000 | Van Stokkum |
| 6,083,199 A | 7/2000 | Thorley |
| 6,083,200 A | 7/2000 | Grimm |
| 6,086,562 A | 7/2000 | Jacobsen |
| 6,086,569 A | 7/2000 | Schweizer |
| 6,090,077 A | 7/2000 | Shaw |
| 6,090,078 A | 7/2000 | Erskine |
| 6,090,080 A | 7/2000 | Jost |
| 6,093,172 A | 7/2000 | Funderburk |
| 6,099,500 A | 8/2000 | Dysarz |
| 6,099,503 A | 8/2000 | Stradella |
| 6,099,504 A | 8/2000 | Gross |
| 6,102,844 A | 8/2000 | Ravins |
| 6,113,574 A | 9/2000 | Spinello |
| 6,117,112 A | 9/2000 | Mahurkar |
| 6,117,113 A | 9/2000 | Novacek |
| 6,126,637 A | 10/2000 | Kriesel |
| 6,129,710 A | 10/2000 | Padgett |
| 6,142,972 A | 11/2000 | Cheikh |

(56) References Cited

U.S. PATENT DOCUMENTS

| | | |
|---|---|---|
| 6,149,626 A | 11/2000 | Bachynsky |
| 6,149,629 A | 11/2000 | Wilson |
| 6,156,008 A | 12/2000 | Castellano |
| 6,156,010 A | 12/2000 | Kuracina |
| 6,156,013 A | 12/2000 | Mahurkar |
| 6,156,015 A | 12/2000 | DeMichele |
| 6,159,161 A | 12/2000 | Hodosh |
| 6,159,181 A | 12/2000 | Crossman |
| 6,159,185 A | 12/2000 | Tanihata |
| 6,171,284 B1 | 1/2001 | Kao |
| 6,179,812 B1 | 1/2001 | Botich |
| 6,183,444 B1 | 2/2001 | Glines |
| 6,183,446 B1 | 2/2001 | Jeanbourquin |
| 6,186,980 B1 | 2/2001 | Marc |
| 6,192,891 B1 | 2/2001 | Gravel |
| 6,193,695 B1 | 2/2001 | Ripstein, Jr. |
| RE37,110 E | 3/2001 | Holliste |
| 6,206,856 B1 | 3/2001 | Mahurkar |
| 6,206,857 B1 | 3/2001 | Chen |
| 6,210,369 B1 | 4/2001 | Wilmot |
| 6,217,550 B1 | 4/2001 | Capes |
| 6,217,559 B1 | 4/2001 | Foster |
| 6,221,044 B1 | 4/2001 | Greco |
| 6,221,051 B1 | 4/2001 | Hjertman |
| 6,221,052 B1 | 4/2001 | Caizza |
| 6,224,576 B1 | 5/2001 | Thorne |
| 6,228,054 B1 | 5/2001 | Dysarz |
| 6,228,055 B1 | 5/2001 | Foerster |
| 6,235,006 B1 | 5/2001 | Dillon |
| 6,241,707 B1 | 6/2001 | Dysarz |
| 6,241,708 B1 | 6/2001 | Reilly |
| RE37,252 E | 7/2001 | Hollister |
| 6,254,575 B1 | 7/2001 | Thome |
| 6,254,580 B1 | 7/2001 | Svedman |
| 6,258,056 B1 | 7/2001 | Turley |
| 6,261,264 B1 | 7/2001 | Tamaro |
| 6,261,265 B1 | 7/2001 | Mosseri |
| 6,267,748 B1 | 7/2001 | Gulliksen |
| 6,270,472 B1 | 8/2001 | Antaki |
| 6,270,479 B1 | 8/2001 | Bergens |
| 6,270,481 B1 | 8/2001 | Mason |
| 6,273,870 B1 | 8/2001 | Garvin |
| 6,280,399 B1 | 8/2001 | Rossin |
| 6,280,420 B1 | 8/2001 | Ferguson |
| 6,280,421 B1 | 8/2001 | Fritz |
| 6,283,941 B1 | 9/2001 | Schoenfeld |
| 6,293,925 B1 | 9/2001 | Safabash |
| 6,299,601 B1 | 10/2001 | Hjertman |
| 6,309,374 B1 | 10/2001 | Hecker |
| 6,309,375 B1 | 10/2001 | Glines |
| 6,312,409 B1 | 11/2001 | Gross |
| 6,315,113 B1 | 11/2001 | Britton |
| 6,319,233 B1 | 11/2001 | Jansen |
| 6,319,234 B1 | 11/2001 | Restelli |
| 6,322,536 B1 | 11/2001 | Rosengart |
| RE37,487 E | 12/2001 | Reilly |
| 6,325,781 B1 | 12/2001 | Takagi |
| 6,325,789 B1 | 12/2001 | Janzen |
| 6,331,173 B1 | 12/2001 | Ljungquist |
| 6,332,875 B2 | 12/2001 | Inkpen |
| 6,344,031 B1 | 2/2002 | Novacek |
| 6,356,783 B1 | 3/2002 | Hubbard, Jr. |
| 6,361,525 B2 | 3/2002 | Capes |
| 6,368,303 B1 | 4/2002 | Caizza |
| 6,371,938 B1 | 4/2002 | Reilly |
| 6,371,939 B2 | 4/2002 | Bergens |
| 6,379,336 B1 | 4/2002 | Asbaghi |
| 6,387,078 B1 | 5/2002 | Gillespie, III |
| 6,402,716 B1 | 6/2002 | Ryoo |
| 6,409,701 B1 | 6/2002 | Cohn |
| 6,409,703 B1 | 6/2002 | Lu |
| 6,409,706 B1 | 6/2002 | Loy |
| 6,412,490 B1 | 7/2002 | Lee |
| 6,413,236 B1 | 7/2002 | Van Dyke |
| 6,413,237 B1 | 7/2002 | Caizza |
| 6,416,323 B1 | 7/2002 | Grenfell |
| 6,416,497 B1 | 7/2002 | Kirk |
| 6,419,658 B1 | 7/2002 | Restelli |
| 6,428,463 B1 | 8/2002 | Ravins |
| 6,428,517 B1 | 8/2002 | Hochman |
| 6,432,035 B1 | 8/2002 | Ravins |
| 6,432,082 B1 | 8/2002 | Chen |
| 6,432,087 B1 | 8/2002 | Hoeck |
| 6,436,068 B1 | 8/2002 | Bardy |
| 6,440,098 B1 | 8/2002 | Luscher |
| 6,443,929 B1 | 9/2002 | Kuracina |
| 6,447,480 B1 | 9/2002 | Brunel |
| 6,454,743 B1 | 9/2002 | Weber |
| 6,458,105 B1 | 10/2002 | Rippstein, Jr. |
| 6,461,331 B1 | 10/2002 | Van Antwerp |
| 6,461,333 B1 | 10/2002 | Frezza |
| 6,468,247 B1 | 10/2002 | Zamoyski |
| 6,475,194 B2 | 11/2002 | Domici, Jr. |
| 6,478,780 B1 | 11/2002 | Shields |
| 6,482,176 B1 | 11/2002 | Wich |
| 6,485,469 B1 | 11/2002 | Stewart |
| 6,485,474 B1 | 11/2002 | Heinz |
| 6,494,863 B1 | 12/2002 | Shaw |
| 6,500,155 B2 | 12/2002 | Sasso |
| 6,508,755 B1 | 1/2003 | Ravins |
| 6,511,454 B1 | 1/2003 | Nakao |
| 6,514,230 B1 | 2/2003 | Munk |
| 6,517,516 B1 | 2/2003 | Caizza |
| 6,517,517 B1 | 2/2003 | Farrugia |
| 6,520,425 B1 | 2/2003 | Reneker |
| 6,524,278 B1 | 2/2003 | Campbell |
| 6,527,734 B2 | 3/2003 | Cragg |
| 6,527,742 B1 | 3/2003 | Malenchek |
| 6,530,896 B1 | 3/2003 | Elliott |
| 6,530,903 B2 | 3/2003 | Wang |
| 6,530,904 B1 | 3/2003 | Edwards |
| 6,537,249 B2 | 3/2003 | Kriesell |
| 6,537,252 B1 | 3/2003 | Hansen |
| 6,544,234 B1 | 4/2003 | Gabriel |
| 6,547,764 B2 | 4/2003 | Larsen |
| 6,551,275 B2 | 4/2003 | Fontayne |
| 6,551,276 B1 | 4/2003 | Mann |
| 6,551,278 B1 | 4/2003 | Geitz |
| 6,554,798 B1 | 4/2003 | Mann |
| 6,558,351 B1 | 5/2003 | Steil |
| 6,558,357 B1 | 5/2003 | Hoeck |
| 6,565,533 B1 | 5/2003 | Smith |
| 6,565,538 B2 | 5/2003 | Quinn |
| 6,569,115 B1 | 5/2003 | Barker |
| 6,572,584 B1 | 6/2003 | Shaw |
| 6,572,585 B2 | 6/2003 | Choi |
| 6,572,590 B1 | 6/2003 | Stevens |
| 6,575,939 B1 | 6/2003 | Marc |
| 6,579,256 B2 | 6/2003 | Hughes |
| 6,582,405 B2 | 6/2003 | Kawagishi |
| 6,584,910 B1 | 7/2003 | Plass |
| 6,585,690 B1 | 7/2003 | Hoeck |
| 6,585,693 B1 | 7/2003 | Dischler |
| 6,585,702 B1 | 7/2003 | Marc |
| 6,589,158 B2 | 7/2003 | Winkler |
| 6,592,508 B1 | 7/2003 | Ravins |
| 6,592,555 B1 | 7/2003 | Wang |
| 6,592,556 B1 | 7/2003 | Thorne |
| 6,595,962 B1 | 7/2003 | Perthu |
| 6,599,268 B1 | 7/2003 | Townsend |
| 6,599,269 B1 | 7/2003 | Lewandowski |
| 6,599,272 B1 | 7/2003 | Hjertman |
| 6,605,058 B1 | 8/2003 | Wich |
| 6,605,067 B1 | 8/2003 | Larsen |
| 6,605,073 B1 | 8/2003 | Pressly, Sr. |
| 6,607,508 B2 | 8/2003 | Knauer |
| 6,607,509 B2 | 8/2003 | Bobroff |
| 6,613,019 B2 | 9/2003 | Munk |
| 6,613,022 B1 | 9/2003 | Doyle |
| 6,616,630 B1 | 9/2003 | Woehr |
| 6,616,638 B2 | 9/2003 | Peters, III |
| 6,616,639 B2 | 9/2003 | Gagnieux |
| 6,620,136 B1 | 9/2003 | Pressly, Sr. |
| 6,620,137 B2 | 9/2003 | Kirchhofer |

(56) References Cited

U.S. PATENT DOCUMENTS

| | | |
|---|---|---|
| 6,620,138 B1 | 9/2003 | Marrgi |
| 6,623,455 B2 | 9/2003 | Small |
| 6,623,458 B2 | 9/2003 | Woehr |
| 6,623,459 B1 | 9/2003 | Doyle |
| 6,626,864 B2 | 9/2003 | Jansen |
| 6,629,957 B1 | 10/2003 | Wiklund |
| 6,629,959 B2 | 10/2003 | Kuracina |
| 6,632,198 B2 | 10/2003 | Caizza |
| 6,637,587 B2 | 10/2003 | Britton |
| 6,638,248 B1 | 10/2003 | Brewer |
| 6,638,255 B1 | 10/2003 | Weber |
| 6,641,561 B1 | 11/2003 | Hill |
| 6,645,181 B1 | 11/2003 | Lavi |
| 6,652,482 B2 | 11/2003 | Hochman |
| 6,656,164 B1 | 12/2003 | Smith |
| 6,659,975 B2 | 12/2003 | Amano |
| 6,659,982 B2 | 12/2003 | Douglas |
| 6,663,593 B2 | 12/2003 | Ito |
| 6,669,666 B2 | 12/2003 | Lu |
| 6,673,034 B2 | 1/2004 | Castellano |
| 6,673,044 B2 | 1/2004 | Righi |
| 6,673,049 B2 | 1/2004 | Hommann |
| 6,678,550 B2 | 1/2004 | Hubbard, Jr. |
| 6,679,863 B2 | 1/2004 | Bush, Jr. |
| 6,679,864 B2 | 1/2004 | Gagnieux |
| 6,685,676 B2 | 2/2004 | Jansen |
| 6,685,677 B2 | 2/2004 | Green |
| 6,689,091 B2 | 2/2004 | Bui |
| 6,689,106 B2 | 2/2004 | Bush, Jr. |
| 6,689,107 B1 | 2/2004 | Choudhary |
| 6,689,108 B2 | 2/2004 | Lavi |
| 6,692,470 B2 | 2/2004 | Sanpietro |
| 6,692,471 B2 | 2/2004 | Boudreaux |
| 6,699,218 B2 | 3/2004 | Flaherty |
| 6,702,784 B1 | 3/2004 | Sheckler |
| 6,706,011 B1 | 3/2004 | Murphy-Chutorian |
| 6,706,015 B2 | 3/2004 | Bang |
| 6,706,019 B1 | 3/2004 | Chui |
| 6,709,416 B2 | 3/2004 | Hjertman |
| 6,712,787 B1 | 3/2004 | Dysarz |
| 6,712,788 B2 | 3/2004 | Righi |
| 6,716,191 B2 | 4/2004 | Sergio |
| 6,716,197 B2 | 4/2004 | Svendsen |
| 6,716,198 B2 | 4/2004 | Larsen |
| 6,719,721 B1 | 4/2004 | Okazaki |
| 6,719,728 B2 | 4/2004 | Mason |
| 6,719,730 B2 | 4/2004 | Hubert |
| 6,723,068 B2 | 4/2004 | Lavi |
| 6,723,072 B2 | 4/2004 | Christopher |
| 6,726,655 B1 | 4/2004 | Lieberman |
| 6,726,658 B2 | 4/2004 | Hochman |
| 6,726,661 B2 | 4/2004 | Munk |
| 6,726,662 B2 | 4/2004 | Altman |
| 6,730,059 B2 | 5/2004 | Caizza |
| 6,736,800 B2 | 5/2004 | Rindlisbacher |
| 6,740,059 B2 | 5/2004 | Flaherty |
| 6,743,203 B1 | 6/2004 | Pickhard |
| 6,749,833 B2 | 6/2004 | Raghavan |
| 6,752,782 B2 | 6/2004 | Liao |
| 6,752,784 B2 | 6/2004 | Tsai |
| 6,752,798 B2 | 6/2004 | McWethy |
| 6,761,706 B2 | 7/2004 | Vaillancourt |
| 6,767,336 B1 | 7/2004 | Kaplan |
| 6,960,194 B2 | 11/2005 | Hommann |
| 7,097,634 B2 | 8/2006 | Gilbert |
| 7,112,187 B2 | 9/2006 | Karlsson |
| 7,128,728 B2 | 10/2006 | Kirchhofer |
| 7,300,420 B2 | 11/2007 | Doyle |
| 7,357,790 B2 | 4/2008 | Hommann |
| 7,357,791 B2 | 4/2008 | Kirchhofer |
| 7,442,185 B2 | 10/2008 | Amark |
| 7,442,186 B2 | 10/2008 | Blomquist |
| 7,476,217 B2 | 1/2009 | Martin |
| 7,500,964 B2 | 3/2009 | Law |
| 7,569,035 B1 | 8/2009 | Wilmot |
| 7,695,453 B2 | 4/2010 | Marshall |
| 7,717,877 B2 | 5/2010 | Lavi |
| 7,736,333 B2 | 6/2010 | Gillespie |
| 7,785,292 B2 | 8/2010 | Harrison |
| 7,794,432 B2 | 9/2010 | Young |
| 7,875,006 B2 | 1/2011 | Pessin |
| 7,905,866 B2 | 3/2011 | Haider |
| 7,931,625 B2 | 4/2011 | Kirchhofer |
| 7,931,626 B2 | 4/2011 | Kirchhofer |
| 8,070,741 B2 | 12/2011 | Jansen |
| 8,313,466 B2 | 11/2012 | Edwards |
| 8,343,110 B2 | 1/2013 | Burnell |
| 8,372,031 B2 | 2/2013 | Gunnar |
| 8,409,149 B2 | 4/2013 | Hommann |
| 8,449,498 B2 | 5/2013 | Marshall |
| 8,529,510 B2 | 9/2013 | Giambattista |
| 8,568,359 B2 | 10/2013 | Carrel |
| 8,591,465 B2 | 11/2013 | Hommann |
| 8,734,393 B2 | 5/2014 | Cleathero |
| 8,858,508 B2 | 10/2014 | Tsais |
| 8,932,265 B2 | 1/2015 | Korisch |
| 8,945,049 B2 | 2/2015 | Hommann |
| 8,968,236 B2 | 3/2015 | Jennings |
| 9,095,660 B2 | 8/2015 | Larsen |
| 9,302,054 B2 | 4/2016 | Marshall |
| 9,314,575 B2 | 4/2016 | Chevalier |
| 9,427,528 B2 | 8/2016 | Hommann |
| 9,486,582 B2 | 11/2016 | Abry |
| 9,586,010 B2 | 3/2017 | Hills |
| 9,675,757 B2 | 6/2017 | Nigel |
| 9,855,392 B2 | 1/2018 | Hommann |
| 10,166,334 B2 | 1/2019 | Wyrick |
| 10,493,213 B2 | 12/2019 | Scherer |
| 10,518,041 B2 | 12/2019 | Burnell |
| 2002/0133122 A1 | 9/2002 | Giambattista |
| 2003/0093036 A1 | 5/2003 | Crossman |
| 2003/0105430 A1 | 6/2003 | Lavi |
| 2004/0039336 A1 | 2/2004 | Amark |
| 2004/0054327 A1 | 3/2004 | Gillespie |
| 2004/0215151 A1 | 10/2004 | Marshall |
| 2007/0129686 A1 | 6/2007 | Daily |
| 2008/0312590 A1 | 12/2008 | Burnell |
| 2009/0204076 A1 | 8/2009 | Liversidge |
| 2010/0121272 A1 | 5/2010 | Marshall |
| 2011/0098641 A1 | 4/2011 | Haider |
| 2011/0196339 A1 | 8/2011 | Hirschel |
| 2016/0074585 A1 | 3/2016 | Hommann |
| 2016/0184530 A1 | 6/2016 | Schenker |
| 2016/0325044 A1 | 11/2016 | Tschirren |
| 2018/0221589 A1 | 8/2018 | Vogt |

FOREIGN PATENT DOCUMENTS

| | | |
|---|---|---|
| CN | 1867368 B | 7/2010 |
| CN | 102014991 B | 11/2013 |
| CN | 102149419 B | 4/2014 |
| CN | 101547713 B | 6/2016 |
| CN | 106413778 A | 2/2017 |
| CN | 104056327 B | 5/2017 |
| DE | 1000814 | 1/1957 |
| DE | 10009814 | 9/2001 |
| DE | 102004060146 A1 | 8/2005 |
| DE | 10342058 B4 | 10/2007 |
| DE | 10066400 B4 | 1/2012 |
| EP | 1349590 B1 | 5/2006 |
| EP | 1680162 A1 | 7/2006 |
| EP | 1703929 B1 | 10/2009 |
| EP | 1654020 B1 | 3/2010 |
| EP | 620748 B1 | 7/2010 |
| EP | 1568388 B2 | 7/2010 |
| EP | 1590023 B1 | 5/2011 |
| EP | 2624882 A1 | 8/2013 |
| EP | 2331510 B1 | 5/2014 |
| EP | 1518575 B2 | 6/2014 |
| EP | 2745866 A1 | 6/2014 |
| EP | 2217308 | 7/2016 |
| EP | 3189867 A1 | 7/2017 |
| EP | 2902057 | 1/2020 |
| JP | 4230698 B2 | 2/2009 |

(56) References Cited

FOREIGN PATENT DOCUMENTS

| | | | |
|---|---|---|---|
| JP | 4377880 | B2 | 12/2009 |
| JP | 4695084 | B2 | 6/2011 |
| JP | 4783763 | B2 | 9/2011 |
| JP | 6334717 | B2 | 5/2018 |
| WO | 0247746 | | 6/2002 |
| WO | 03011378 | | 2/2003 |
| WO | WO 03037663 | | 5/2003 |
| WO | 2004047890 | | 6/2004 |
| WO | 2005021070 | | 3/2005 |
| WO | 2005023341 | | 3/2005 |
| WO | 2005025636 | | 3/2005 |
| WO | 2005035029 | | 4/2005 |
| WO | 2005058396 | | 6/2005 |
| WO | 2012045350 | | 4/2012 |
| WO | 2013016832 | | 2/2013 |
| WO | 2017219157 | | 12/2017 |
| WO | 2018130944 | | 7/2018 |

OTHER PUBLICATIONS

An office action dated Jul. 7, 2011, which issued during the prosecution of Canadian Paten Application No. 2,539,315.

An Office action dated Jan. 19, 2012, which issued during the prosecution of Indian Patent Application No. 426/MUMNP/2006.

An Office Action dated Mar. 19, 2012, which issued during the prosecution of U.S. Appl. No. 12/741,628.

An Examination Report dated Feb. 10, 2012, which issued during the prosecution of European Patent Application No. 04770522,3.

An International Search Report and a Written Opinion both dated Feb. 28, 2006, which issued during the prosecution of Applican'ts PCT/I12004/000851.

A Hearing Notice in Reference dated Jan. 19, 2012, which issued during the prosecution of Indian Patent Application No. 426/MUMNP/2006.

An International Preliminary Report on Patentability dated Jan. 5, 2007, which issued during the prosecution of Applicant's PCT/IL2004/000851.

U.S. Appl. No. 60/853,411, filed Oct. 19, 2006.

European Search Report for EP 13175764 dated Nov. 6, 2013, 6 pages.

International Search Report and Written Opinion in International Appln. No. PCT/IL2007/001258, dated Aug. 8, 2008, 4 pages.

International Search Report and Written Opinion in International Appln. No. PCT/IL2014/050375, dated Aug. 5, 2014, 15 pages.

U.S. Office Action in U.S. Appl. No. 12/446,168, dated Dec. 31, 2013, 11 pages.

* cited by examiner

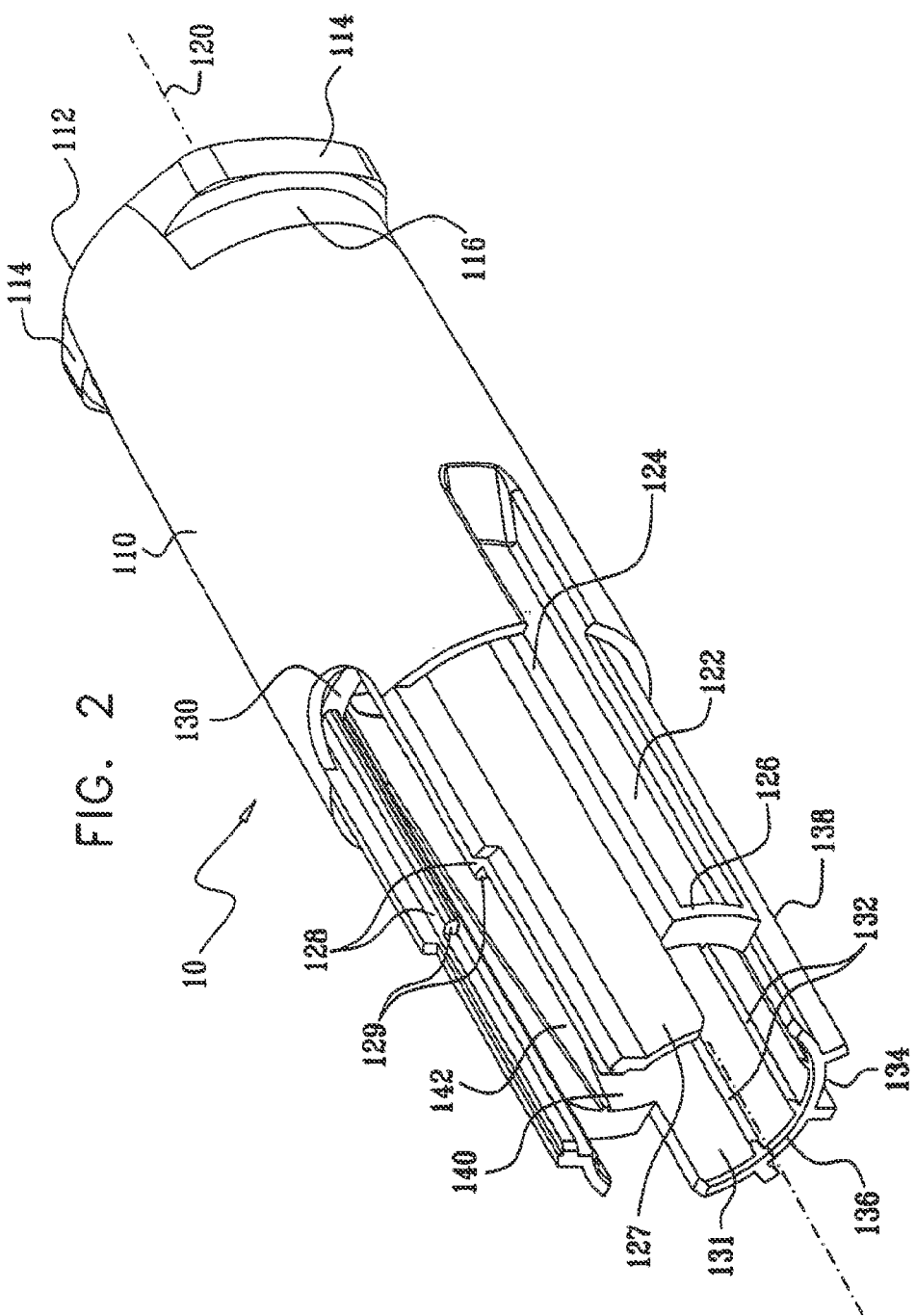

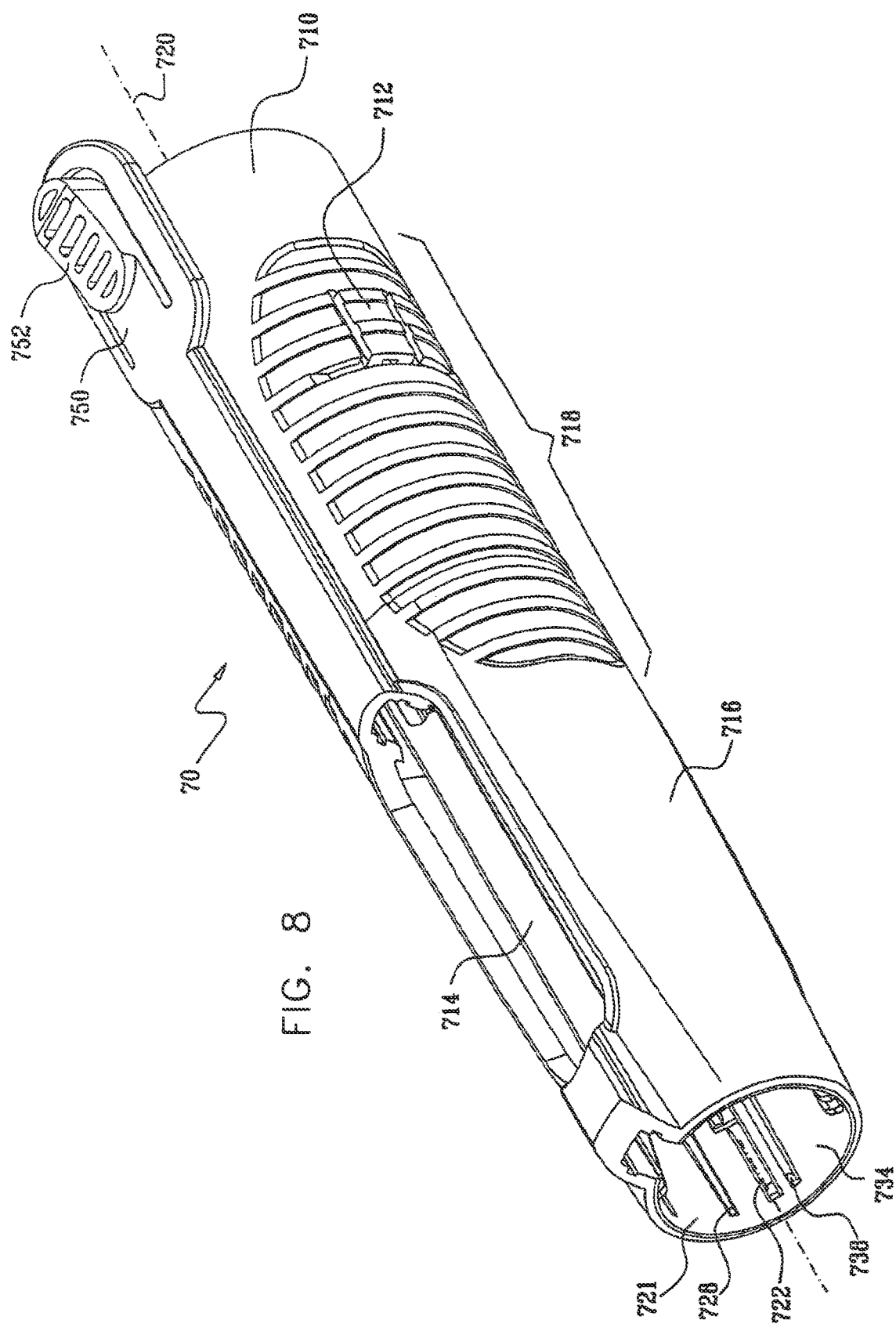

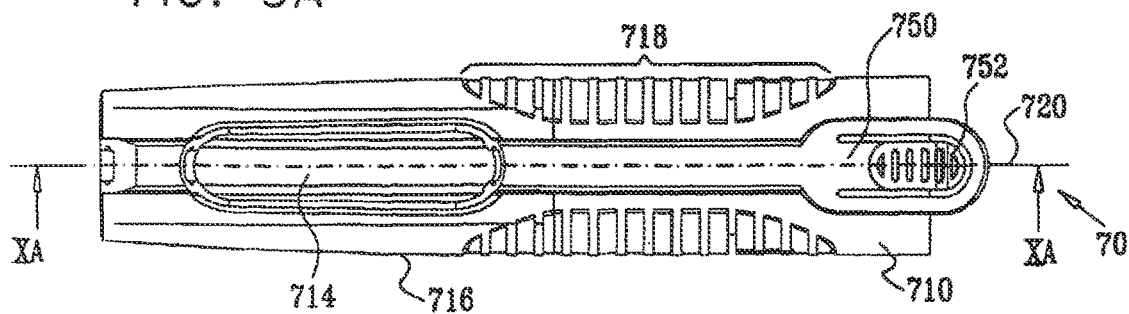
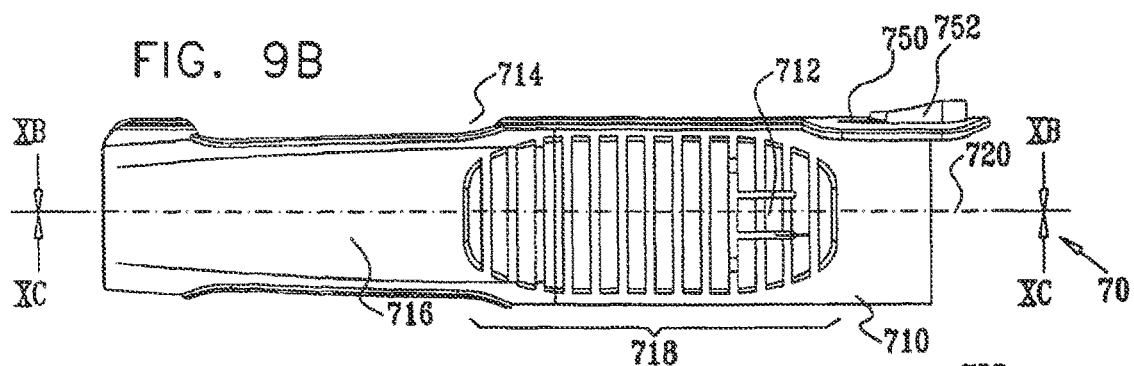
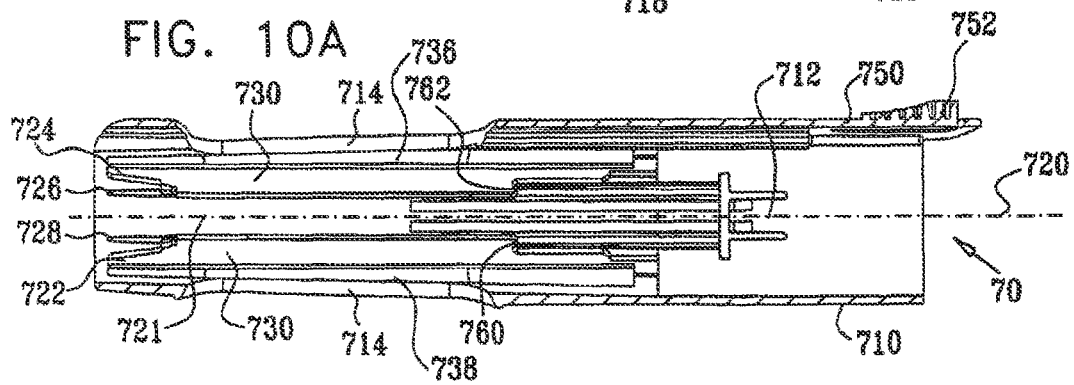
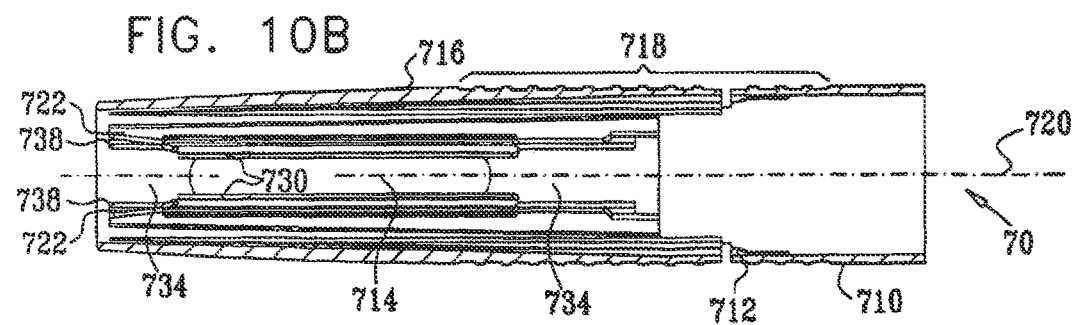
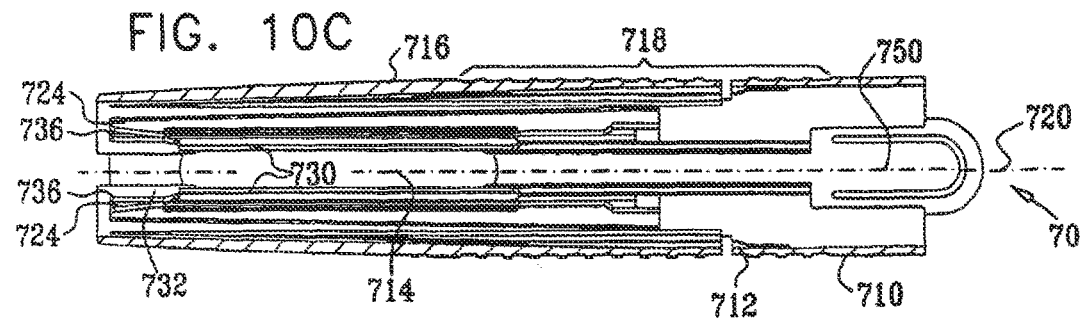

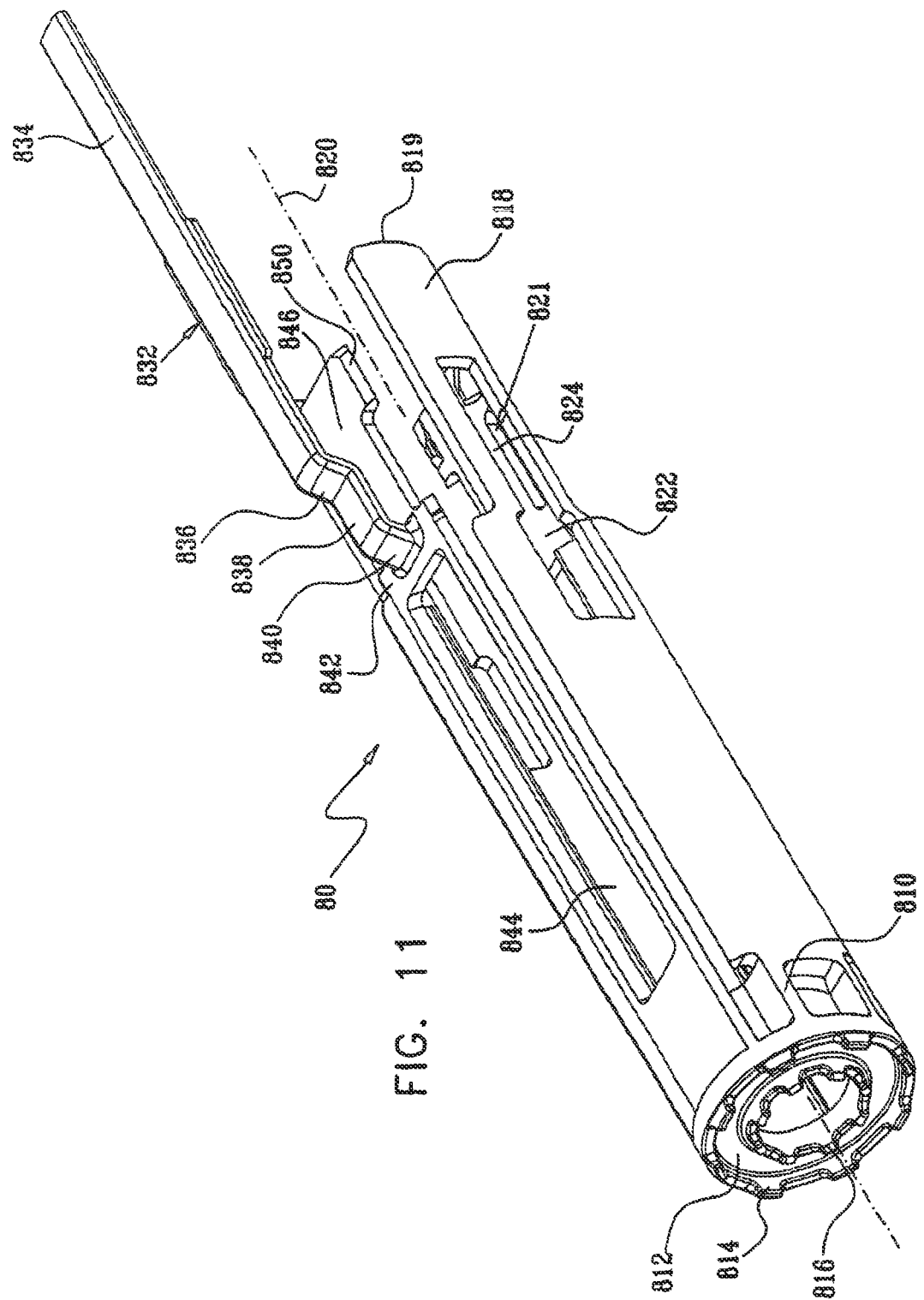

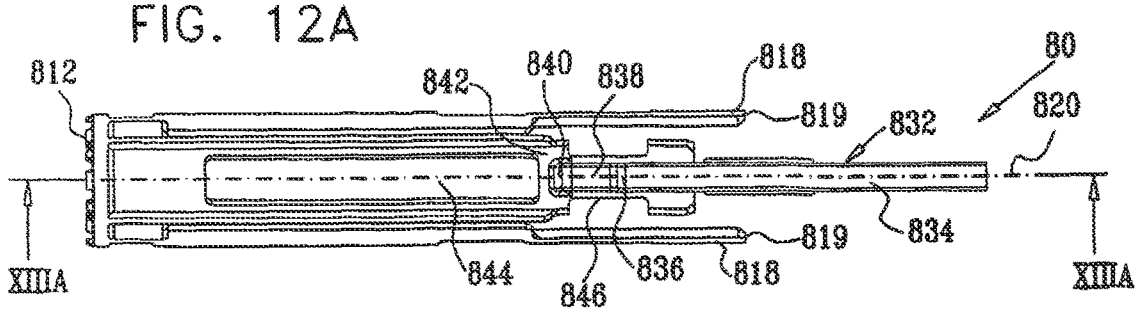
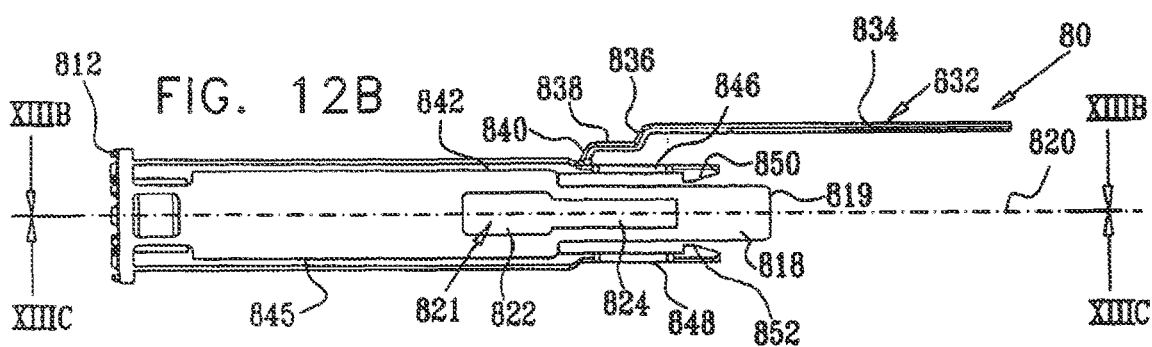
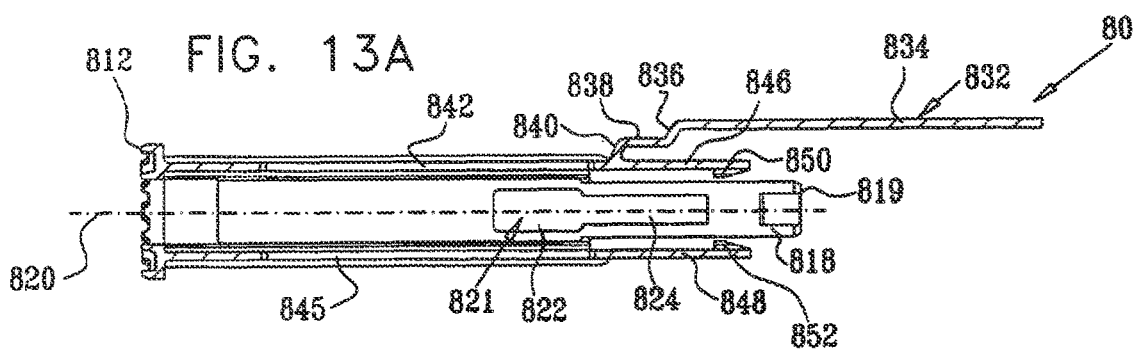
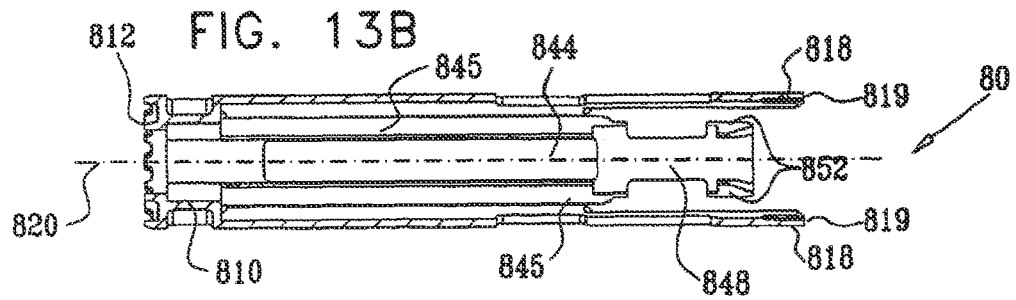
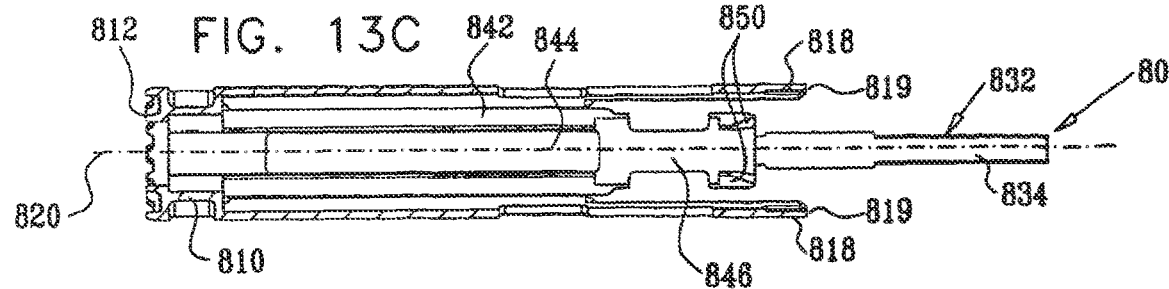

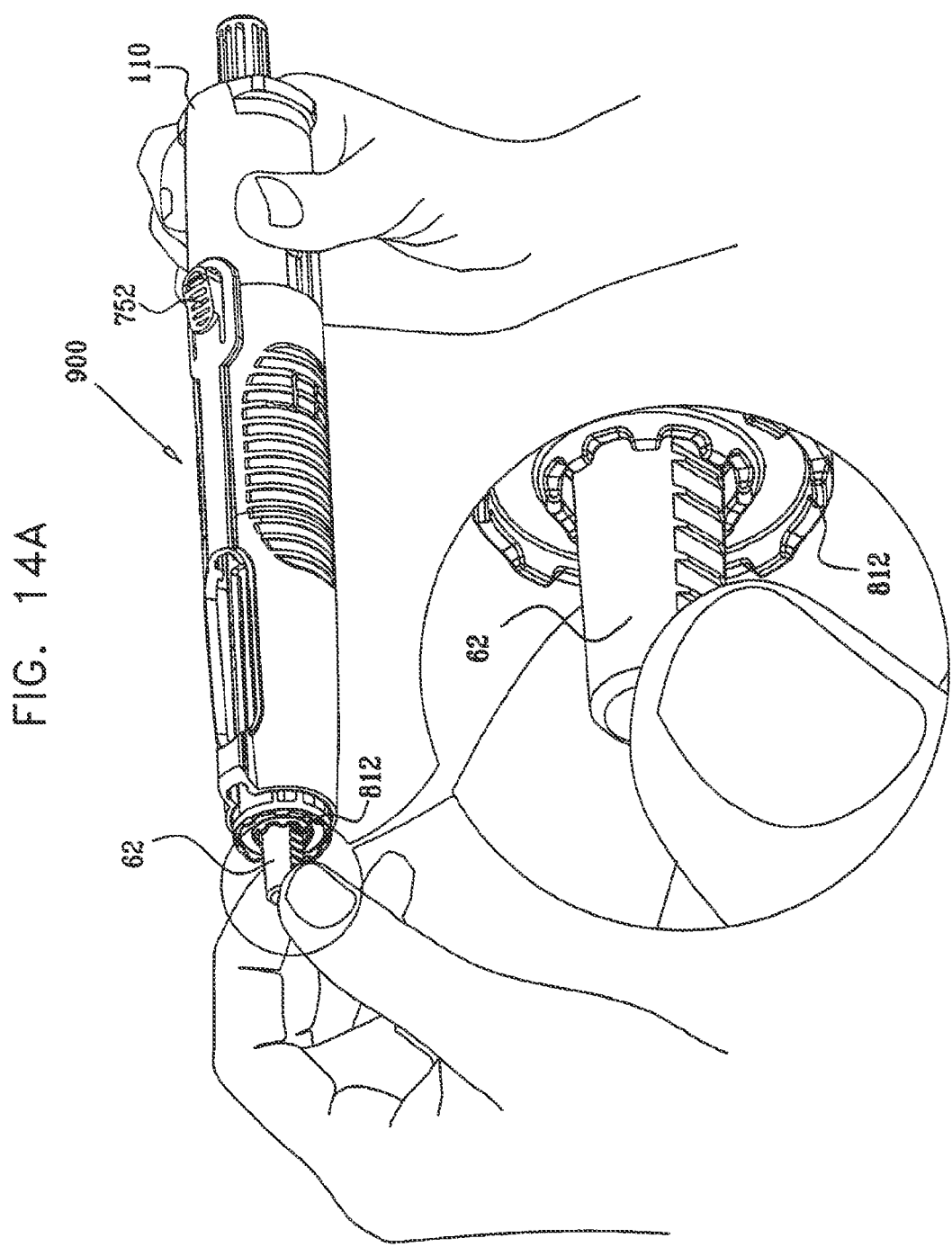

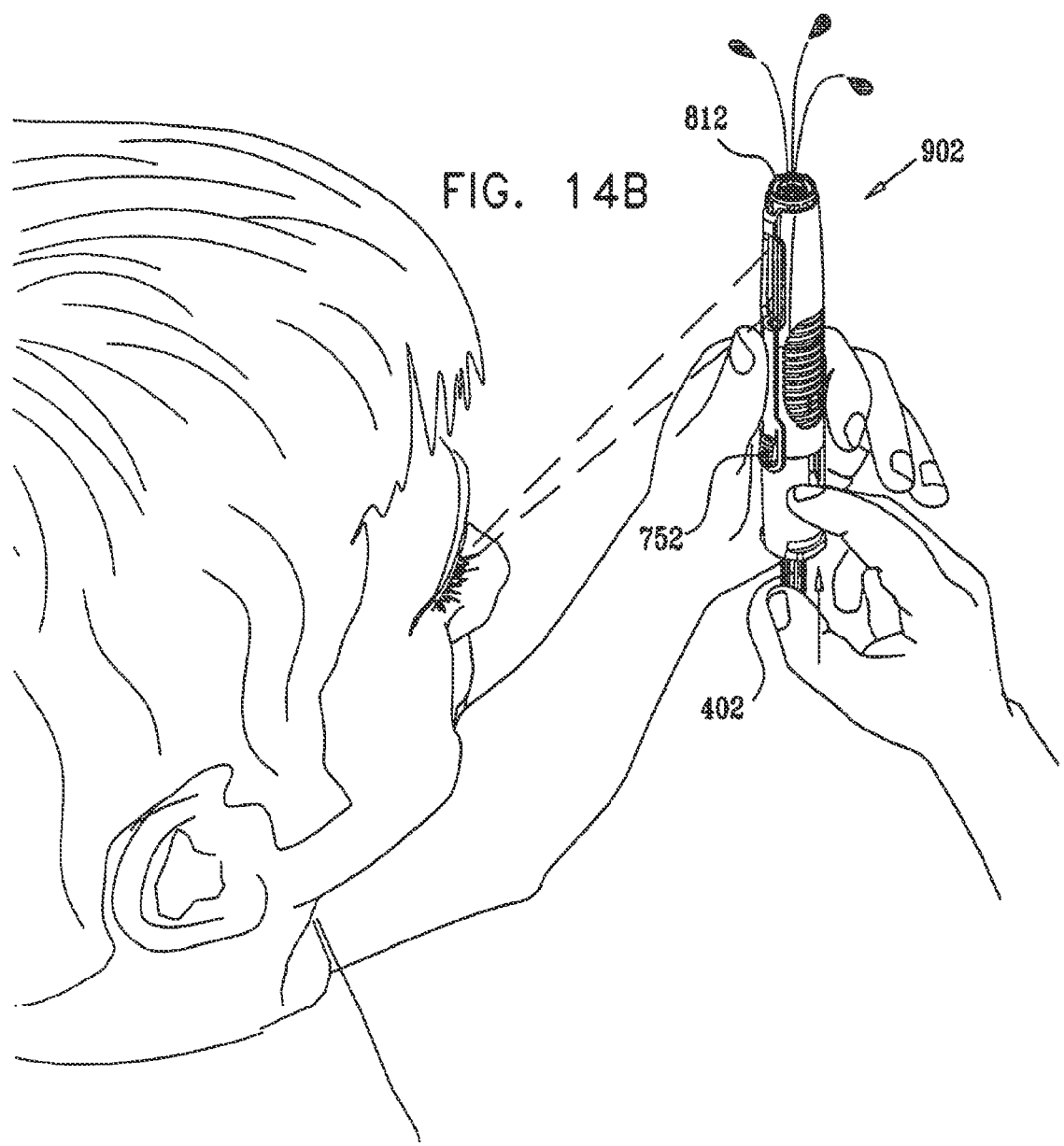

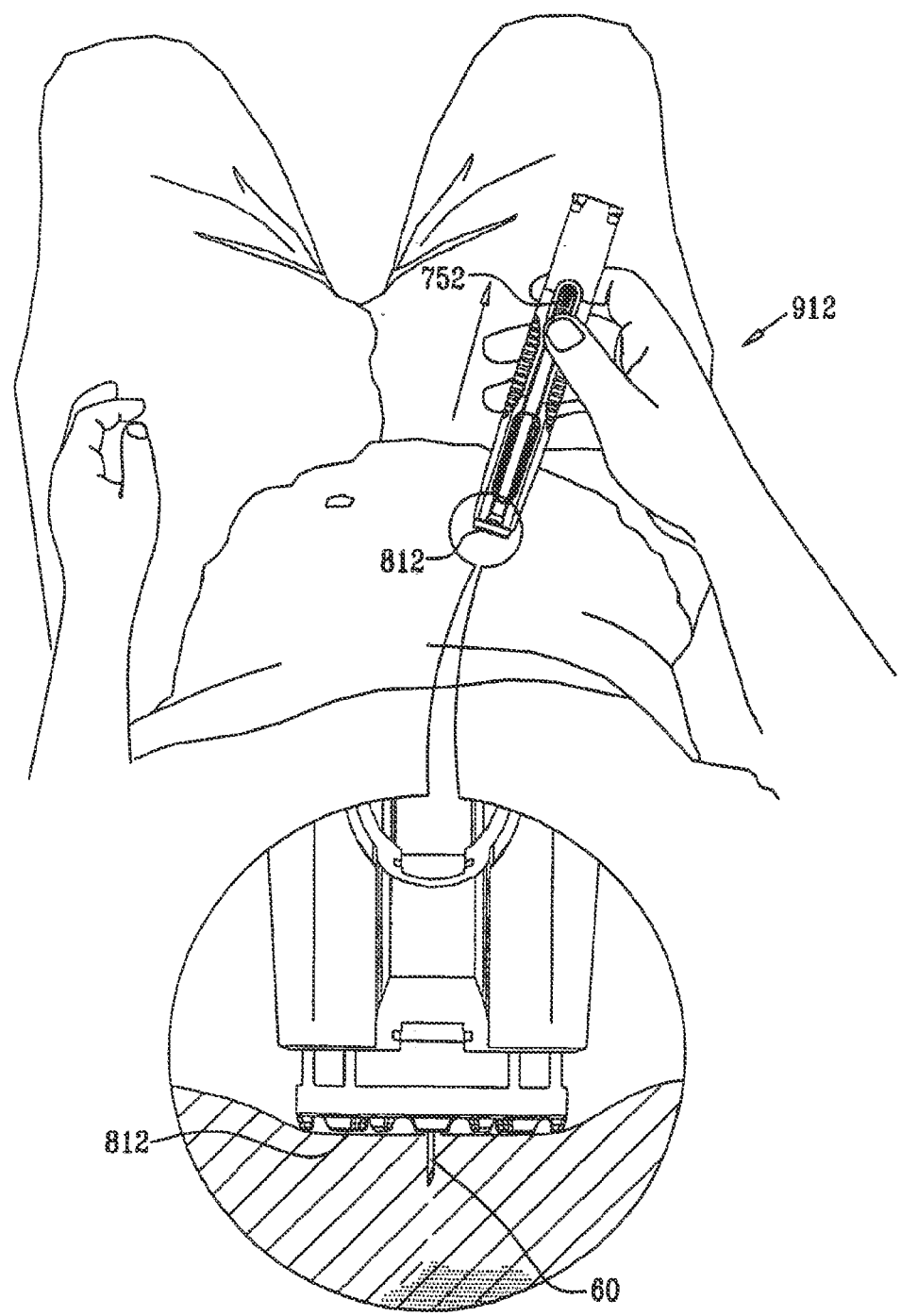

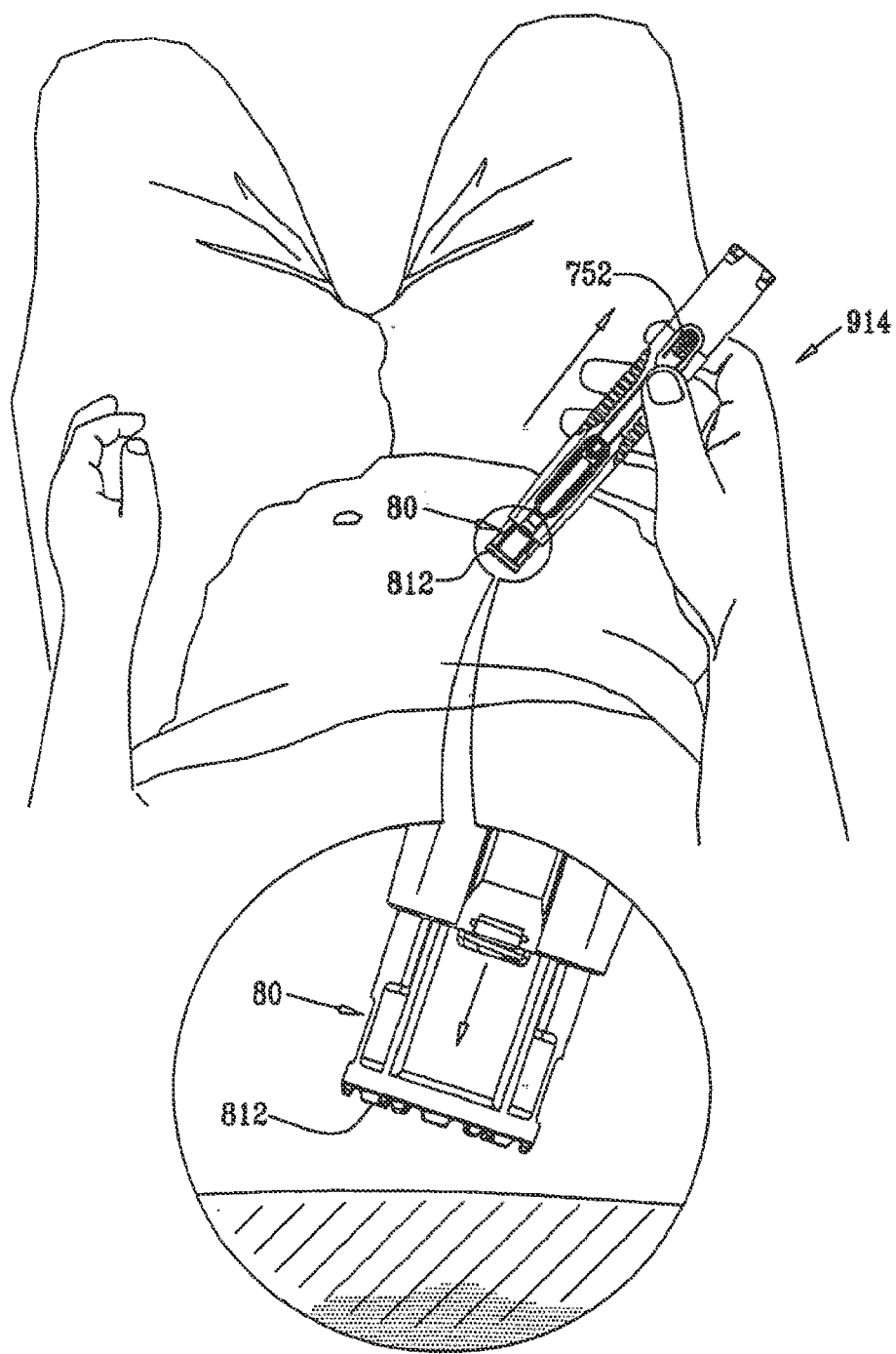

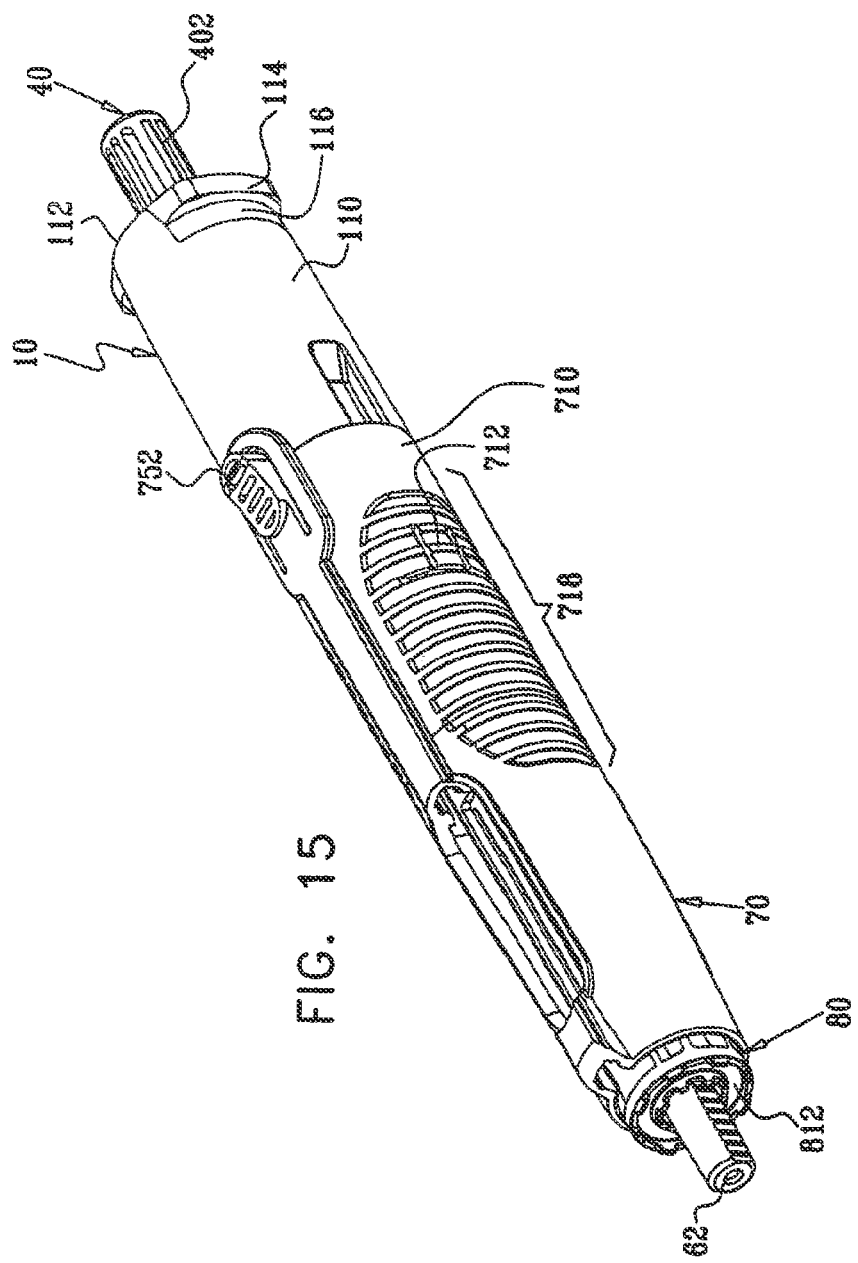

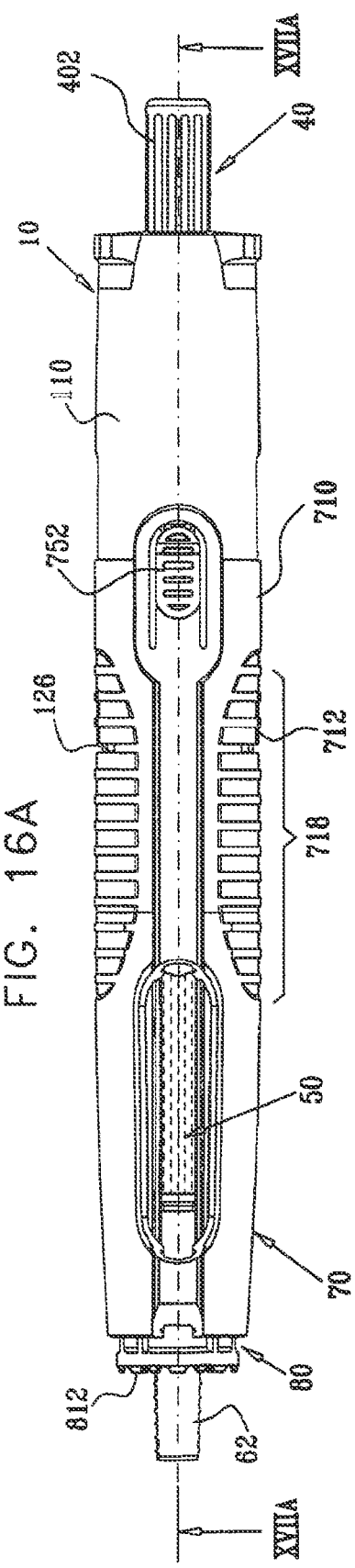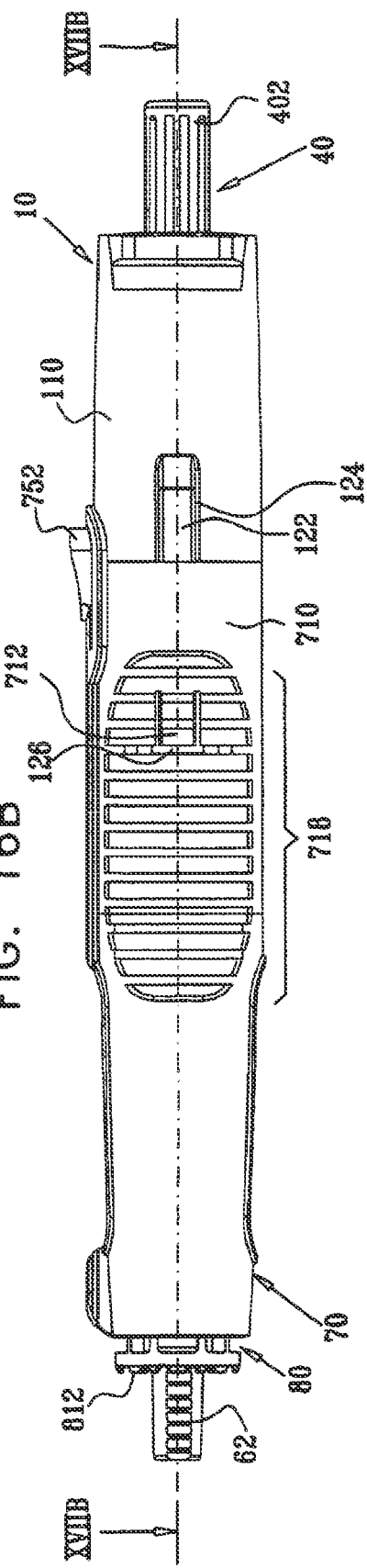

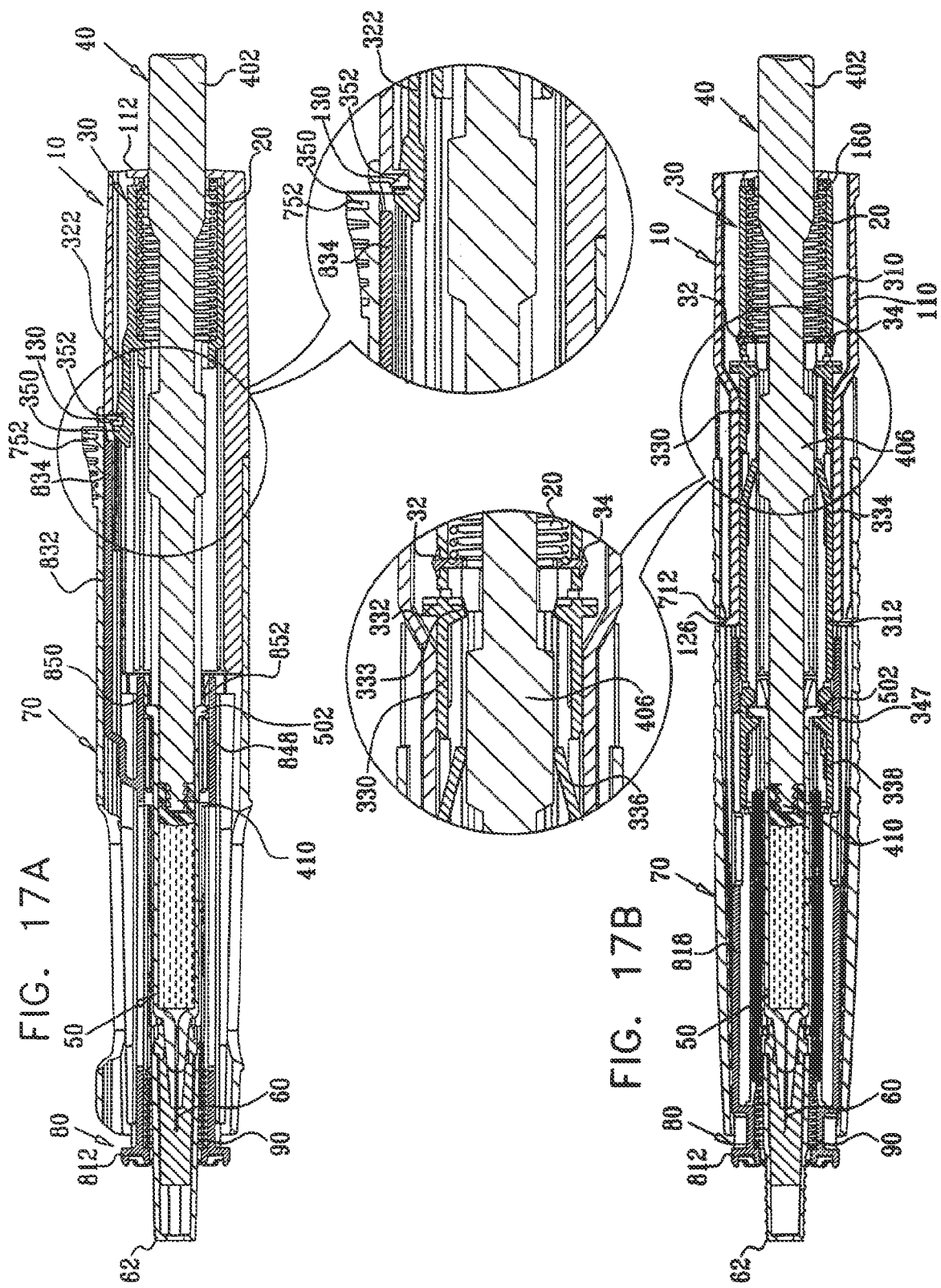

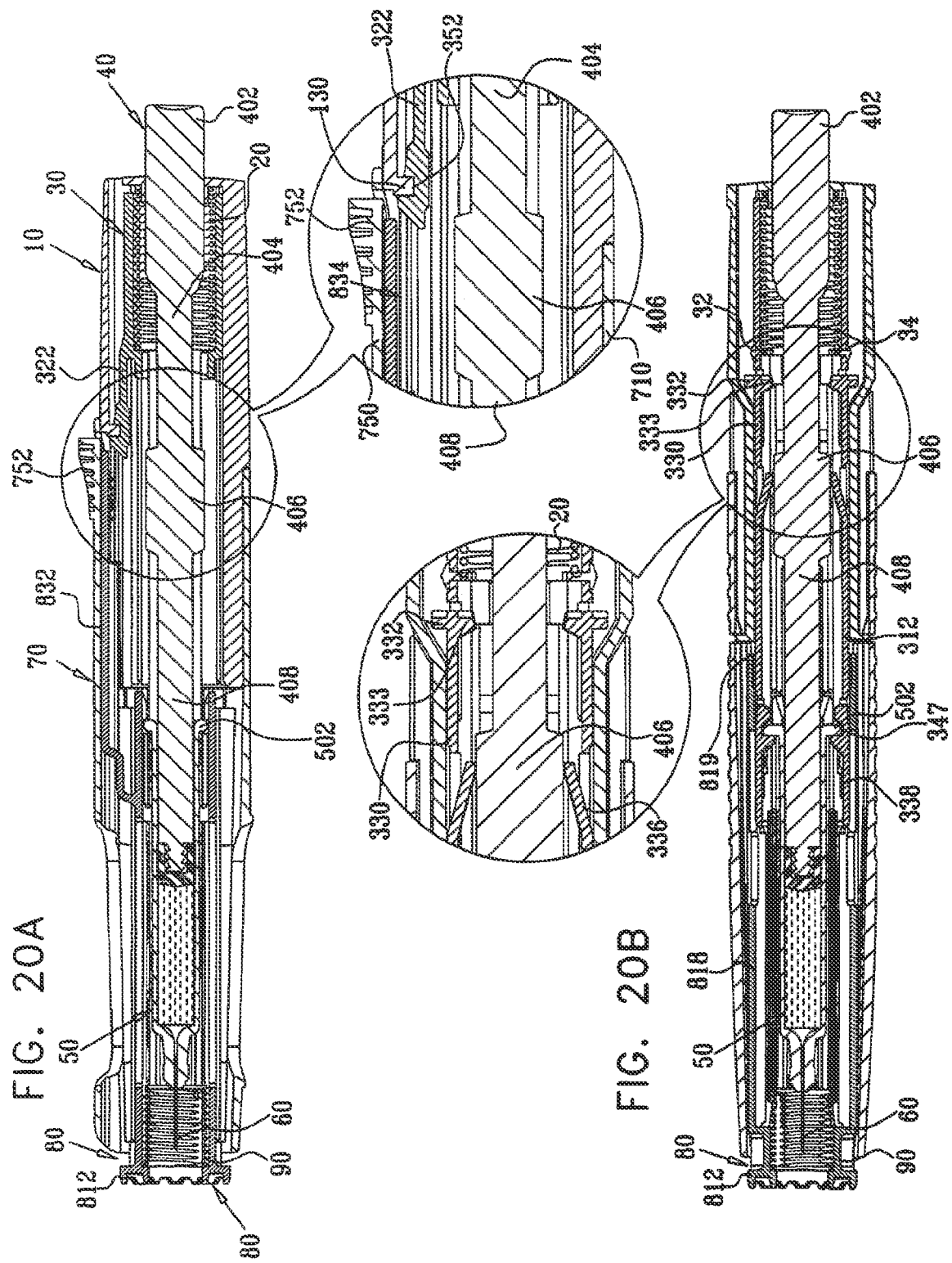

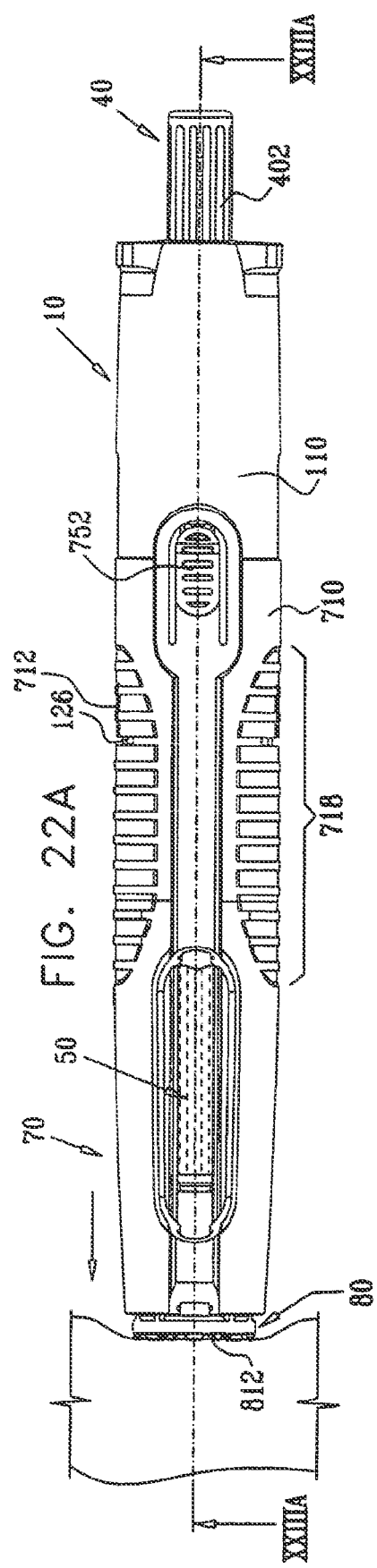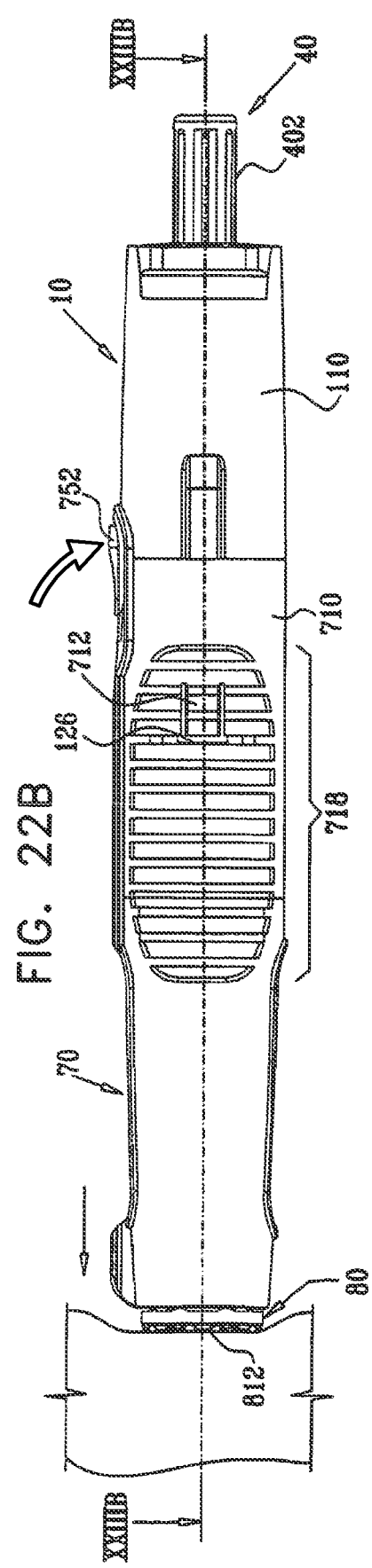

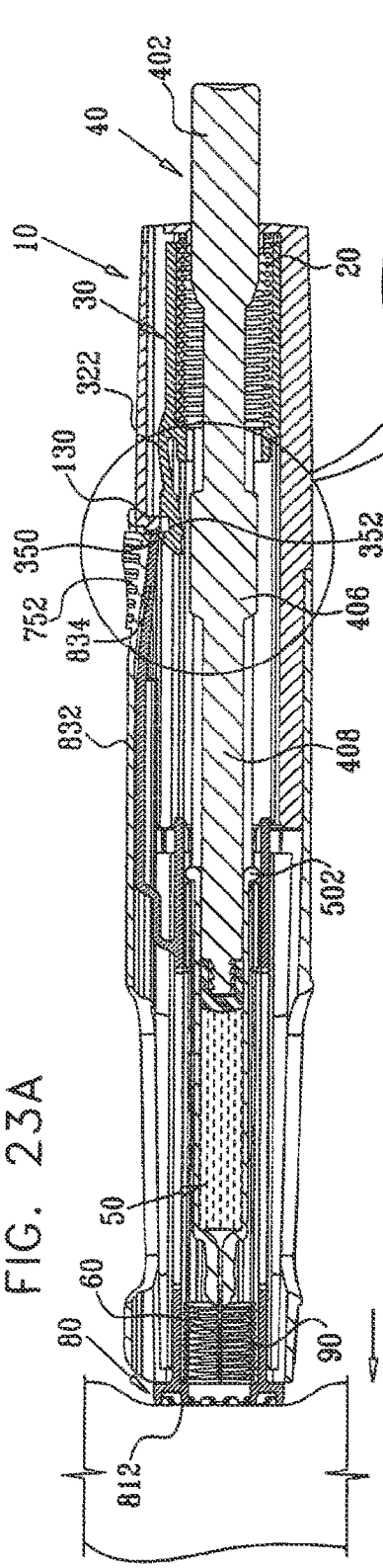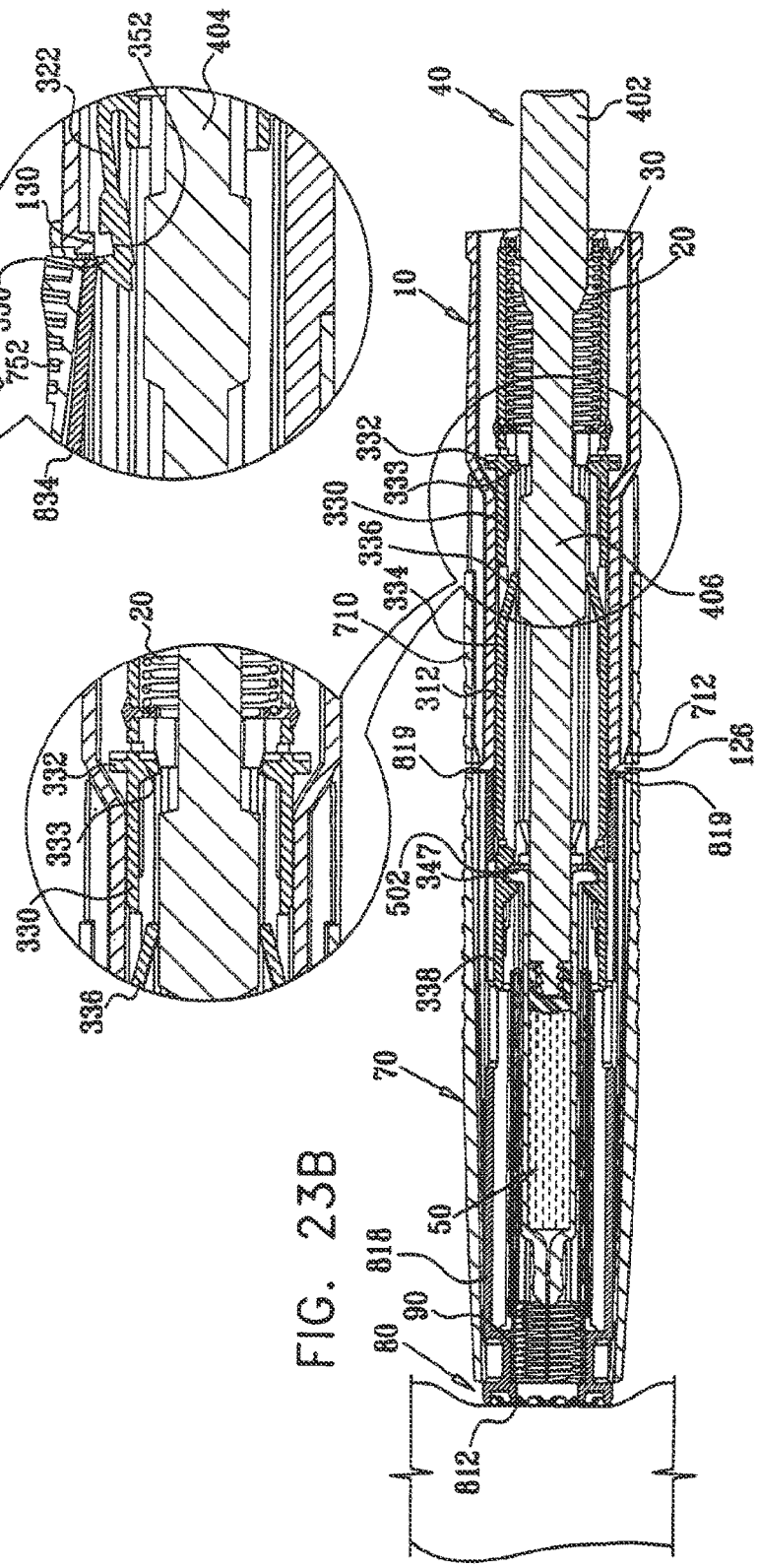

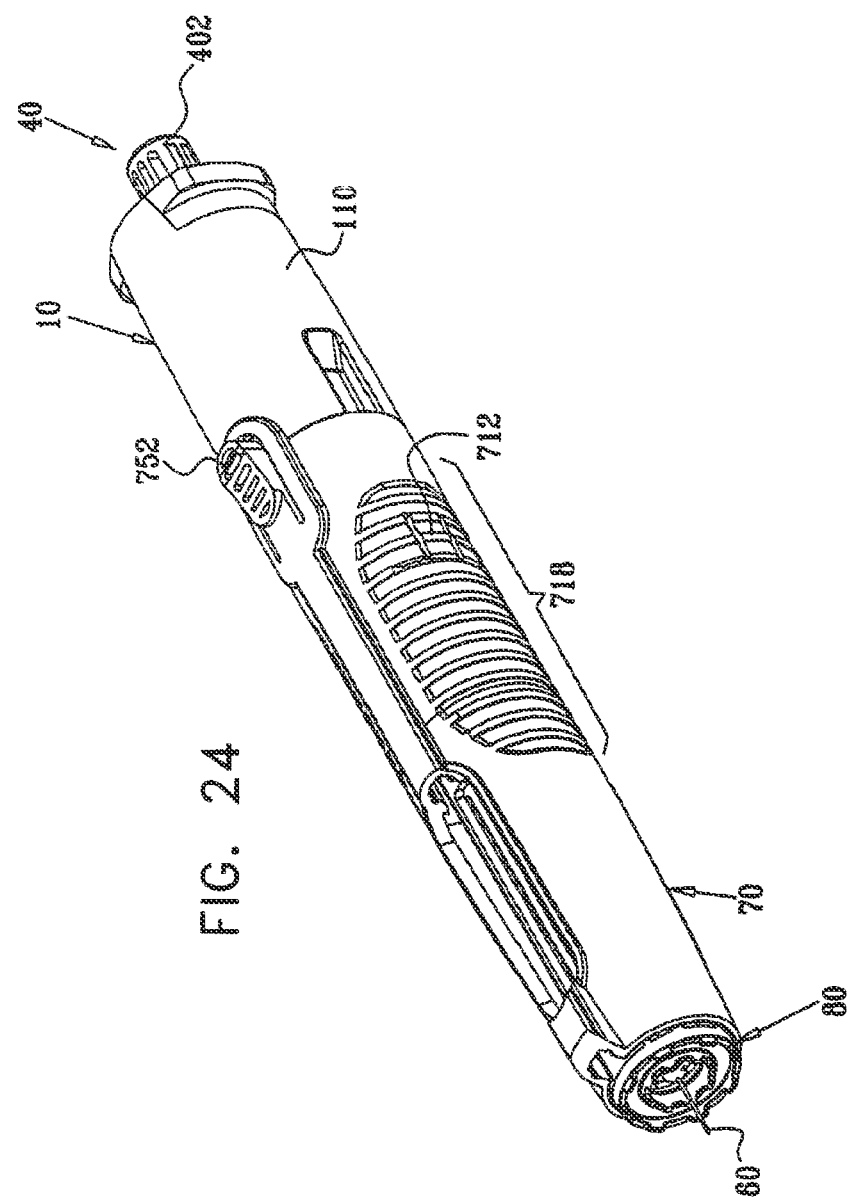

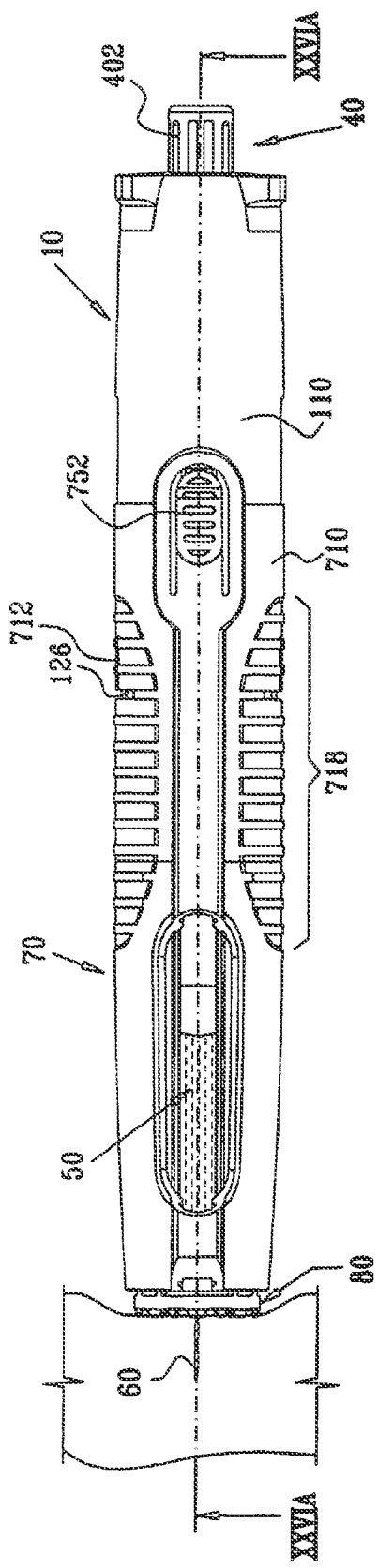
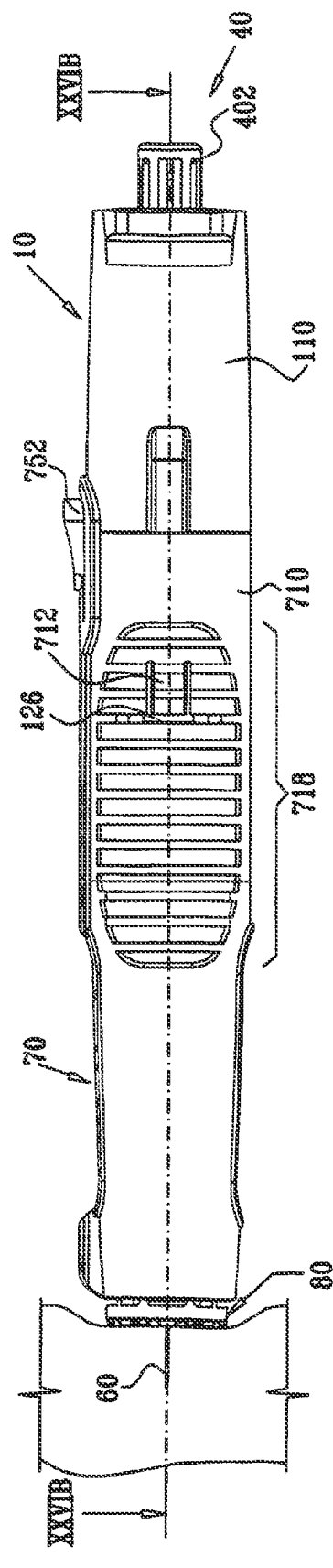

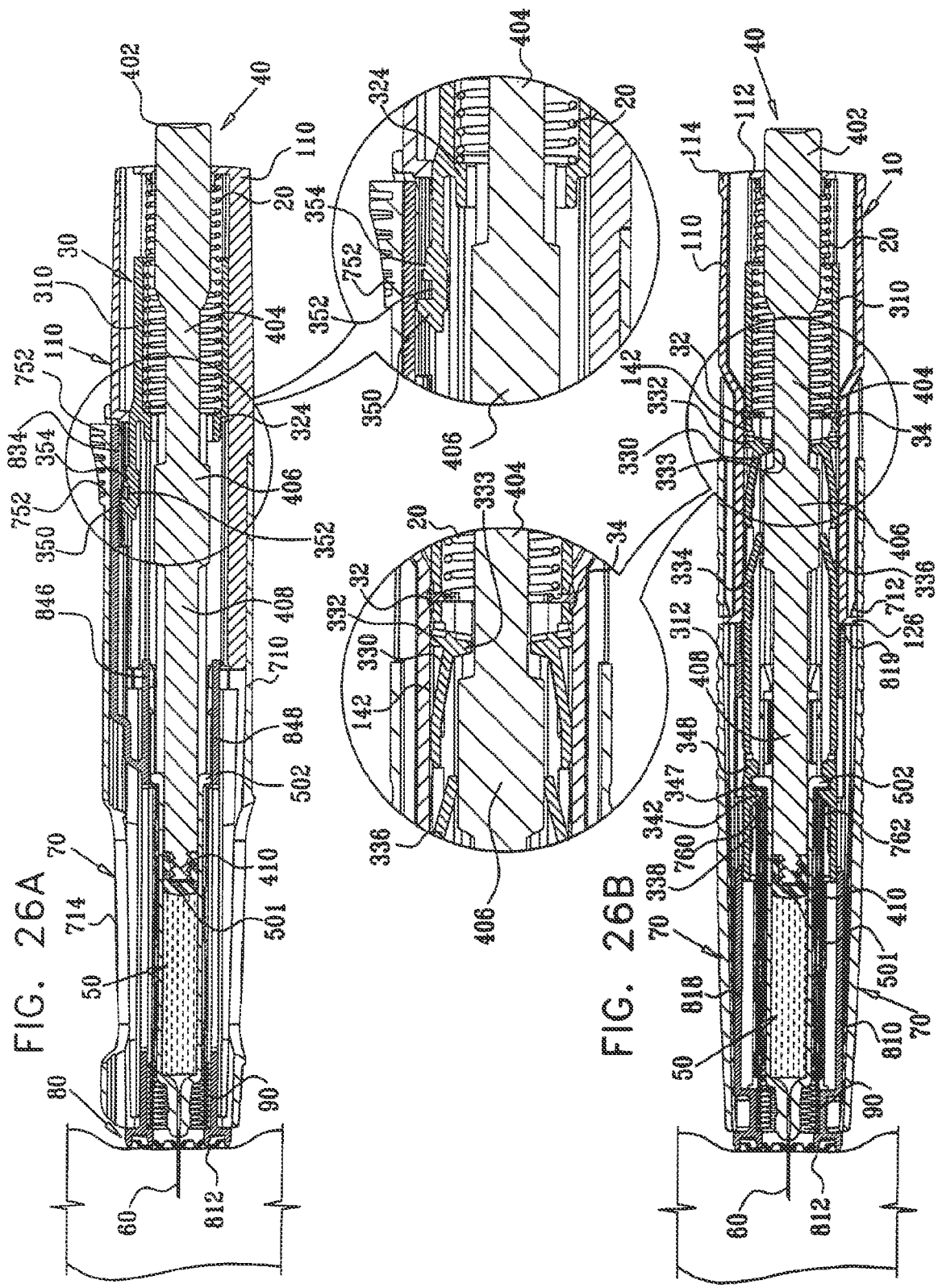

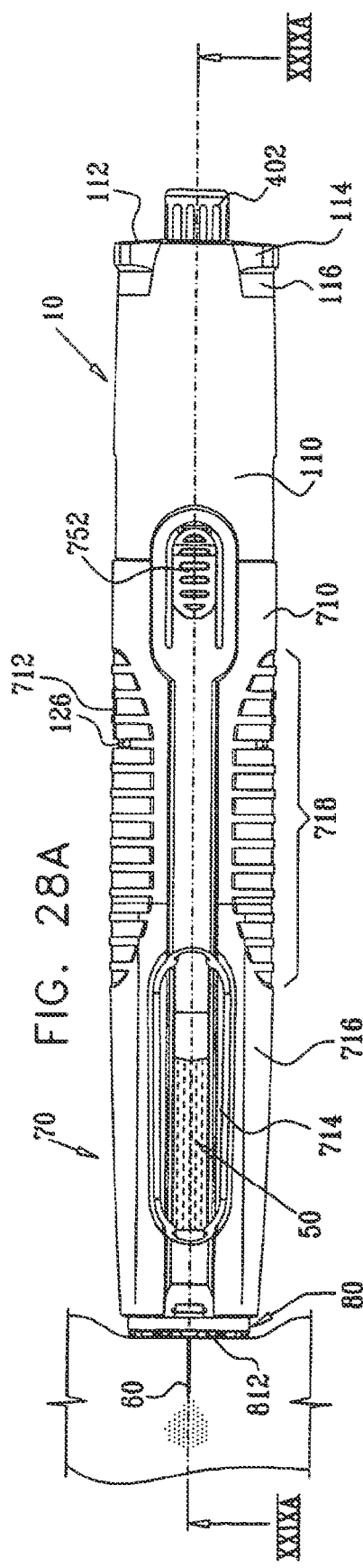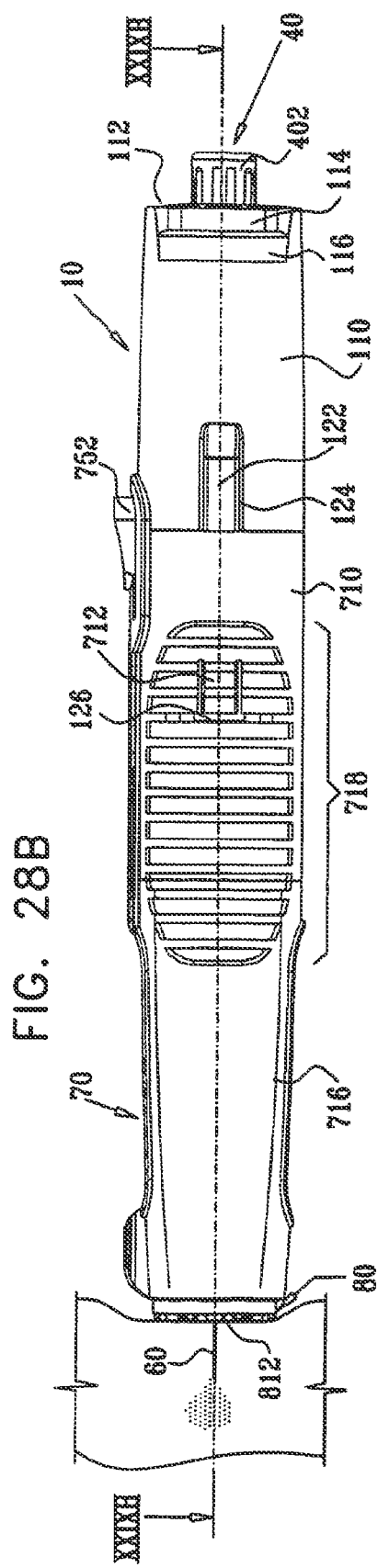

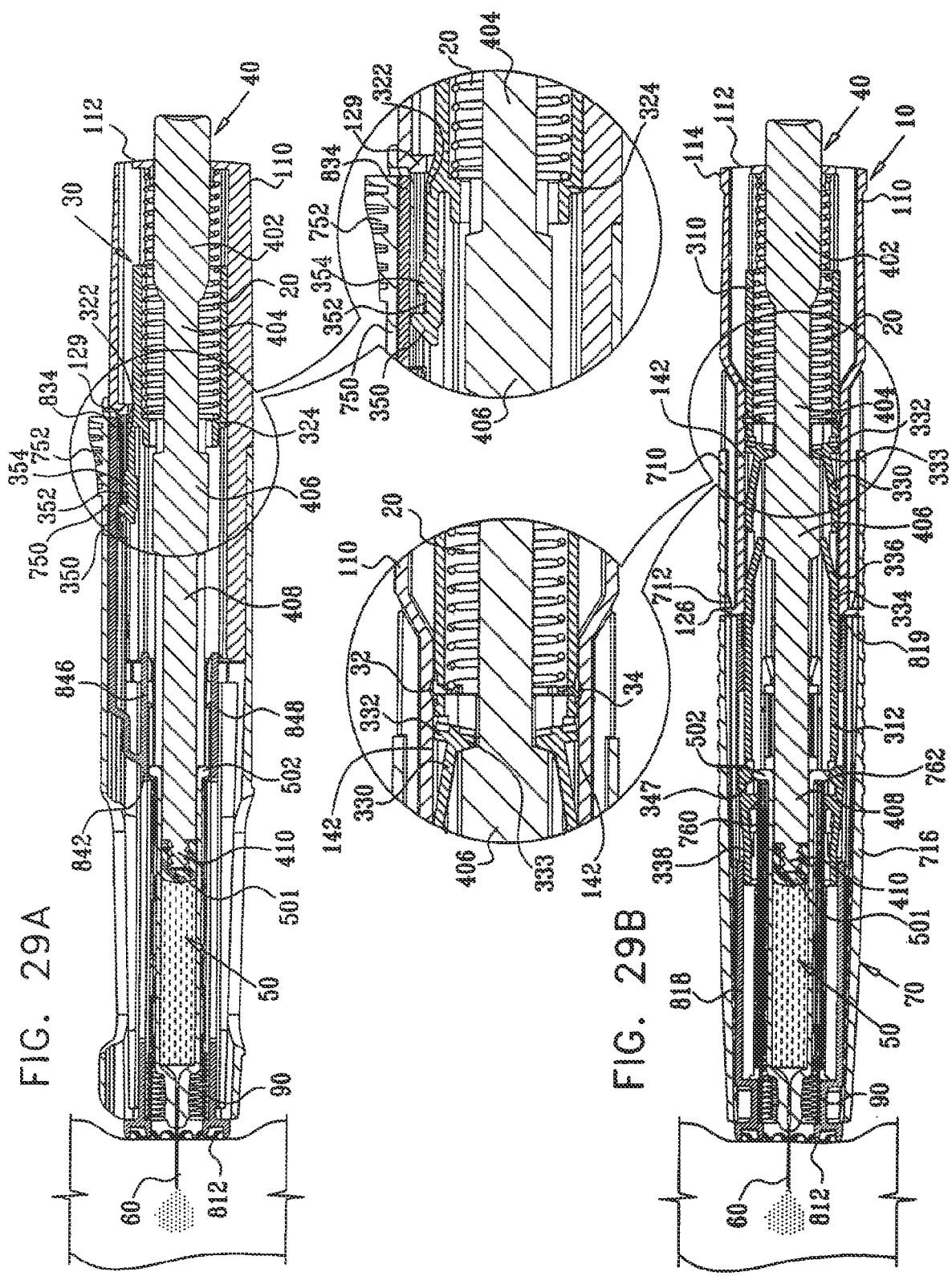

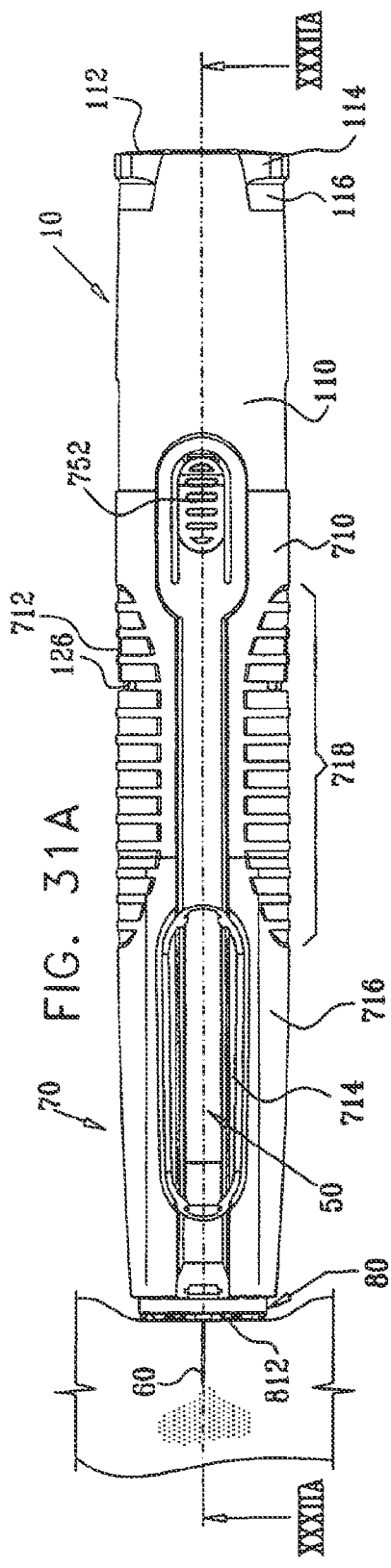
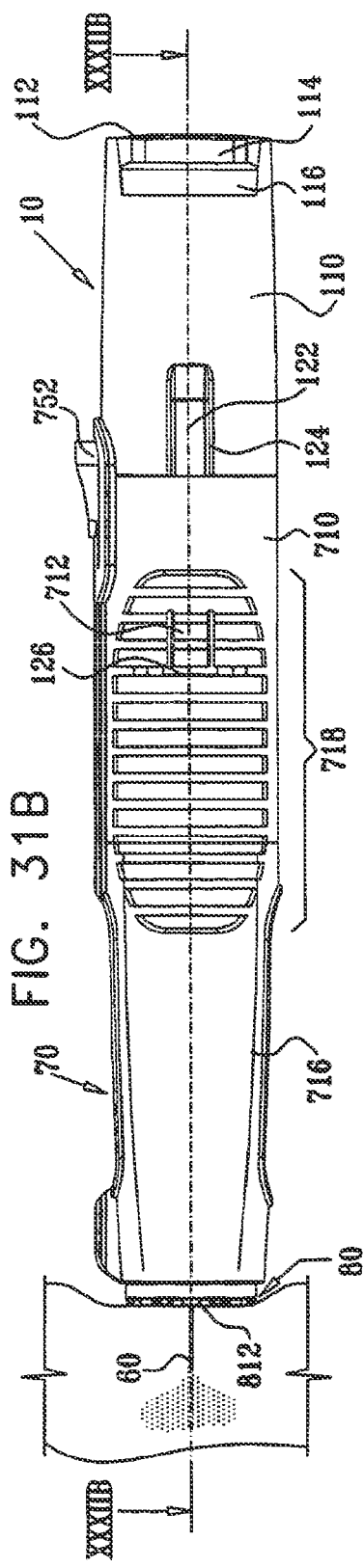

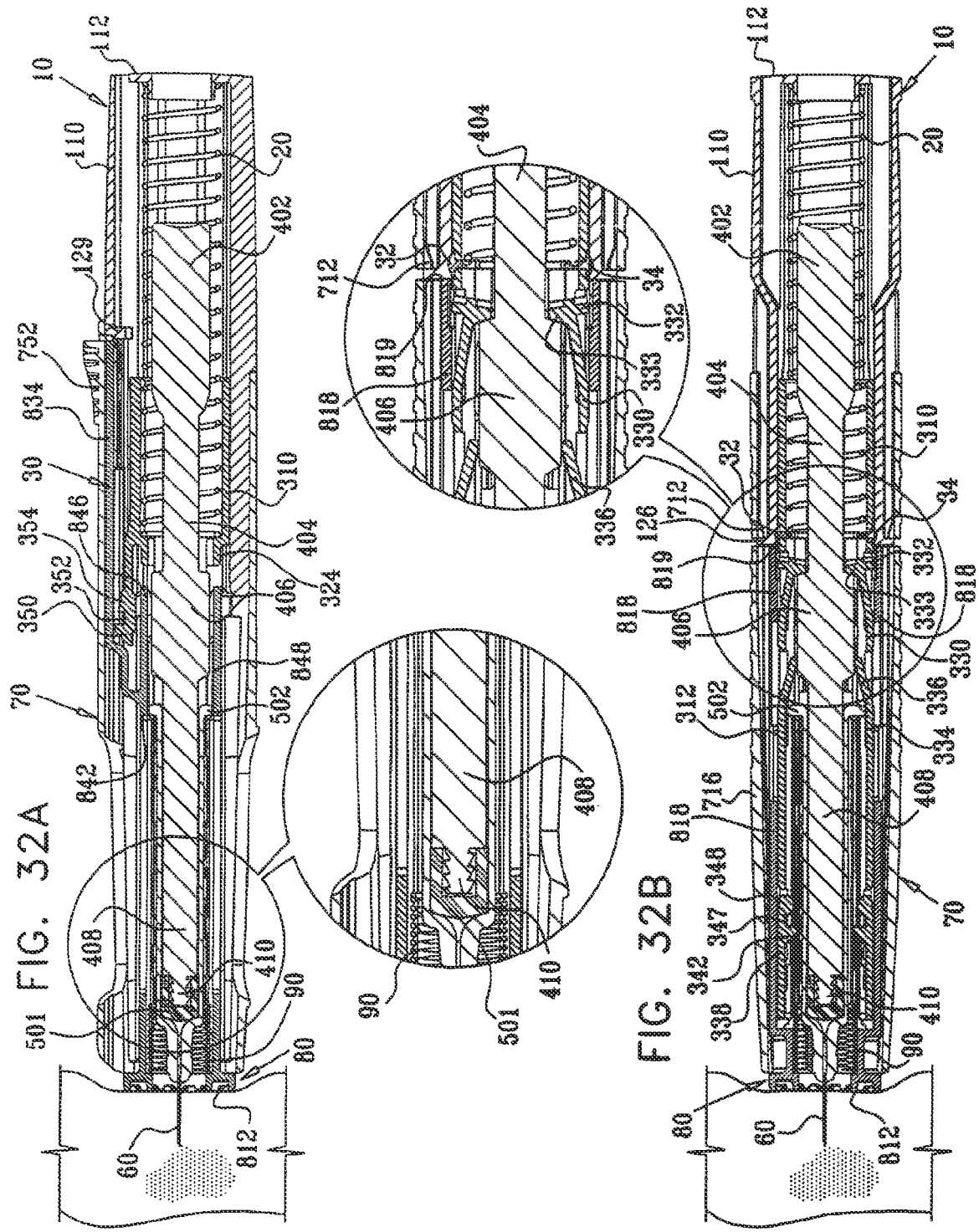

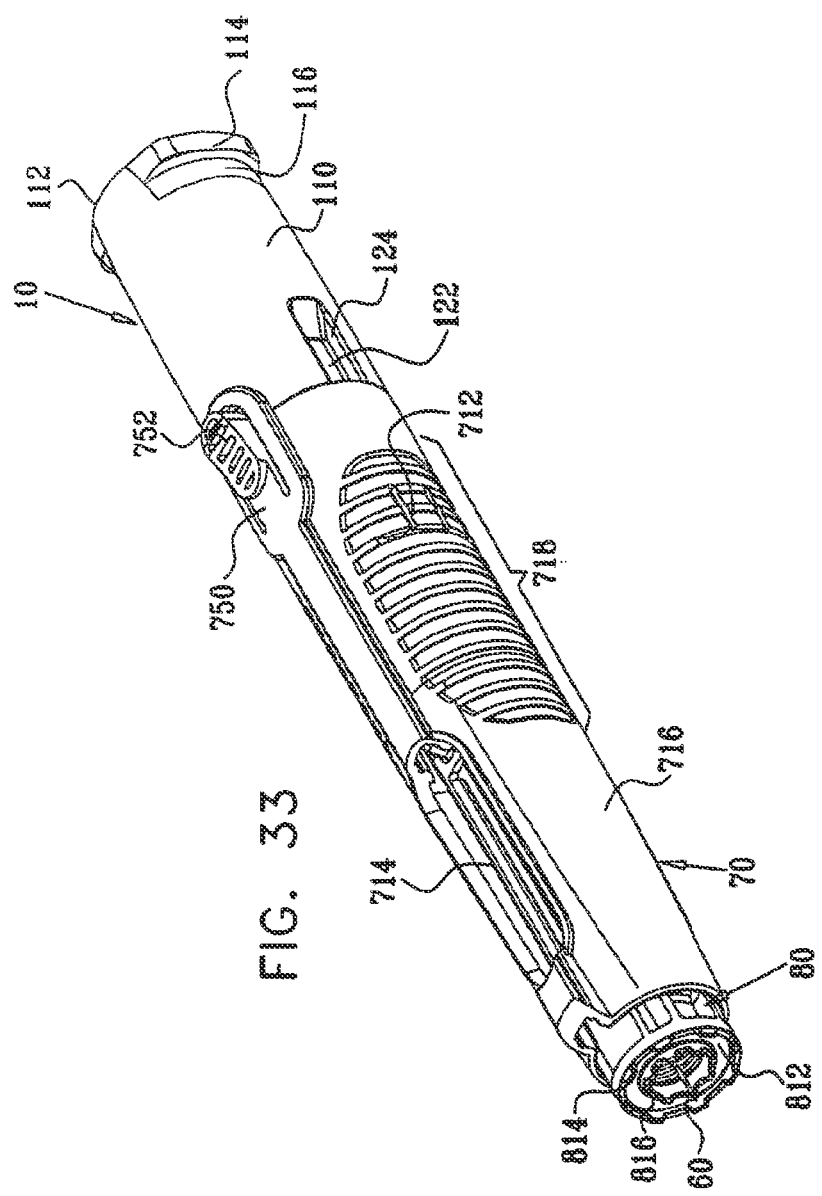

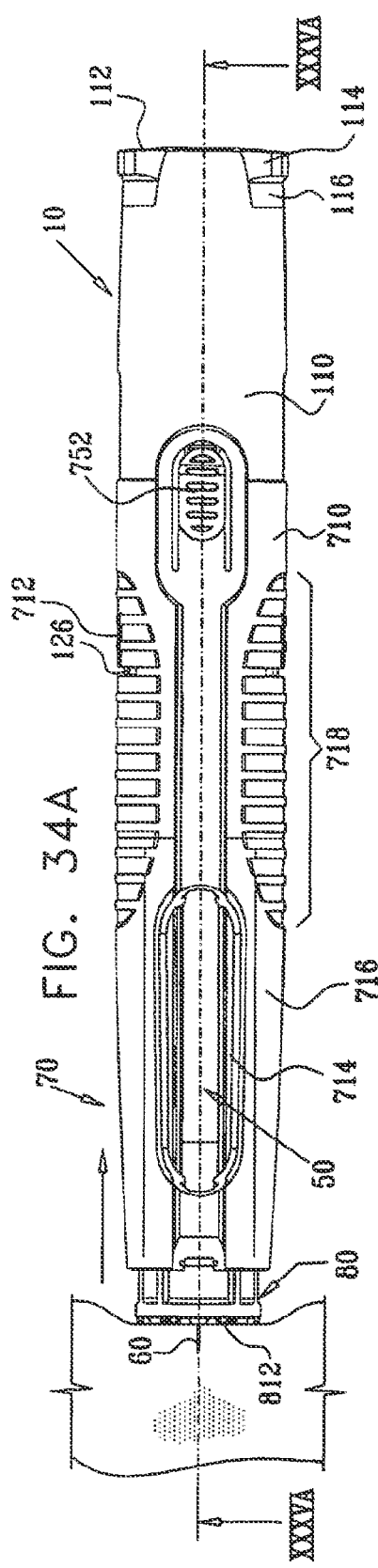
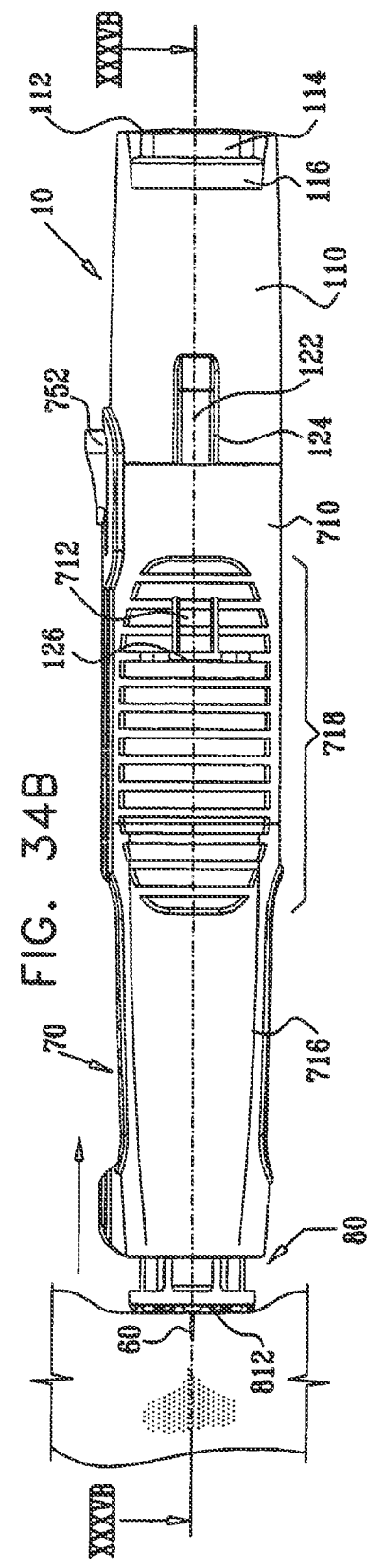
FIG. 34A
FIG. 34B

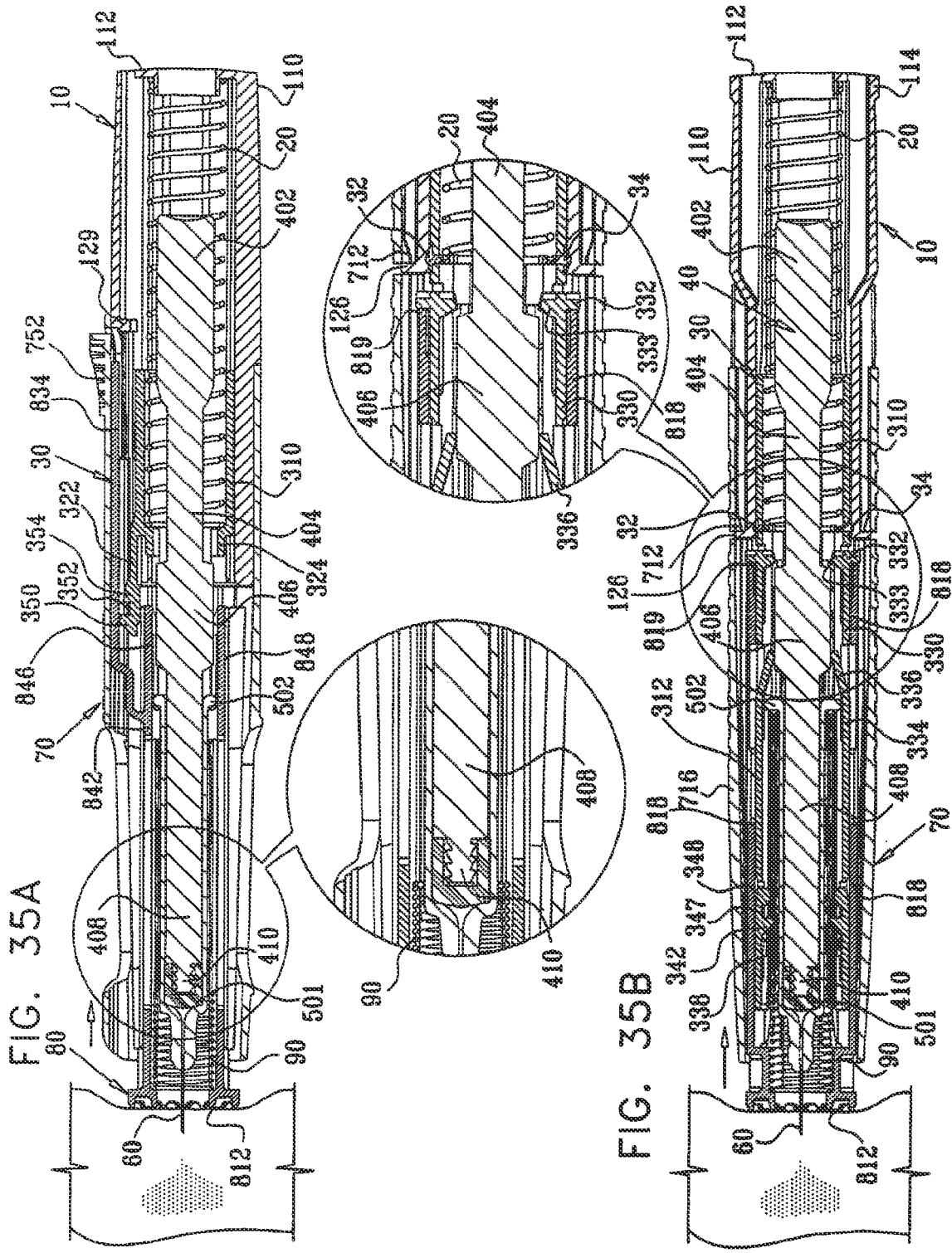

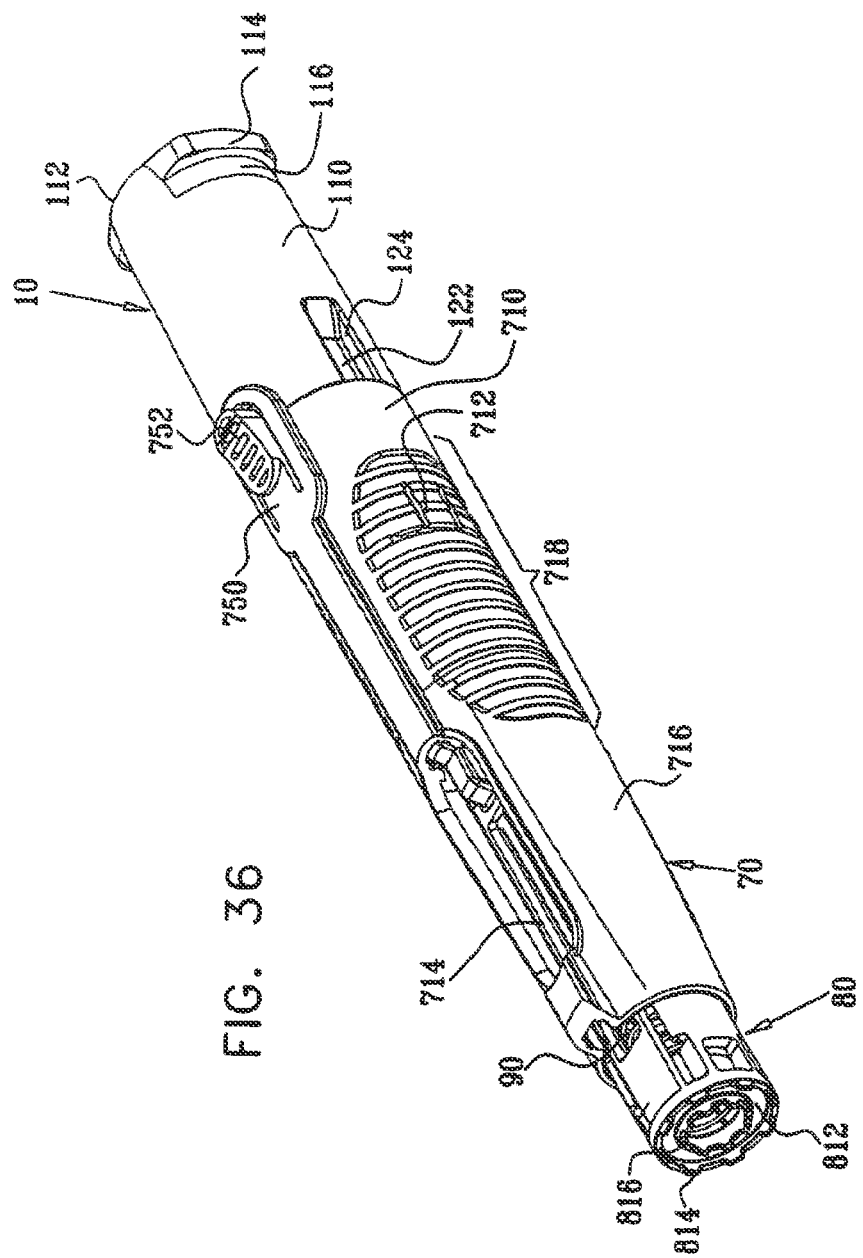

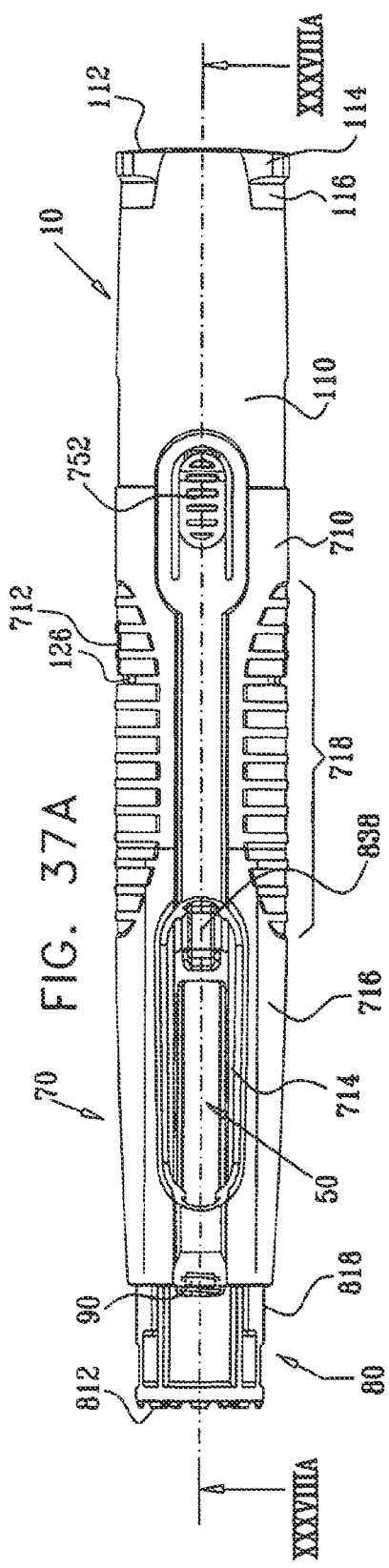
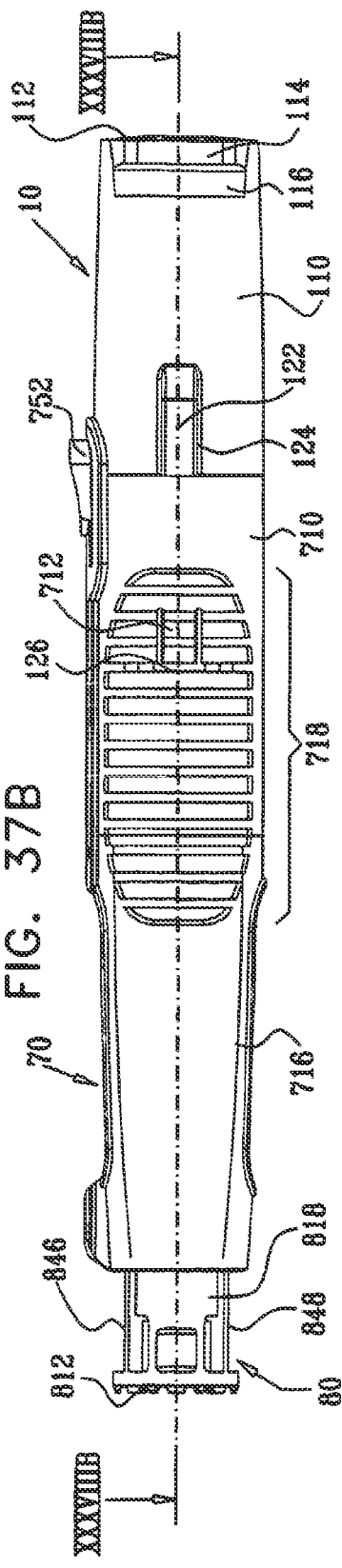
FIG. 37A
FIG. 37B

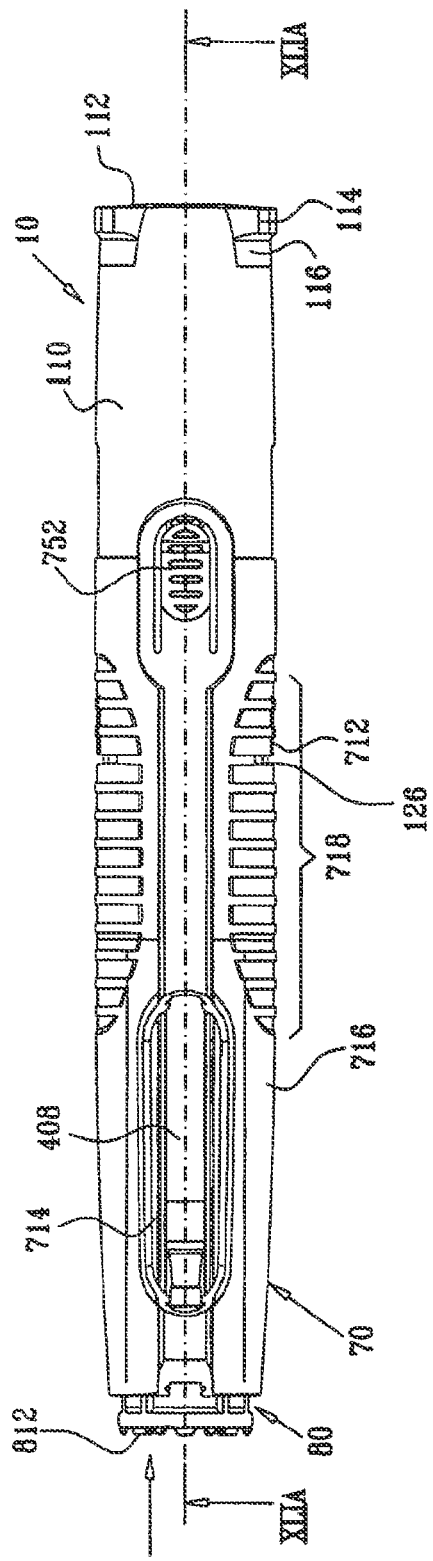
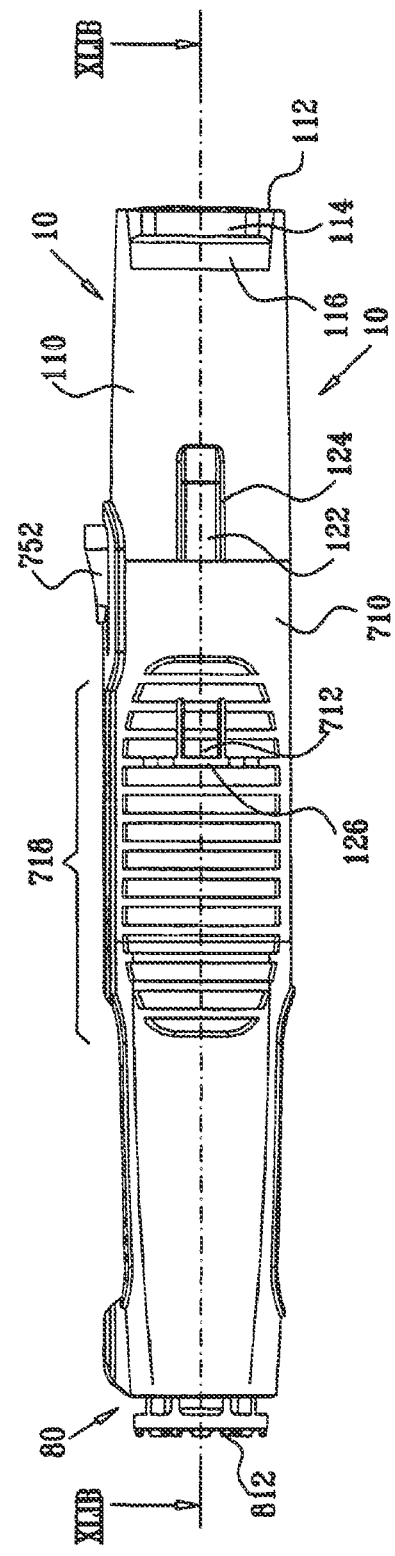
FIG. 40A
FIG. 40B

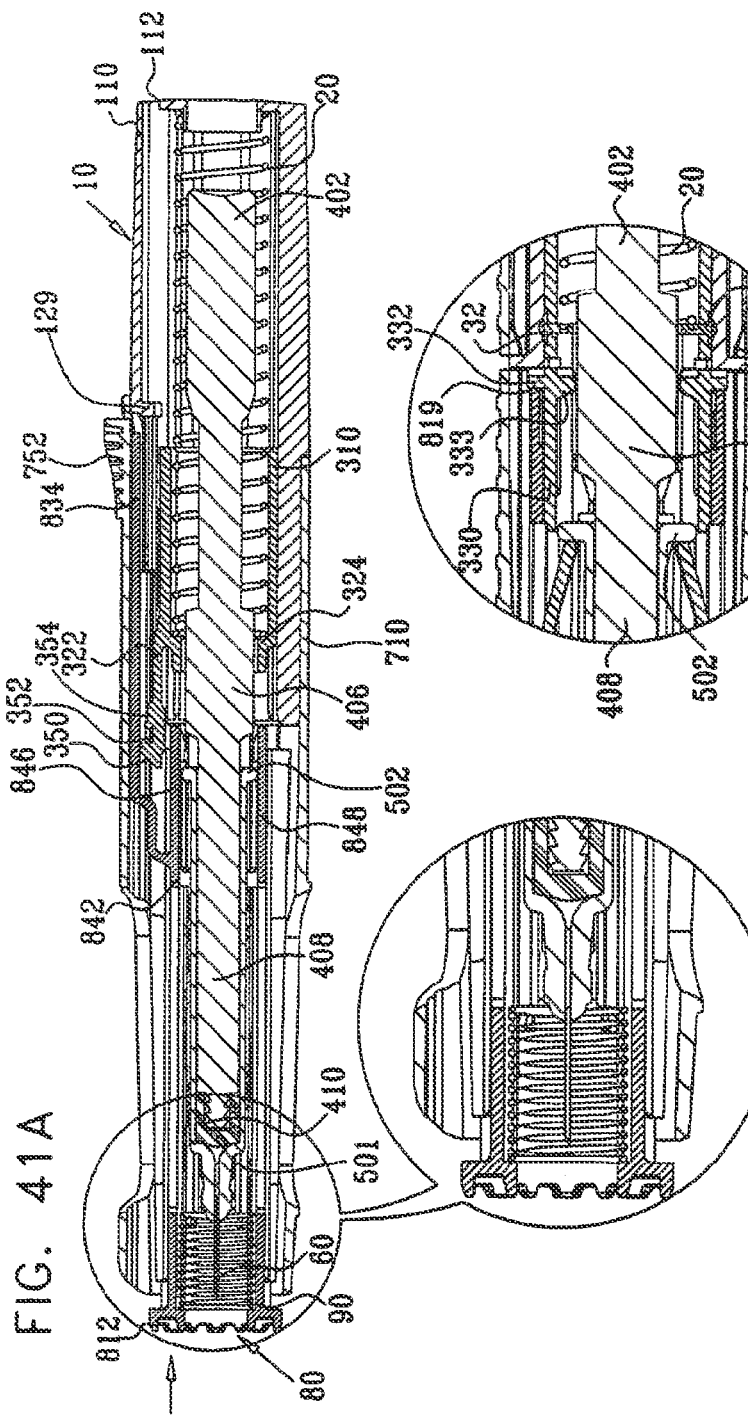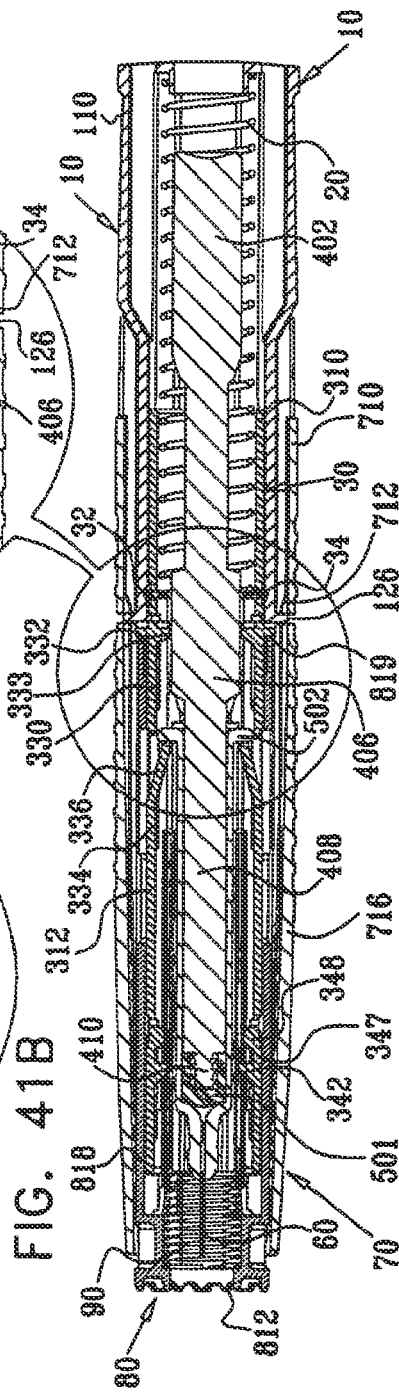

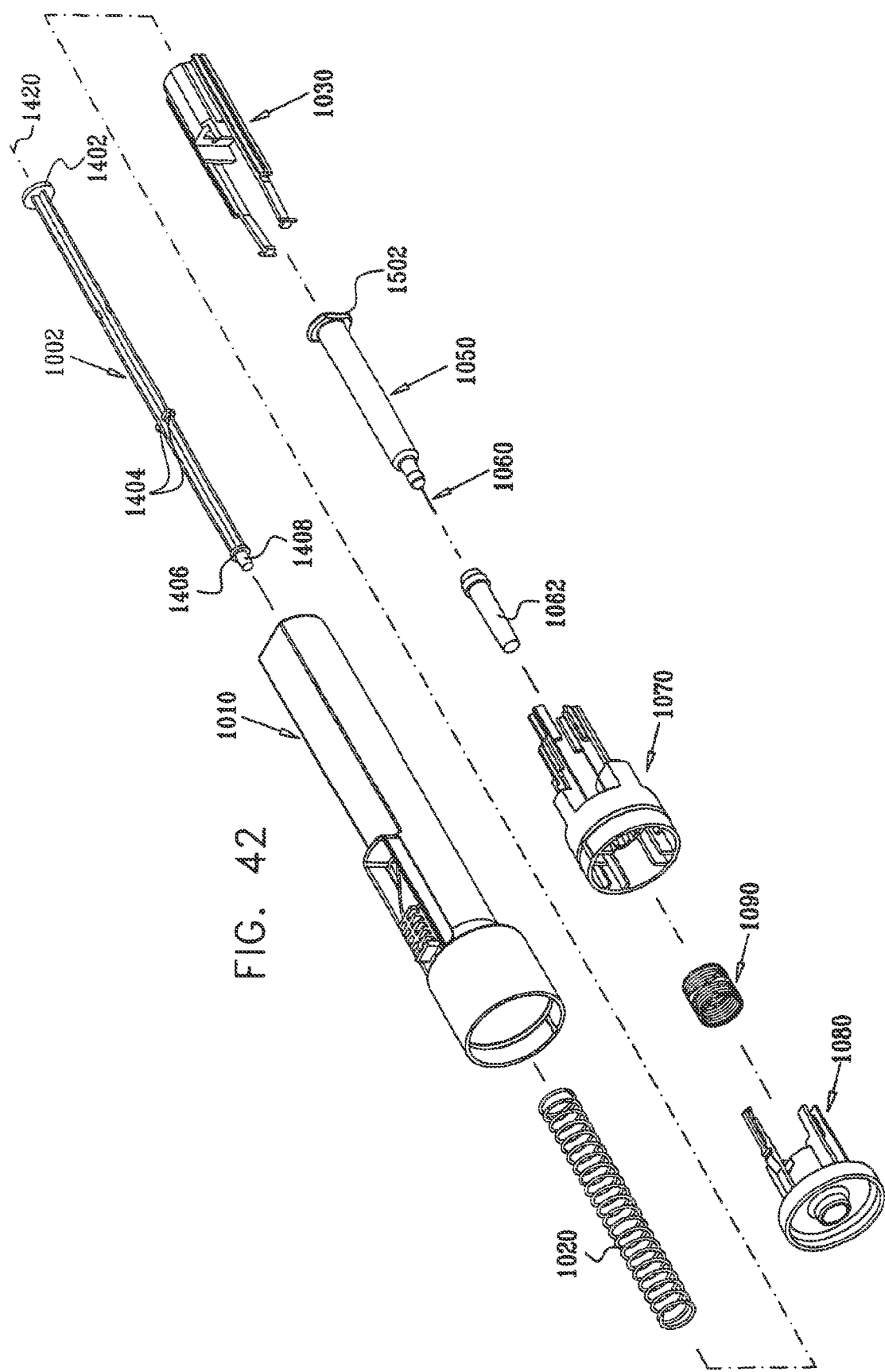

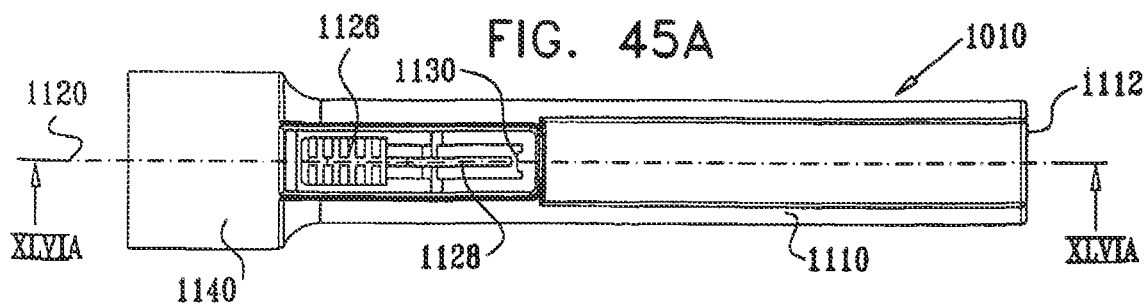
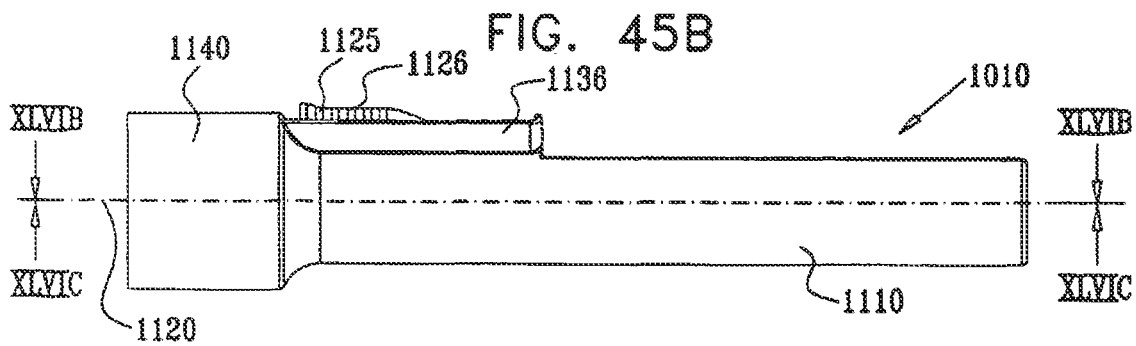
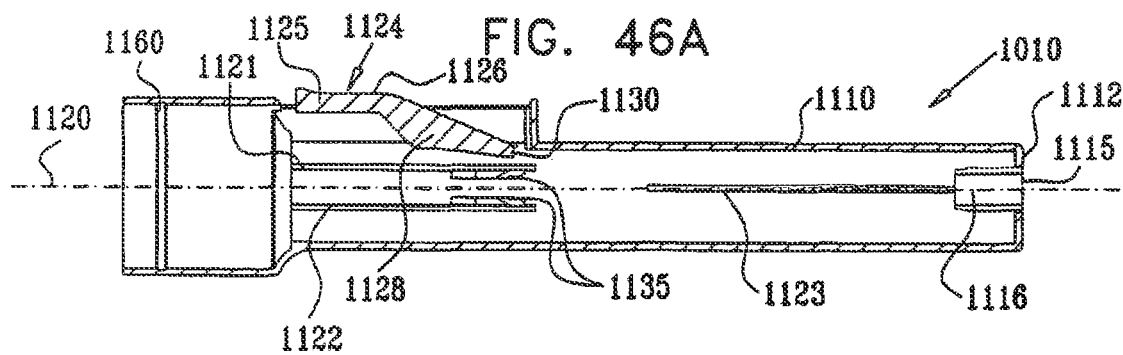
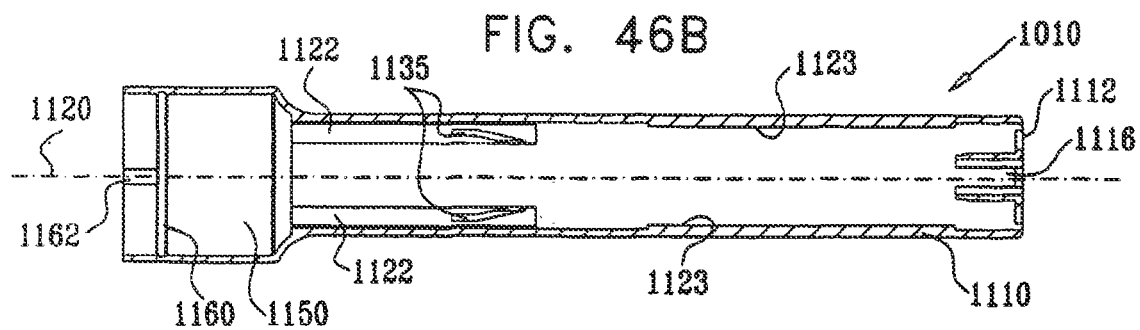
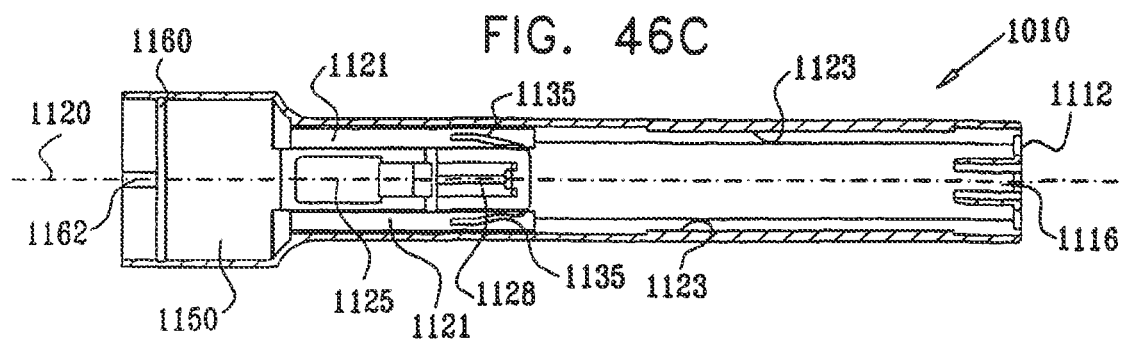

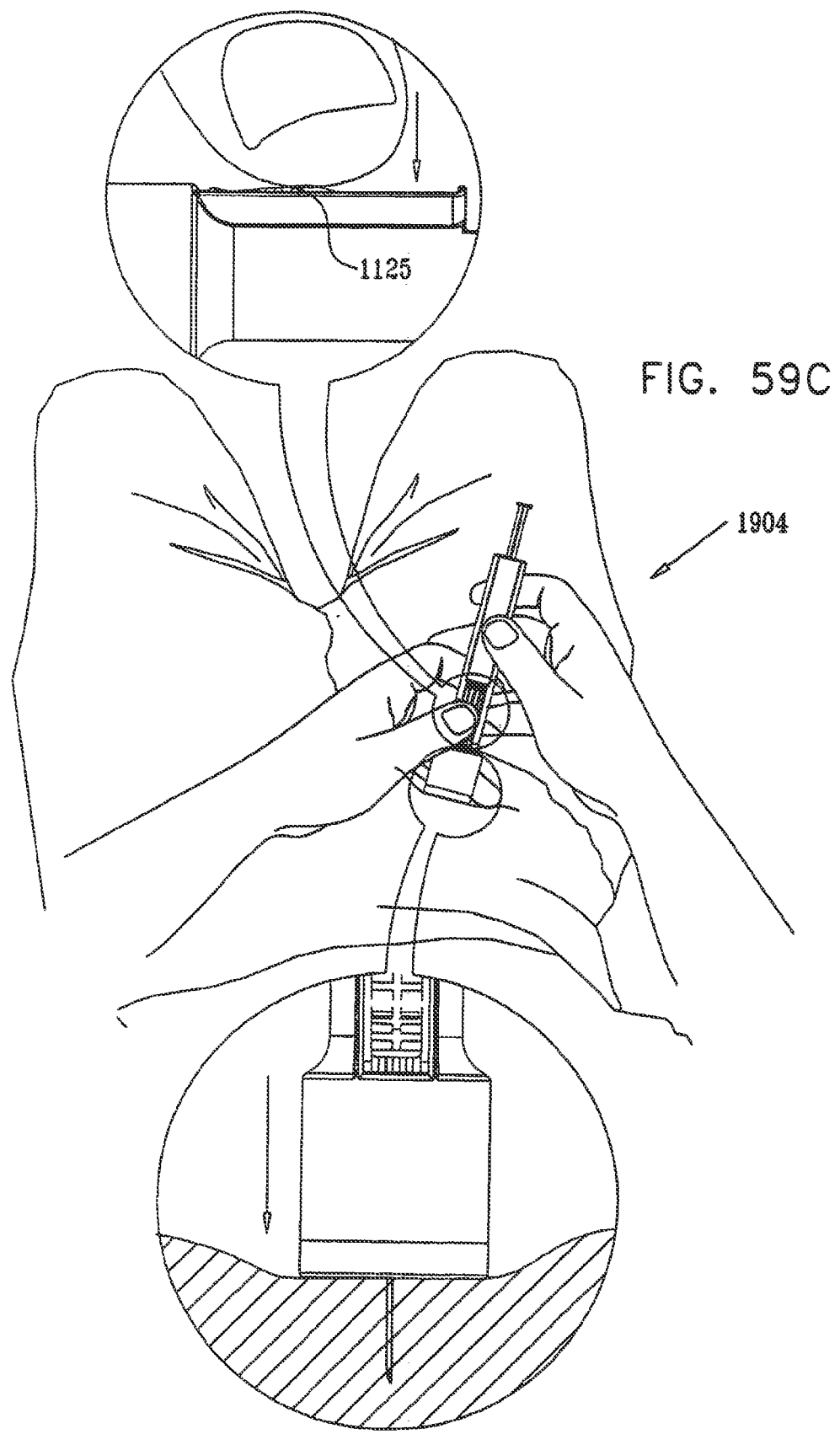

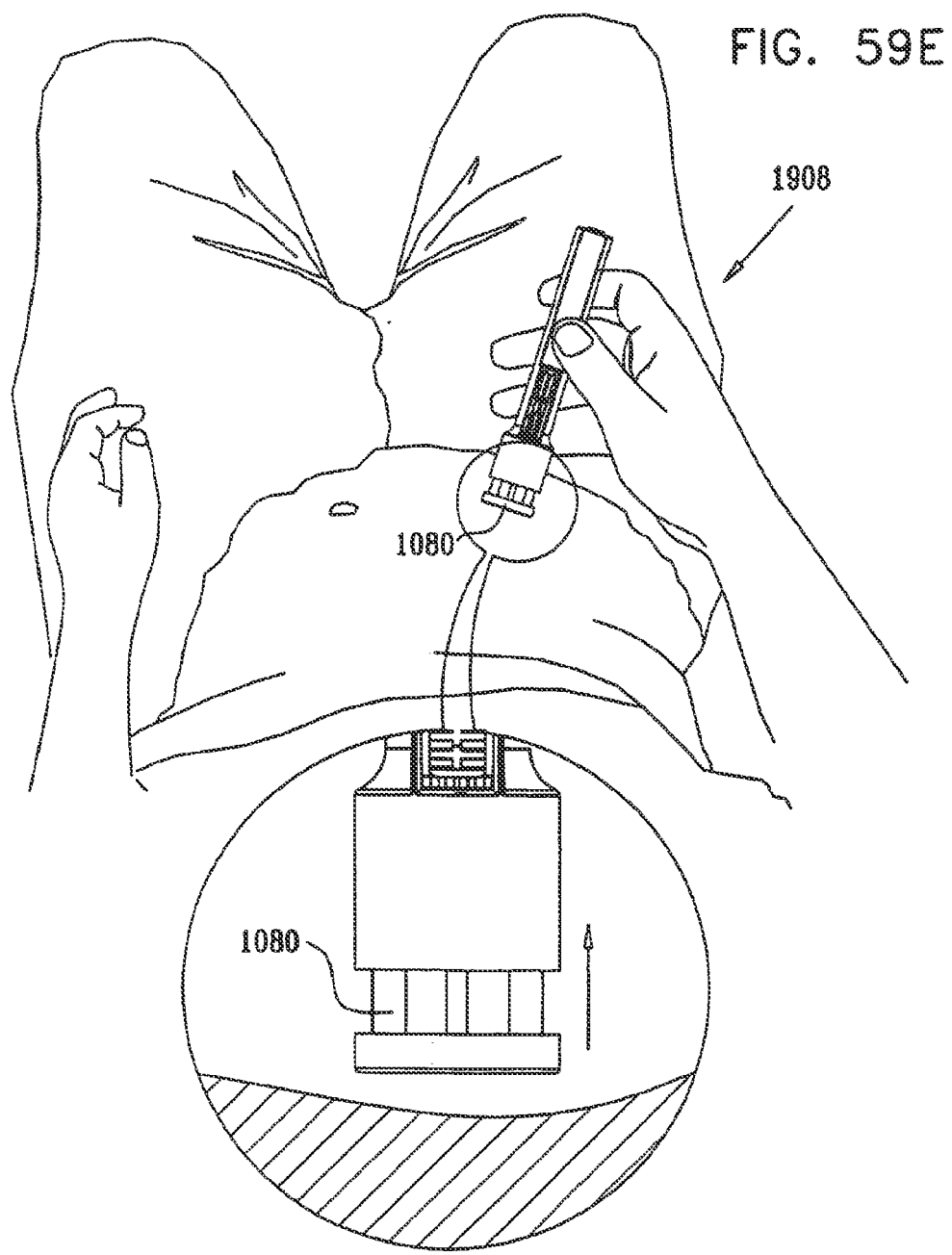

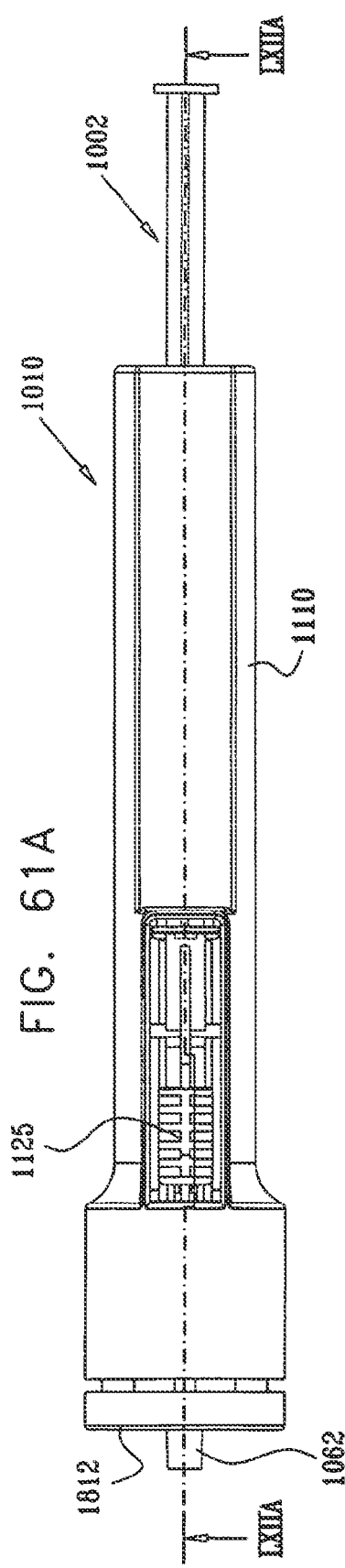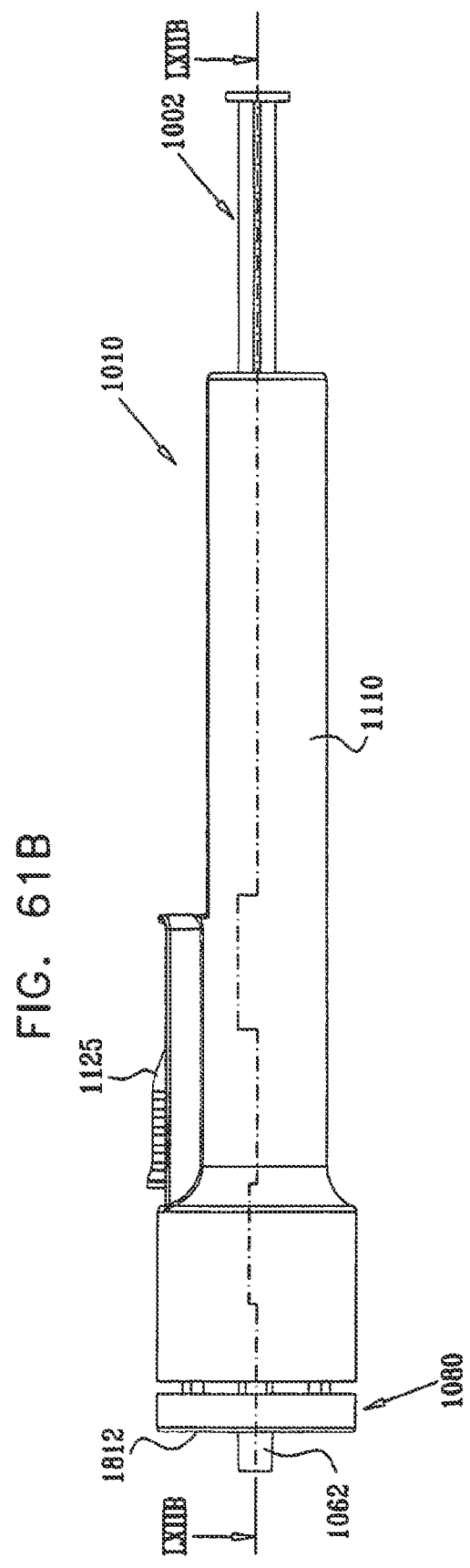

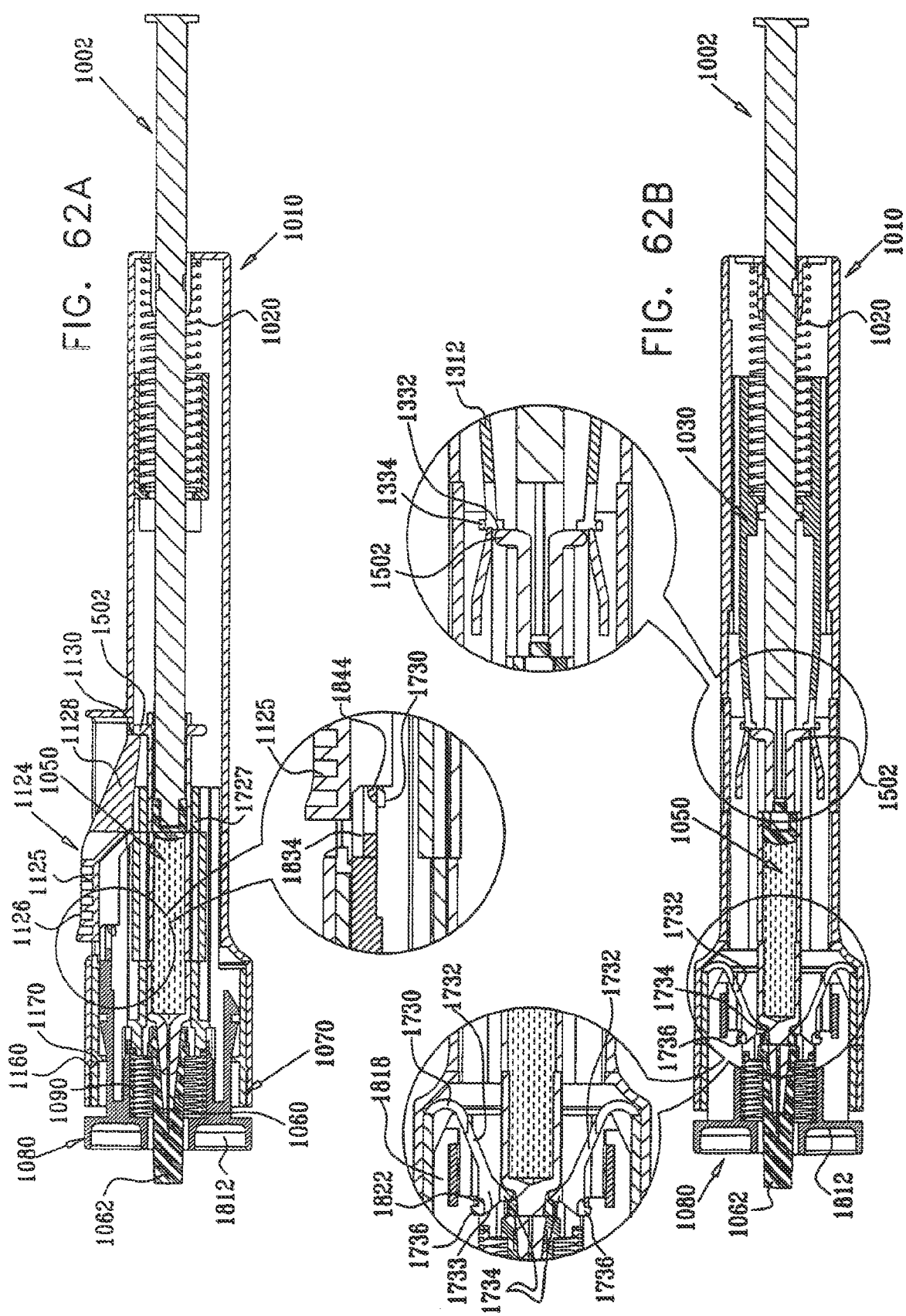

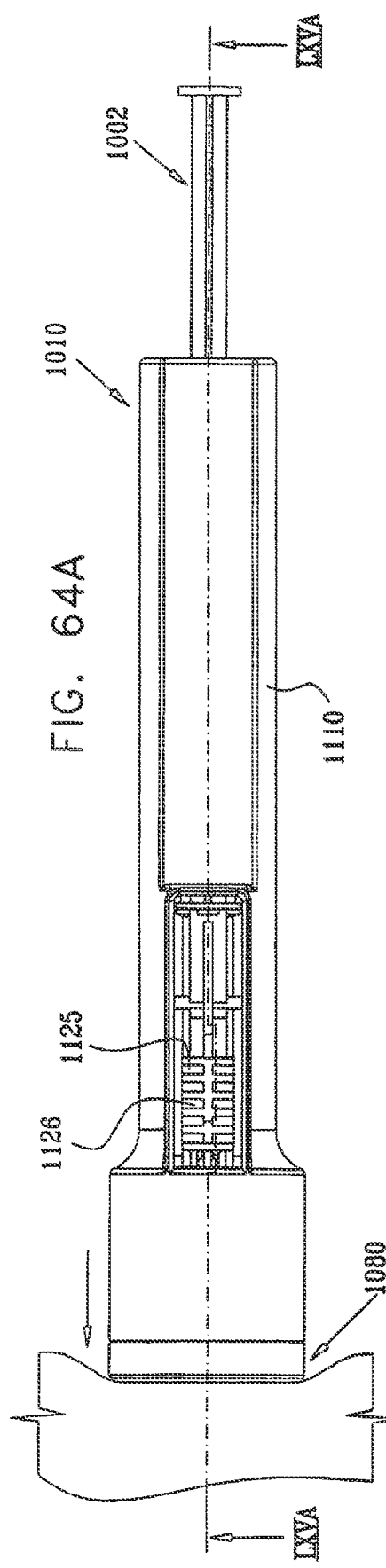
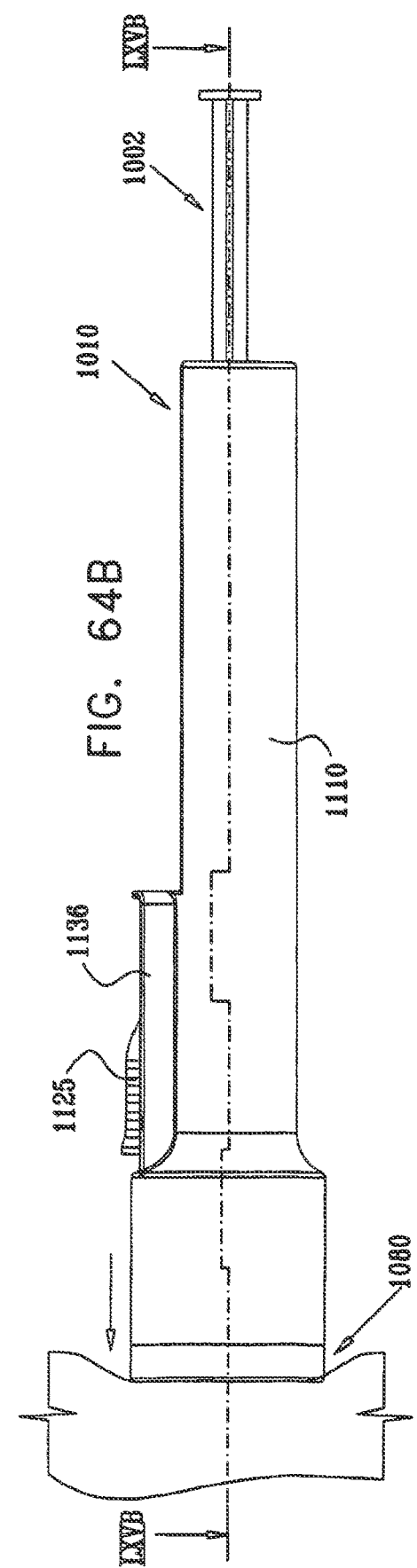

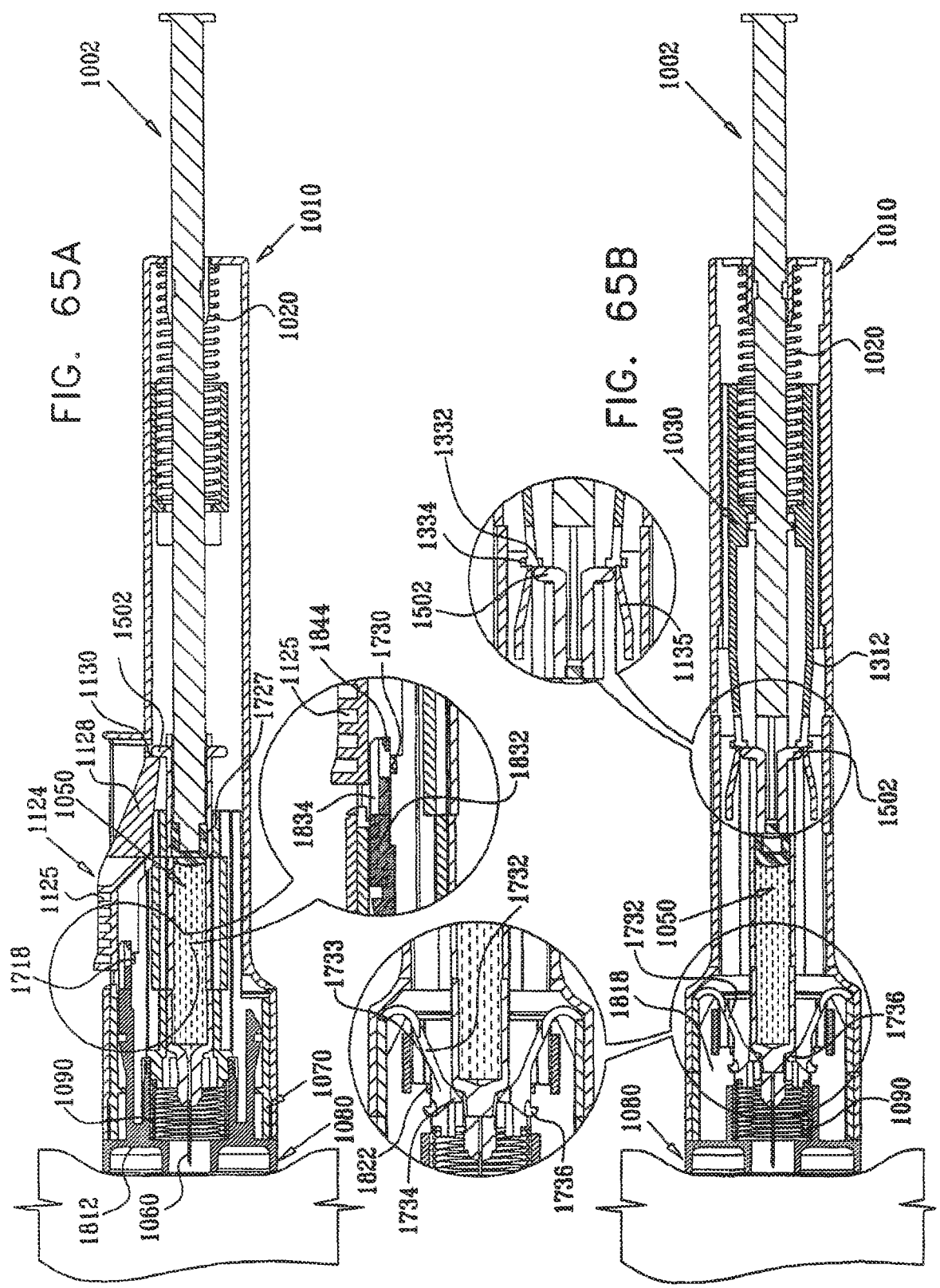

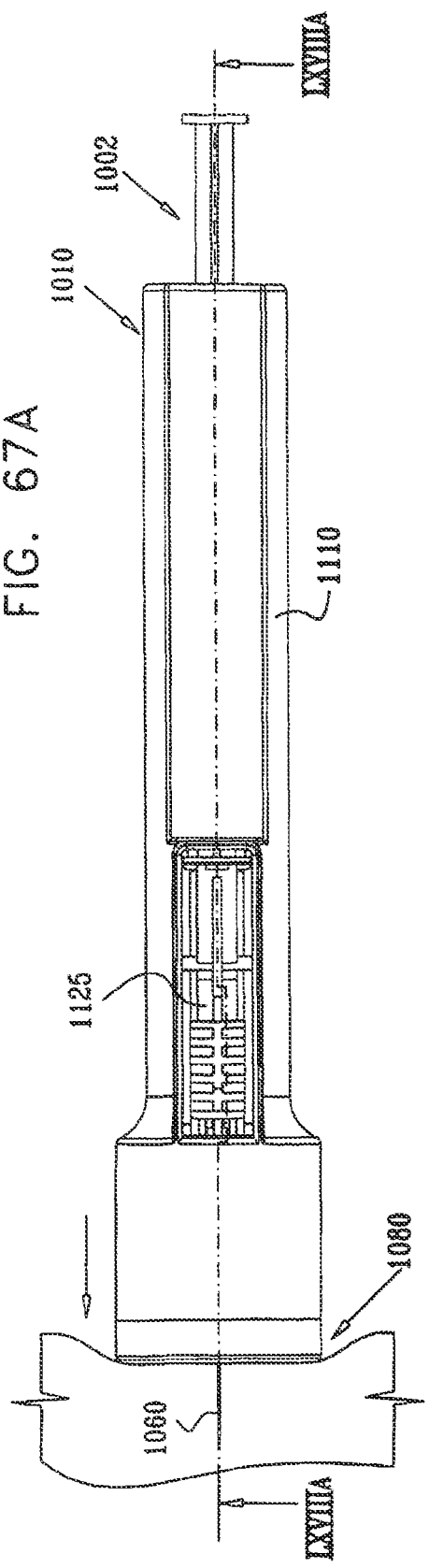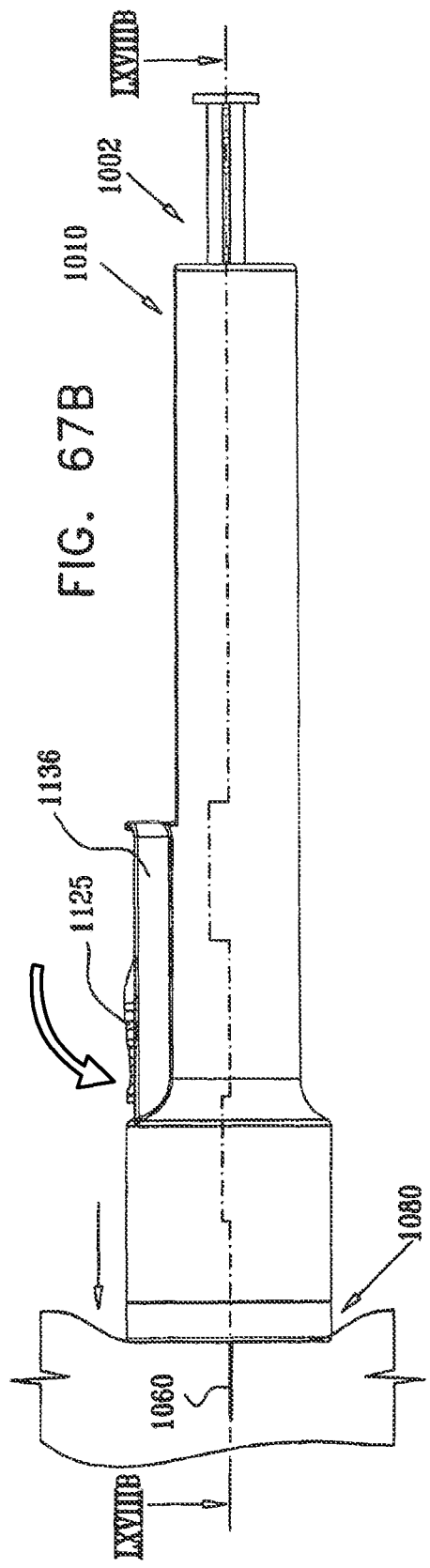

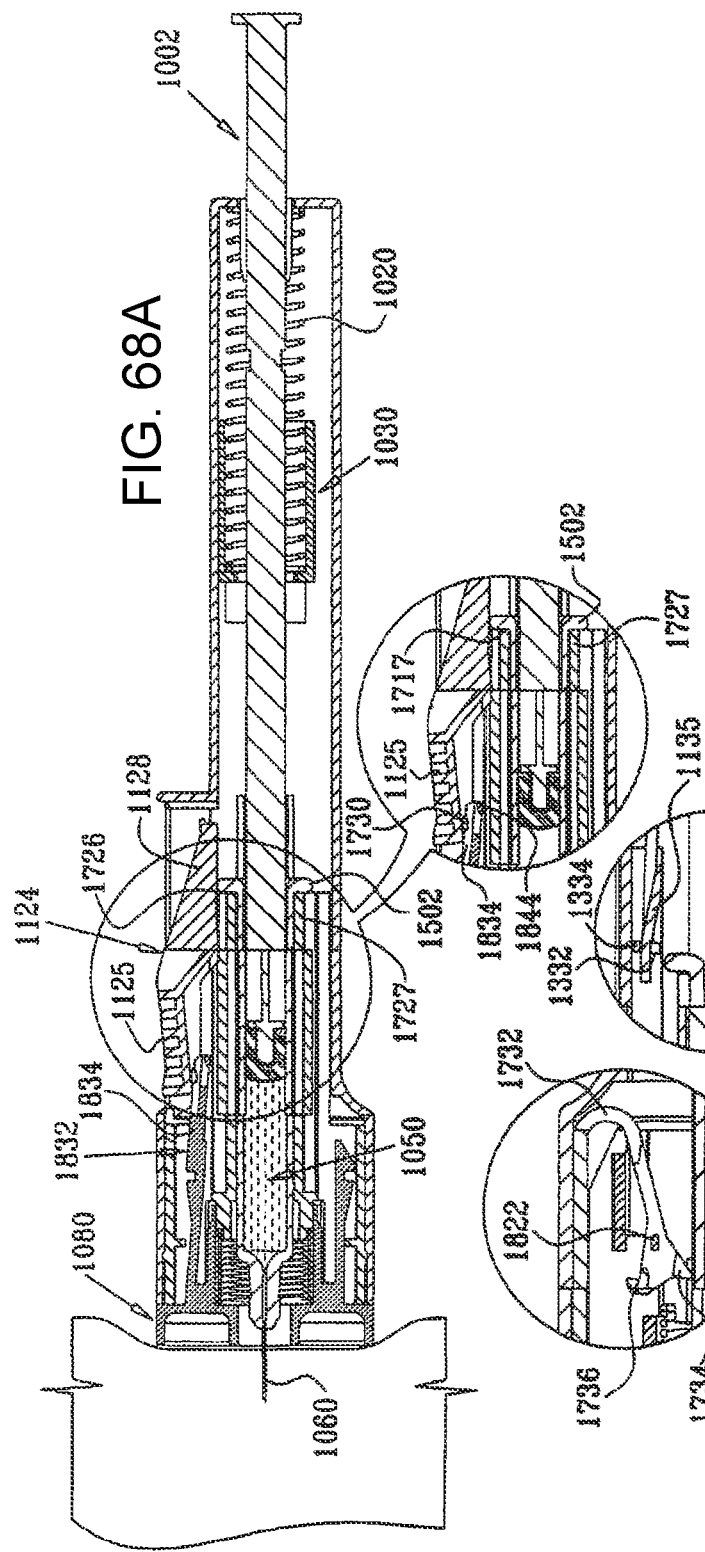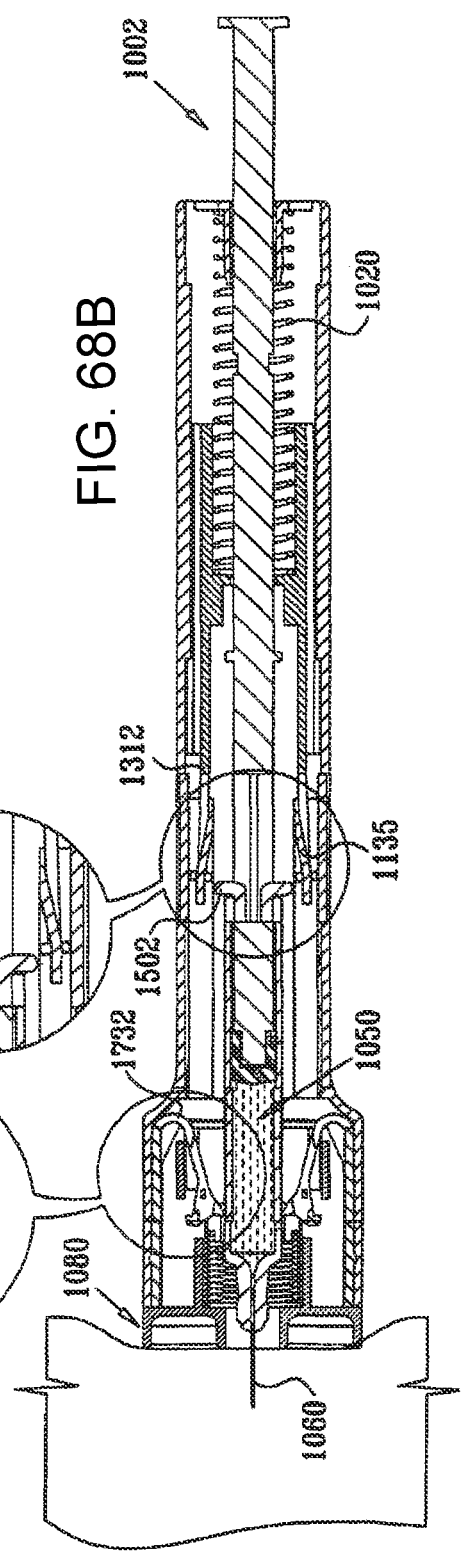

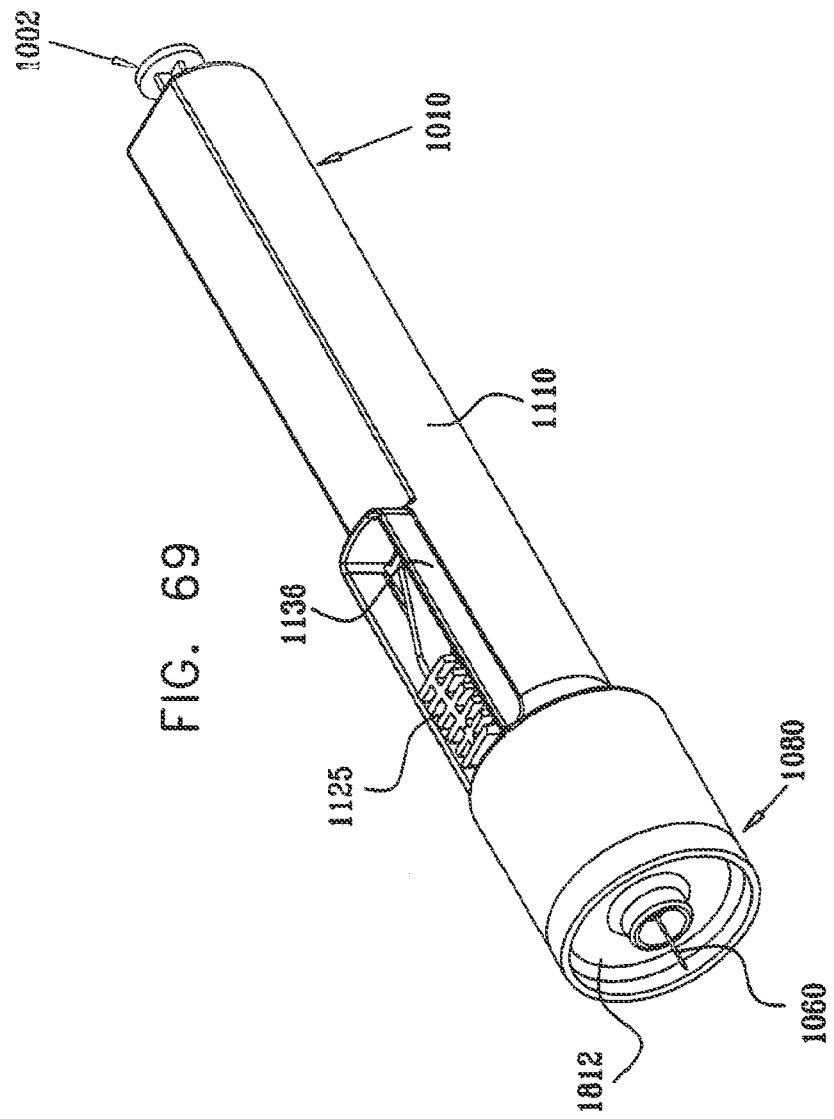

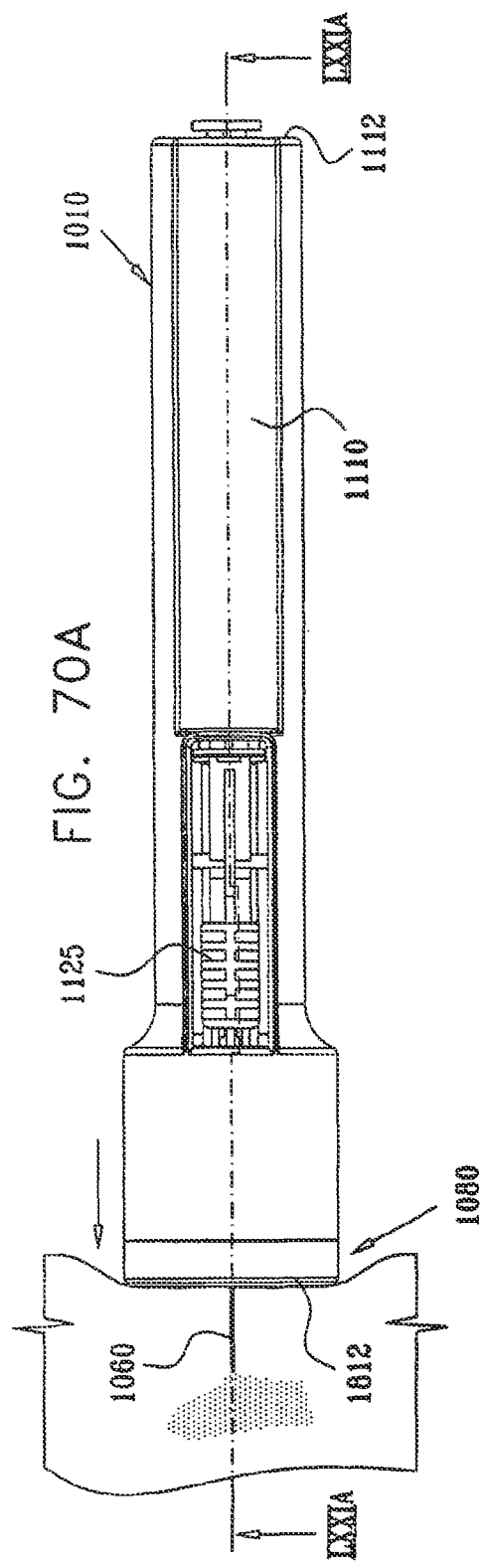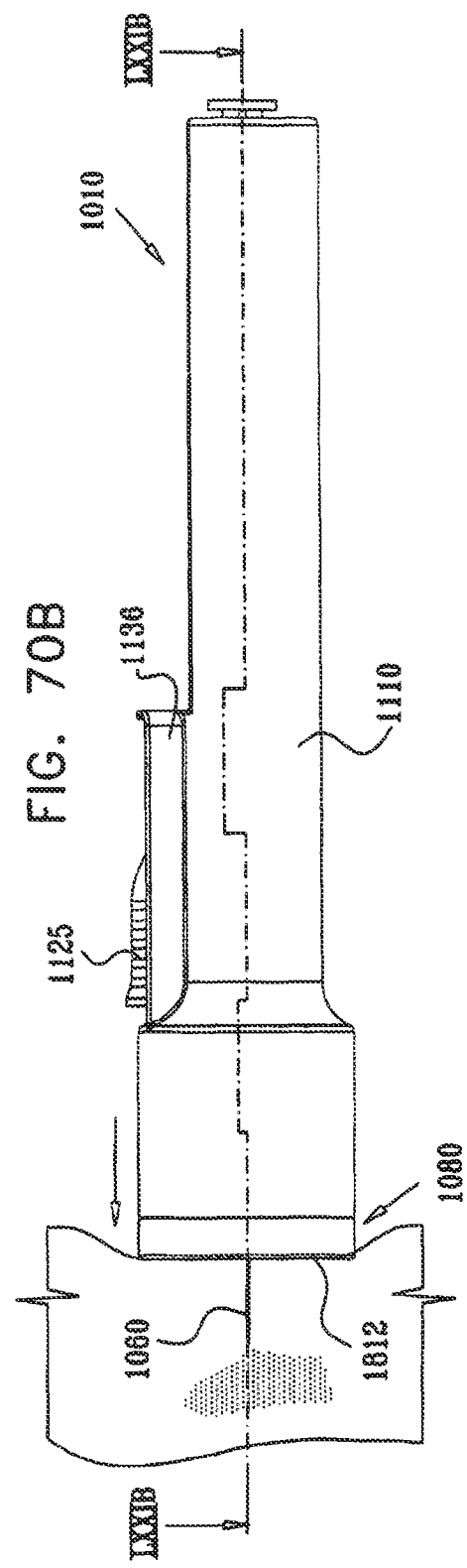

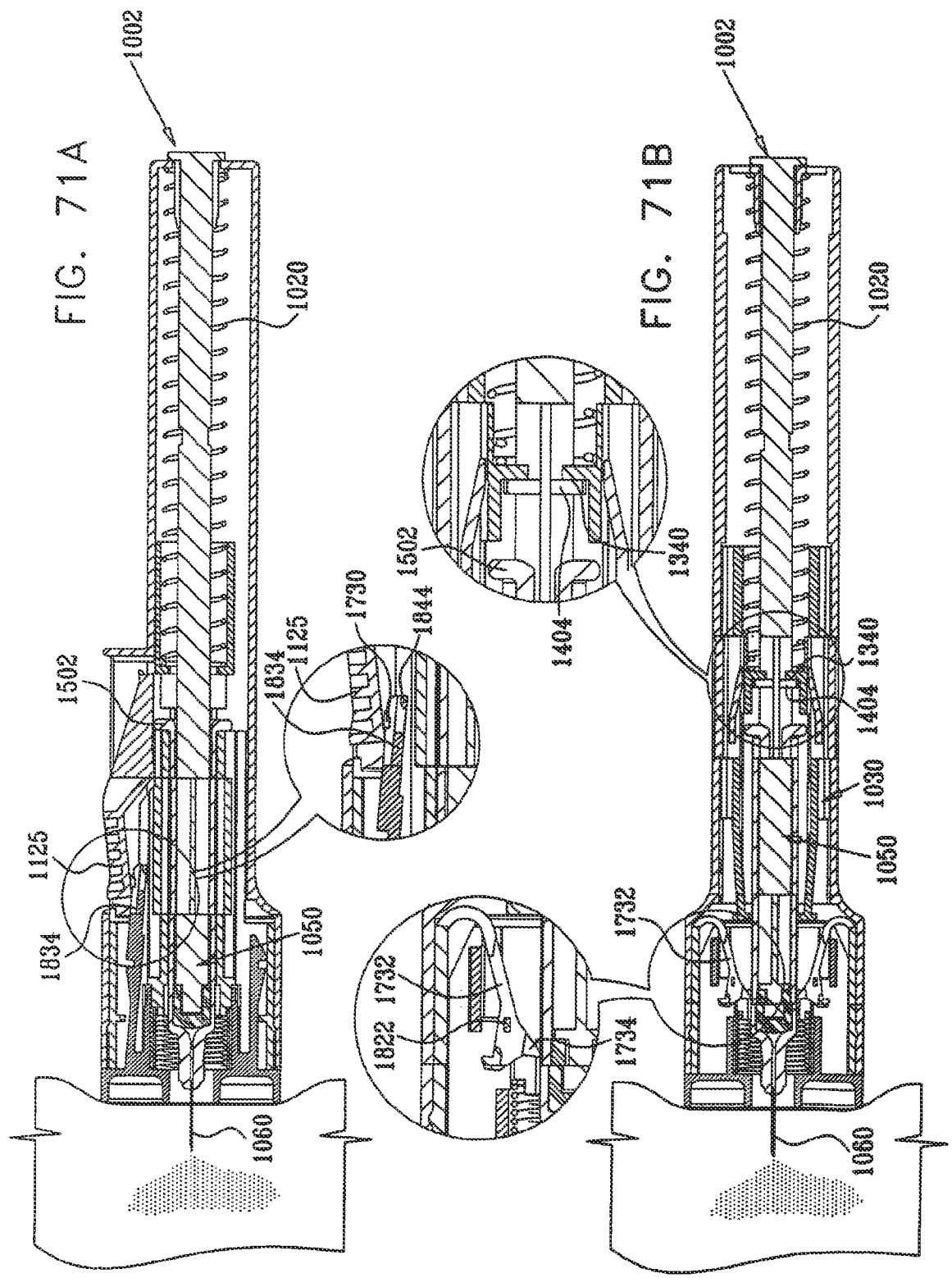

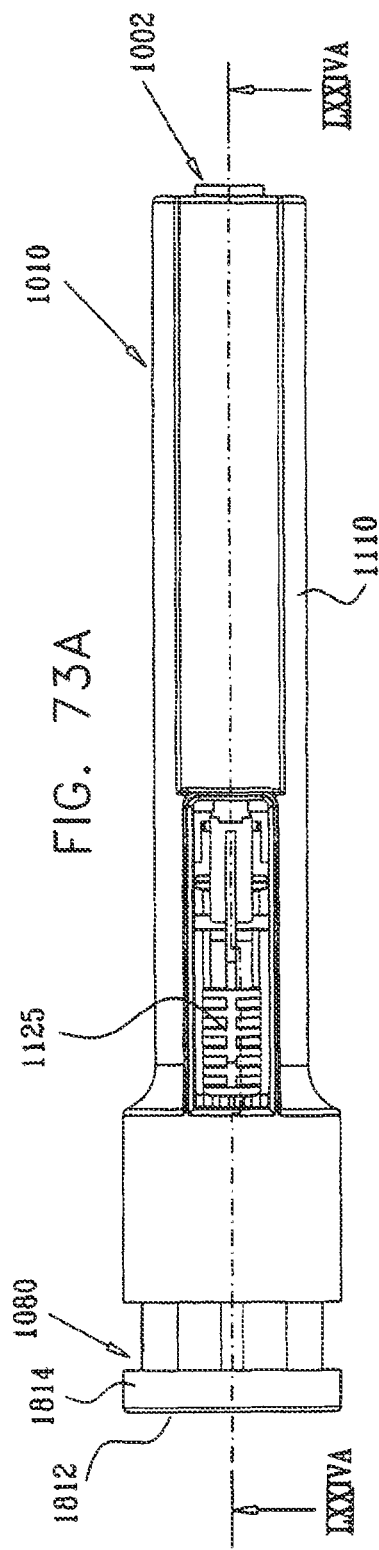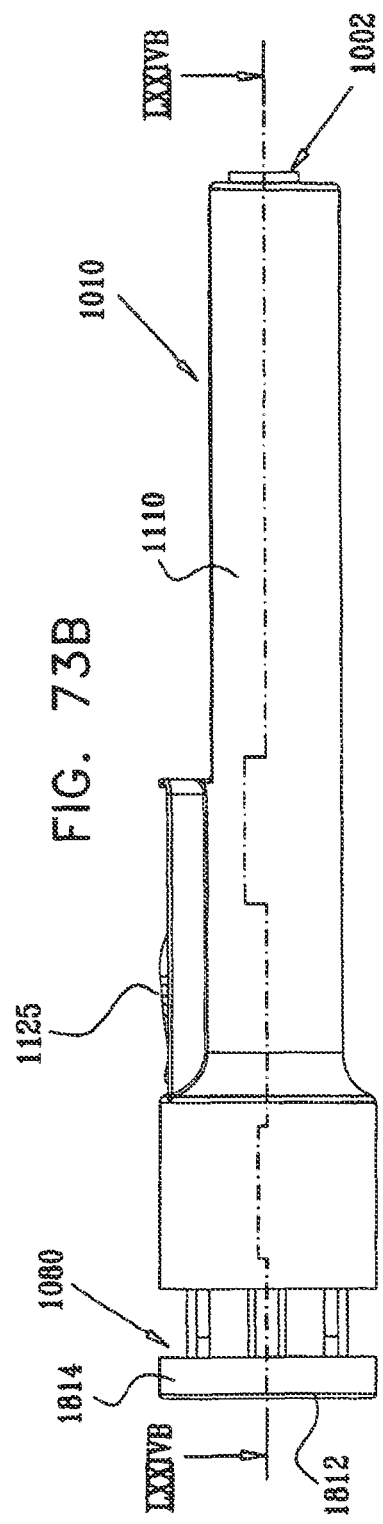

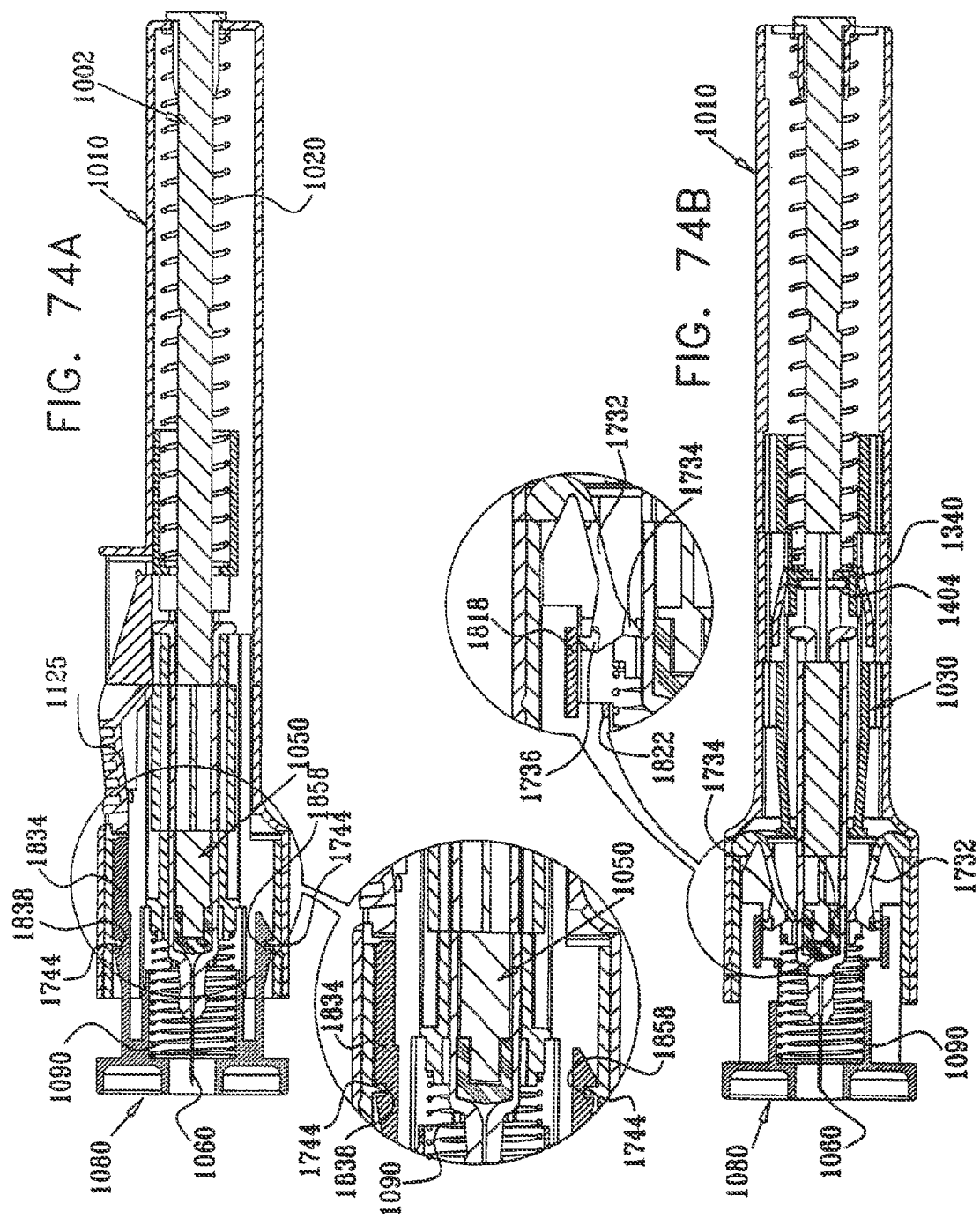

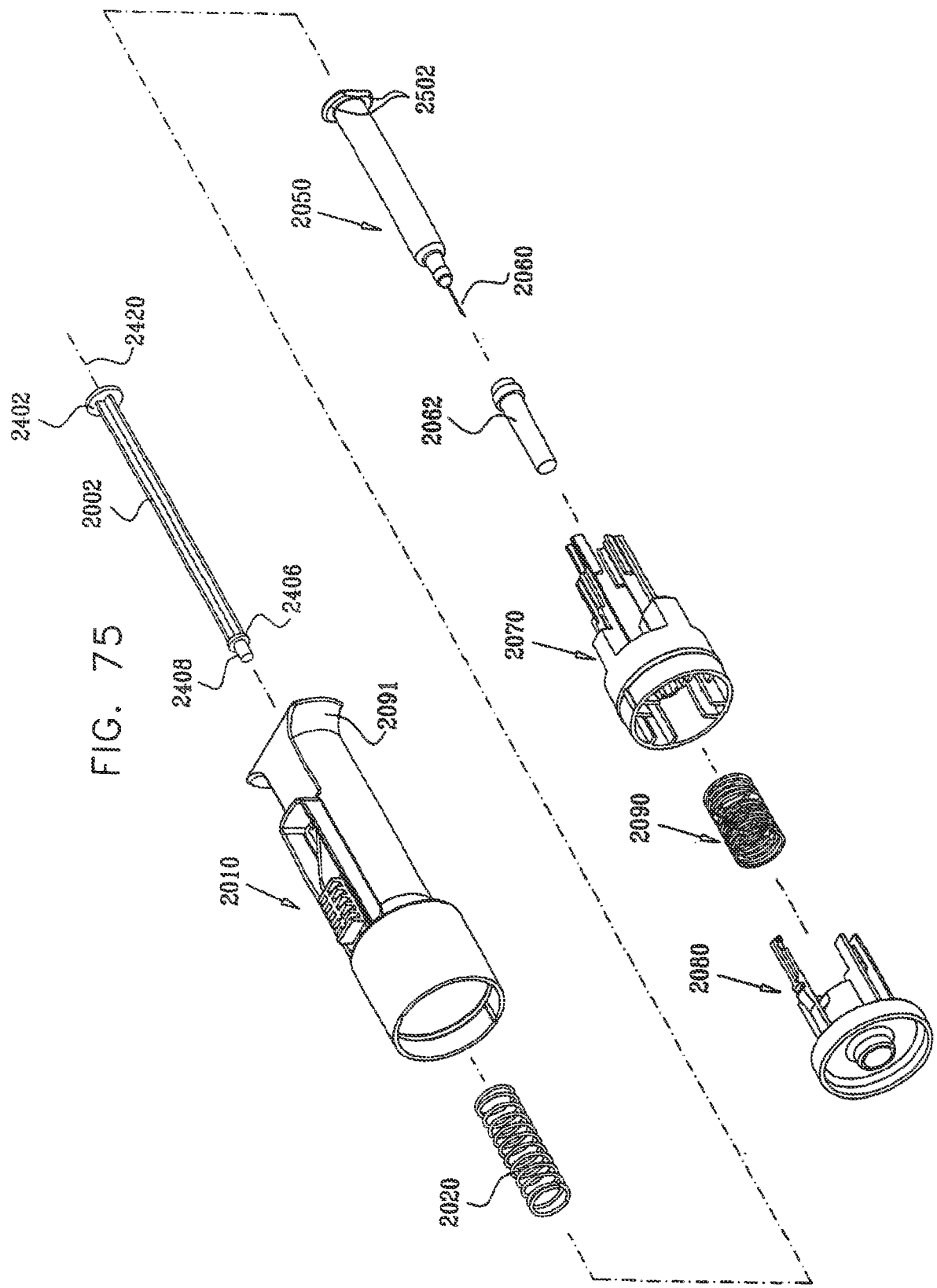

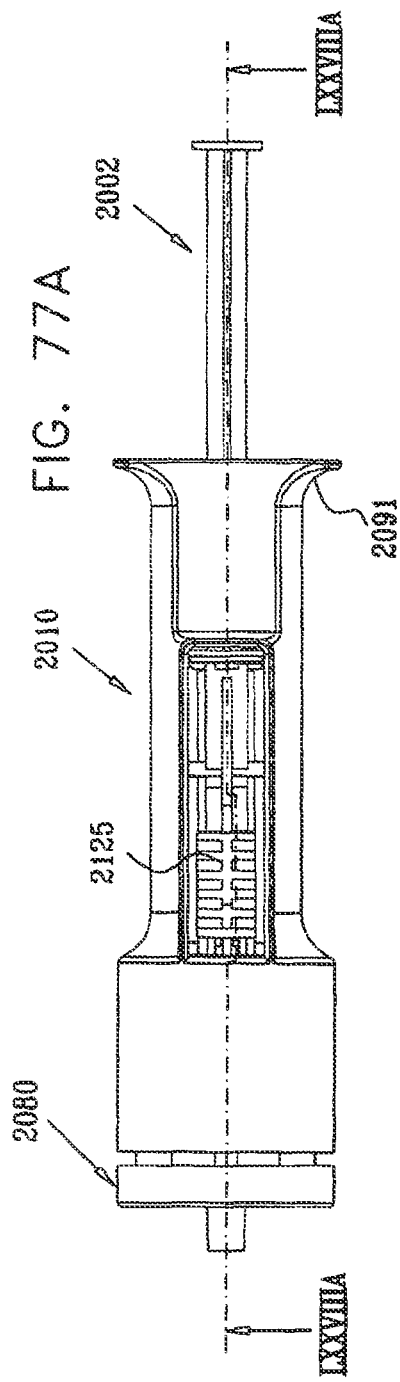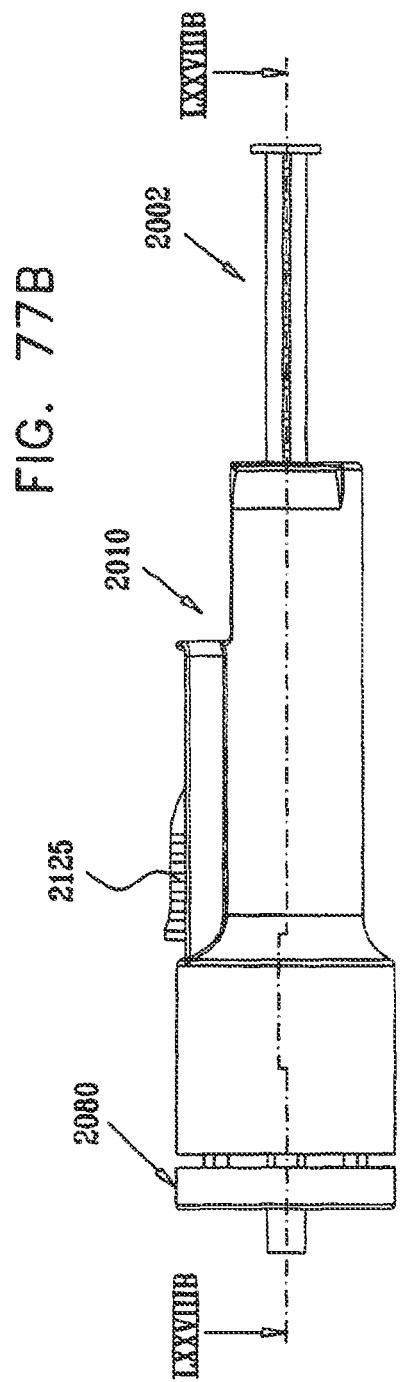

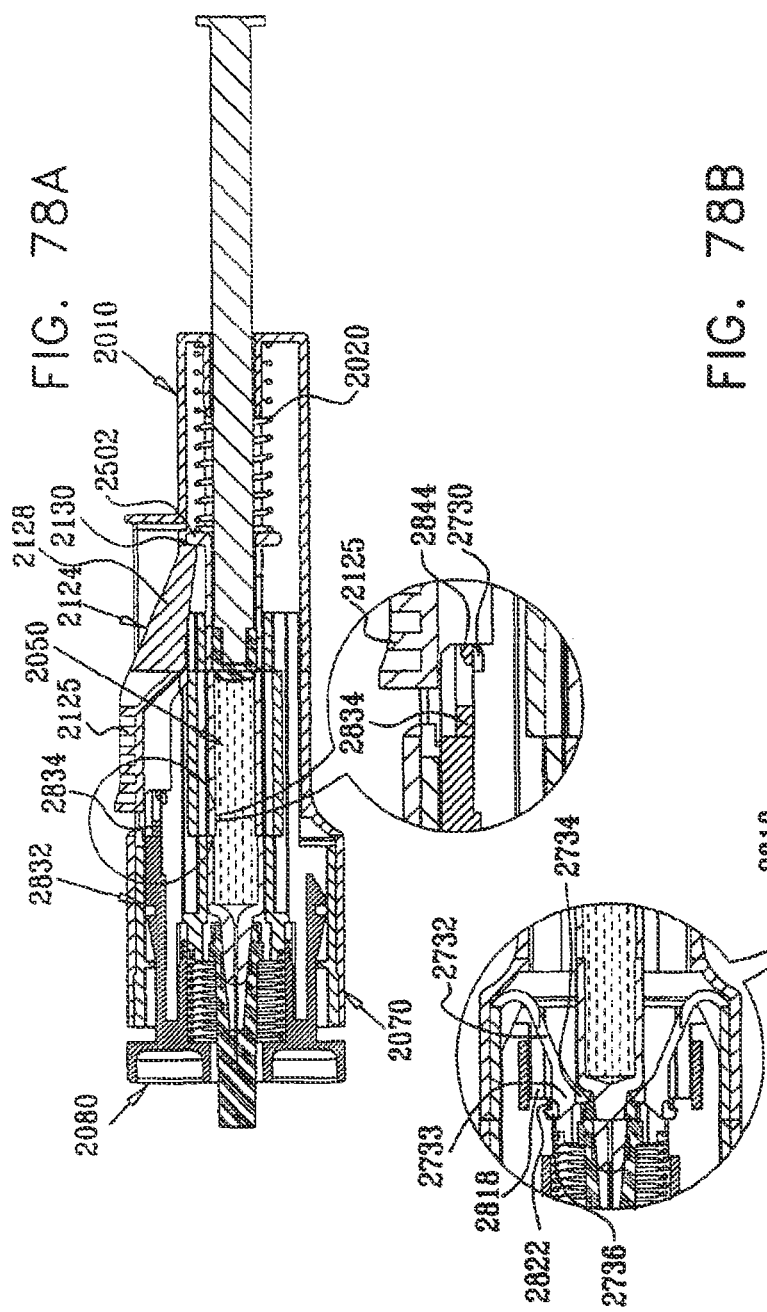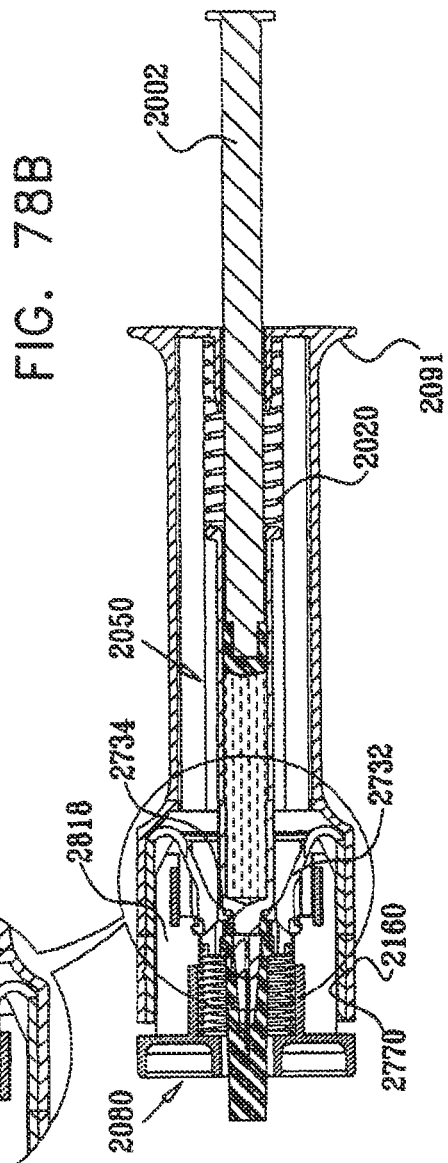

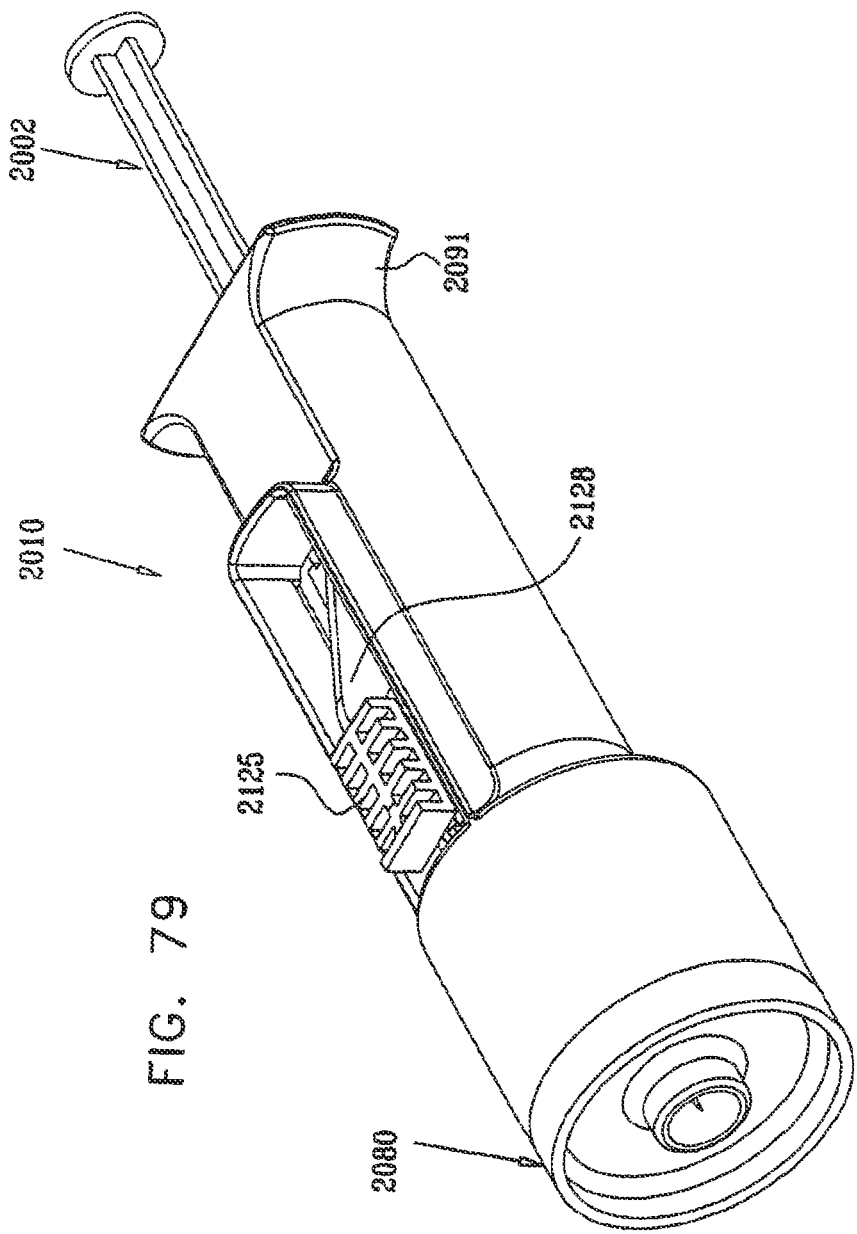

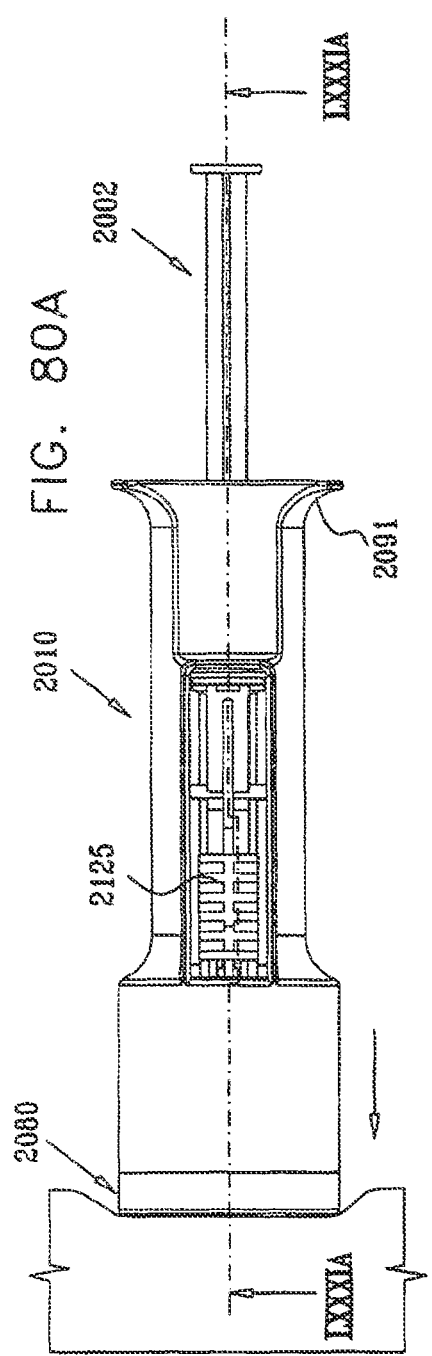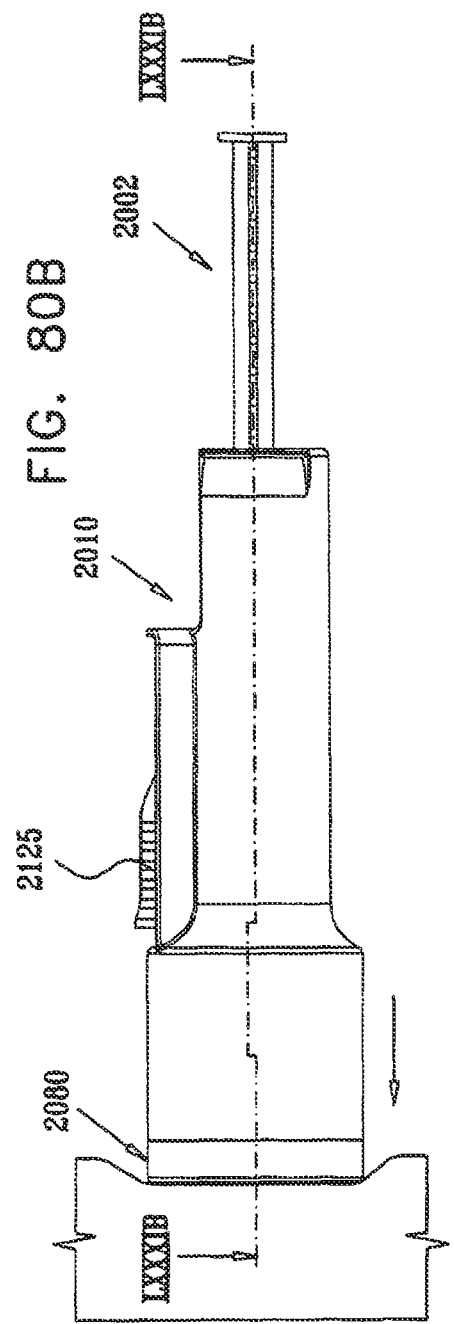

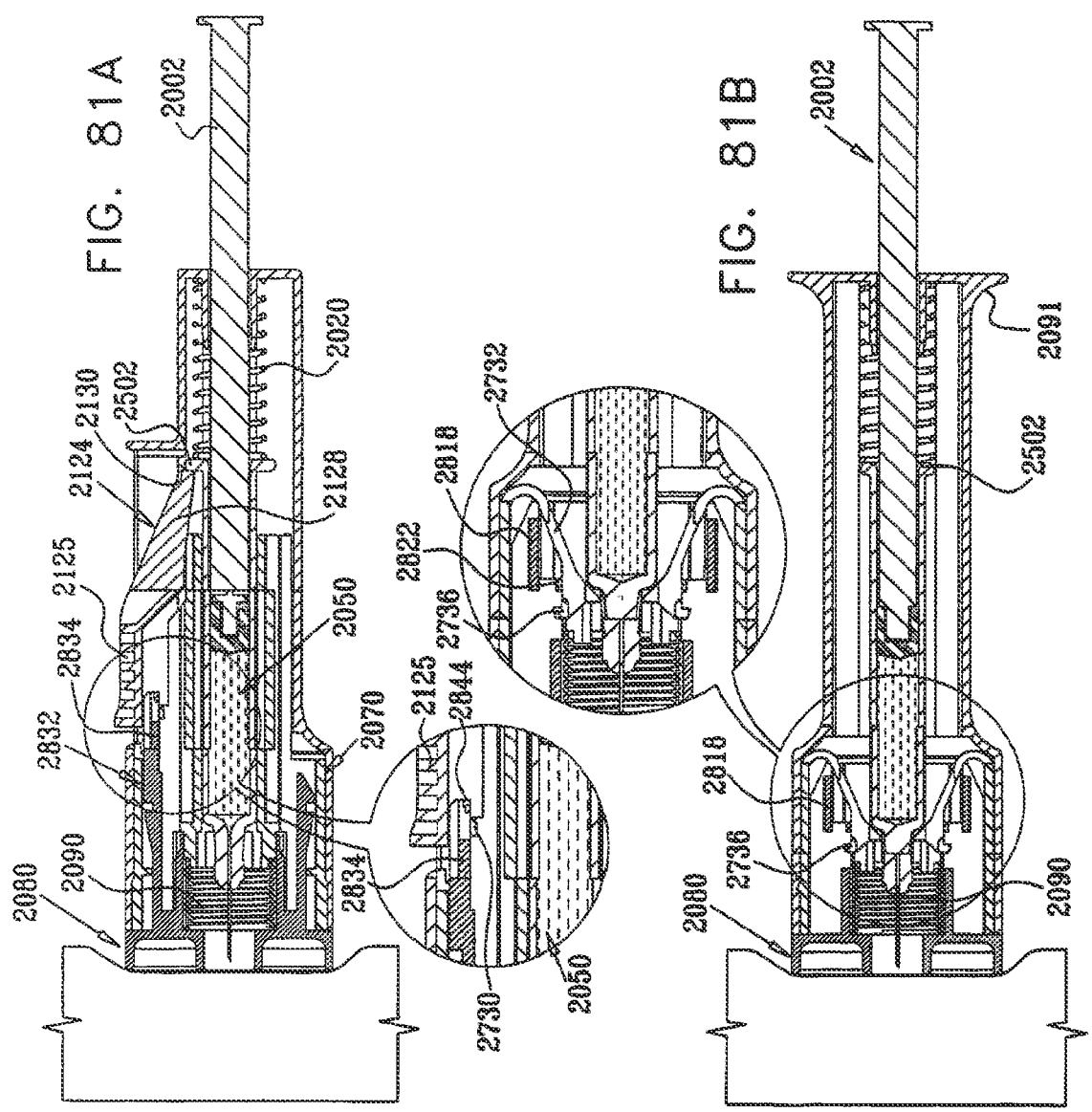

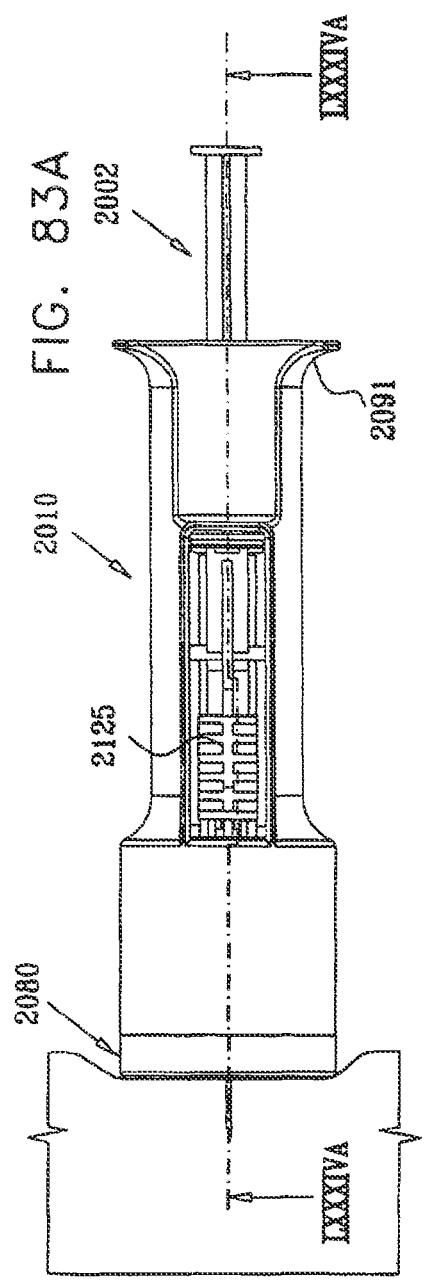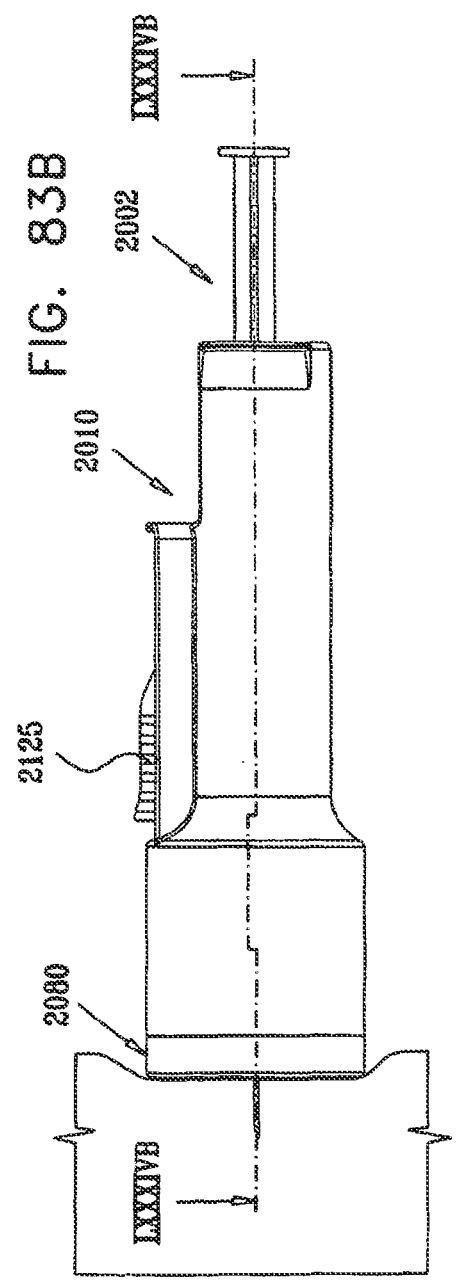

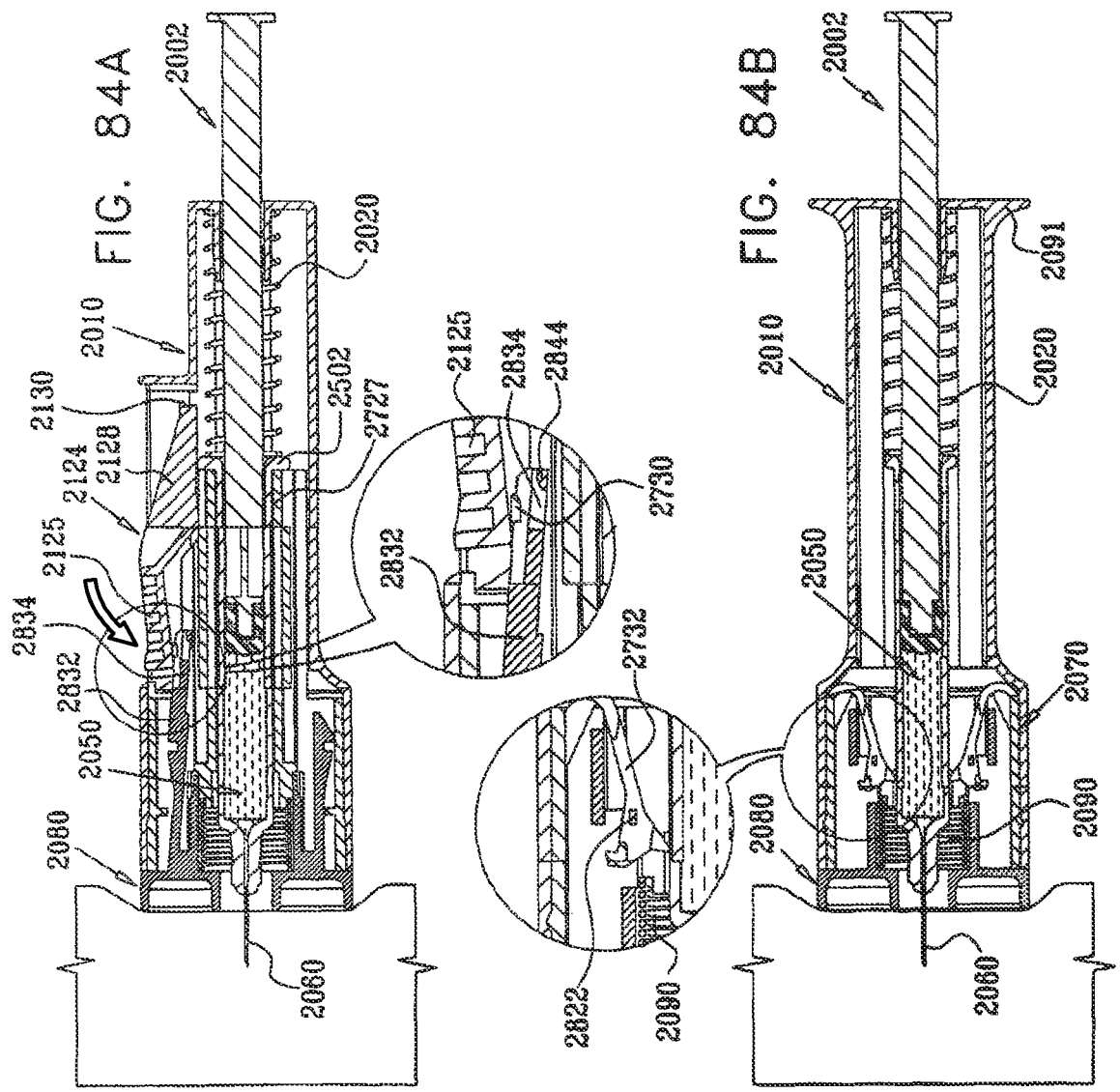

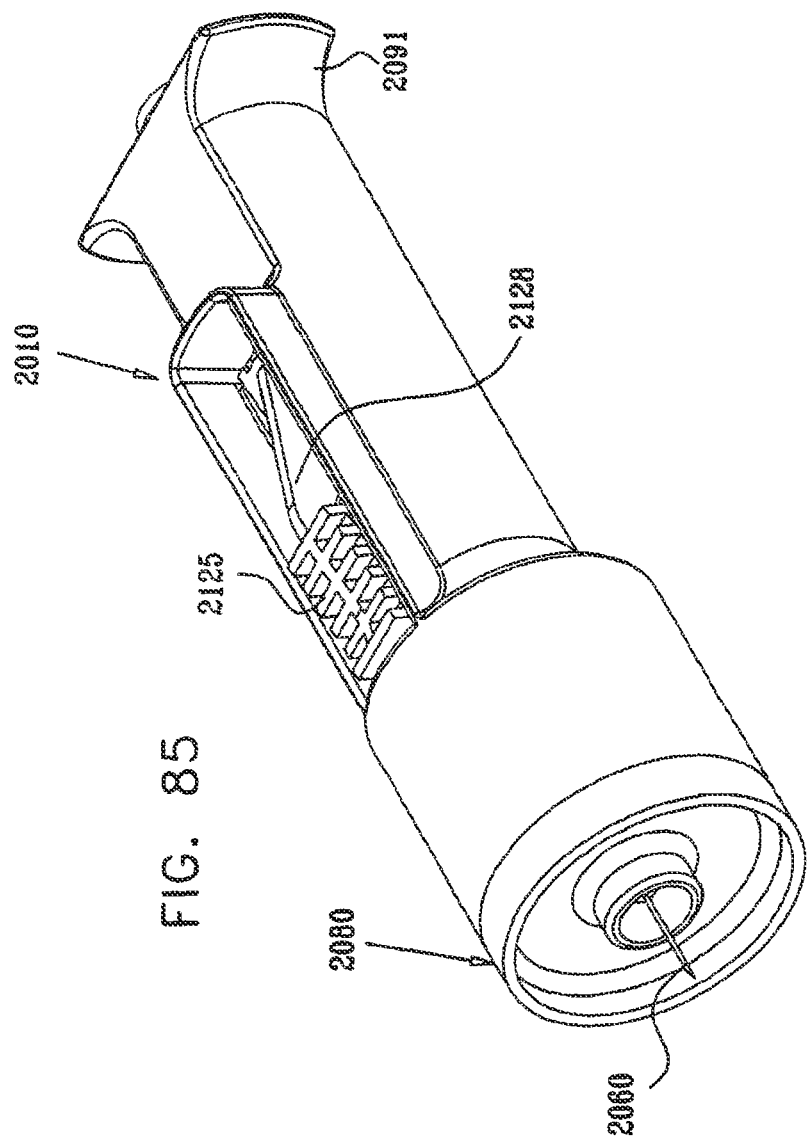

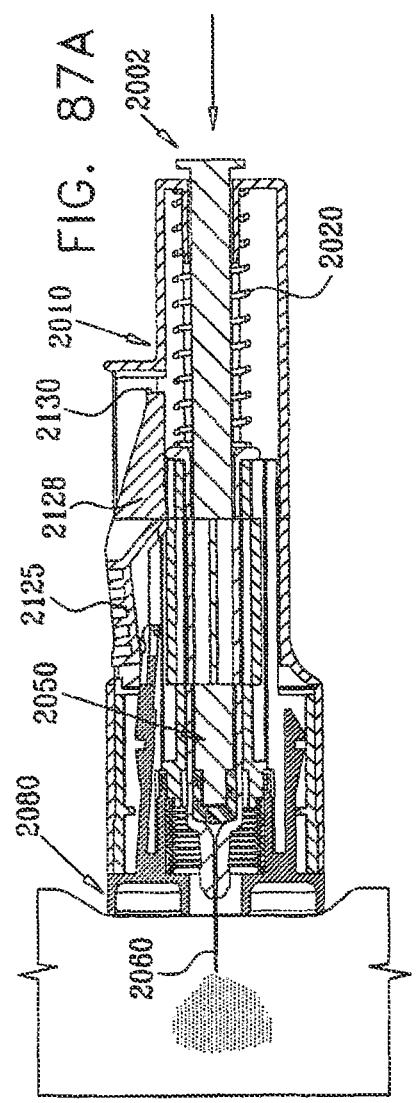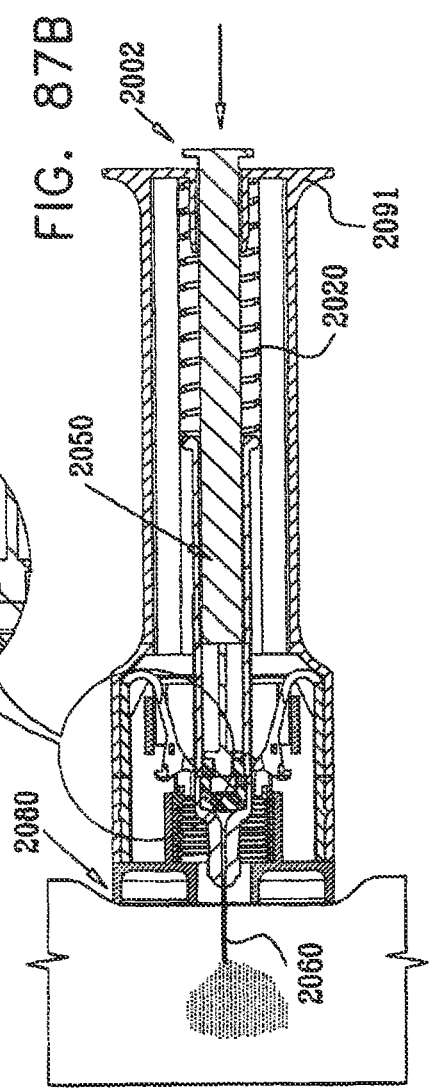

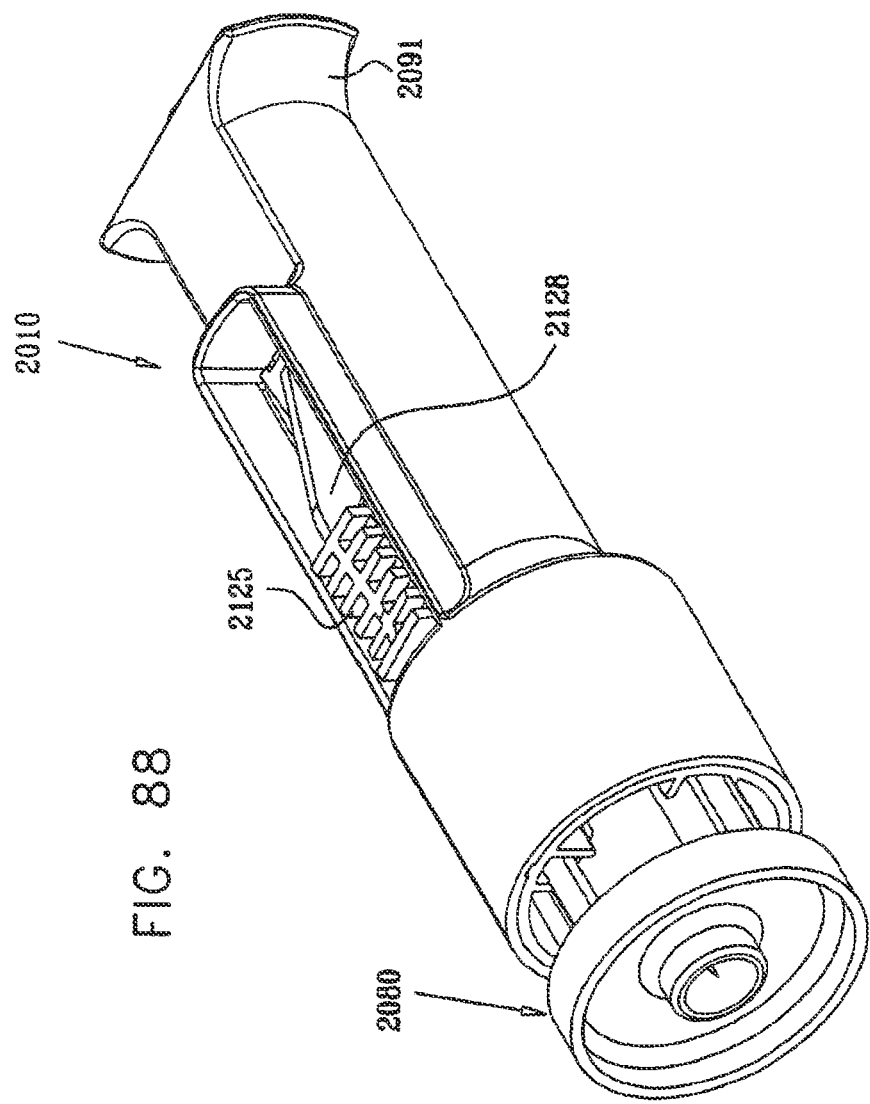

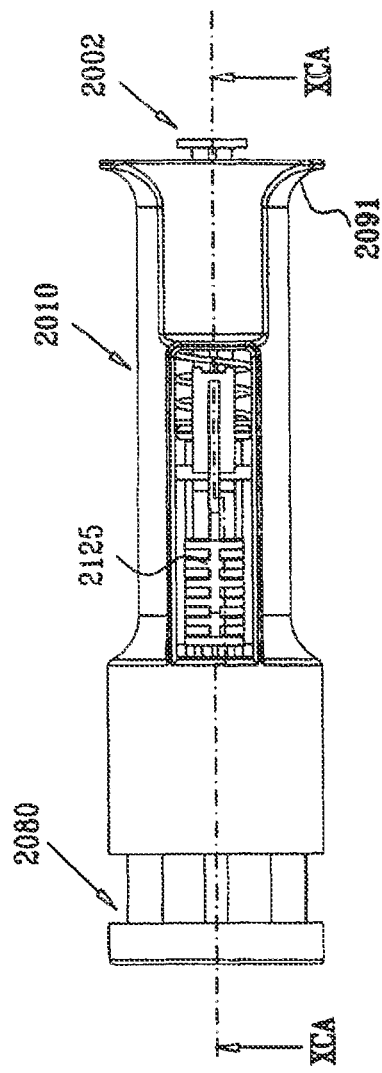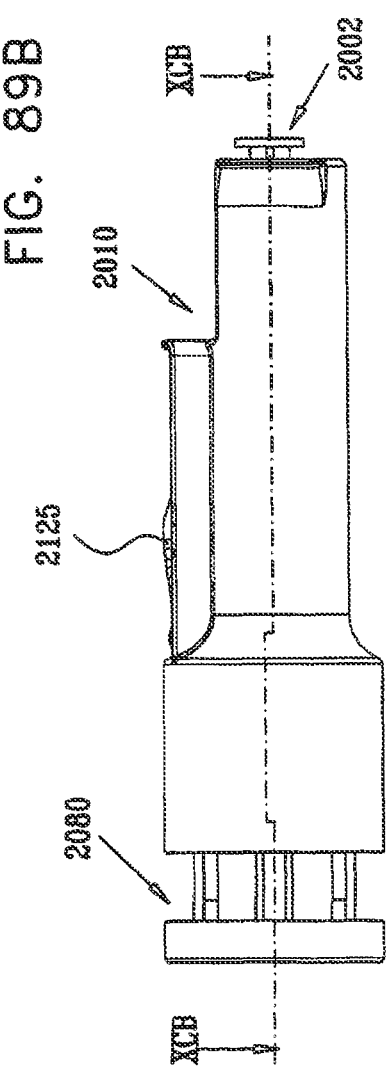

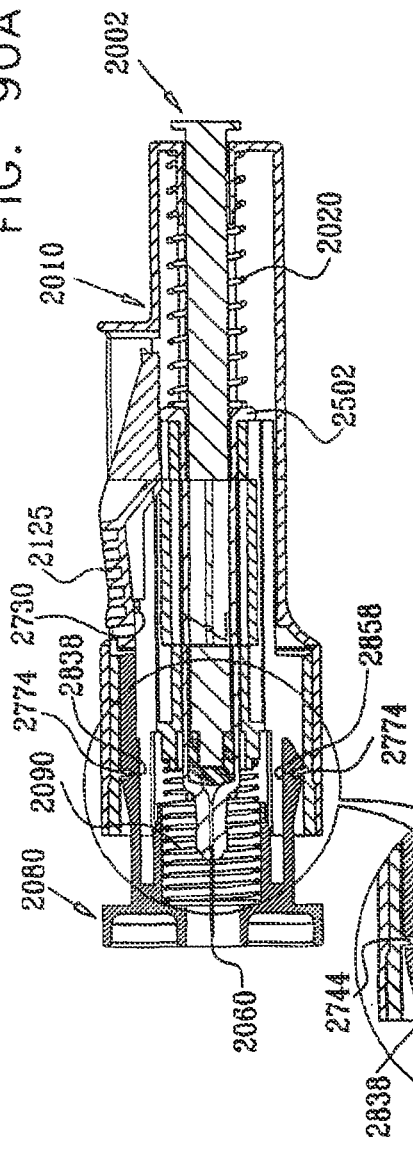
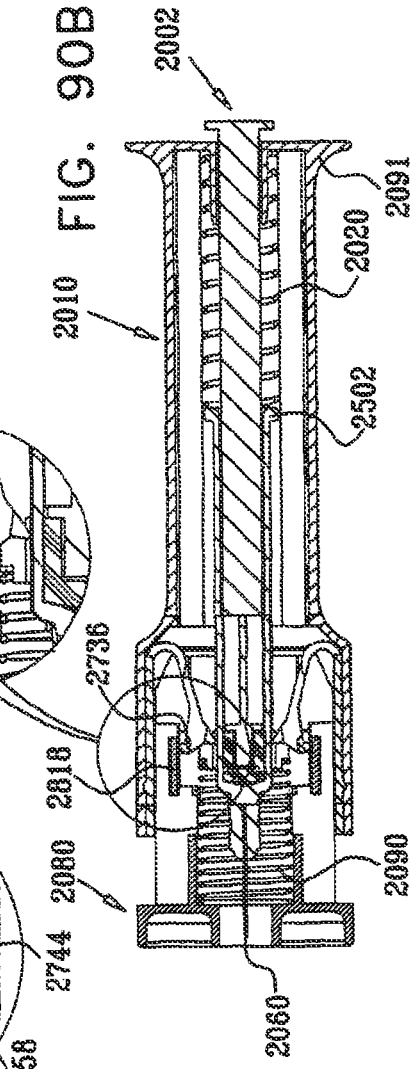
FIG. 90A
FIG. 90B

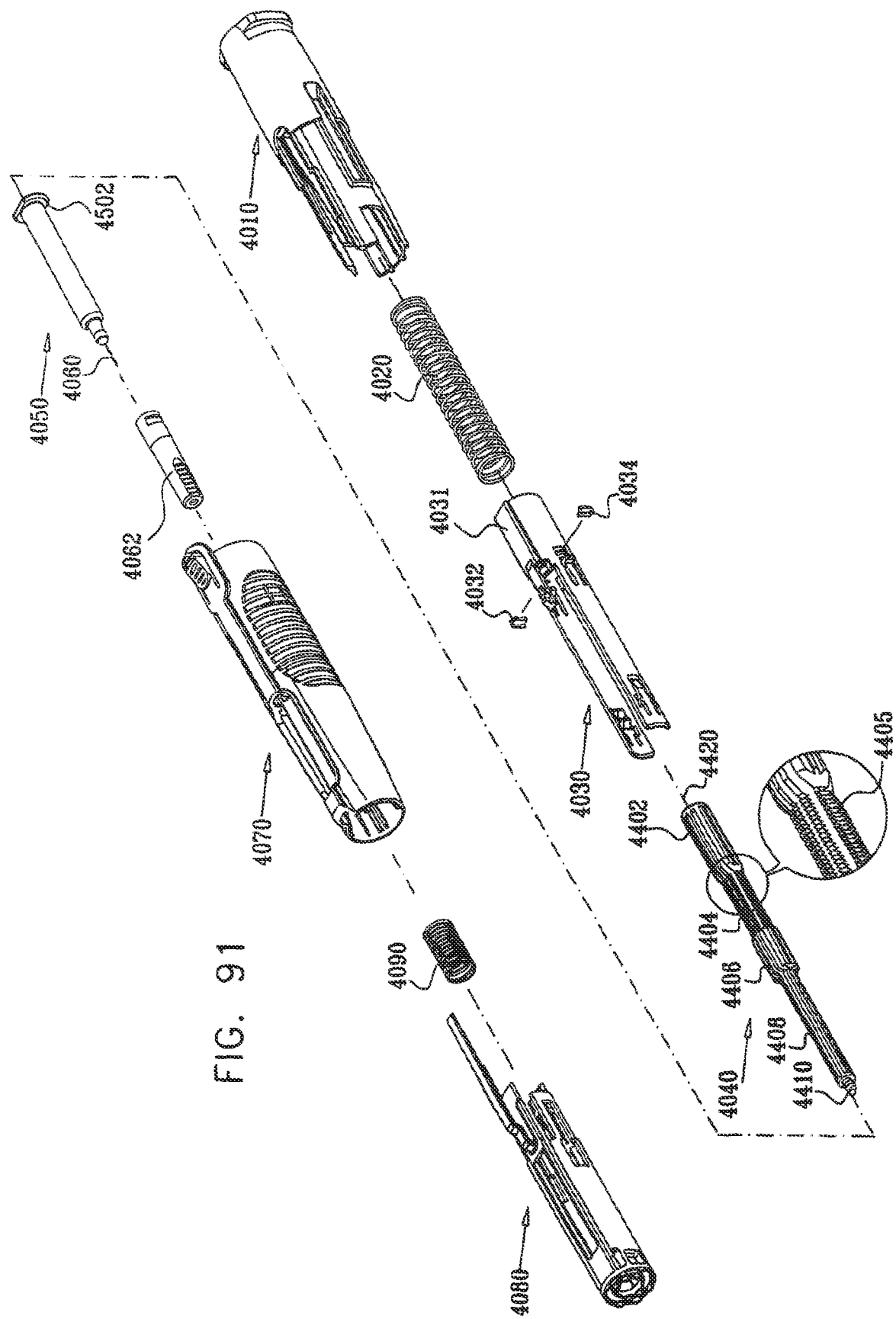

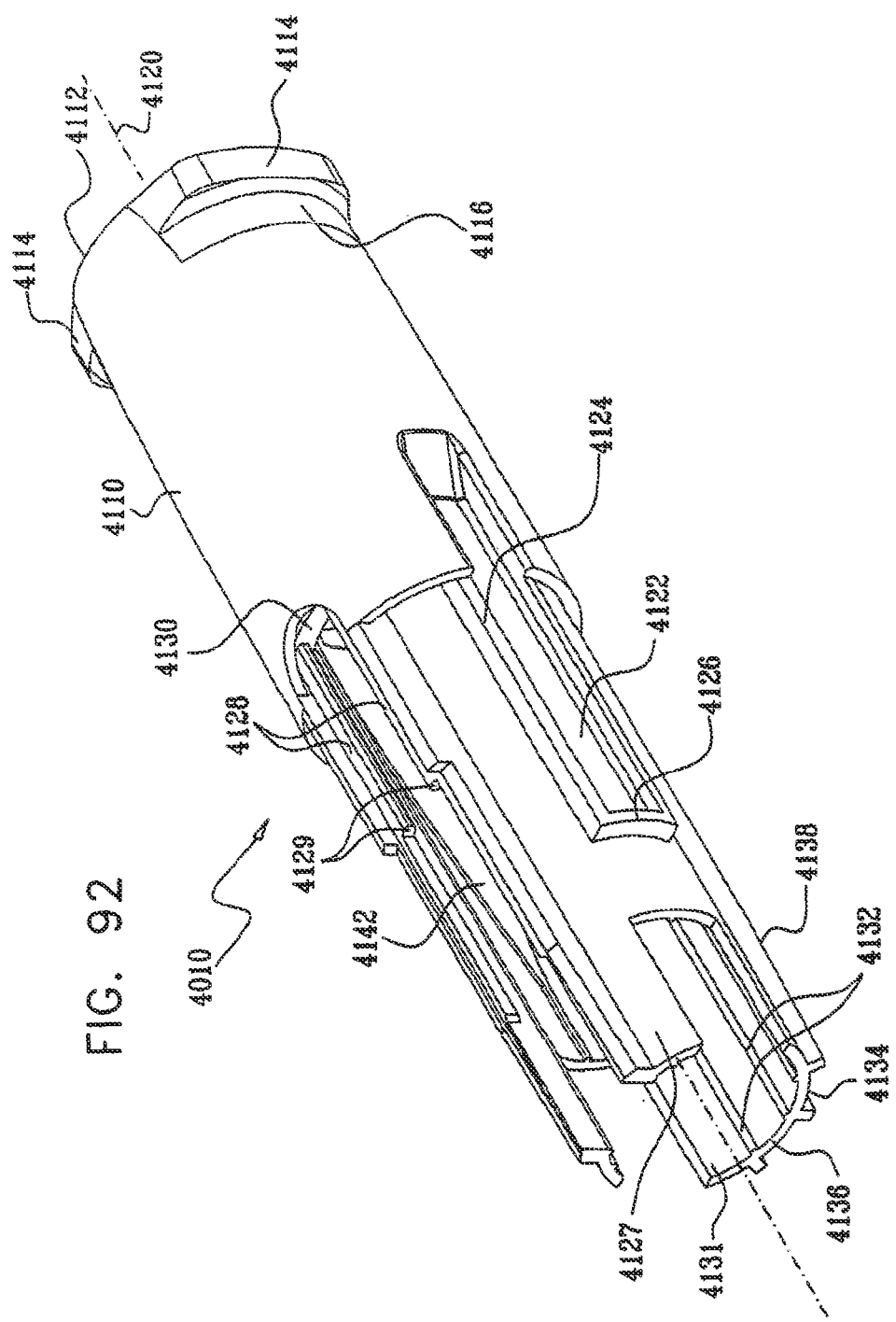

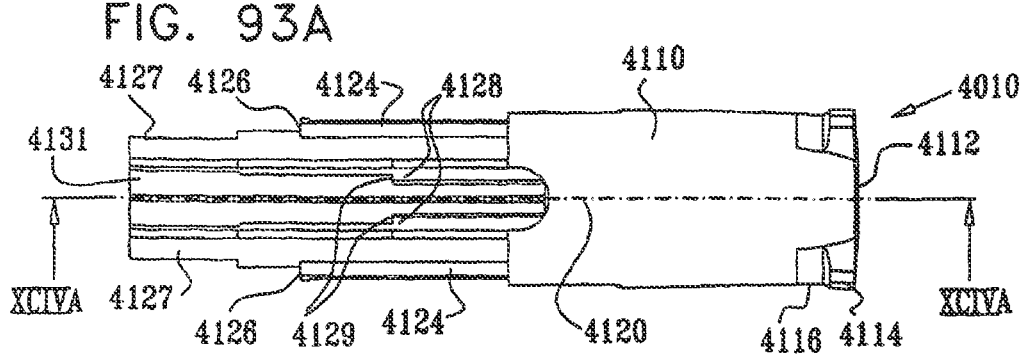
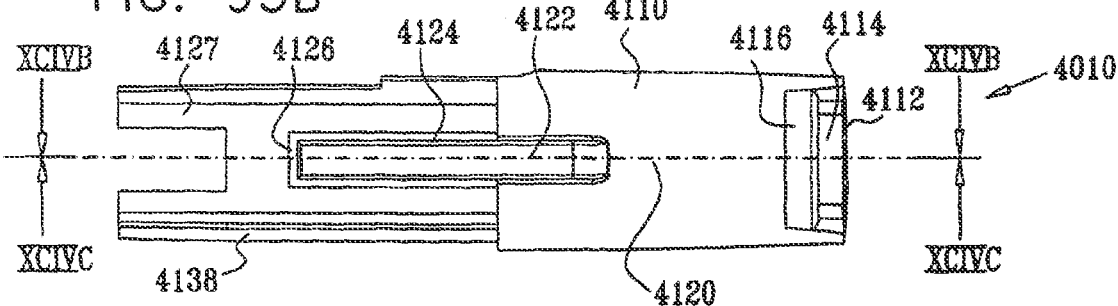
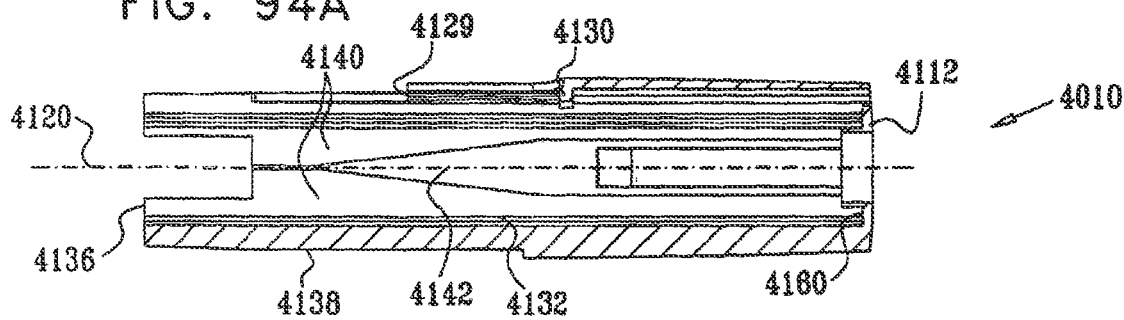
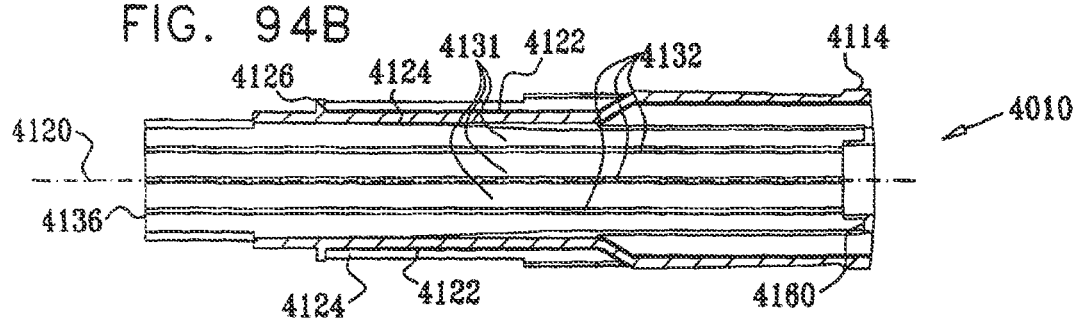
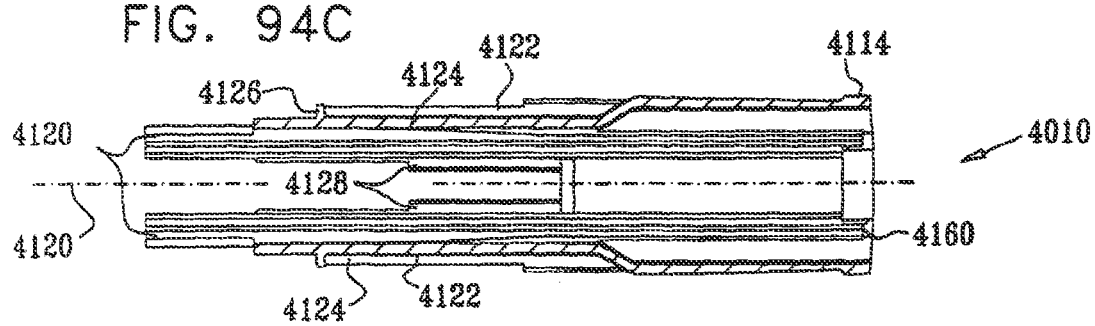

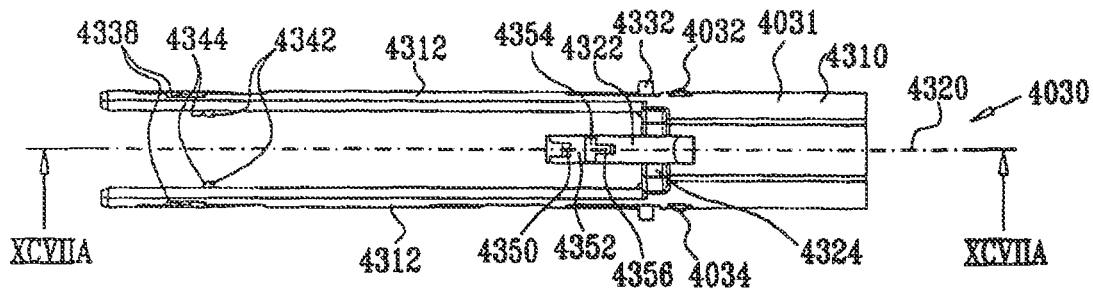
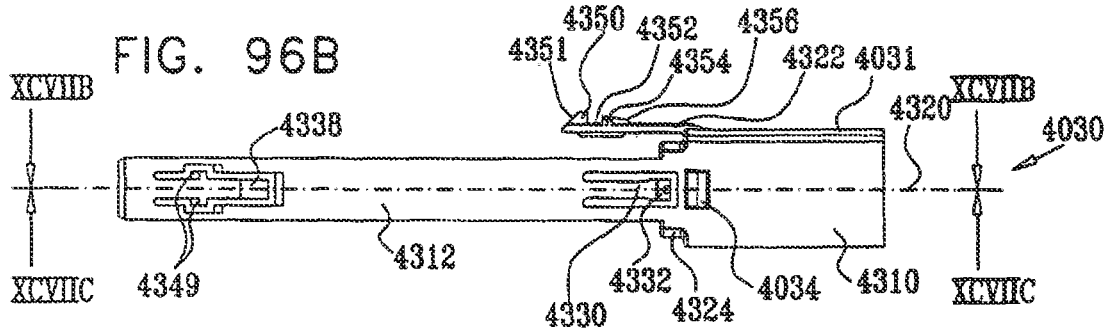
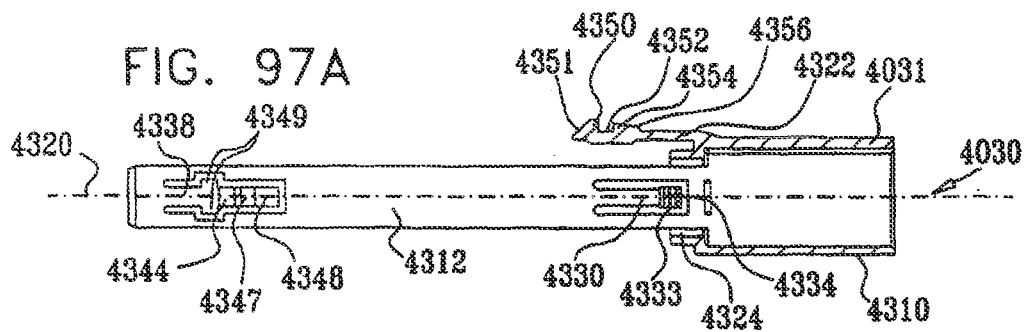
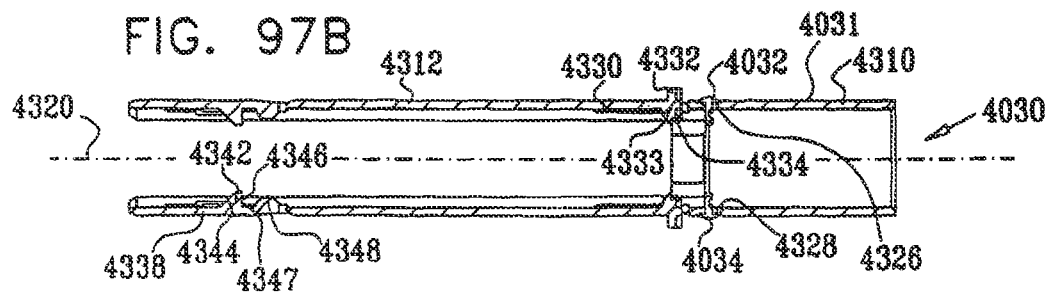
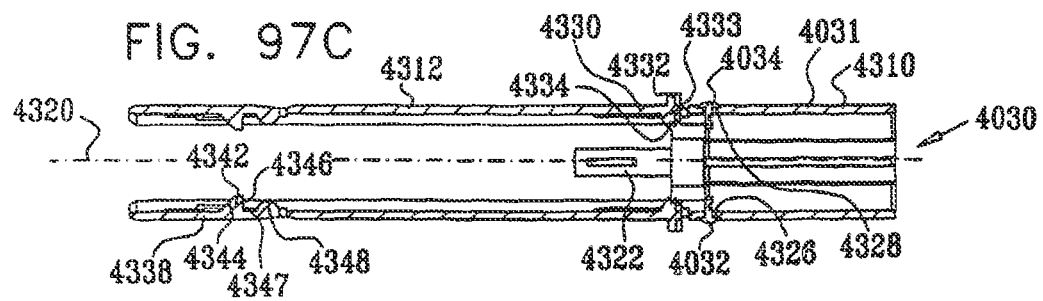

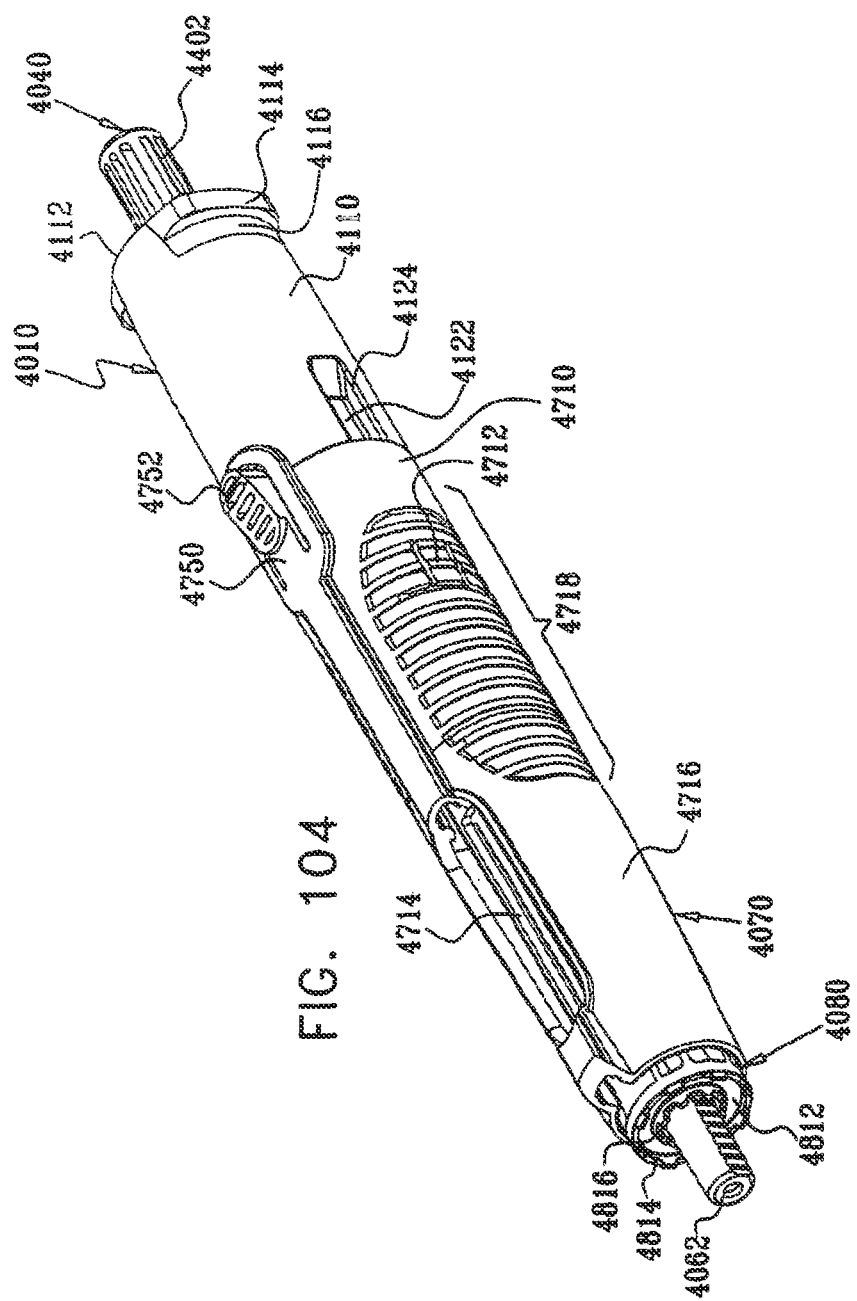

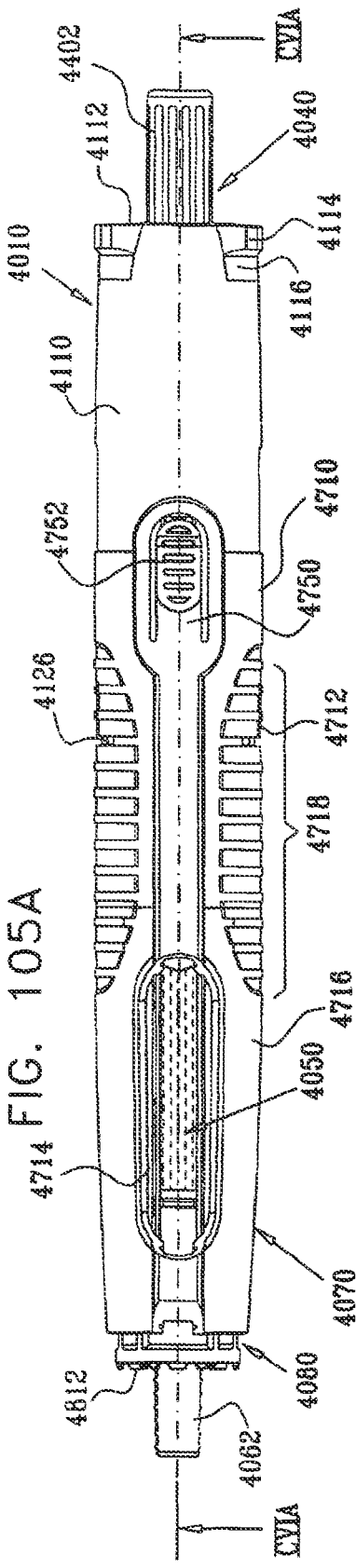
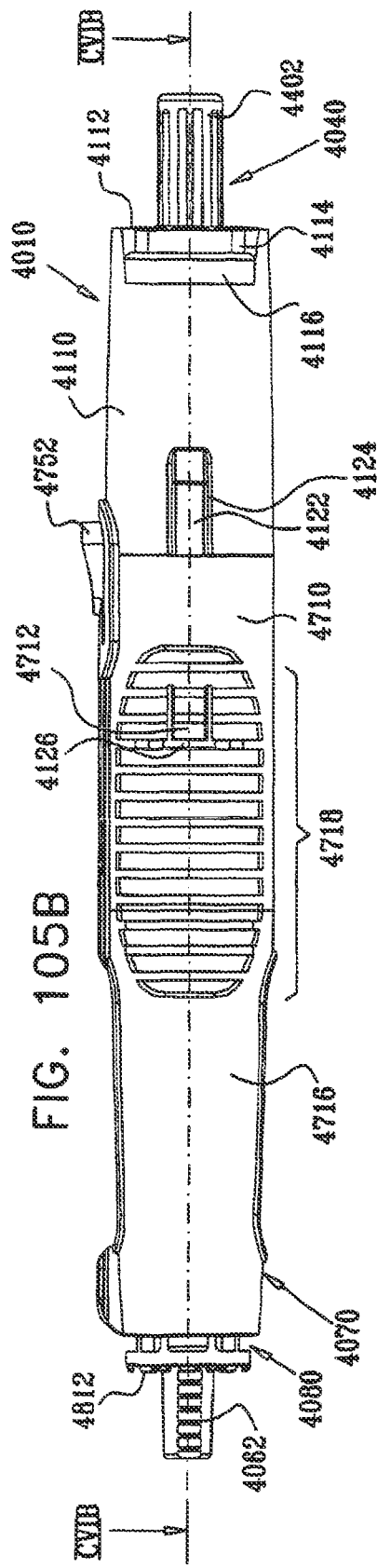
FIG. 105A
FIG. 105B

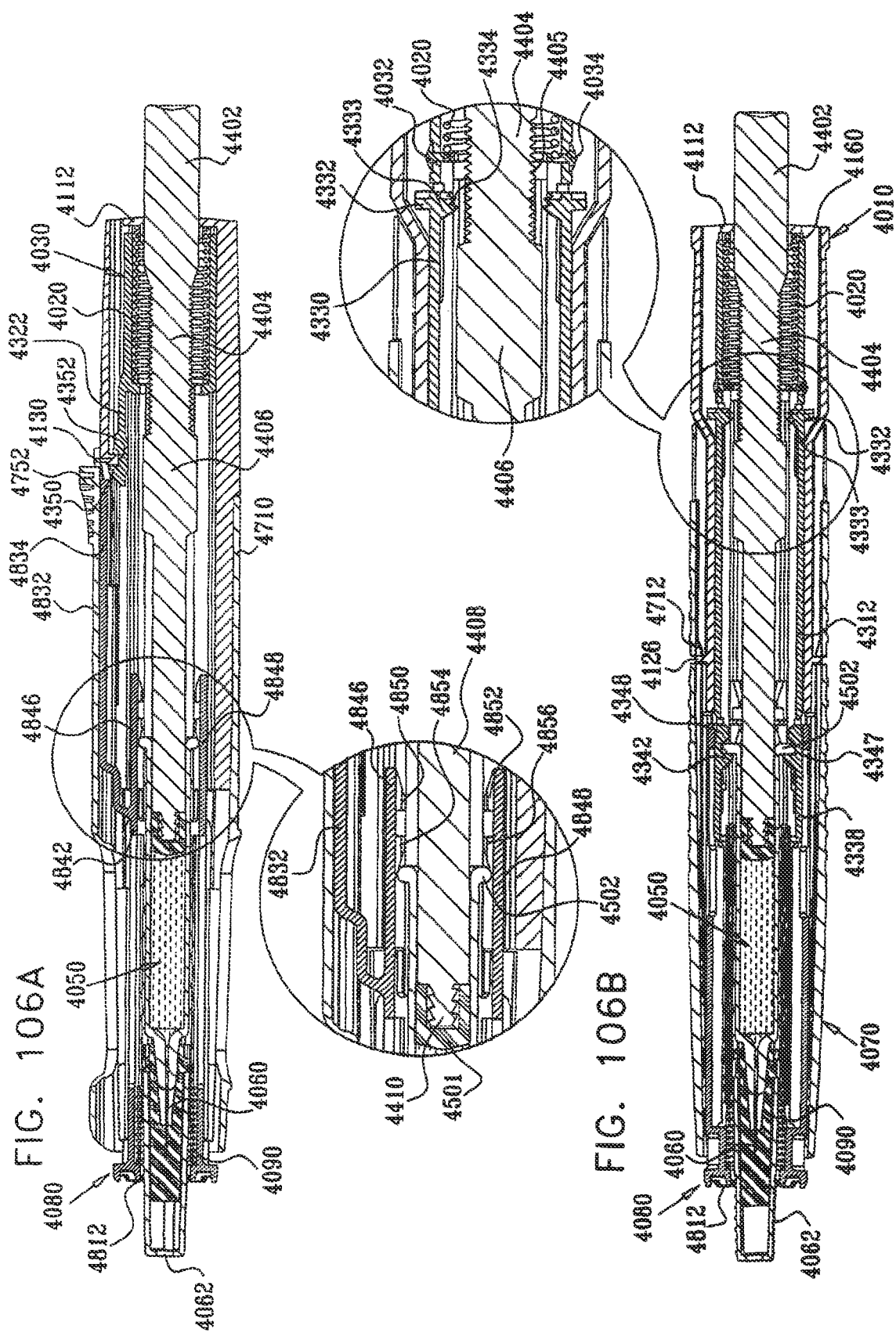

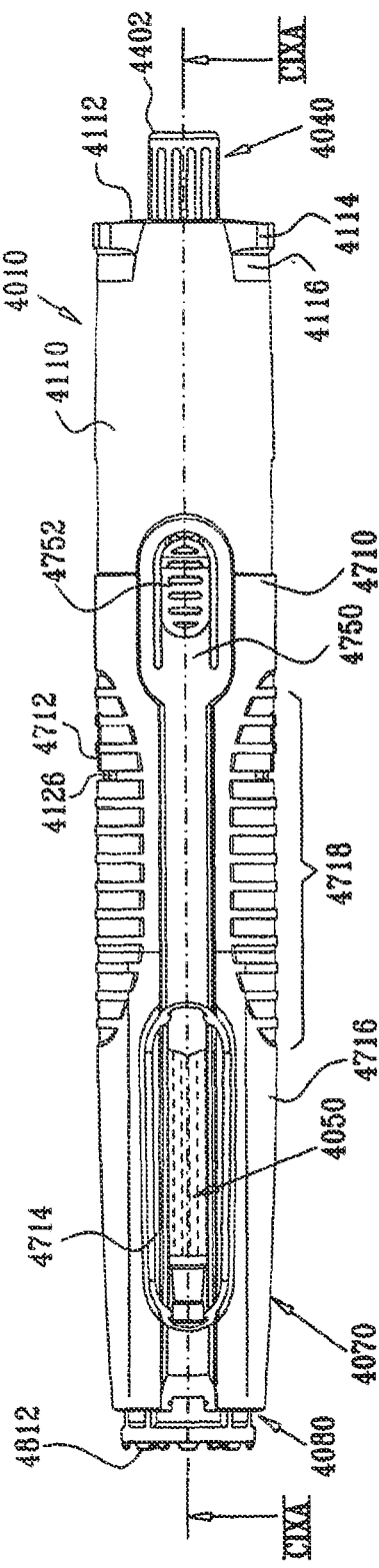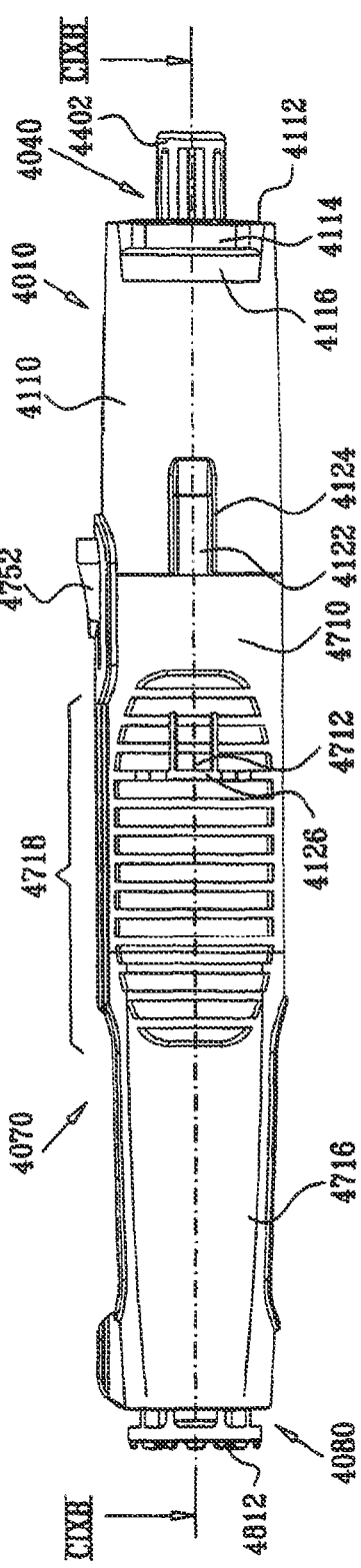
FIG. 108A
FIG. 108B

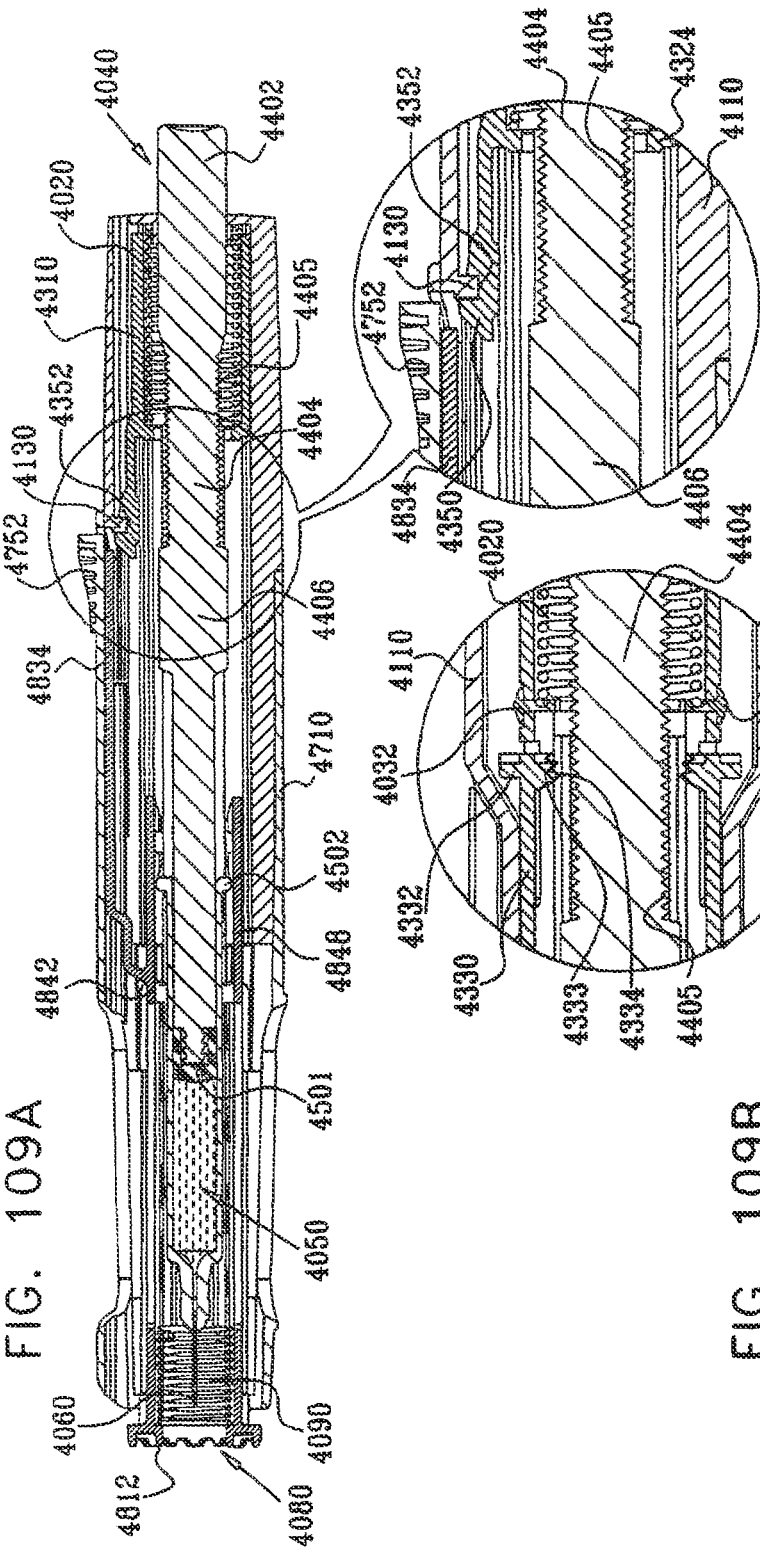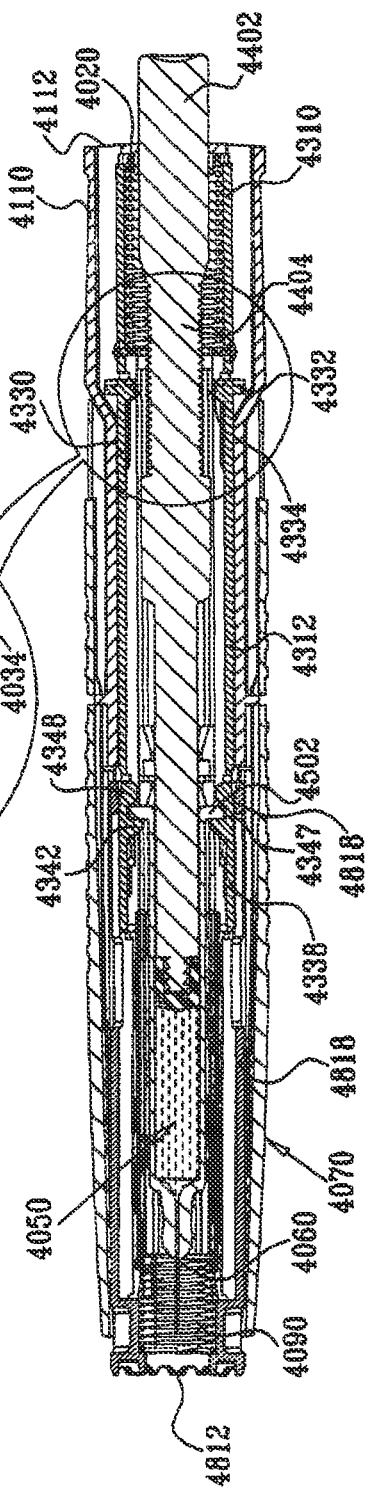
FIG. 109A
FIG. 109B

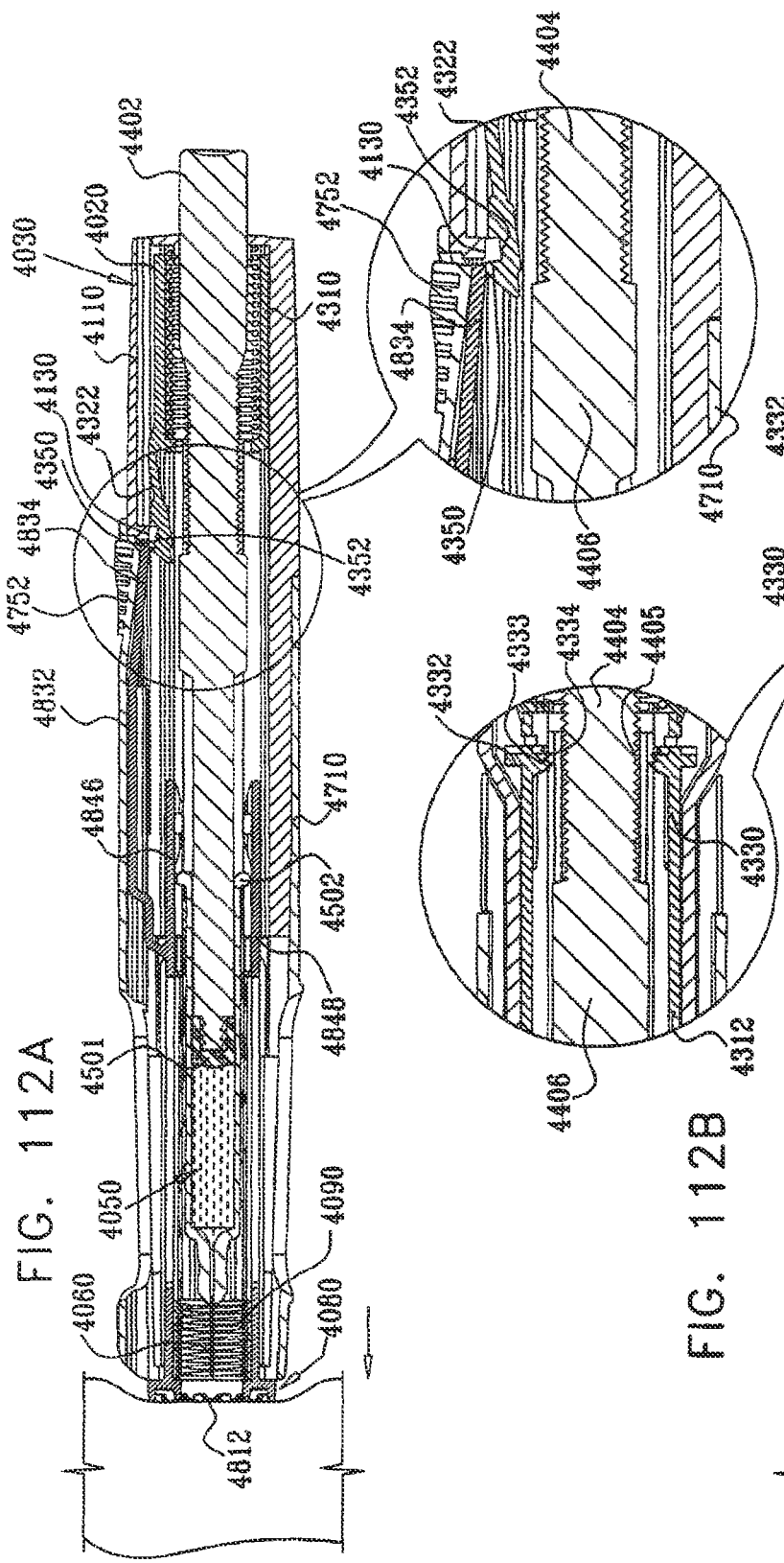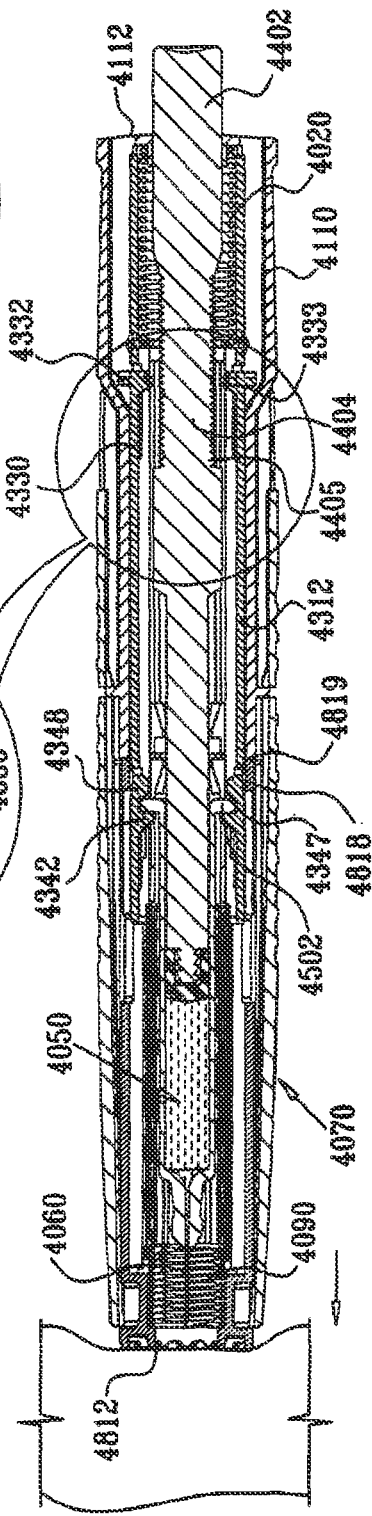

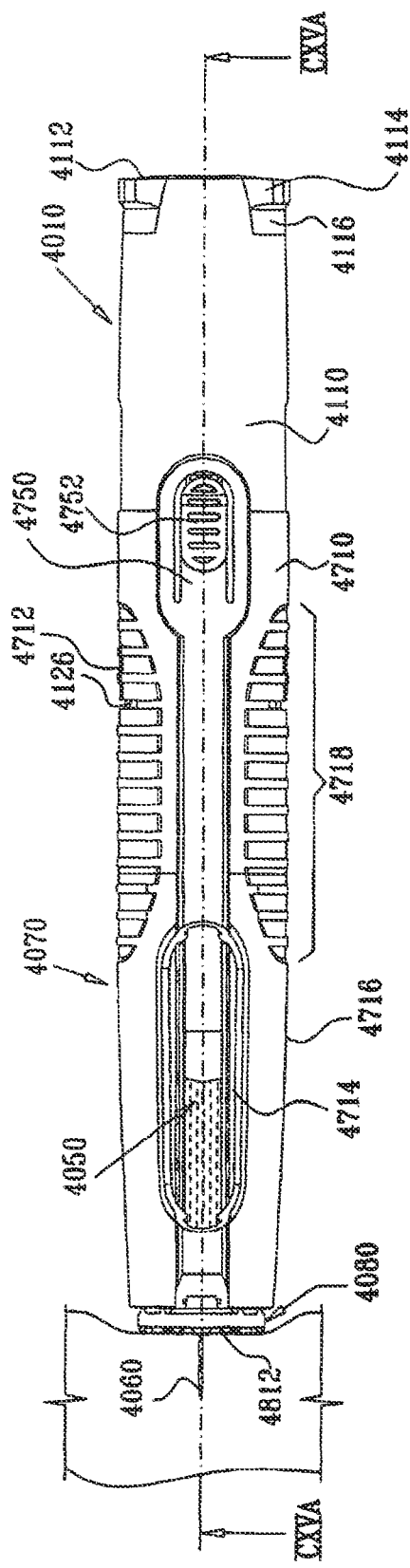
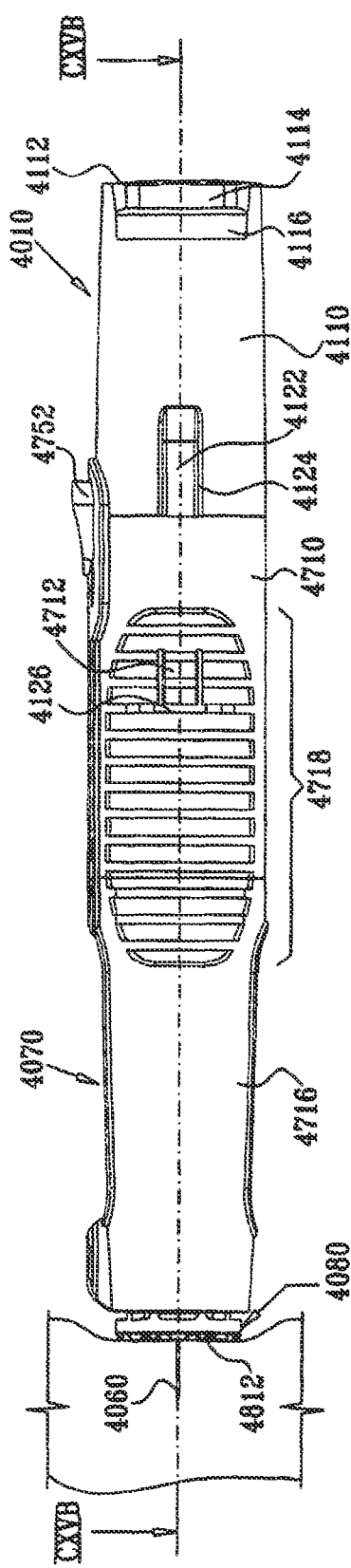
FIG. 114A
FIG. 114B

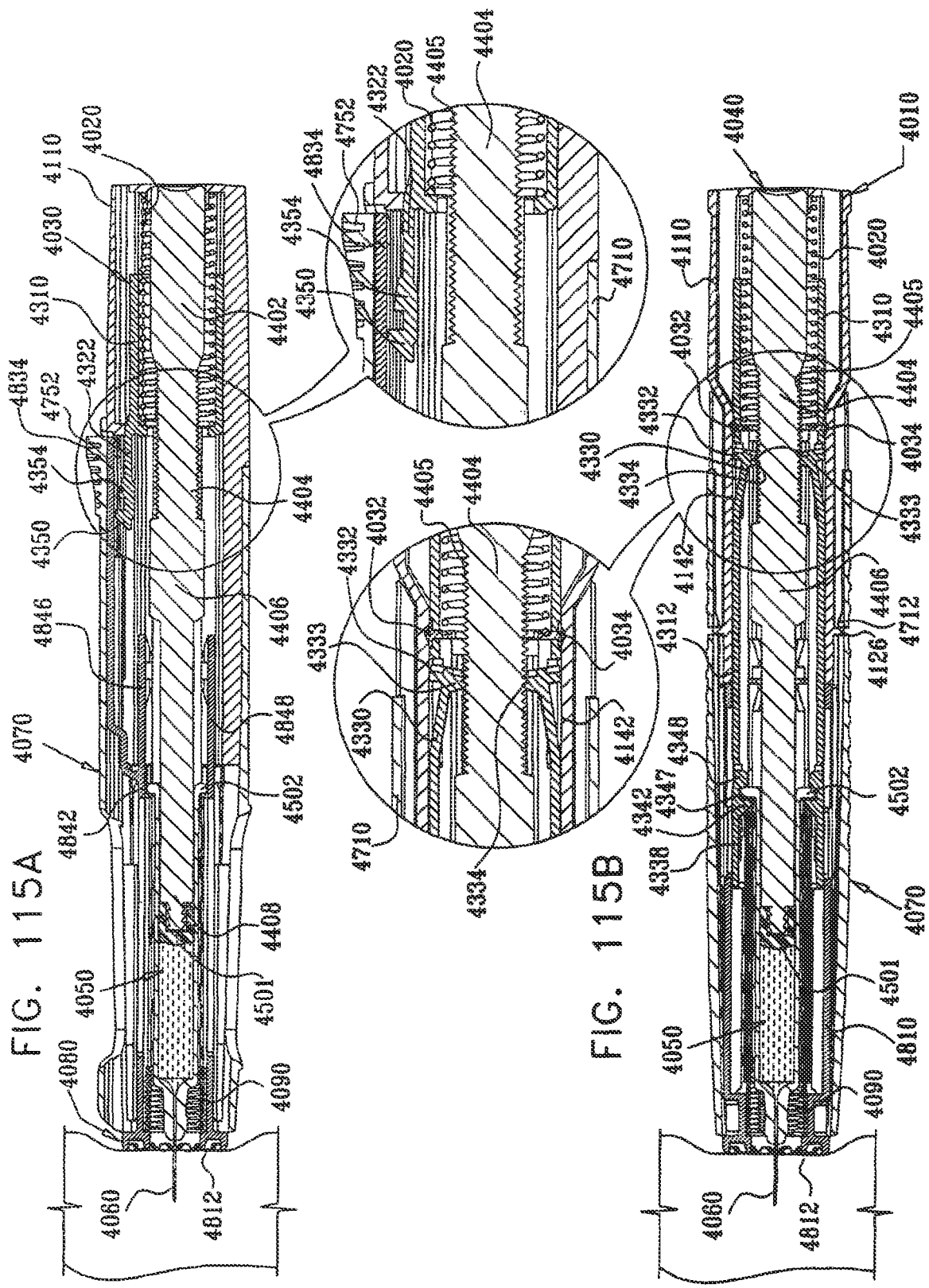

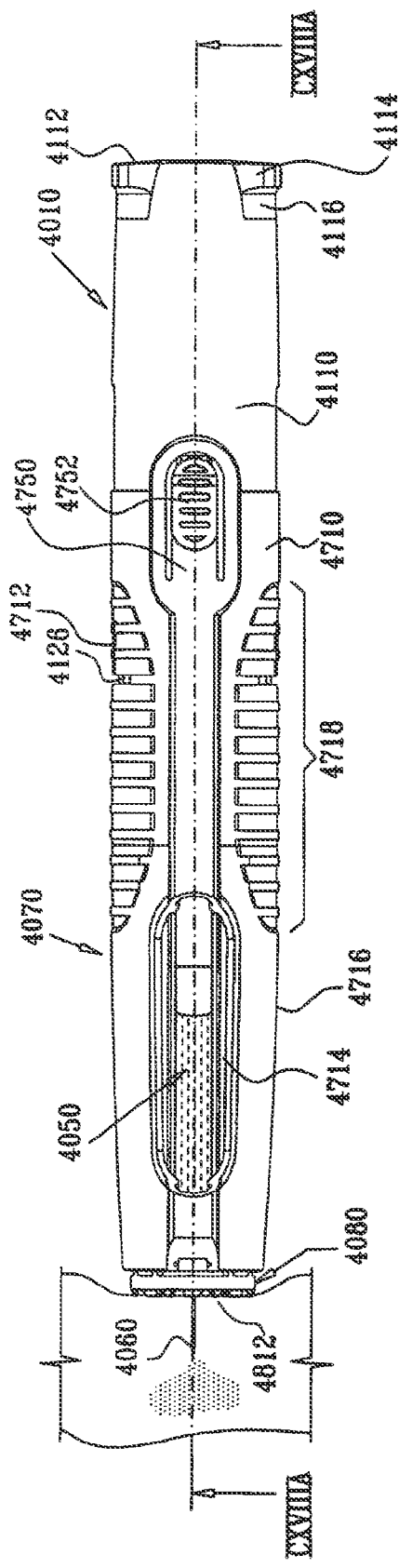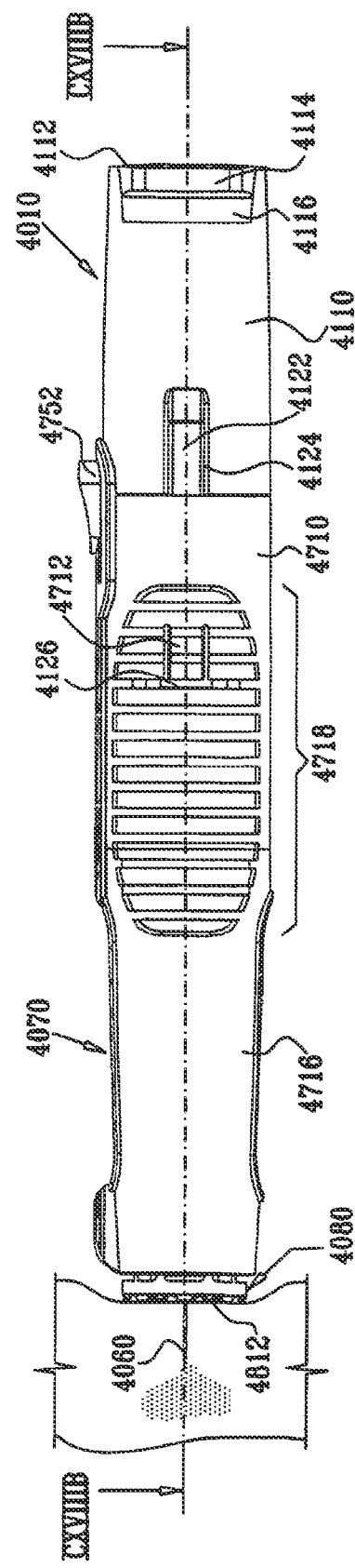

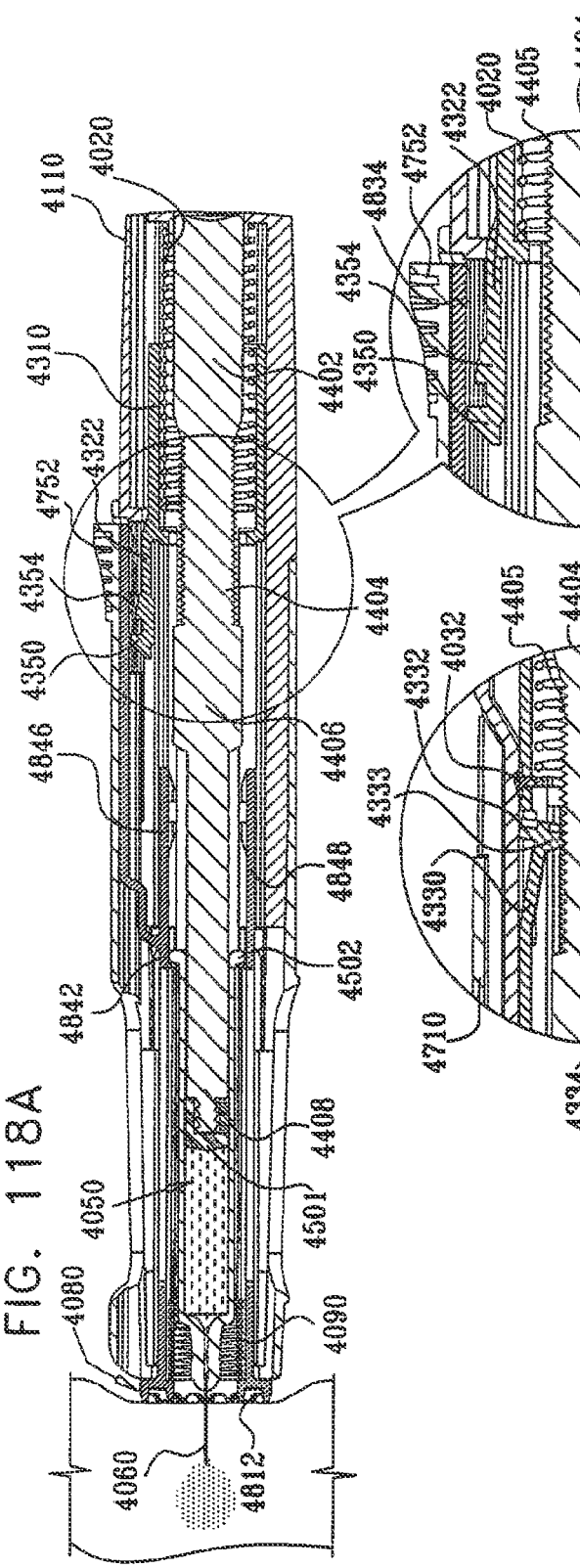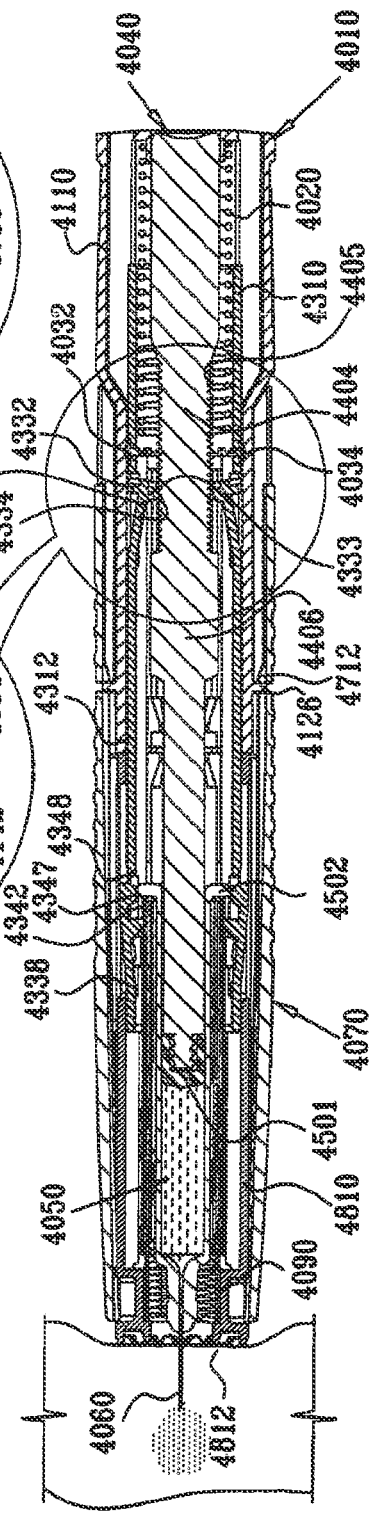
FIG. 118A
FIG. 118B

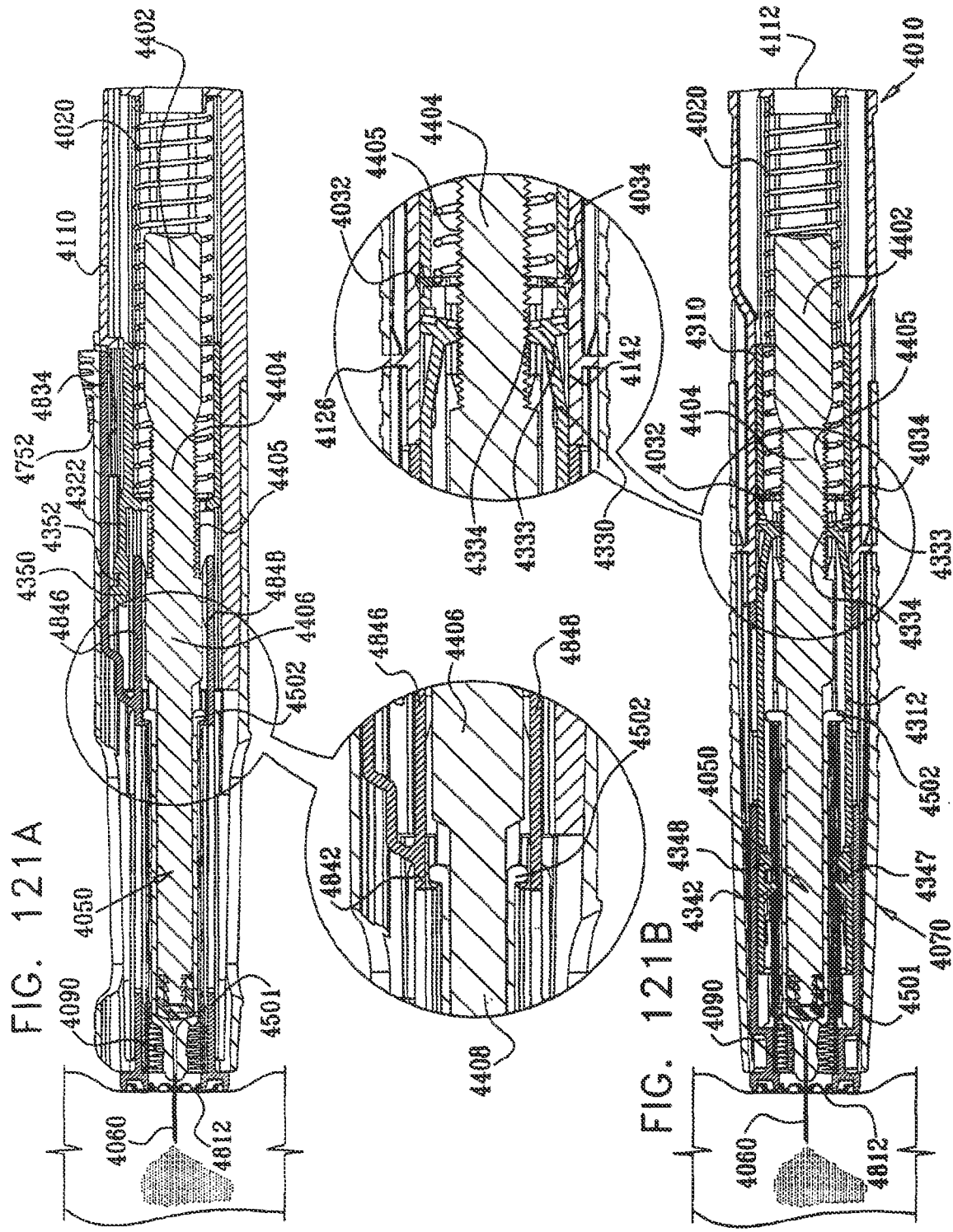

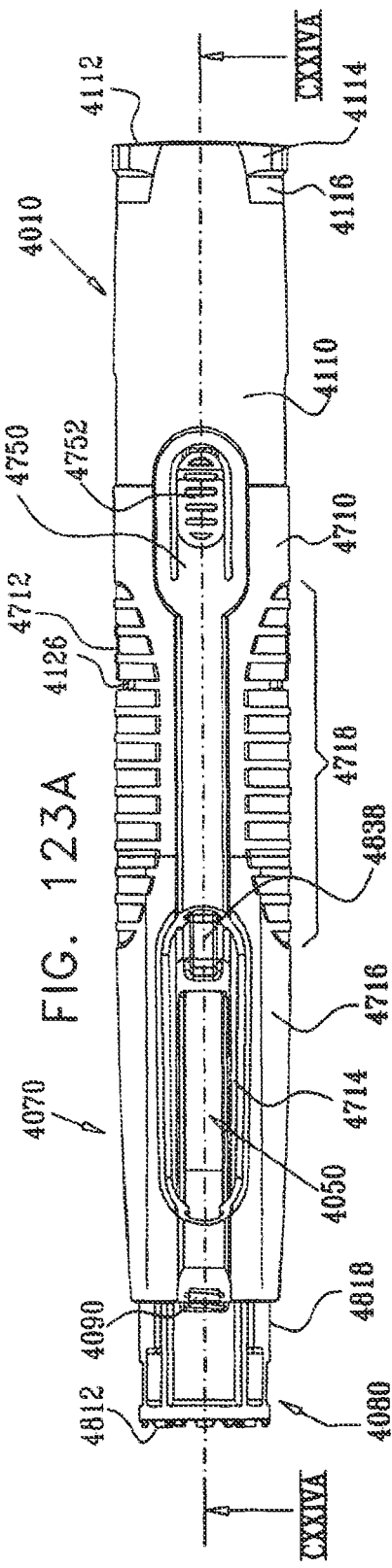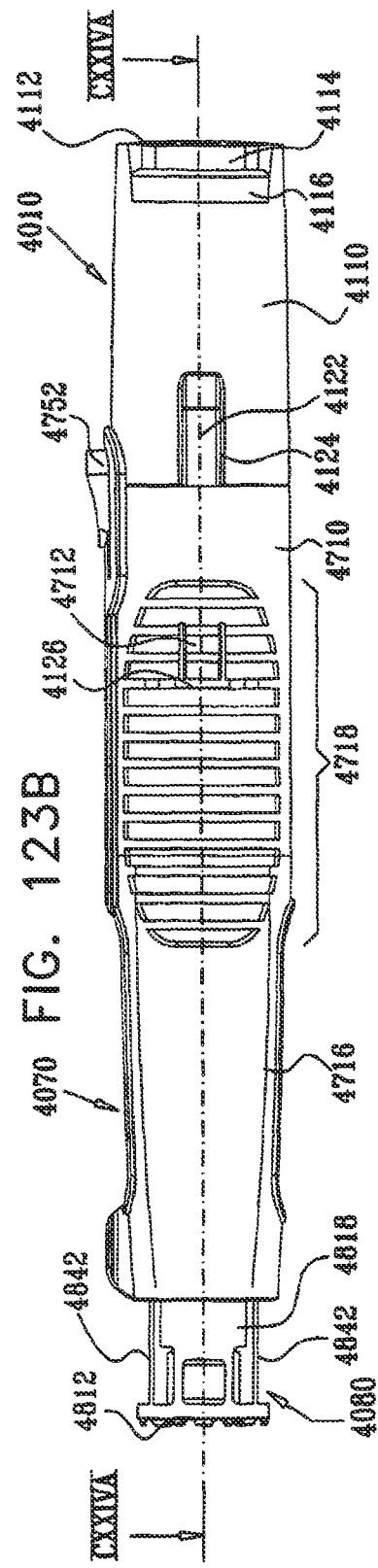

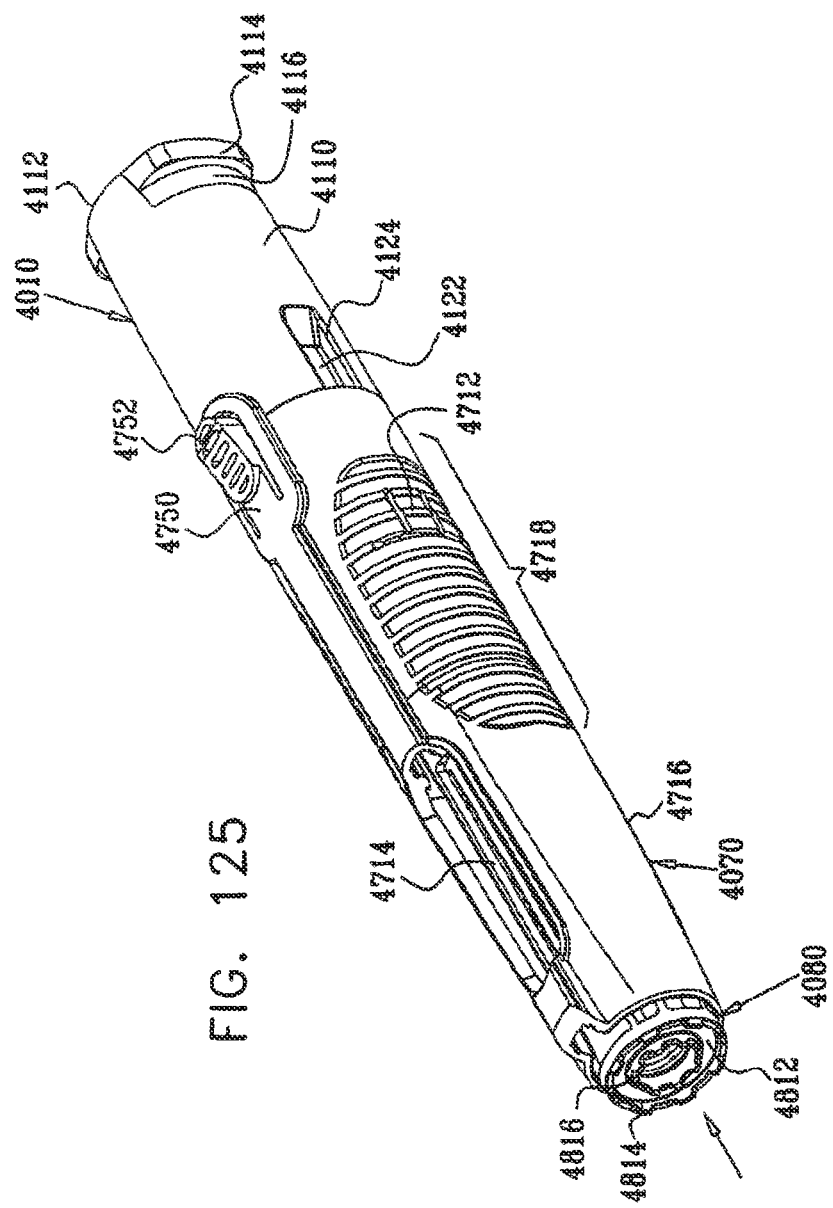

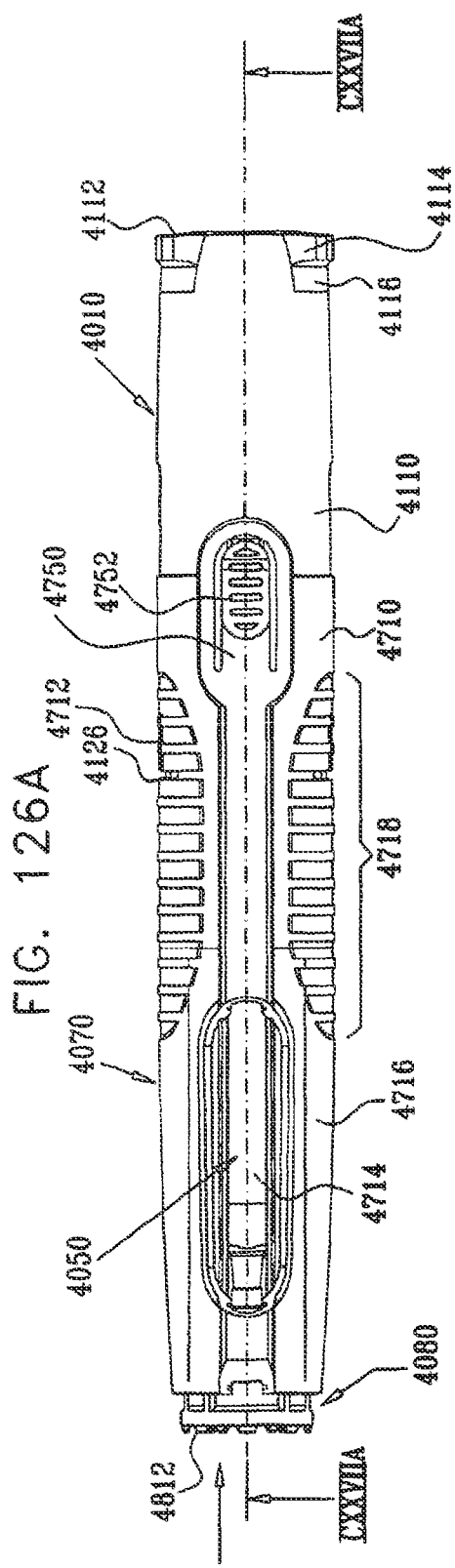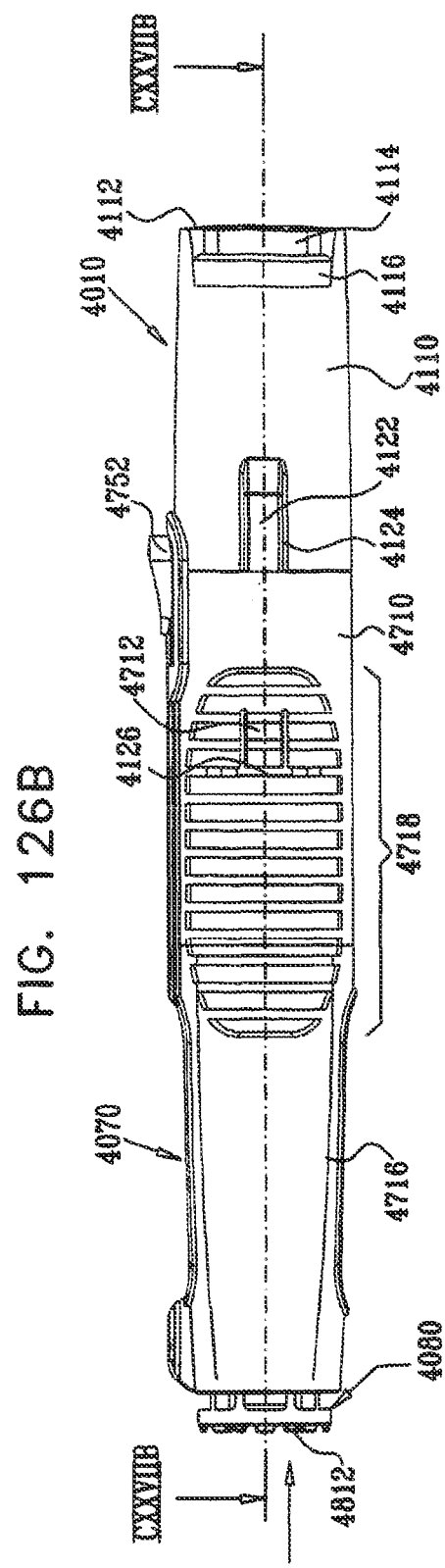

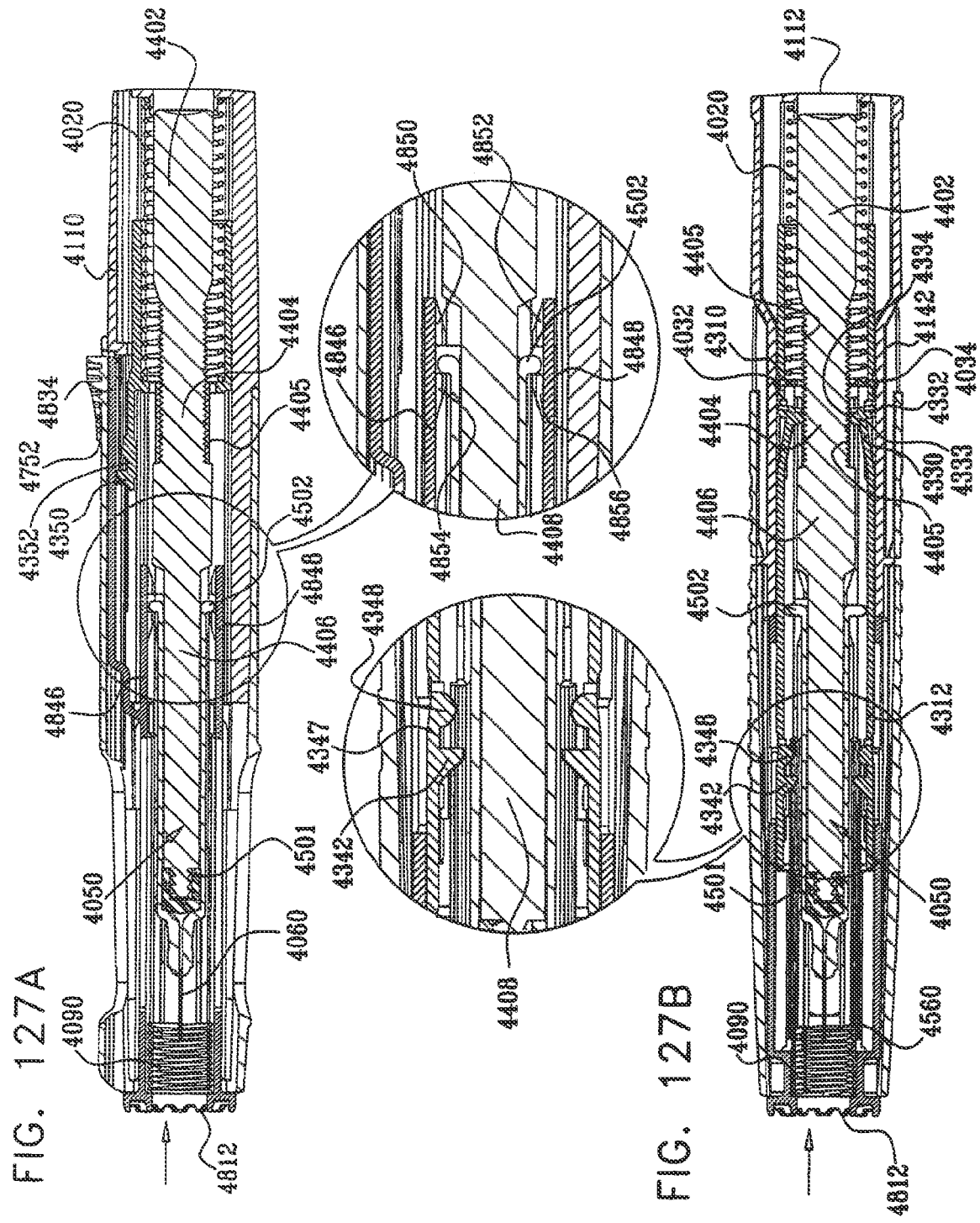

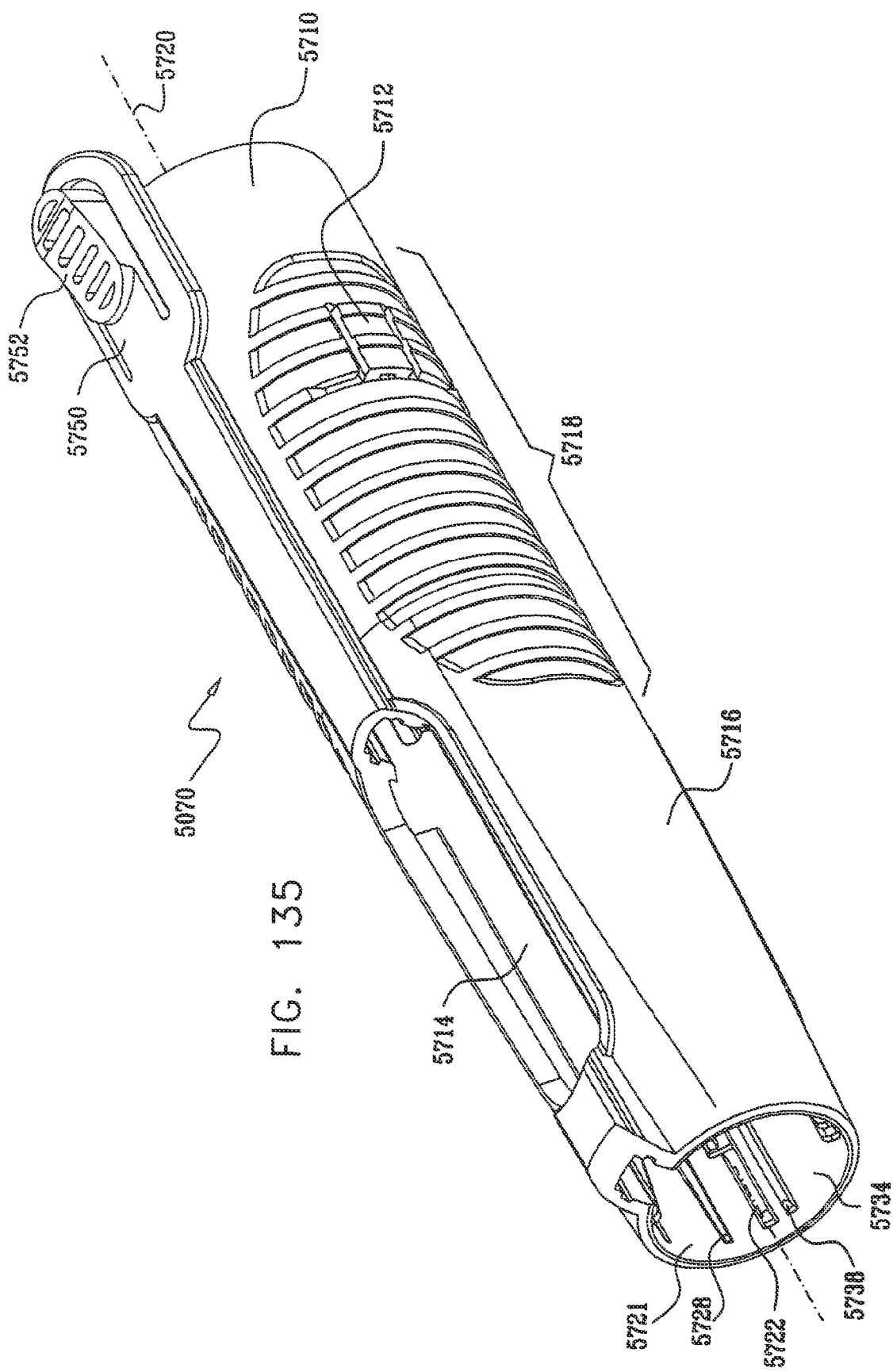

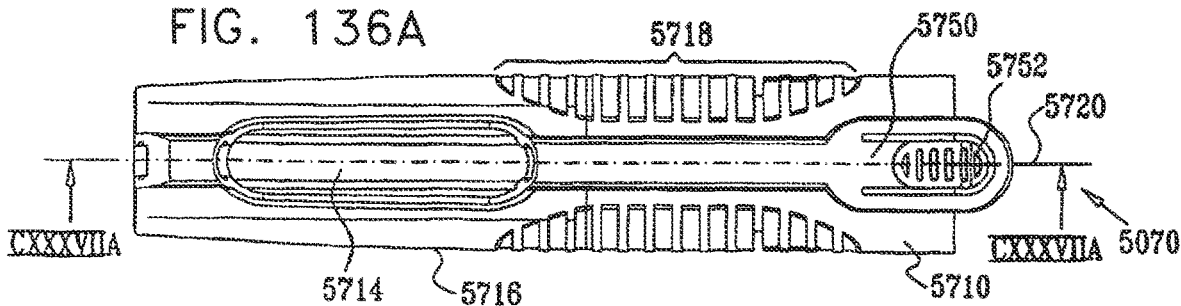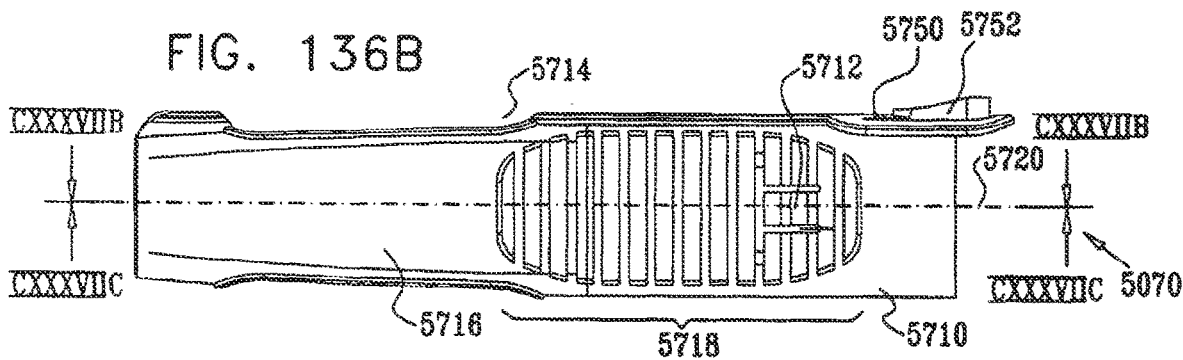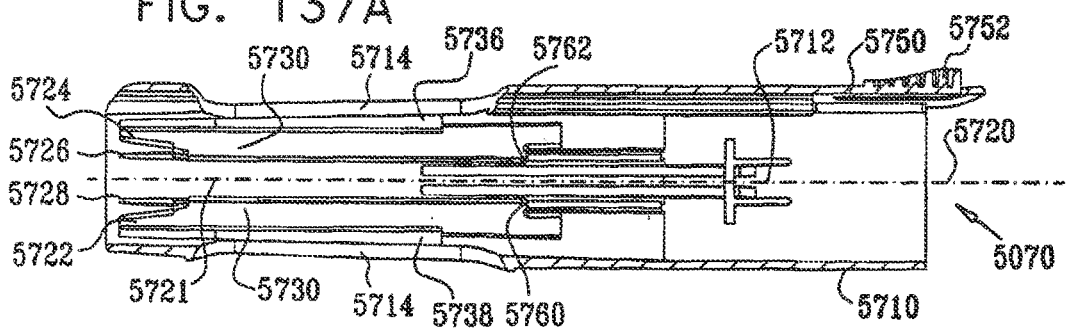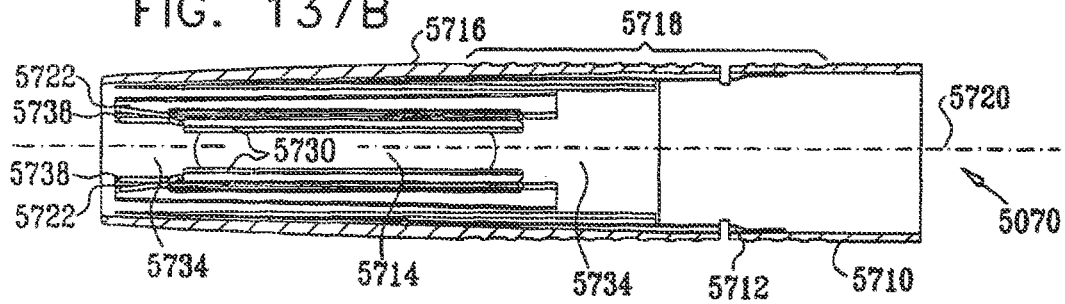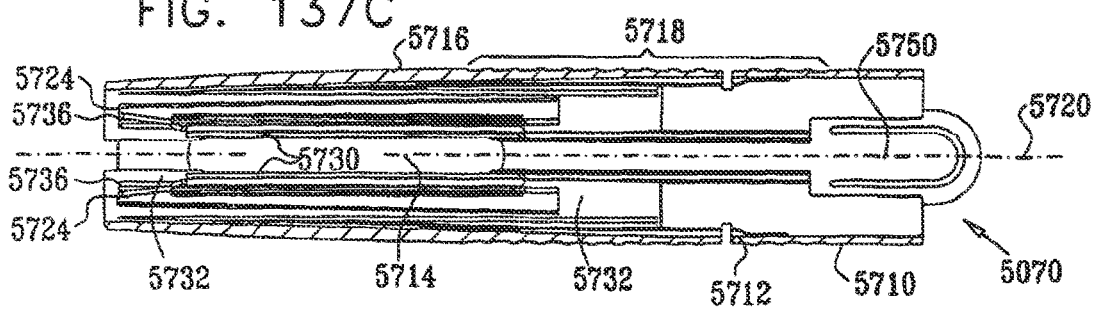

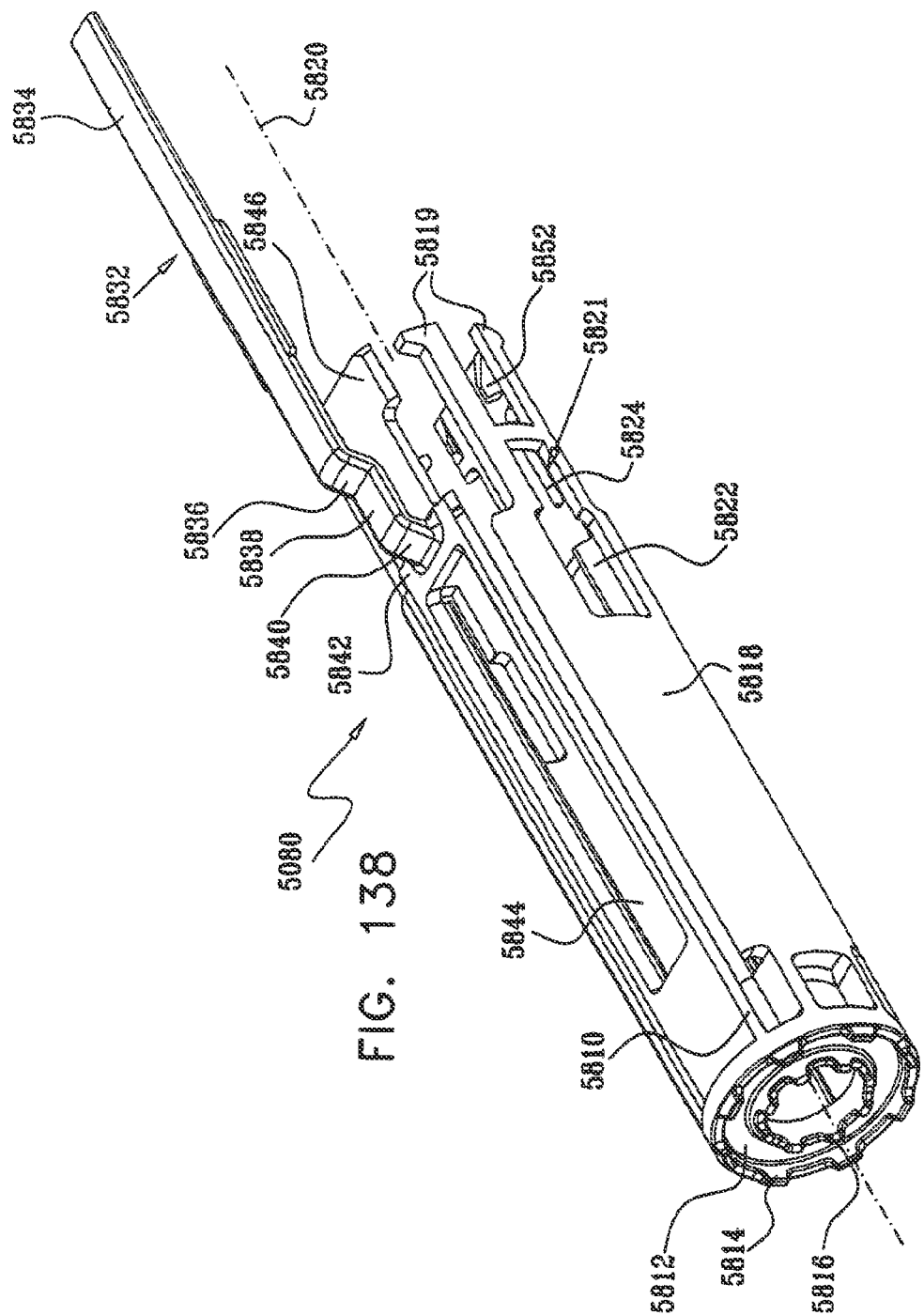

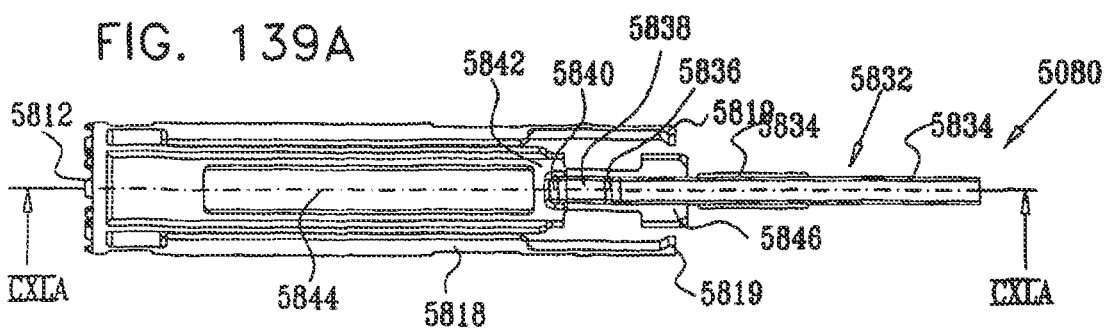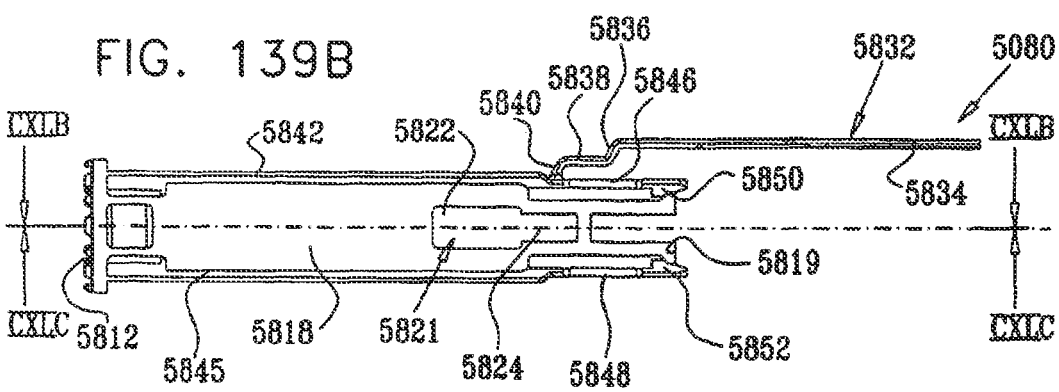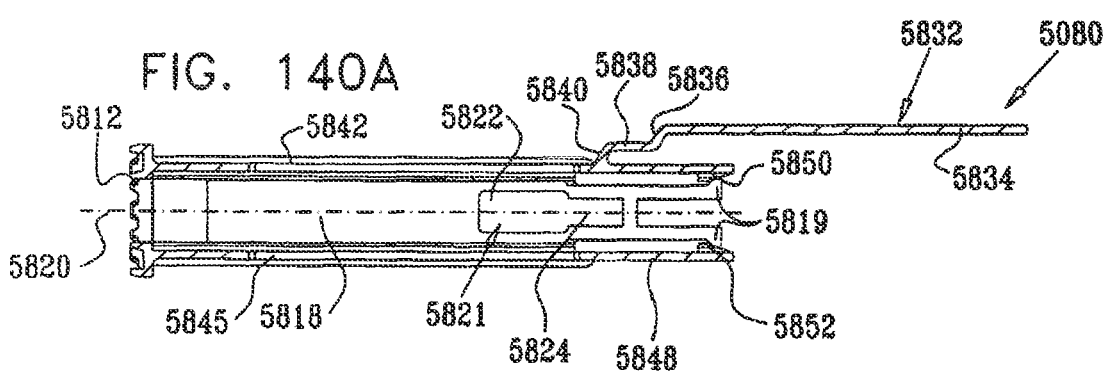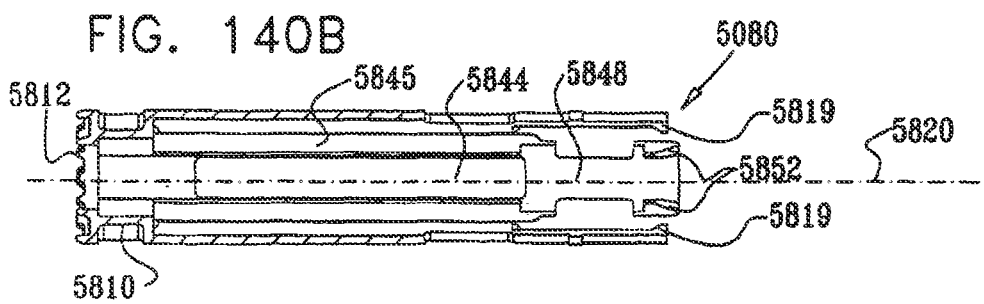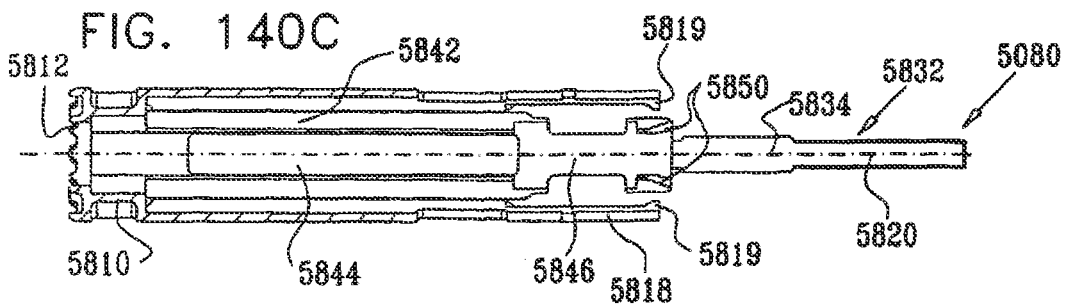

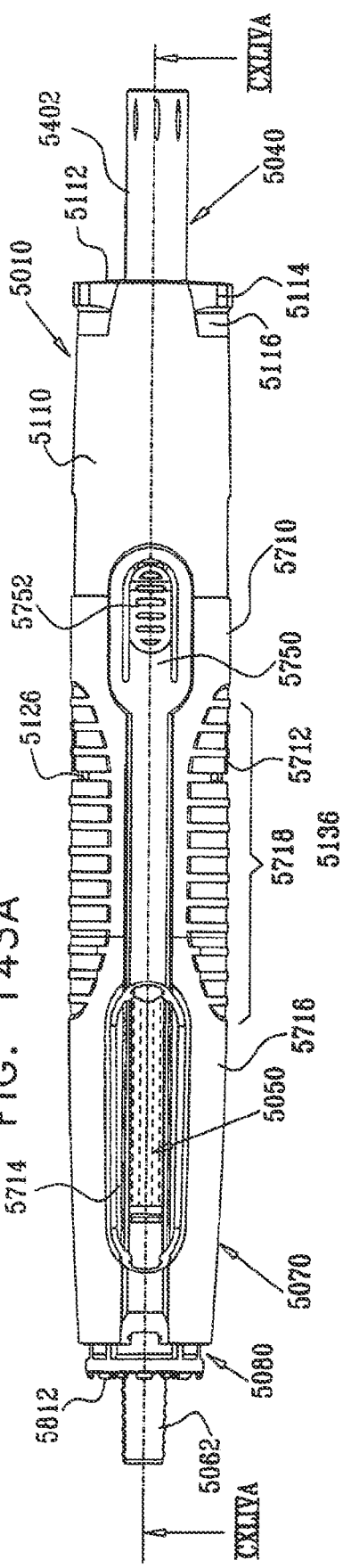
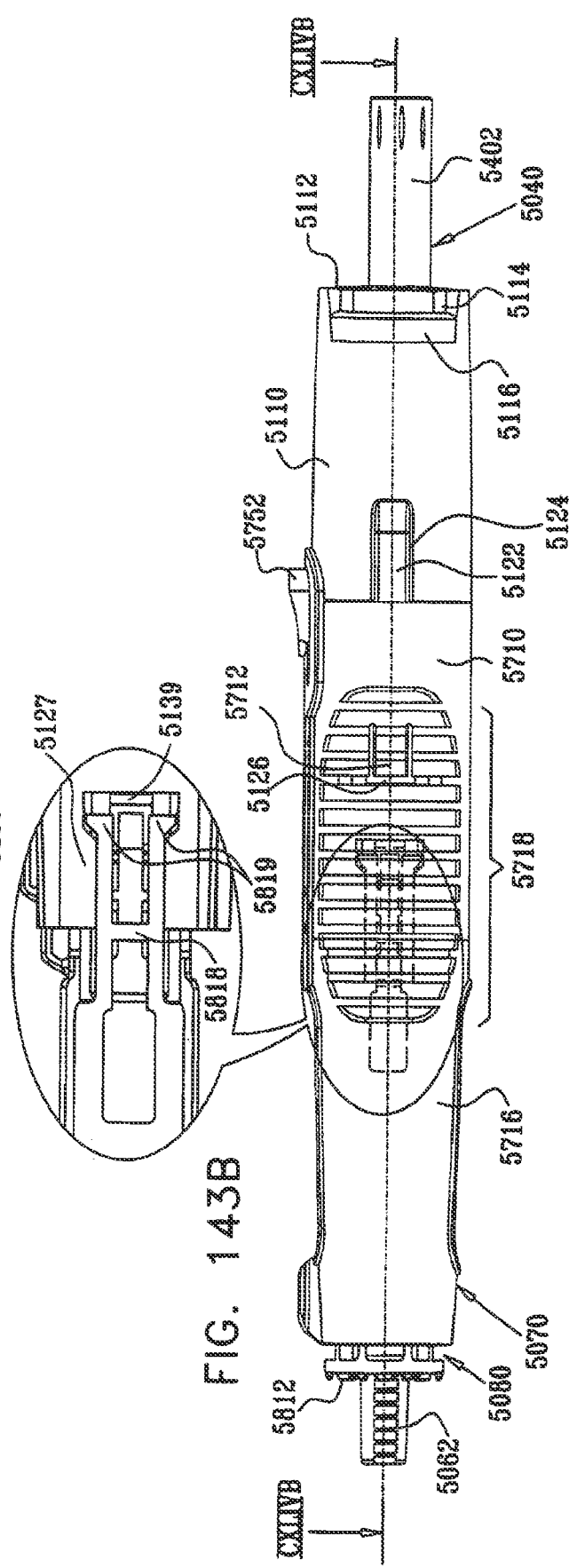
FIG. 143A
FIG. 143B

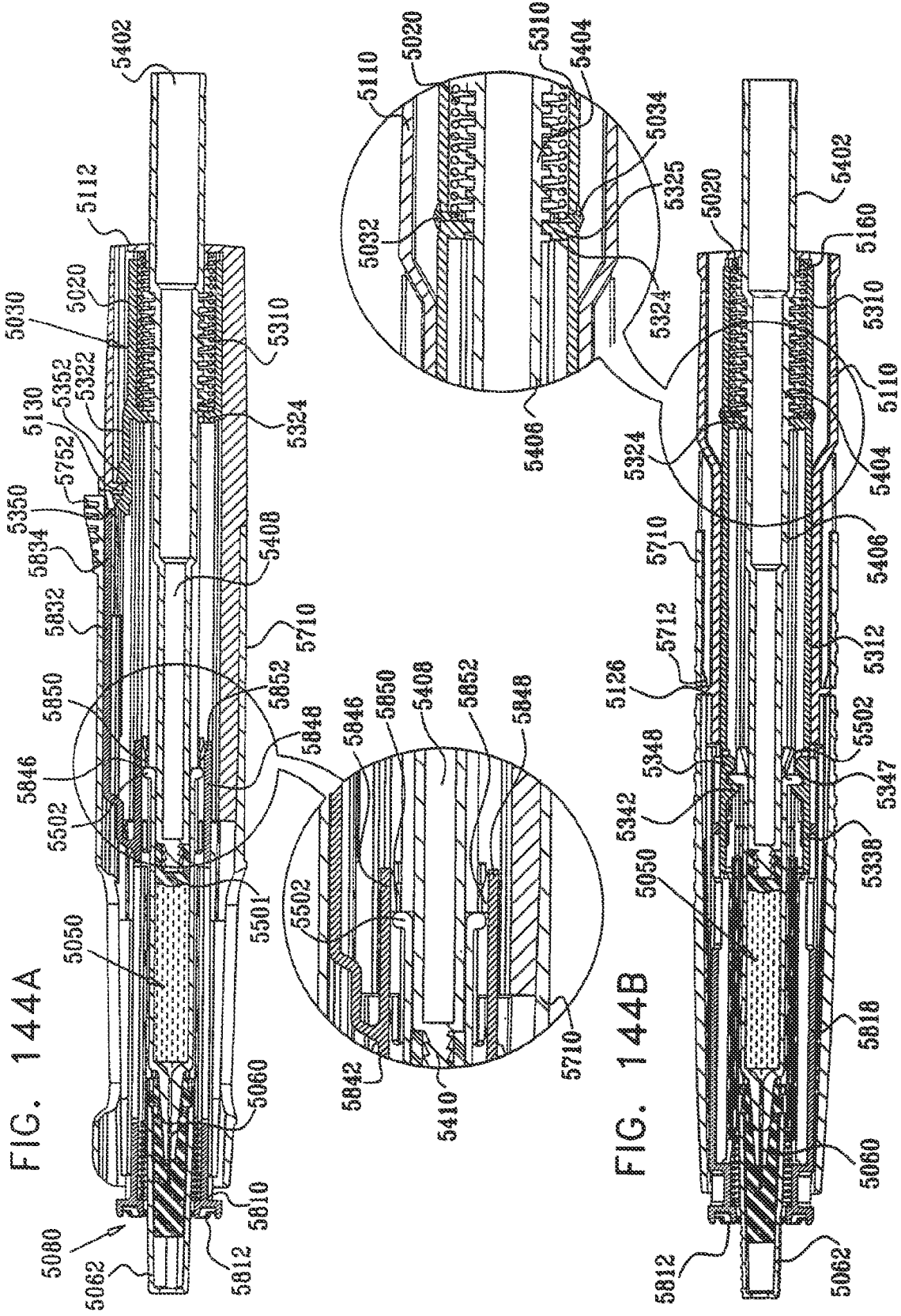

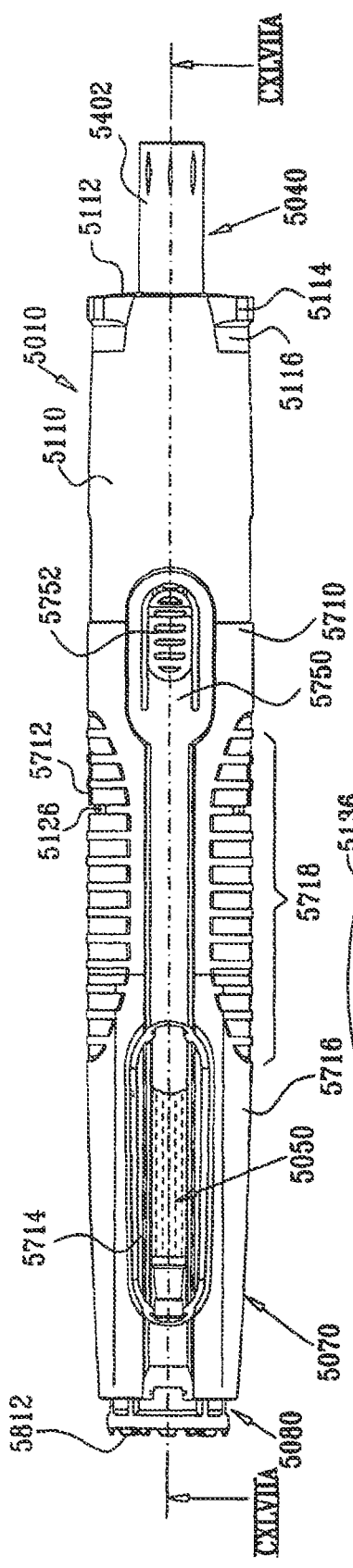
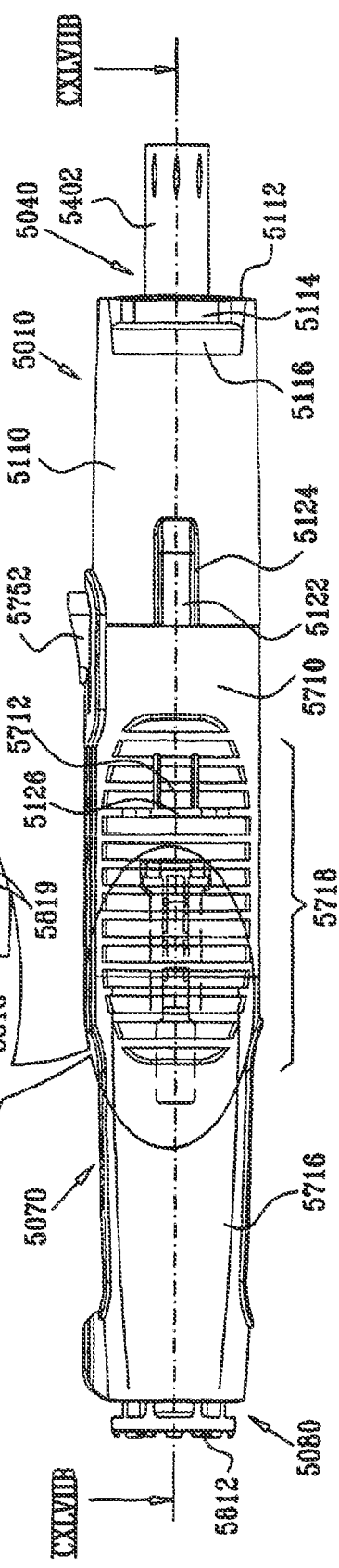
FIG. 146A
FIG. 146B

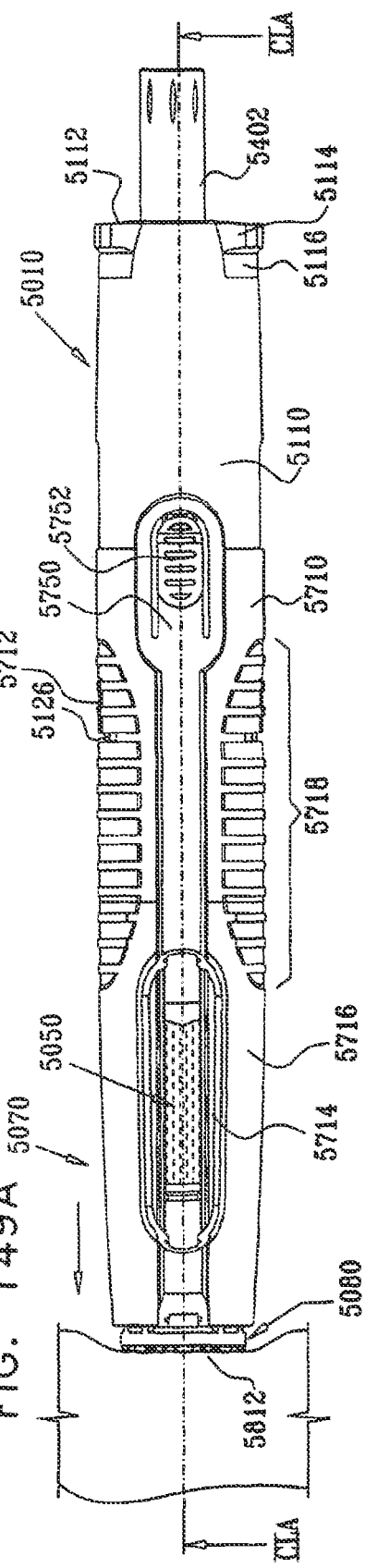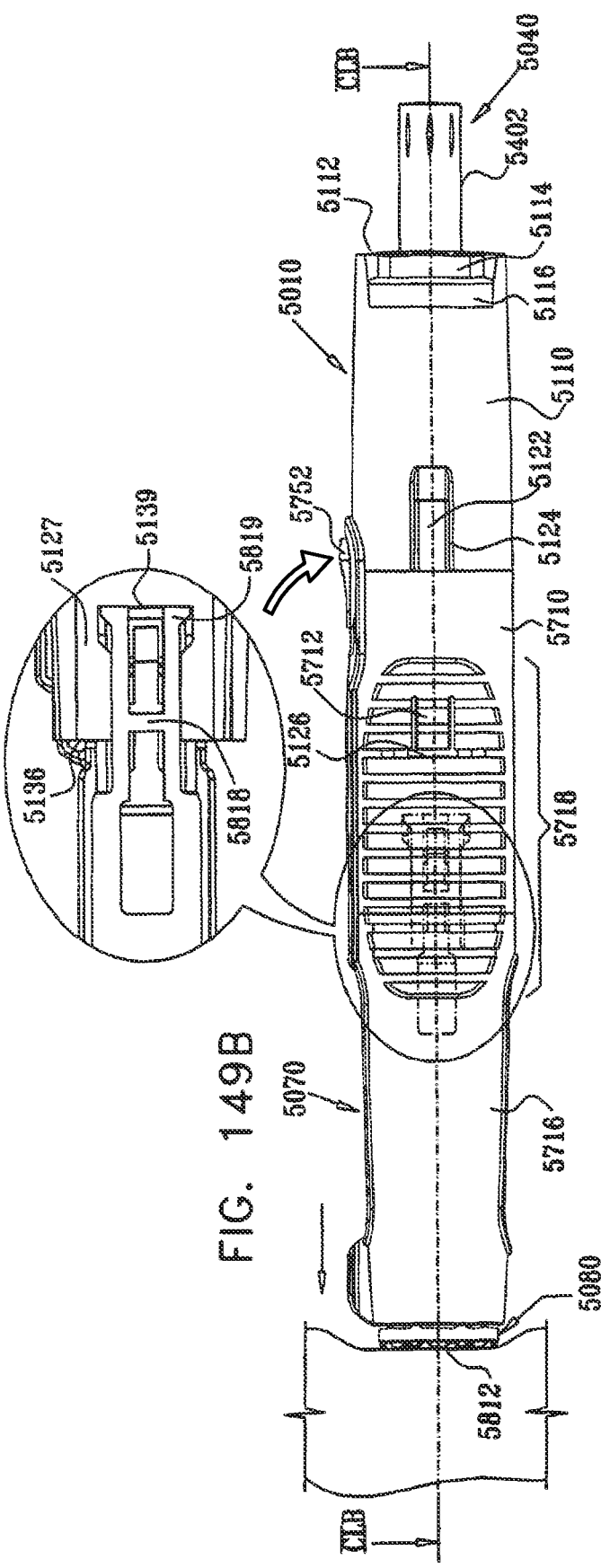

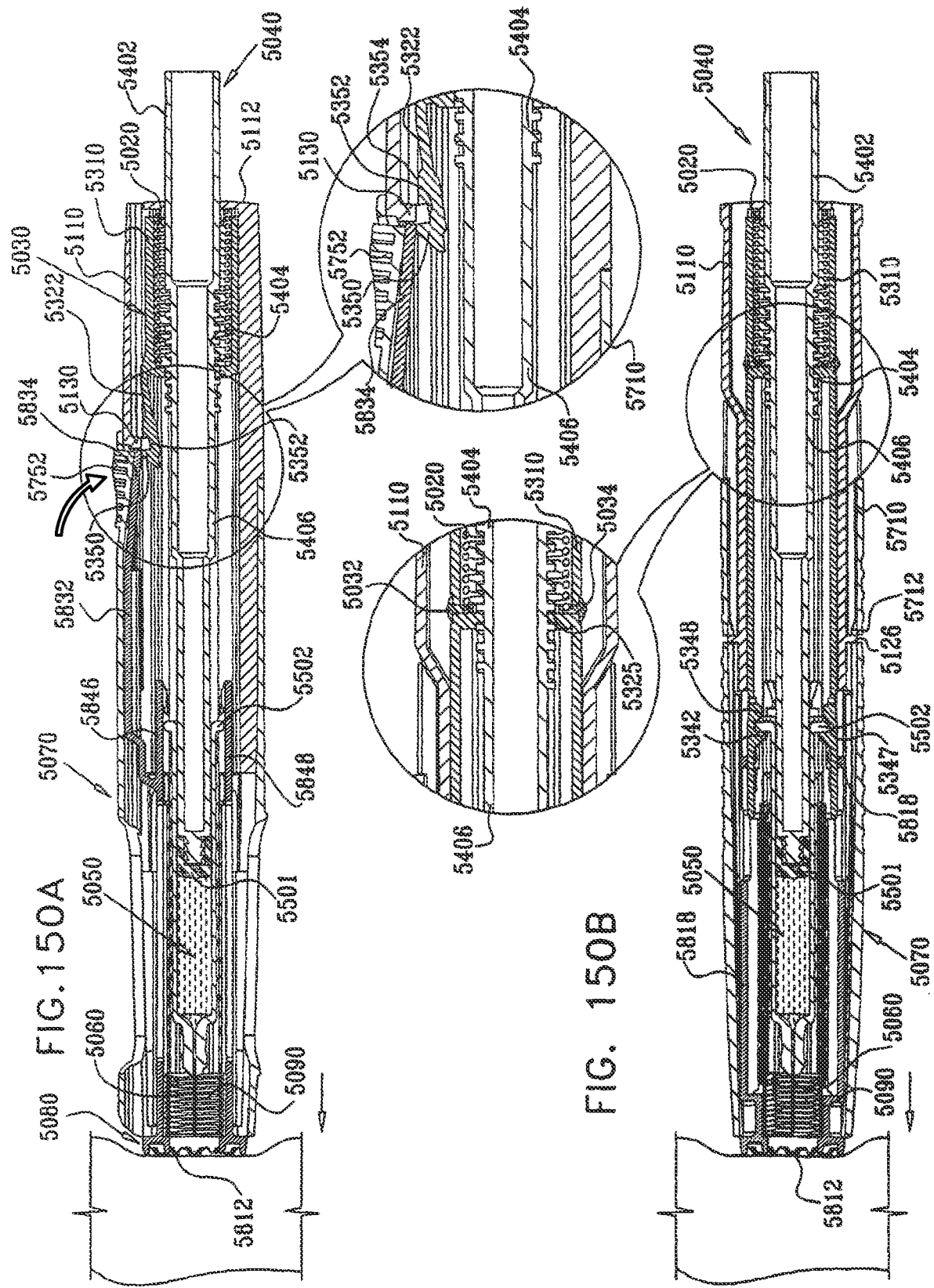

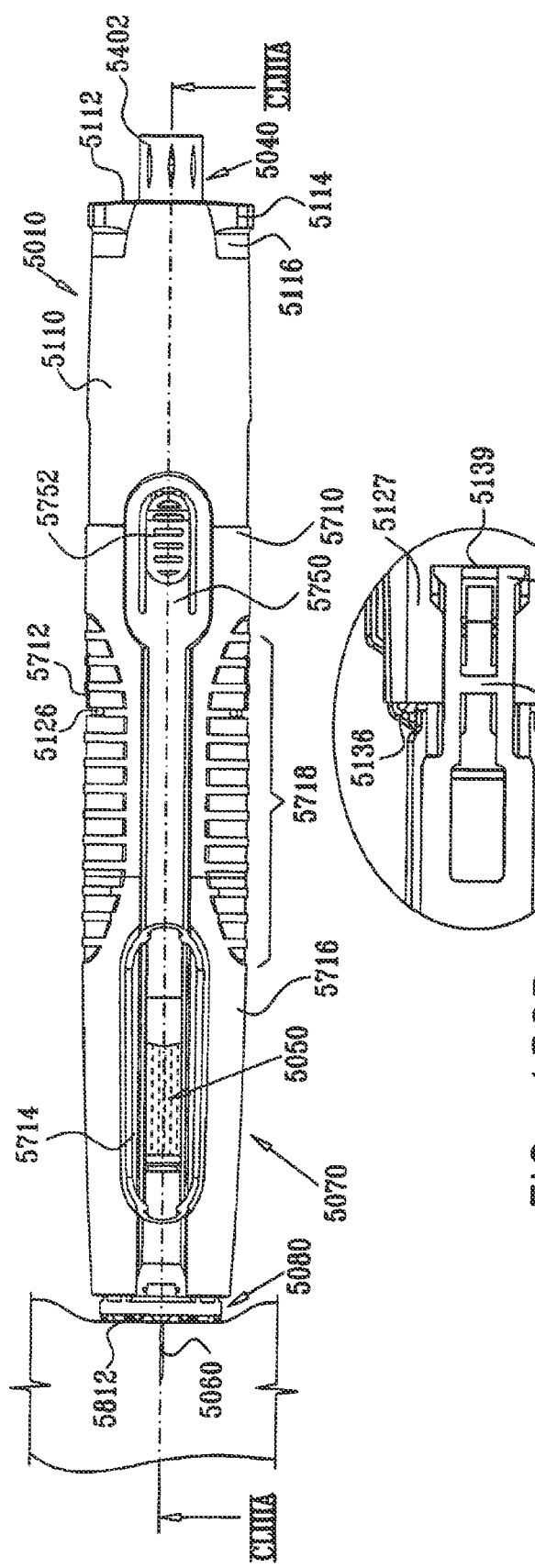
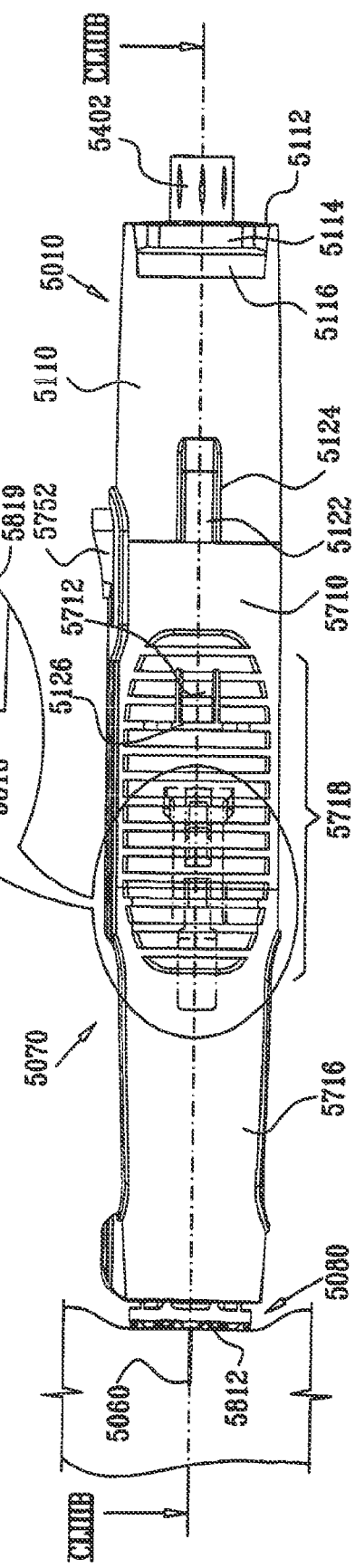
FIG. 152A
FIG. 152B

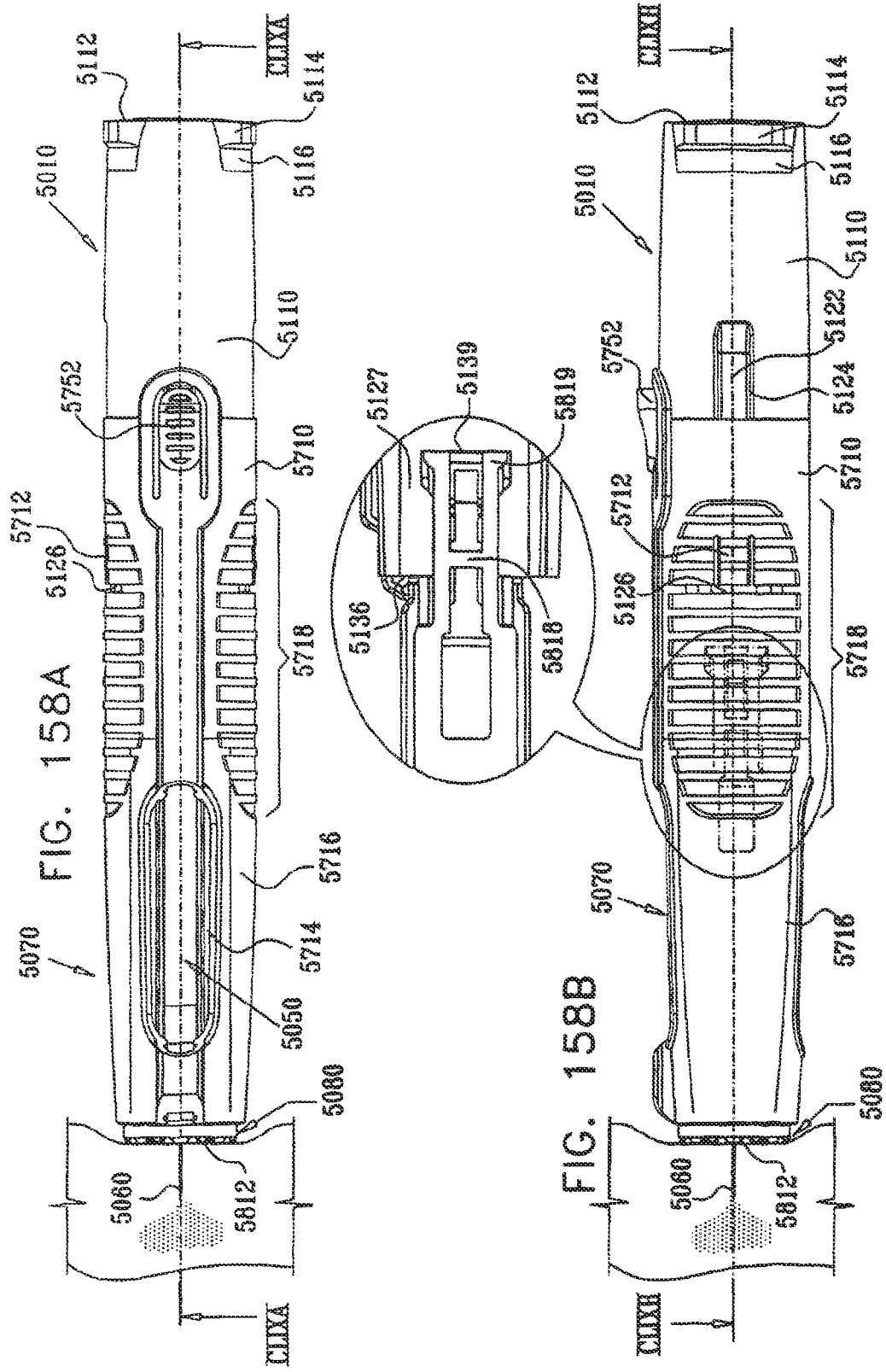

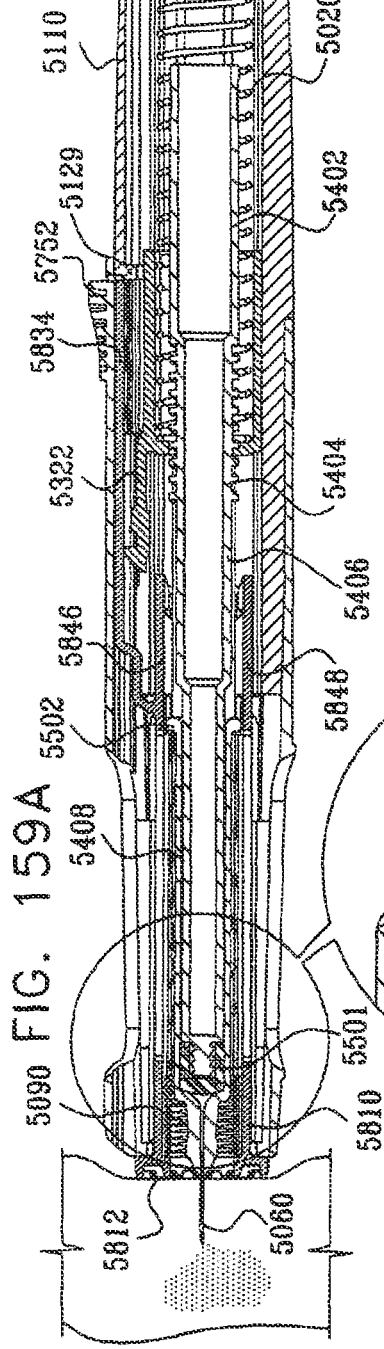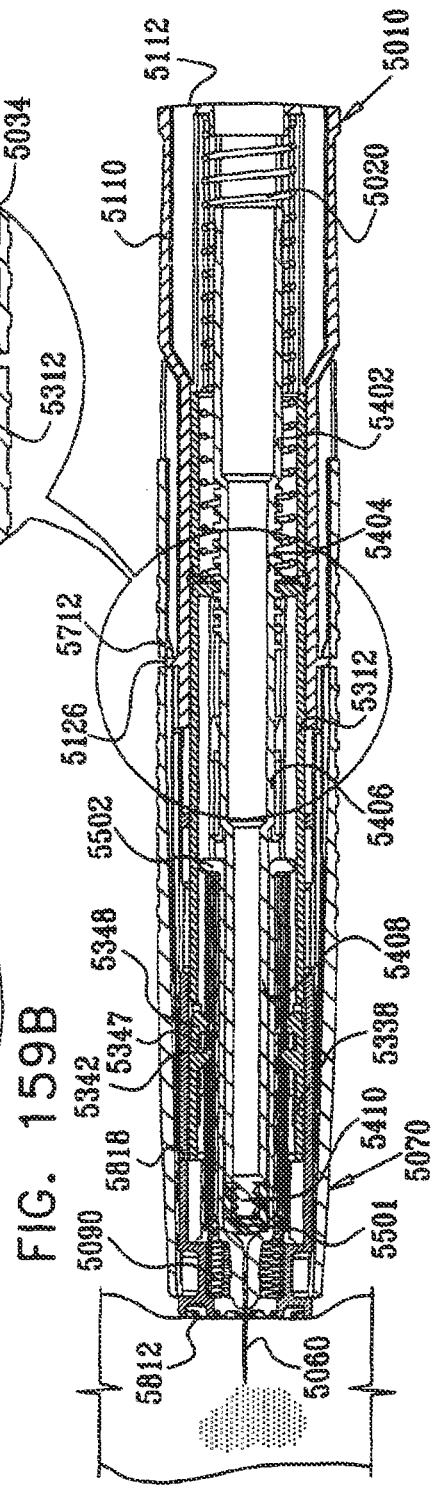

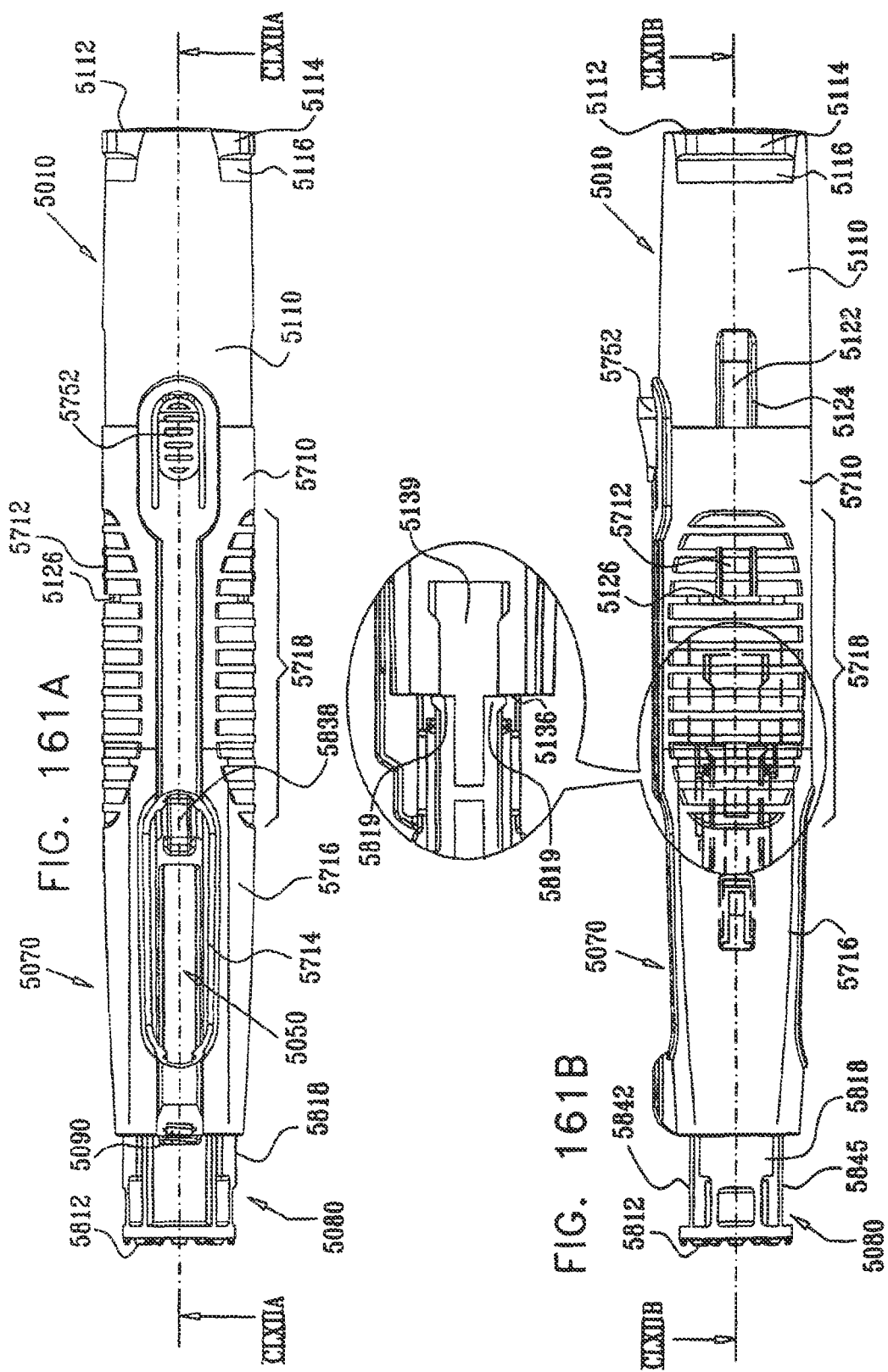

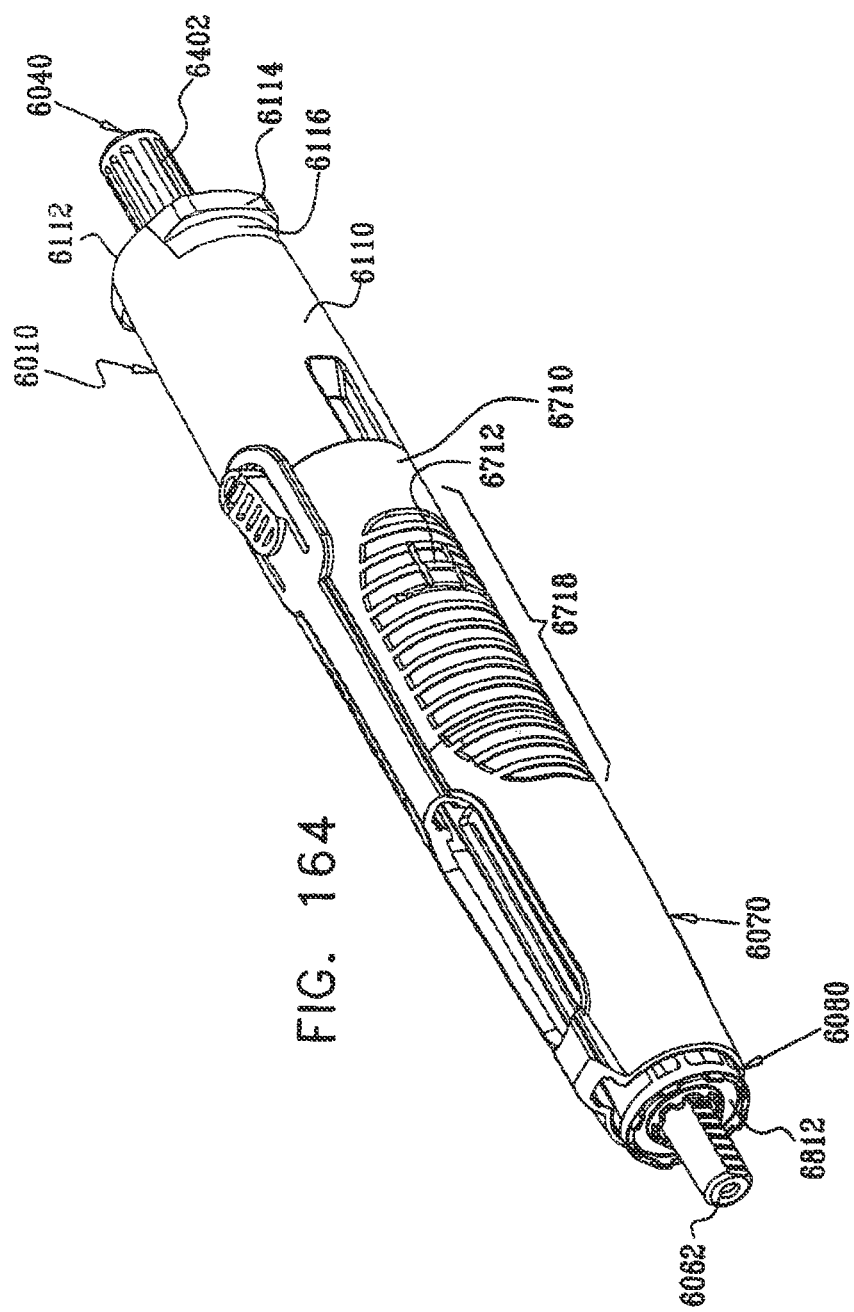

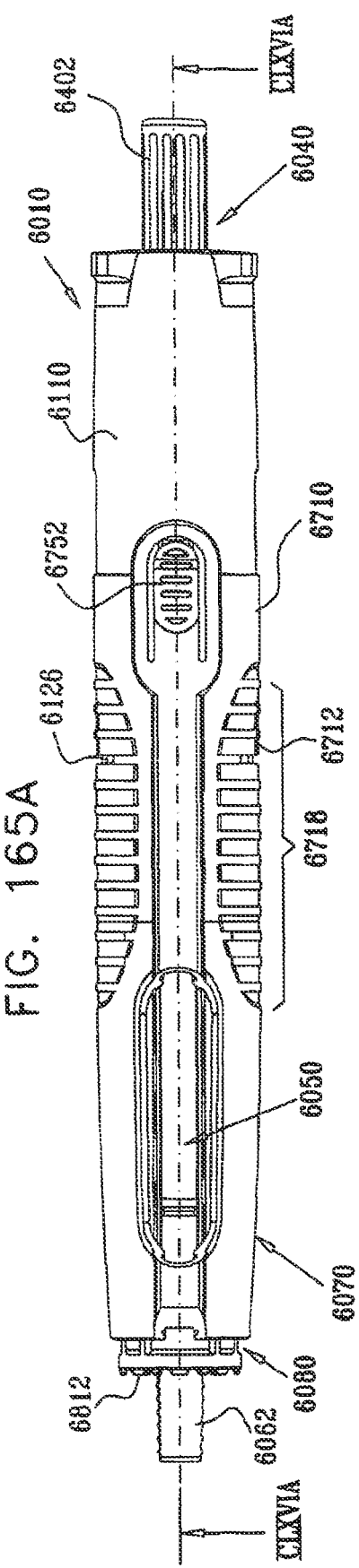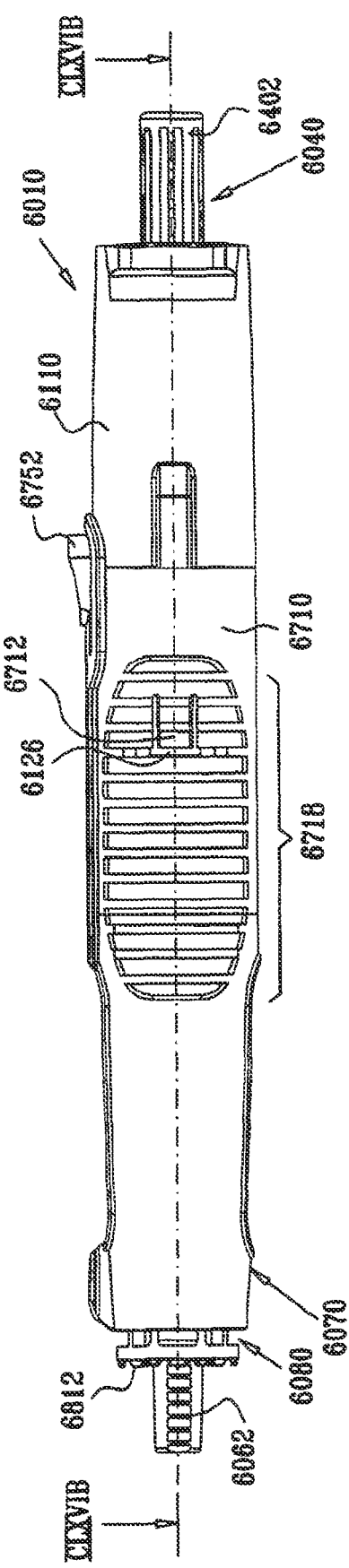
FIG. 165A
FIG. 165B

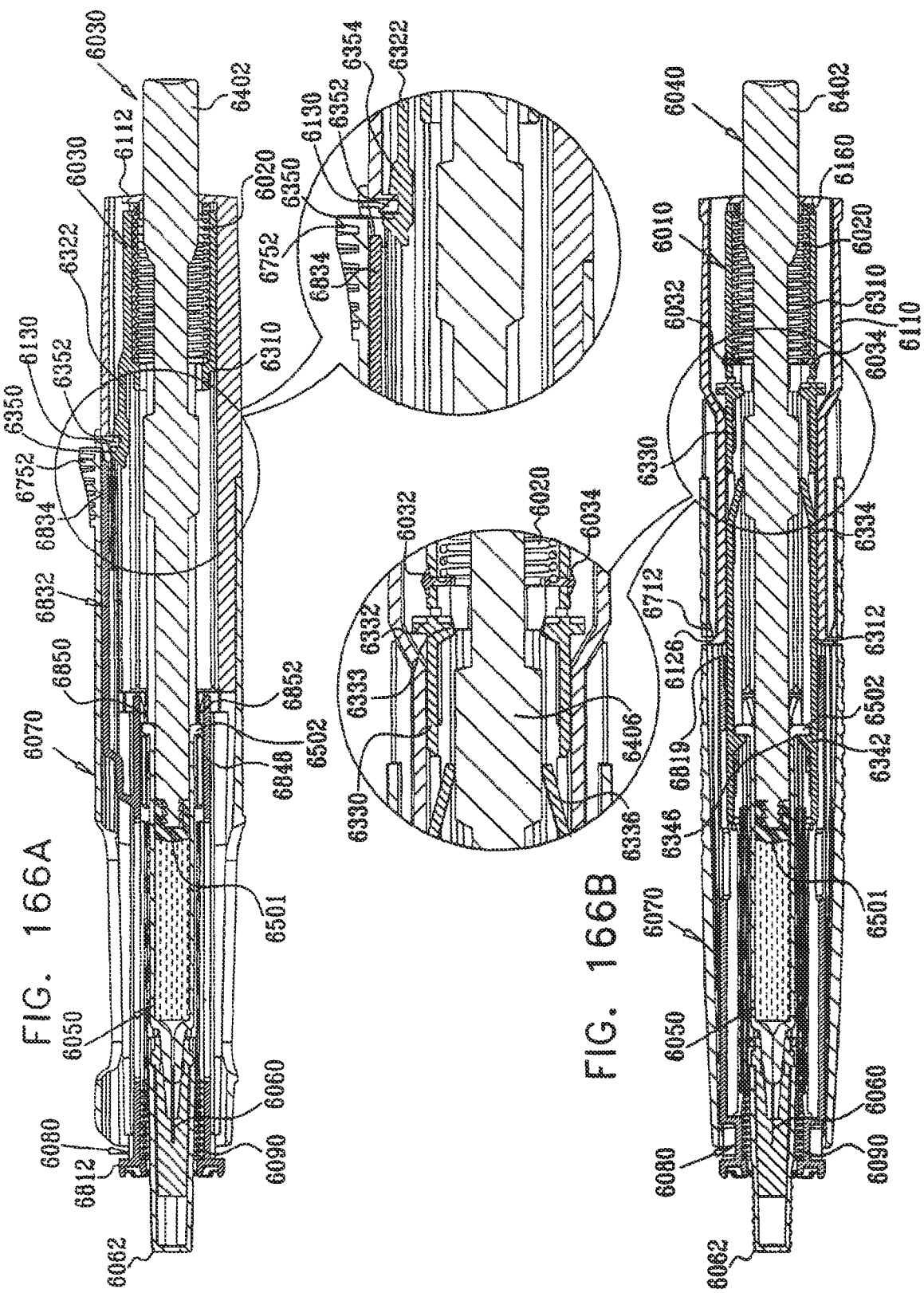

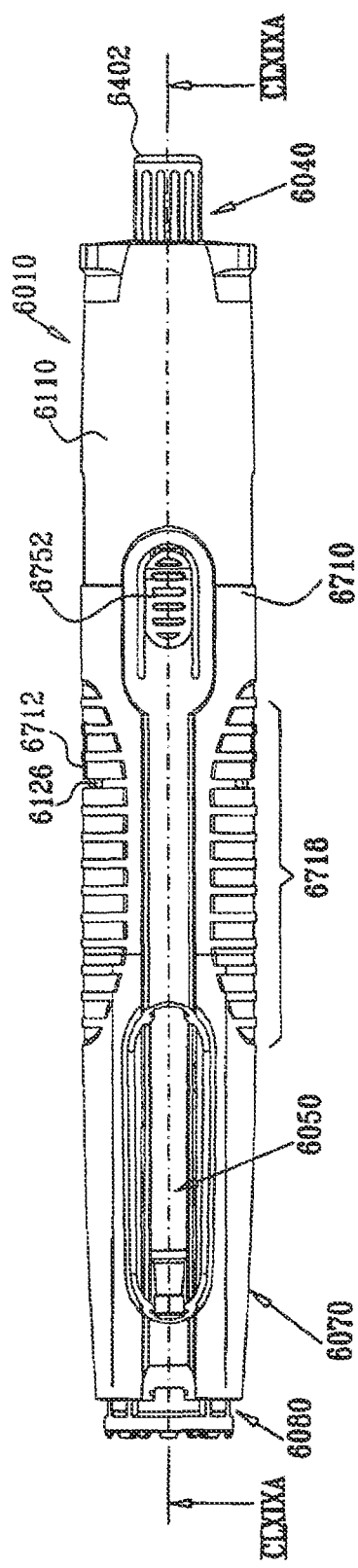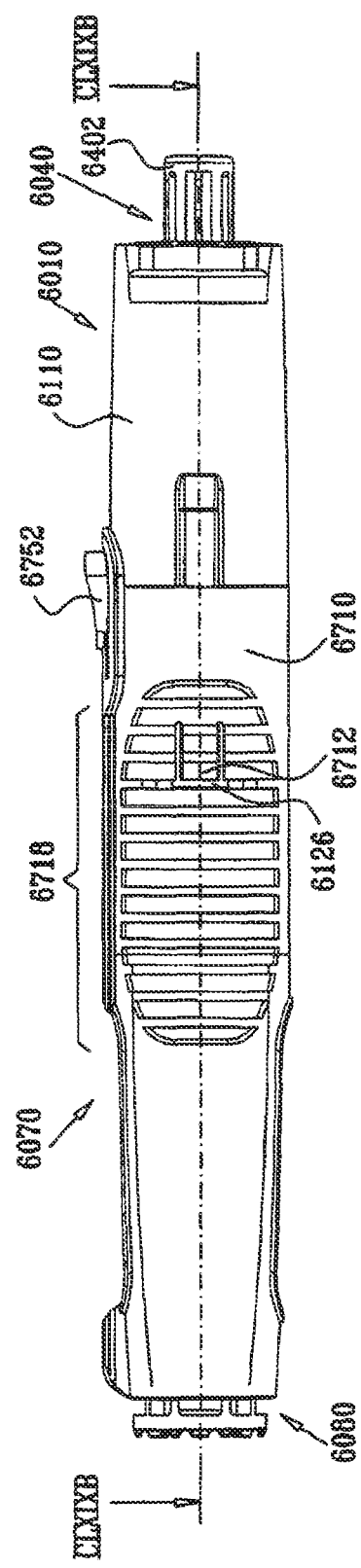
FIG. 168A
FIG. 168B

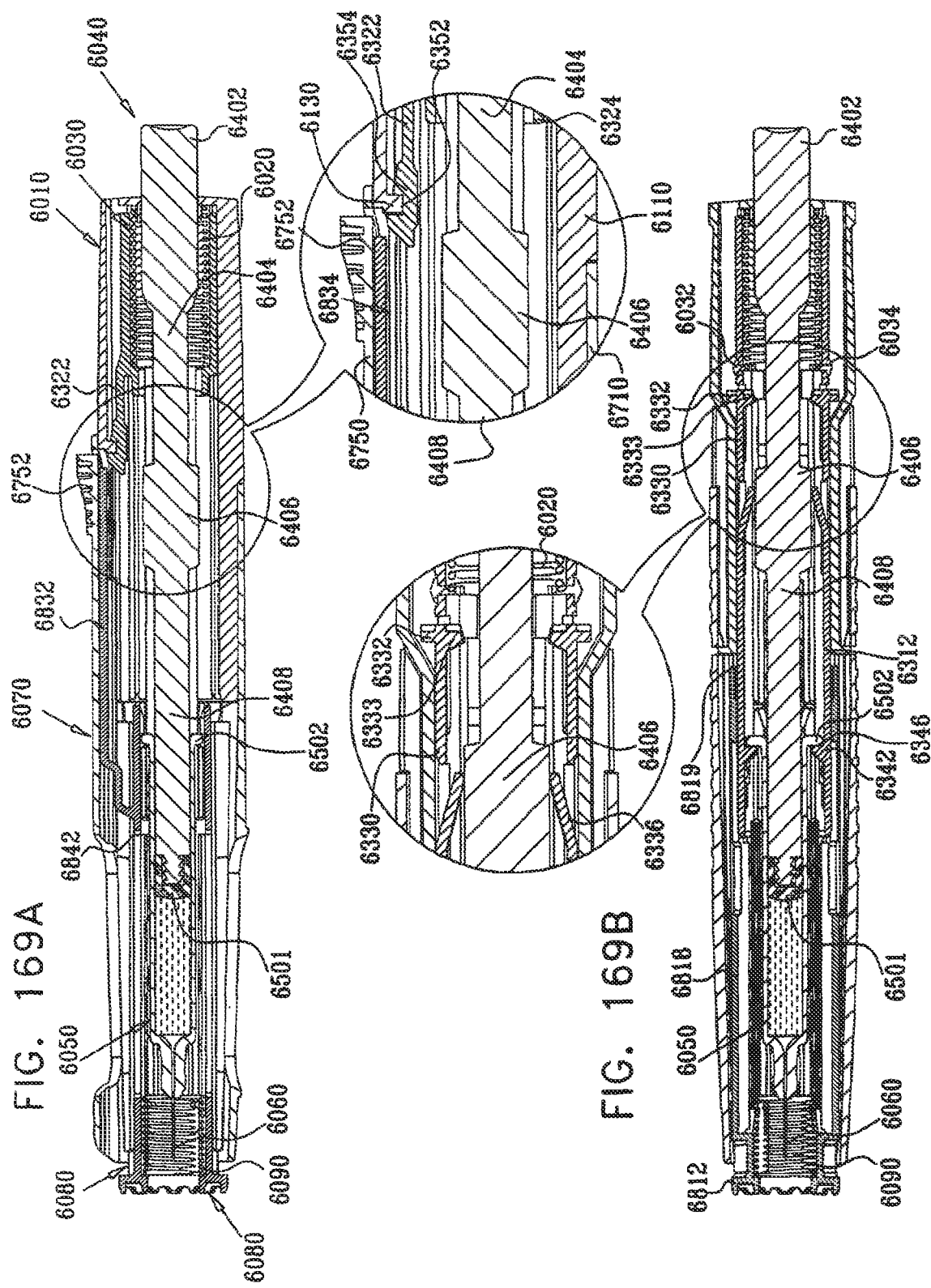

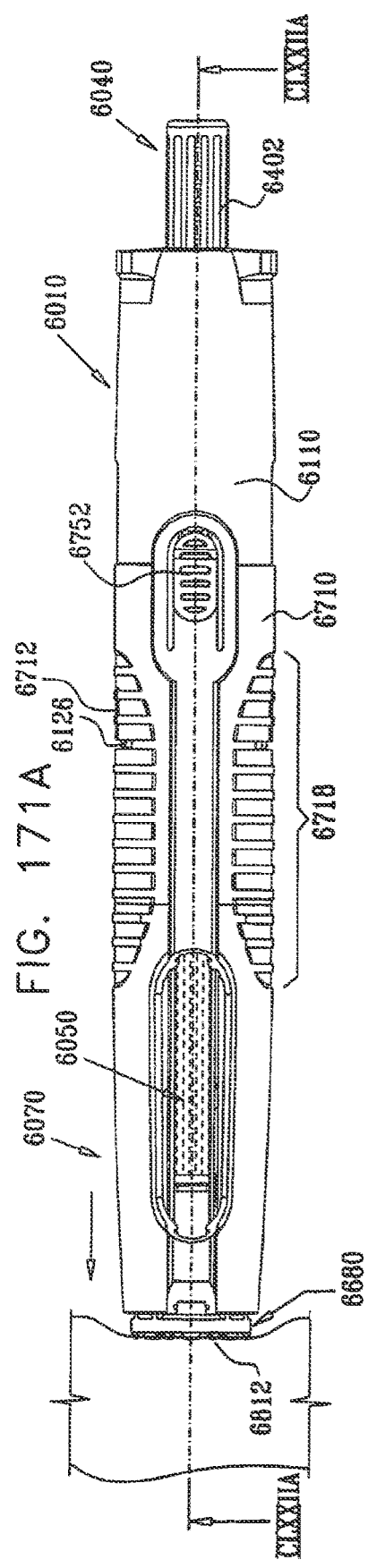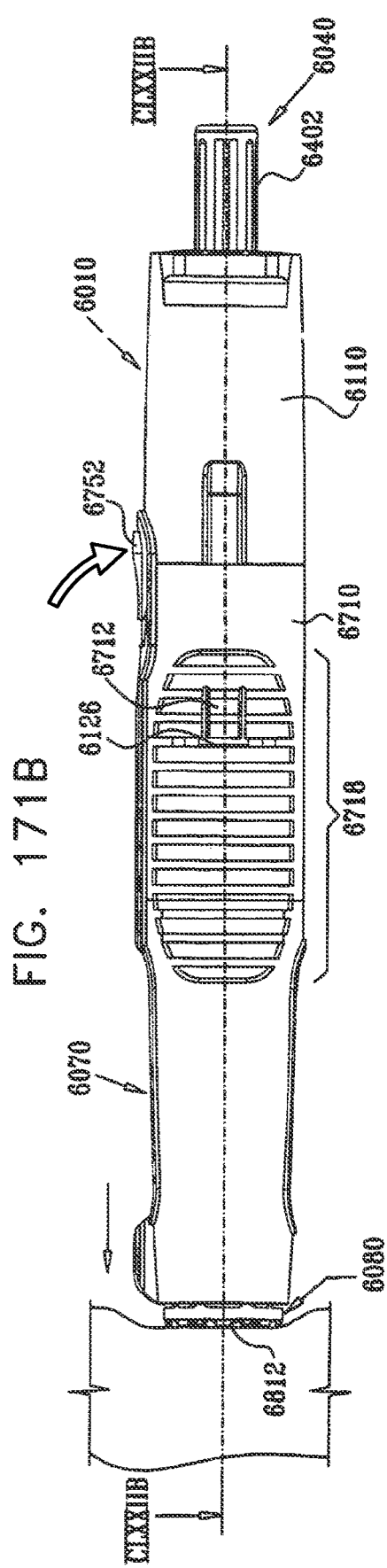

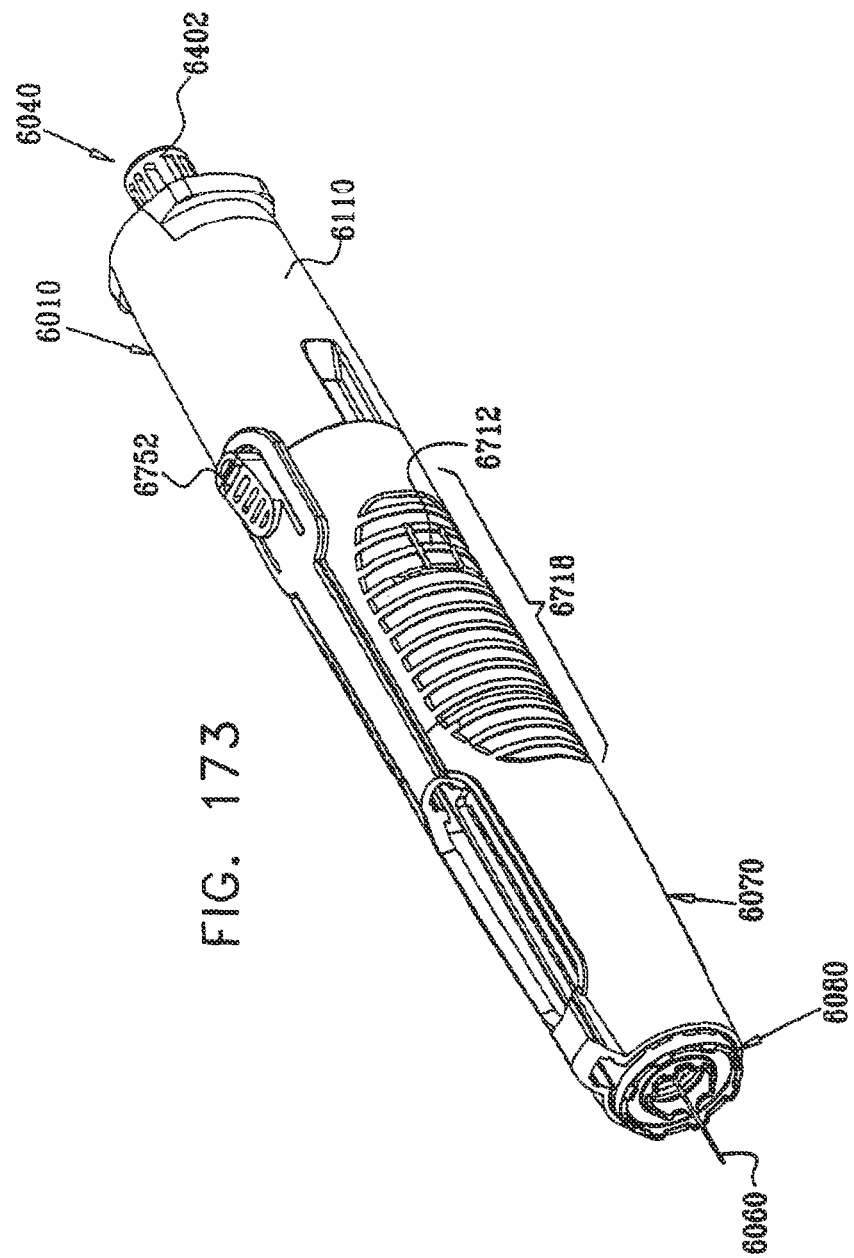

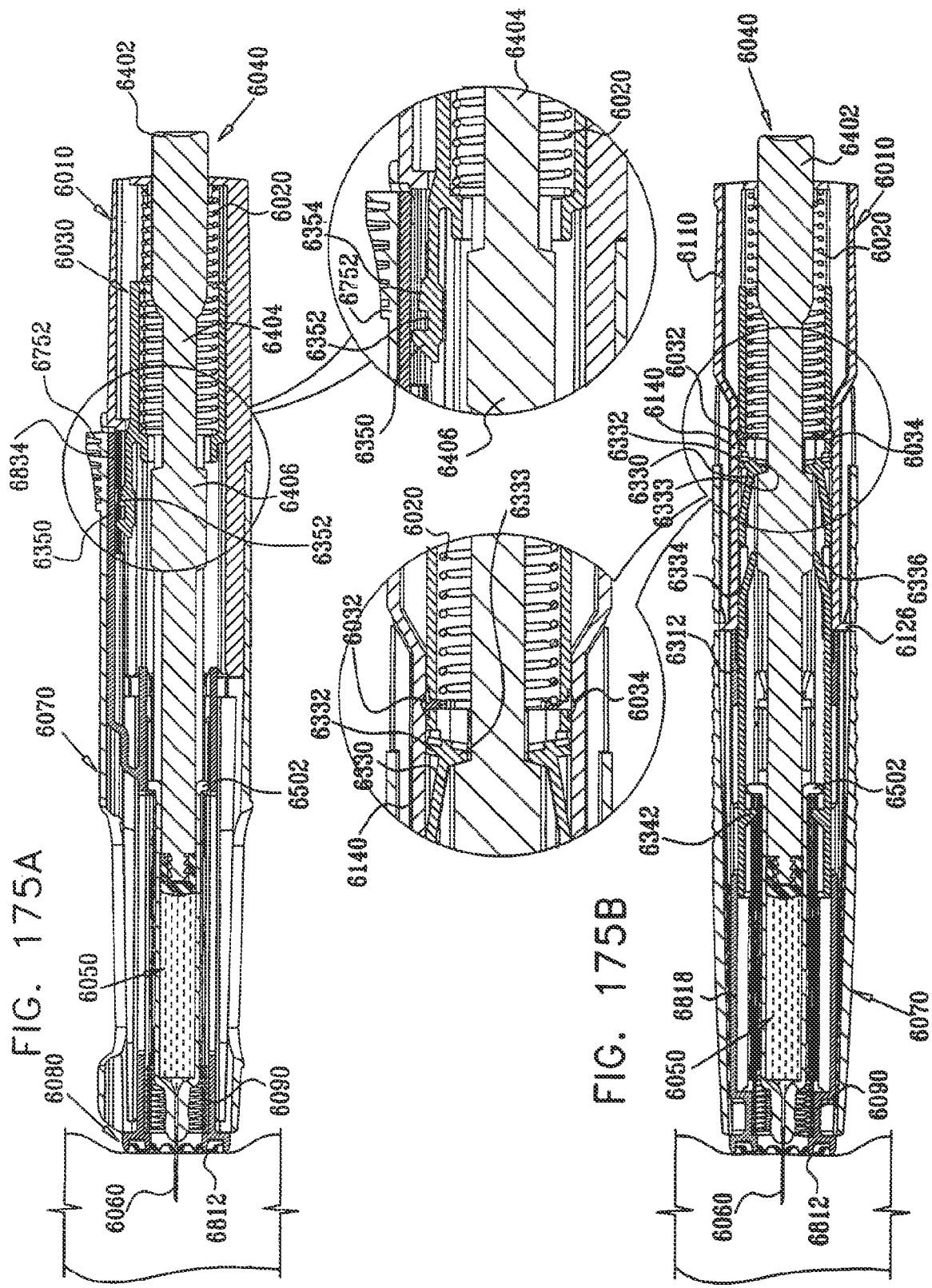

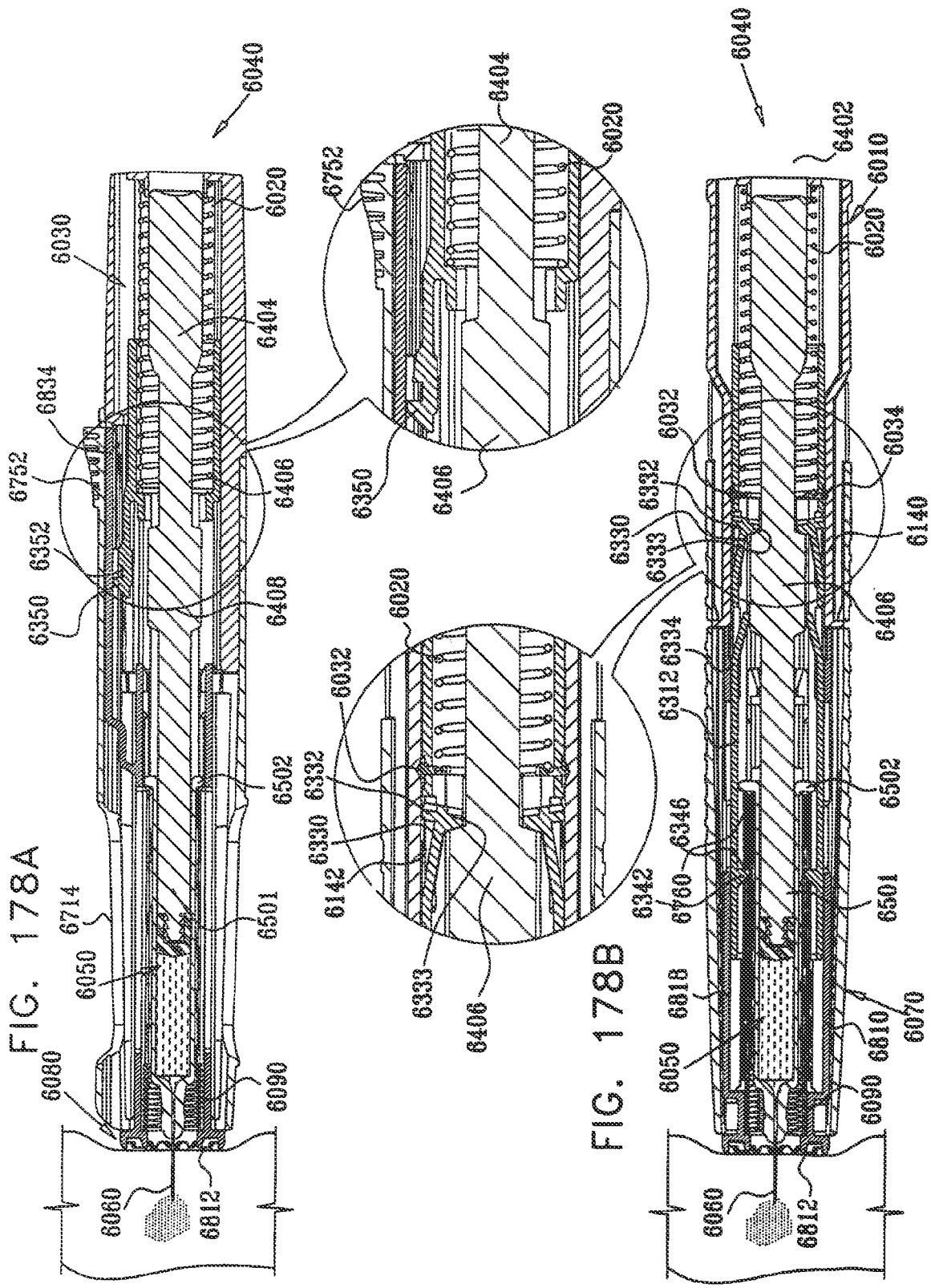

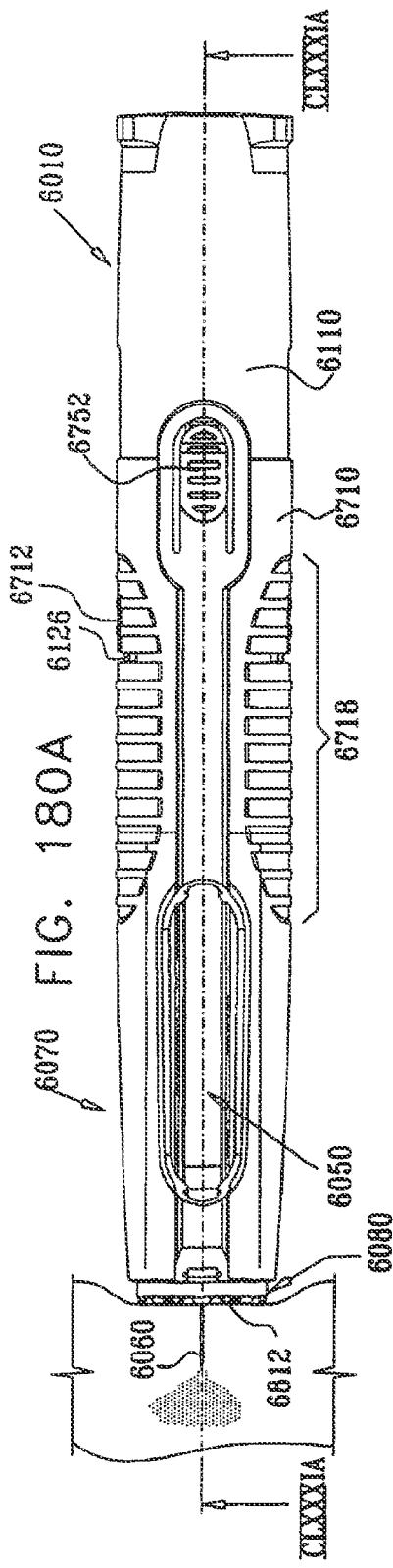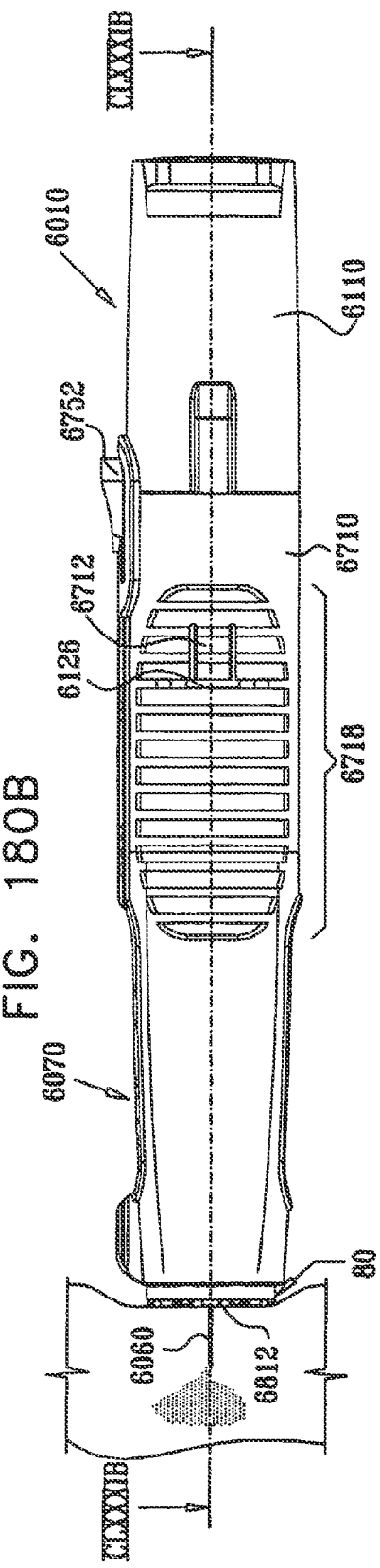

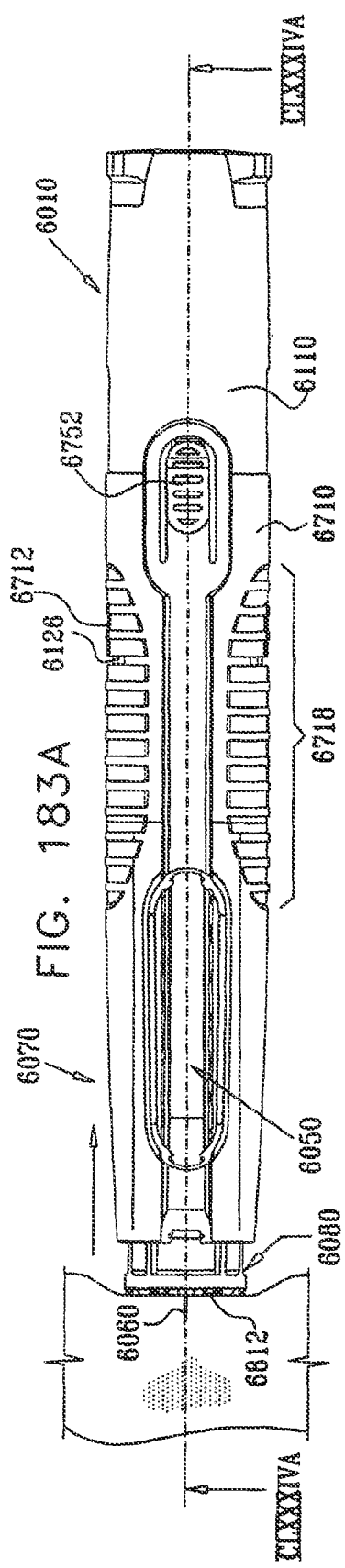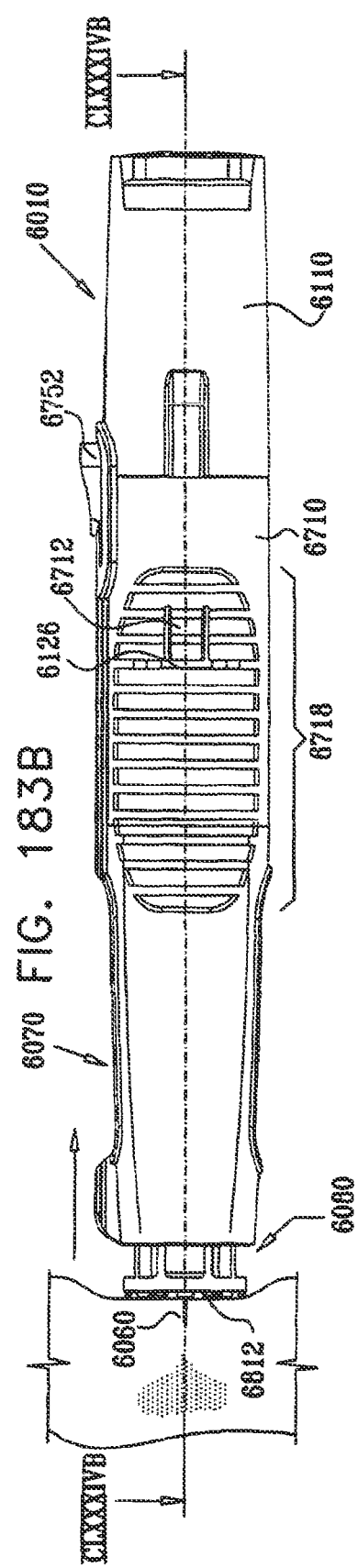

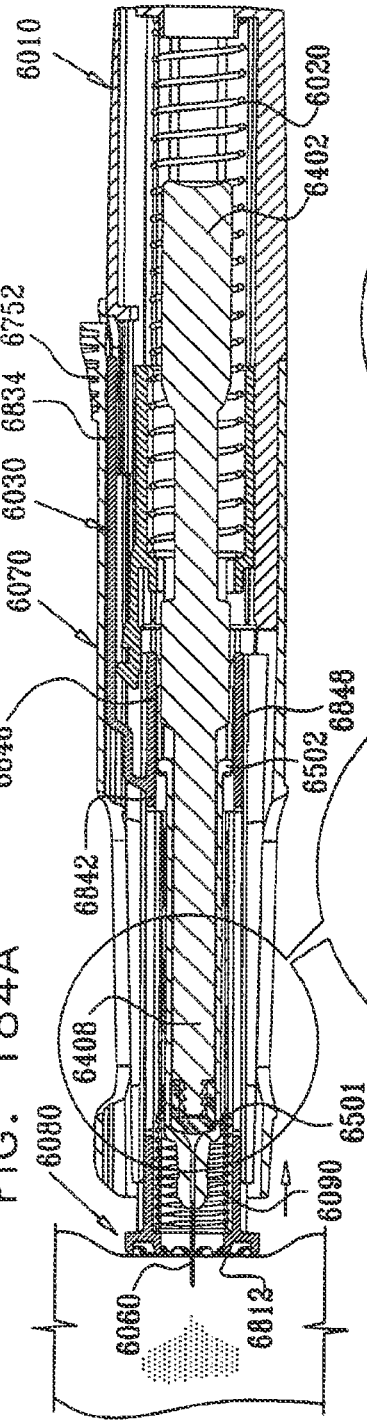
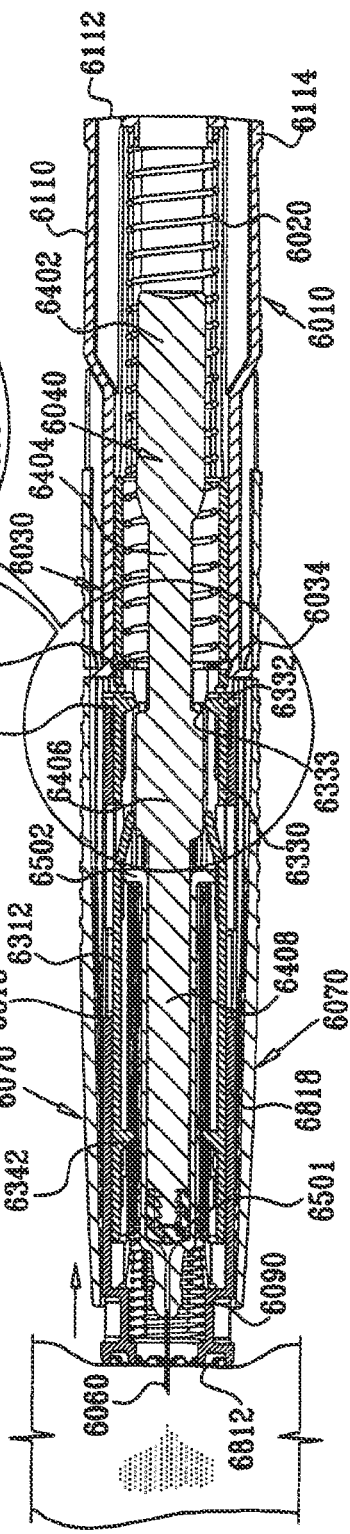
FIG. 184A
FIG. 184B

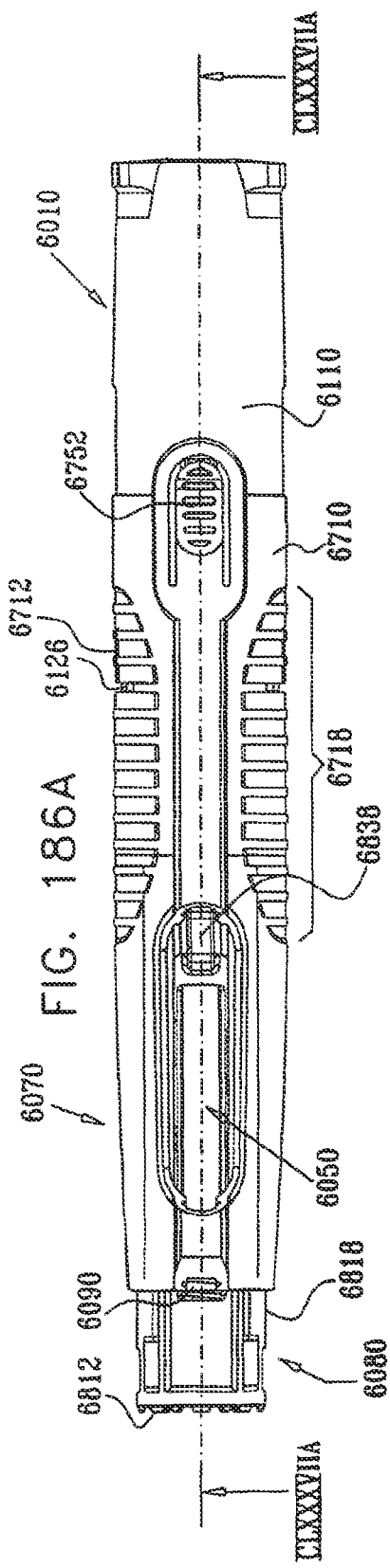
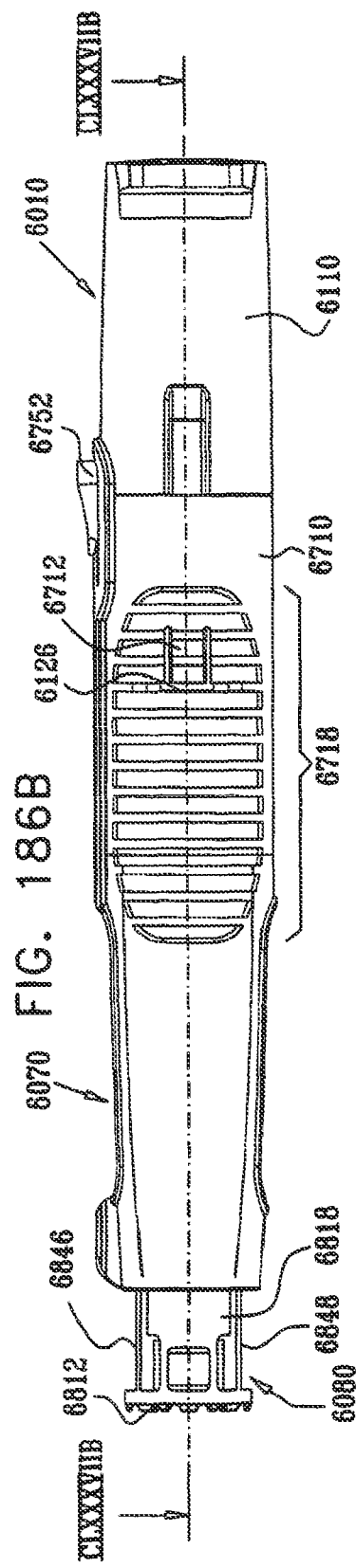

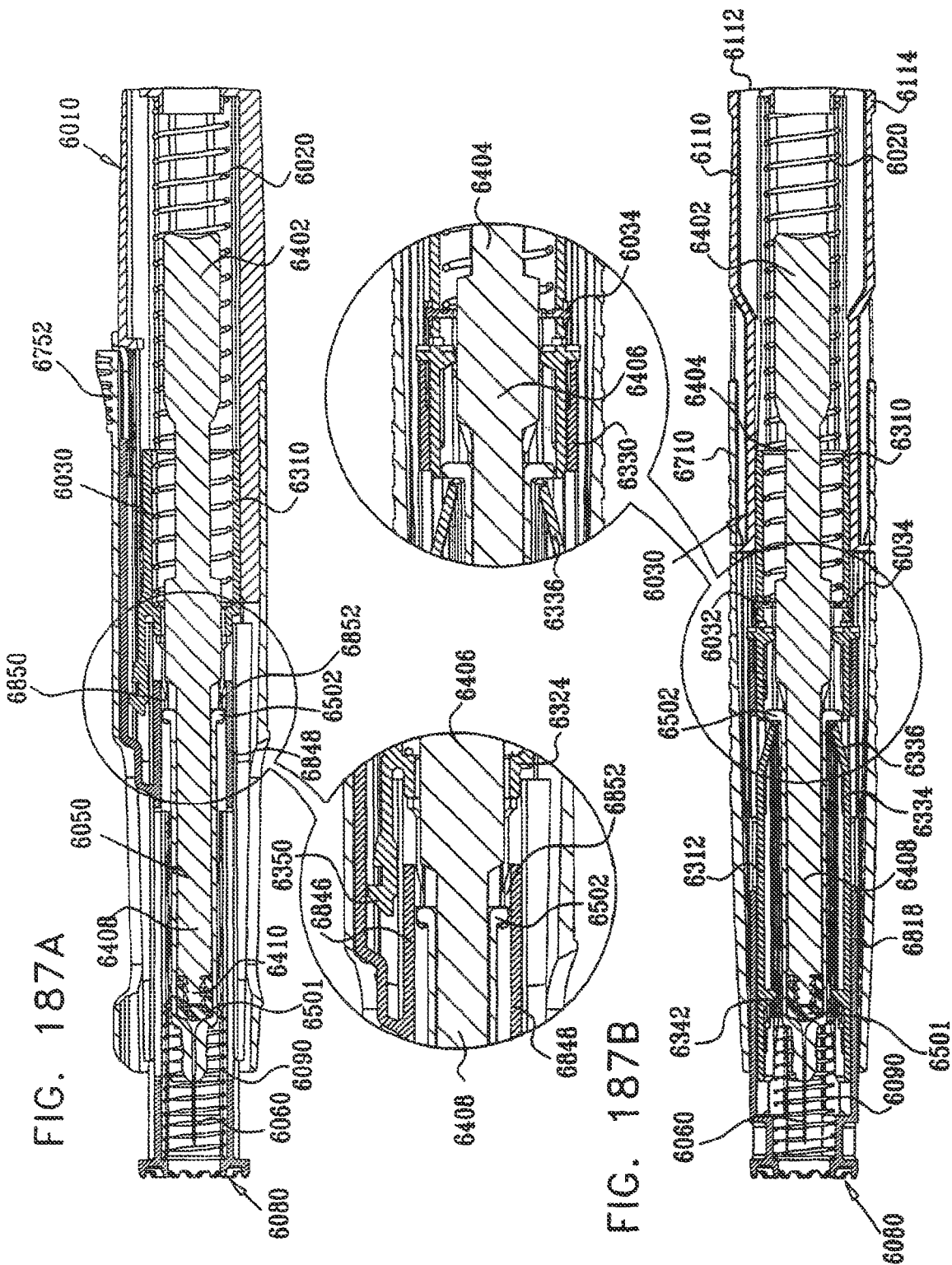

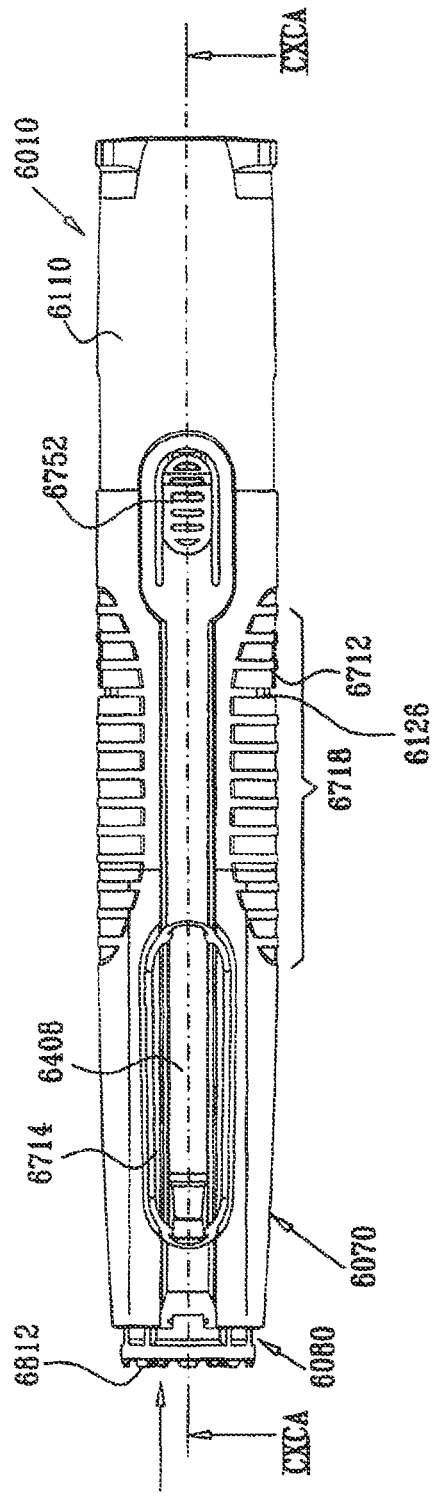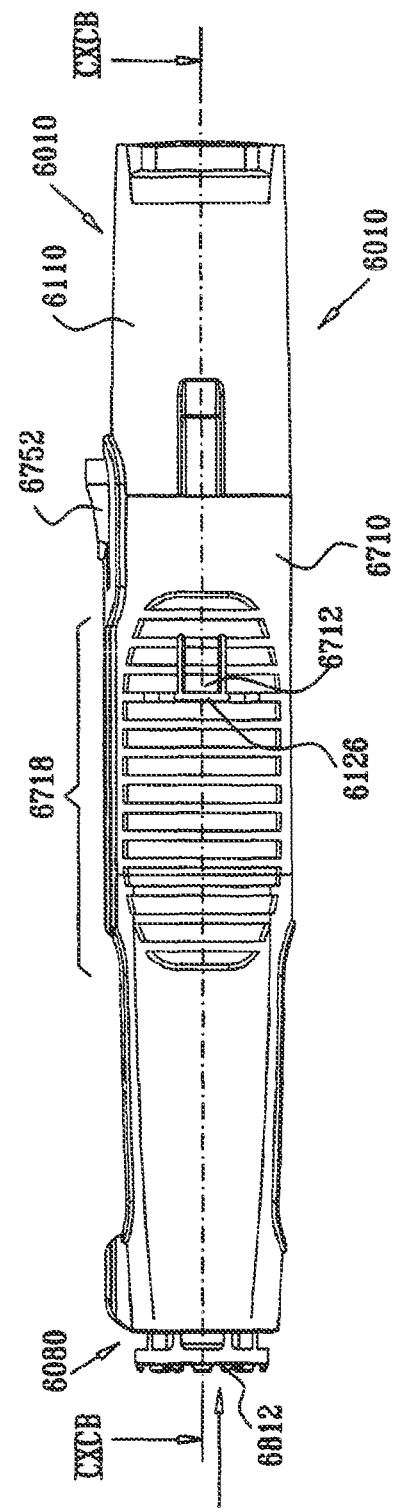

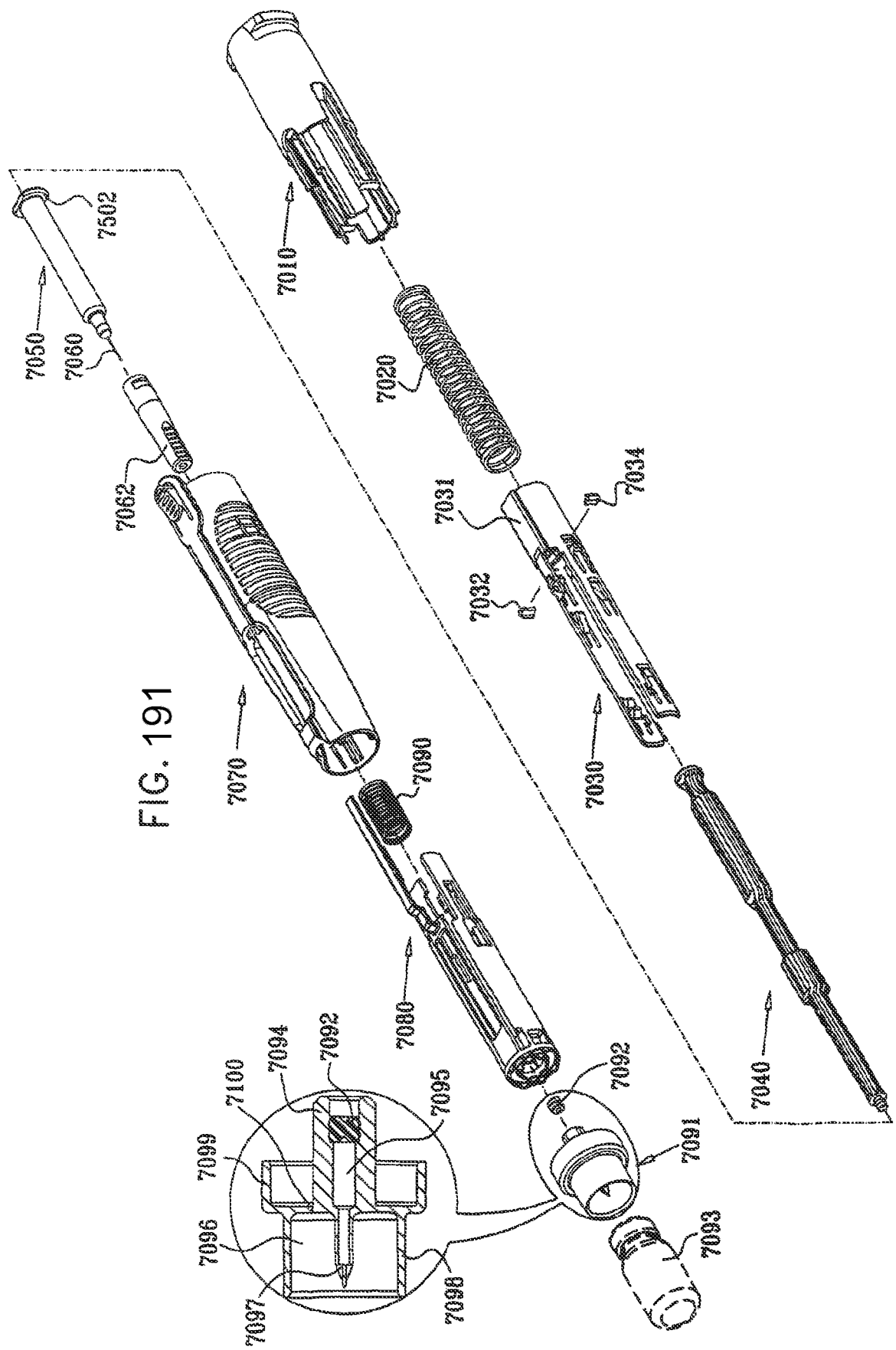

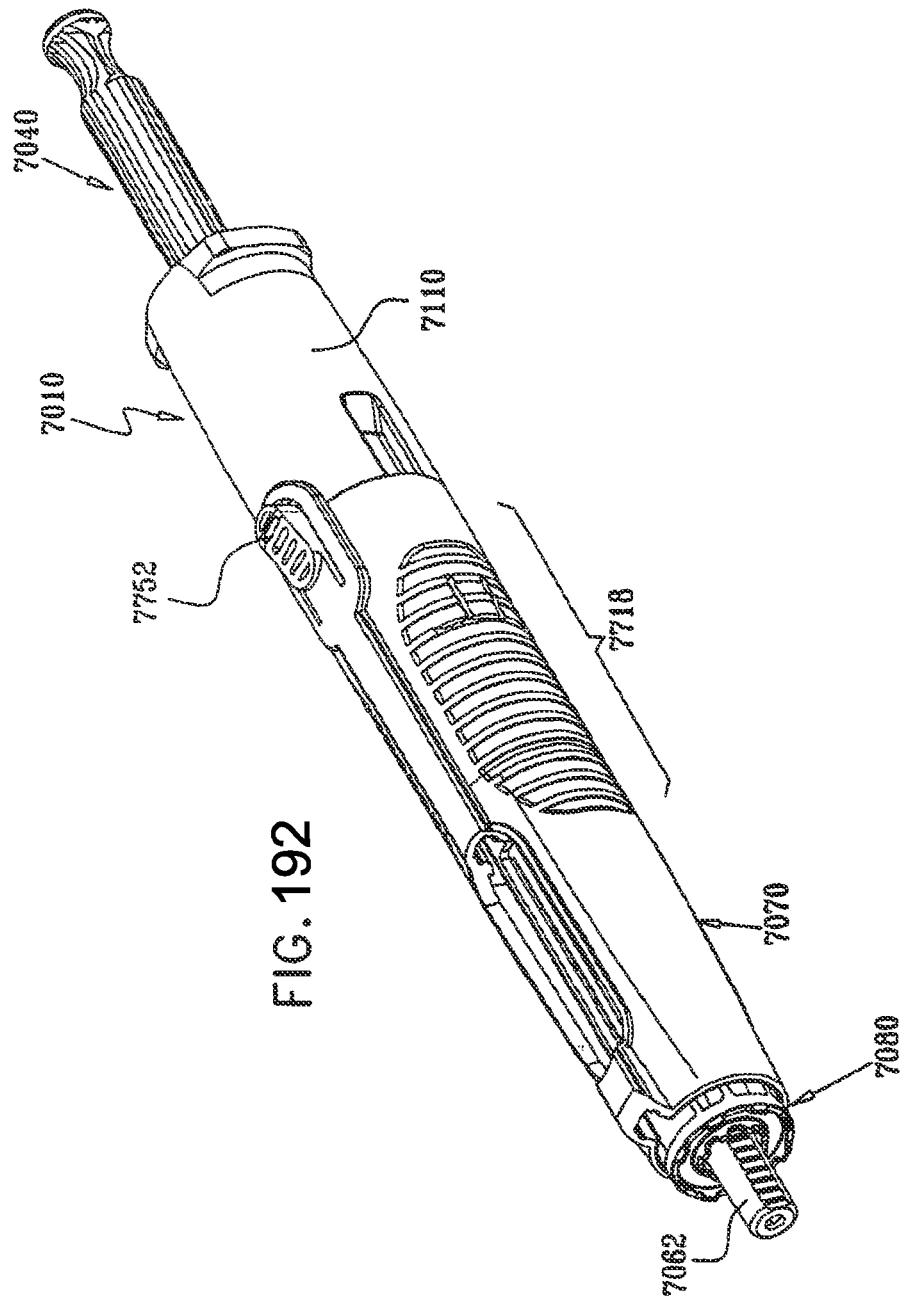

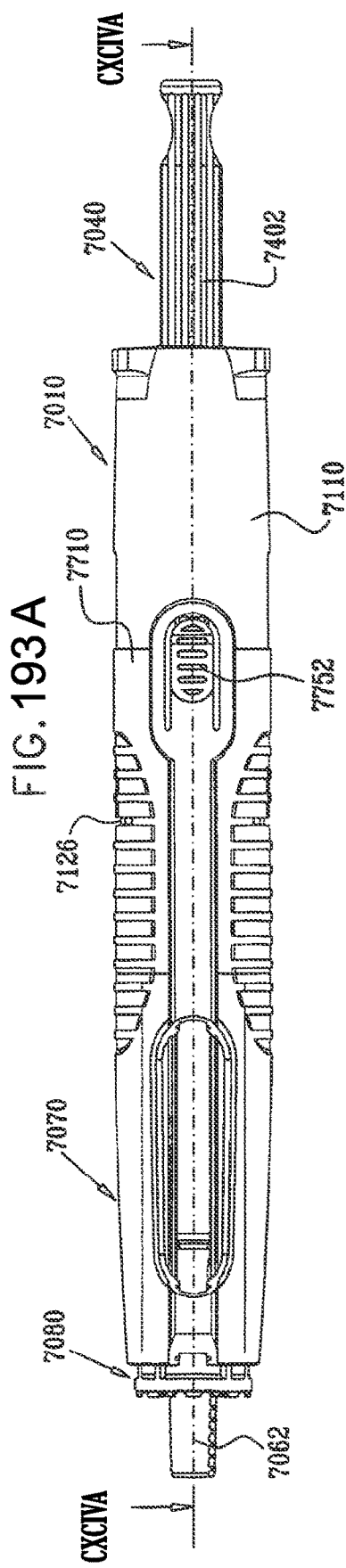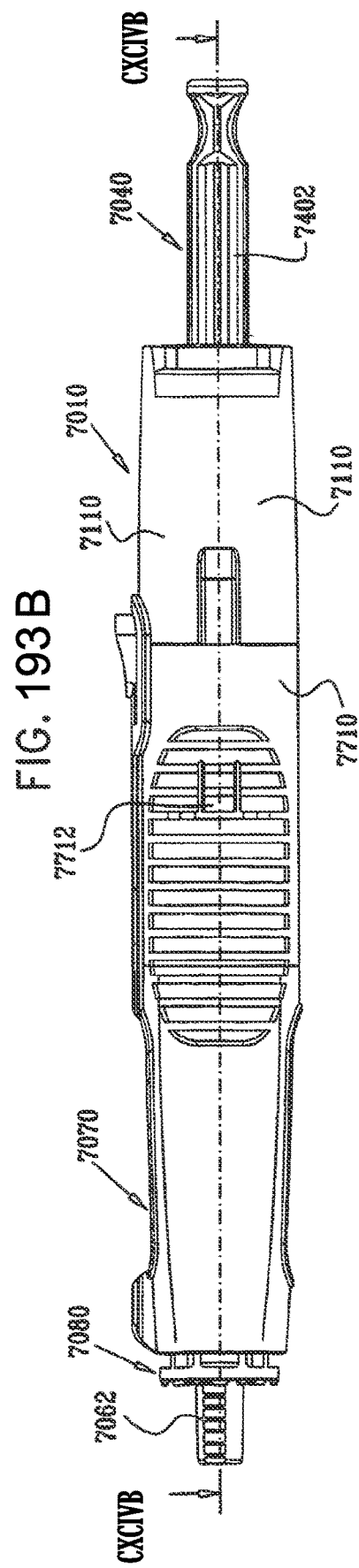

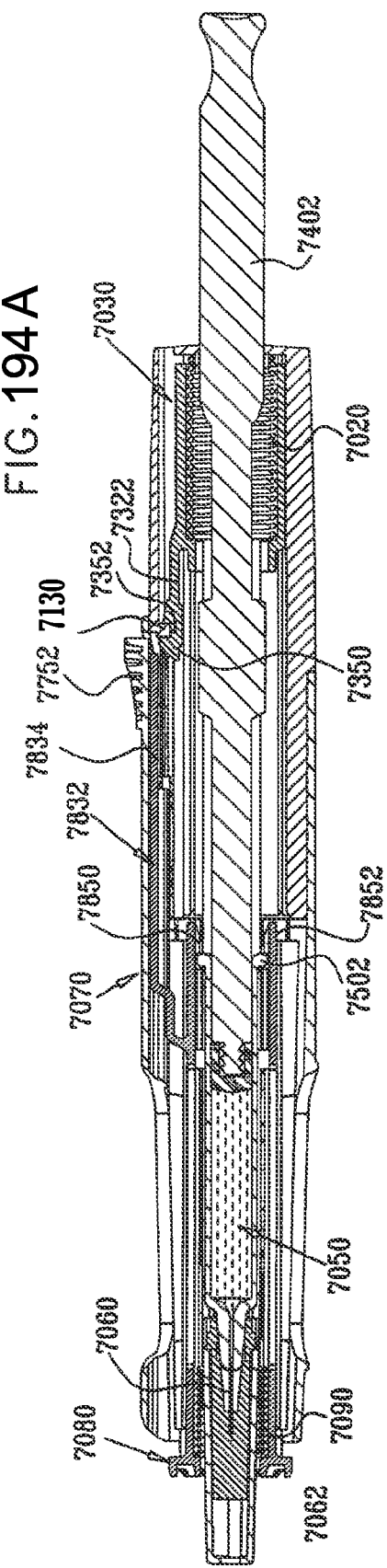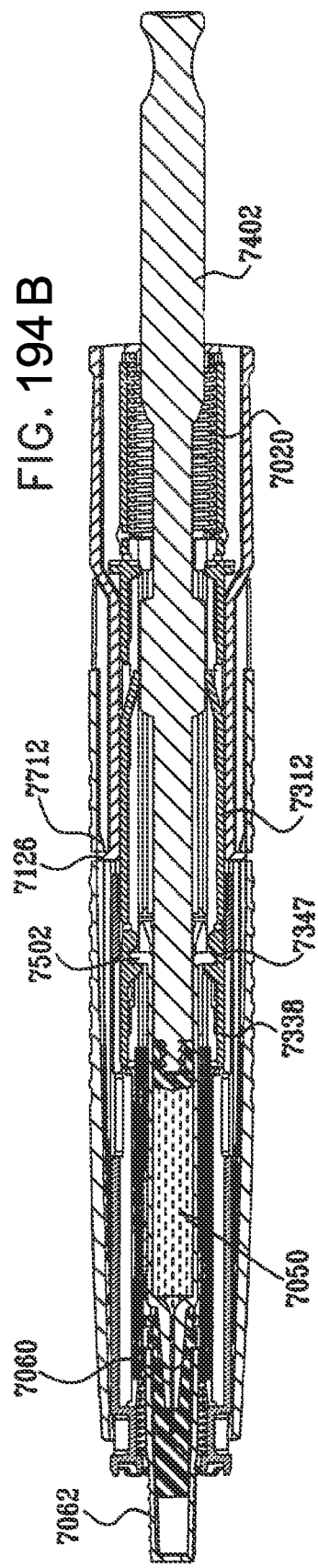

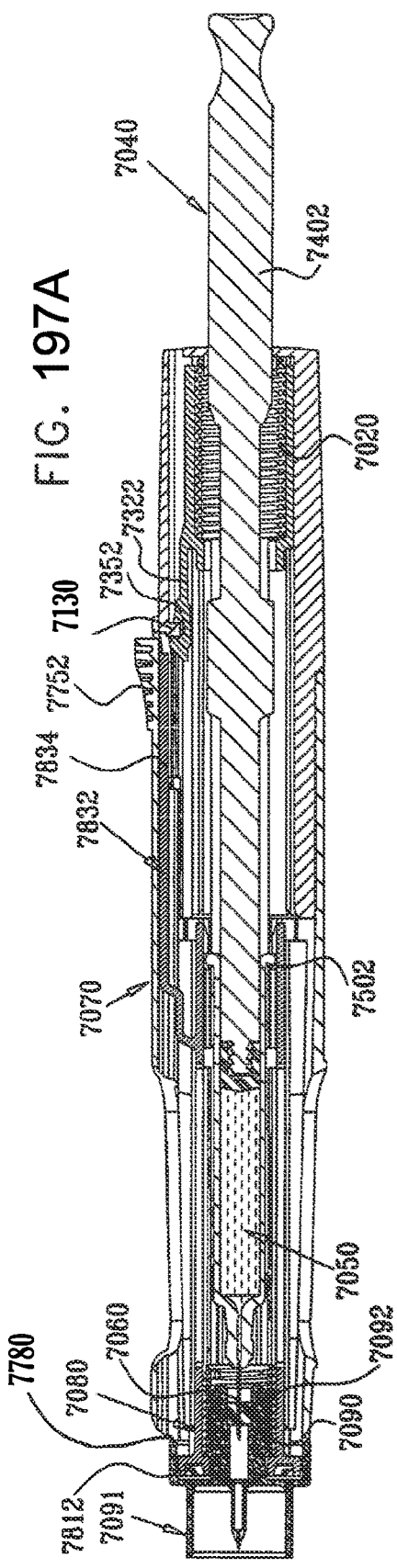
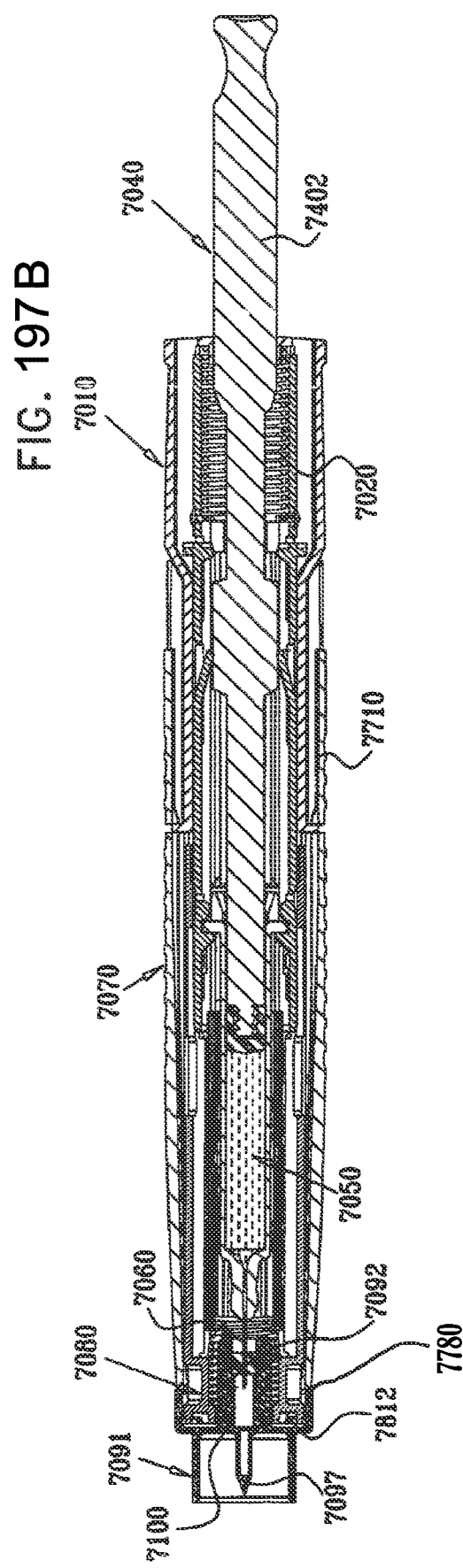

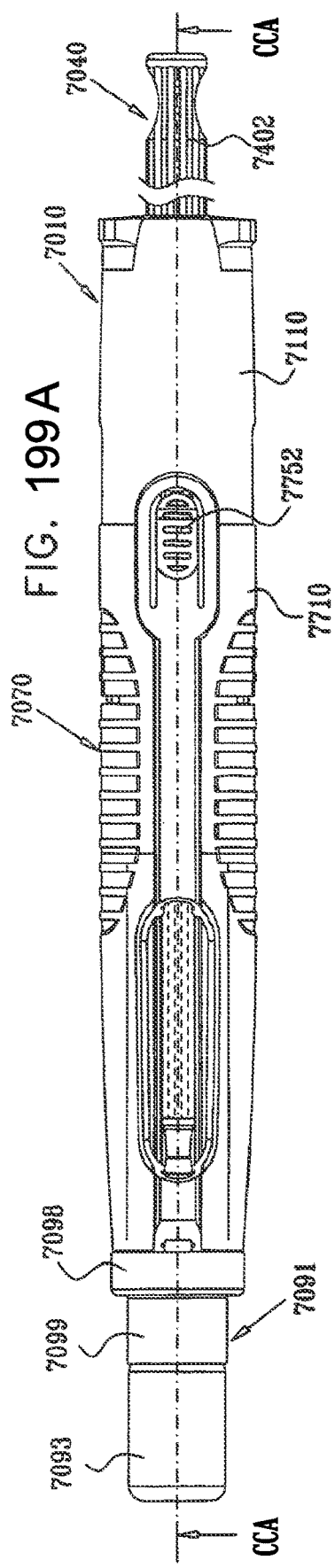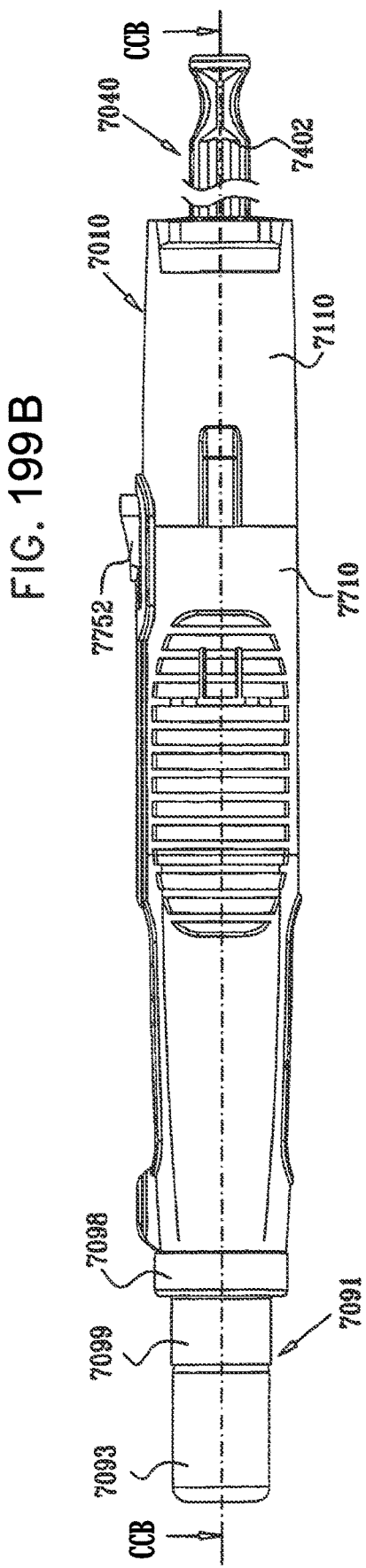

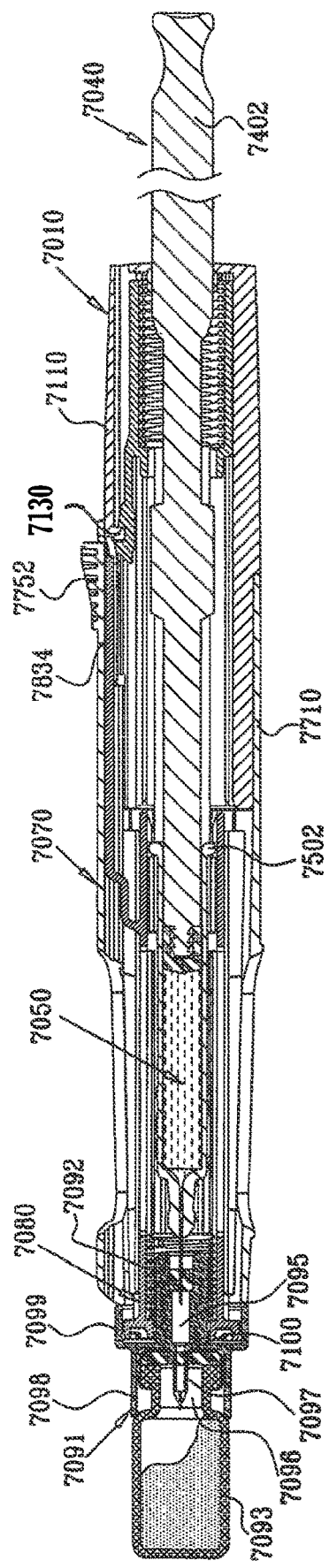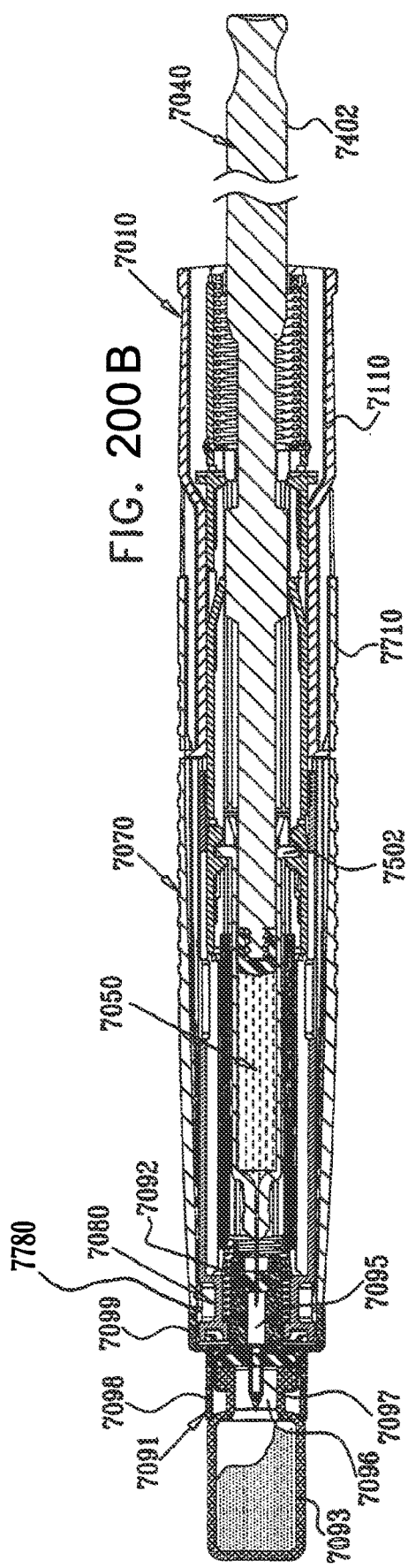

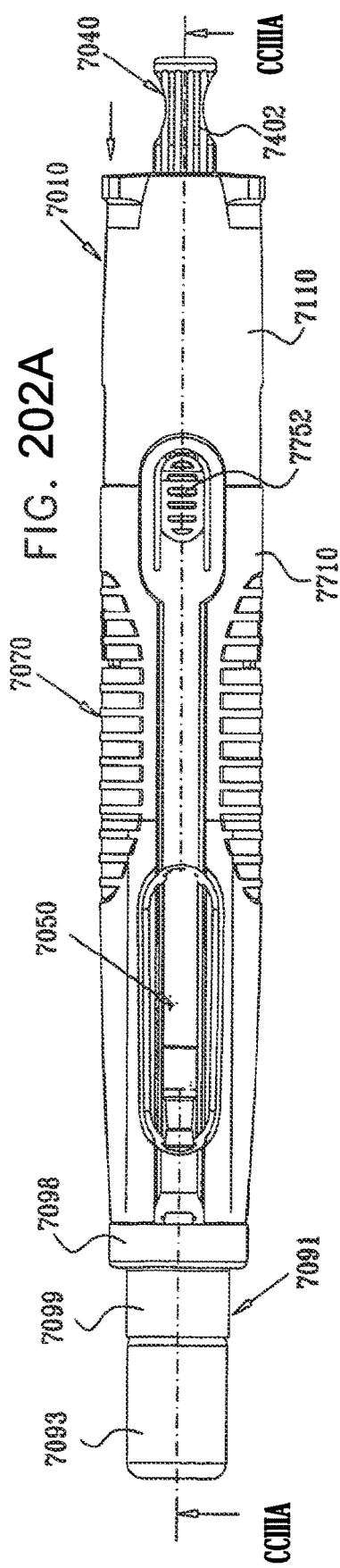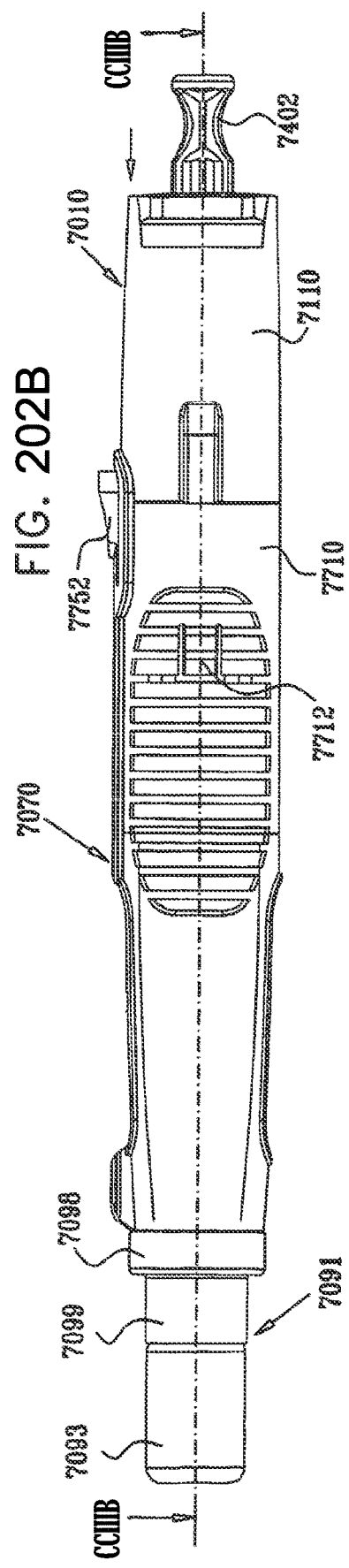

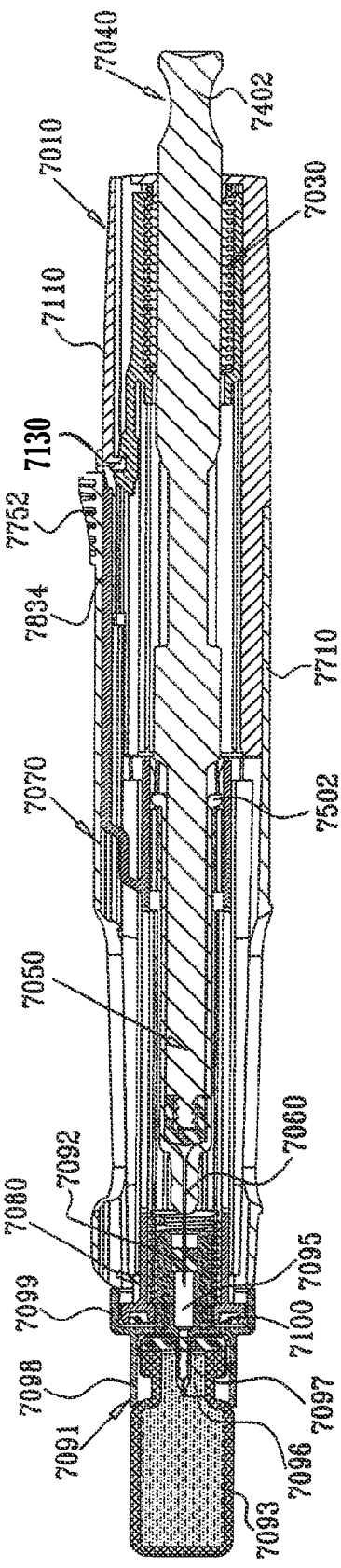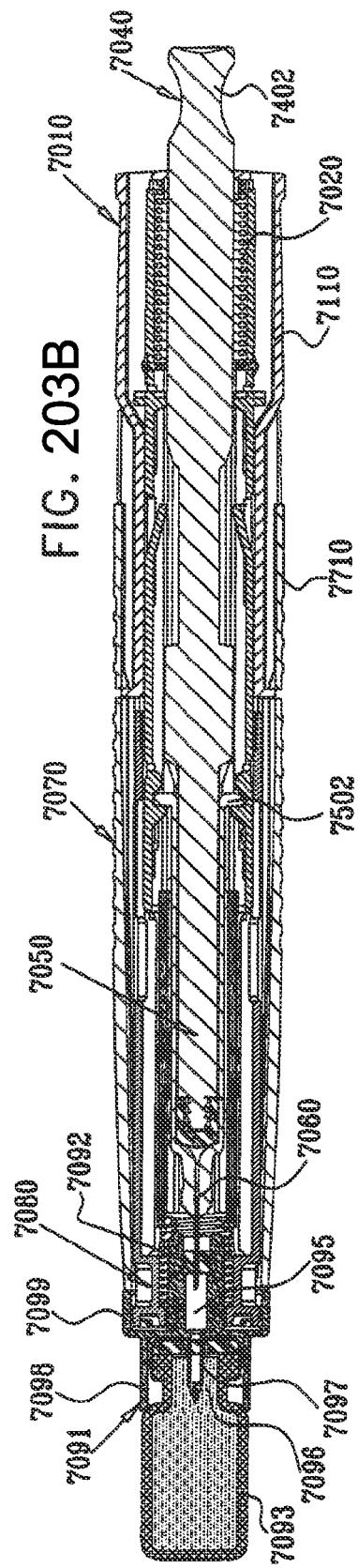

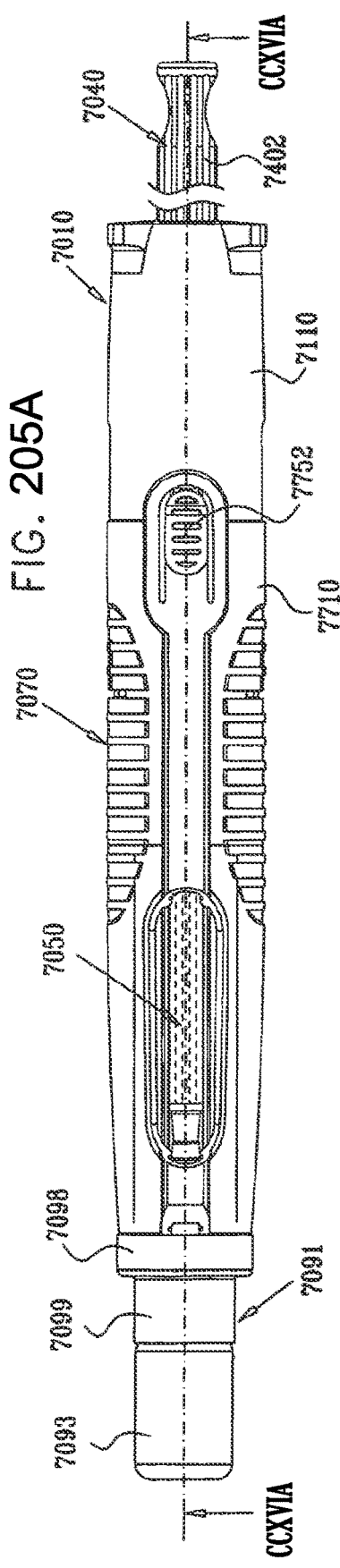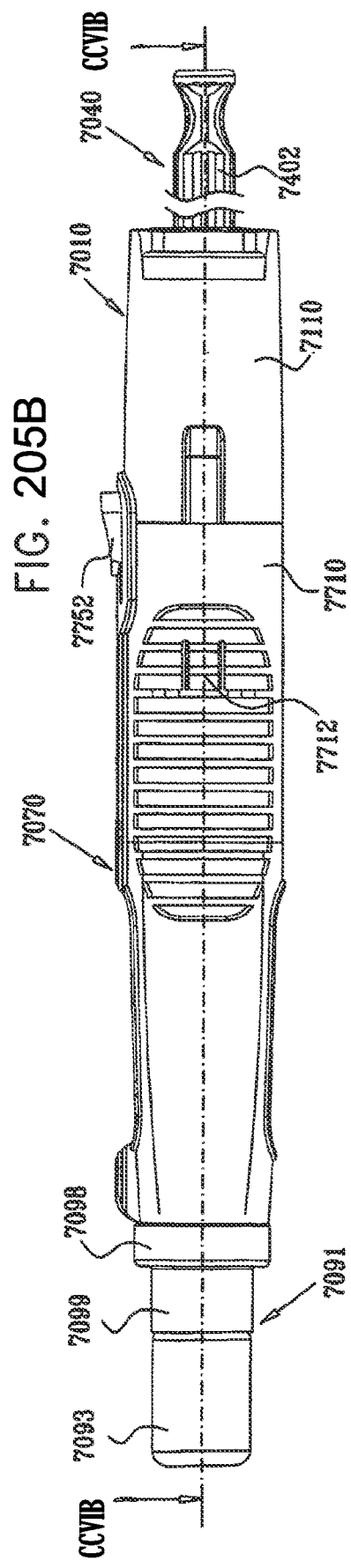

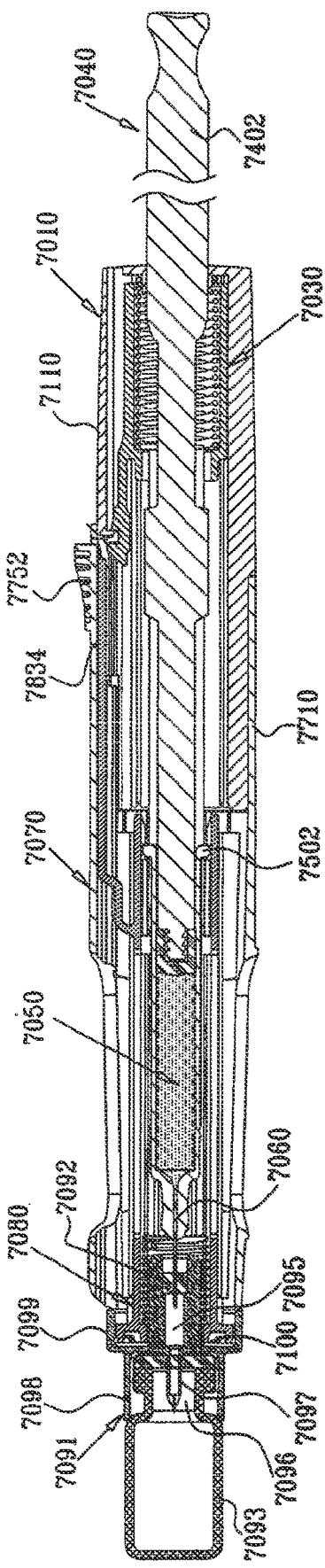

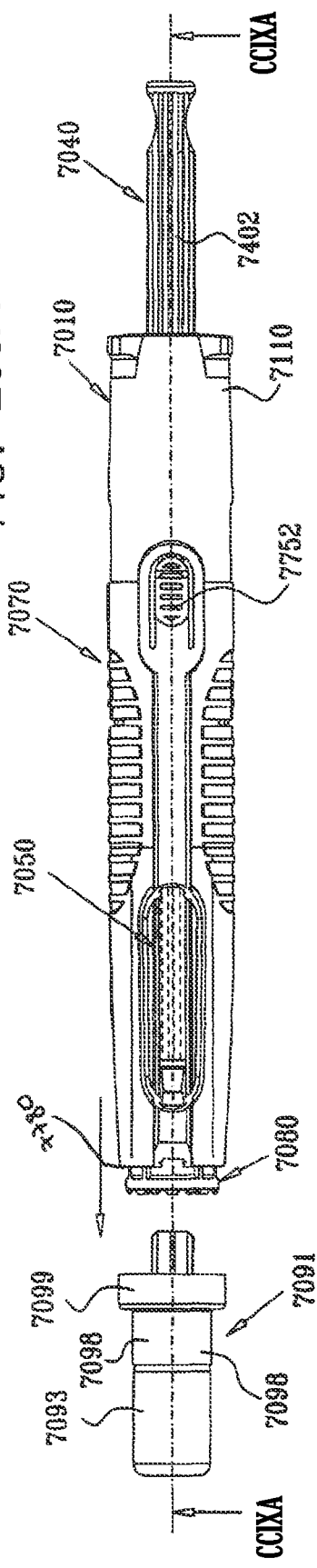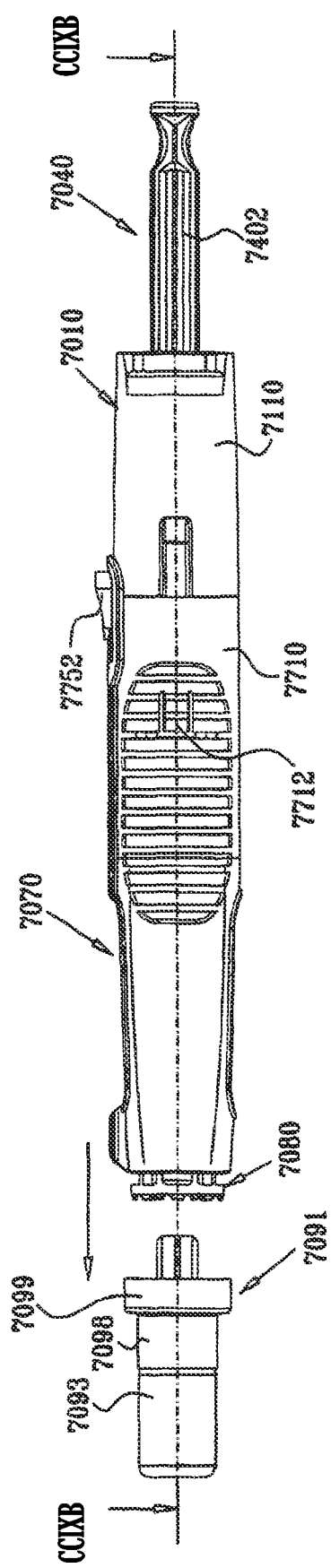

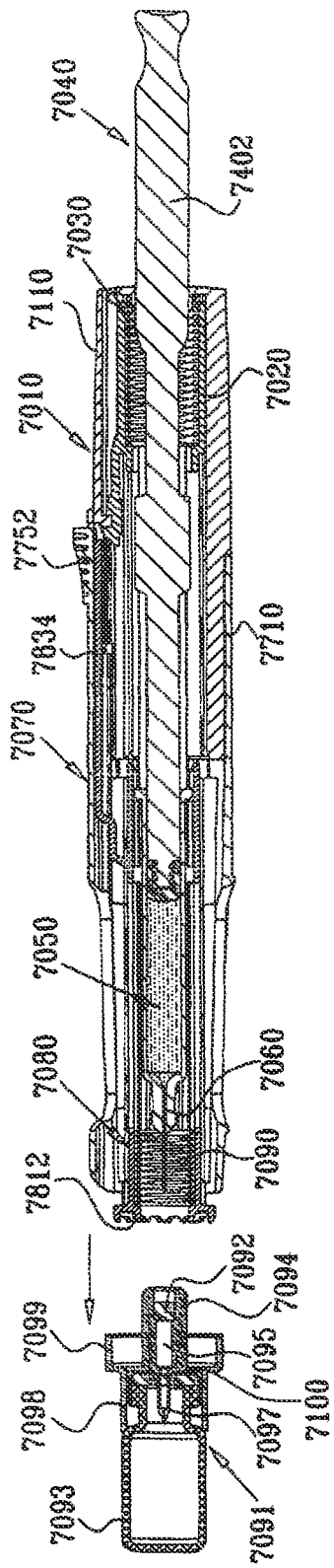
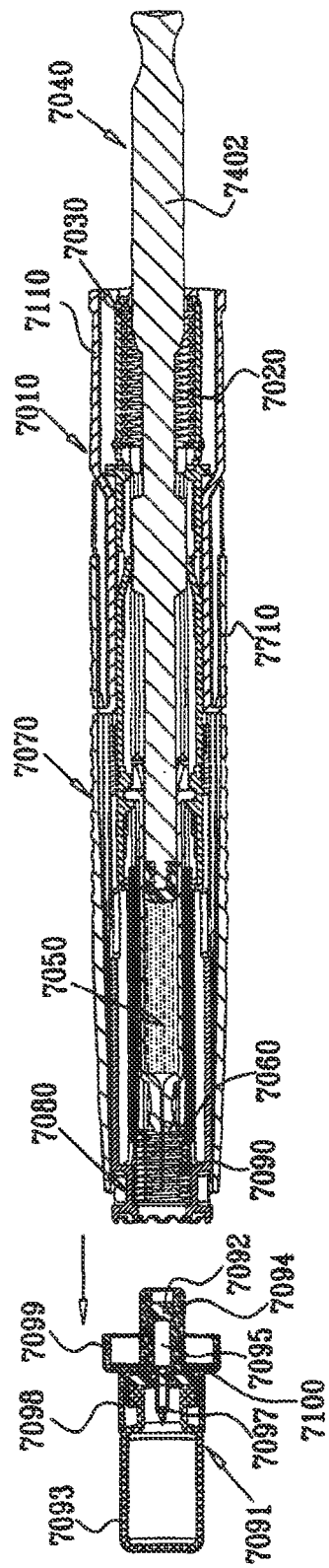
FIG. 209A
FIG. 209B

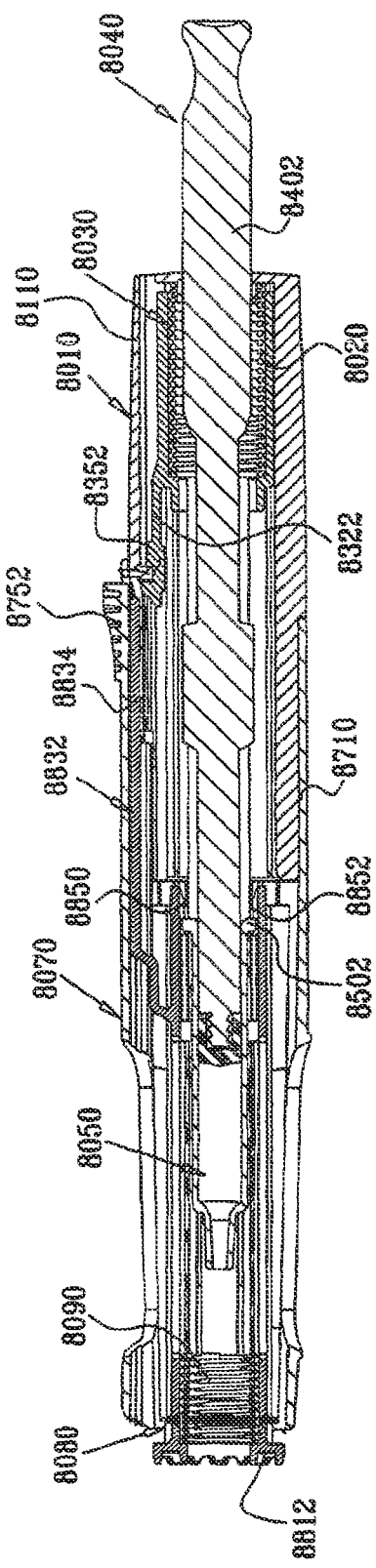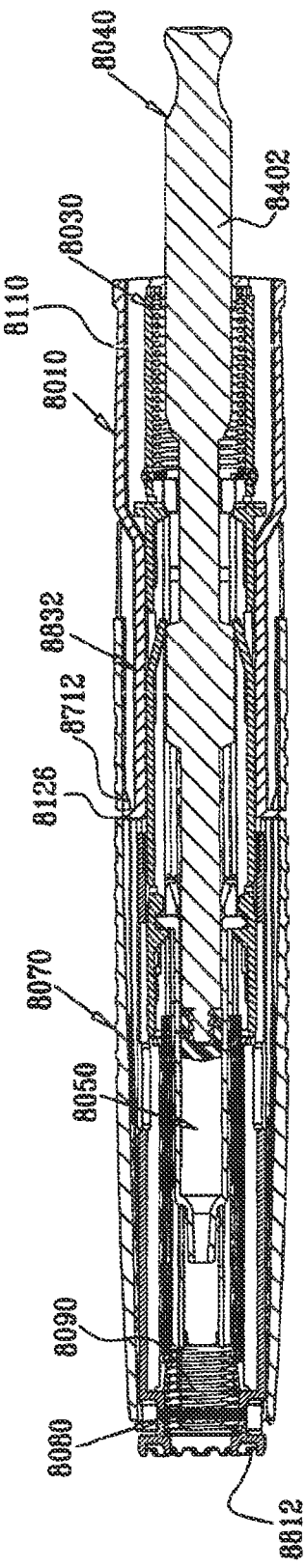
FIG. 213A
FIG. 213B

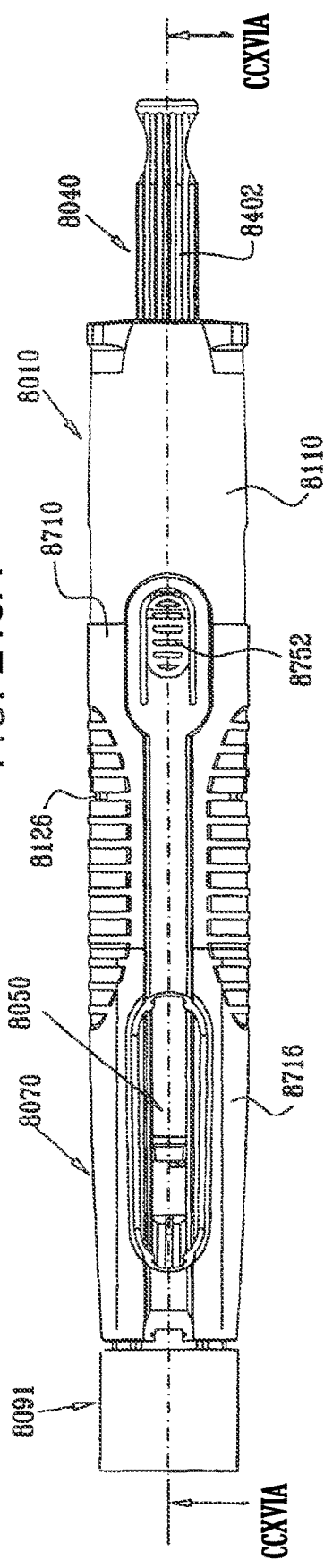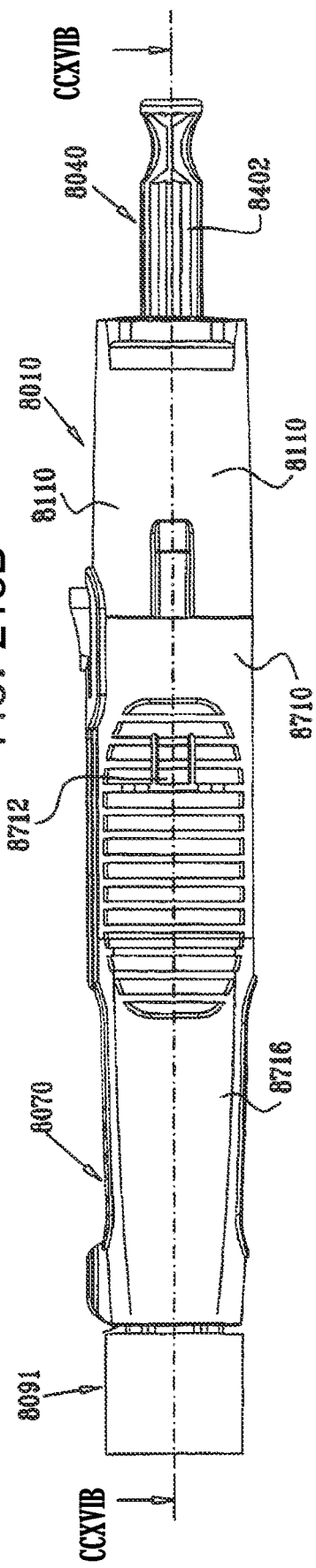

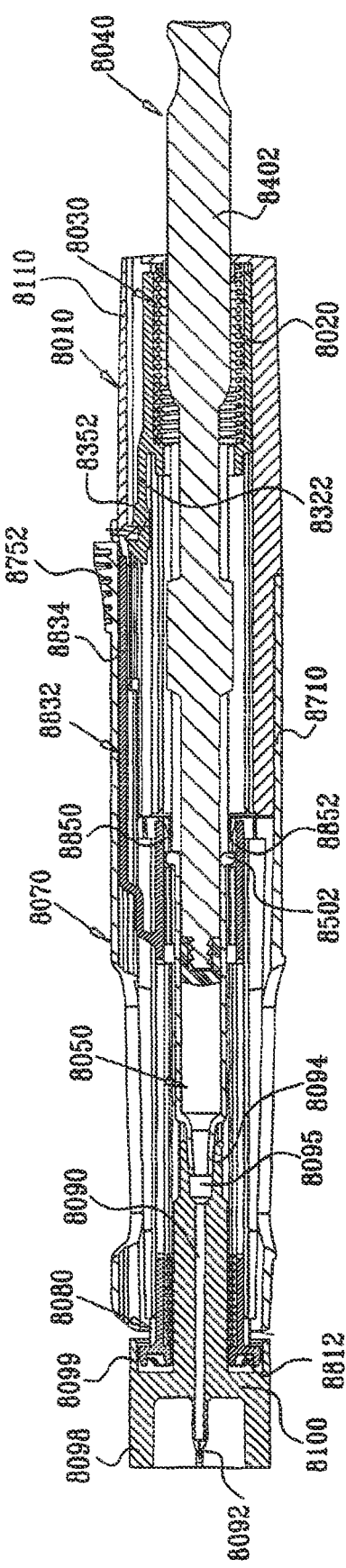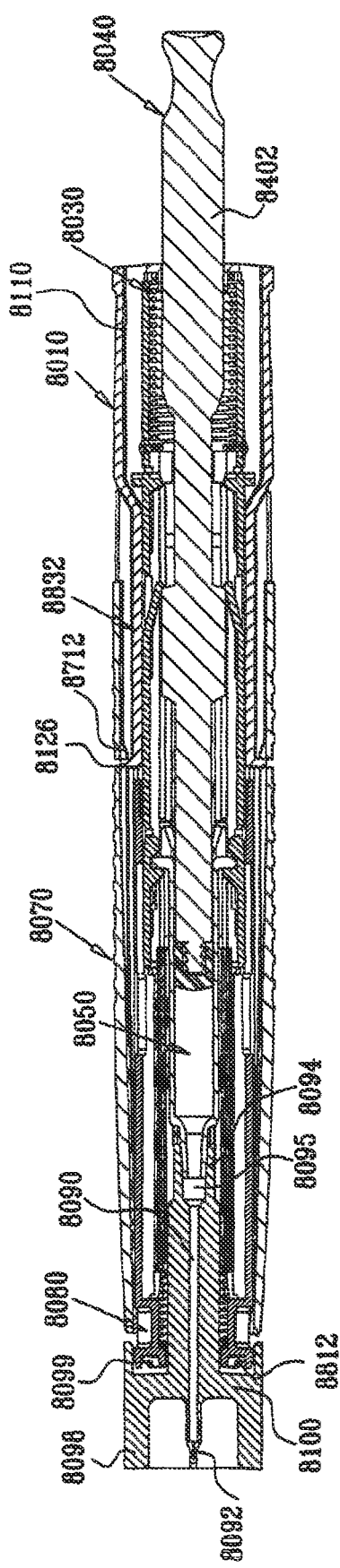

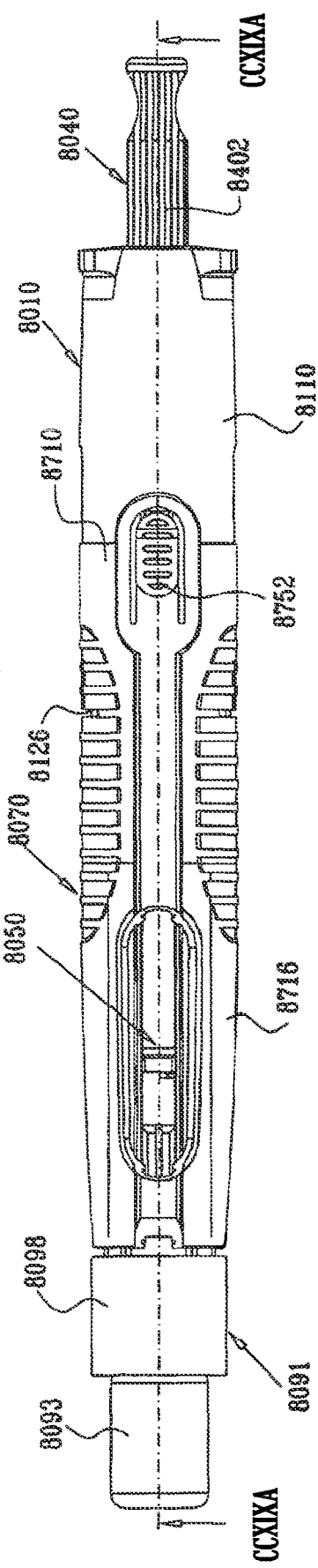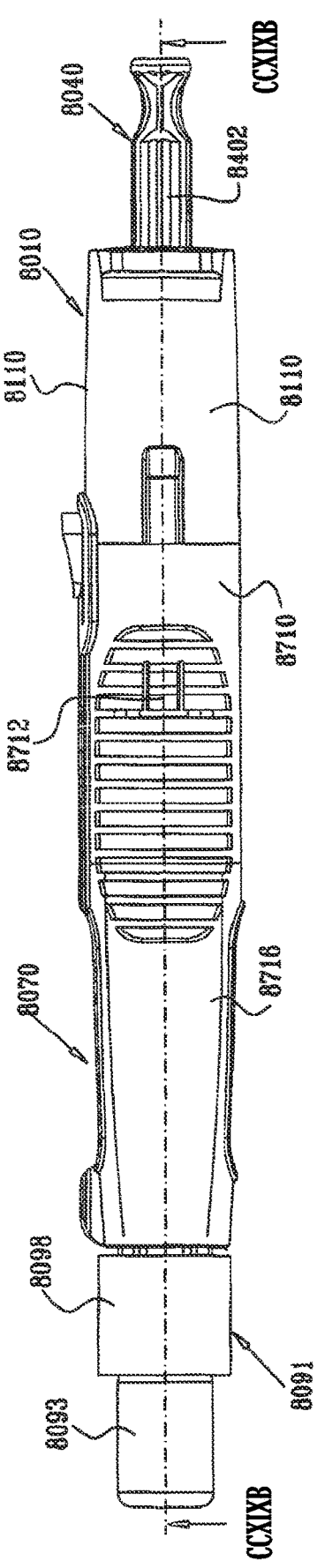

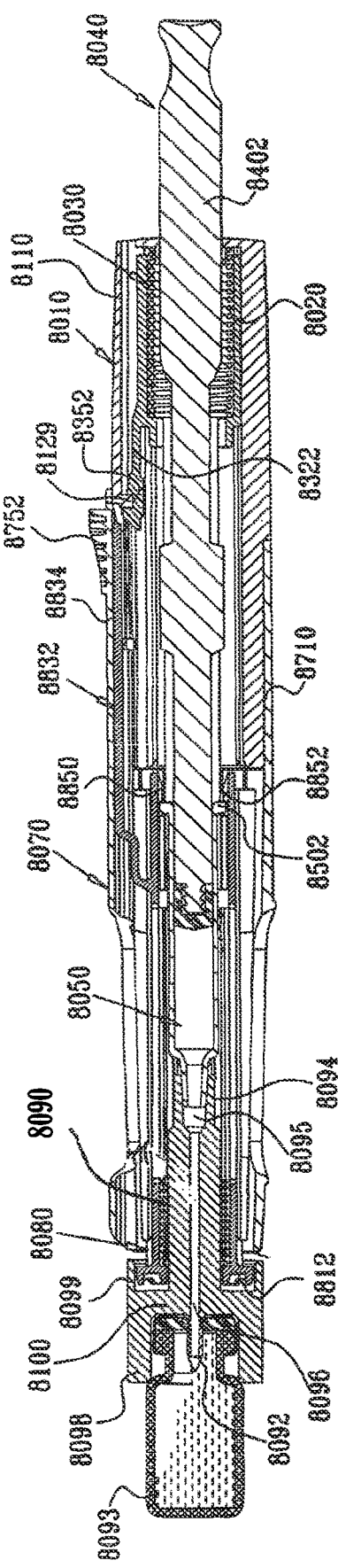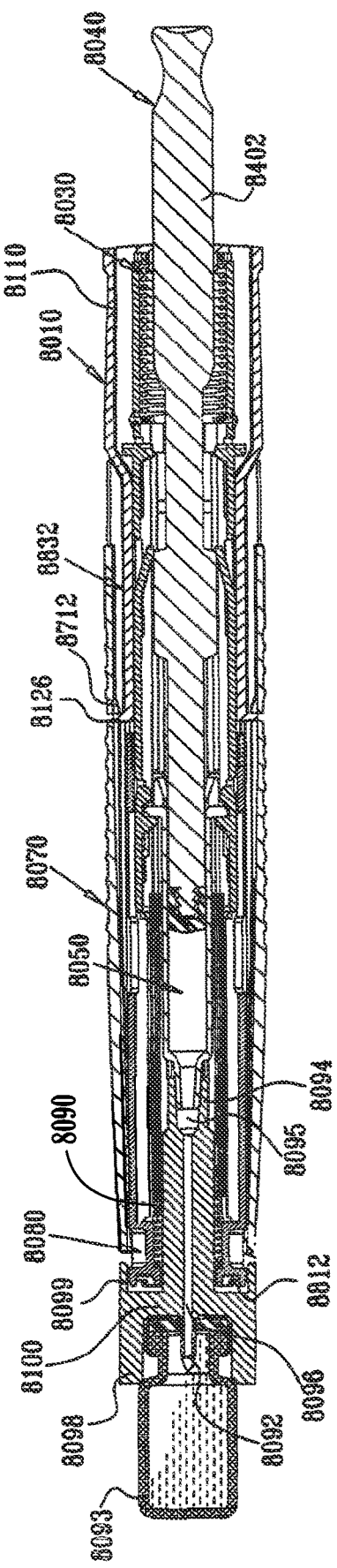

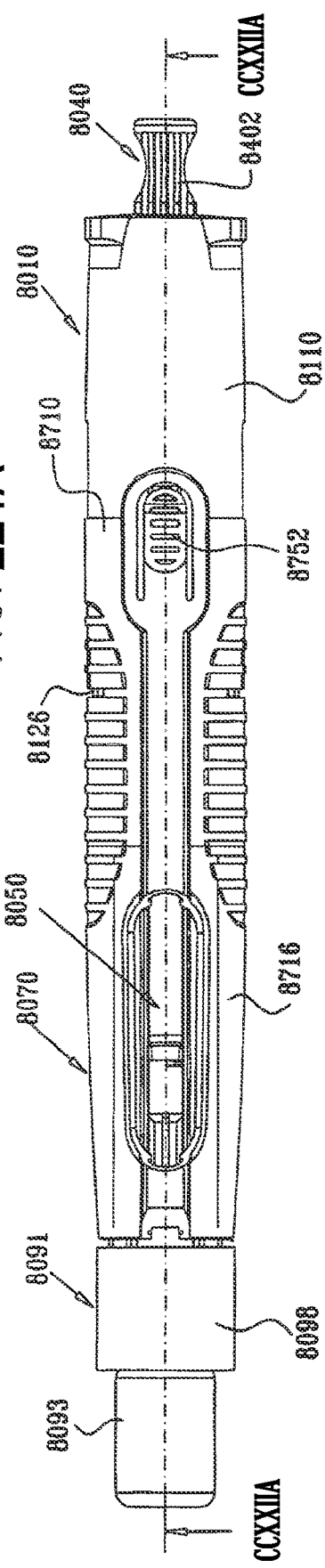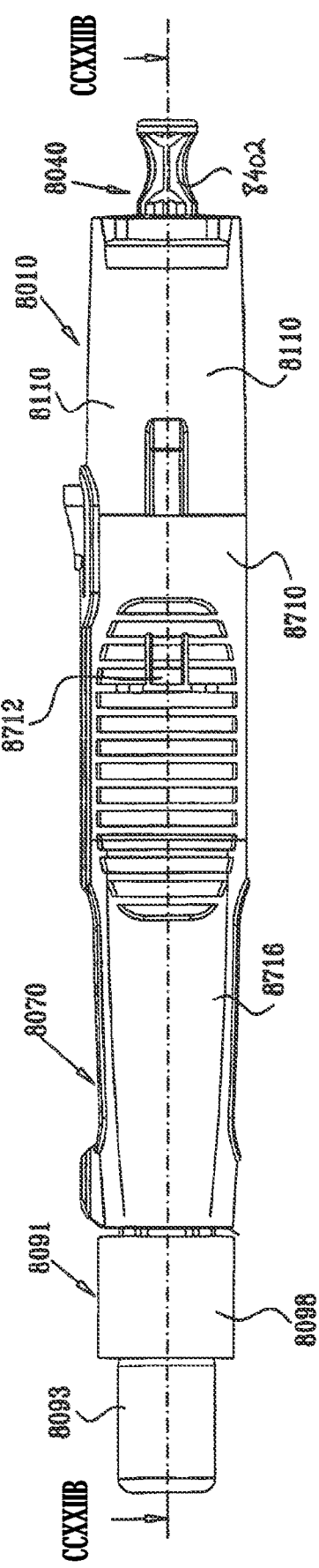

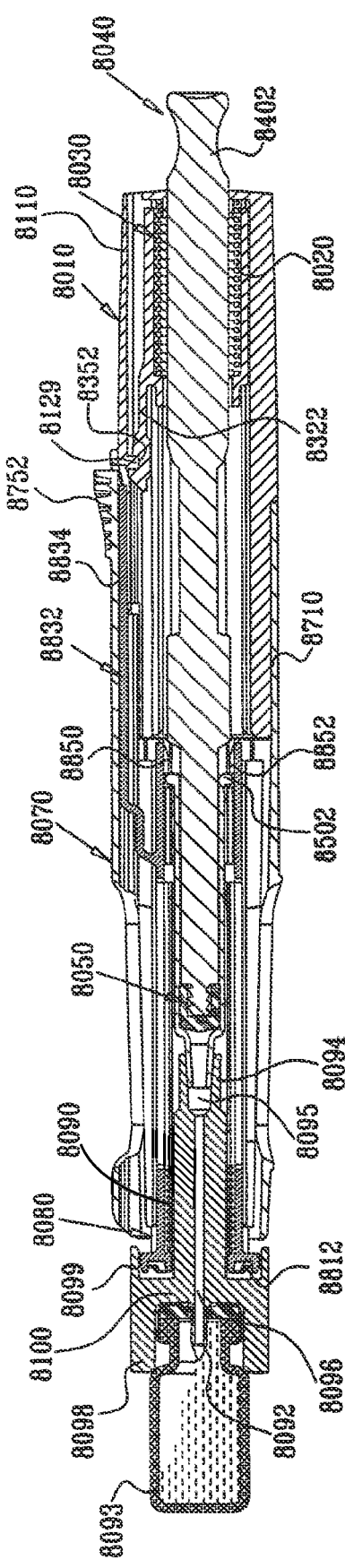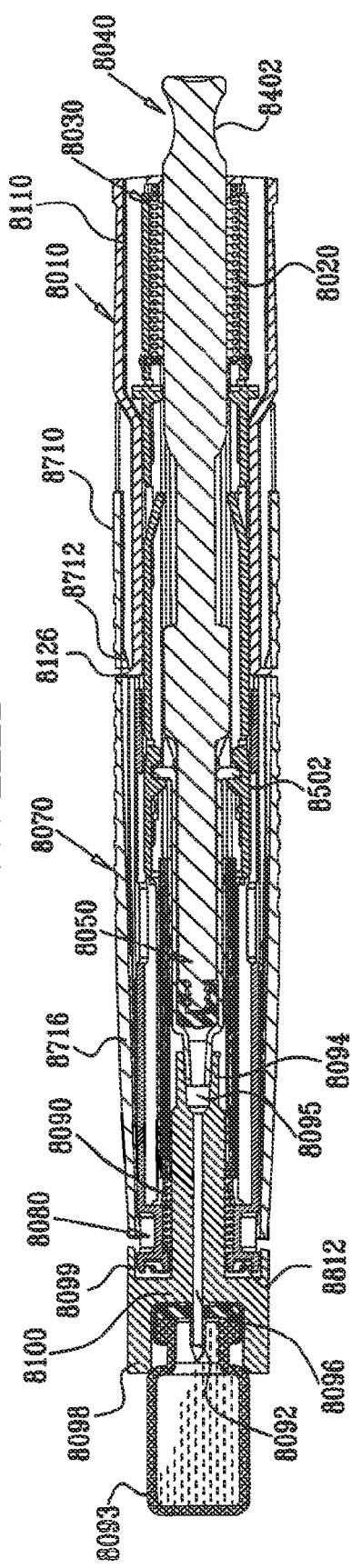

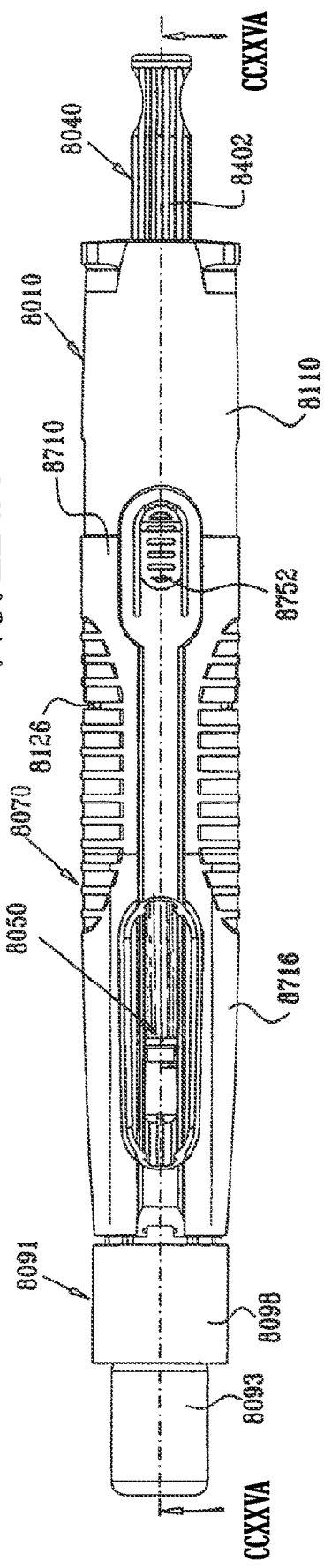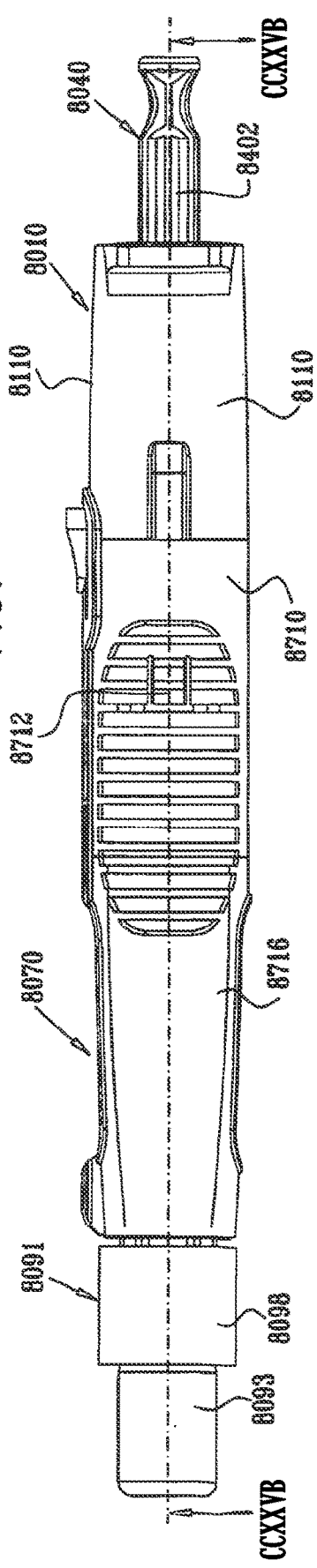

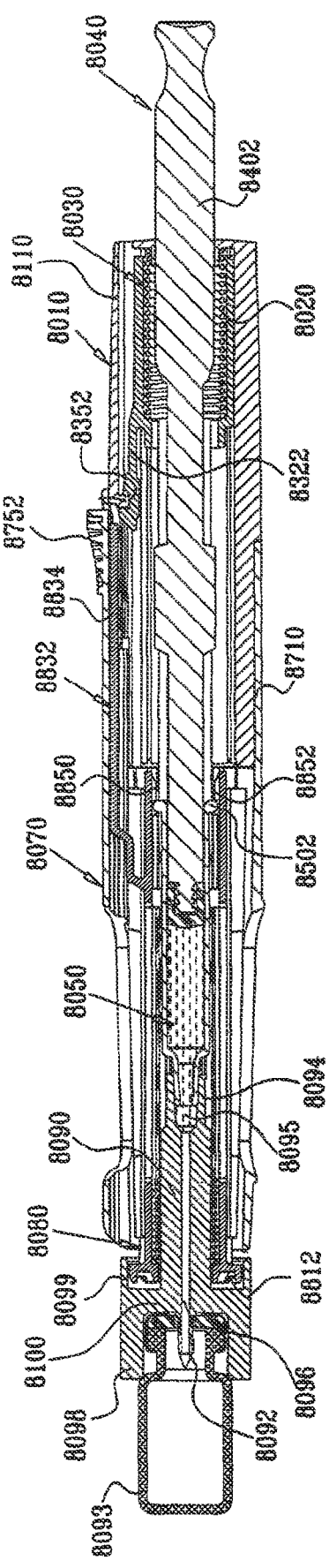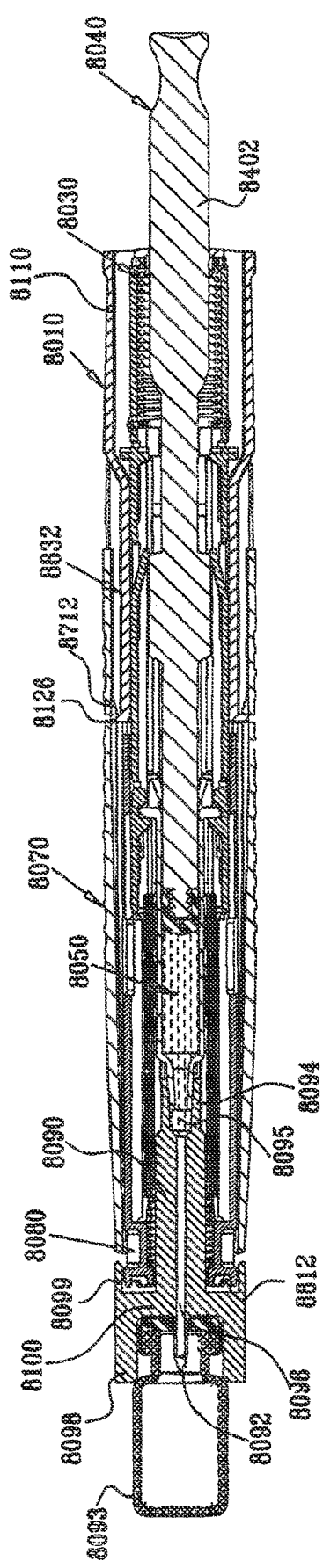

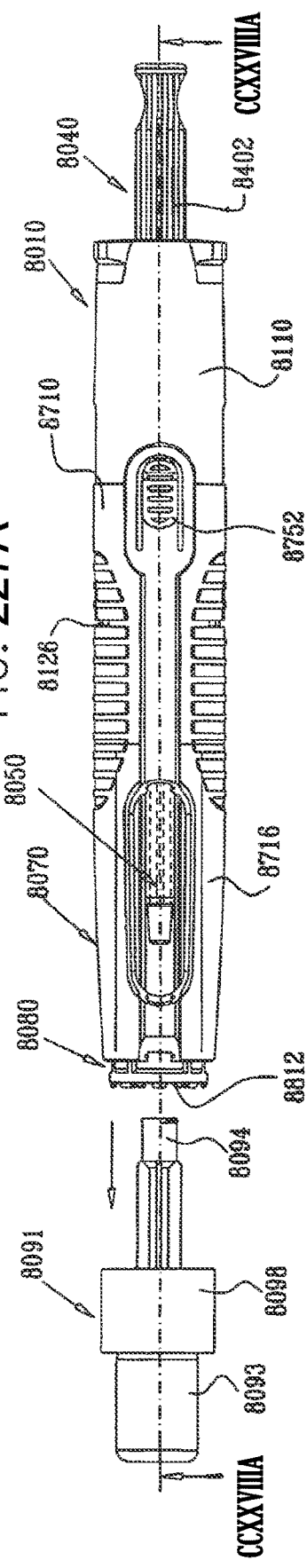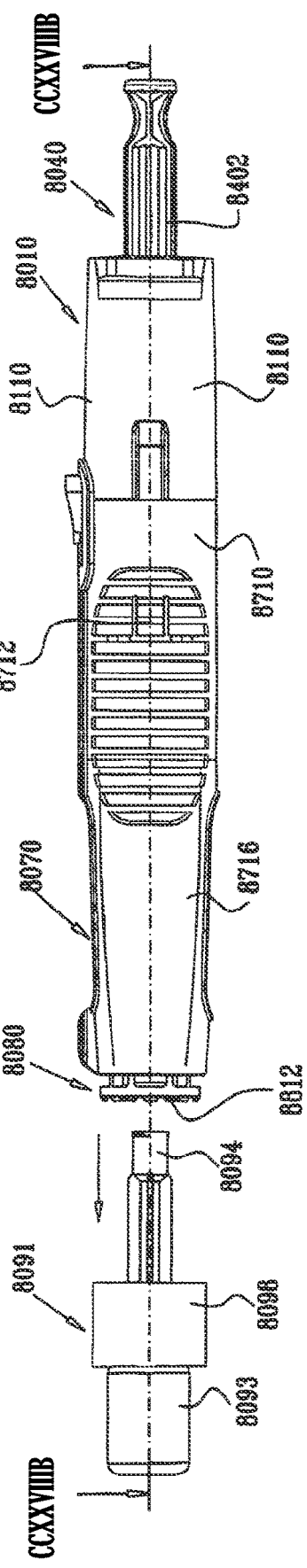

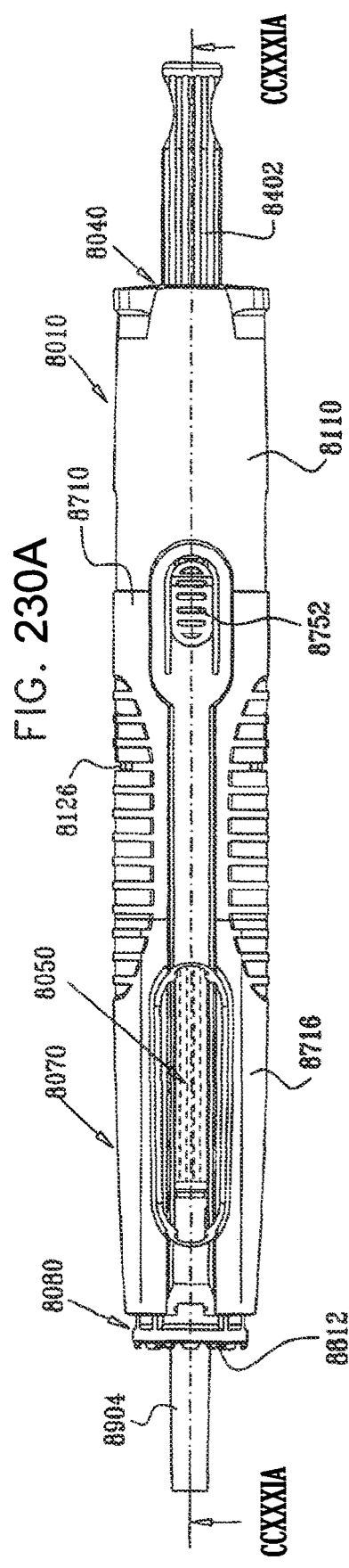
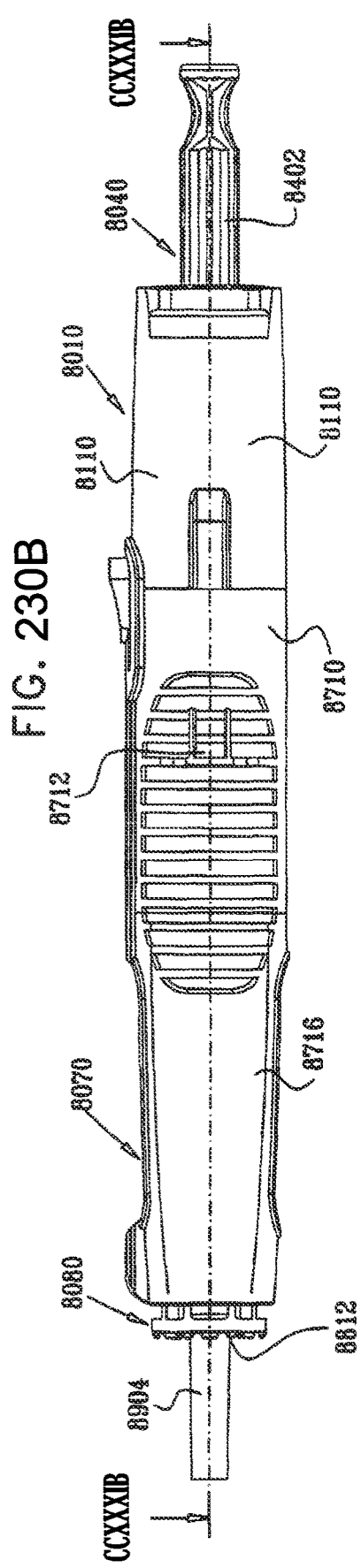

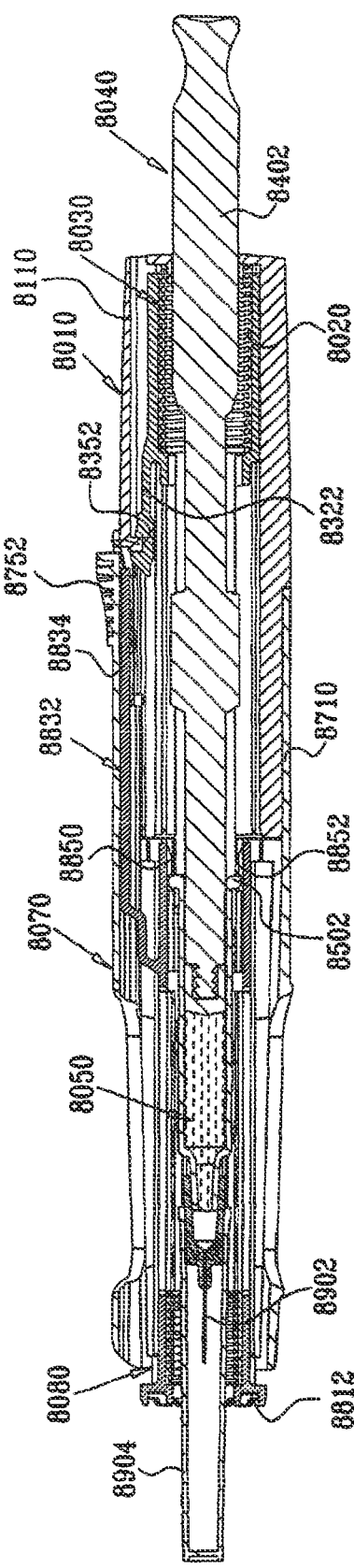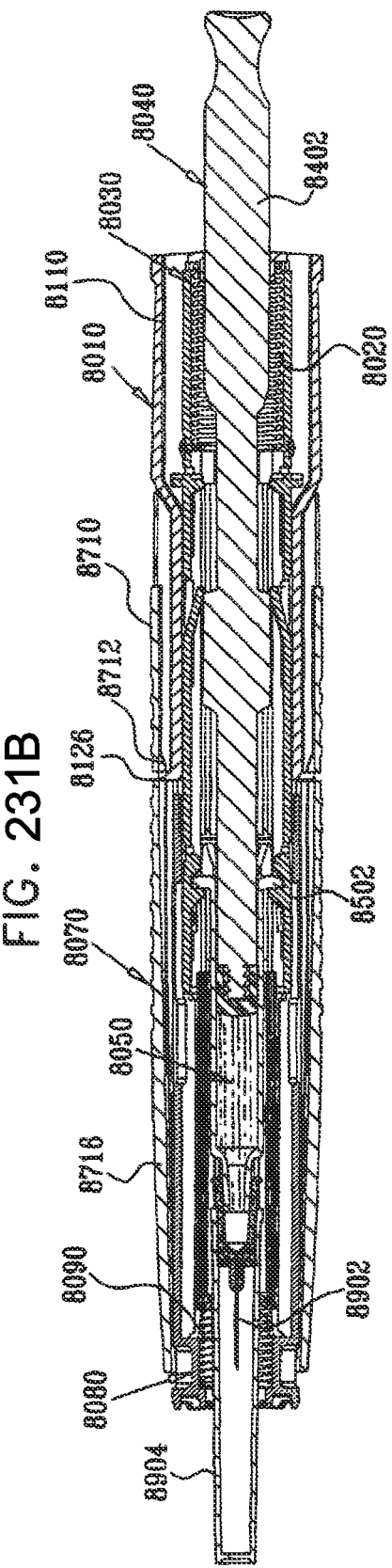

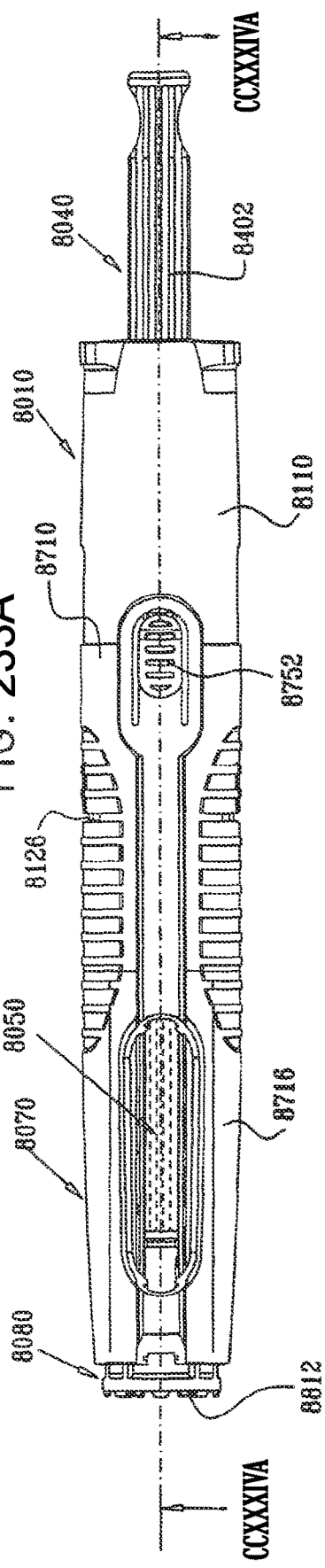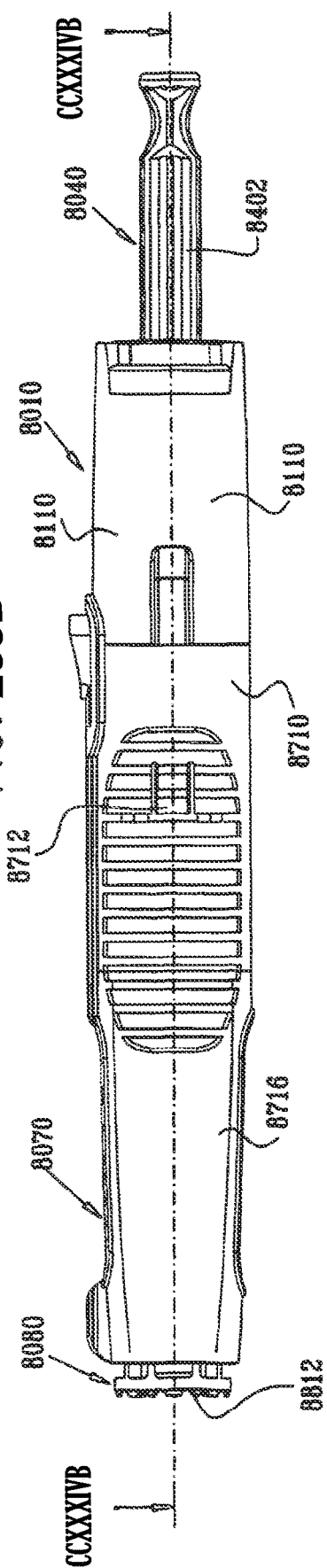

AUTOMATIC INJECTION DEVICE

REFERENCE TO RELATED APPLICATIONS

This application is a continuation application of U.S. patent application Ser. No. 13/611,899, filed on Sep. 12, 2012 which is a divisional application of U.S. patent application Ser. No. 10/572,214, filed on Sep. 15, 2006, entitled "AUTOMATIC INJECTION DEVICE", which is the U.S. National Phase application of International Patent Application No. PCT/IL2004/00851, filed on Sep. 15, 2004, the disclosures of which are hereby incorporated by reference.

FIELD OF THE INVENTION

The present invention relates to automatic injection devices for hypodermic syringes generally.

BACKGROUND OF THE INVENTION

The following U.S. patents are believed to represent the current state of the art: U.S. Pat. Nos. 4,474,572; 4,475,906; 4,484,910; 4,487,602; 4,505,710; 4,512,767; 4,515,590; 4,518,387; 4,529,401; 4,529,403; 4,530,695; 4,534,759; 4,547,189; 4,553,962; 4,573,970; 4,573,976; 4,578,061; 4,578,064; 4,580,561; 4,592,744; 4,594,073; 4,596,558; 4,597,753; 4,600,403; 4,601,708; 4,613,328; 4,620,540; 4,620,847; 4,624,660; 4,650,468; 4,658,830; 4,659,326; 4,664,651; 4,664,654; 4,666,436; 4,672,967; 4,681,565; 4,687,465; 4,687,467; 4,689,042; 4,699,614; 4,710,170; 4,723,937; 4,735,618; 4,738,663; 4,743,234; 4,744,955; 4,745,907; 4,747,829; 4,747,831; 4,753,636; 4,755,169; 4,758,227; 4,758,230; 4,758,231; 4,766,908; 4,767,407; 4,767,413; 4,770,655; 4,781,683; 4,781,685; 4,781,688; 4,784,640; 4,787,384; 4,787,893; 4,790,823; 4,790,827; 4,795,432; 4,795,433; 4,798,587; 4,799,921; 4,804,370; 4,808,169; 4,813,937; 4,813,940; 4,820,275; 4,820,286; 4,826,484; 4,826,489; 4,826,490; 4,828,548; 4,832,682; 4,832,693; 4,834,704; 4,834,718; 4,842,598; 4,846,811; 4,850,961; 4,850,968; 4,850,971; 4,850,976; 4,850,977; 4,850,994; 4,861,338; 4,863,427; 4,863,435; 4,863,436; 4,865,592; 4,874,372; 4,874,382; 4,883,466; 4,883,472; 4,886,499; 4,887,998; 4,892,107; 4,892,523; 4,894,054; 4,894,055; 4,898,589; 4,900,303; 4,900,307; 4,900,311; 4,902,279; 4,904,242; 4,906,236; 4,908,022; 4,909,794; 4,909,795; 4,911,706; 4,913,702; 4,915,702; 4,917,672; 4,919,146; 4,919,657; 4,923,443; 4,923,445; 4,927,414; 4,929,237; 4,929,241; 4,931,040; 4,932,944; 4,932,946; 4,932,947; 4,935,013; 4,935,014; 4,936,830; 4,941,879; 4,944,723; 4,944,725; 4,946,441; 4,950,240; 4,950,241; 4,950,250; 4,950,252; 4,955,866; 4,955,868; 4,955,869; 4,955,870; 4,961,728; 4,966,589; 4,966,592; 4,966,593; 4,973,310; 4,973,317; 4,976,704; 4,988,335; 4,988,339; 4,994,045; 4,998,921; 4,998,922; 5,000,736; 5,000,737; 5,002,548; 5,007,903; 5,011,475; 5,015,240; 5,017,187; 5,019,043; 5,019,044; 5,019,047; 5,019,048; 5,021,059; 5,024,665; 5,026,349; 5,030,208; 5,034,003; 5,037,306; 5,037,382; 5,037,393; 5,037,400; 5,041,094; 5,042,977; 5,045,066; 5,047,016; 5,049,133; 5,049,136; 5,053,010; 5,053,018; 5,055,102; 5,057,086; 5,057,089; 5,059,180; 5,059,185; 5,061,249; 5,061,251; 5,064,419; 5,067,490; 5,067,948; 5,071,353; 5,080,104; 5,084,027; 5,084,029; 5,084,030; 5,085,640; 5,085,641; 5,085,642; 5,088,986; 5,088,988; 5,092,843; 5,092,851; 5,092,852; 5,092,853; 5,098,382; 5,098,400; 5,098,401; 5,102,393; 5,102,397; 5,104,378; 5,104,380; 5,104,384; 5,104,385; 5,106,370; 5,106,372; 5,106,379; 5,108,378; 5,108,379; 5,112,307; 5,112,316; 5,114,404; 5,120,310; 5,120,314; 5,120,321; 5,122,118; 5,122,124; 5,125,898; 5,125,899; 5,127,910; 5,135,507; 5,135,510; 5,137,515; 5,137,516; 5,141,496; 5,143,414; 5,147,311; 5,147,326; 5,147,327; 5,149,323; 5,152,751; 5,156,599; 5,160,326; 5,163,916; 5,163,917; 5,163,918; 5,167,632; 5,167,641; 5,169,389; 5,169,392; 5,176,641; 5,176,655; 5,176,656; 5,176,657; 5,183,468; 5,183,469; 5,188,614; 5,190,526; 5,193,552; 5,195,982; 5,195,983; 5,195,985; 5,199,952; 5,201,708; 5,201,710; 5,205,826; 5,205,827; 5,207,646; 5,207,699; 5,209,739; 5,211,628; 5,211,629; 5,215,524; 5,215,533; 5,215,534; 5,215,535; 5,215,536; 5,217,437; 5,219,338; 5,221,262; 5,222,943; 5,222,947; 5,222,974; 5,224,936; 5,226,882; 5,228,883; 5,232,457; 5,232,458; 5,238,654; 5,242,388; 5,242,401; 5,242,416; 5,242,420; 5,246,428; 5,250,031; 5,256,152; 5,257,976; 5,261,894; 5,263,933; 5,267,961; 5,267,963; 5,269,761; 5,269,762; 5,269,766; 5,273,532; 5,273,538; 5,273,539; 5,273,541; 5,273,544; 5,279,554; 5,279,566; 5,279,577; 5,279,579; 5,279,581; 5,279,582; 5,279,583; 5,279,590; 5,282,793; 5,282,822; 5,282,827; 5,284,479; 5,290,233; 5,290,239; 5,290,240; 5,290,254; 5,292,314; 5,295,963; 5,295,965; 5,295,972; 5,295,973; 5,295,974; 5,295,975; 5,300,029; 5,300,030; 5,300,040; 5,300,045; 5,304,137; 5,304,138; 5,306,251; 5,306,258; 5,308,332; 5,311,841; 5,312,353; 5,312,366; 5,312,368; 5,312,370; 5,312,371; 5,312,372; 5,314,503; 5,318,538; 5,320,609; 5,322,517; 5,324,265; 5,328,475; 5,328,482; 5,328,484; 5,330,430; 5,334,149; 5,334,158; 5,334,173; 5,336,180; 5,336,187; 5,336,199; 5,338,303; 5,338,311; 5,342,310; 5,342,320; 5,344,407; 5,344,408; 5,346,475; 5,346,480; 5,346,481; 5,348,544; 5,352,200; 5,352,202; 5,352,203; 5,354,287; 5,356,387; 5,358,489; 5,360,410; 5,364,362; 5,364,370; 5,366,447; 5,368,568; 5,368,570; 5,368,571; 5,370,619; 5,370,626; 5,374,250; 5,378,240; 5,383,857; 5,385,550; 5,385,551; 5,385,557; 5,389,076; 5,389,085; 5,391,151; 5,391,183; 5,395,317; 5,395,337; 5,399,163; 5,401,246; 5,401,249; 5,401,251; 5,403,286; 5,403,287; 5,405,326; 5,405,327; 5,407,436; 5,409,466; 5,411,487; 5,415,638; 5,415,645; 5,415,648; 5,419,766; 5,419,773; 5,423,746; 5,425,715; 5,425,722; 5,429,611; 5,429,612; 5,429,613; 5,431,631; 5,431,632; 5,433,712; 5,445,618; 5,445,620; 5,451,210; 5,458,576; 5,458,580; 5,460,611; 5,462,531; 5,466,223; 5,468,227; 5,474,687; 5,478,314; 5,478,316; 5,478,328; 5,480,385; 5,480,387; 5,480,390; 5,482,039; 5,484,414; 5,486,163; 5,486,164; 5,487,732; 5,487,733; 5,487,734; 5,489,272; 5,492,536; 5,496,278; 5,501,672; 5,512,048; 5,512,050; 5,514,097; 5,514,107; 5,520,639; 5,520,649; 5,522,797; 5,522,812; 5,527,283; 5,527,284; 5,527,307; 5,529,189; 5,531,691; 5,531,692; 5,531,694; 5,531,704; 5,531,706; 5,533,975; 5,533,984; 5,536,243; 5,536,253; 5,536,257; 5,538,506; 5,538,508; 5,540,664; 5,540,666; 5,542,920; 5,542,927; 5,549,558; 5,549,568; 5,549,570; 5,549,572; 5,549,708; 5,558,648; 5,562,623; 5,562,624; 5,562,626; 5,562,631; 5,569,202; 5,569,203; 5,573,513; 5,575,770; 5,578,011; 5,578,014; 5,578,015; 5,582,591; 5,586,976; 5,591,133; 5,591,134; 5,591,138; 5,593,387; 5,593,390; 5,599,309; 5,599,313; 5,599,316; 5,599,318; 5,601,532; 5,601,535; 5,605,544; 5,609,577; 5,611,781; 5,611,782; 5,613,500; 5,613,951; 5,613,952; 5,615,771; 5,616,123; 5,616,132; 5,616,134; 5,616,135; 5,620,422; 5,620,425; 5,624,401; 5,624,405; 5,628,765; 5,630,803; 5,632,730; 5,632,733; 5,634,906; 5,634,909; 5,634,937; 5,637,092; 5,637,094; 5,643,220; 5,643,222; 5,647,851; 5,649,622; 5,651,774; 5,653,687; 5,653,688; 5,653,693; 5,656,031; 5,658,256; 5,658,257; 5,658,258; 5,658,259; 5,662,610; 5,662,617; 5,665,071; 5,665,075; 5,669,889; 5,672,155; 5,672,161;

5,681,291; 5,681,295; 5,688,240; 5,688,251; 5,693,016;
5,693,022; 5,693,023; 5,695,472; 5,704,911; 5,704,921;
5,707,393; 5,709,662; 5,709,667; 5,709,668; 5,713,866;
5,713,871; 5,713,872; 5,720,727; 5,725,498; 5,738,655;
5,741,223; 5,743,879; 5,743,887; 5,743,888; 5,743,891;
5,746,718; 5,749,854; 5,749,860; 5,755,692; 5,769,822;
5,769,827; 5,779,675; 5,779,677; 5,779,684; 5,788,677;
5,788,713; 5,792,107; 5,792,121; 5,792,122; 5,795,336;
5,797,885; 5,800,403; 5,807,334; 5,807,345; 5,807,352;
5,810,775; 5,810,784; 5,817,054; 5,817,070; 5,820,602;
5,823,997; 5,823,998; 5,827,293; 5,830,130; 5,836,911;
5,836,920; 5,843,036; 5,843,047; 5,848,990; 5,851,197;
5,853,390; 5,853,393; 5,855,839; 5,858,000; 5,865,227;
5,865,804; 5,868,711; 5,879,337; 5,882,342; 5,885,257;
5,891,052; 5,891,092; 5,891,097; 5,891,105; 5,897,508;
5,899,885; 5,899,886; 5,908,404; 5,908,408; 5,910,131;
5,911,706; 5,919,166; 5,921,959; 5,921,960; 5,921,961;
5,921,963; 5,921,964; 5,925,019; 5,928,188; 5,928,194;
5,928,205; 5,931,813; 5,938,638; 5,938,639; 5,941,850;
5,944,692; 5,944,693; 5,951,522; 5,954,699; 5,957,892;
5,957,895; 5,957,897; 5,960,797; 5,961,491; 5,971,953;
5,976,111; 5,980,487; 5,980,488; 5,980,491; 5,980,494;
5,984,899; 5,984,900; 5,989,219; 5,989,221; 5,993,417;
5,993,418; 5,997,500; 5,997,511; 5,997,513; 6,001,080;
6,007,474; 6,010,486; 6,010,487; 6,015,396; 6,015,438;
6,017,325; 6,022,337; 6,033,386; 6,033,387; 6,036,674;
6,039,713; 6,050,974; 6,050,977; 6,056,716; 6,056,724;
6,056,734; 6,063,040; 6,063,053; 6,066,115; 6,068,616;
6,074,360; 6,074,369; 6,074,370; 6,077,245; 6,080,135;
6,083,199; 6,083,200; 6,086,562; 6,086,569; 6,090,077;
6,090,078; 6,090,080; 6,093,172; 6,099,500; 6,099,503;
6,099,504; 6,102,844; 6,113,574; 6,117,112; 6,117,113;
6,126,637; 6,129,710; 6,142,972; 6,149,626; 6,149,629;
6,156,008; 6,156,010; 6,156,013; 6,156,015; 6,159,161;
6,159,181; 6,159,185; 6,171,284; 6,179,812; 6,183,444;
6,183,446; 6,186,980; 6,192,891; 6,193,695; 6,206,856;
6,206,857; 6,210,369; 6,217,550; 6,217,559; 6,221,044;
6,221,051; 6,221,052; 6,224,576; 6,228,054; 6,228,055;
6,235,006; 6,241,707; 6,241,708; 6,254,575; 6,254,580;
6,258,056; 6,261,264; 6,261,265; 6,267,748; 6,270,472;
6,270,481; 6,273,870; 6,280,399; 6,280,420; 6,280,421;
6,283,941; 6,293,925; 6,299,601; 6,309,374; 6,309,375;
6,312,409; 6,315,113; 6,319,233; 6,319,234; 6,322,536;
6,325,781; 6,325,789; 6,331,173; 6,332,875; 6,344,031;
6,356,783; 6,361,525; 6,368,303; 6,371,938; 6,379,336;
6,387,078; 6,402,716; 6,409,701; 6,409,703; 6,409,706;
6,412,490; 6,413,236; 6,413,237; 6,416,323; 6,416,497;
6,419,658; 6,428,463; 6,428,517; 6,432,035; 6,432,082;
6,432,087; 6,436,068; 6,440,098; 6,443,929; 6,447,480;
6,454,743; 6,458,105; 6,461,331; 6,461,333; 6,468,247;
6,475,194; 6,478,780; 6,482,176; 6,485,469; 6,485,474;
6,494,863; 6,500,155; 6,508,755; 6,511,454; 6,514,230;
6,517,516; 6,517,517; 6,524,278; 6,527,734; 6,527,742;
6,530,896; 6,530,904; 6,537,249; 6,537,252; 6,544,234;
6,547,764; 6,551,275; 6,551,276; 6,551,278; 6,554,798;
6,558,351; 6,558,357; 6,565,533; 6,565,538; 6,569,115;
6,572,584; 6,572,585; 6,575,939; 6,579,256; 6,582,405;
6,584,910; 6,585,690; 6,585,693; 6,585,702; 6,589,158;
6,592,508; 6,592,555; 6,592,556; 6,595,962; 6,599,268;
6,599,269; 6,599,272; 6,605,058; 6,605,067; 6,605,073;
6,607,508; 6,607,509; 6,613,019; 6,613,022; 6,616,630;
6,616,638; 6,616,639; 6,620,136; 6,620,137; 6,620,138;
6,623,455; 6,623,458; 6,623,459; 6,626,864; 6,629,957;
6,629,959; 6,632,198; 6,637,587; 6,638,248; 6,638,255;
6,641,561; 6,645,181; 6,652,482; 6,656,164; 6,659,975;
6,659,982; 6,663,593; 6,669,666; 6,673,034; 6,673,044;
6,673,049; 6,678,550; 6,679,863; 6,679,864; 6,685,676;
6,685,677; 6,689,091; 6,689,106; 6,689,107; 6,689,108;
6,692,470; 6,692,471; 6,699,218; 6,702,784; 6,706,011;
6,706,015; 6,706,019; 6,709,416; 6,712,787; 6,712,788;
6,716,191; 6,716,197; 6,716,198; 6,719,721; 6,719,728;
6,719,730; 6,723,068; 6,723,072; 6,726,655; 6,726,658;
6,726,661; 6,726,662; 6,730,059; 6,736,800; 6,740,059;
6,743,203; 6,749,833; 6,752,782; 6,752,784; 6,752,798;
6,761,706; 6,767,336; RE 33,585; RE 34,335; RE 34,936;
RE36,398; RE 36,447; RE 37,110; RE 37,252 and RE 37,487.

SUMMARY OF THE INVENTION

The present invention seeks to provide an improved automatic injection device.

There is thus provided in accordance with a preferred embodiment of the present invention an automatic injection device including a housing element, at least one resilient element arranged to be located within the housing element, a syringe including at least one syringe piston, a needle guard adapted for selectable positioning with respect to the housing element and a selectable driving element adapted, when actuated, to be driven by the at least one resilient element for initially displacing the syringe relative to the housing element from a non-penetration position to a penetration position and thereafter displacing the at least one syringe piston in the syringe to effect drug delivery and displacing the needle guard into a needle guarding position.

There is also provided in accordance with another preferred embodiment of the present invention an automatic injection device including a housing element, at least one resilient element arranged to be located within the housing element, a syringe including at least one syringe piston and a selectable driving element adapted, prior to being actuated, to retain the syringe in a non-penetration position and, when actuated, to be driven by the at least one resilient element for initially displacing the syringe relative to the housing element from a non-penetration position to a penetration position and thereafter displacing the at least one syringe piston in the syringe to effect drug delivery.

Preferably, the automatic injection device also includes a needle guard adapted for selectable positioning with respect to the housing element and wherein the selectable driving element is also operative for displacing the needle guard into a needle guarding position.

There is further provided in accordance with yet another preferred embodiment of the present invention an automatic injection device including a housing element, at least one resilient element arranged to be located within the housing element, a syringe including at least one syringe piston, a needle guard adapted for selectable positioning with respect to the housing element and a selectable driving element adapted, when actuated, to be driven by the at least one resilient element for displacing the syringe relative to the housing element from a non-penetration position to a penetration position, the needle guard being operative to permit actuation of the selectable driving element for displacing the syringe relative to the housing element from the non-penetration position to the penetration position.

Preferably, the selectable driving element is also operative when actuated, following suitable displacement of the needle guard relative to the housing element and resulting displacement of the syringe relative to the housing element from the non-penetration position to the penetration position, to be driven by the at least one resilient element for displacing the at least one syringe piston in the syringe to effect drug delivery.

There is yet further provided in accordance with still another preferred embodiment of the present invention an automatic injection device including a housing element, at least one resilient element arranged to be located within the housing element, a syringe including at least one syringe piston, a selectable driving element adapted, when actuated, to be driven by the at least one resilient element for initially displacing the syringe relative to the housing element from a non-penetration position to a penetration position and a motion damper operative to limit impact on the syringe produced by motion of the selectable driving element.

Preferably, the selectable driving element is also operative for displacing the at least one syringe piston in the syringe to effect drug delivery and displacing the needle guard into a needle guarding position.

Preferably, the motion damper is operative to limit impact on the at least one syringe piston produced by motion of the selectable driving element. Additionally or alternatively, the motion damper is operative to limit impact on a flange of the syringe produced by motion of the selectable driving element.

Preferably, the motion damper includes at least one elastomeric element. Additionally, the at least one elastomeric element is operative to damp relative axial motion between the housing element and the selectable driving element. Additionally or alternatively, relative axial motion between the at least one elastomeric element and a surface of varying cross-sectional area produces an extent of damping which varies with the relative axial positions of the housing element and the selectable driving element.

Preferably, the motion damper provides decreasing damping as the selectable driving element moves forwardly relative to the housing element. Additionally, the decreasing damping is produced by engagement of the at least one elastomeric element with a surface of decreasing cross-sectional area as a function of forward displacement of the selectable driving element relative to the housing element.

There is still further provided in accordance with yet another preferred embodiment of the present invention an automatic injection device including a housing element, at least one resilient element arranged to be located within the housing element, a syringe including at least one syringe piston, a plunger operative for displacing the at least one syringe piston, the plunger extending in and rearwardly of the housing element and a selectable driving element adapted, when actuated, to be driven by the at least one resilient element for initially displacing the syringe relative to the housing element from a non-penetration position to a penetration position.

Preferably, the selectable driving element is also operative for displacing the at least one syringe piston in the syringe to effect drug delivery. Additionally or alternatively, the plunger is manually operable for displacing the at least one syringe piston.

In accordance with still another preferred embodiment of the present invention the automatic injection device also includes a vial adaptor adapted for operative association with the syringe and with a drug vial for effecting fluid transfer between the syringe and the vial.

There is further provided in accordance with another preferred embodiment of the present invention an automatic injection device including a housing element, a syringe including at least one syringe piston, a plunger operative for displacing the at least one syringe piston, the plunger extending in and rearwardly of the housing element and a selectable driving element adapted, when actuated, for initially displacing the syringe relative to the housing element from a non-penetration position to a penetration position and a vial adaptor adapted for operative association with the syringe and with a drug vial for effecting fluid transfer between the syringe and the vial.

There is even further provided in accordance with yet another preferred embodiment of the present invention an automatic injection device including a housing element, at least one resilient element arranged to be located within the housing element, a syringe and a needle guard adapted for positioning with respect to the syringe in a mutually locked orientation, whereby displacement of the needle guard relative to the housing requires corresponding displacement of the syringe There is still further provided in accordance with yet another preferred embodiment of the present invention an automatic injection device including a housing element, at least one resilient element arranged to be located within the housing element, a syringe and a needle guard adapted for positioning with respect to the syringe and with respect to the housing element in a mutually locked needle guarding orientation, whereby displacement of the needle guard in a first direction relative to the housing is prevented by engagement of the needle guard with the syringe and displacement of the needle guard in a second direction relative to the housing, opposite to the first direction, is prevented by engagement of the needle guard with the housing element.

Preferably, the housing element includes at least one window permitting contents of the syringe to be viewed from outside the housing element. In accordance with another preferred embodiment of the present invention the needle guard includes at least one window permitting contents of the syringe to be viewed from outside the needle guard. Additionally or alternatively, the housing element includes at least one transparent portion permitting contents of the syringe to be viewed from outside the housing element. Alternatively or additionally, the needle guard includes at least one transparent portion permitting contents of the syringe to be viewed from outside the needle guard.

There is yet further provided in accordance with another preferred embodiment of the present invention an automatic injection device including a housing element, at least one resilient element arranged to be located within the housing element, a syringe including at least one syringe piston, a plunger operative to selectably drive the at least one syringe piston in axial motion relative to the housing element and a selectable driving element threadably engaging the plunger and adapted, when actuated, to be driven by the at least one resilient element for initially axially displacing the syringe relative to the housing element from a non-penetration position to a penetration position and thereafter displacing the at least one syringe piston in the syringe to effect drug delivery, wherein manual rotation of the plunger relative to the selectable driving element also produces axial movement of the plunger.

There is further provided in accordance with yet another preferred embodiment of the present invention an automatic injection device including a housing element, at least one resilient element arranged to be located within the housing element, a syringe including at least one syringe piston, a plunger operative to selectably drive the at least one syringe piston in axial motion relative to the housing element and a selectable driving element adapted, when actuated, to be driven by the at least one resilient element for initially displacing the syringe relative to the housing element from a non-penetration position to a penetration position and at least partially coincidentally therewith engaging the plunger.

Preferably, the vial adaptor includes a rearward facing portion configured such that upon mounting of the vial adaptor, rearward movement of the needle guard is prevented.

There is still further provided in accordance with still another preferred embodiment of the present invention an automatic injection device including a housing element, a syringe including at least one syringe piston, a needle guard adapted for selectable positioning with respect to the housing element and a resilient selectable driving element adapted, when actuated, for displacing the syringe relative to the housing element from a non-penetration position to a penetration position, the needle guard being operative to permit actuation of the selectable driving element for displacing the syringe relative to the housing element from the non-penetration position to the penetration position.

There is even further provided in accordance with yet another preferred embodiment of the present invention an automatic injection device including a housing element, a syringe including at least one syringe piston, a needle guard adapted for selectable positioning with respect to the housing element and a selectable driving element adapted, when actuated, to be driven for displacing the syringe relative to the housing element from a non-penetration position to a penetration position, the needle guard being operative to permit displacing the syringe relative to the housing element from the non-penetration position to the penetration position.

BRIEF DESCRIPTION OF THE DRAWINGS

The present invention will be understood and appreciated more fully from the following detailed description, taken in conjunction with the drawings in which:

FIG. 2 is a simplified pictorial illustration of a rear housing element which forms part of the automatic injection device of FIG. 1;

FIG. 8 is a simplified pictorial illustration of a forward housing and actuator element which forms part of the automatic injection device of FIG. 1;

FIGS. 9A and 9B are respective top and side view simplified planar illustrations of the forward housing and actuator element of FIG. 8;

FIGS. 10A, 10B and 10C are sectional illustrations taken along respective section lines and directions XA-XA, XB-XB and XC-XC in FIGS. 9A and 9B;

FIG. 11 is a simplified pictorial illustration of a needle guard element which forms part of the automatic injection device of FIG. 1;

FIGS. 12A and 12B are respective top and side view simplified planar illustrations of the needle guard element of FIG. 11;

FIGS. 13A, 13B and 13C are sectional illustrations taken along respective section lines and directions XIIIA-XIIIA, XIIIB-XIIIB and XIIIC-XIIIC in FIGS. 12A and 12B;

FIGS. 14A, 14B, 14C, 14D, 14E, 14F, 14G, 14H and 14I are simplified pictorial illustration of various stages of typical use of the automatic injection device of FIG. 1;

FIG. 15 is a simplified assembled view illustration of the automatic injection device of FIGS. 1 and 14A in a pre-use operative orientation;

FIGS. 16A and 16B are respective top and side view simplified planar illustrations of the automatic injection device of FIG. 15;

FIGS. 17A and 17B are sectional illustrations taken along respective section lines and directions XVIIA-XVIIA and XVIIB-XVIIB in FIGS. 16A and 16B;

FIGS. 20A and 20B are sectional illustrations taken along respective section lines and directions XXA-XXA and XXB-XXB in FIGS. 19A and 19B;

FIGS. 22A and 22B are respective top and side view simplified planar illustrations of the automatic injection device of FIG. 21;

FIGS. 23A and 23B are sectional illustrations taken along respective section lines and directions XXIIIA-XXIIIA and XXIIIB-XXIIIB in FIGS. 22A and 22B;

FIG. 24 is a simplified pictorial illustration of the automatic injection device of FIGS. 1 and 14D in a needle penetration, pre-drug delivery operative orientation;

FIGS. 25A and 25B are respective top and side view simplified planar illustrations of the automatic injection device of FIG. 24;

FIGS. 26A and 26B are sectional illustrations taken along respective section lines and directions XXVIA-XXVIA and XXVIB-XXVIB in FIGS. 25A and 25B;

FIGS. 28A and 28B are respective top and side view simplified planar illustrations of the automatic injection device of FIG. 27;

FIGS. 29A and 29B are sectional illustrations taken along respective section lines and directions XXIXA-XXIXA and XXIXB-XXIXB in FIGS. 28A and 28B;

FIGS. 31A and 31B are respective top and side view simplified planar illustrations of the automatic injection device of FIG. 30;

FIGS. 32A and 32B are sectional illustrations taken along respective section lines and directions XXXIIA-XXXIIA and XXXIIB-XXXIIB in FIGS. 31A and 31B;

FIG. 33 is a simplified pictorial illustration of the automatic injection device of FIGS. 1 and 14G in its operation orientation as it is being disengaged from an injection site;

FIGS. 34A and 34B are respective top and side view simplified planar illustrations of the automatic injection device of FIG. 33;

FIGS. 35A and 35B are sectional illustrations taken along respective section lines and directions XXXVA-XXXVA and XXXVB-XXXVB in FIGS. 34A and 34B;

FIG. 36 is a simplified pictorial illustration of the automatic injection device of FIGS. 1 and 14H in a needle protected operational orientation;

FIGS. 37A and 37B are respective top and side view simplified planar illustrations of the automatic injection device of FIG. 36;

FIGS. 40A and 40B are respective top and side view simplified planar illustrations of the automatic injection device of FIG. 39;

FIGS. 41A and 41B are sectional illustrations taken along respective section lines and directions XLIA-XLIA and XLIB-XLIB in FIGS. 40A and 40B;

FIG. 42 is a simplified exploded view illustration of an automatic injection device constructed and operative in accordance with another preferred embodiment of the present invention;

FIGS. 45A and 45B are respective top and side view simplified planar illustrations of the main housing element of FIGS. 43A-44B;

FIGS. 46A, 46B and 46C are sectional illustrations taken along respective section lines and directions XLVIA-XLVIA, XLVIB-XLVIB and XLVIC-XLVIC in FIGS. 45A and 45B;

FIGS. 59A, 59B, 59C, 59D and 59E are simplified pictorial illustrations of various stages of typical use of the automatic injection device of FIG. 42;

FIGS. 61A and 61B are respective top and side view simplified planar illustrations of the automatic injection device of FIG. 60;

FIGS. 62A and 62B are sectional illustrations taken along respective section lines and directions LXIIA-LXIIA and LXIIB-LXIIB in FIGS. 61A and 61B;

FIGS. 64A and 64B are respective top and side view simplified planar illustrations of the automatic injection device of FIG. 63;

FIGS. 65A and 65B are sectional illustrations taken along respective section lines and directions LXVA-LXVA and LXVB-LXVB in FIGS. 64A and 64B;

FIGS. 67A and 67B are respective top and side view simplified planar illustrations of the automatic injection device of FIG. 66;

FIGS. 68A and 68B are sectional illustrations taken along respective section lines and directions LXVIIIA-LXVIIIA and LXVIIIB-LXVIIIB in FIGS. 67A and 67B;

FIG. 69 is a simplified pictorial illustration of the automatic injection device of FIGS. 42 and 59D in a post-drug delivery operative orientation;

FIGS. 70A and 70B are respective top and side view simplified planar illustrations of the automatic injection device of FIG. 69;

FIGS. 71A and 71B are sectional illustrations taken along respective section lines and directions LXXIA-LXXIA and LXXIB-LXXIB in FIGS. 70A and 70B;

FIGS. 73A and 73B are respective top and side view simplified planar illustrations of the automatic injection device of FIG. 72;

FIGS. 74A and 74B are sectional illustrations taken along respective section lines and directions LXXIVA-LXXIVA and LXXIVB-LXXIVB in FIGS. 73A and 73B;

FIG. 75 is a simplified exploded view illustration of an automatic injection device constructed and operative in accordance with yet another preferred embodiment of the present invention;

FIGS. 77A and 77B are respective top and side view simplified planar illustrations of the automatic injection device of FIG. 76;

FIGS. 78A and 78B are sectional illustrations taken along respective section lines and directions LXXVIIIA-LXXVIIIA and LXXVIIIB-LXXVIIIB in FIGS. 77A and 77B;

FIG. 79 is a simplified pictorial illustration of the automatic injection device of FIG. 75 in an actuatable operative orientation;

FIGS. 80A and 80B are respective top and side view simplified planar illustrations of the automatic injection device of FIG. 79;

FIGS. 81A and 81B are sectional illustrations taken along respective section lines and directions LXXXIA-LXXXIA and LXXXIB-LXXXIB in FIGS. 80A and 80B;

FIGS. 83A and 83B are respective top and side view simplified planar illustrations of the automatic injection device of FIG. 82;

FIGS. 84A and 84B are sectional illustrations taken along respective section lines and directions LXXXIVA-LXXXIVA and LXXXIVB-LXXXIVB in FIGS. 83A and 83B;

FIG. 85 is a simplified pictorial illustration of the automatic injection device of FIG. 75 in a post-drug delivery operative orientation;

FIGS. 86A and 86B are respective top and side view simplified planar illustrations of the automatic injection device of FIG. 85;

FIGS. 87A and 87B are sectional illustrations taken along respective section lines and directions LXXXVIIA-LXXXVIIA and LXXXVIIB-LXXXVIIB in FIGS. 86A and 86B;

FIG. 88 is a simplified pictorial illustration of the automatic injection device of FIG. 75 in post injection site disengagement operational orientation;

FIGS. 89A and 89B are respective top and side view simplified planar illustrations of the automatic injection device of FIG. 88;

FIGS. 90A and 90B are sectional illustrations taken along respective section lines and directions XCA-XCA and XCB-XCB in FIGS. 89A and 89B;

FIG. 91 is a simplified exploded view illustration of an automatic injection device constructed and operative in accordance with a further preferred embodiment of the present invention;

FIG. 92 is a simplified pictorial illustration of a rear housing element which forms part of the automatic injection device of FIG. 91;

FIGS. 93A and 93B are respective top and side view simplified planar illustrations of the rear housing element of FIG. 92;

FIGS. 94A, 94B and 94C are sectional illustrations taken along respective section lines and directions XCIVA-XCIVA, XCIVB-XCIVB and XCIVC-XCIVC in FIGS. 93A and 93B;

FIGS. 96A and 96B are respective top and side view simplified planar illustrations of the selectable driving assembly of FIG. 95;

FIGS. 97A, 97B and 97C are sectional illustrations taken along respective section lines and directions XCVIIA-XCVIIA, XCVIIB-XCVIIB and XCVIIC-XCVIIC in FIGS. 96A and 96B;

FIG. 104 is a simplified assembled view illustration of the automatic injection device of FIG. 91 in a pre-use operative orientation;

FIGS. 105A and 105B are respective top and side view simplified planar illustrations of the automatic injection device of FIG. 104;

FIGS. 106A and 106B are sectional illustrations taken along respective section lines and directions CVIA-CVIA and CVIB-CVIB in FIGS. 105A and 105B;

FIGS. 108A and 108B are respective top and side view simplified planar illustrations of the automatic injection device of FIG. 107;

FIGS. 109A and 109B are sectional illustrations taken along respective section lines and directions CIXA-CIXA and CIXB-CIXB in FIGS. 108A and 108B;

FIGS. 112A and 112B are sectional illustrations taken along respective section lines and directions CXIIA-CXIIA and CXIIB-CXIIB in FIGS. 111A and 111B;

FIGS. 114A and 114B are respective top and side view simplified planar illustrations of the automatic injection device of FIG. 113;

FIGS. 115A and 115B are sectional illustrations taken along respective section lines and directions CXVA-CXVA and CXVB-CXVB in FIGS. 114A and 114B;

FIGS. 117A and 117B are respective top and side view simplified planar illustrations of the automatic injection device of FIG. 116;

FIGS. 118A and 118B are sectional illustrations taken along respective section lines and directions CXVIIIA-CXVIIIA and CXVIIIB-CXVIIIB in FIGS. 117A and 117B;

FIG. 119 is a simplified pictorial illustration of the automatic injection device of FIG. 91 in an immediate post-drug delivery operational orientation;

FIGS. 120A and 120B are respective top and side view simplified planar illustrations of the automatic injection device of FIG. 119;

FIGS. 121A and 121B are sectional illustrations taken along respective section lines and directions CXXIA-CXXIA and CXXIB-CXXIB in FIGS. 120A and 120B;

FIG. 122 is a simplified pictorial illustration of the automatic injection device of FIG. 91 in a needle protected operational orientation;

FIGS. 123A and 123B are respective top and side view simplified planar illustrations of the automatic injection device of FIG. 122;

FIGS. 124A and 124B are sectional illustrations taken along respective section lines and directions CXXIVA-CXXIVA and CXXIVB-CXXIVB in FIGS. 123A and 123B;

FIG. 125 is a simplified pictorial illustration of the automatic injection device of FIG. 91 in a needle-guard push back misuse operational orientation;

FIGS. 126A and 126B are respective top and side view simplified planar illustrations of the automatic injection device of FIG. 125;

FIGS. 127A and 127B are sectional illustrations taken along respective section lines and directions CXXVIIA-CXXVIIA and CXXVIIB-CXXVIIB in FIGS. 126A and 126B;

FIG. 128 is a simplified exploded view illustration of an automatic injection device constructed and operative in accordance with a still further preferred embodiment of the present invention;

FIG. 129 is a simplified pictorial illustration of a rear housing element which forms part of the automatic injection device of FIG. 128;

FIGS. 130A and 130B are respective top and side view simplified planar illustrations of the rear housing element of FIG. 129;

Figure 128:
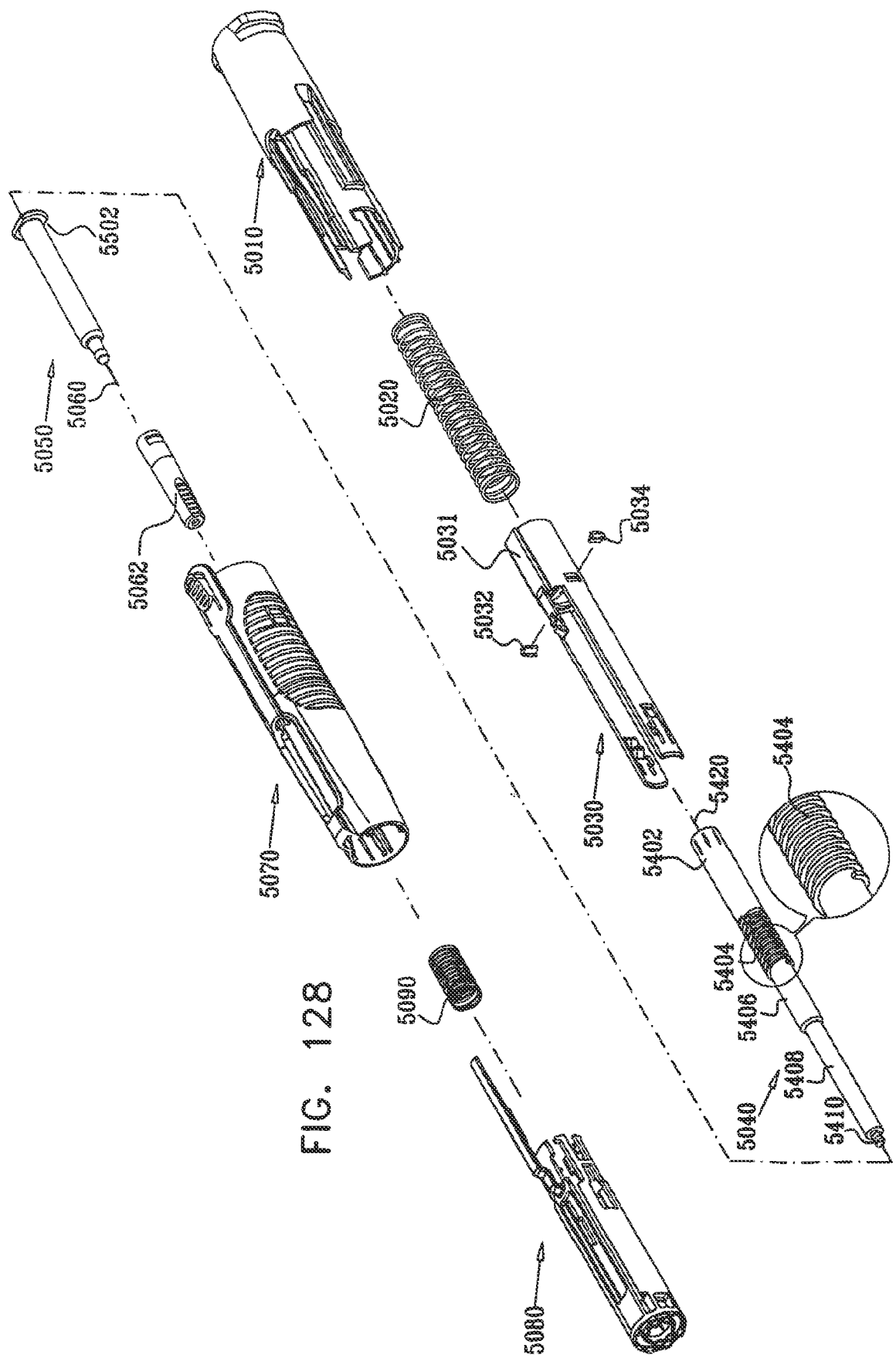
Figure 130A:
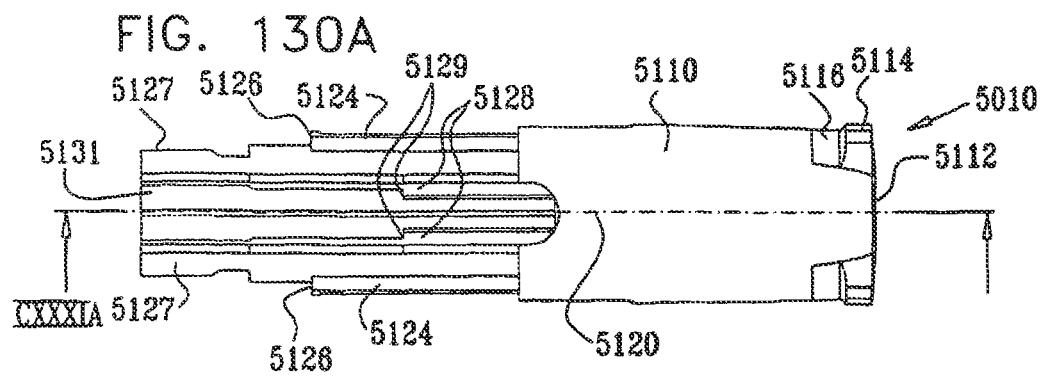
Figure 130B:
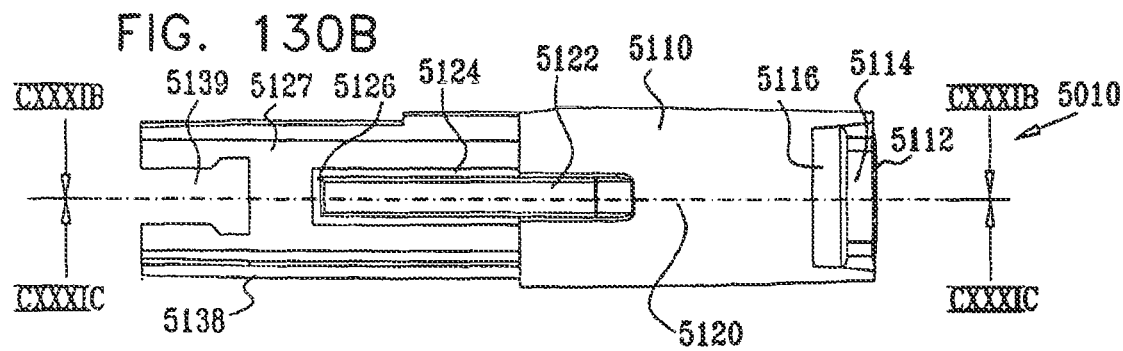
Figure 131A:
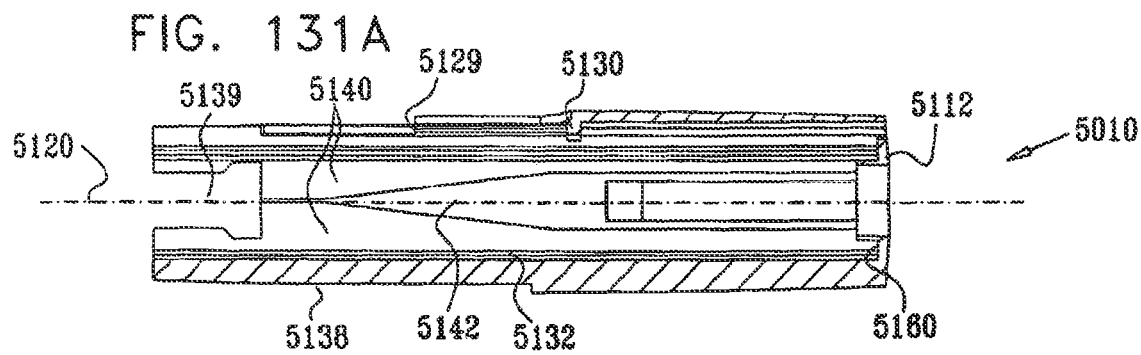
Figure 131B:
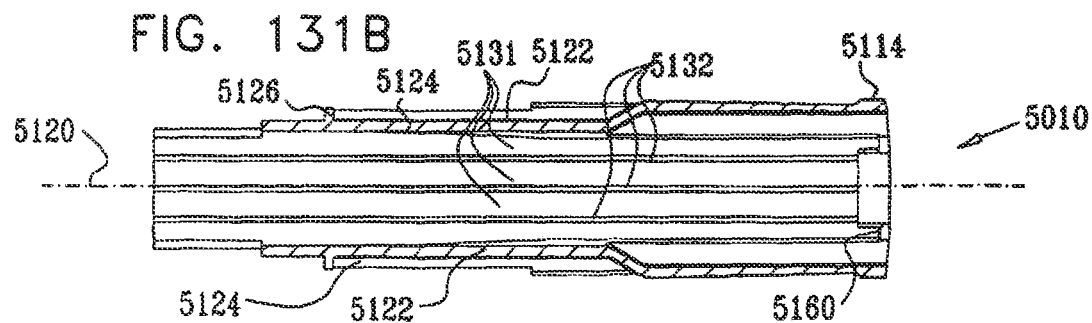
Figure 131C:
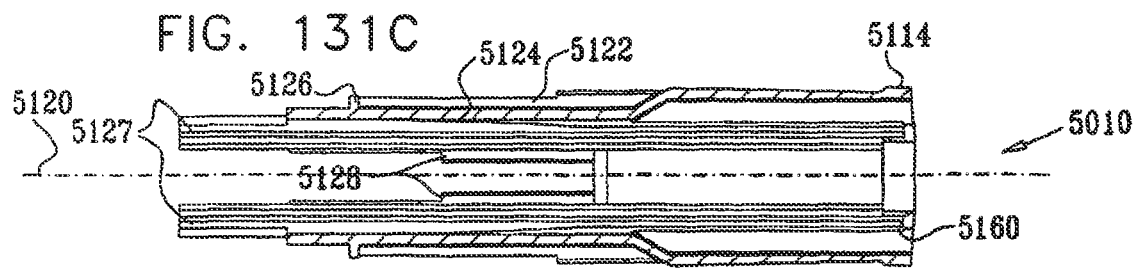
Figure 132:
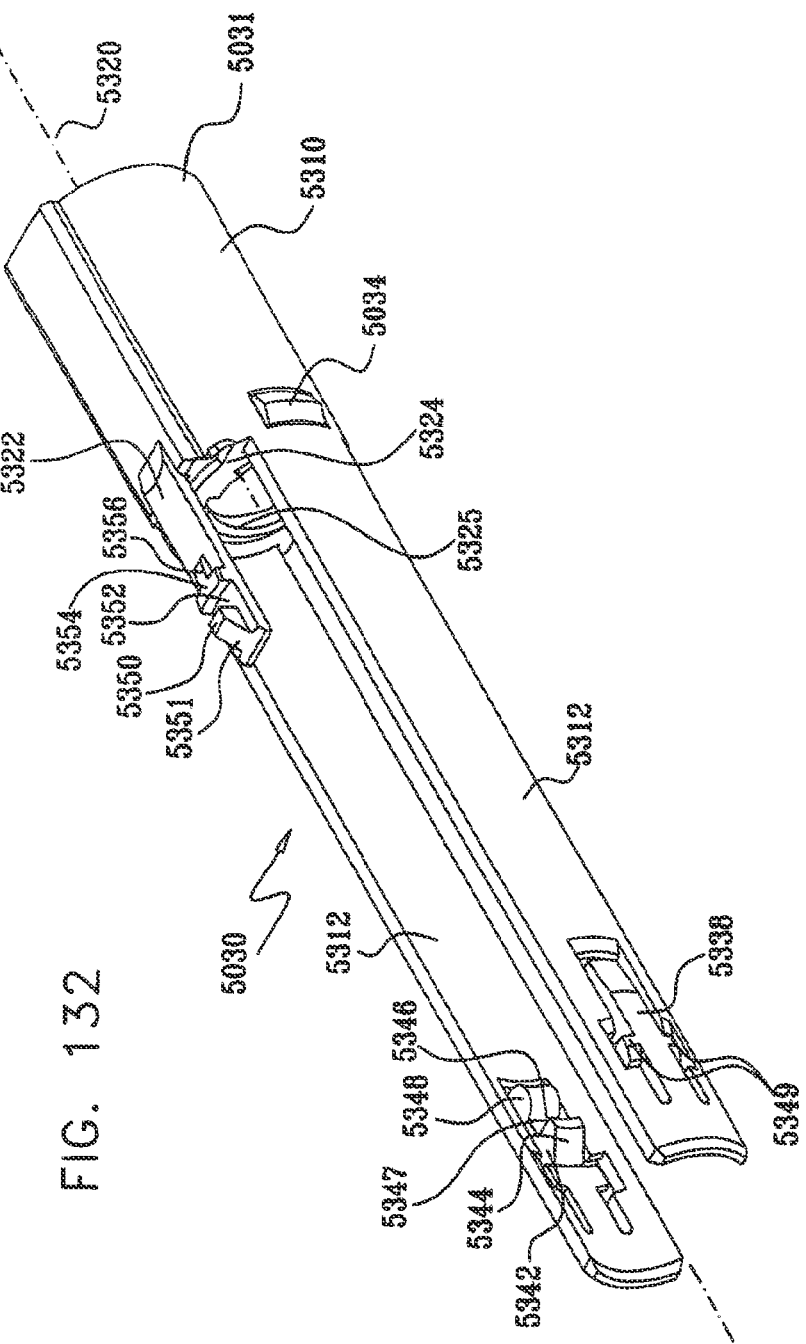
Figure 133A:
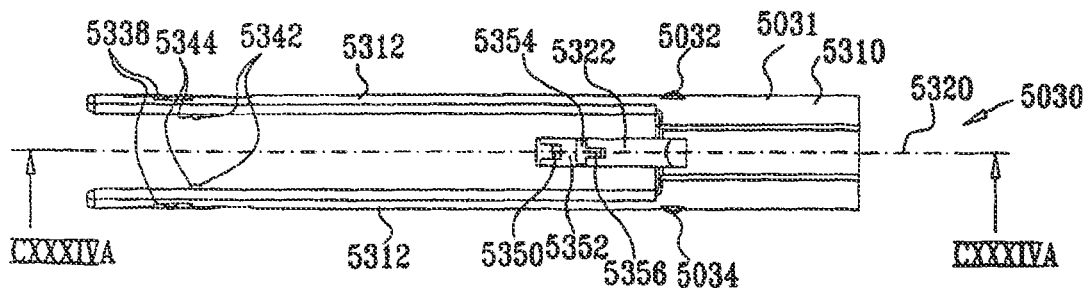
Figure 133B:
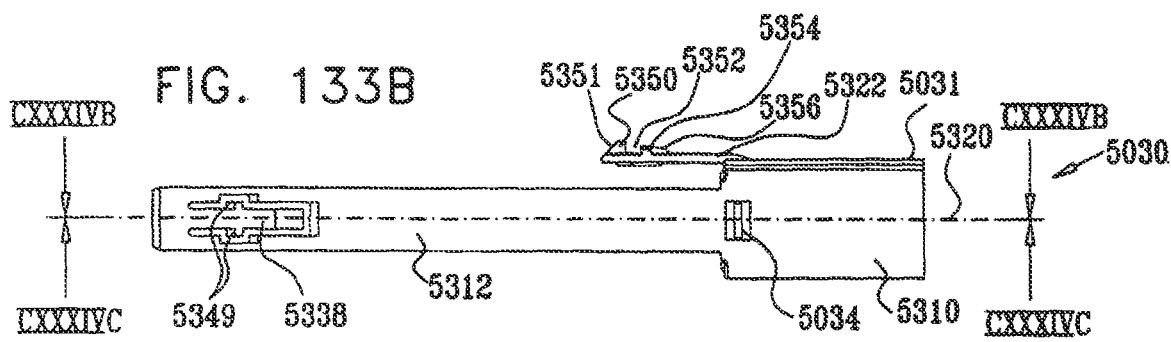
Figure 134A:
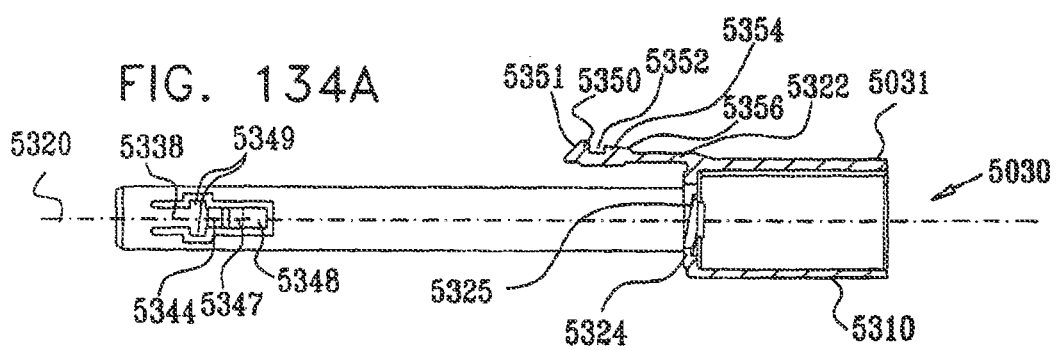
Figure 134B:
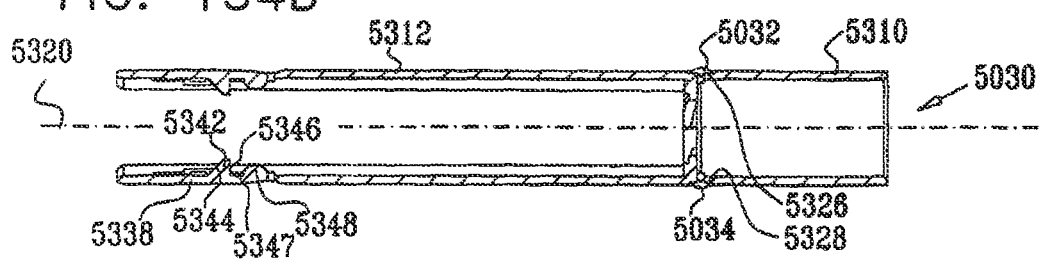
Figure 134C:
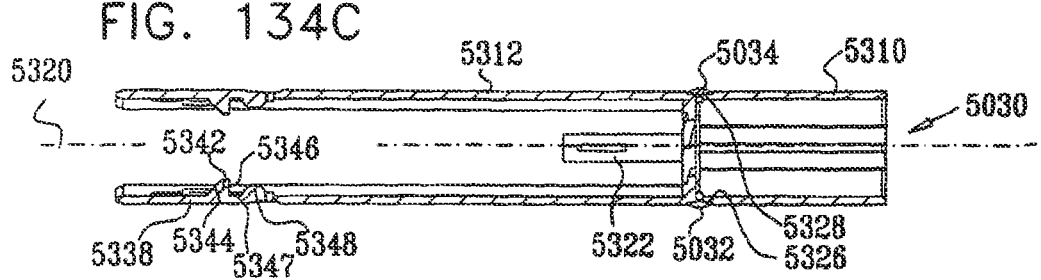
Figure 141A:
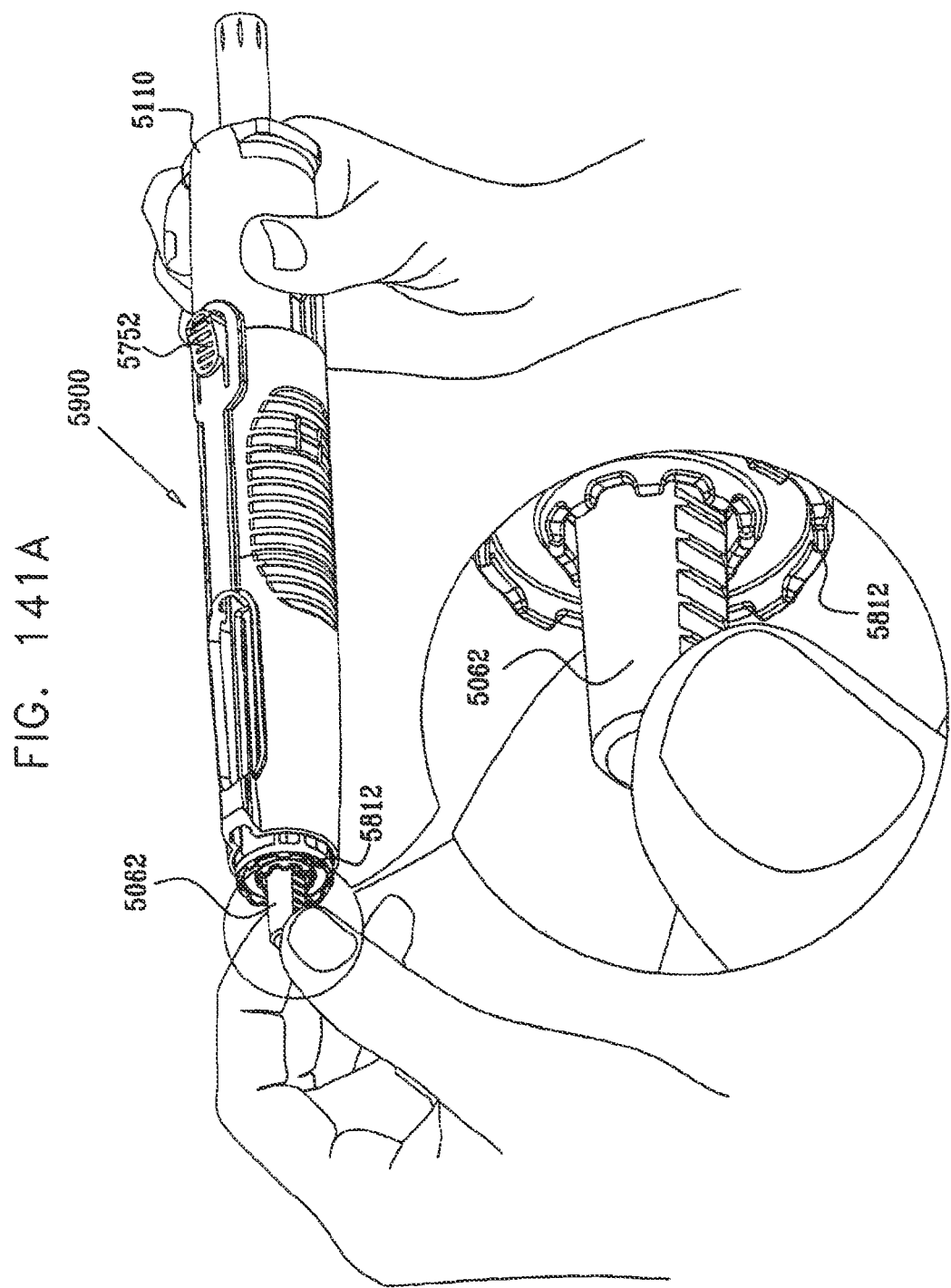
Figure 141B:
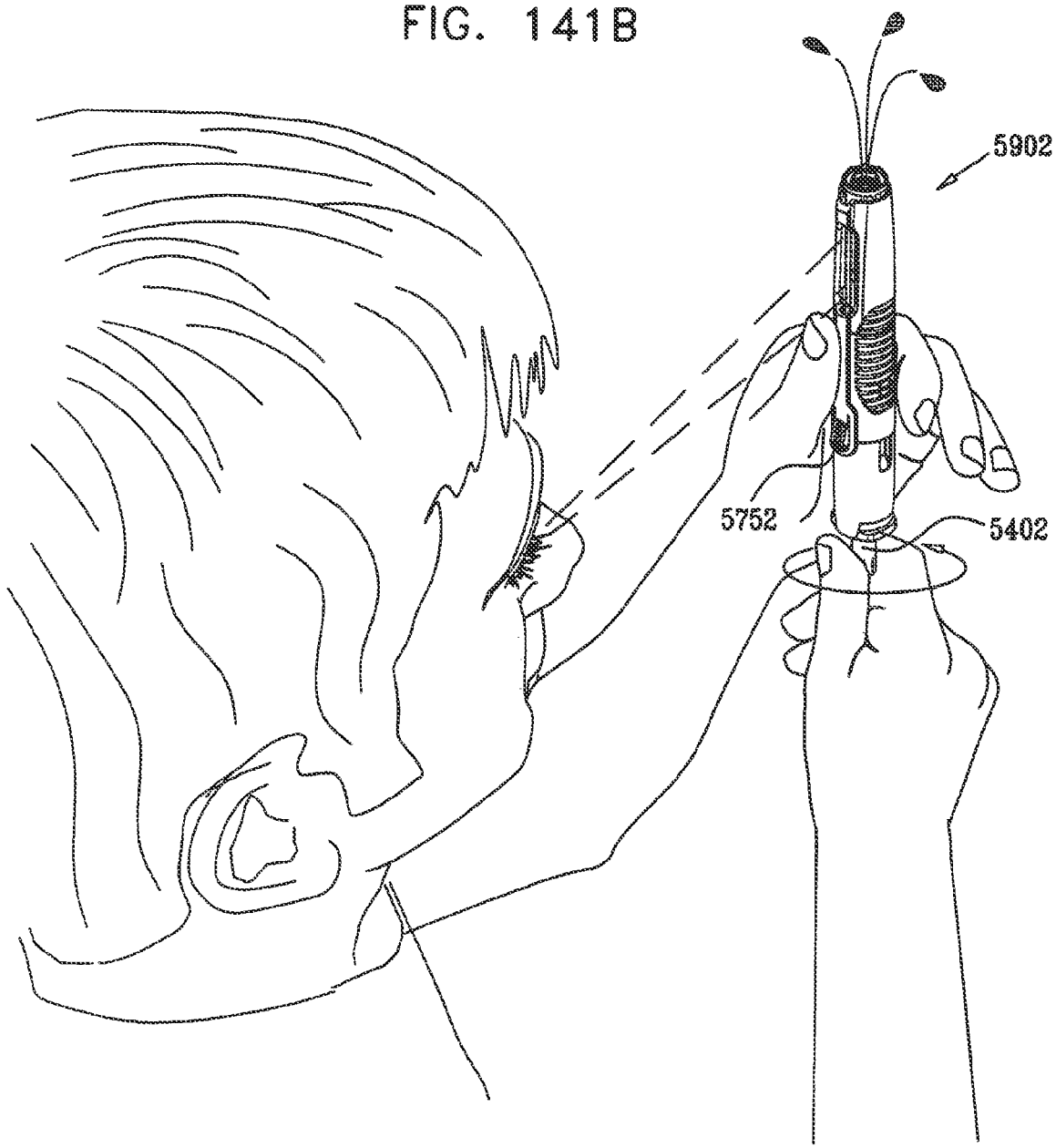
Figure 141C:
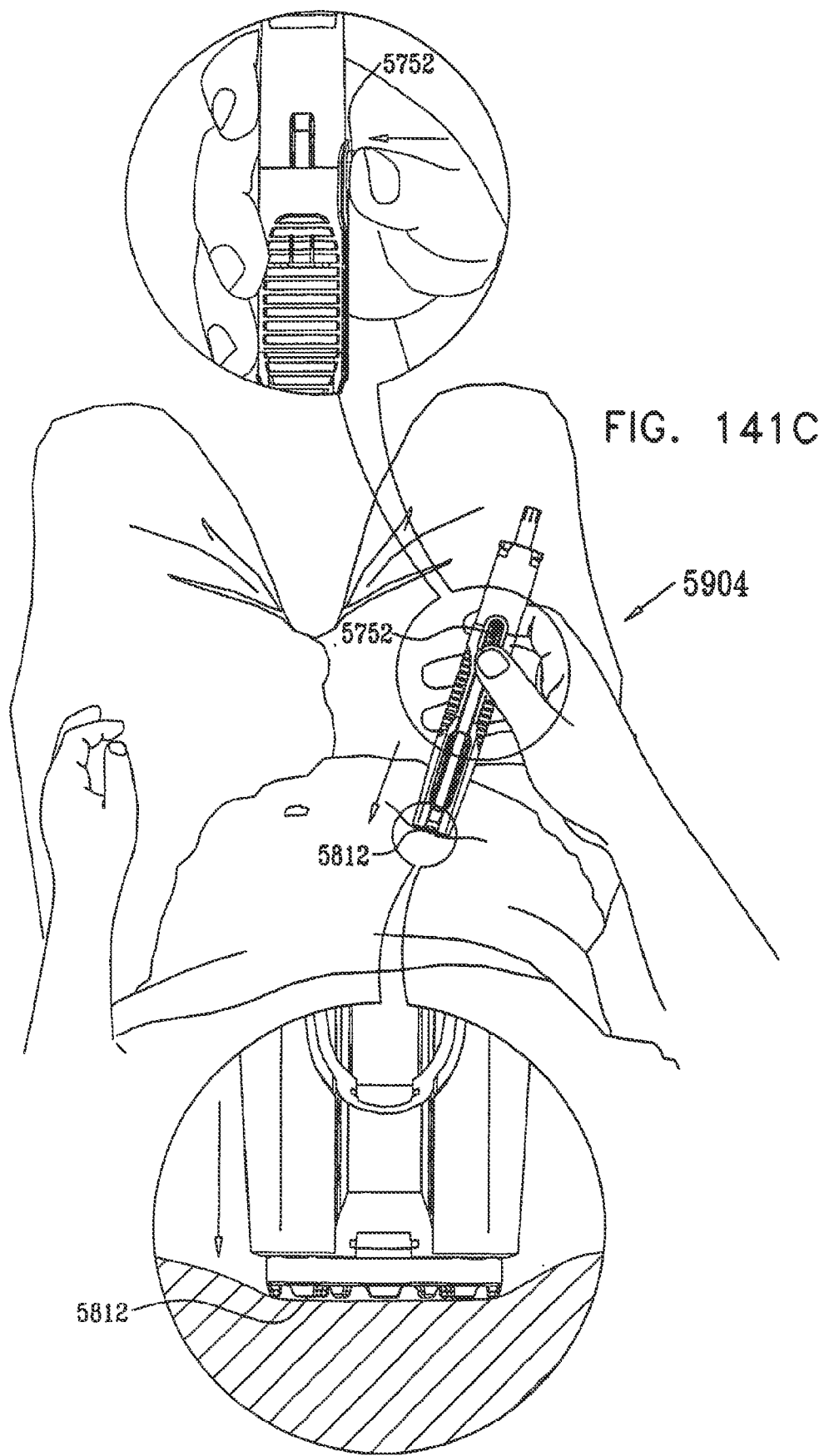
Figure 141D:
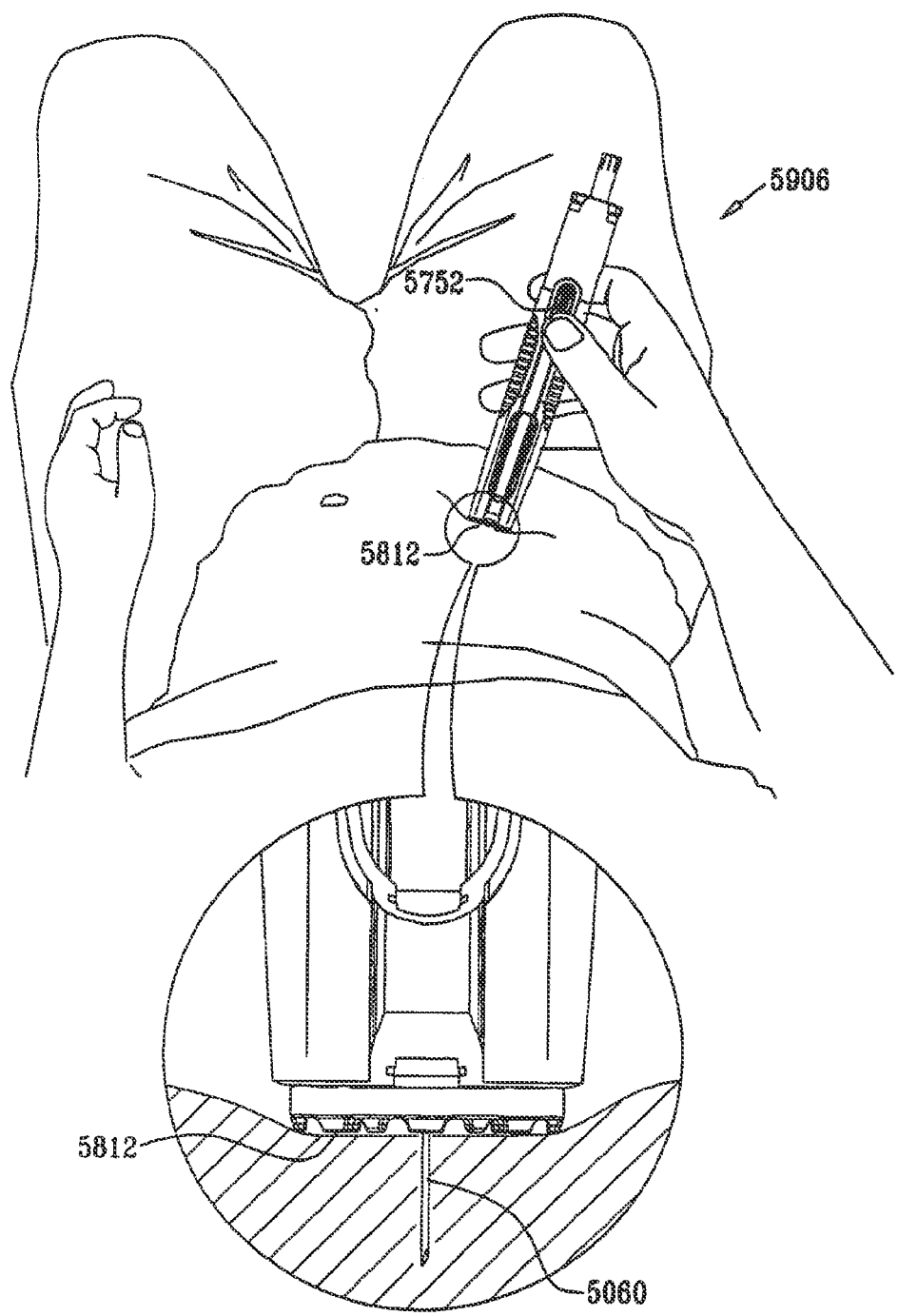
Figure 141E:
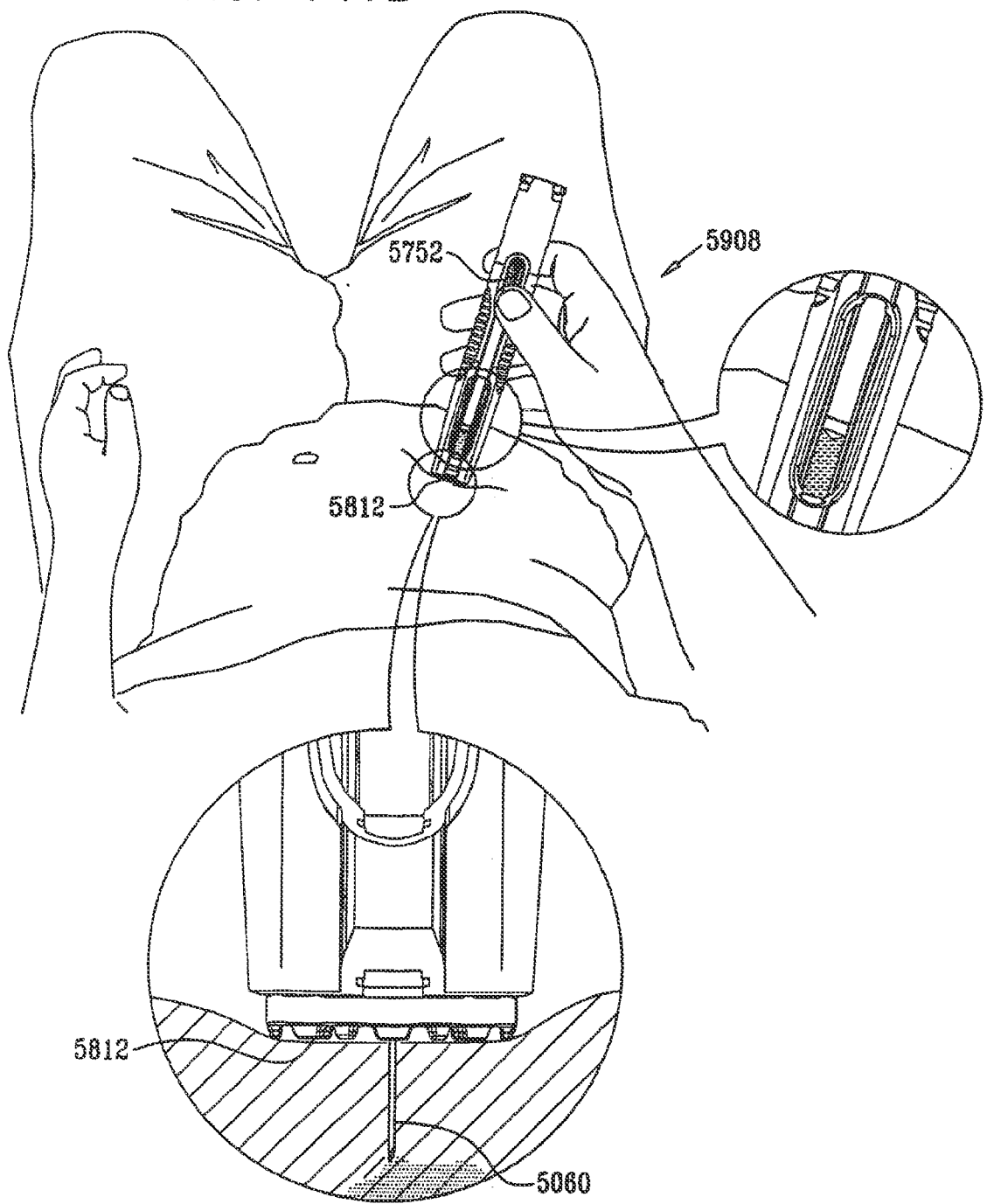
Figure 141F:
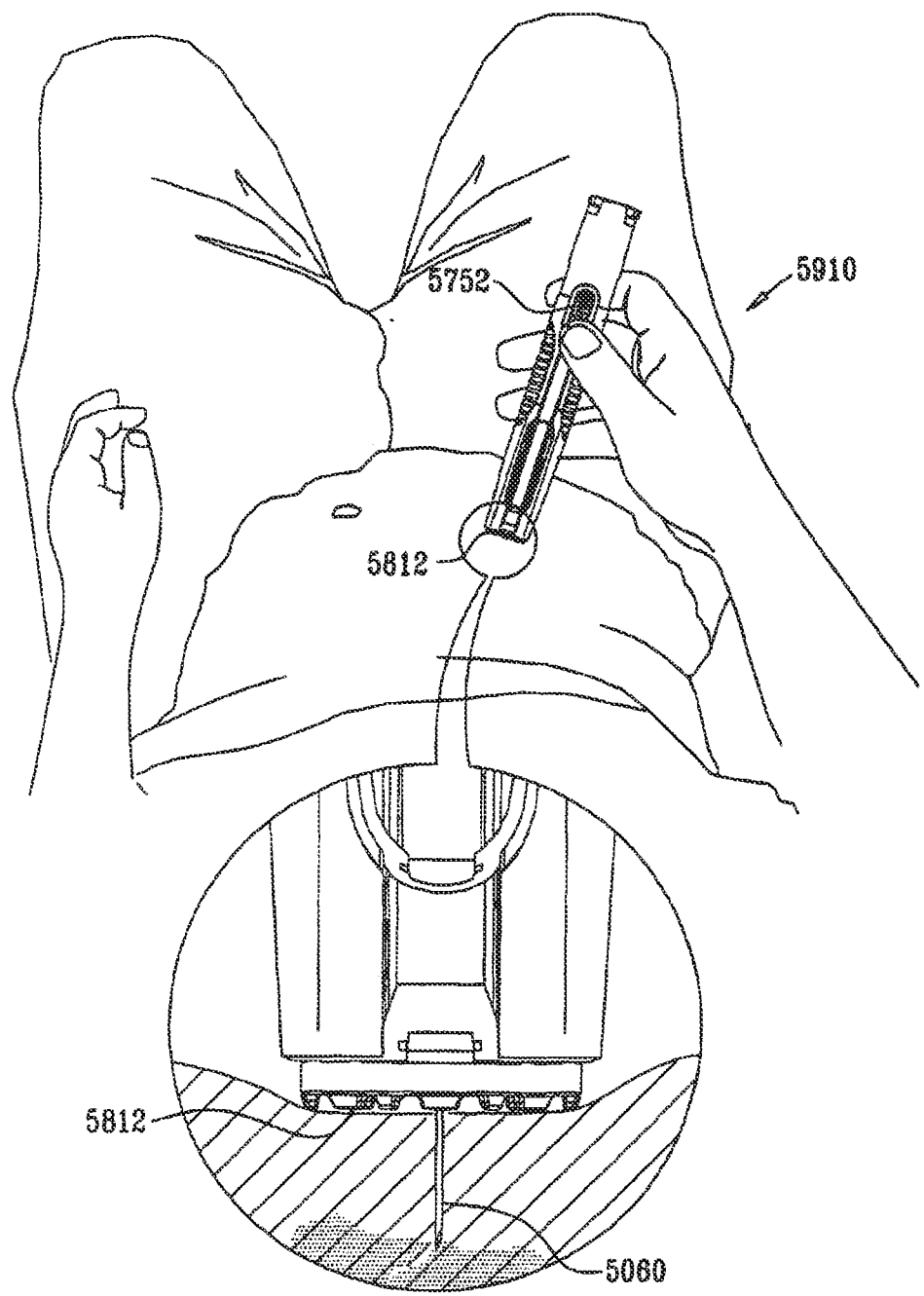
Figure 141G:
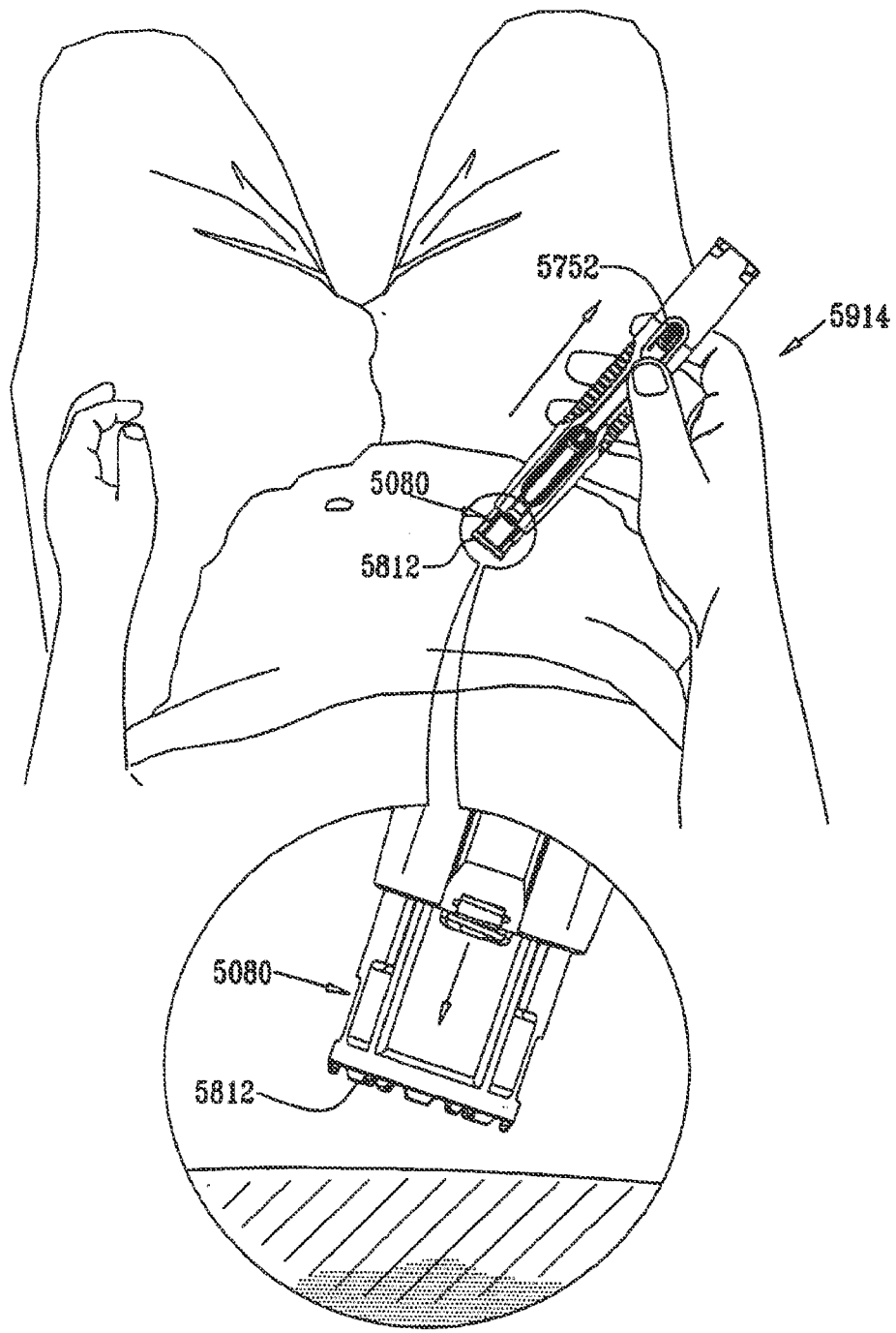
Figure 142:
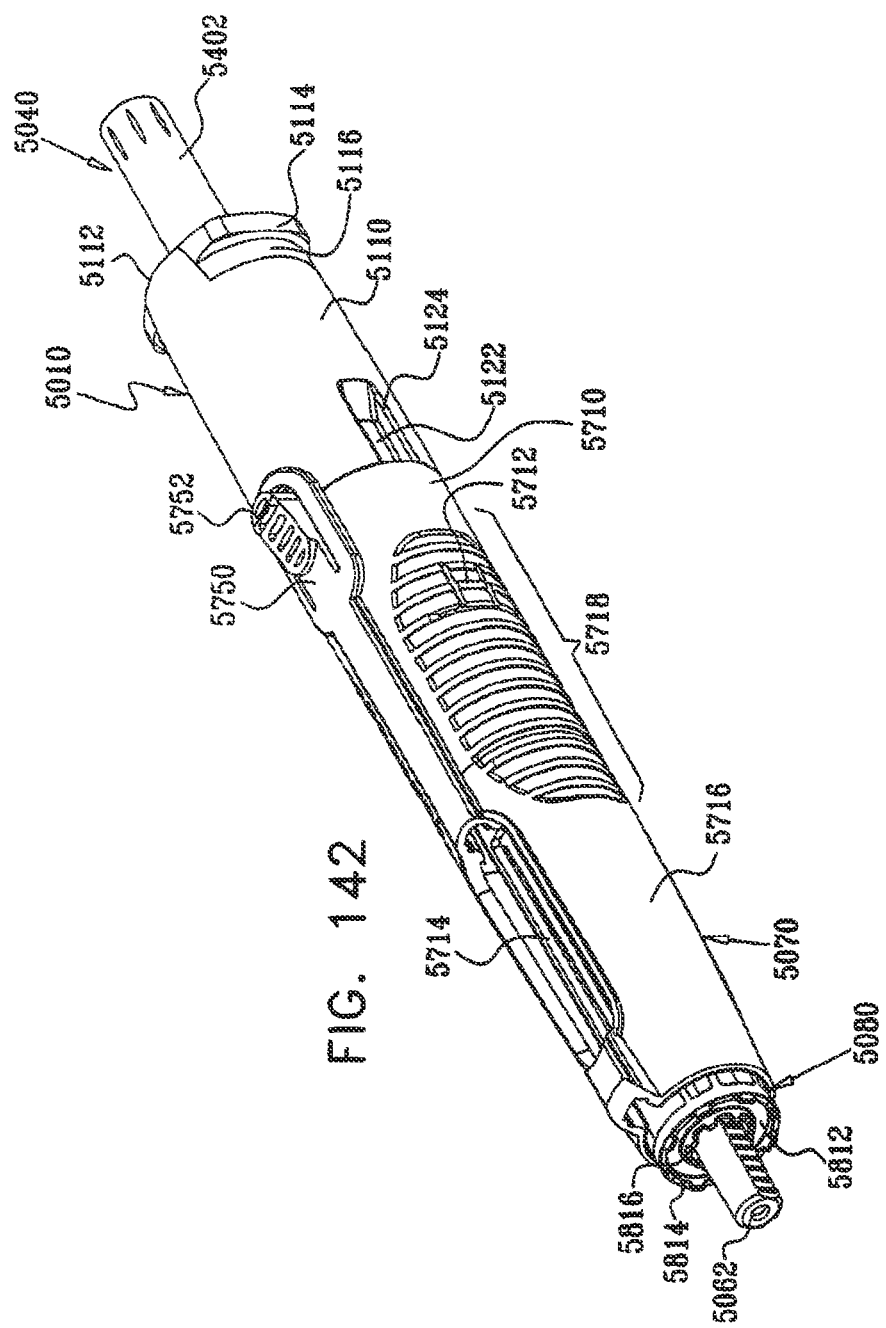
Figure 145:
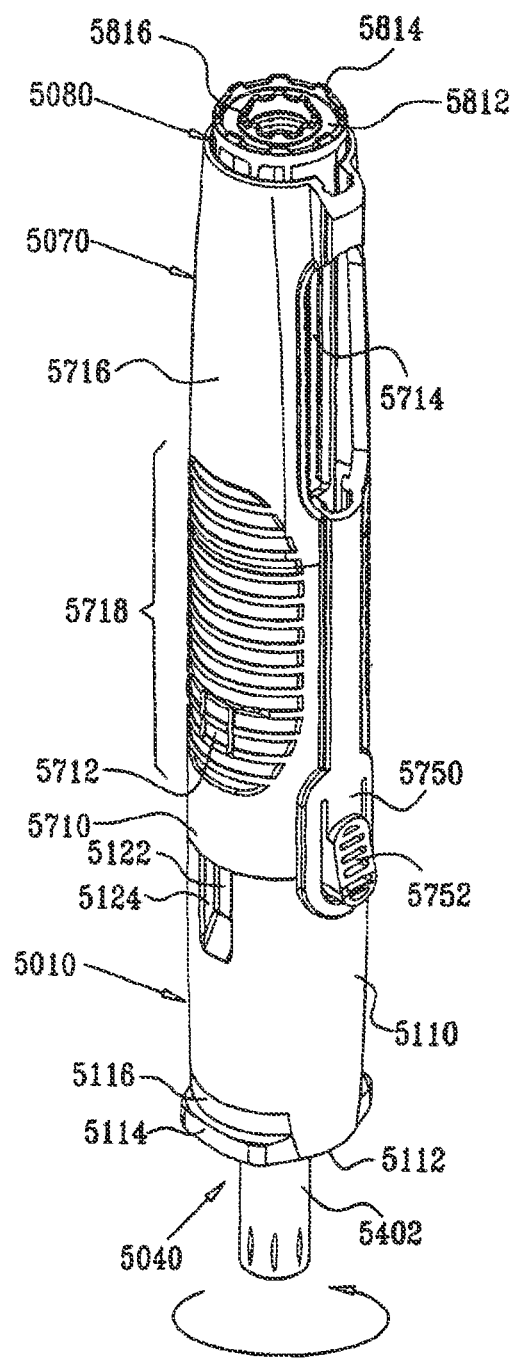
Figure 147A:
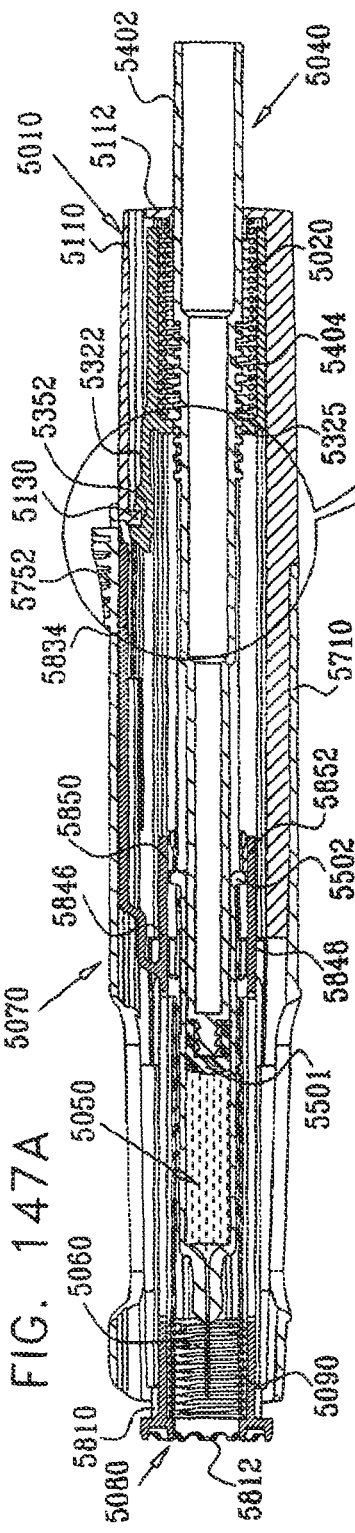
Figure 147B:
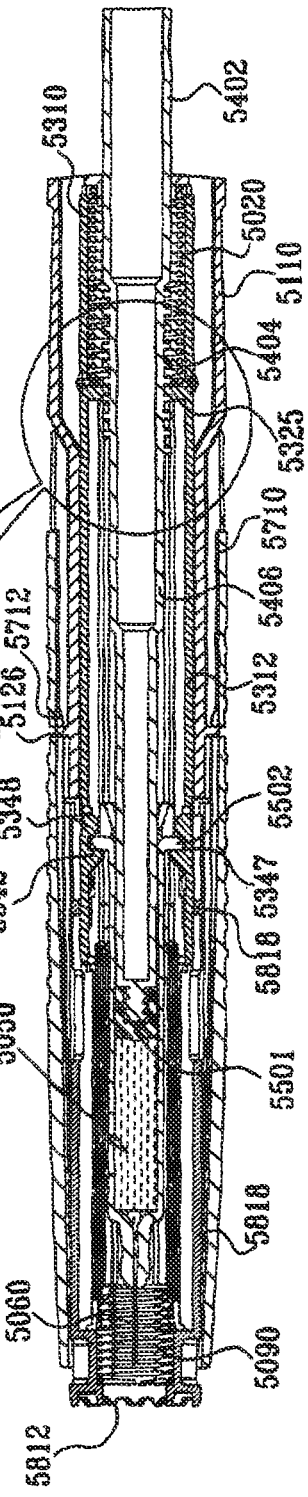
Figure 148:
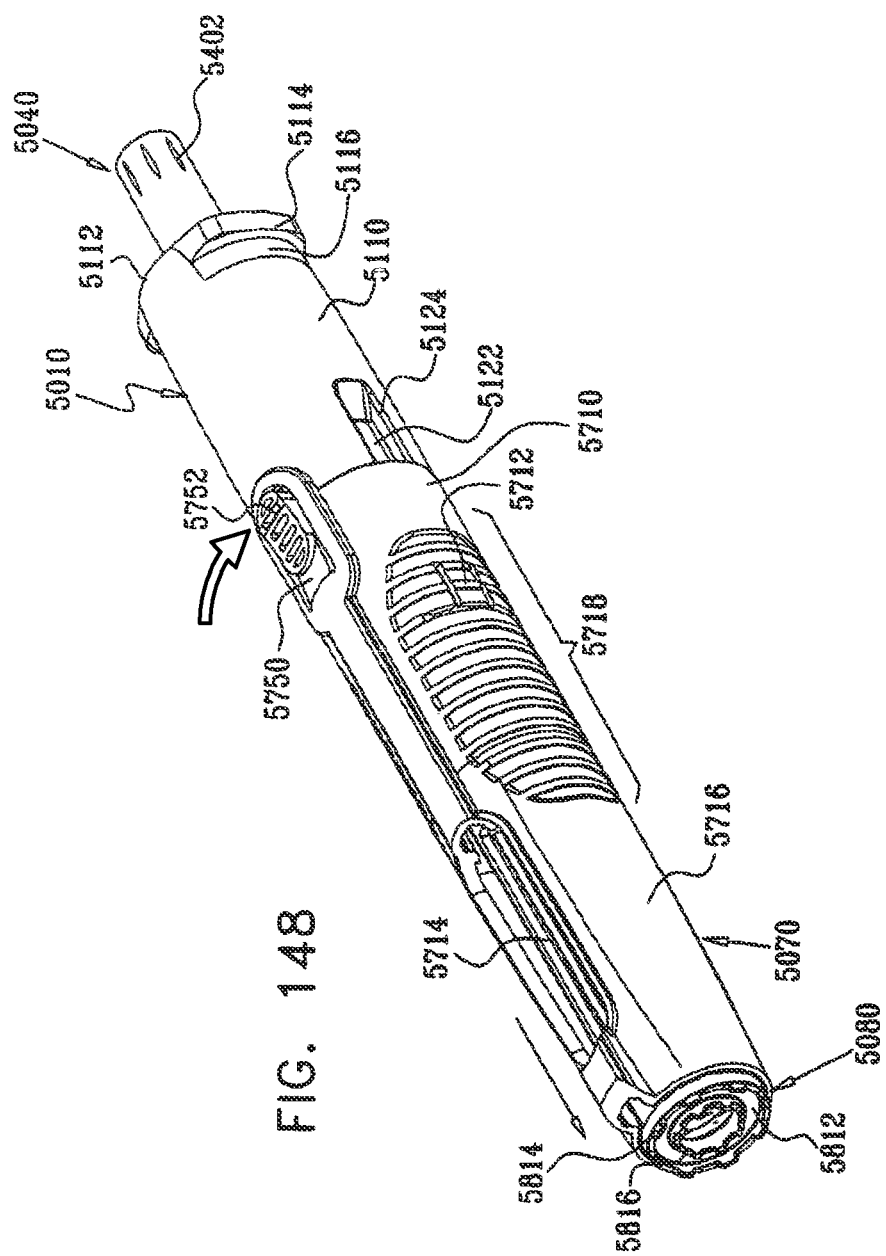
Figure 151:
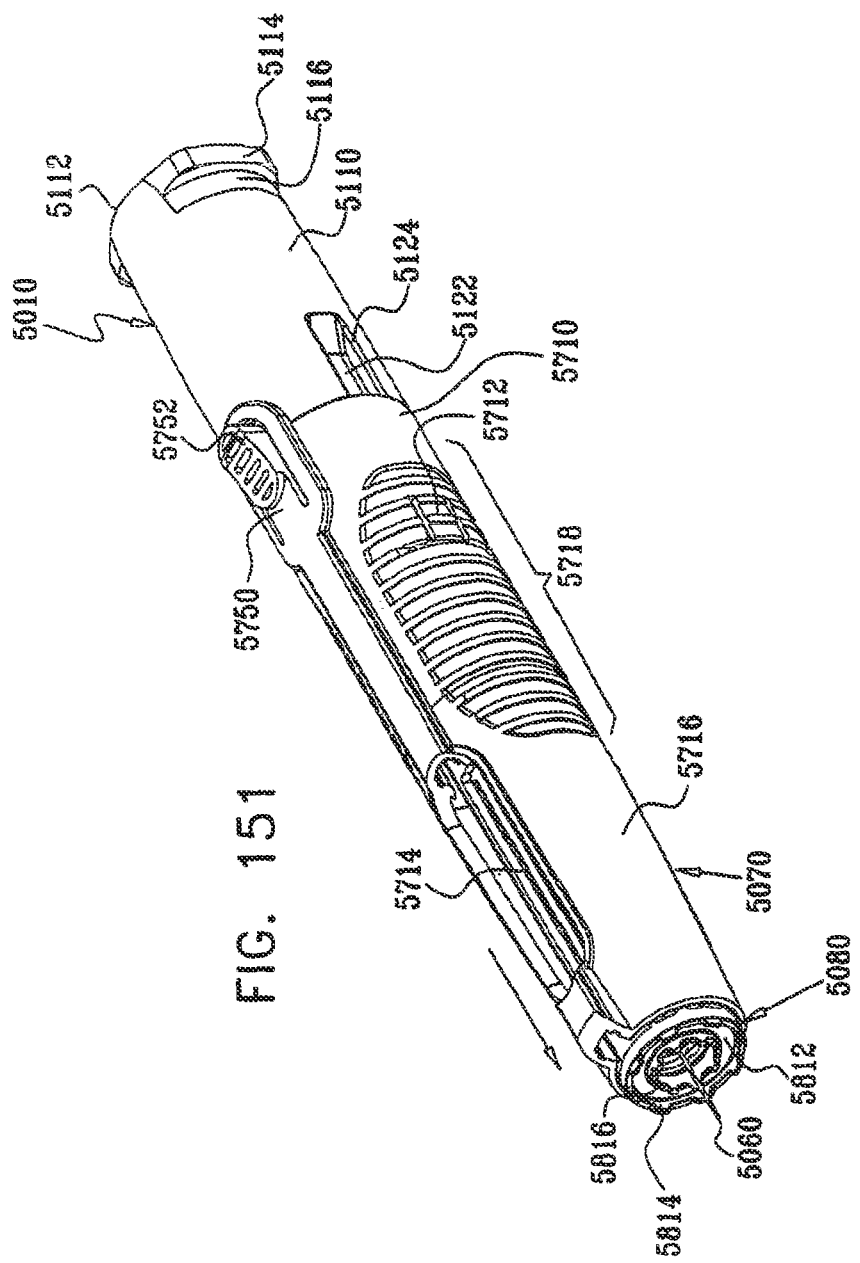
Figure 153A:
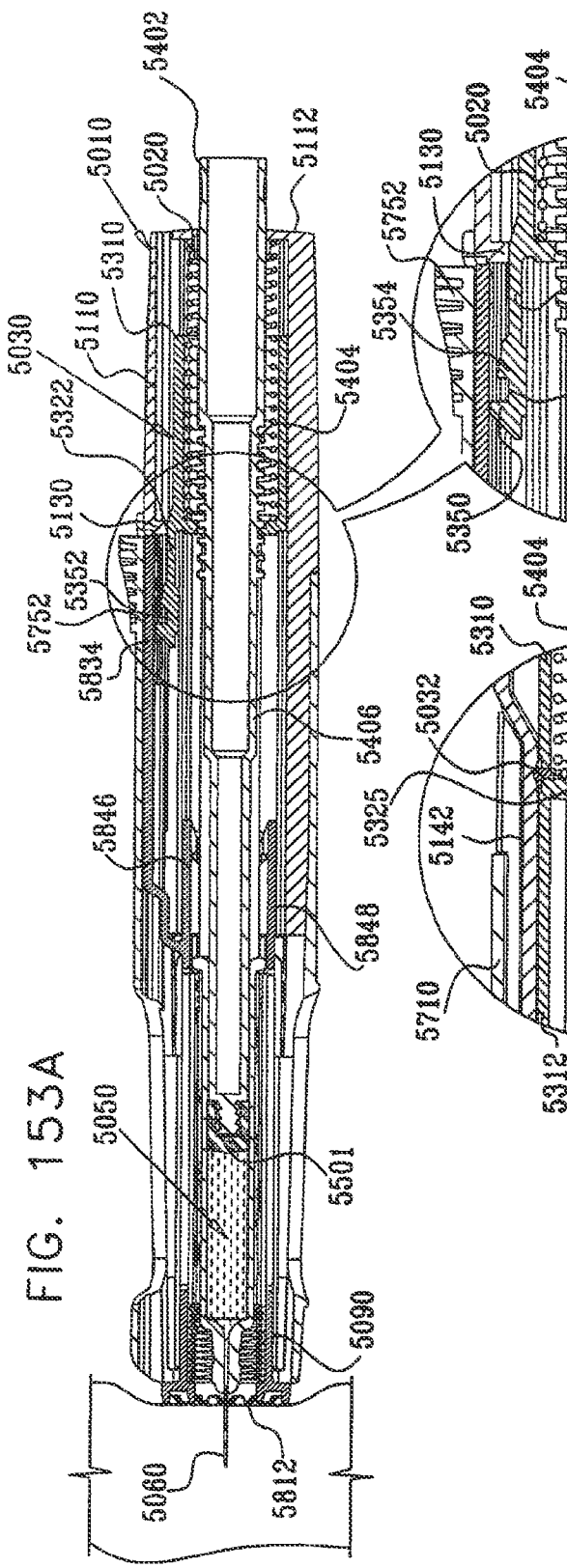
Figure 153B:
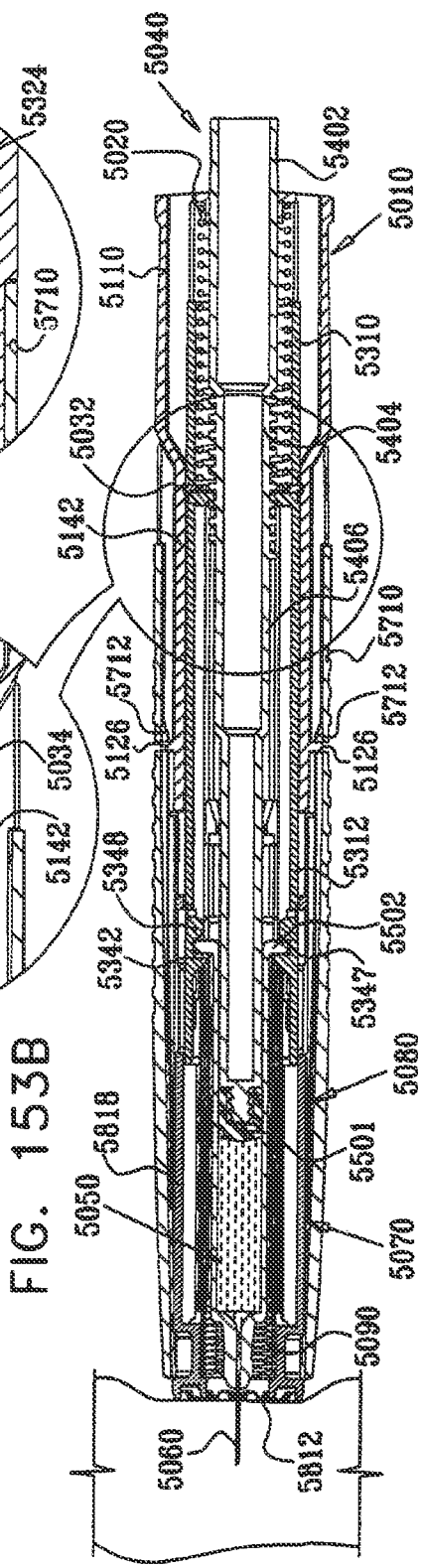
Figure 154:
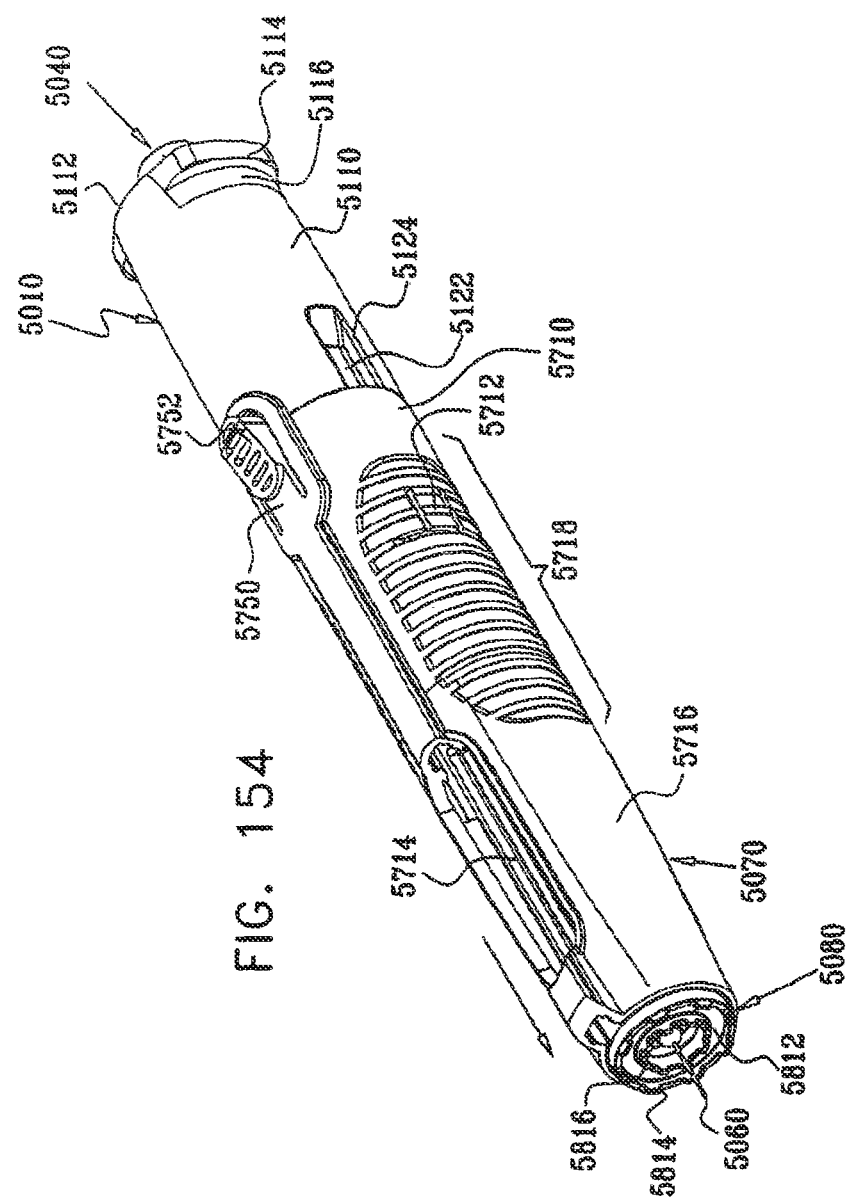
Figure 155:
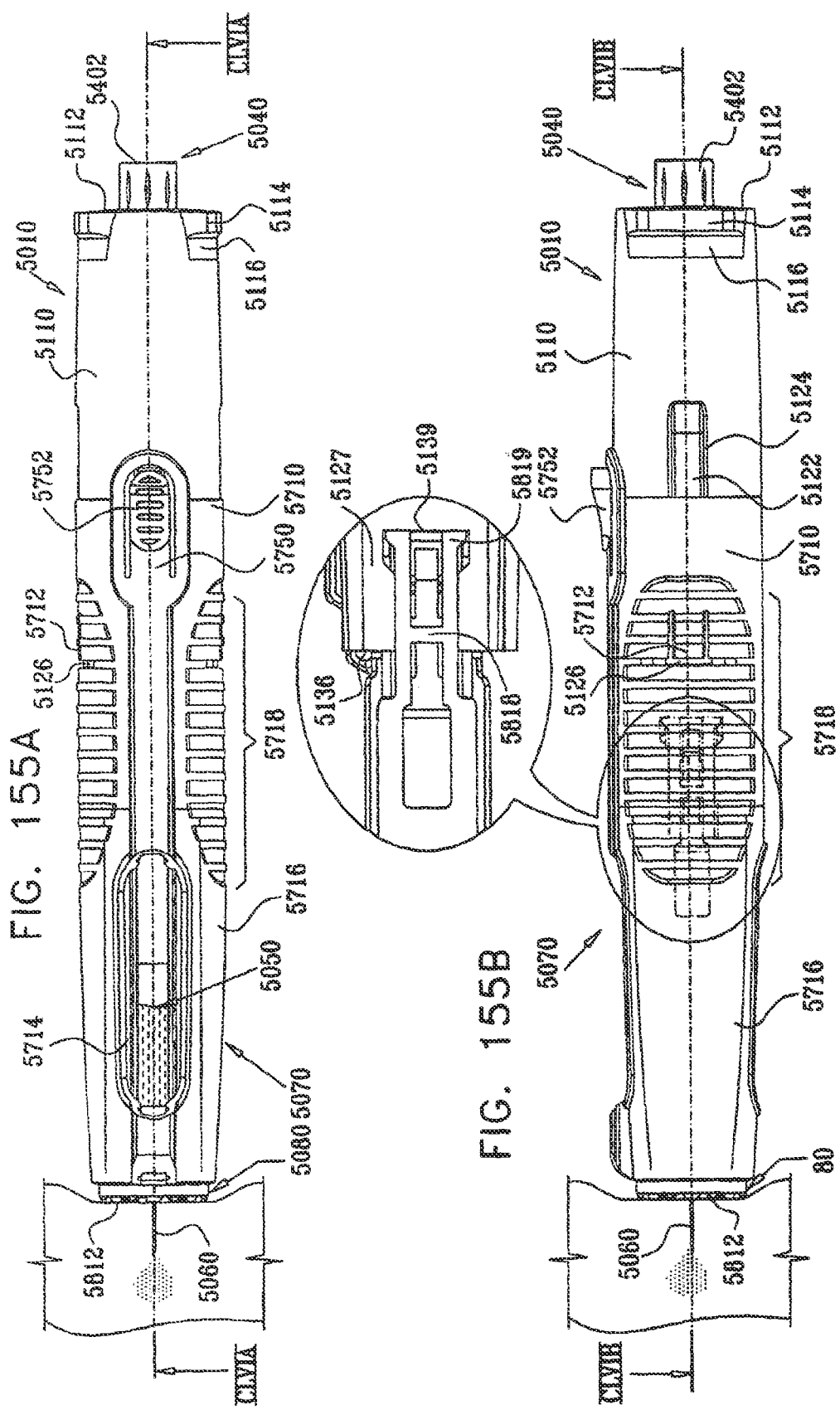
Figure 156:
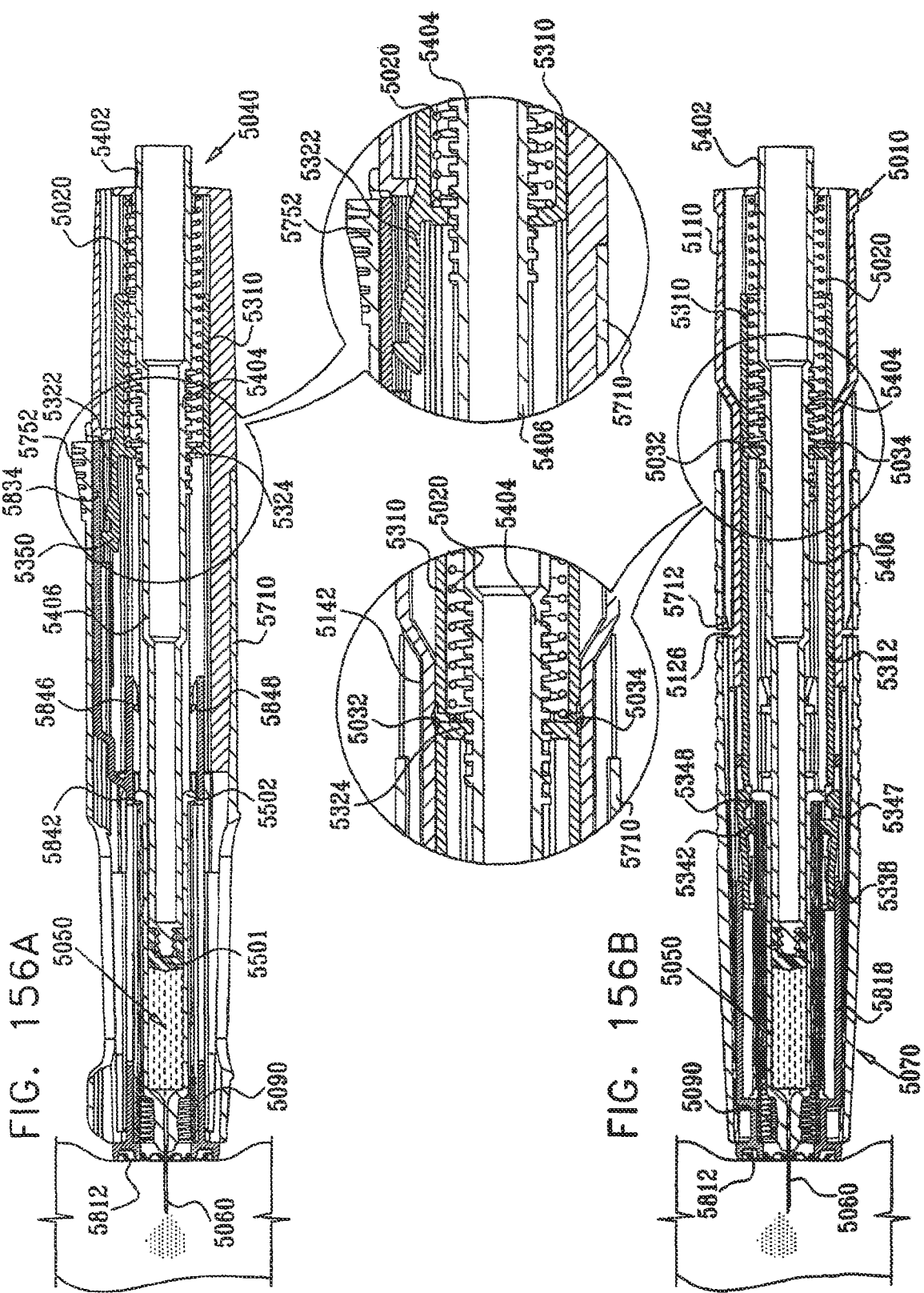
Figure 157:
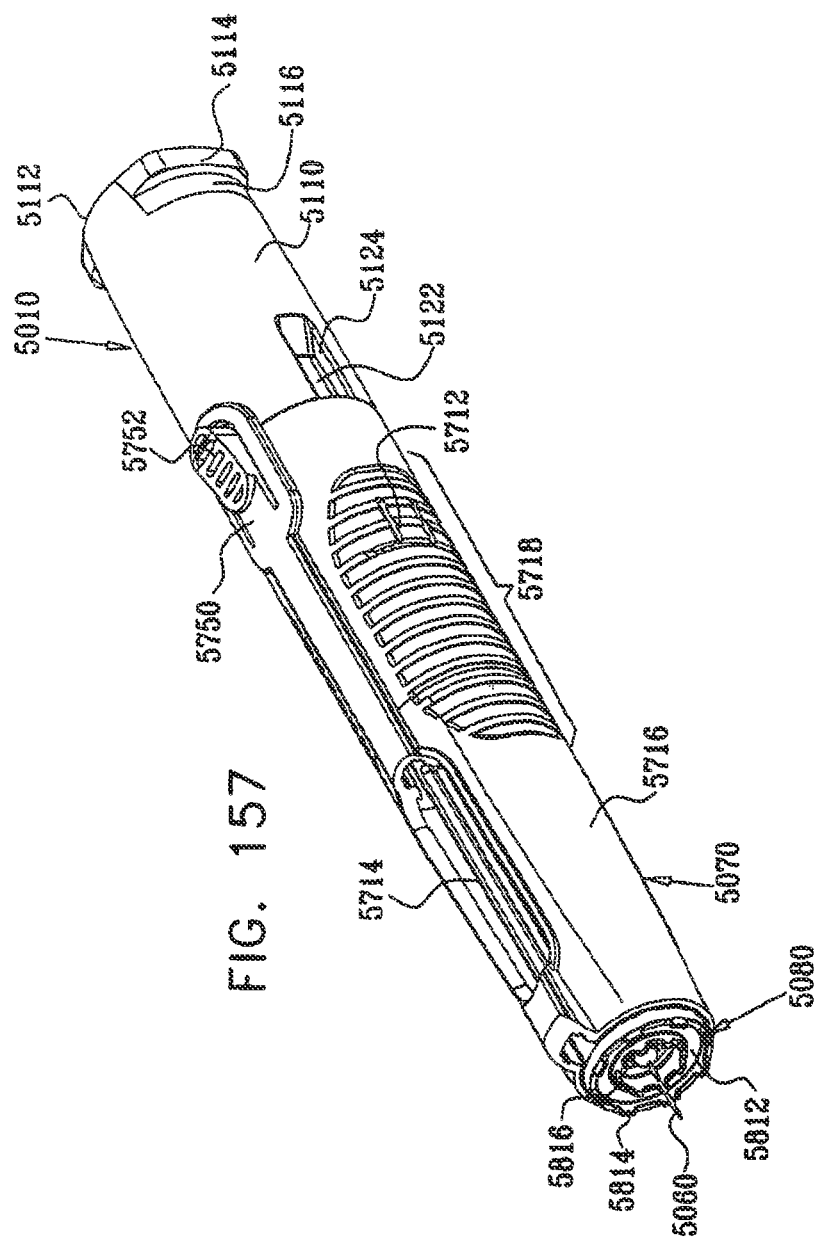
Figure 160:
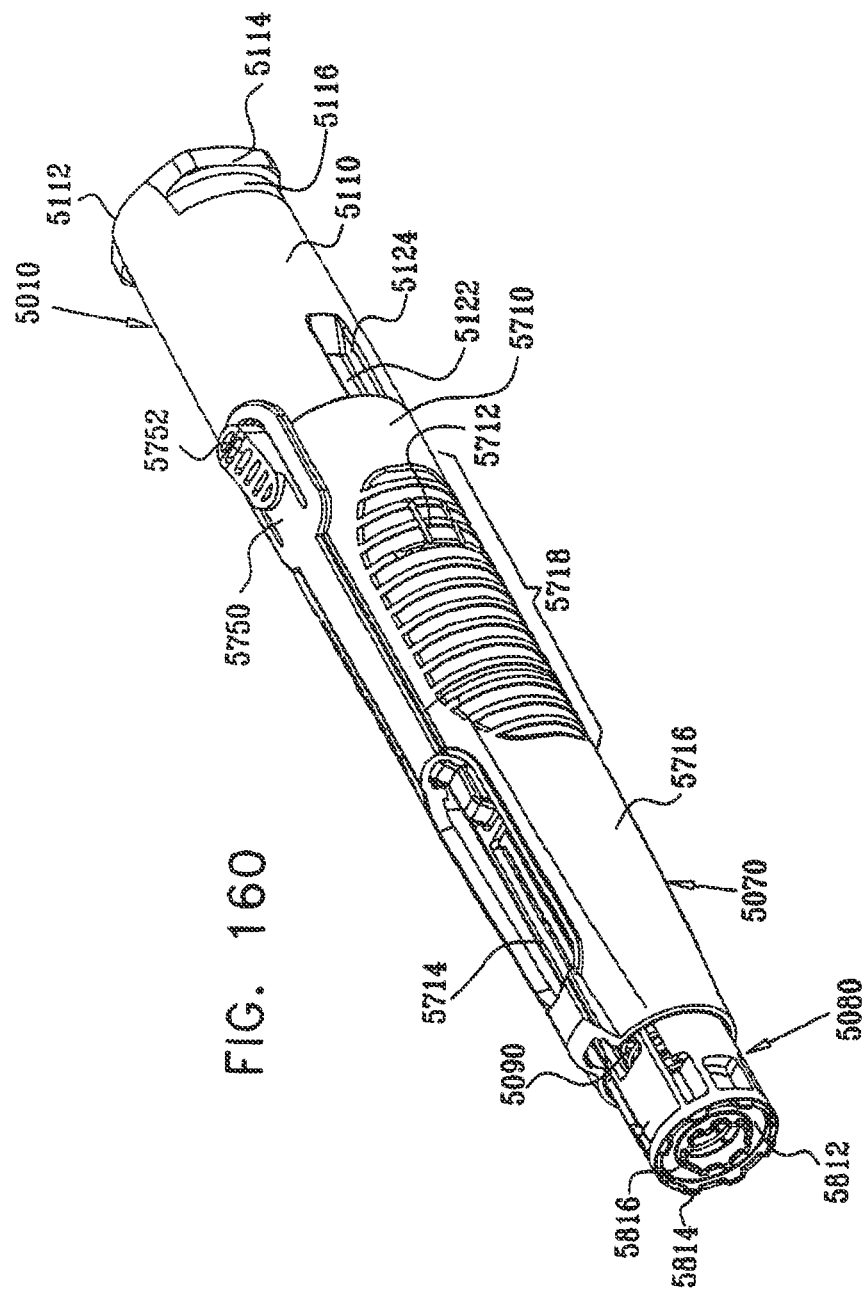
Figure 162A:
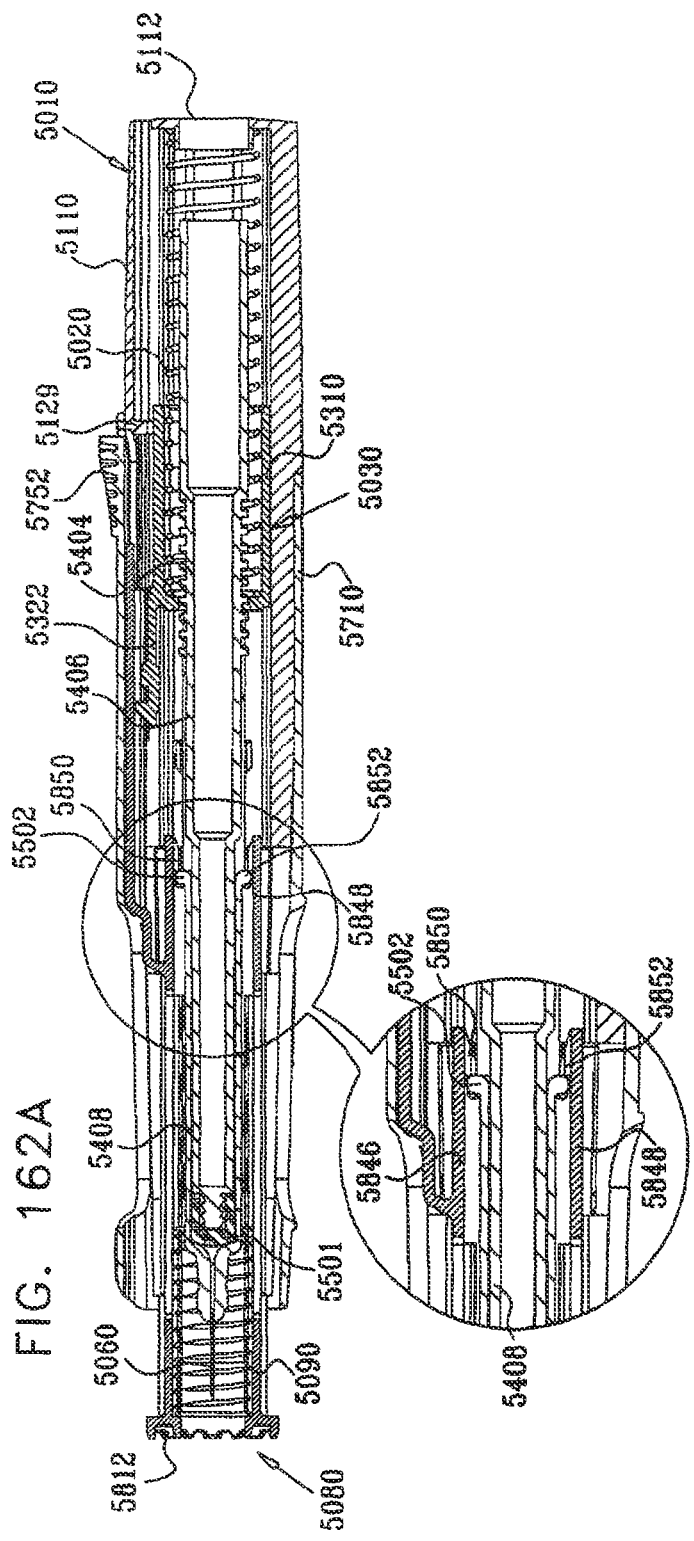
Figure 162B:
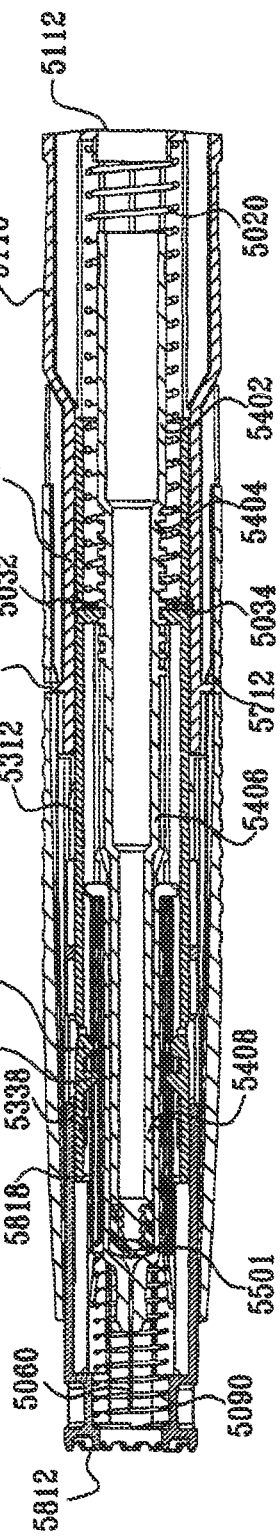
Figure 163:
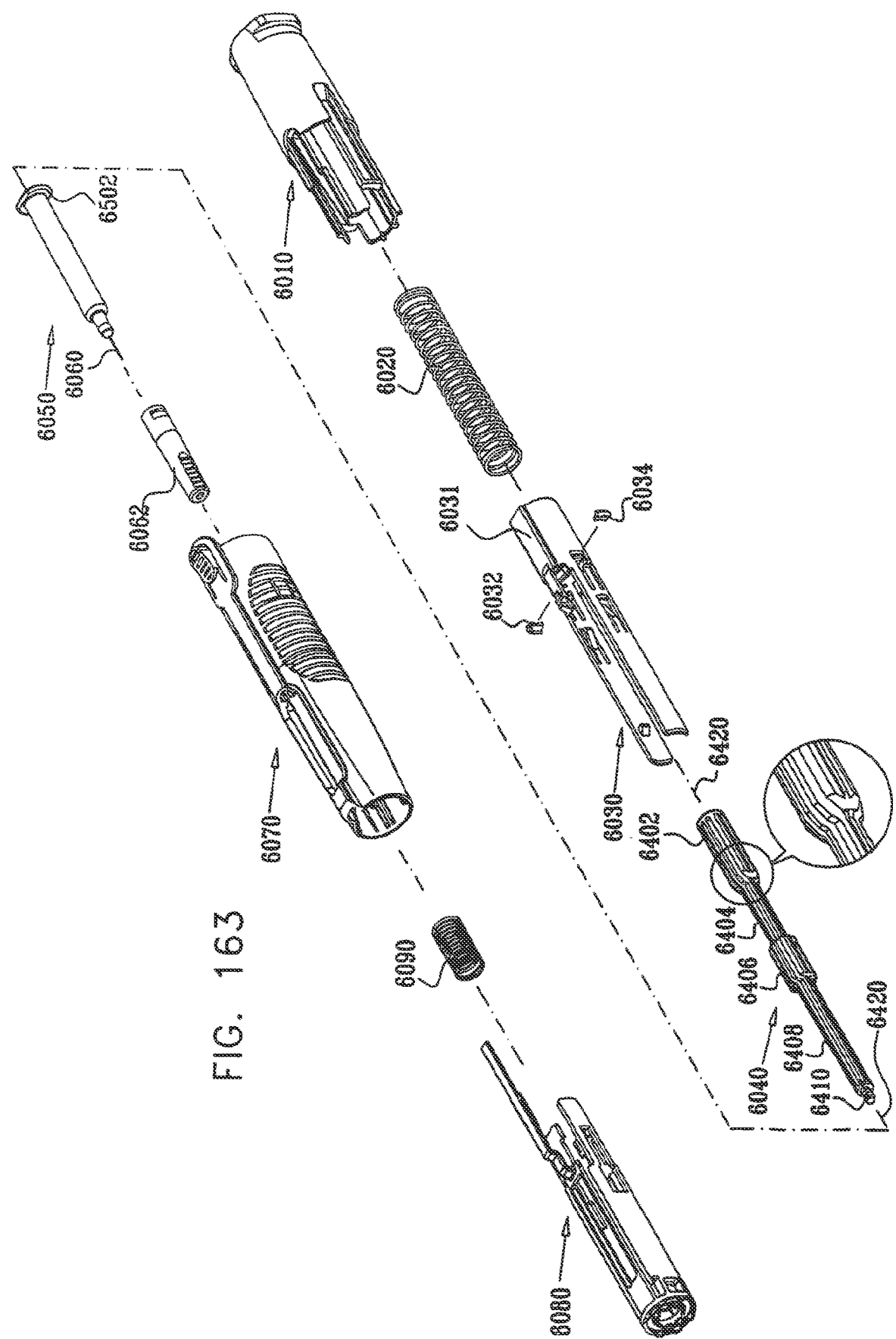
Figure 167:
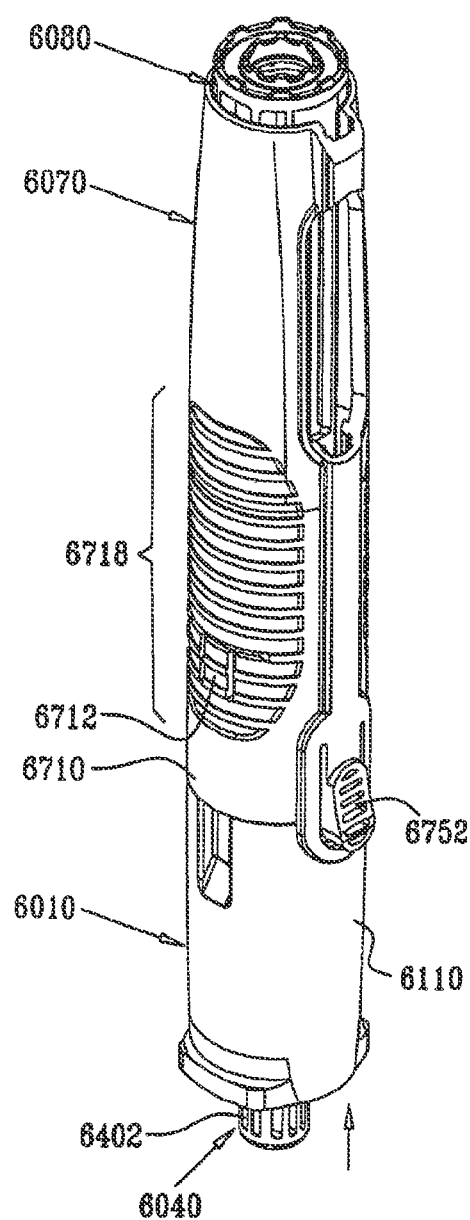
Figure 170:
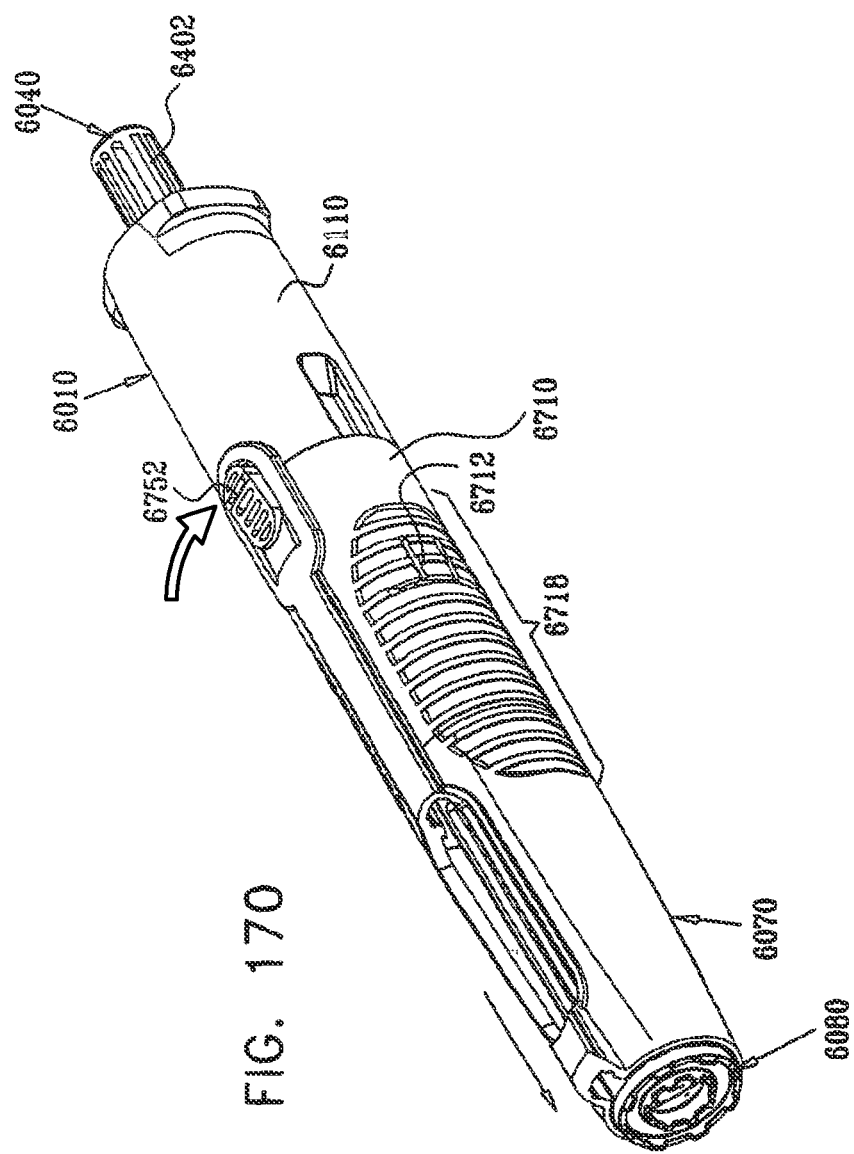
Figures 172A, 172B:
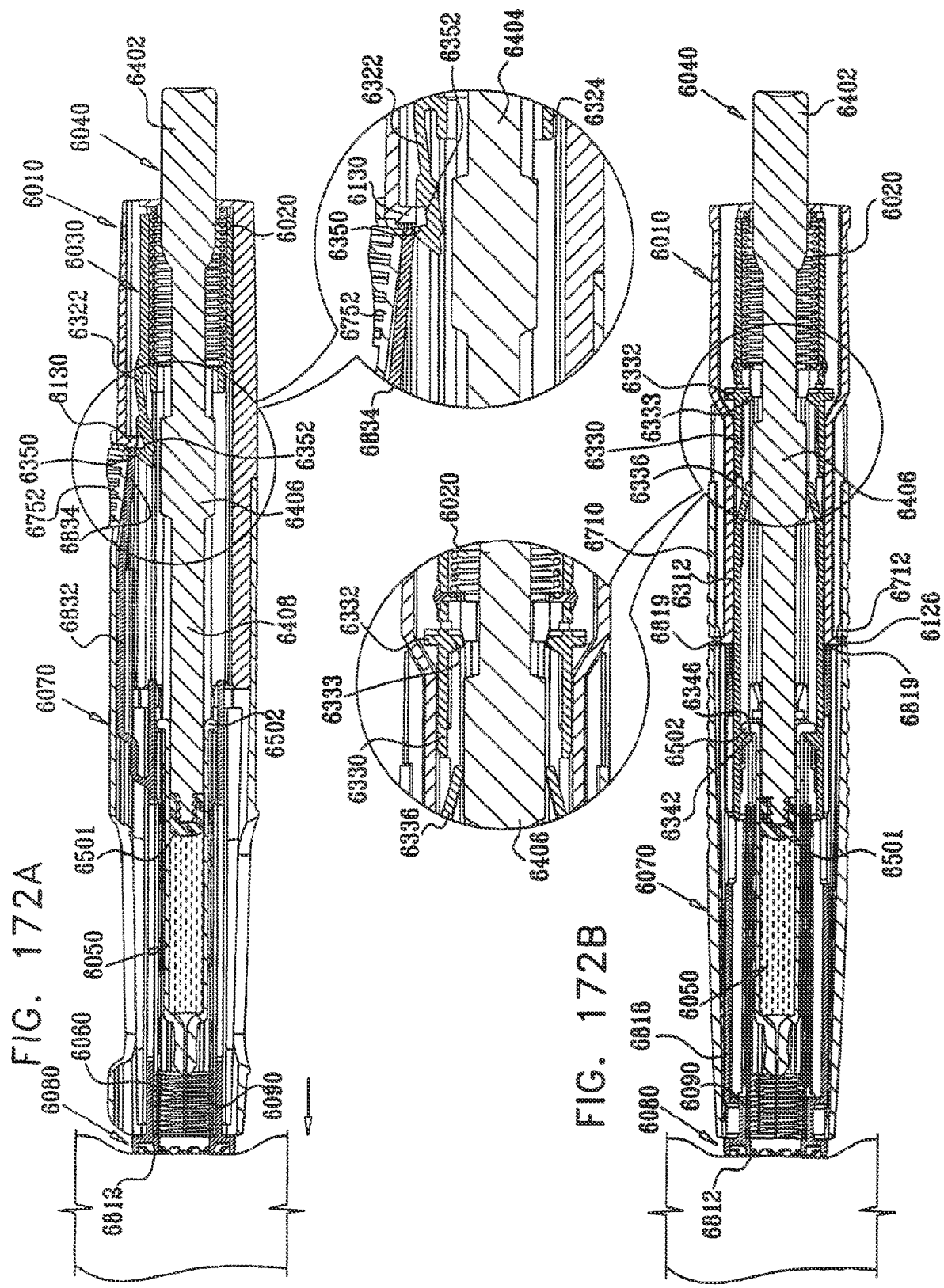
Figure 174A:
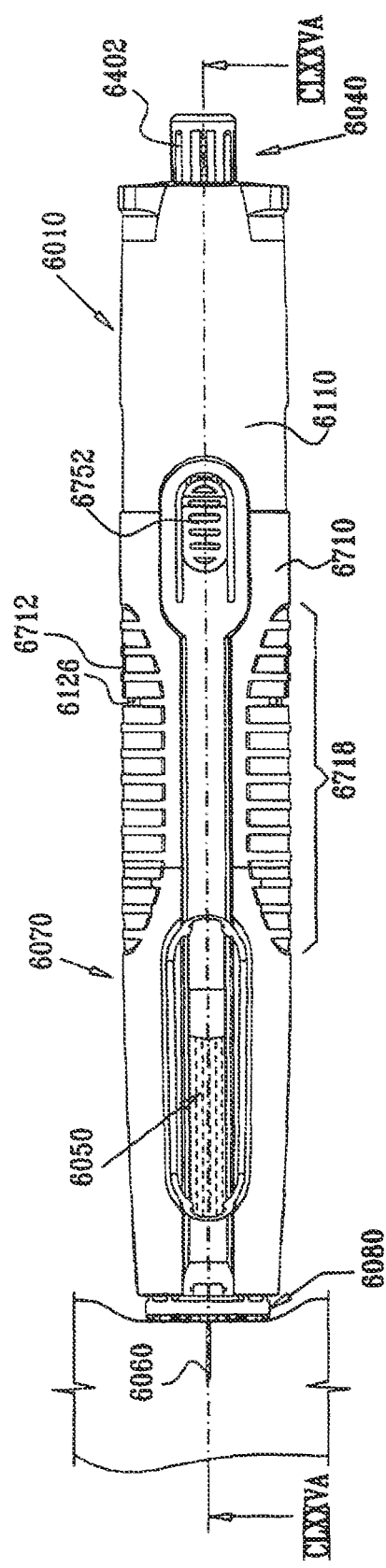
Figure 174B:
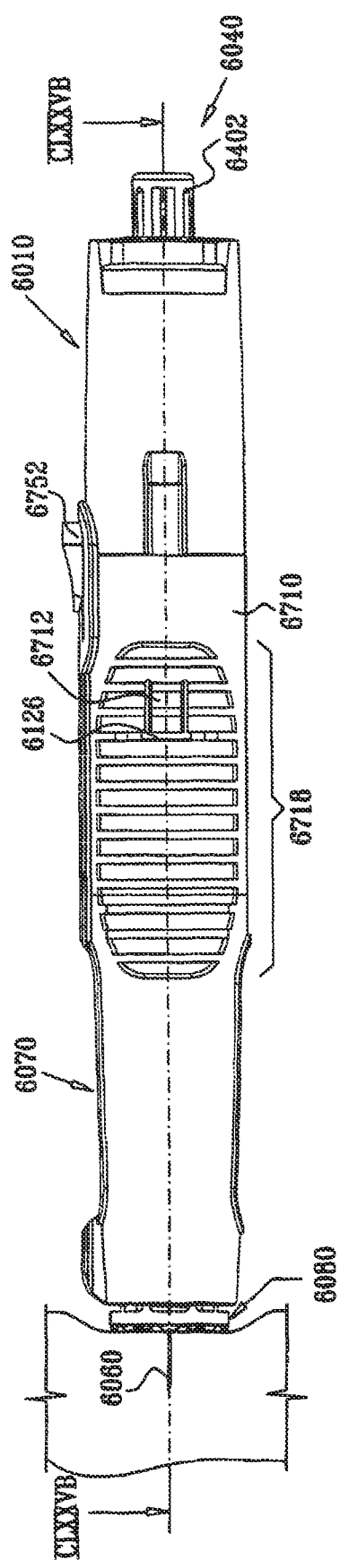
Figure 176:
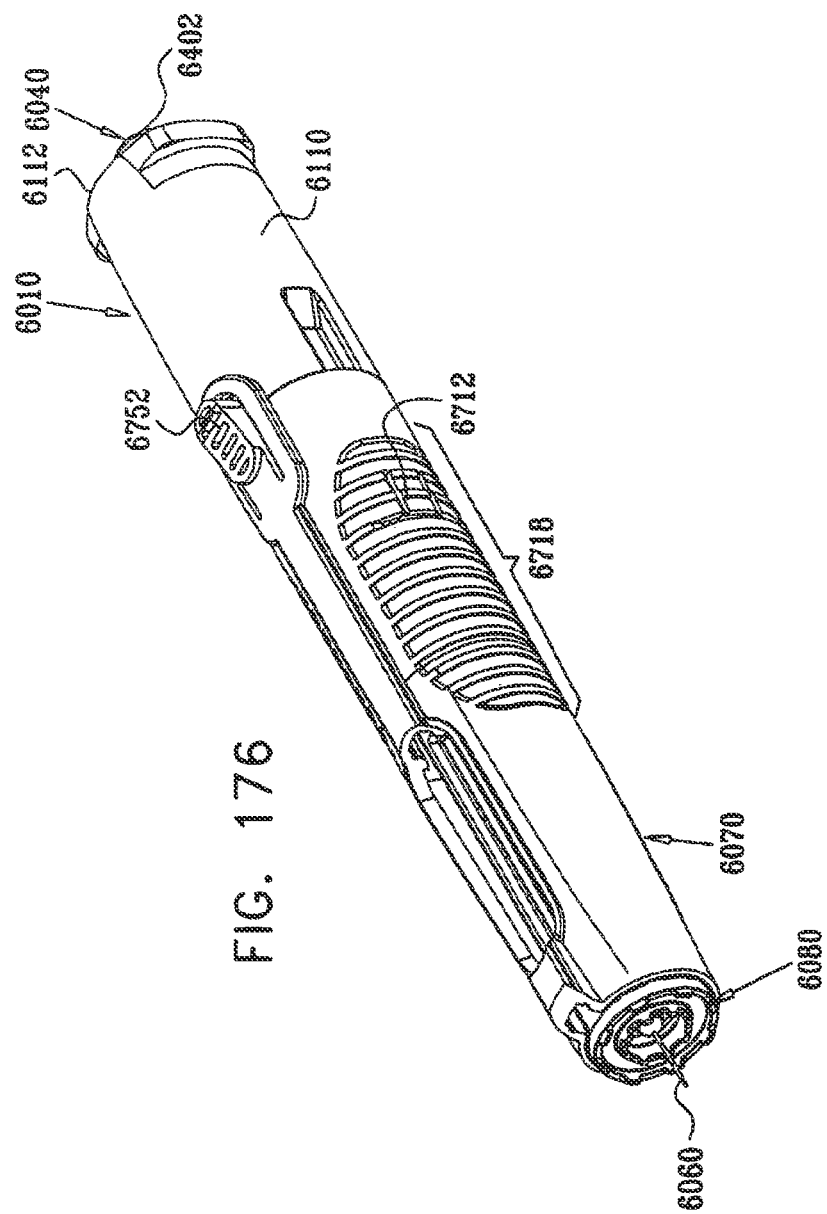
Figure 177A:
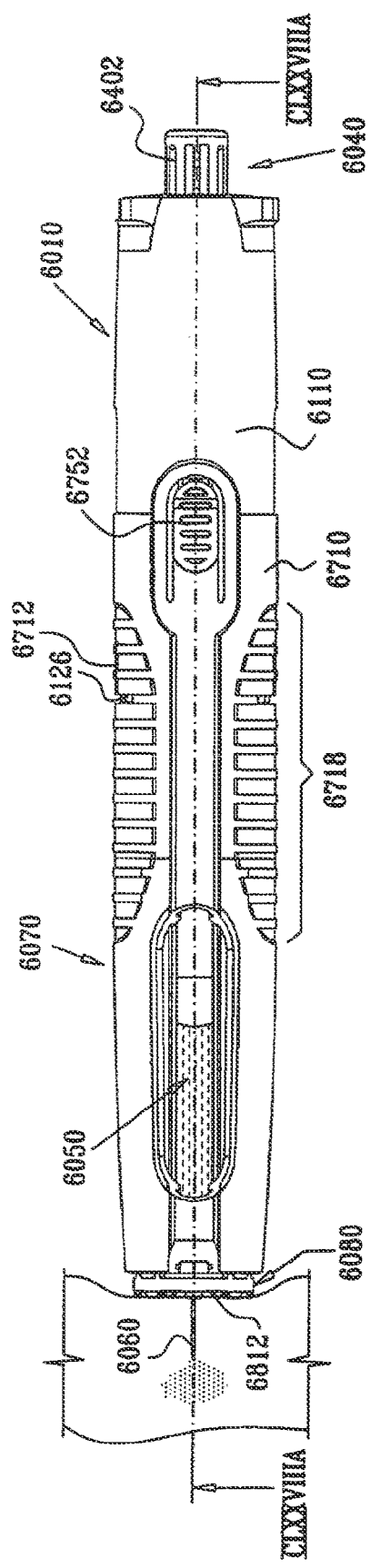
Figure 177B:
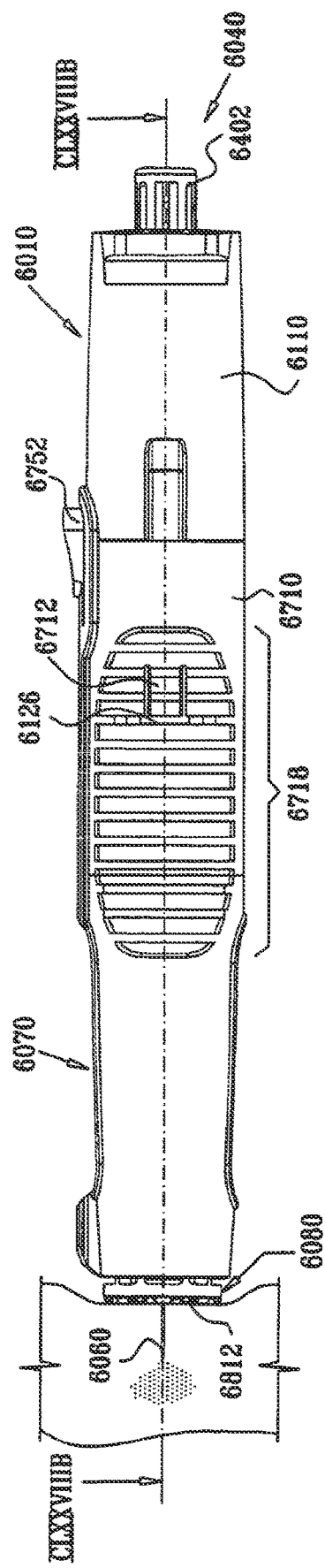
Figure 179:
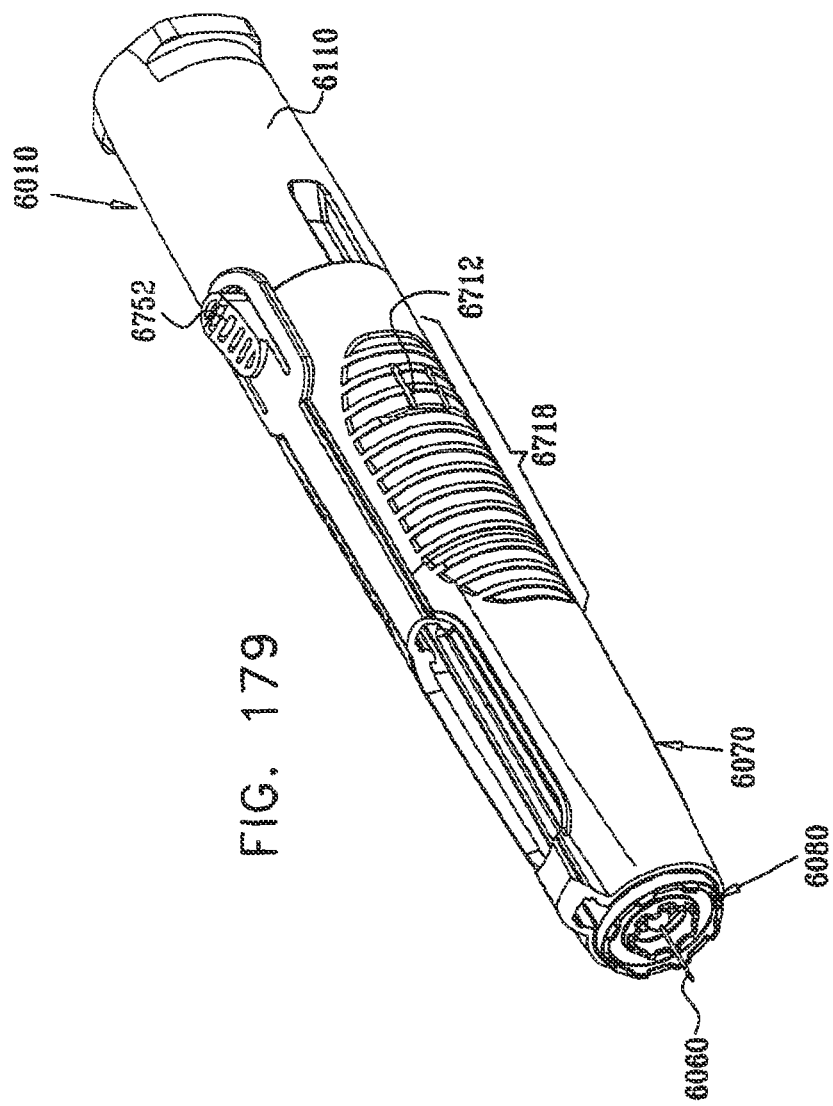
Figures 181A, 181B:
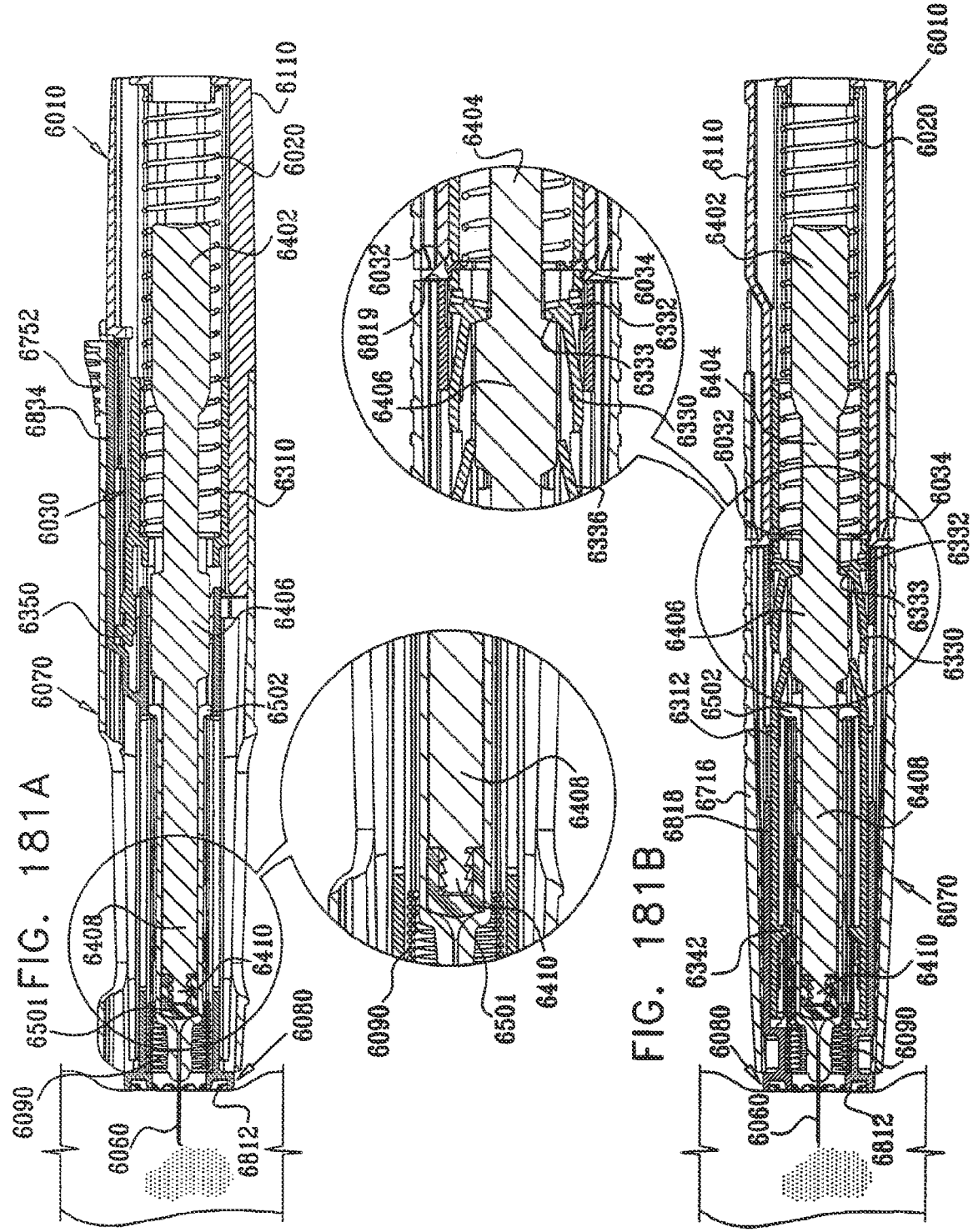
Figure 182:
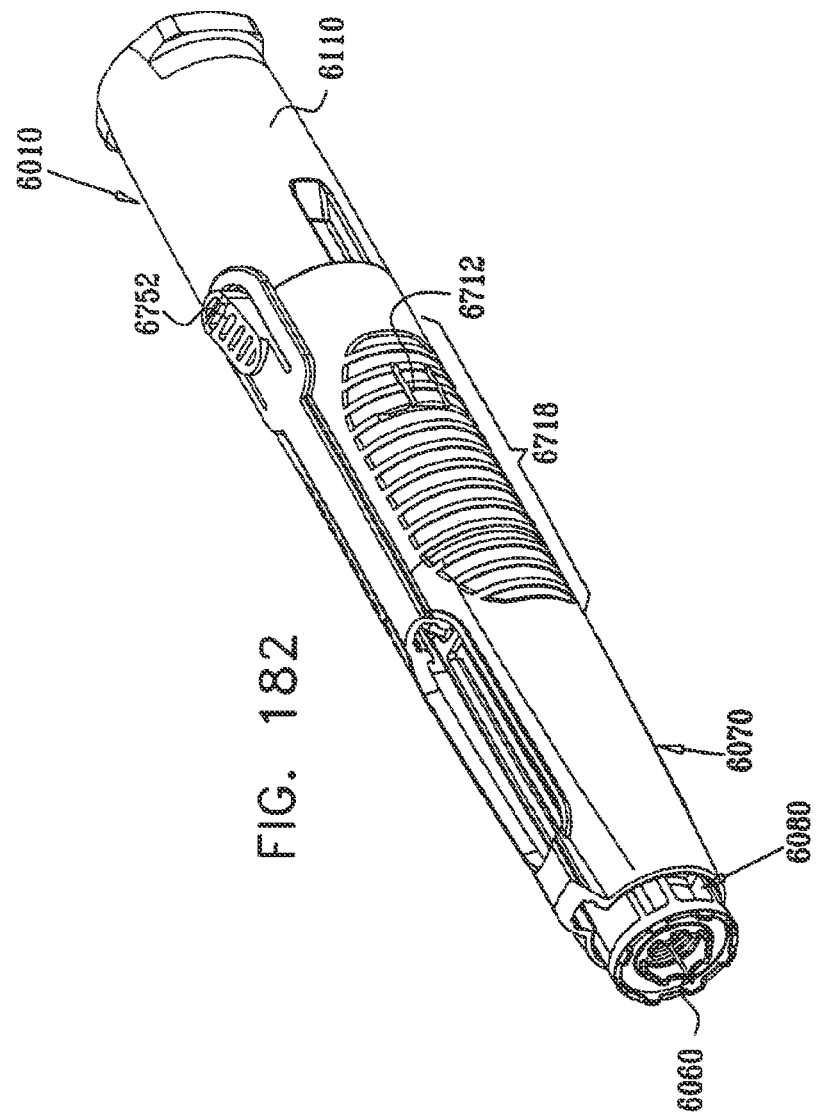
Figure 185:
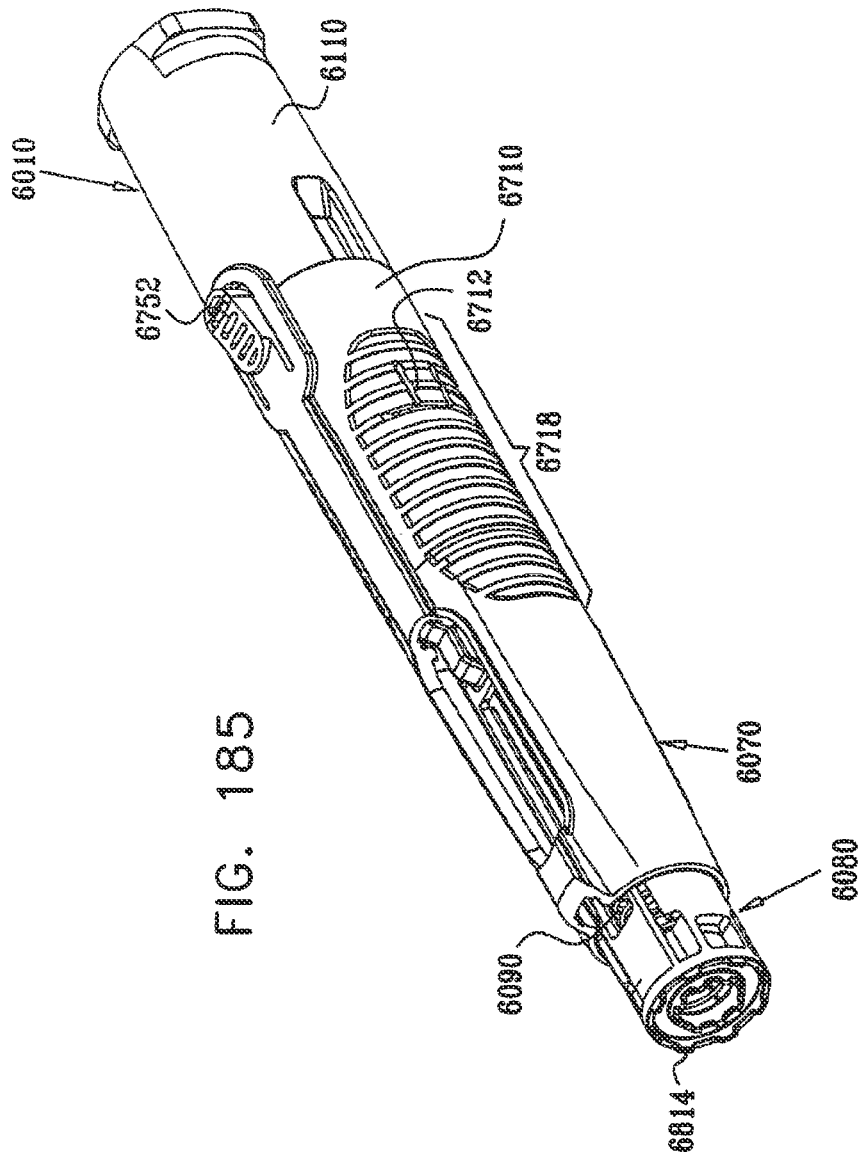
Figure 188:
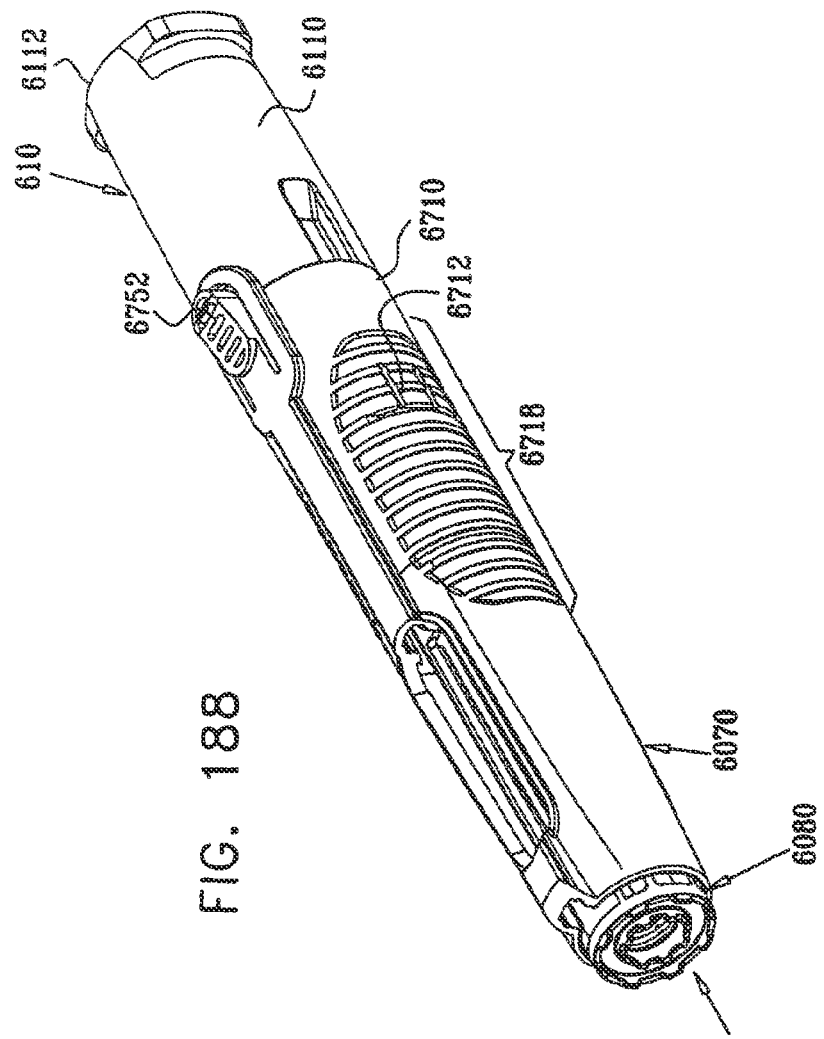
Figure 190A:
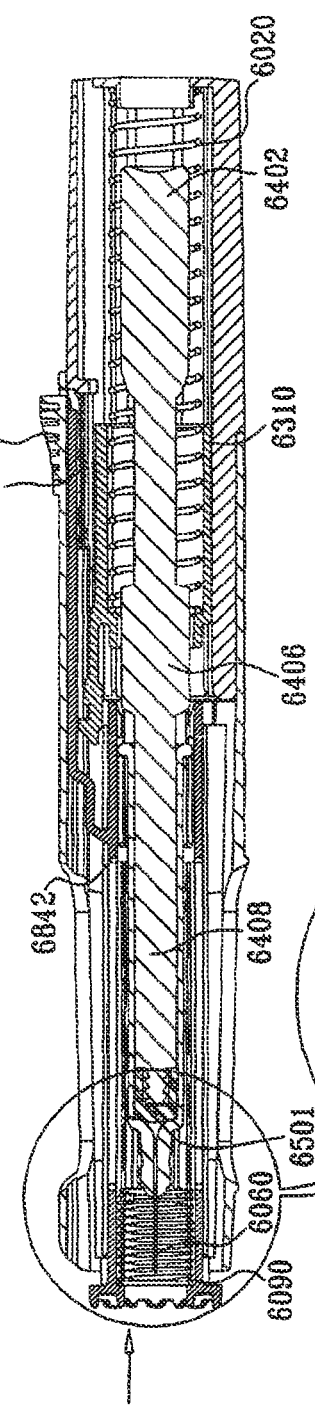
Figure 190B:
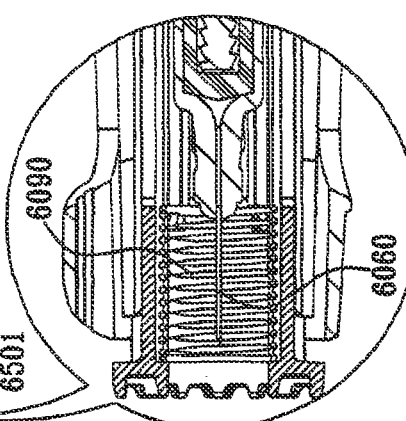
Figure 195:
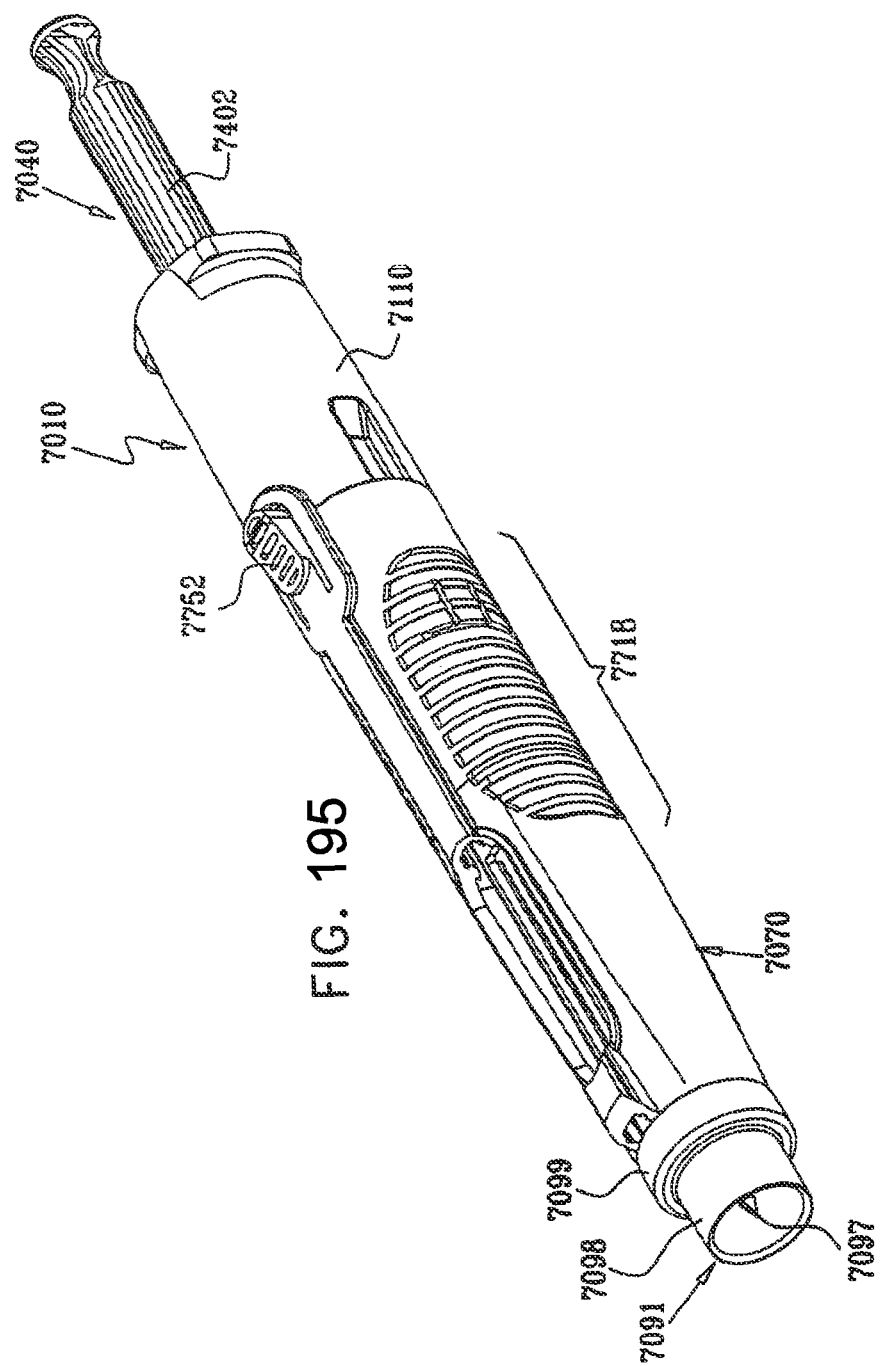
Figure 196A:
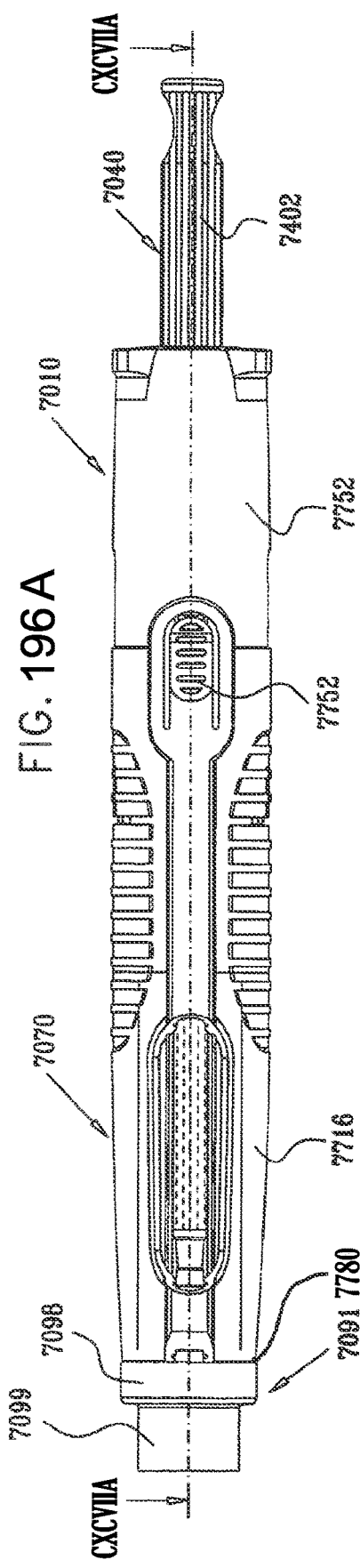
Figure 196B:
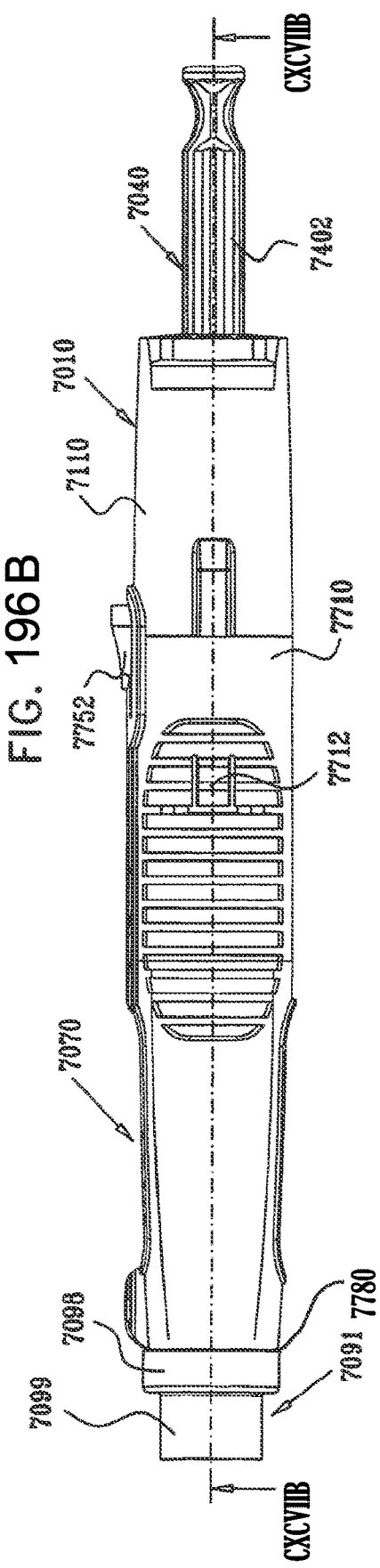
Figure 198:
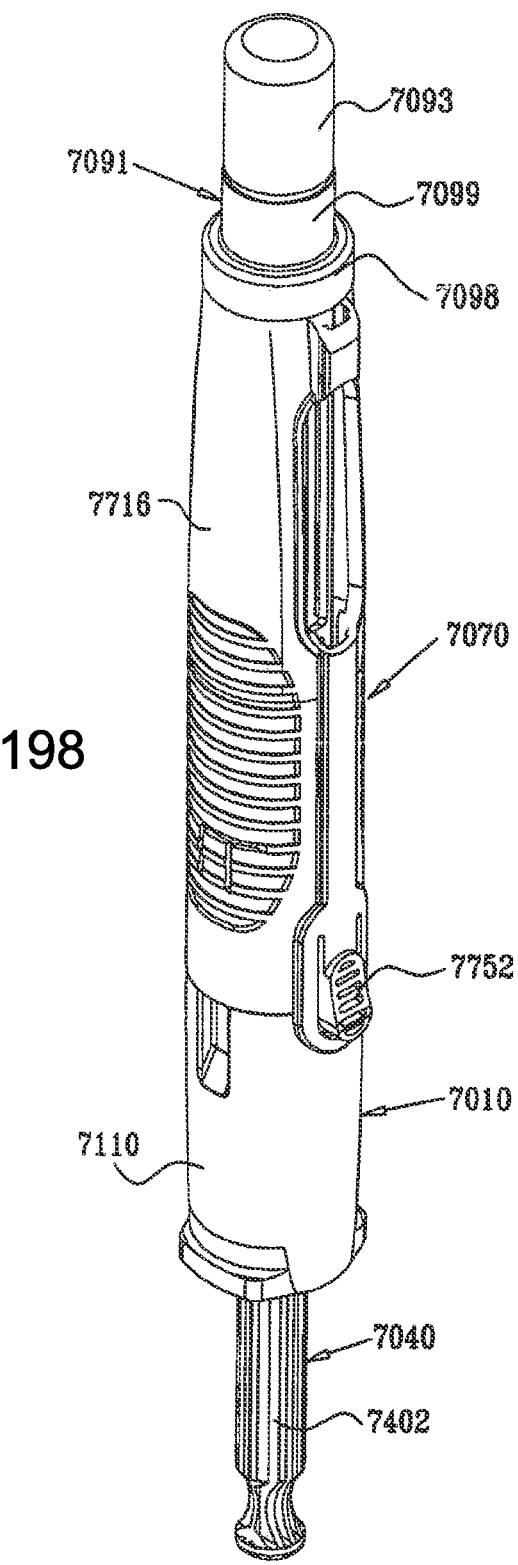
Figure 201:
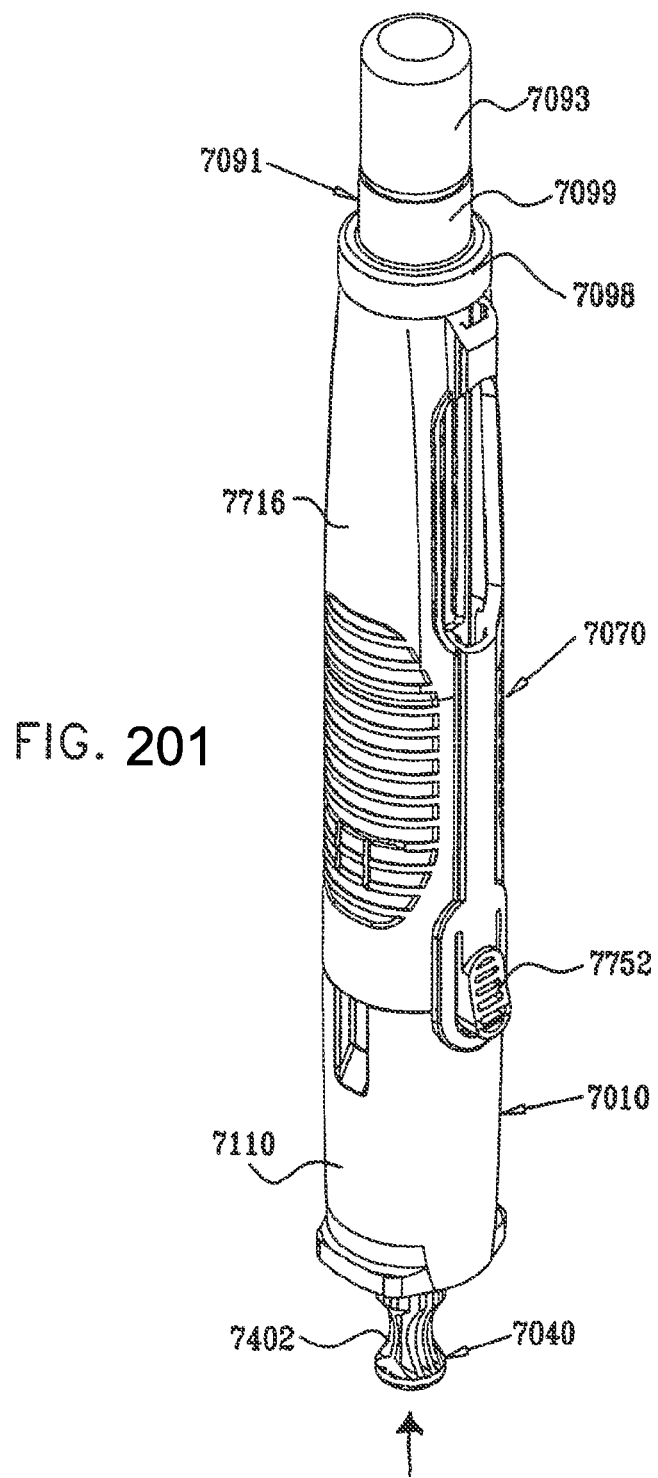
Figure 204:
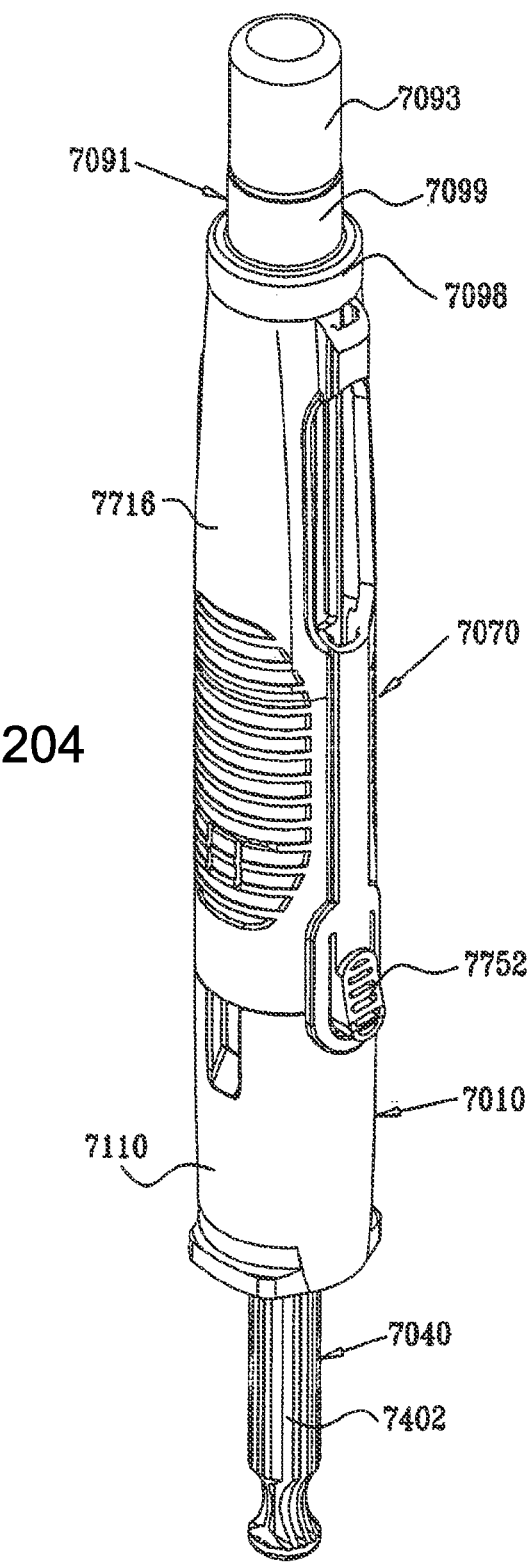
Figure 207:
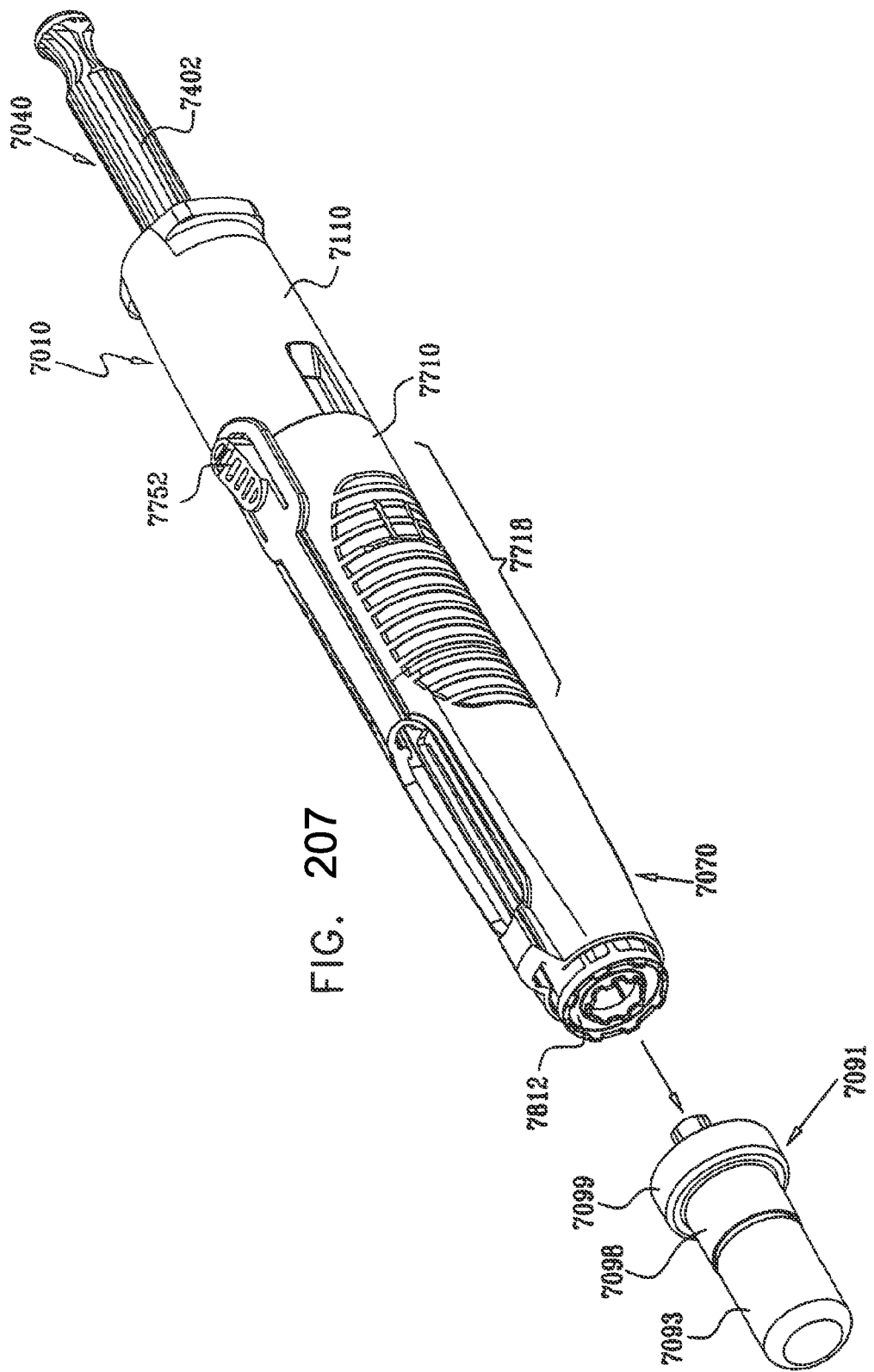
Figure 210:
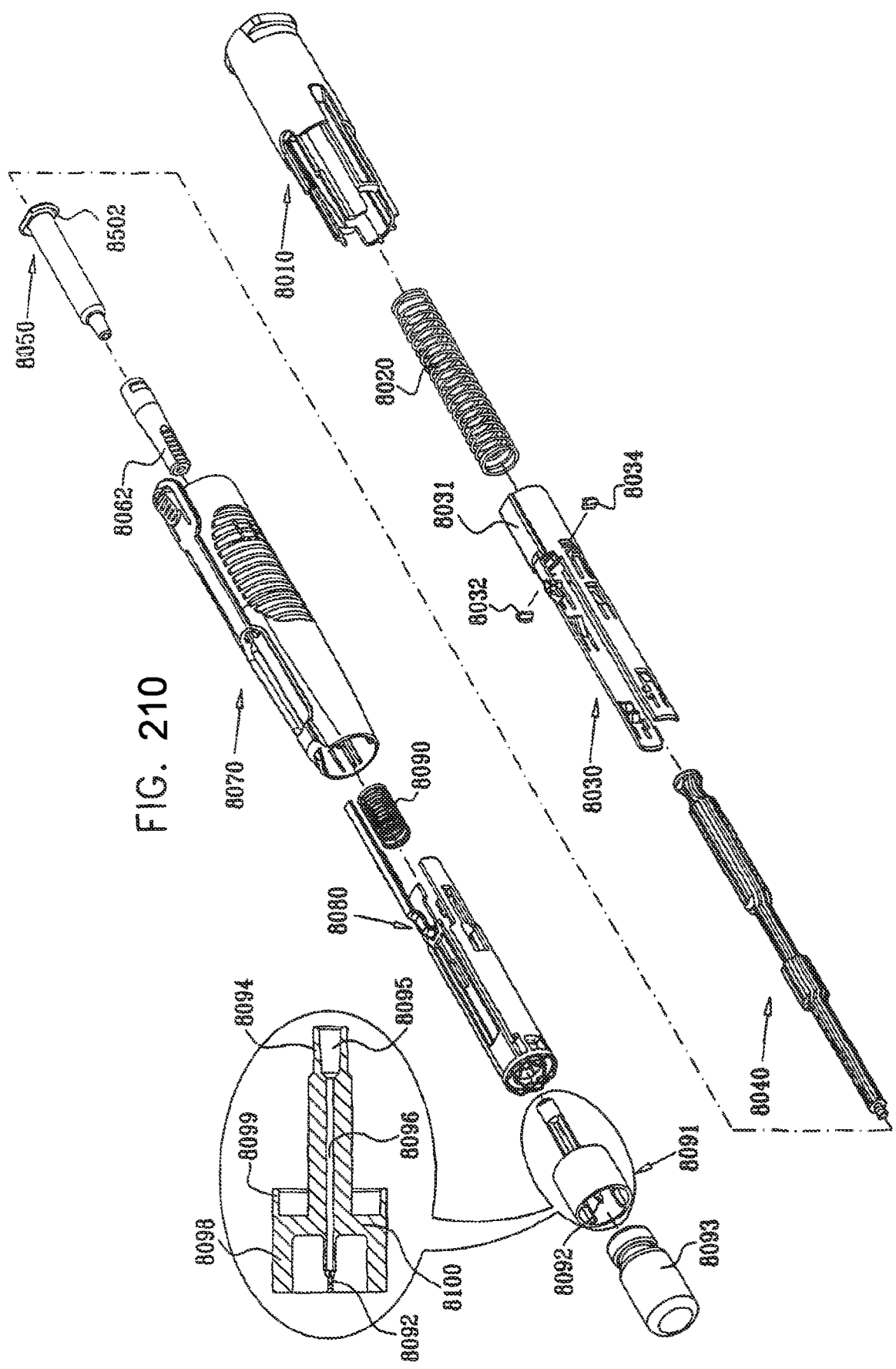
Figure 211:
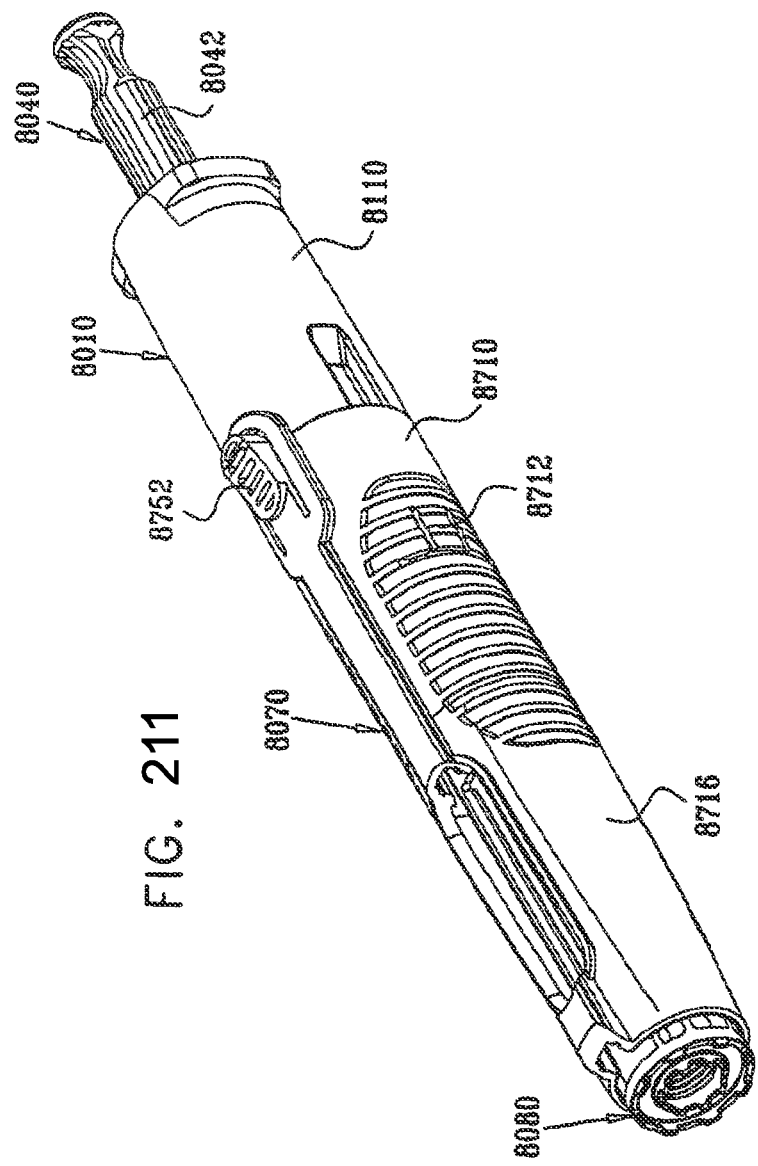
Figure 212A:
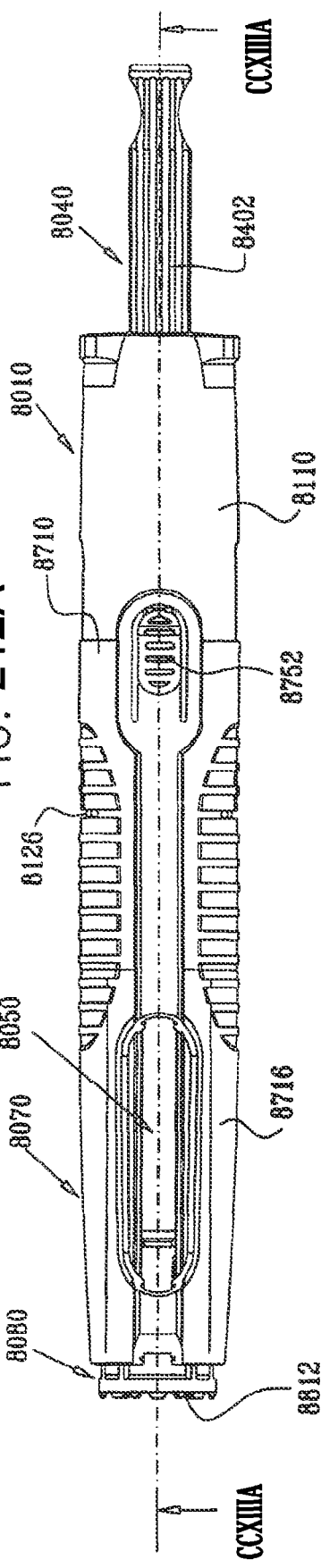
Figure 212B:
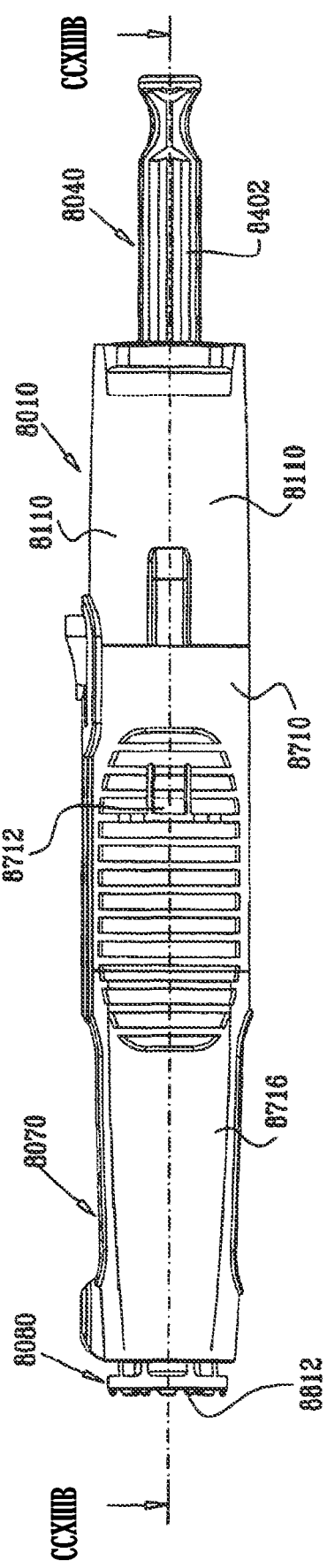
Figure 214:
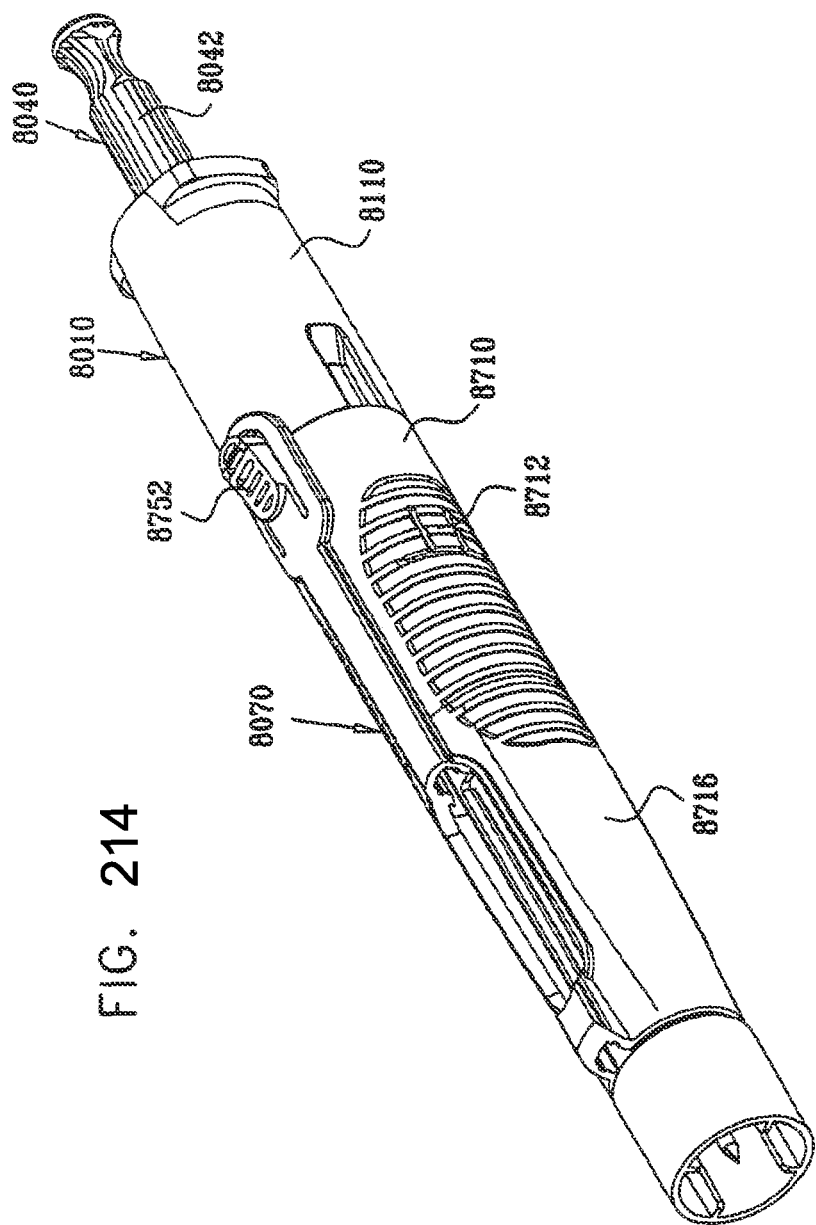
Figure 217:
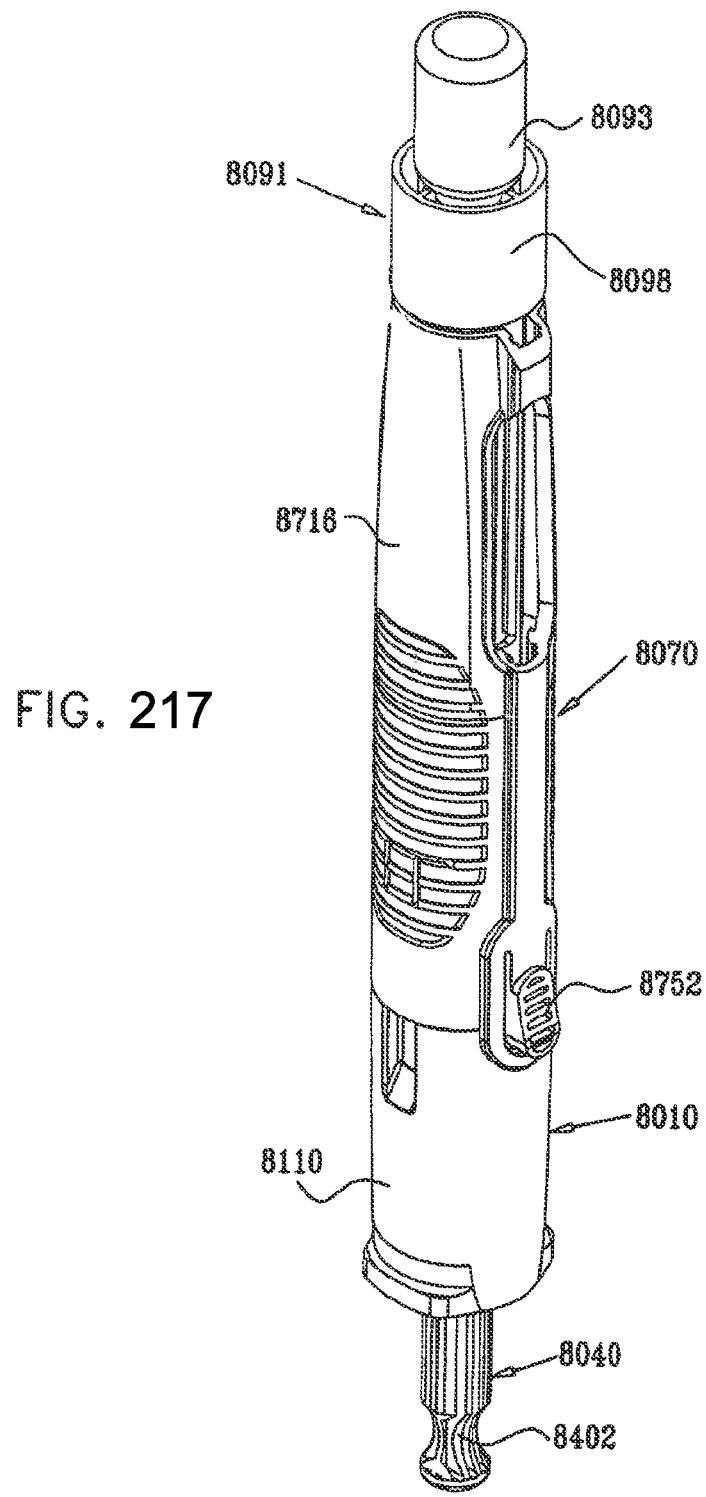
Figure 220:
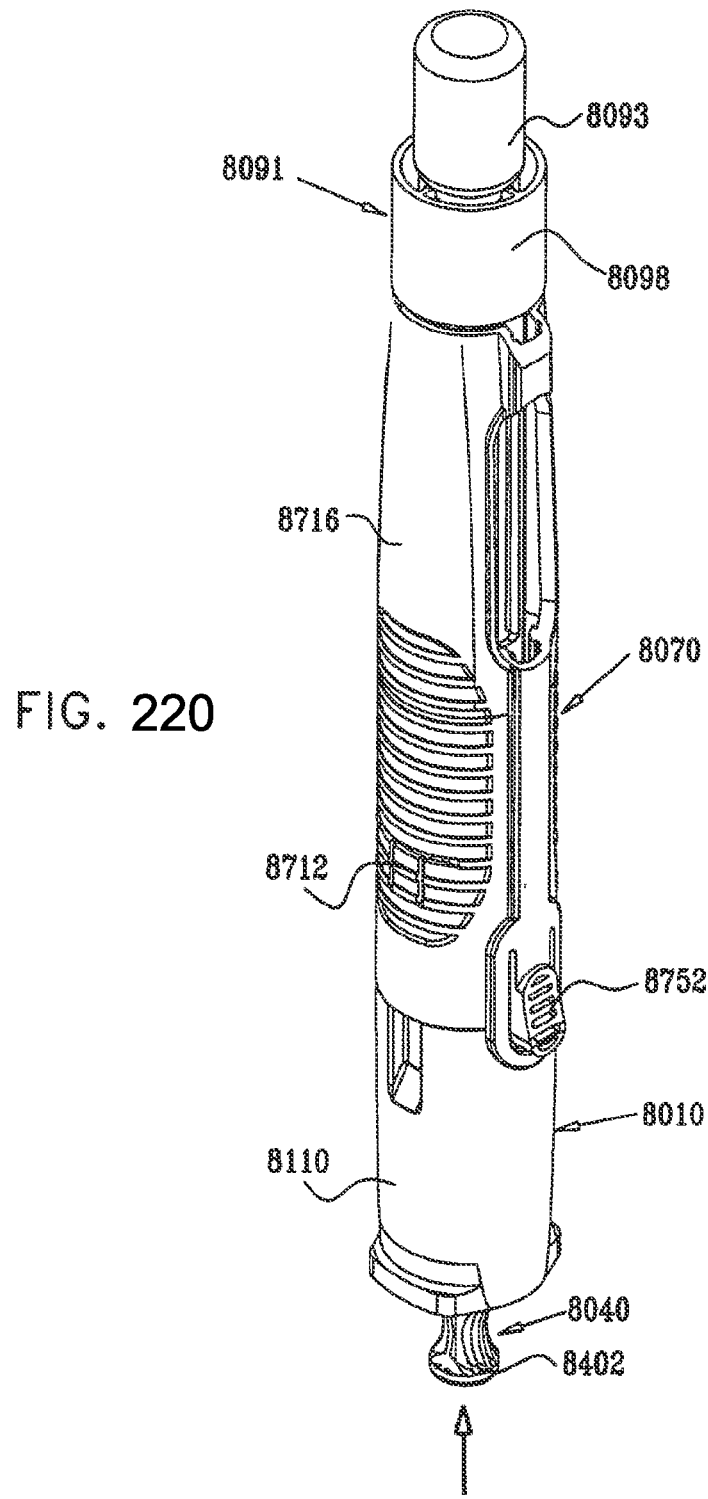
Figure 223:
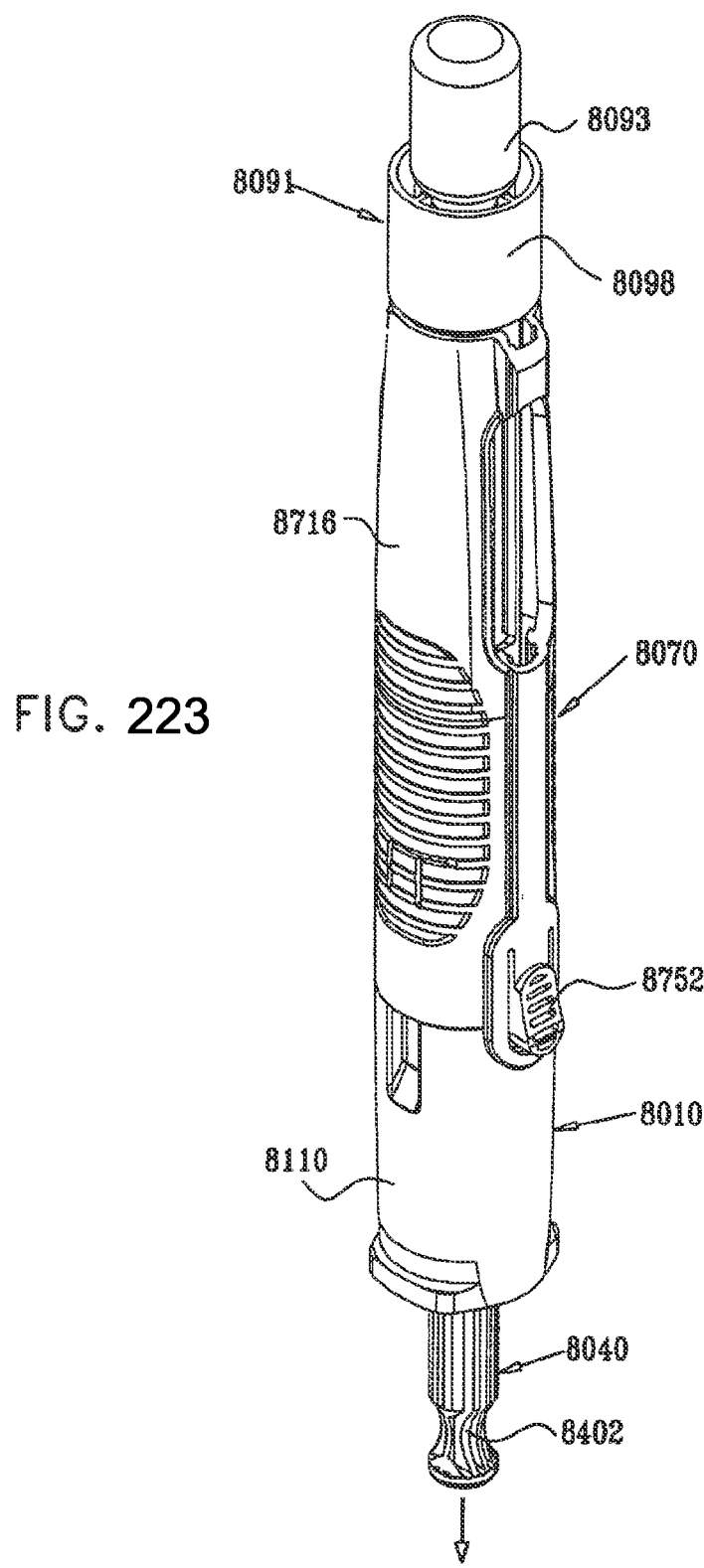
Figure 226:
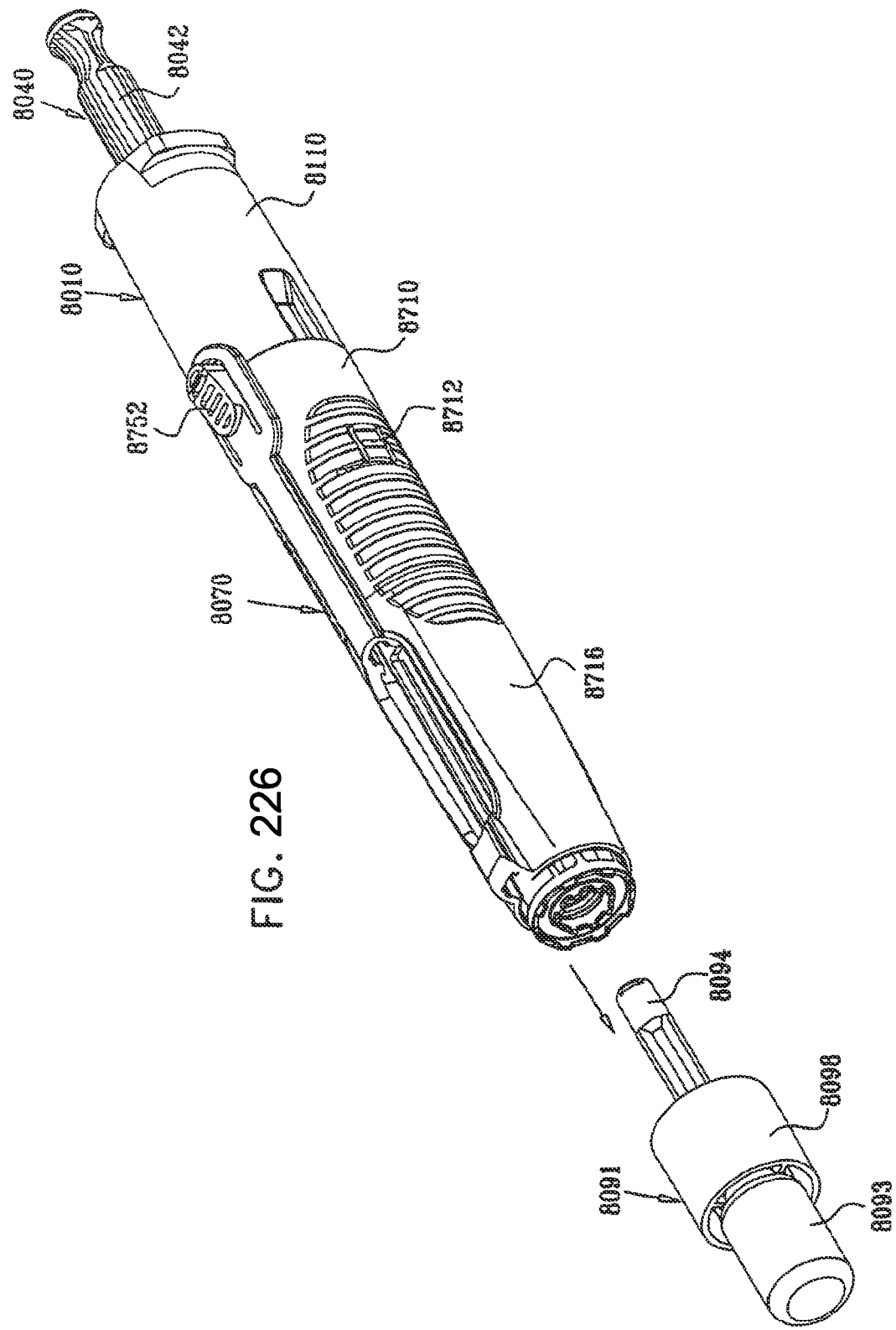
Figure 228A:
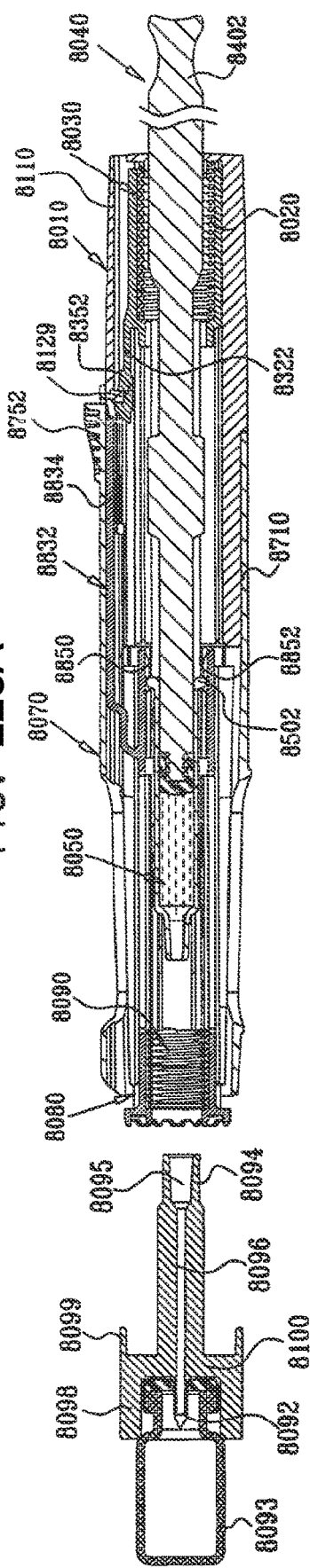
Figure 228B:
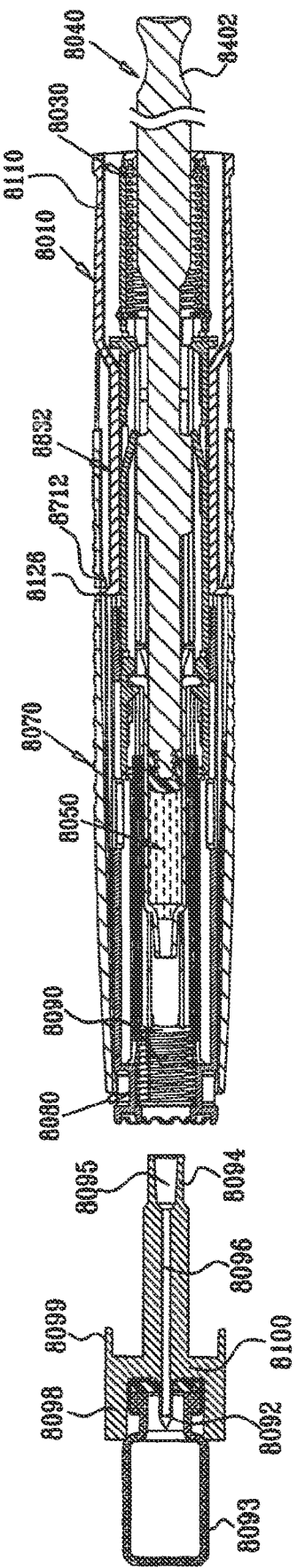
Figures 229A, 229B:
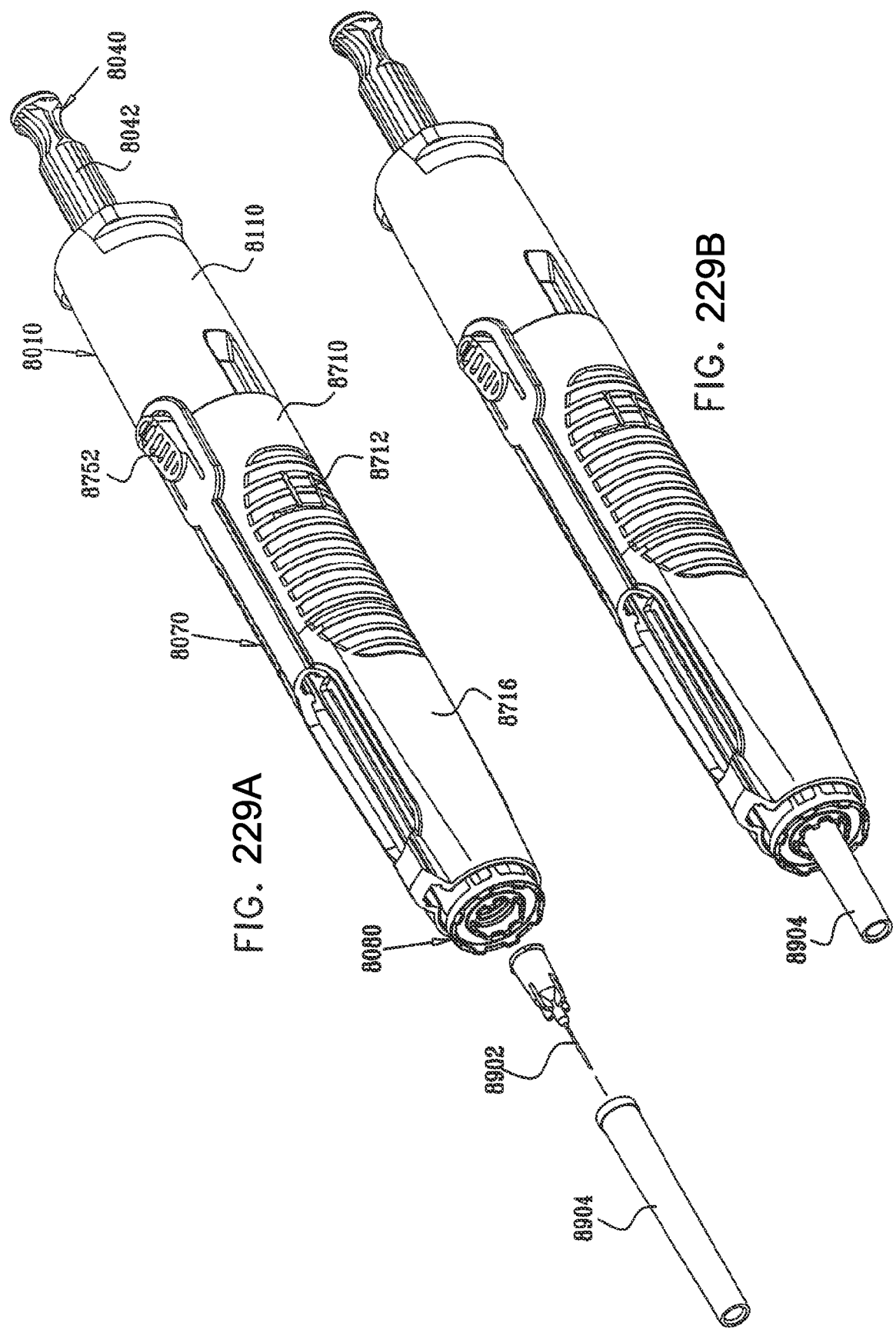
Figure 232:
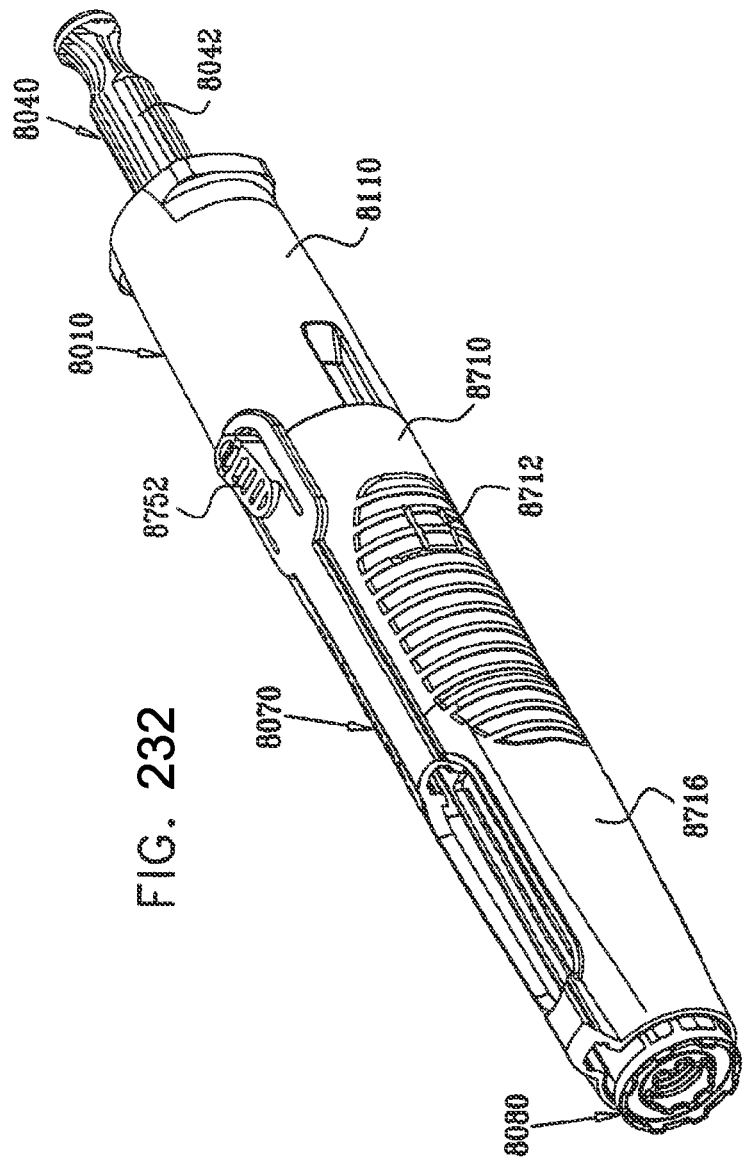
Figure 234A:
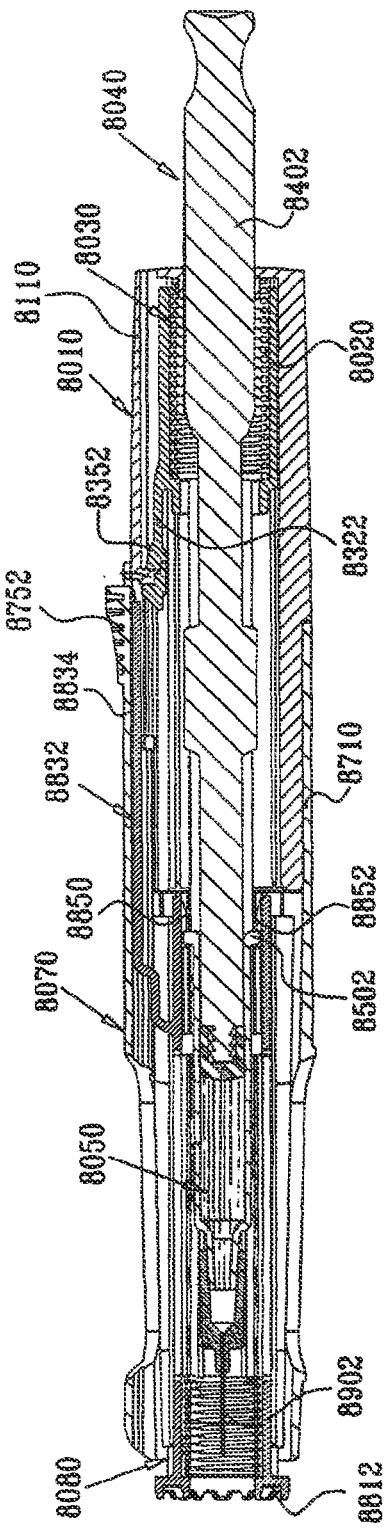
Figure 234B:
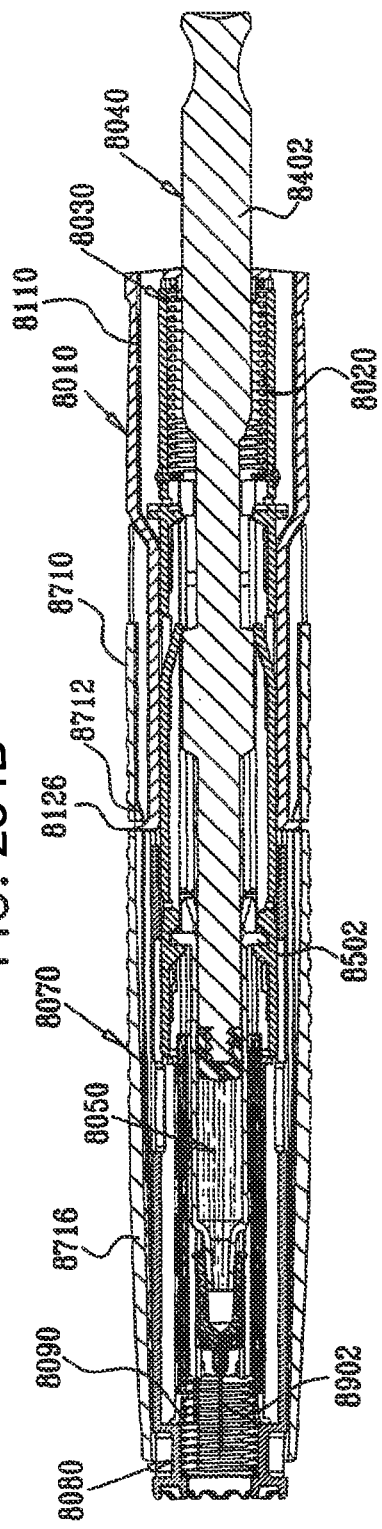

FIGS. 131A, 131B and 131C are sectional illustrations taken along respective section lines and directions CXXXIA-CXXXIA, CXXXIB-CXXXIB and CXXXIC-CXXXIC in FIGS. 130A and 130B;

FIG. 132 is a simplified pictorial illustration of a selectable driving assembly which forms part of the automatic injection device of FIG. 128;

FIGS. 133A and 133B are respective top and side view simplified planar illustrations of the selectable driving assembly of FIG. 132;

FIGS. 134A, 134B and 134C are sectional illustrations taken along respective section lines and directions CXXXIVA-CXXXIVA, CXXXIVB-CXXXIVB and CXXXIVC-CXXXIVC in FIGS. 133A and 133B;

FIG. 135 is a simplified pictorial illustration of a forward housing and actuator element which forms part of the automatic injection device of FIG. 128;

FIGS. 136A and 136B are respective top and side view simplified planar illustrations of the forward housing and actuator element of FIG. 135;

FIGS. 137A, 137B and 137C are sectional illustrations taken along respective section lines and directions CXXXVIIA-CXXXVIIA, CXXXVIIB-CXXXVIIB and CXXXVIIC-CXXXVIIC in FIGS. 136A and 136B;

FIG. 138 is a simplified pictorial illustration of a needle guard element which forms part of the automatic injection device of FIG. 128;

FIGS. 139A and 139B are respective top and side view simplified planar illustrations of the needle guard element of FIG. 138;

FIGS. 140A, 140B and 140C are sectional illustrations taken along respective section lines and directions CXLA-CXLA, CXLB-CXLB and CXLC-CXLC in FIGS. 139A and 139B;

FIGS. 141A, 141B, 141C, 141D, 141E, 141F and 141G are simplified pictorial illustration of various stages of typical use of the automatic injection device of FIG. 128;

FIG. 142 is a simplified assembled view illustration of the automatic injection device of FIGS. 128 and 141A in a pre-use operative orientation;

FIGS. 143A and 143B are respective top and side view simplified planar illustrations of the automatic injection device of FIG. 142;

FIGS. 144A and 144B are sectional illustrations taken along respective section lines and directions CXLIVA-CXLIVA and CXLIVB-CXLIVB in FIGS. 143A and 143B;

FIG. 145 is a simplified pictorial illustration of the automatic injection device of FIGS. 128 and 141B in an optional titration operative orientation;

FIGS. 146A and 146B are respective top and side view simplified planar illustrations of the automatic injection device of FIG. 145;

FIGS. 147A and 147B are sectional illustrations taken along respective section lines and directions CXLVIIA-CXLVIIA and CXLVIM-CXLVIIB in FIGS. 146A and 146B;

FIG. 148 is a simplified pictorial illustration of the automatic injection device of FIGS. 128 and 141C in an actuated operative orientation;

FIGS. 149A and 149B are respective top and side view simplified planar illustrations of the automatic injection device of FIG. 148;

FIGS. 150A and 150B are sectional illustrations taken along respective section lines and directions CLA-CLA and CLB-CLB in FIGS. 149A and 149B;

FIG. 151 is a simplified pictorial illustration of the automatic injection device of FIGS. 128 and 141D in a needle penetration, pre-drug delivery operative orientation;

FIGS. 152A and 152B are respective top and side view simplified planar illustrations of the automatic injection device of FIG. 151;

FIGS. 153A and 153B are sectional illustrations taken along respective section lines and directions CLIIIA-CLIIIA and CLIIIB-CLIIIB in FIGS. 152A and 152B;

FIG. 154 is a simplified pictorial illustration of the automatic injection device of FIGS. 128 and 141E in drug delivery operational orientation;

FIGS. 155A and 155B are respective top and side view simplified planar illustrations of the automatic injection device of FIG. 154;

FIGS. 156A and 156B are sectional illustrations taken along respective section lines and directions CLVIA-CLVIA and CLVIB-CLVIB in FIGS. 155A and 155B;

FIG. 157 is a simplified pictorial illustration of the automatic injection device of FIGS. 128 and 141F in an immediate post-drug delivery operational orientation;

FIGS. 158A and 158B are respective top and side view simplified planar illustrations of the automatic injection device of FIG. 157;

FIGS. 159A and 159B are sectional illustrations taken along respective section lines and directions CLIXA-CLIXA and CLIXB-CLIXB in FIGS. 158A and 158B;

FIG. 160 is a simplified pictorial illustration of the automatic injection device of FIGS. 128 and 141G in its operation orientation as it is being disengaged from an injection site;

FIGS. 161A and 161B are respective top and side view simplified planar illustrations of the automatic injection device of FIG. 160;

FIGS. 162A and 162B are sectional illustrations taken along respective section lines and directions CLXIIA-CLXIIA and CLXIIB-CLXIIB in FIGS. 161A and 161B;

FIG. 163 is a simplified exploded view illustration of an automatic injection device constructed and operative in accordance with a yet further preferred embodiment of the present invention;

FIG. 164 is a simplified assembled view illustration of the automatic injection device of FIG. 163 in a pre-use operative orientation;

FIGS. 165A and 165B are respective top and side view simplified planar illustrations of the automatic injection device of FIG. 164;

FIGS. 166A and 166B are sectional illustrations taken along respective section lines and directions CLXVIA-CLXVIA and CLXVIB-CLXVIB in FIGS. 165A and 165B;

FIG. 167 is a simplified pictorial illustration of the automatic injection device of FIG. 163 in an optional titration operative orientation;

FIGS. 168A and 168B are respective top and side view simplified planar illustrations of the automatic injection device of FIG. 167;

FIGS. 169A and 169B are sectional illustrations taken along respective section lines and directions CLXIXA-CLXIXA and CLXIXB-CLXIXB in FIGS. 168A and 168B;

FIG. 170 is a simplified pictorial illustration of the automatic injection device of FIG. 163 in an actuated operative orientation;

FIGS. 171A and 171B are respective top and side view simplified planar illustrations of the automatic injection device of FIG. 170;

FIGS. 172A and 172B are sectional illustrations taken along respective section lines and directions CLXXIIA-CLXXIIA and CLXXIIB-CLXXIIB in FIGS. 171A and 171B;

FIG. 173 is a simplified pictorial illustration of the automatic injection device of FIG. 163 in a needle penetration, pre-drug delivery operative orientation;

FIGS. 174A and 174B are respective top and side view simplified planar illustrations of the automatic injection device of FIG. 173;

FIGS. 175A and 175B are sectional illustrations taken along respective section lines and directions CLXXVA-CLXXVA and CLXXVB-CLXXVB in FIGS. 174A and 174B;

FIG. 176 is a simplified pictorial illustration of the automatic injection device of FIG. 163 in drug delivery operational orientation;

FIGS. 177A and 177B are respective top and side view simplified planar illustrations of the automatic injection device of FIG. 176;

FIGS. 178A and 178B are sectional illustrations taken along respective section lines and directions CLXXVIIIA-CLXXVIIIA and CLXXVIIIB-CLXXVIIIB in FIGS. 177A and 177B;

FIG. 179 is a simplified pictorial illustration of the automatic injection device of FIG. 163 in an immediate post-drug delivery operational orientation;

FIGS. 180A and 180B are respective top and side view simplified planar illustrations of the automatic injection device of FIG. 179;

FIGS. 181A and 181B are sectional illustrations taken along respective section lines and directions CLXXXIA-CLXXXIA and CLXXXIB-CLXXXIB in FIGS. 180A and 180B;

FIG. 182 is a simplified pictorial illustration of the automatic injection device of FIG. 163 in its operation orientation as it is being disengaged from an injection site;

FIGS. 183A and 183B are respective top and side view simplified planar illustrations of the automatic injection device of FIG. 182;

FIGS. 184A and 184B are sectional illustrations taken along respective section lines and directions CLXXXIVA-CLXXXIVA and CLXXXIVB-CLXXXIVB in FIGS. 183A and 183B;

FIG. 185 is a simplified pictorial illustration of the automatic injection device of FIG. 163 in a needle protected operational orientation;

FIGS. 186A and 186B are respective top and side view simplified planar illustrations of the automatic injection device of FIG. 185;

FIGS. 187A and 187B are sectional illustrations taken along respective section lines and directions CLXXXVIIA-CLXXXVIIA and CLXXXVIIB-CLXXXVIIB in FIGS. 186A and 186B;

FIG. 188 is a simplified pictorial illustration of the automatic injection device of FIG. 163 in a needle-guard push back misuse operational orientation;

FIGS. 189A and 189B are respective top and side view simplified planar illustrations of the automatic injection device of FIG. 188;

FIGS. 190A and 190B are sectional illustrations taken along respective section lines and directions CXCA-CXCA and CXCB-CXCB in FIGS. 189A and 189B;

FIG. 191 is a simplified exploded view illustration of an automatic injection device constructed and operative in accordance with yet another preferred embodiment of the present invention;

FIG. 192 is a simplified assembled view illustration of the automatic injection device of FIG. 191 in a pre-use operative orientation;

FIGS. 193A and 193B are respective top and side view simplified planar illustrations of the automatic injection device of FIG. 192;

FIGS. 194A and 194B are sectional illustrations taken along respective section lines and directions CXCIVA-CXCIVA and CXCIVB-CXCIVB in FIGS. 193A and 193B;

FIG. 195 is a simplified pictorial illustration of the automatic injection device of FIGS. 192-194B in an optional vial adaptor mounted operative orientation;

FIGS. 196A and 196B are respective top and side view simplified planar illustrations of the automatic injection device of FIG. 195;

FIGS. 197A and 197B are sectional illustrations taken along respective section lines and directions CXCVIIA-CXCVIIA and CXCVIIB-CXCVIIB in FIGS. 196A and 196B;

FIG. 198 is a simplified pictorial illustration of the automatic injection device of FIGS. 195-197B in a vial communication operative orientation;

FIGS. 199A and 199B are respective top and side view simplified planar illustrations of the automatic injection device of FIG. 198;

FIGS. 200A and 200B are sectional illustrations taken along respective section lines and directions CCA-CCA and CCB-CCB in FIGS. 199A and 199B;

FIG. 201 is a simplified pictorial illustration of the automatic injection device of FIGS. 198-200B in a vial injection operative orientation;

FIGS. 202A and 202B are respective top and side view simplified planar illustrations of the automatic injection device of FIG. 201;

FIGS. 203A and 203B are sectional illustrations taken along respective section lines and directions CCIIIA-CCIIIA and CCIIIB-CCIIIB in FIGS. 202A and 202B;

FIG. 204 is a simplified pictorial illustration of the automatic injection device of FIGS. 201-203B in a vial aspiration operative orientation;

FIGS. 205A and 205B are respective top and side view simplified planar illustrations of the automatic injection device of FIG. 204;

FIGS. 206A and 206B are sectional illustrations taken along respective section lines and directions CCVIA-CCVIA and CCVIB-CCVIB in FIGS. 205A and 205B;

FIG. 207 is a simplified pictorial illustration of the automatic injection device of FIGS. 204-206B in a vial removed operative orientation;

FIGS. 208A and 208B are respective top and side view simplified planar illustrations of the automatic injection device of FIG. 207;

FIGS. 209A and 209B are sectional illustrations taken along respective section lines and directions CCIXA-CCIXA and CCIXB-CCIXB in FIGS. 208A and 208B;

FIG. 210 is a simplified exploded view illustration of an automatic injection device constructed and operative in accordance with still another preferred embodiment of the present invention;

FIG. 211 is a simplified assembled view illustration of the automatic injection device of FIG. 210 in a pre-use operative orientation;

FIGS. 212A and 212B are respective top and side view simplified planar illustrations of the automatic injection device of FIG. 211;

FIGS. 213A and 213B are sectional illustrations taken along respective section lines and directions CCXIIIA-CCXIIIA and CCXIIIB-CCXIIIB in FIGS. 212A and 212B;

FIG. 214 is a simplified pictorial illustration of the automatic injection device of FIGS. 211-213B in an optional vial adaptor mounted operative orientation;

FIGS. 215A and 215B are respective top and side view simplified planar illustrations of the automatic injection device of FIG. 214;

FIGS. 216A and 216B are sectional illustrations taken along respective section lines and directions CCXVIA-CCXVIA and CCXVIB-CCXVIB in FIGS. 215A and 215B;

FIG. 217 is a simplified pictorial illustration of the automatic injection device of FIGS. 214-216B in a vial communication operative orientation;

FIGS. 218A and 218B are respective top and side view simplified planar illustrations of the automatic injection device of FIG. 217;

FIGS. 219A and 219B are sectional illustrations taken along respective section lines and directions CCXIXA-CCXIXA and CCXIXB-CCXIXB in FIGS. 218A and 218B;

FIG. 220 is a simplified pictorial illustration of the automatic injection device of FIGS. 217-219B in an air injection operative orientation;

FIGS. 221A and 221B are respective top and side view simplified planar illustrations of the automatic injection device of FIG. 220;

FIGS. 222A and 222B are sectional illustrations taken along respective section lines and directions CCXXIIA-CCXXIIA and CCXXIIB-CCXXIIB in FIGS. 221A and 221B;

FIG. 223 is a simplified pictorial illustration of the automatic injection device of FIGS. 220-222B in a vial aspiration operative orientation;

FIGS. 224A and 224B are respective top and side view simplified planar illustrations of the automatic injection device of FIG. 223;

FIGS. 225A and 225B are sectional illustrations taken along respective section lines and directions CCXXVA-CCXXVA and CCXXVB-CCXXVB in FIGS. 224A and 224B;

FIG. 226 is a simplified pictorial illustration of the automatic injection device of FIGS. 223-225B in a vial removed operative orientation;

FIGS. 227A and 227B are respective top and side view simplified planar illustrations of the automatic injection device of FIG. 226;

FIGS. 228A and 228B are sectional illustrations taken along respective section lines and directions CCXXVIIIA-CCXXVIIIA and CCXXVIIIB-CCXXVIIIB in FIGS. 227A and 227B;

FIGS. 229A and 229B are simplified pictorial illustrations of the automatic injection device of FIGS. 226-228B in a needle connection operative orientation;

FIGS. 230A and 230B are respective top and side view simplified planar illustrations of the automatic injection device of FIGS. 229A and 229B;

FIGS. 231A and 231B are sectional illustrations taken along respective section lines and directions CCXXXIA-CCXXXIA and CCXXXIB-CCXXXIB in FIGS. 230A and 230B;

FIG. 232 is a simplified pictorial illustration of the automatic injection device of FIGS. 229A-231B in a needle cover removed operative orientation;

FIGS. 233A and 233B are respective top and side view simplified planar illustrations of the automatic injection device of FIG. 232; and FIGS. 234A and 234B are sectional illustrations taken along respective section lines and directions CCXXXIVA-CCXXXIVA and CCXXXIVB-CCXXXIVB in FIGS. 233A and 233B;

DETAILED DESCRIPTION OF PREFERRED EMBODIMENTS

Reference is now made to FIGS. 1-13C, which illustrate the constituent elements of an automatic injection device constructed and operative in accordance with a preferred embodiment of the present invention.

Figure 1:
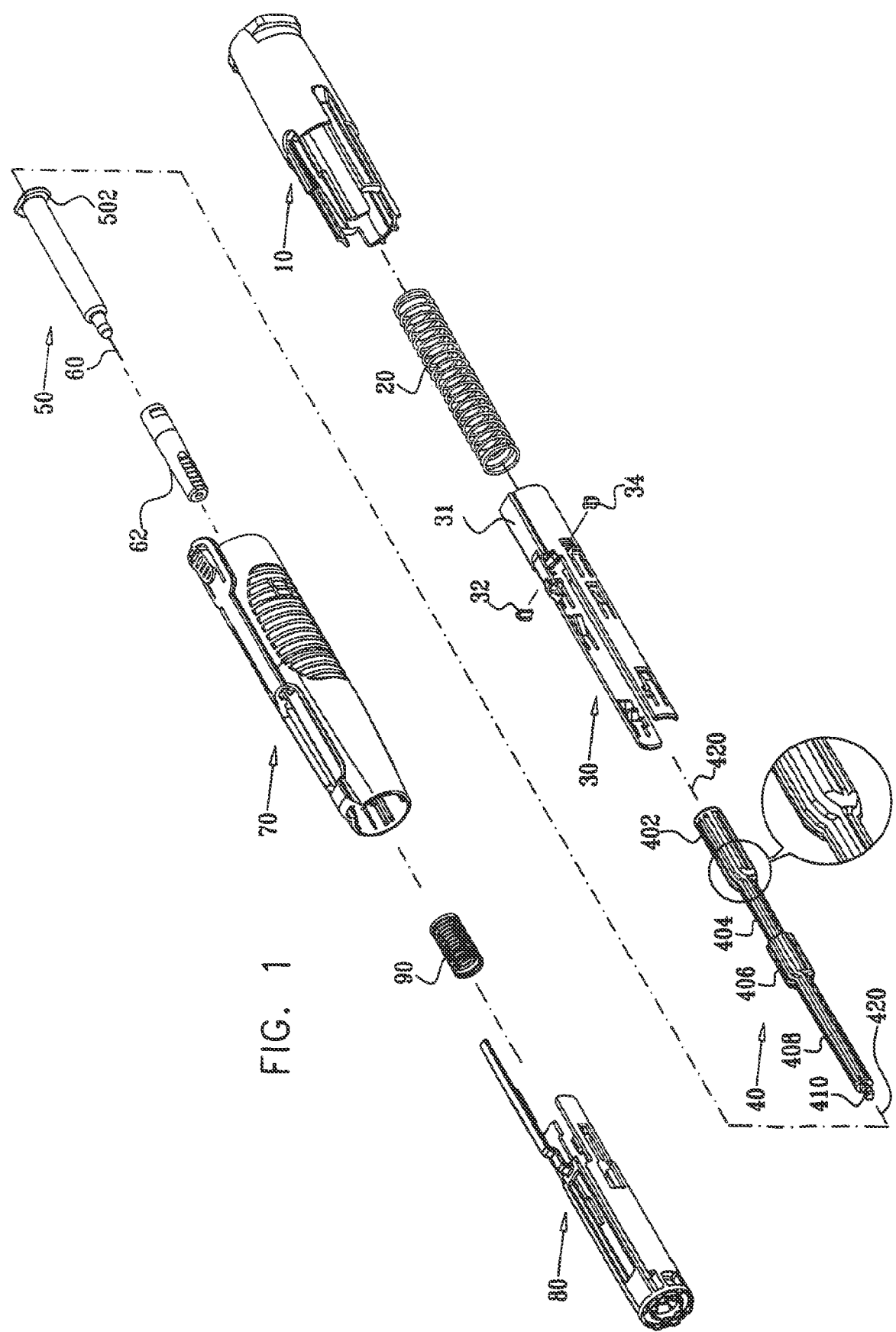
FIG. 1 is a simplified exploded view illustration of an automatic injection device constructed and operative in accordance with a preferred embodiment of the present invention.

As seen with particular clarity in FIG. 1, the automatic injection device comprises a rear housing element 10 in which is seated a main compression spring 20, which provides selectable forward displacement to a selectable driving assembly 30, which includes a selectable driving element 31 and a pair of elastomeric motion damping elements 32 and 34, and selectably engages a plunger 40 and a pre-filled syringe 50 having a hypodermic needle 60 which is covered by a needle protection cover 62. Pre-filled syringe 50 may be a conventional pre-filled syringe, such as a commercially available syringe sold under the catalog designation BD-Hypak™ or may be any other suitable syringe or cartridge.

Plunger 40 also operatively engages pre-filled syringe 50 and is selectably operated by selectable driving assembly 30 to inject liquid contents of pre-filled syringe 50 through hypodermic needle 60.

The forward portion of rear housing element 10 as well as spring 20, selectable driving assembly 30, plunger 40 and pre-filled syringe 50 are located within a forward housing and actuator element 70. At a forward end of the interior of forward housing and actuator element 70 there is provided a needle guard element 80, which is positioned by a compression spring 90.

Figure 3A:
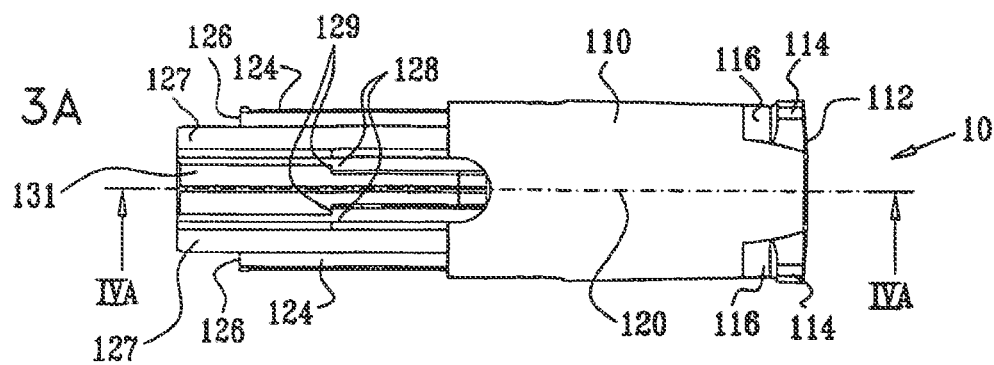
FIGS. 3A and 3B are respective top and side view simplified planar illustrations of the rear housing element of FIG. 2.
Figure 3B:
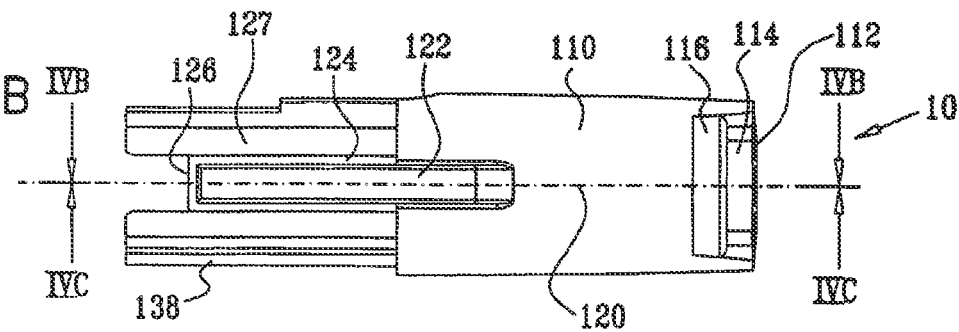
Figure 4A:
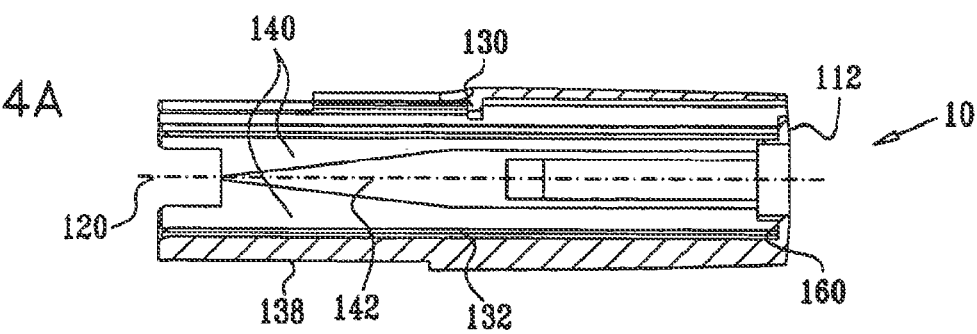
FIGS. 4A, 4B and 4C are sectional illustrations taken along respective section lines and directions IVA-IVA, IVB-IVB and IVC-IVC in FIGS. 3A and 3B.
Figure 4B:
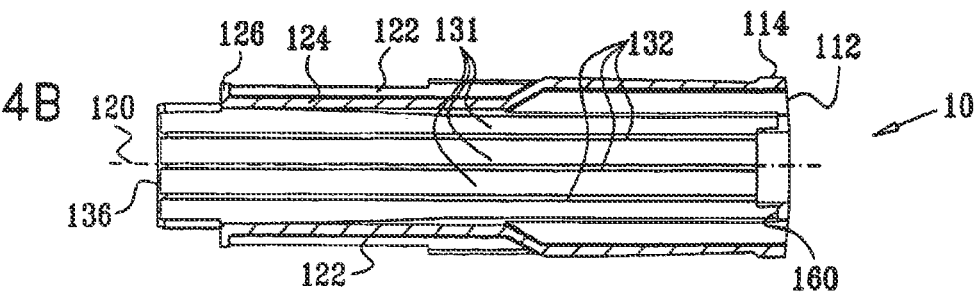
Figure 4C:
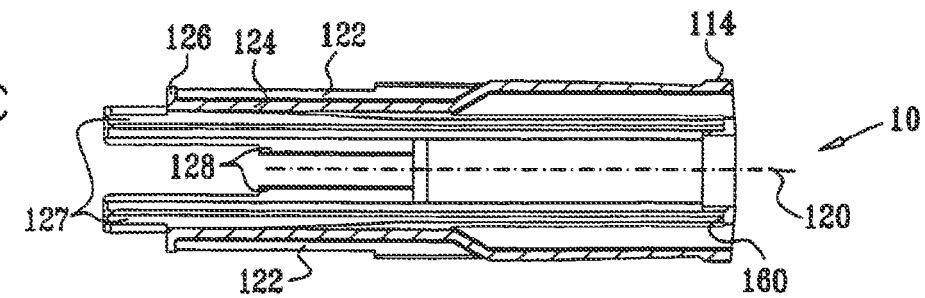

Reference is now made to FIG. 2, which is a simplified pictorial illustration of a preferred rear housing element 10 which forms part of the automatic injection device of FIG. 1, to FIGS. 3A and 3B which are respective top and side view simplified planar illustrations thereof and to FIGS. 4A, 4B and 4C, which are sectional illustrations taken along respective section lines and directions IVA-IVA, IVB-IVB and IVC-IVC in FIGS. 3A and 3B.

As seen in FIGS. 2-4C, the rear housing element 10 preferably is an integrally formed element, preferably injection molded of plastic and preferably has a generally cylindrical configuration including a generally tubular portion 110, which terminates in a back wall 112, defining generally symmetric side-facing tabs 114 in front of which are generally symmetric side facing recesses 116. Tubular portion 110 is preferably side-to-side symmetric about a longitudinal axis 120.

Tubular portion 110 is formed with a pair of generally symmetric side recesses 122 at which corresponding generally elongate engagement shaft portions 124 extend forwardly parallel to longitudinal axis 120, each terminating in an outward facing protrusion 126. Above each engagement shaft portion 124 there is provided an additional shaft portion 127, which extends forwardly of protrusion 126 and has a somewhat curved cross sectional configuration. Shaft portions 127 on the two sides of the rear housing element 10 are separated from each other, as shown. A pair of mutually facing ribs 128 extend from shaft portions 127 parallel to longitudinal axis 120, defining forward facing shoulders 129. As seen particularly in FIGS. 2 and 4A, a central inward facing protrusion 130 is provided at a top interior surface of the rear housing element, between and rearward of ribs 128.

A bottom interior surface 131 of the rear housing element has a generally uniform, slightly concave cross section and includes a plurality of generally radially inwardly directed ribs 132, which extend generally parallel to longitudinal axis 120. A bottom exterior surface 134 of the rear housing element, which is the underside of surface 131, includes a forward edge 136 and a plurality of radially outwardly directed ribs 138 which extend generally parallel to longitudinal axis 120.

Side interior surfaces 140 of the rear housing element 10 each define a forwardly pointed protrusion 142 which is engaged by an outwardly extending protrusion of a first finger of selectable driving assembly 30 and by elastomeric motion damping elements 32 and 34, forming part of selectable driving assembly 30, as described hereinbelow. The interior surface of back wall 112 of the rear housing element 10 further comprises a rear seat 160 for spring 20.

Figure 5:
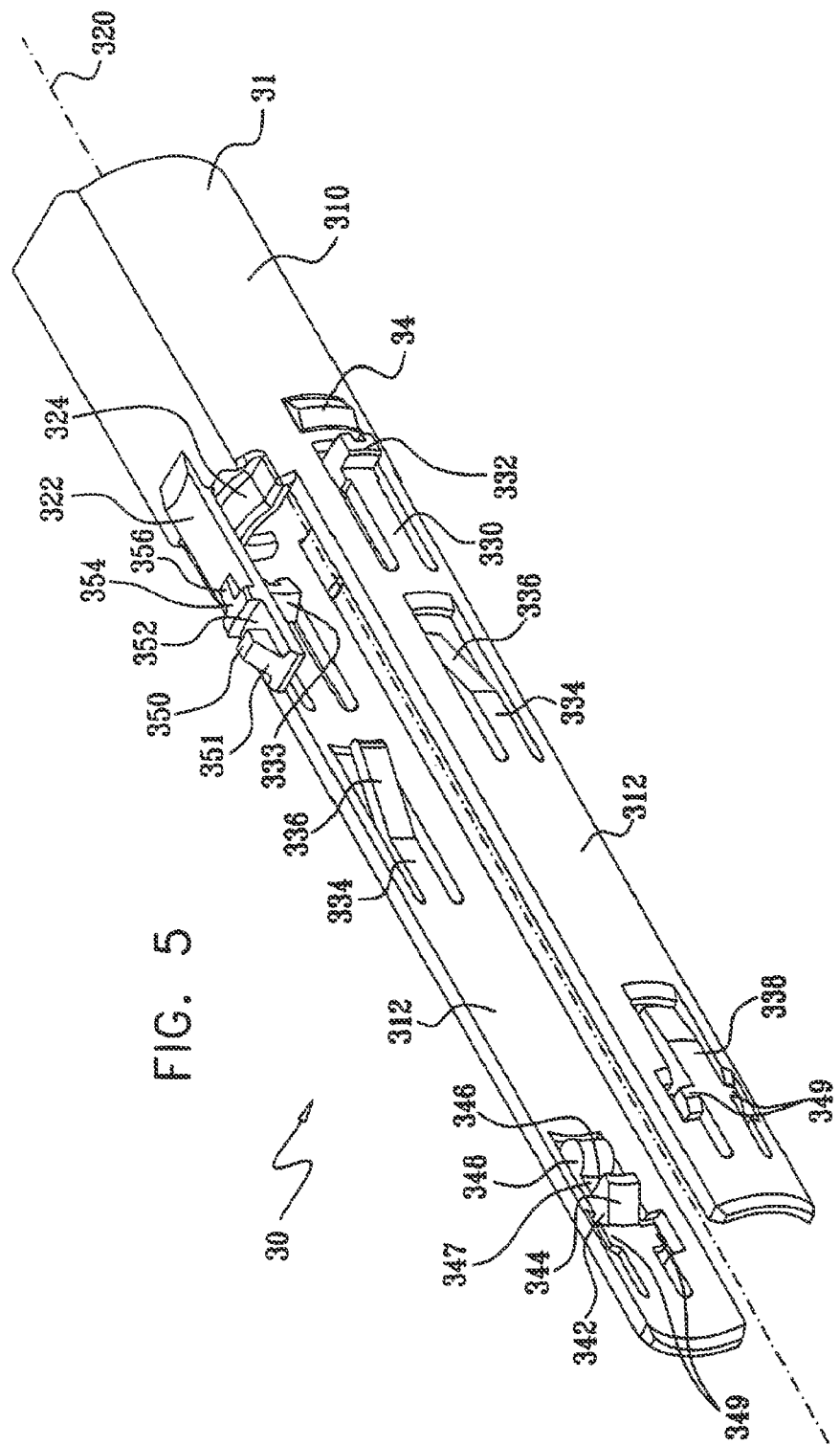
FIG. 5 is a simplified pictorial illustration of a selectable driving assembly which forms part of the automatic injection device of FIG. 1.
Figure 6A:
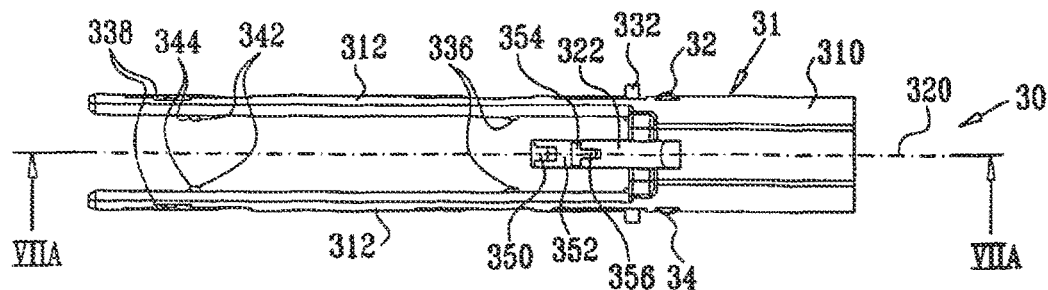
FIGS. 6A and 6B are respective top and side view simplified planar illustrations of the selectable driving assembly of FIG. 5.
Figure 6B:
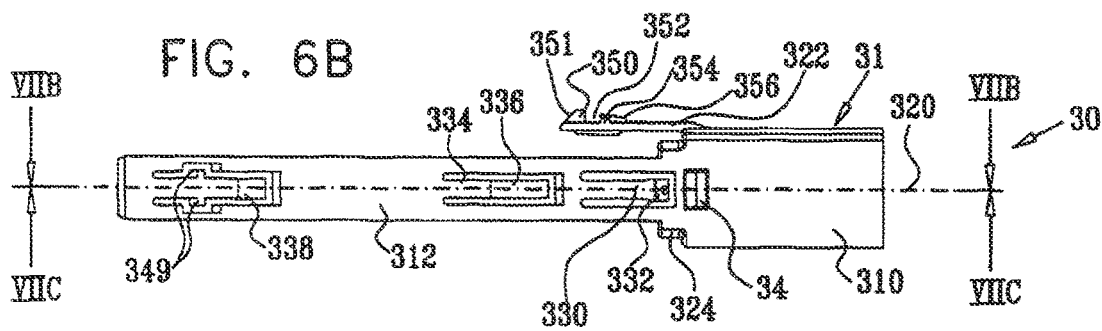
Figure 7A:
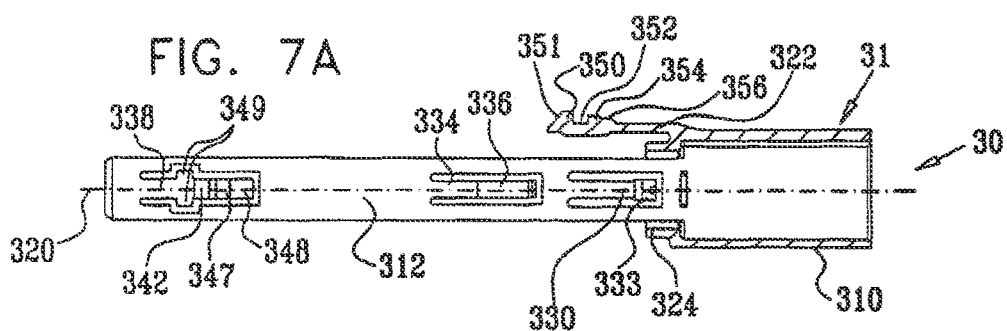
FIGS. 7A, 7B and 7C are sectional illustrations taken along respective section lines and directions VIIA-VIIA, VIIB-VIIB and VIIC-VIIC in FIGS. 6A and 6B.
Figure 7B:
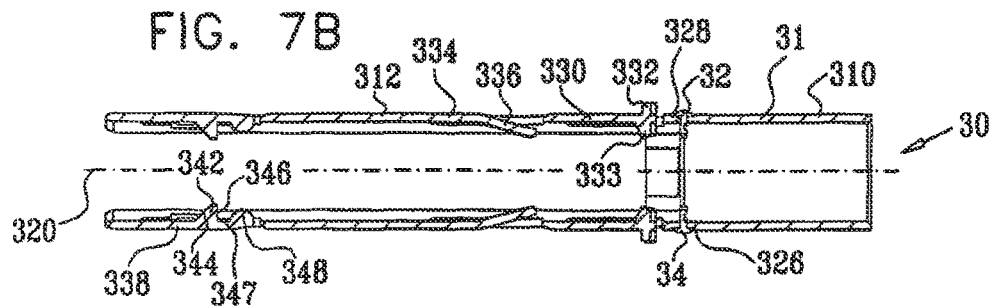
Figure 7C:
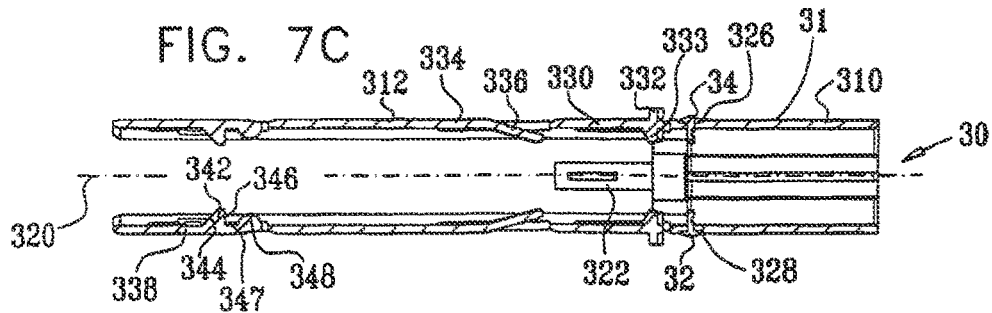

Reference is now made to FIG. 5, which is a simplified pictorial illustration of a preferred selectable driving assembly 30, which forms part of the automatic injection device of FIG. 1, to FIGS. 6A and 6B, which are respective top and side view simplified planar illustrations of the selectable driving assembly and to FIGS. 7A, 7B and 7C, which are sectional illustrations taken along respective section lines and directions VIIA-VIIA, VIIB-VIIB and VIIC-VIIC in FIGS. 6A and 6B.

As seen in FIGS. 5-7C, the selectable driving element 31 preferably is an integrally formed element, preferably injection molded of plastic and preferably has a generally cylindrical configuration including a generally tubular portion 310, having an open back and having a pair of side-to-side symmetric actuation arms 312 which extend forwardly of tubular portion 310 parallel to a longitudinal axis 320, which when selectable driving assembly 30 is assembled with the rear housing element 10, is coaxial with longitudinal axis 120 (FIGS. 2-4C). A top engagement arm 322 also extends forwardly of tubular portion 310. A narrowed tubular neck portion 324 is formed forwardly of tubular portion 310. Elastomeric elements 32 and 34, seated in side recesses 326 and 328 in the selectable driving element 31, are located symmetrically at the junction of the tubular portion 310 and the neck portion 324.

Each of actuation arms 312 has a generally curved cross section and includes a rearwardly facing first finger 330 terminating in an outwardly extending protrusion 332 and an inwardly extending protrusion 333, a second rearwardly extending finger 334 terminating in an inwardly inclined protruding portion 336 and a third rearwardly extending finger 338 having formed thereon, adjacent an extreme outward end thereof, an inwardly facing generally triangular tooth 342 having a forwardly facing inclined surface 344 and a rearwardly facing engagement surface 346 extending generally perpendicular to longitudinal axis 320. Separated from tooth 342 by a notch 347 is an inwardly facing rounded tooth 348. Additionally, third finger 338 has formed thereon top and bottom protrusions 349.

Top engagement arm 322 terminates in an outwardly facing protrusion 350 having an inclined forward facing surface 351. Rearwardly of protrusion 350 and separated therefrom by an outwardly facing notch 352 is an outwardly facing protrusion 354, having an inclined outwardly facing surface 356.

Plunger 40, as seen in FIG. 1, is a generally circularly symmetric element, which is preferably formed in an overall ribbed configuration, as shown. Plunger 40 includes a rear portion 402 having a relatively large circular cross section which tapers forwardly to a neck portion 404, having a relatively small circular cross section. Forwardly of neck portion 404 is an intermediate portion 406, whose circular cross section is typically the same as that of rear portion 402, and a forward portion 408, whose circular cross section is typically the same as that of neck portion 404. Plunger 40 terminates at its forward end in a male threaded protrusion 410 adapted to fit a corresponding female threaded socket formed in a piston described hereinbelow with reference to FIG. 17A which is movably located in pre-filled syringe 50. Plunger 40 is preferably symmetrically disposed about a longitudinal axis 420, which when assembled together with selectable driving assembly 30 and rear housing element 10, is coaxial with longitudinal axes 120 (FIGS. 2-4C) and 320 (FIGS. 5-7C).

As seen in FIG. 1, pre-filled syringe 50 includes a rear flange 502 which selectably engages notches 347 formed in respective third fingers 338 of each of side-to-side symmetric actuation arms 312 of selectable driving assembly 30 (FIGS. 5-7C).

Reference is now made to FIG. 8, which is a simplified pictorial illustration of forward housing and actuator element 70 which forms part of the automatic injection device of FIG. 1, to FIGS. 9A and 9B, which are respective top and side view simplified planar illustrations thereof and to FIGS. 10A, 10B and 10C, which are sectional illustrations taken along respective section lines and directions XA-XA, XB-XB and XC-XC in FIGS. 9A and 9B.

As seen in FIGS. 8-10C, the forward housing and actuator element 70 preferably is an integrally formed element, preferably injection molded of plastic and preferably has a generally truncated conical configuration arranged along a longitudinal axis 720, which when the automatic injection device is assembled, is coaxial with longitudinal axes 120 (FIGS. 2-4C), 320 (FIGS. 5-7C) and 420 (FIG. 1). Forward housing and actuator element 70 includes a generally tubular rear portion 710, having an open back and formed with a pair of side-to-side symmetric snap fit engagement sockets 712 which receive the protrusions 126 of the rear housing element 10 during factory assembly of the automatic injection device.

Forward of tubular rear portion 710 are formed a pair of top-bottom symmetric windows 714, which allow the pre-filled syringe to be viewed, when the automatic injection device is assembled, including during use thereof.

A pair of outer side surfaces 716 of forward housing and actuator element 70 are each formed with ribbed grip regions 718. Corresponding inner side surfaces 721 each define a plurality of longitudinally extending ribs 722, 724, 726 and 728 which are used to slidably guide the needle guard element 80 during axial movement thereof as well as inner facing protrusions 730, which together with ribs 722 and 724 define a forward facing spring seat for spring 90 (FIG. 1). Inner facing protrusions 730 are operative to slidably support pre-filled syringe 50 and to slidably guide actuation arms 312 of selectable driving assembly 30.

Inner top and bottom surfaces 732 and 734 define respective pairs of ribs 736 and 738 which are operative to slidably guide the needle guard 80 during axial movement thereof. A cantilevered rearwardly extending actuation lever 750 extends from a location rearward of top window 714 and defines, at an extreme rearward top facing surface thereof, an actuation button 752.

As best seen in FIG. 10A, inner facing protrusions 730 define at rearward facing portions thereof protrusions 760 and 762 which form a stopping point for flange 502, thus limiting the forward movement of the pre-filled syringe 50.

Reference is now made to FIG. 11, which is a simplified pictorial illustration of a needle guard element 80 which forms part of the automatic injection device of FIG. 1, to FIGS. 12A and 12B, which are respective top and side view simplified planar illustrations thereof and to FIGS. 13A, 13B and 13C, which are sectional illustrations taken along respective section lines and directions XIIIA-XIIIA, XIIIB-XIIIB and XIIIC-XIIIC in FIGS. 12A and 12B.

As seen in FIGS. 11-13C, the needle guard element 80 preferably is an integrally formed element, preferably injection molded of plastic and preferably has a generally cylindrical configuration including a generally tubular portion 810, having a forward facing body engaging surface 812 including a pair of concentric ribbed circumferential forward facing rings 814 and 816. The internal surface, located opposite from body engaging surface 812, forms a spring-seat for spring 90.

Needle guard element 80 has a pair of side-to-side symmetric mounting arms 818 having rearwardmost ends 819, arranged symmetrically about a longitudinal axis 820. Each of arms 818 is formed with a rectangular window 821 having a relatively wider forward portion 822 and a relatively narrower rear portion 824. Arms 818 extend along and rearwardly of tubular portion 810 parallel to longitudinal axis 820, which when the automatic injection device is assembled, is coaxial with longitudinal axes 120 (FIGS. 2-4C), 320 (FIGS. 5-7C), 420 (FIG. 1) and 720 (FIGS. 8-10C).

A top engagement arm 832 also extends rearwardly of tubular portion 810 and includes a rearwardmost axial portion 834, an inclined intermediate portion 836, an axial intermediate portion 838 and an inclined mounting portion 840, which extends from a top mounting arm 842, formed with an elongate window 844. An equivalent elongate window, also referenced by numeral 844, is formed on a bottom mounting arm 845. Elongate windows 844 and top-bottom symmetric windows 714 of forward housing and actuator element 70 are positioned in respective parallel locations, such that pre-filled syringe 50 is visible through the windows.

Top and bottom engagement portions 846 and 848 are each formed with inwardly directed teeth, here designated by reference numerals 850 and 852 respectively.

Reference is now made to FIGS. 14A, 14B, 14C, 14D, 14E, 14F, 14G, 14H and 14I which are simplified pictorial illustrations of various stages of typical use of the automatic injection device of FIG. 1.

As seen in FIG. 14A, the automatic injection device of FIG. 1 is stored prior to use, as indicated by reference numeral 900, in a pre-use operative orientation, described hereinbelow with reference to FIGS. 15-17B. While the automatic injection device is stored, it is preferably covered by needle protection cover 62.

As seen in FIG. 14B, prior to use, after removing the needle protection cover 62, air bubbles or some of the drug contained in pre-filled syringe 50 may optionally be manually expelled via the needle, as indicated by reference numeral 902. The operative orientation of the automatic injection device for this functionality is described hereinbelow with reference to FIGS. 18-20B.

A user actuates the automatic injection device by pushing it against an injection site and depressing actuation button 752 (FIGS. 8-10C), as indicated by reference numeral 904 shown in FIG. 14C and as described hereinbelow with reference to FIGS. 21-23B. In response to user actuation, needle penetration takes place at the injection site, as indicated by reference numeral 906 shown in FIG. 14D. The operative orientation of the automatic injection device at this stage is described hereinbelow with reference to FIGS. 24-26B.

Figure 14C:
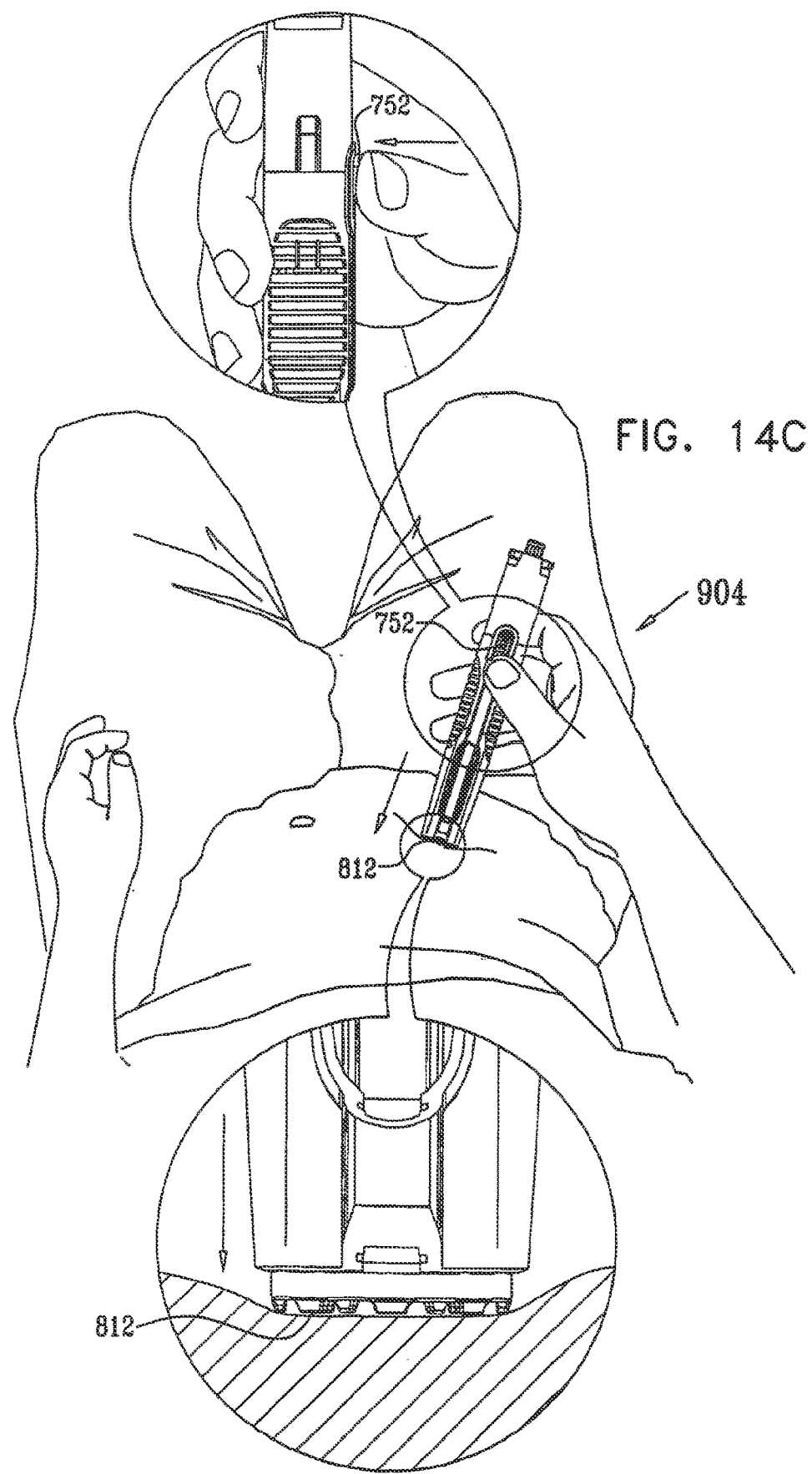
Figure 14D:
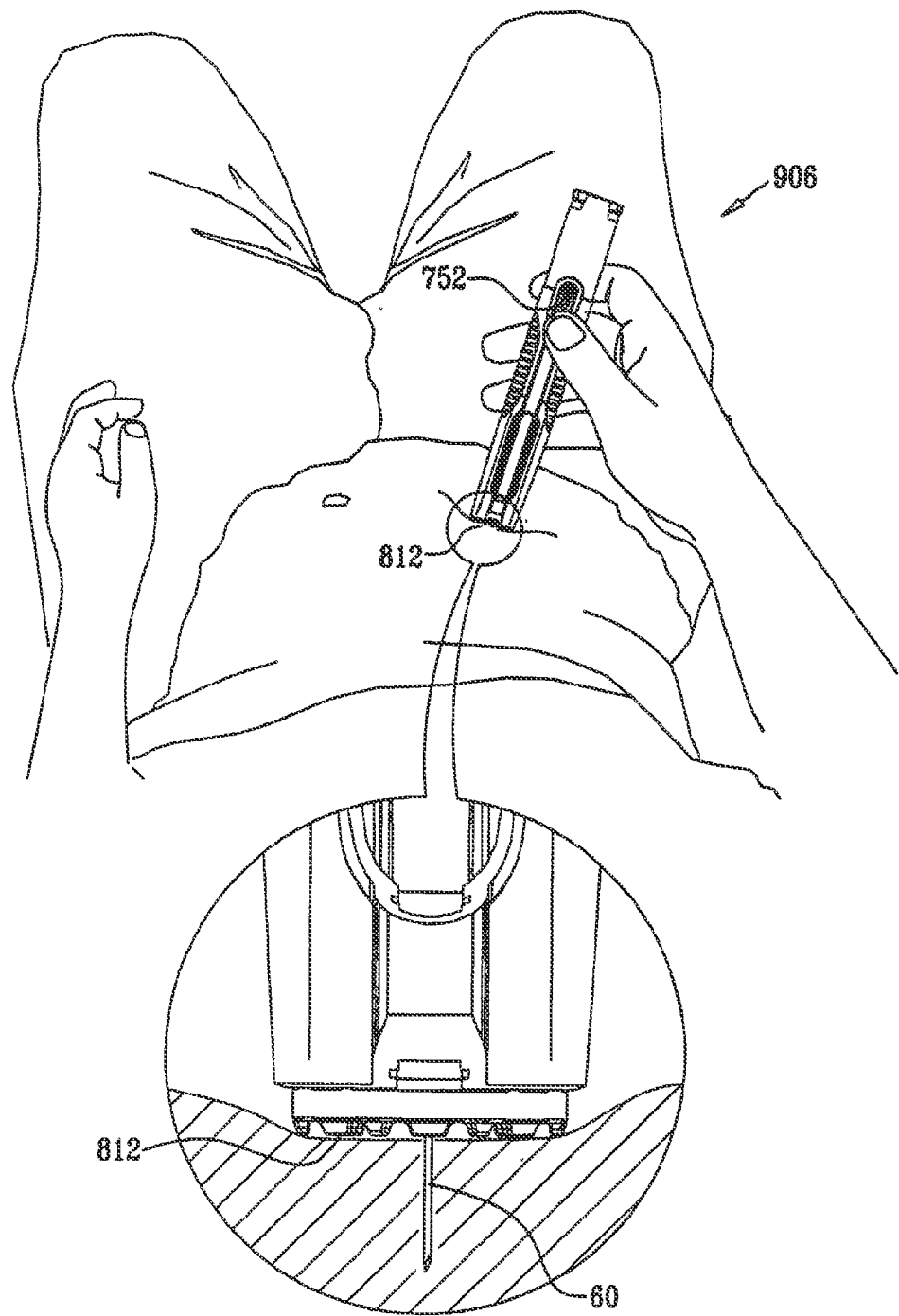
Figure 14E:
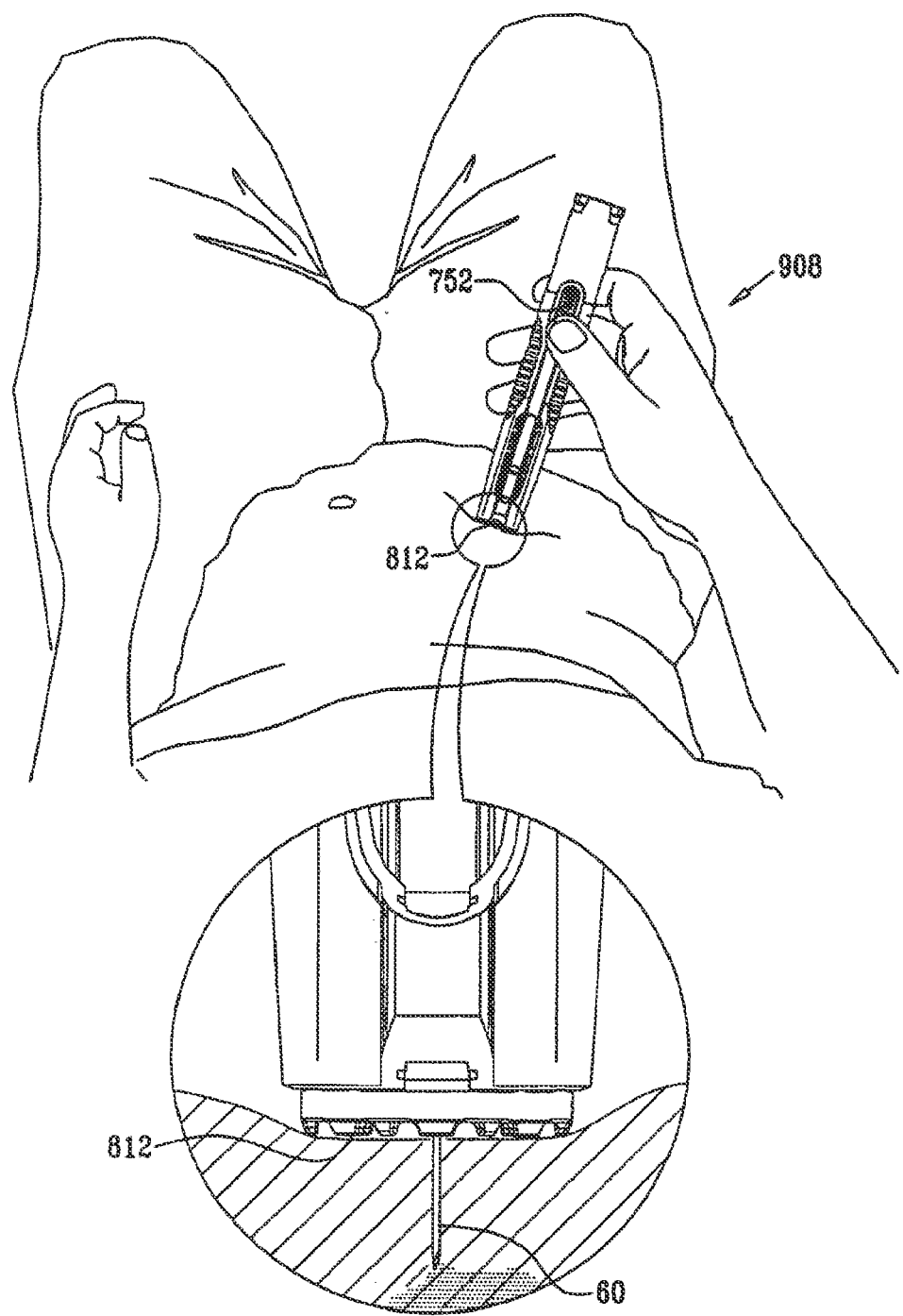

As seen in FIG. 14E, immediately following needle penetration, drug delivery takes place, as indicated by reference numeral 908. The operative orientation of the automatic injection device at this stage is described hereinbelow with reference to FIGS. 27-29B. The operative orientation of the automatic injection device immediately following completion of drug delivery is indicated by reference numeral 910 shown in FIG. 14F, as described hereinbelow with reference to FIGS. 30-32B.

As seen in FIG. 14G, the automatic injection device is then manually disengaged from the injection site, as indicated by reference numeral 912, during which time the needle guard 80 is automatically deployed. The operative orientation of the automatic injection device at this stage is described hereinbelow with reference to FIGS. 33-35B. Immediately upon disengagement, the needle is automatically protected by the needle guard element 80, as indicated by reference numeral 914 shown in FIG. 14H. The operative orientation of the automatic injection device at this stage is described hereinbelow with reference to FIGS. 36-38B.

Figure 14F:
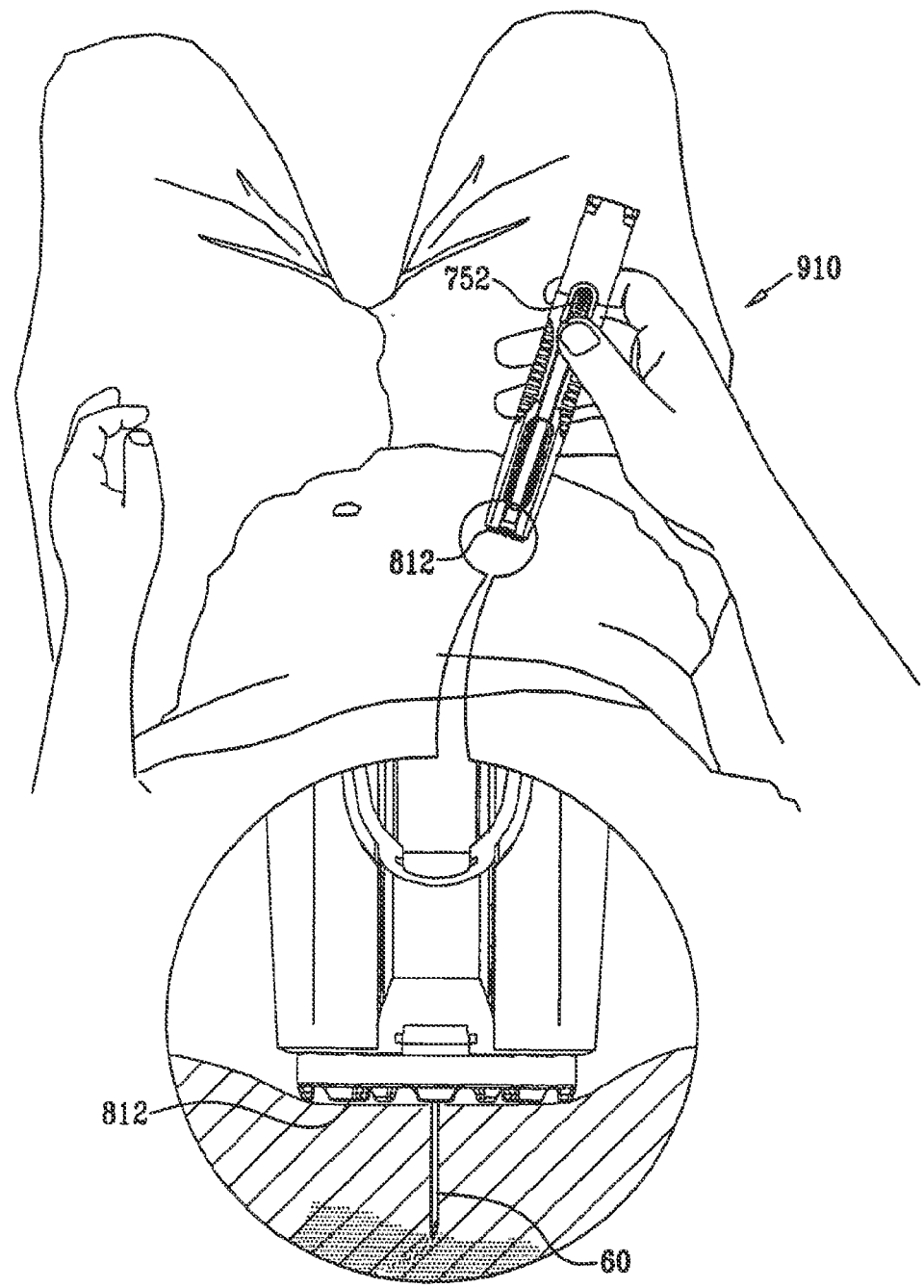
Figure 14I:
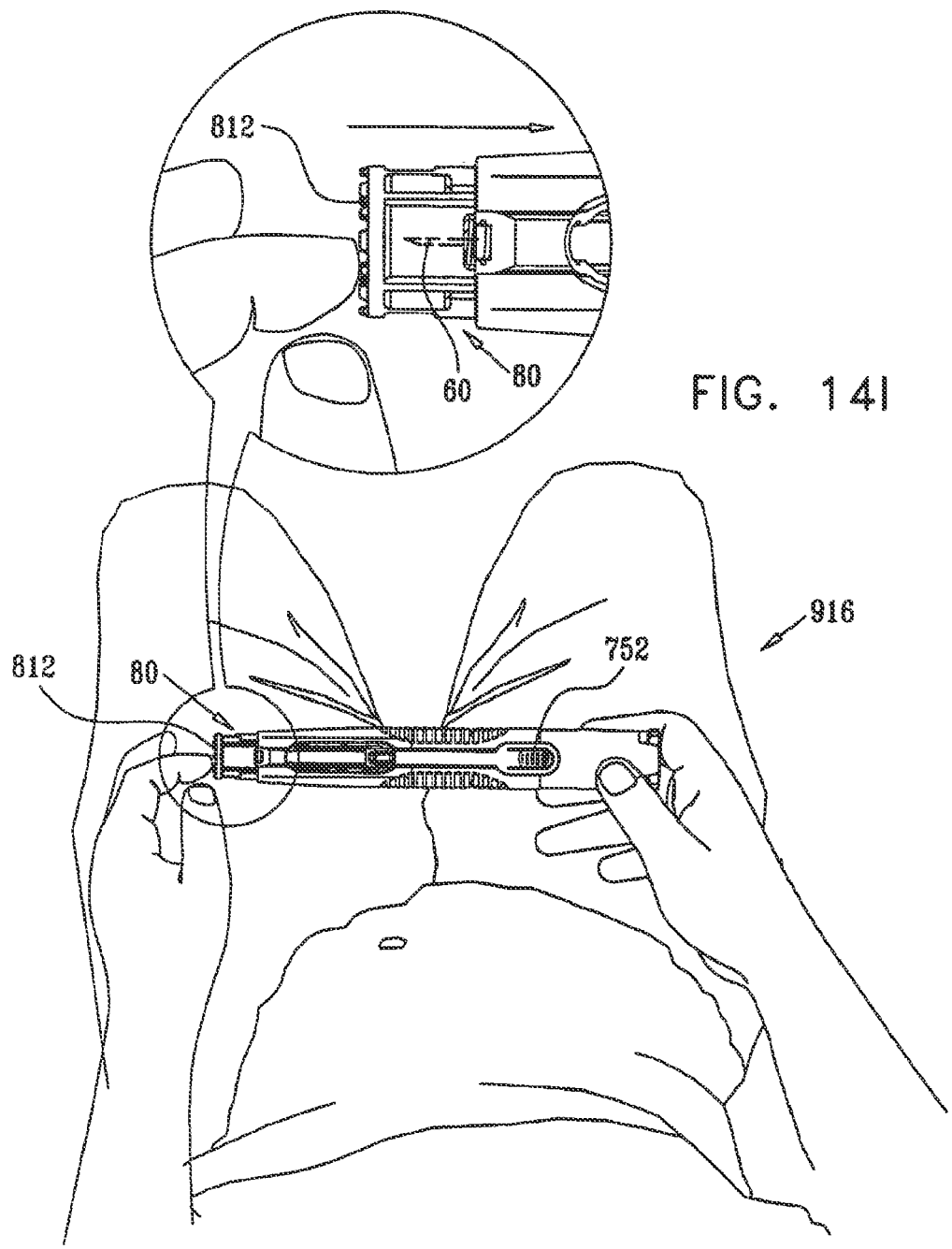

As seen in FIG. 14I, should the needle guard be forced axially rearward due to misuse, as indicated by reference numeral 916, its rearward movement produces corresponding rearward motion of the syringe 50, thus keeping the needle protected. The operative orientation of the automatic injection device in this case is described hereinbelow with reference to FIGS. 39-41B.

Reference is now made to FIG. 15, which is a simplified assembled view illustration of the automatic injection device of FIGS. 1 and 14A in a pre-use operative orientation, to FIGS. 16A and 16B, which are respective top and side view simplified planar illustrations thereof and to FIGS. 17A and 17B, which are sectional illustrations taken along respective section lines and directions XVIIA-XVIIA and XVIIB-XVIIB in FIGS. 16A and 16B.

As seen in FIGS. 15-17B, in a pre-use operative orientation of the automatic injection device which is suitable for storage, the rear housing element 10 is joined to the forward housing and actuator element 70 by snap fit engagement of protrusions 126 of rear housing element 10 in the engagement sockets 712 formed in the forward housing and actuator element 70.

Selectable driving assembly 30 is retained in its axial position by engagement of inward facing protrusion 130 (FIG. 4A) with outwardly facing notch 352 of top engagement arm 322 (FIG. 7A) of selectable driving assembly 30, as shown particularly in the enlarged portion of FIG. 17A. In this arrangement, spring 20 is in a relatively compressed state and is held in that state by the selectable driving assembly 30.

Also seen in the enlarged portion of FIG. 17A is that the rearwardmost axial portion 834 of the top engagement arm 832 of the needle guard 80 (FIGS. 11-13C) is in a relatively forward position, only partially underlying actuation button 752 of forward housing and actuator element 70 (FIGS. 8-10C). Additionally, inward displacement of actuation button 752 is limited by ribs 128 (FIGS. 2-4C), thus ensuring that actuation button 752 does not directly engage protrusion 350 of engagement arm 322. Accordingly, in this orientation of the needle guard 80, inadvertent pressing of button 752 does not actuate the automatic injection device.

The pre-filled syringe 50 is retained in a retracted orientation by engagement of flange 502 thereof with notches 347 formed in respective third fingers 338 of each of side-to-side symmetric actuation arms 312 of selectable driving assembly 30 (FIGS. 5-7C).

Needle guard 80 is retained in its axial position, and is prevented from moving forward by engagement of inwardly directed teeth 850 and 852 with the flange 502 of the pre-filled syringe 50. It is appreciated that in this operative orientation spring 90 is either at rest or in a semi-compressed state.

Figure 18:
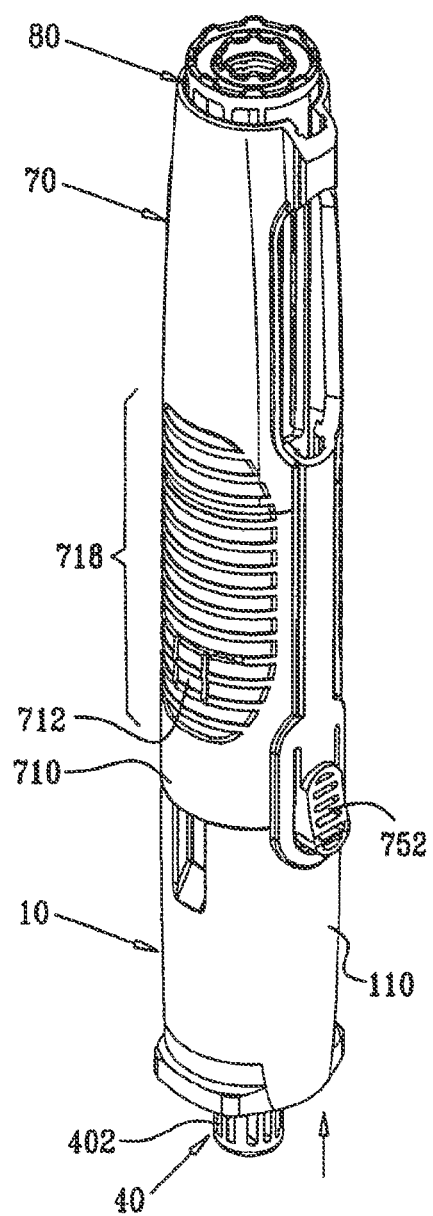
FIG. 18 is a simplified pictorial illustration of the automatic injection device of FIGS. 1 and 14B in an optional titration operative orientation.
Figure 19A:
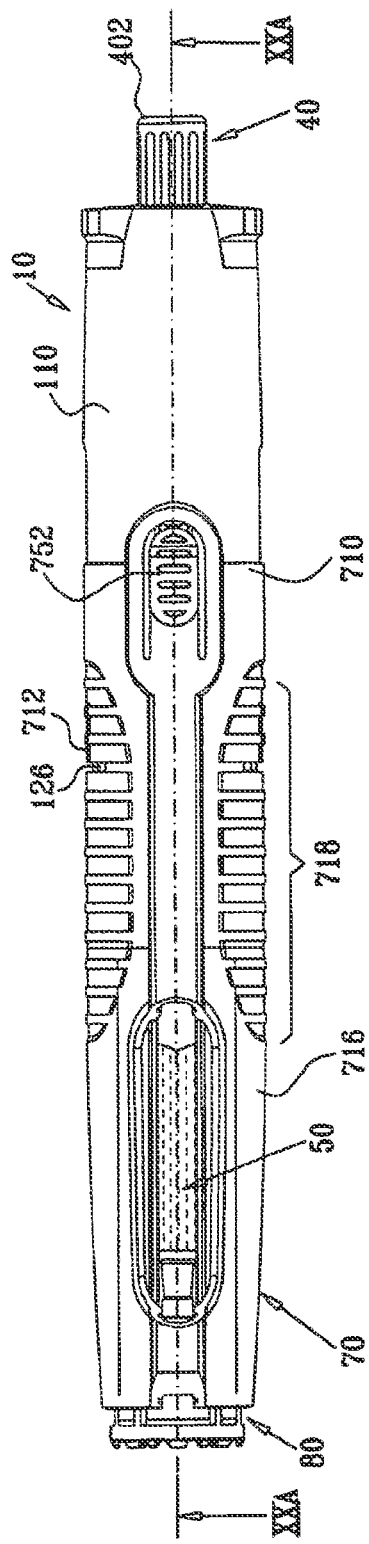
FIGS. 19A and 19B are respective top and side view simplified planar illustrations of the automatic injection device of FIG. 18.
Figure 19B:
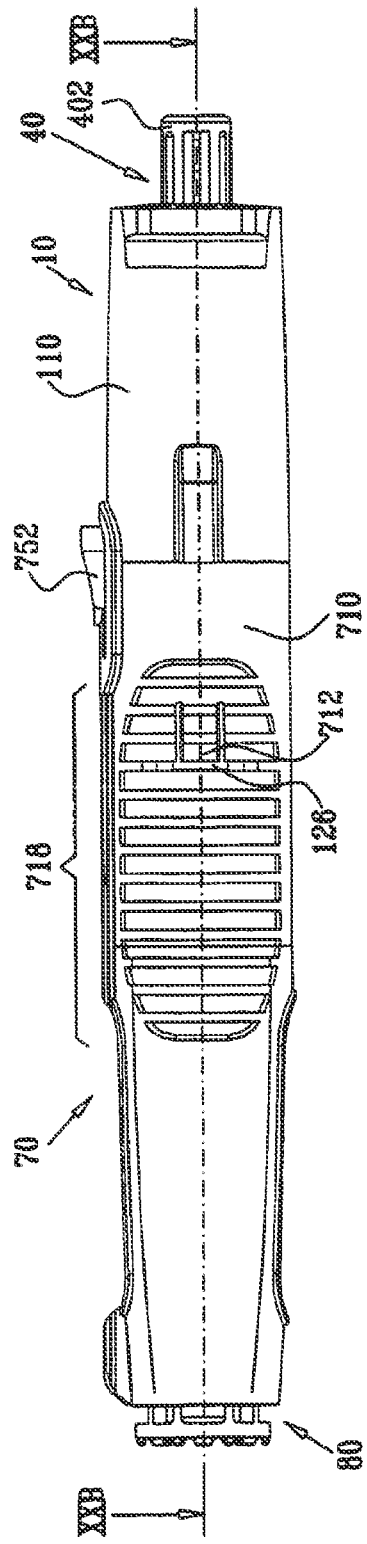

Reference is now made to FIG. 18, which is a simplified pictorial illustration of the automatic injection device of FIGS. 1 and 14B in an optional titration operative orientation, to FIGS. 19A and 19B, which are respective top and side view simplified planar illustrations thereof and to FIGS. 20A and 20B, which are sectional illustrations taken along respective section lines and directions XXA-XXA and XXB-XXB in FIGS. 19A and 19B.

In an optional titration step, after the protective needle cover has been removed and while the needle guard 80 points upwards, a user may push rear portion 402 of plunger 40 forwardly as the syringe 50 is retained in place. This forces air bubbles and/or liquid out of the syringe via the needle 60. At this stage, protrusions 349 formed on third fingers 338 (FIGS. 5-7C) engage the defining walls of narrower rear portion 824 of rectangular window 821 (FIGS. 11-13C), thus limiting the third fingers 338 from bending outward and therefore flange 502 continues to engage notches 347 thus inhibiting premature movement of syringe 50. It is appreciated that except for the forward movement of the plunger 40, the remainder of the operative orientation of the automatic injection device remains identical to the pre-use operative orientation.

Figure 21:
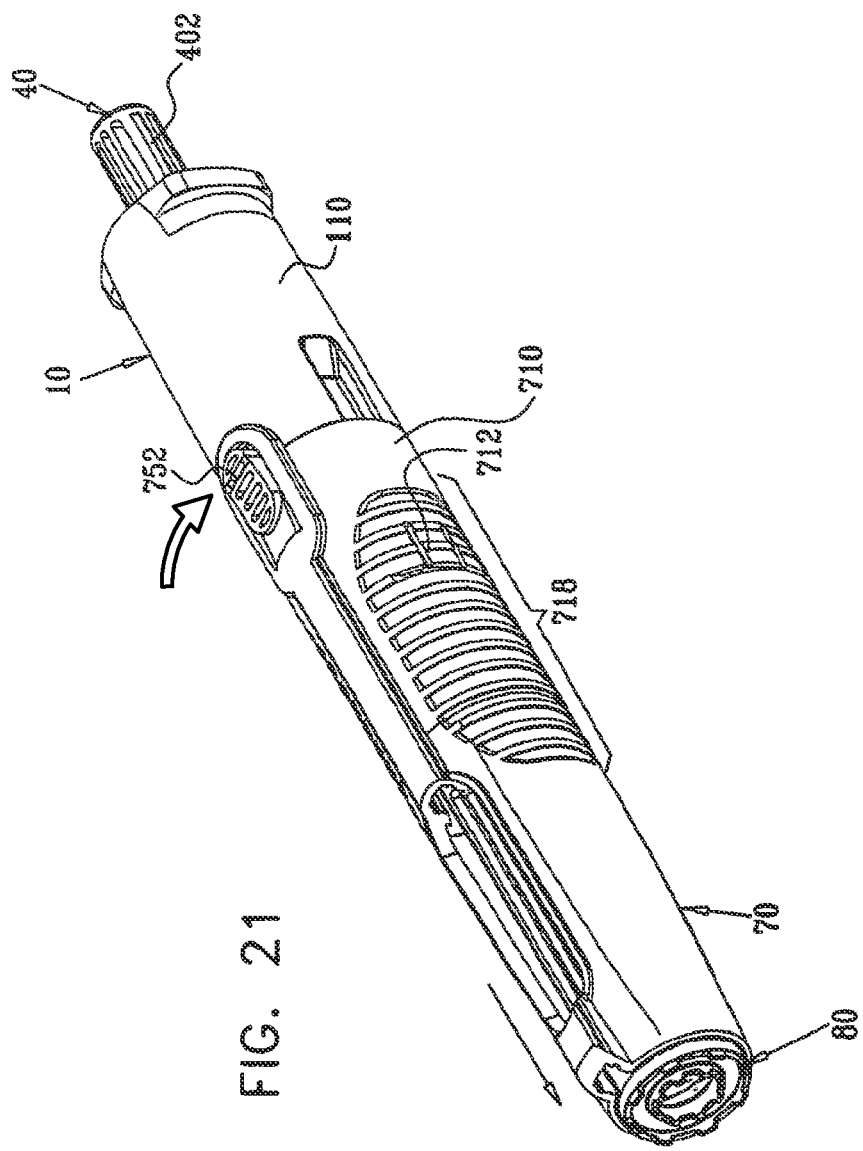
FIG. 21 is a simplified pictorial illustration of the automatic injection device of FIGS. 1 and 14C in an actuated operative orientation.

Reference is now made to FIG. 21, which is a simplified pictorial illustration of the automatic injection device of FIGS. 1 and 14C in an actuated operative orientation, to FIGS. 22A and 22B which are respective top and side view simplified planar illustrations thereof and to FIGS. 23A and 23B which are sectional illustrations taken along respective section lines and directions XXIIIA-XXIIIA and XXIIIB-XXIIIB in FIGS. 22A and 22B.

As seen particularly in the enlarged portion of FIG. 23A, due to engagement of the needle guard 80 with an injection site on a body, the needle guard 80 is forced to move axially in a rearward direction with respect to the remainder of the automatic injection device, thus compressing spring 90 and causing the rearwardmost axial portion 834 of the top engagement arm 832 of the needle guard 80 (FIGS. 11-13C) to assume a relatively rearward position, generally underlying actuation button 752 of forward housing and actuator element 70 (FIGS. 8-10C). The rearward motion of the needle guard 80 is limited by engagement of rearwardmost ends 819 of arms 818 of the needle guard and the forward facing edge of outward facing protrusion 126 rear housing element 10 (FIG. 23B).

In this orientation of the needle guard 80, pressing of button 752 does actuate the automatic injection device, by causing portion 834 to engage protrusion 350, thus disengaging notch 352 from protrusion 130 (FIG. 4A) and thus disengaging engagement arm 322 from the rear housing element 10 and permitting forward axial movement of the selectable driving assembly 30 under the urging of spring 20.

Reference is now made to FIG. 24, which is a simplified pictorial illustration of the automatic injection device of FIGS. 1 and 14D in a needle penetration, pre-drug delivery operative orientation, to FIGS. 25A and 25B, which are respective top and side view simplified planar illustrations thereof and to FIGS. 26A and 26B, which are sectional illustrations taken along respective section lines and directions XXVIA-XXVIA and XXVIB-XXVIB in FIGS. 25A and 25B.

FIGS. 24-26B illustrate an initial stage in the forward motion of the selectable driving assembly 30 under the urging of spring 20 following user actuation of button 752. It is seen that the axial forward motion of the selectable driving assembly 30 produces equivalent axial forward motion of the syringe 50, due to engagement of flange 502 in notches 347 formed in respective third fingers 338 of each of side-to-side symmetric actuation arms 312 of selectable driving assembly 30 (FIGS. 5-7C).

This forward motion results in forward motion of the needle 60 and needle penetration at the injection site as shown. The forward motion of syringe 50 and needle penetration stops as flange 502 reaches protrusions 760 and 762 of forward housing and actuator element 70. During needle penetration, elastomeric elements 32 and 34 engage forwardly pointed protrusion 142 of side interior surface 140 causing friction therebetween, thus compensating for the force of spring 20 and resulting in damping of the needle movement and absorbance of the shock applied by protrusions 760 and 762 on the flange 502. The forward motion of the selectable driving assembly 30 causes the outwardly extending protrusion 332 to engage forwardly pointed protrusion 142 of side interior surface 140, thus bending the first finger 330 inwards. As will be described hereinbelow, drug delivery follows needle penetration.

Figure 27:
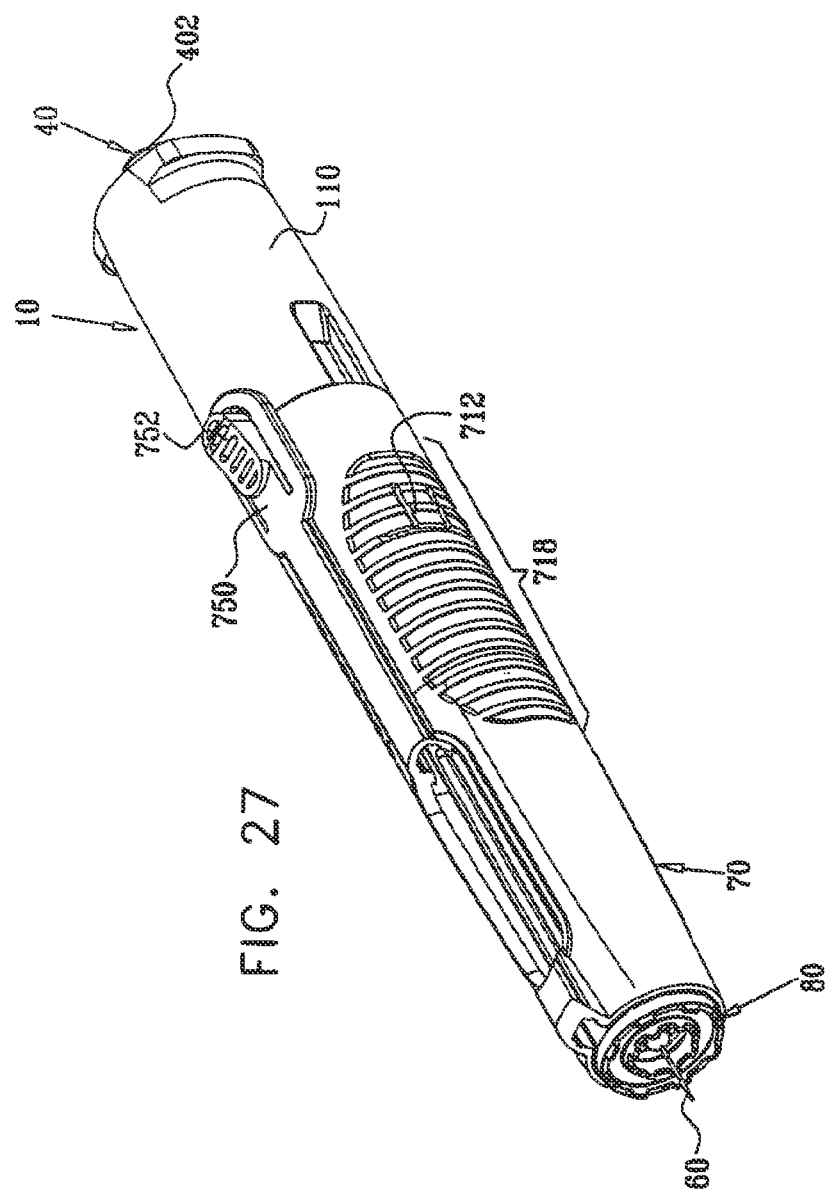
FIG. 27 is a simplified pictorial illustration of the automatic injection device of FIGS. 1 and 14E in drug delivery operational orientation.

Reference is now made to FIG. 27, which is a simplified pictorial illustration of the automatic injection device of FIGS. 1 and 14E in drug delivery operational orientation, to FIGS. 28A and 28B which are respective top and side view simplified planar illustrations thereof and to FIGS. 29A and 29B, which are sectional illustrations taken along respective section lines and directions XXIXA-XXIXA and XXIXB-XXIXB in FIGS. 28A and 28B.

FIGS. 27-29B illustrate a further stage in the forward motion of the selectable driving assembly under the urging of spring 20 following user actuation of button 752. It is seen that the axial forward motion of the selectable driving assembly 30 does not produce equivalent axial forward motion of the syringe 50, due to engagement of flange 502 of syringe 50 with protrusions 760 and 762 of ribs of the forward housing and actuator element 70 (FIG. 10A).

Continued urging of spring 20 and the selectable driving assembly 30 causes protrusions 349 formed on third fingers 338 (FIGS. 5-7C) to disengage the defining walls of narrower rear portion 824 of rectangular window 821, and bend outward into the space formed by the wider forward portion 822 of the rectangular window (FIGS. 11-13C), resulting in disengagement of flange 502 and notches 347 formed in respective third fingers 338 of each of side-to-side symmetric actuation arms 312 of selectable driving assembly 30 (FIGS. 5-7C). This allows the inwardly extending protrusion 333 of the bended first finger 330 of the selectable driving assembly 30 to engage intermediate portion 406 of plunger 40, causing it to continue its forward motion together with a piston 501, which is threaded thereto.

Forward motion of piston 501 forces the drug out of syringe 50 through needle 60 into the injection site. During drug delivery, the forward motion of the piston 501 is governed by friction between elastomeric elements 32 and 34 and forwardly pointed protrusions 142 of side interior surface 140. The amount of friction may be selected by appropriately shaping the forwardly pointed protrusion and the elastomeric elements 32 and 34.

The forwardly pointed shape of the protrusions, causes a reduction in friction as selectable driving assembly 30 advances, which compensates for the reduction in the force applied by spring 20 as it extends. Friction between the protrusion and elastomeric elements 32 and 34 also damps shock resulting from engagement of inwardly extending protrusion 333 with intermediate portion 406 of plunger 40, which is then transferred to flange 502 of the pre-filled syringe 50, and may help control the drug injection rate.

Figure 30:
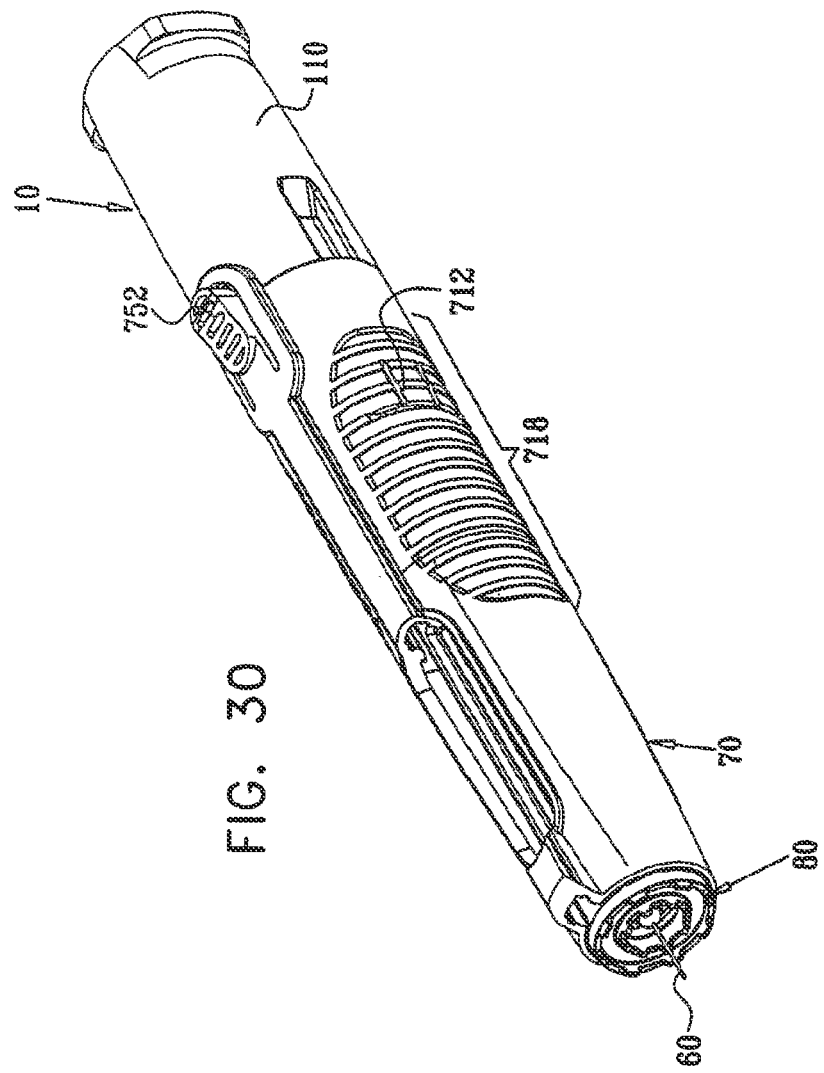
FIG. 30 is a simplified pictorial illustration of the automatic injection device of FIGS. 1 and 14F in an immediate post-drug delivery operational orientation.

Reference is now made to FIG. 30, which is a simplified pictorial illustration of the automatic injection device of FIGS. 1 and 14F in an immediate post-drug delivery operational orientation, to FIGS. 31A and 31B, which are respective top and side view simplified planar illustrations thereof and to FIGS. 32A and 32B, which are sectional illustrations taken along respective section lines and directions XXXIIA-XXXIIA and XXXIIB-XXXIIB in FIGS. 31A and 31B.

Prior to this stage, forward motion of piston 501 in the syringe continued until the piston cannot move forward any more, thus terminating drug delivery. Additionally, outwardly extending protrusions 332 of first fingers 330 no longer engage the forwardly pointed protrusions, and are now supported by the internal surfaces of mounting arms 818. Reference is now made to FIG. 33, which is a simplified pictorial illustration of the automatic injection device of FIGS. 1 and 14G in its operation orientation as it is being disengaged from an injection site, to FIGS. 34A and 34B which are respective top and side view simplified planar illustrations thereof and to FIGS. 35A and 35B which are sectional illustrations taken along respective section lines and directions XXXVA-XXXVA and XXXVB-XXXVB in FIGS. 34A and 34B.

At this stage, the automatic injection device is being removed from the injection site and the needle guard 80 is moving axially forward under the urging of spring 90, so that the exposed portion of the needle 60 is protected by the needle guard 80. Subsequent to the initial forward movement of the needle guard 80 forward, the first fingers 330 of each of side-to-side symmetric actuation arms 312 of the selectable driving assembly 30 are released and bend outwards to their initial position, thus disengaging from the plunger 40 and engaging the rearwardmost ends 819 of arms 818 of the needle guard 80.

At this stage the spring 20 applies more force than does spring 90 and thus pushes the needle guard 80 further forward. It is therefore appreciated that even if spring 90 were to be replaced by a shorter spring, for example a short plastic spring integrated with either forward housing and actuator element 70 or needle guard 80, spring 20 would guarantee that needle guard 80 would be fully deployed, such that the auto injection device would be maintained in a protected position.

Figures 38A, 38B:
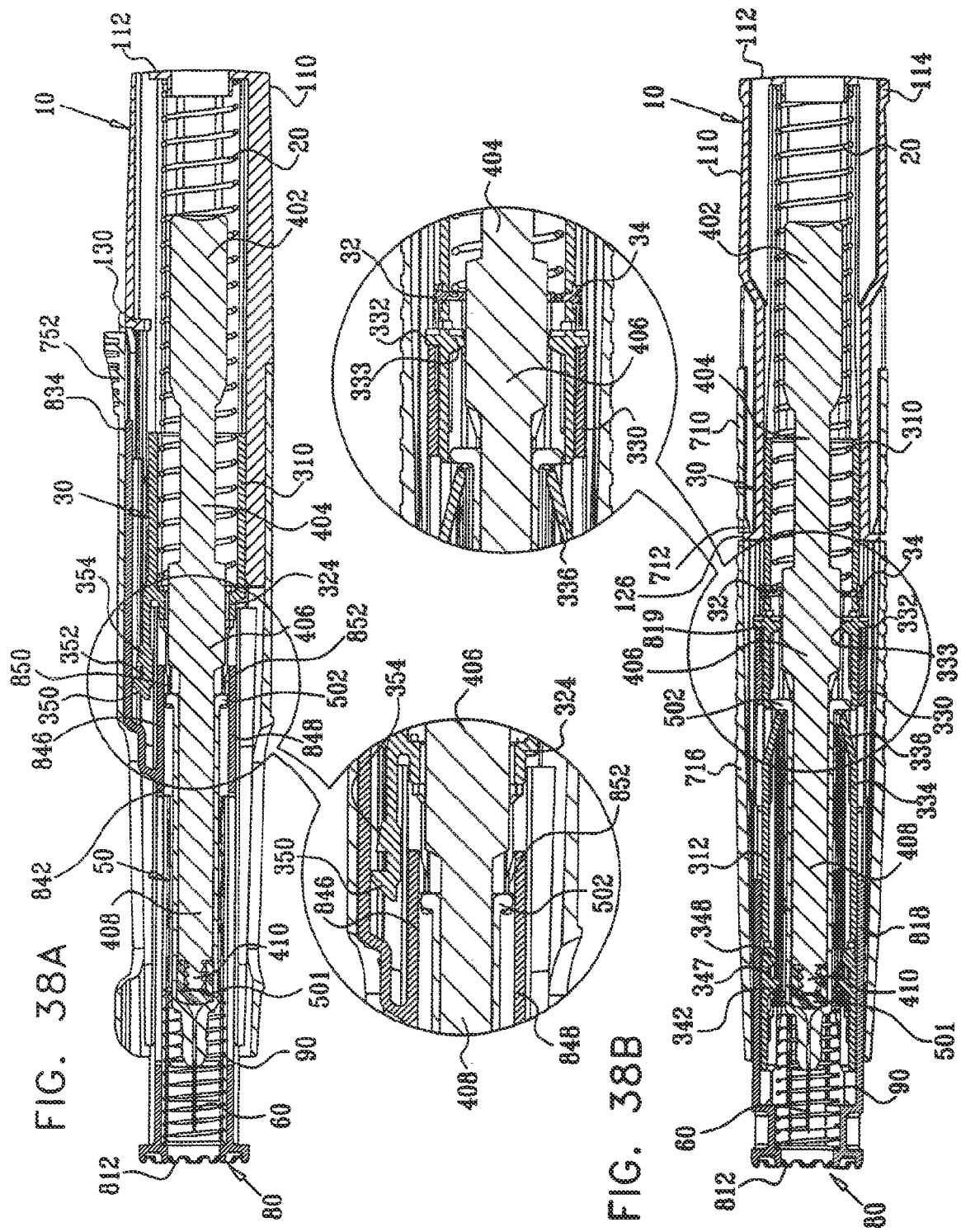
FIGS. 38A and 38B are sectional illustrations taken along respective section lines and directions XXXVIIIA-XXXVIIIA and XXXVIIIB-XXXVIIIB in FIGS. 37A and 37B.

Reference is now made to FIG. 36, which is a simplified pictorial illustration of the automatic injection device of FIGS. 1 and 14H in a needle protected operational orientation, to FIGS. 37A and 37B which are respective top and side view simplified planar illustrations thereof and to FIGS. 38A and 38B which are sectional illustrations taken along respective section lines and directions XXXVIIIA-XXXVIIIA and XXXVIIIB-XXXVIIIB in FIGS. 37A and 37B.

At this stage, the automatic injection device is fully disengaged from the injection site and the needle guard 80 is fully extended to fully enclose the needle 60. When the needle guard is fully extended it is locked onto the syringe 50 by engagement of inwardly directed teeth 850 and 852 and flange 502 of the pre-filled syringe 50, thus inhibiting further movement outwards of the needle guard 80. During the movement of needle guard 80 and due to force exerted by spring 20, inwardly extending protruding portions 336 of second fingers 334 snap over flange 502 within the narrower rear portion 824 of rectangular window 821, thus enabling further locking of the needle guard as described hereinbelow.

Figure 39:
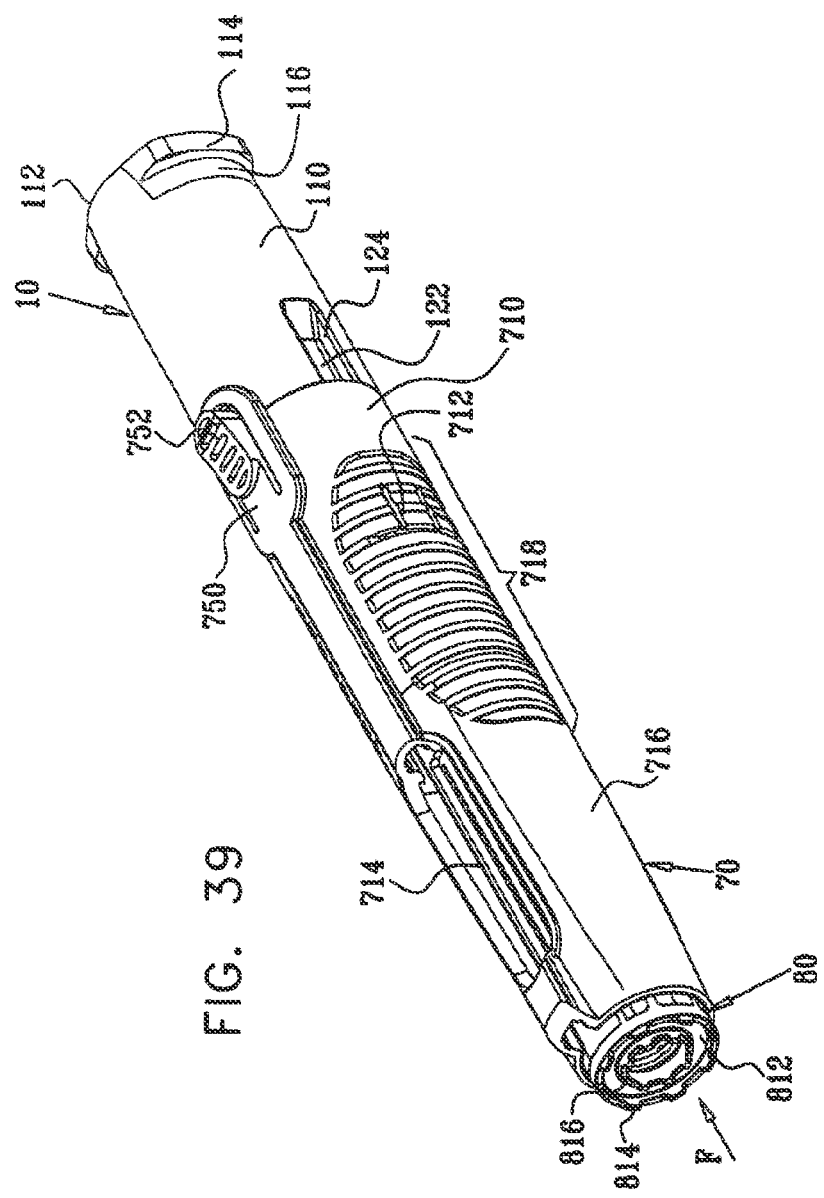
FIG. 39 is a simplified pictorial illustration of the automatic injection device of FIGS. 1 and 14I in a needle-guard push back misuse operational orientation.

Reference is now made to FIG. 39, which is a simplified pictorial illustration of the automatic injection device of FIGS. 1 and 14I in a needle-guard push back misuse operational orientation, to FIGS. 40A and 40B which are respective top and side view simplified planar illustrations thereof and to FIGS. 41A and 41B which are sectional illustrations taken along respective section lines and directions XLIA-XLIA and XLIB-XLIB in FIGS. 40A and 40B.

FIGS. 39-41B illustrate an important feature of the present invention provided by the locking of inwardly extending protruding portion 336 of second finger 334 of the selectable driving assembly 30 and the flange 502 of the pre-filled syringe 50. Should the needle guard 80 be pushed rearwardly with respect to the forward housing and actuator element 70, the rearwardmost ends 819 of arms 818 of the needle guard 80 push against protrusion 332 of the selectable driving assembly 30. Selectable driving assembly 30 is therefore forced to move rearwardly together with the needle guard.

Due to engagement of second fingers 334 and flange 502, the selectable driving assembly 30 forces the needle 60 and syringe to 50 move rearwardly together with selectable driving assembly 30, so that the needle 60 does not protrude from the needle guard 80. During this rearward movement, first fingers 330 cannot bend inwards to cause outwardly extending protrusions 332 to disengage from rearwardmost ends 819 of arms 818, since the inwardly extending protrusions 333 of first fingers 330 are supported by intermediate portion 406 of the plunger 40.

Reference is now made to FIGS. 42-58C, which illustrate the constituent elements of an automatic injection device constructed and operative in accordance with another preferred embodiment of the present invention.

As seen with particular clarity in FIG. 42, the automatic injection device comprises a plunger 1002 which is partially located within a main housing element 1010 into which is seated a main compression spring 1020, which provides selectable forward displacement to a selectable driving element 1030, which selectably engages plunger 1002 and a pre-filled syringe 1050 having a hypodermic needle 1060 which is covered by a needle protection cover 1062. Pre-filled syringe 1050 may be a conventional pre-filled syringe, such as a commercially available syringe sold under the catalog designation BD-Hypak™ or may be any other suitable syringe or cartridge.

Plunger 1002 also operatively engages pre-filled syringe 1050 and is selectably operated by selectable driving element 1030 to inject the liquid contents of pre-filled syringe 1050 through hypodermic needle 1060. The forward portion of main housing element 1010 surrounds and is engaged with a forward housing element 1070. At the forward end of the interior of forward housing element 1070 there is provided a needle guard element 1080, which is positioned by a compression spring 1090.

Figure 43A:
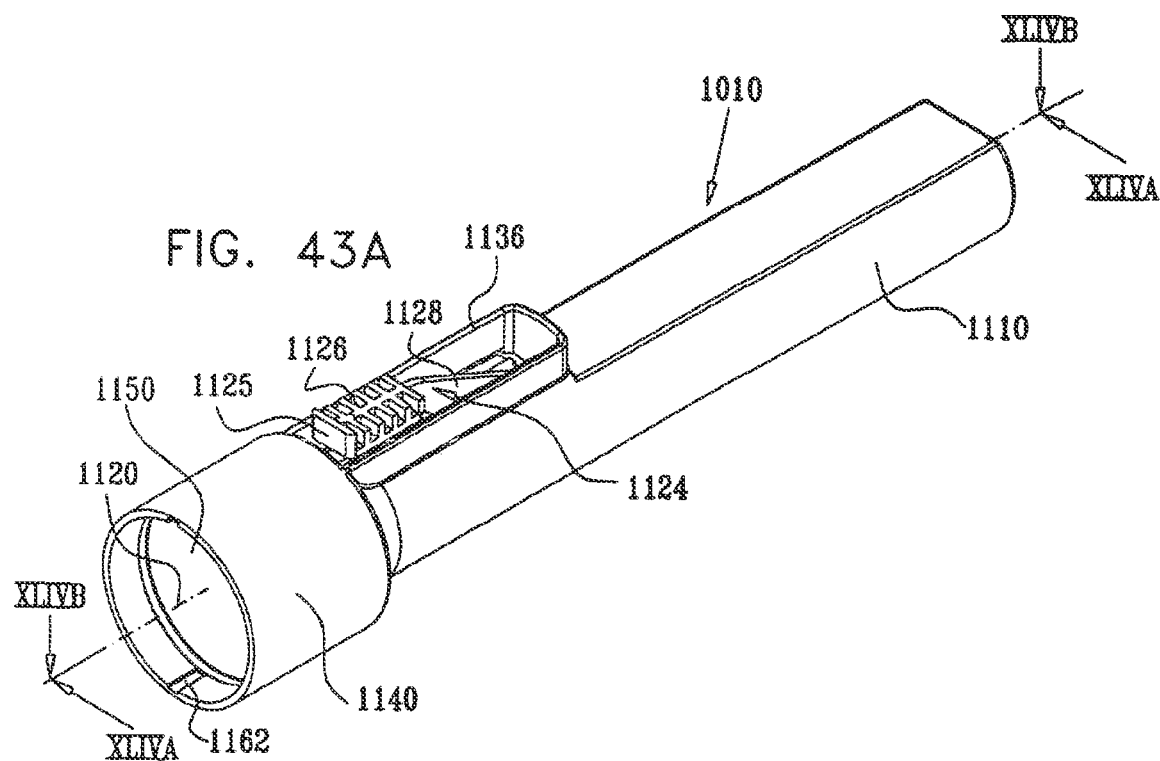
FIGS. 43A and 43B are simplified pictorial illustrations of a main housing element which forms part of the automatic injection device of FIG. 42.
Figure 43B:
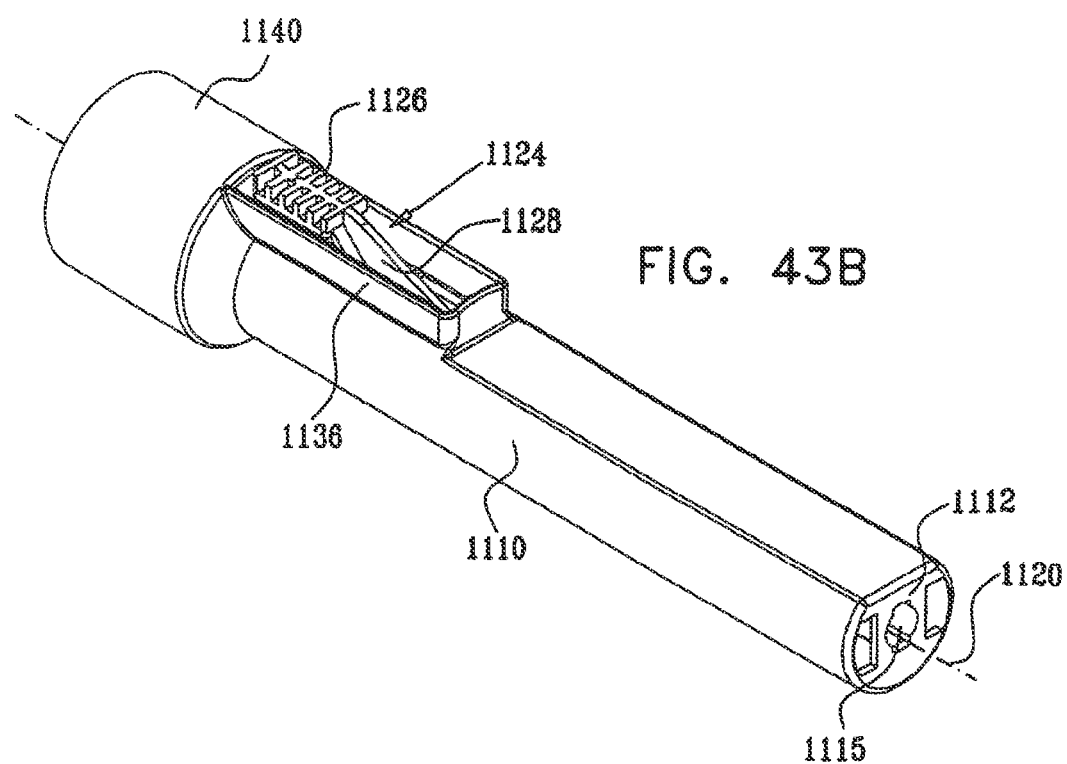
Figure 44A:
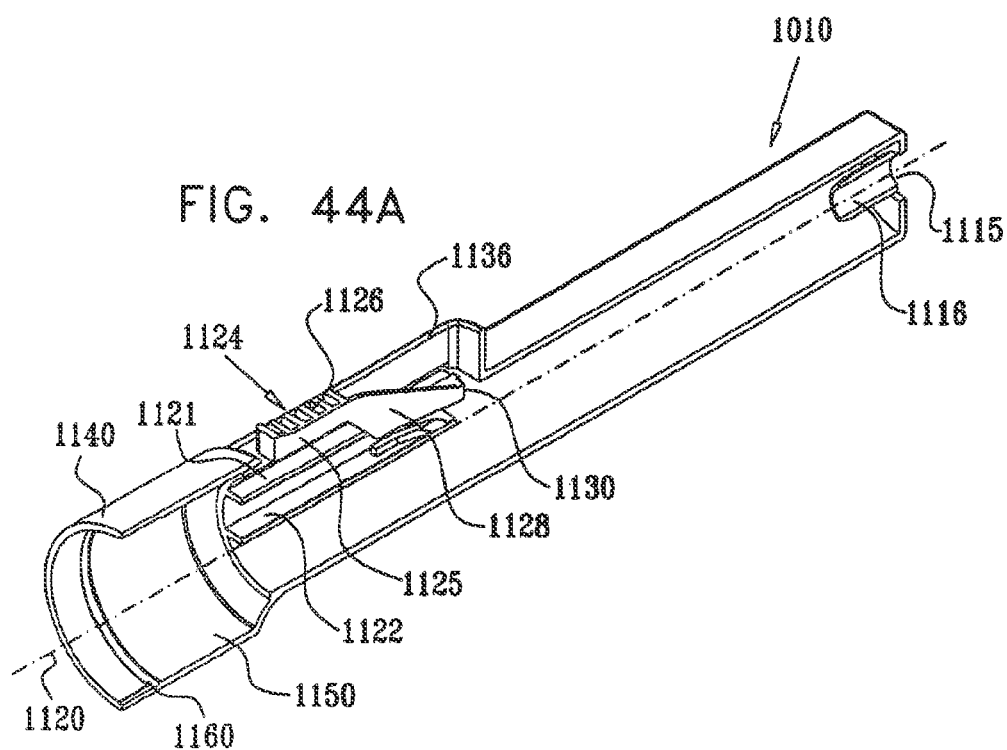
FIGS. 44A and 44B are simplified pictorial sectional illustrations of the main housing element of FIGS. 43A and 43B, taken along lines XLIVA-XLIVA and XLIVB-XLIVB in FIG. 43A.
Figure 44B:
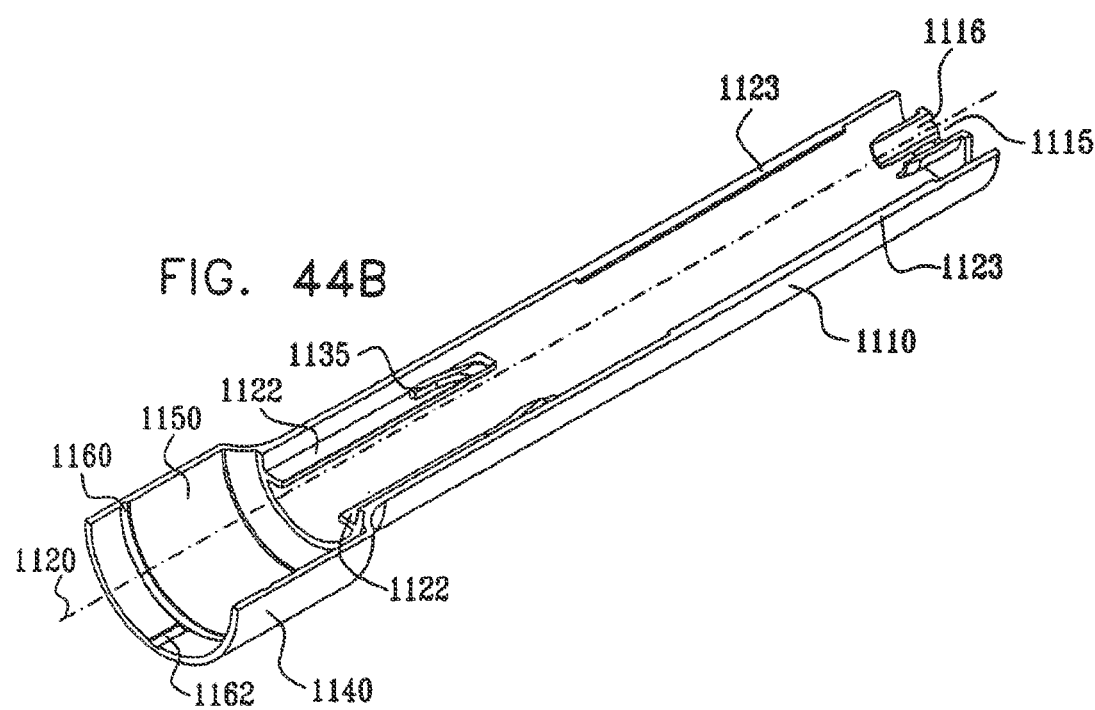

Reference is now made to FIGS. 43A and 43B, which are simplified pictorial illustrations of a preferred main housing element 1010 which forms part of the automatic injection device of FIG. 42, to FIGS. 44A and 44B which are simplified pictorial sectional illustrations of the main housing element 1010 of FIGS. 43A and 43B, taken along lines XLIVA-XLIVA and XLIVB-XLIVB in FIG. 43A, to FIGS. 45A and 45B, which are respective top and side view simplified planar illustrations of the main housing element of FIGS. 43A-44B and to FIGS. 46A, 46B and 46C which are sectional illustrations taken along respective section lines and directions XLVIA-XLVIA, XLVIB-XLVIB and XLVIC-XLVIC in FIGS. 45A and 45B.

As seen in FIGS. 43A-46C, the main housing element 1010 preferably is an integrally formed element, preferably injection molded of plastic and preferably has a generally cylindrical configuration including a rearward generally cylindrical portion 1110, having a nearly circular cross section, which terminates in a back wall 1112, defining a rearward-facing central opening 1115 communicating with a cylindrical bore 1116. An interior surface of back wall 1112 defines a spring seat for spring 1020, while bore 1116 slidably accommodates plunger 1002. Rearward generally cylindrical portion 1110 is preferably side-to-side symmetric about a longitudinal axis 1120.

Rearward generally cylindrical portion 1110 is preferably formed on an interior surface thereof with a pair of generally symmetric axially extending upper interior ribs 1121 and a pair of generally symmetric axially extending lower interior ribs 1122 on each side of the interior surface. Also formed on opposite sides of an interior surface of rearward generally cylindrical portion 1110 are side-to-side symmetric axially extending guiding ribs 1123. Cantilevered onto rearward generally cylindrical portion 1110 is an actuation button portion 1124 including a forward actuation button defining portion 1125 having a slightly curved finger engagement surface 1126, defining an actuation button and a selectable syringe engagement portion 1128 having a rearward facing surface 1130 which selectably engages a forward facing surface of pre-filled syringe 1050 for selectably retaining it against forward axial motion. Actuation button portion 1124 is pivotally mounted with respect to the remainder of the main housing element 1010 about a pivot axis, transverse to longitudinal axis 1120, which lies intermediate portion 1125 and portion 1128, such that inward displacement of portion 1125 causes portion 1128 to move outwardly.

Formed onto upper ribs 1121 and lower ribs 1122 are forwardly facing, outwardly extending ribs 1135. A peripheral outwardly facing guard protrusion 1136 is formed around actuation button portion 1124. Forwardly of actuation button portion 1124 and of protrusion 1136 there is formed a forwardly facing circular cylindrical portion 1140.

Circular cylindrical portion 1140 defines on an interior surface 1150 thereof a peripheral groove 1160, which is in contact with top and bottom axial grooves 1162.

Figure 47A:
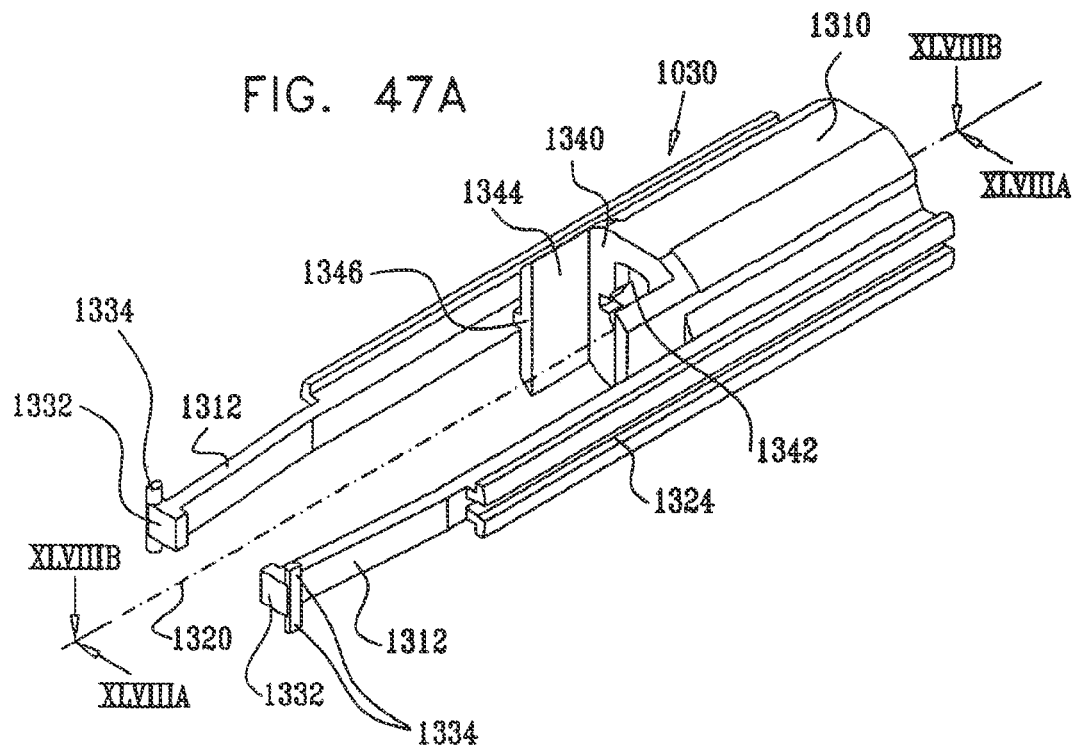
FIGS. 47A and 47B are a simplified pictorial illustrations of a selectable driving element which forms part of the automatic injection device of FIG. 42.
Figure 47B:
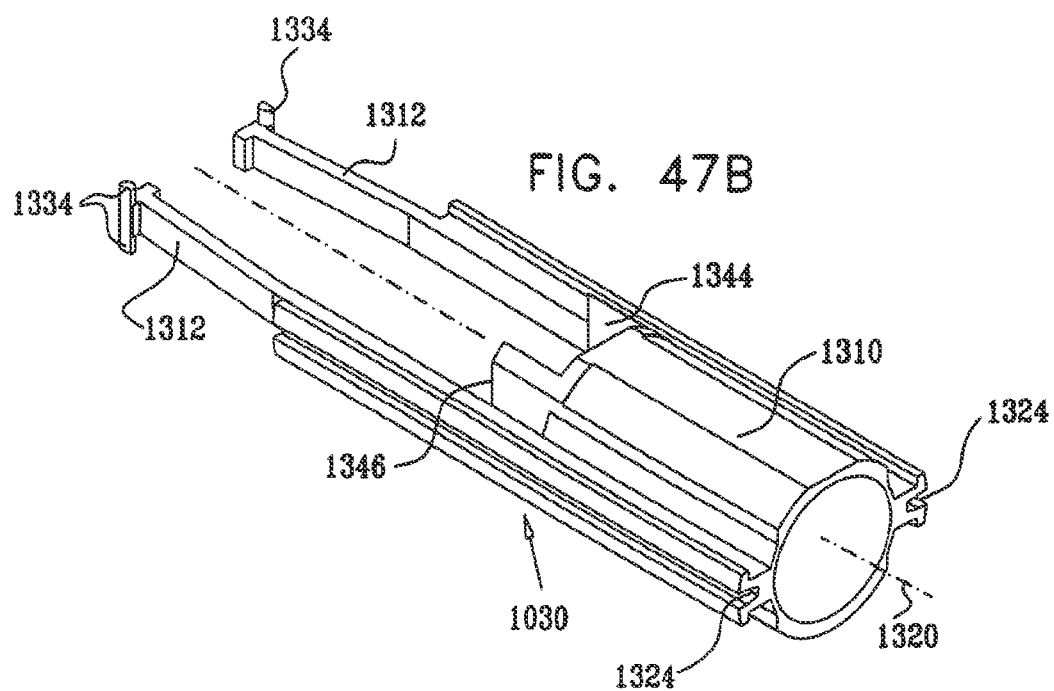
Figure 48A:
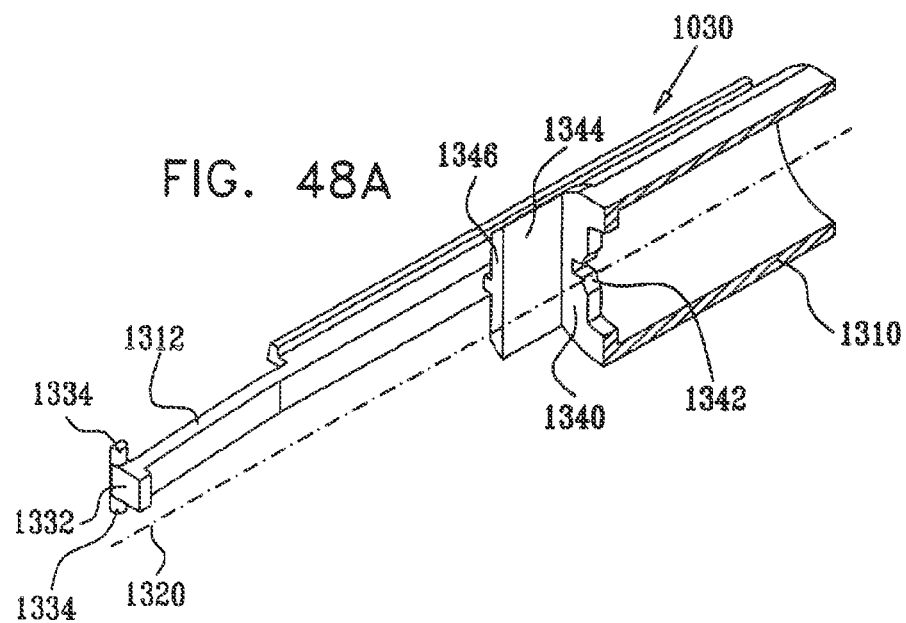
FIGS. 48A and 48B are simplified pictorial sectional illustrations of the selectable driving element of FIGS. 47A and 47B, taken along lines XLVIIIA-XLVIIIA and XLVIIIB-XLVIIIB in FIG. 47A.
Figure 48B:
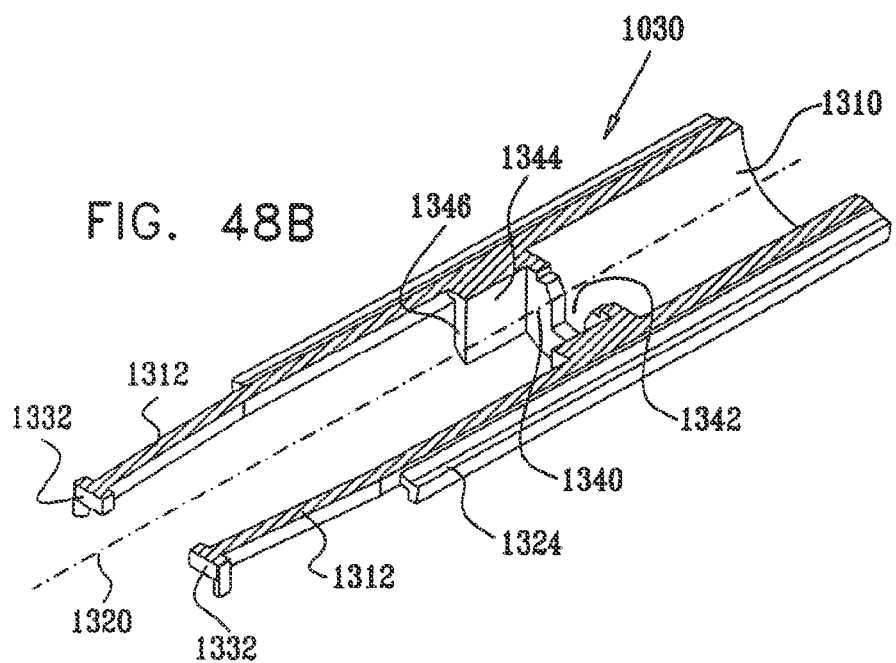
Figure 49A:
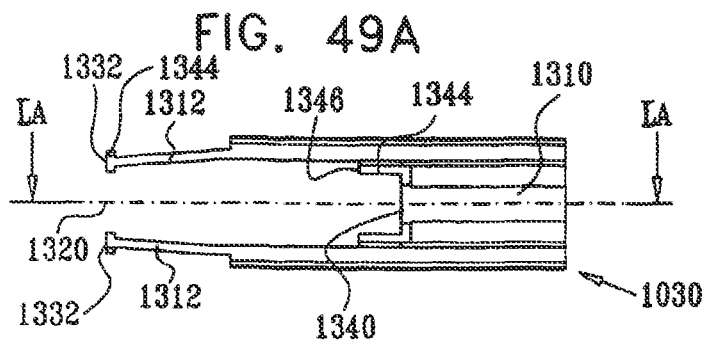
FIGS. 49A and 49B are respective top and side view simplified planar illustrations of the selectable driving element of FIGS. 47A-48B.
Figure 49B:
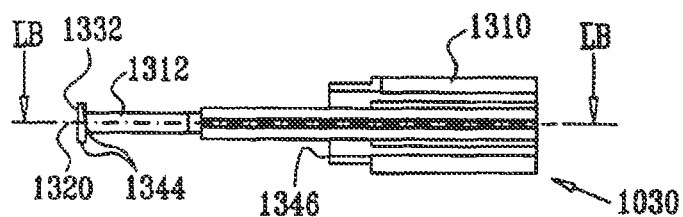
Figure 50A:
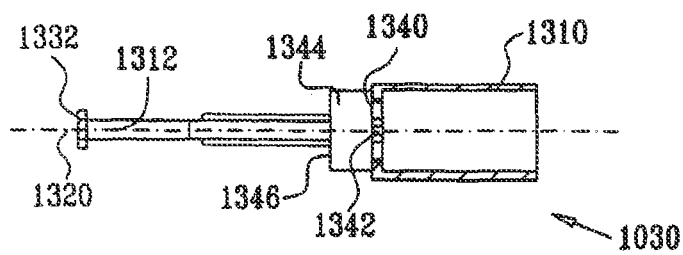
FIGS. 50A and 50B are sectional illustrations taken along respective section lines and directions LA-LA and LB-LB in FIGS. 49A and 49B.
Figure 50B:
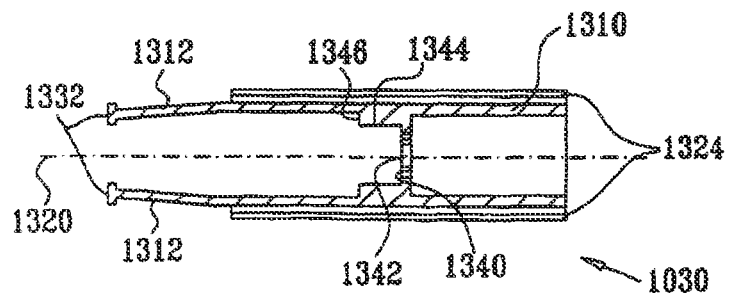

Reference is now made to FIGS. 47A and 47B, which are simplified pictorial illustrations of a selectable driving element 1030 which forms part of the automatic injection device of FIG. 42, to FIGS. 48A and 48B, which are simplified pictorial sectional illustrations of the selectable driving element of FIGS. 47A and 47B, taken along lines XLVIIIA-XLVIIIA and XLVIIIB-XLVIIIB in FIG. 47A, to FIGS. 49A and 49B, which are respective top and side view simplified planar illustrations of the selectable driving element of FIGS. 47A-48B and to FIGS. 50A and 50B, which are sectional illustrations taken along respective section lines and directions LA-LA and LB-LB in FIGS. 49A and 49B.

As seen in FIGS. 47A-50B, the selectable driving element 1030 preferably is an integrally formed element, preferably injection molded of plastic and preferably has a generally cylindrical configuration including a generally tubular portion 1310, having an open back and having a pair of side-to-side symmetric actuation arms 1312 which extend forwardly of tubular portion 1310 generally parallel to a longitudinal axis 1320, which when selectable driving element 1030 is assembled with the main housing element 1010, is coaxial with longitudinal axis 1120 (FIGS. 43-46C). Overlying part of each actuation arm 1312 and extending axially rearwardly thereof along an outer surface of generally tubular portion 1310 is a guiding slot 1324. Guiding slots 1324 cooperate with ribs 1123 formed on main housing element 1010 for guiding axial motion of the selectable driving element 1030 with respect to the main housing element 1010.

Each of actuation arms 1312 terminates in a forwardly facing end surface 1332 having oppositely directed transversely extending protrusions 1334 and defines a shoulder along the length of each arm 1312.

The selectable tubular portion 1310 defines a forward wall 1340 having an aperture 1342 for selectable slidable engagement with plunger 1002. Forward of wall is formed a pair of side-to-side symmetric forward-facing tabs 1344, each defining a forward shoulder surface 1346. A rear facing surface of forward wall 1340 defines a spring seat for spring 1020.

Plunger 1002, as seen in FIG. 42 is a generally circularly symmetric element, which is preferably formed in an overall ribbed configuration, as shown. Plunger 1002 includes a rear wall portion 1402. Forwardly of rear wall portion 1402 by approximately two thirds of the length of plunger 1002, there are provided a pair of side-to-side symmetric, sideways extending protrusions 1404. At a forward end of plunger 1002 there is provided a peripheral protrusion 1406 forward of which is provided a threaded end 1408. Plunger 1002 is arranged along a longitudinal axis 1420, which when the automatic injector device is assembled, is coaxial with longitudinal axes 1120 (FIGS. 43-46C), and 1320 (FIGS. 47-50C).

As seen in FIG. 42, pre-filled syringe includes a rear flange 1502 which engages forwardly facing end surface 1332 formed in each of side-to-side symmetric actuation arms 1312 of selectable driver element 1030 (FIGS. 47-50C).

Figure 51A:
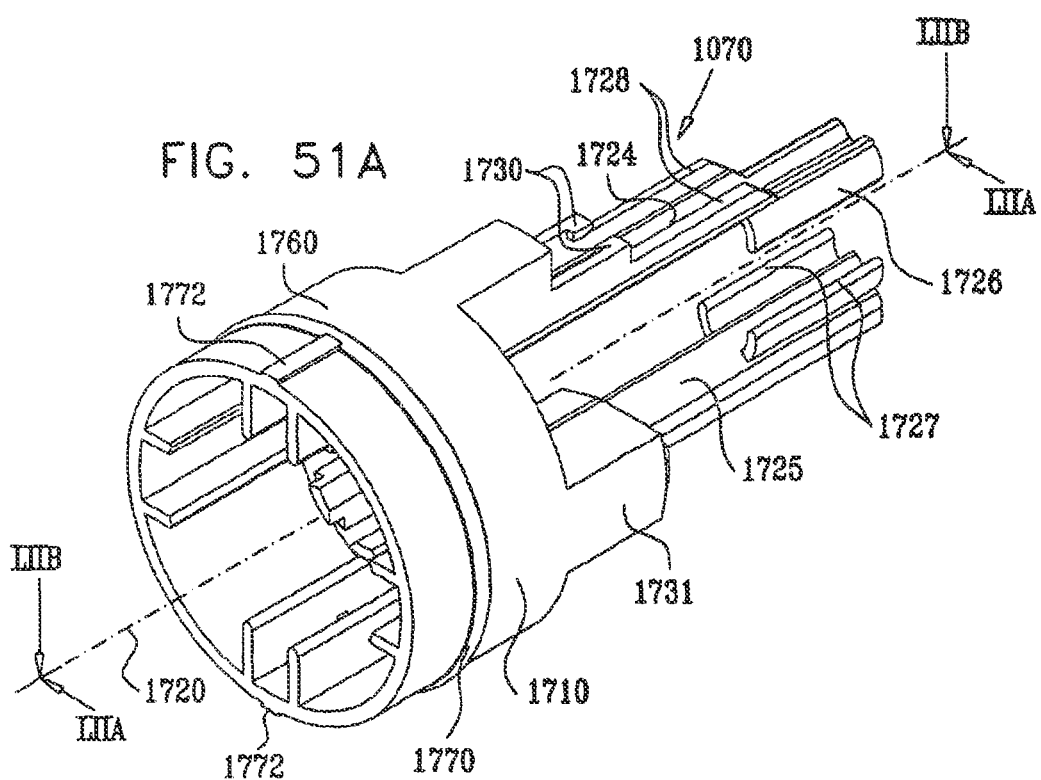
FIGS. 51A and 51B are simplified pictorial illustrations of a forward housing element which forms part of the automatic injection device of FIG. 42.
Figure 51B:
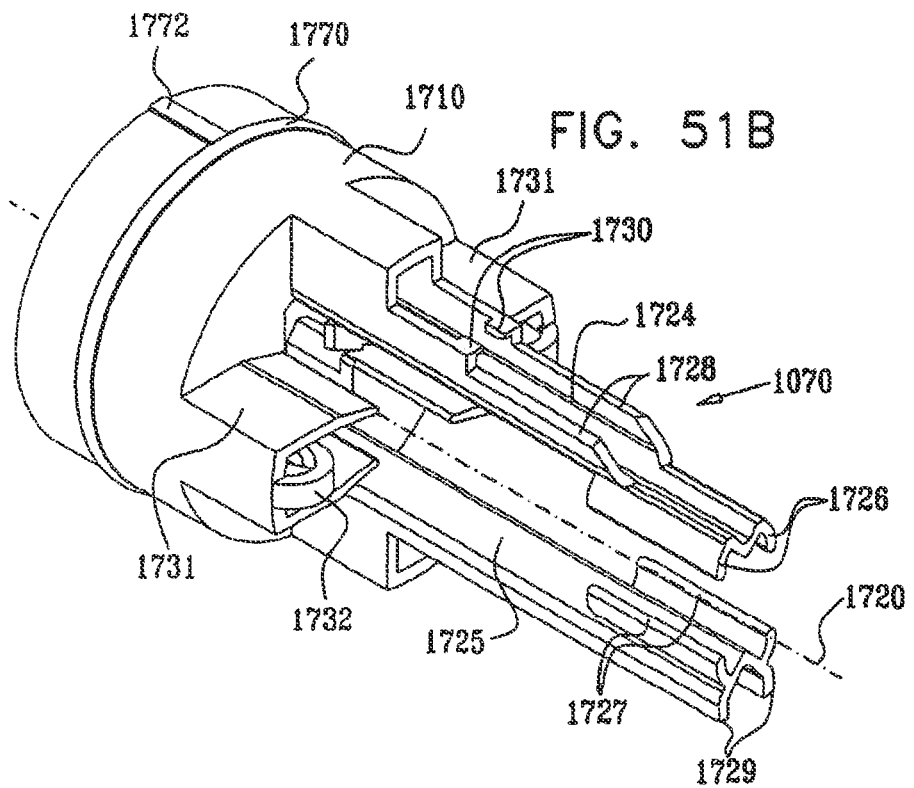
Figure 52A:
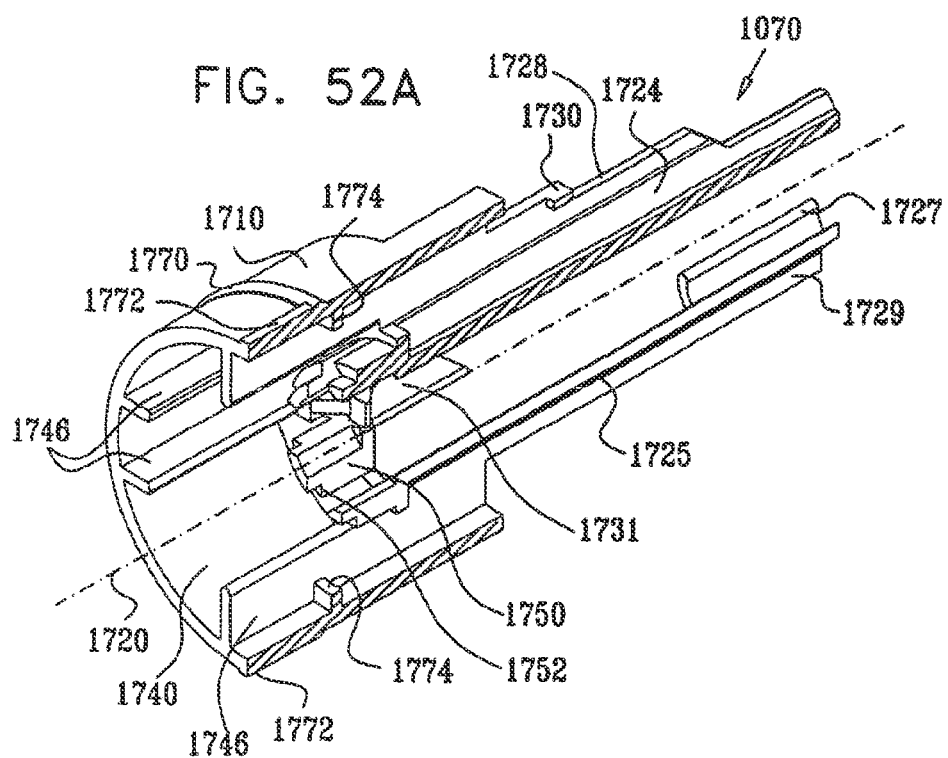
FIGS. 52A and 52B are simplified pictorial sectional illustrations of the forward housing element of FIGS. 51A and 51B, taken along lines LIIA-LIIA and LIIB-LIIB in FIG. 51A.
Figure 52B:
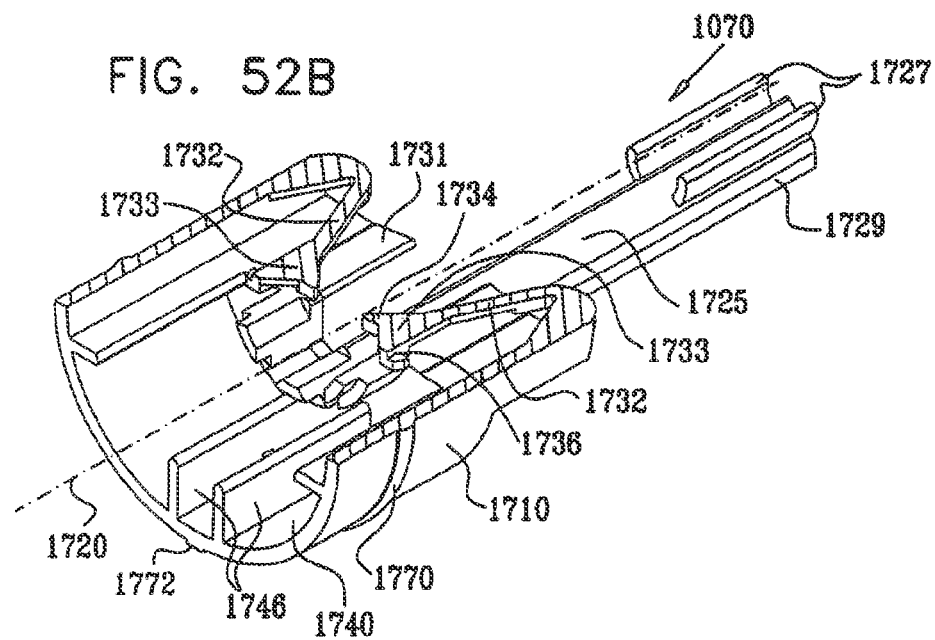
Figure 53A:
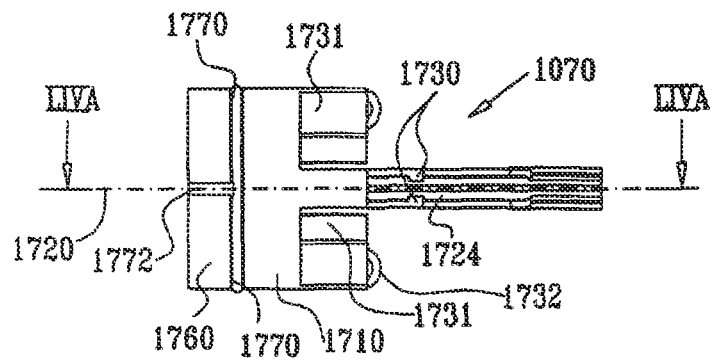
FIGS. 53A and 53B are respective top and side view simplified planar illustrations of the forward housing element of FIGS. 51A-51B.
Figure 53B:
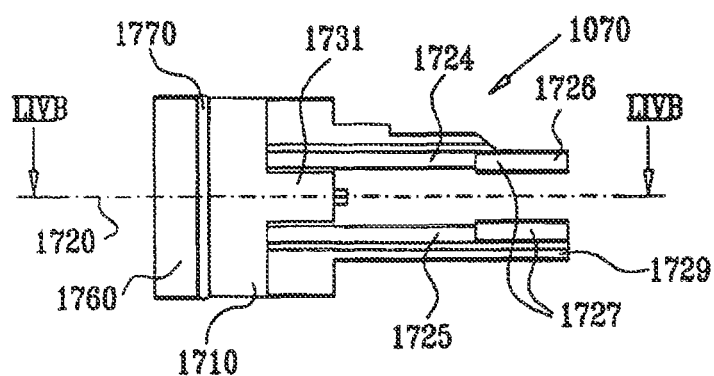
Figure 54A:
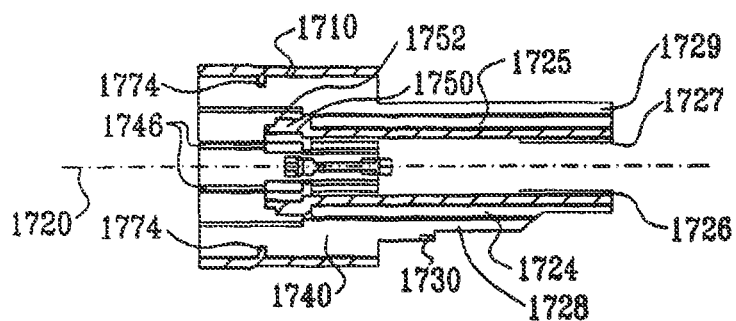
FIGS. 54A and 54B are sectional illustrations taken along respective section lines and directions LIVA-LIVA and LIVB-LIVB in FIGS. 53A and 53B.
Figure 54B:
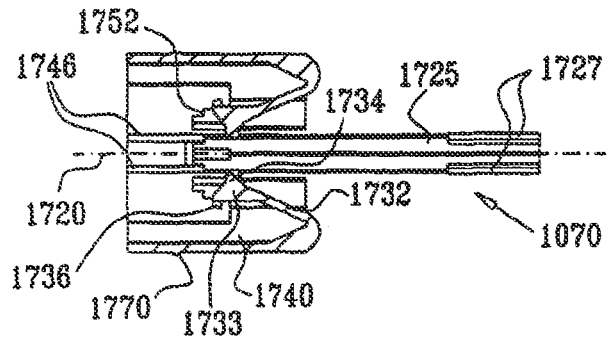

Reference is now made to FIGS. 51A and 51B, which are simplified pictorial illustrations of a forward housing element 1070 which forms part of the automatic injection device of FIG. 42, to FIGS. 52A and 52B, which are simplified pictorial sectional illustrations of the forward housing element of FIGS. 51A and 51B, taken along lines LIIA-LIIA and LIIB-LIIB in FIG. 51A, to FIGS. 53A and 53B, which are respective top and side view simplified planar illustrations of the forward housing element of FIGS. 51A-52B and to FIGS. 54A and 54B which are sectional illustrations taken along respective section lines and directions LIVA-LIVA and LIVB-LIVB in FIGS. 53A and 53B.

As seen in FIGS. 51A-54B, the forward housing element 1070 preferably is an integrally formed element, preferably injection molded of plastic and preferably has a generally circular cylindrical truncated conical configuration arranged along a longitudinal axis 1720, which when the automatic injector device is assembled, is coaxial with longitudinal axes 1120 (FIGS. 43-46C), 1320 (FIGS. 47-50C) and 1420 (FIG. 1).

Forward housing element 1070 includes a generally tubular forward portion 1710, having an open front and having formed rearward thereof a top axially extending arm 1724 and a bottom axially extending arm 1725. Each of arms 1724 and 1725 is formed with a pair of inwardly facing protrusions, respectively designated by reference numerals 1726 and 1727 and with a pair of outwardly facing protrusions, respectively designated by reference numerals 1728 and 1729. Outwardly facing protrusions 1728 extend rearwardly only partially along the length of arm 1724, while outwardly facing protrusions 1727 extend rearwardly along substantially the entire length of arm 1725. Inwardly facing protrusions 1726 and 1727 are adapted to stop the forward motion of flange 1502 of pre-filled syringe 1050 following actuation as described hereinbelow with reference to FIGS. 66-68A.

A pair of teeth 1730 are formed on top of axially extending arms 1724, which are operative to prevent premature activation of the automatic injection device as described hereinbelow with reference to FIGS. 63-65B.

A pair of side-to-side symmetric partial enclosures 1731 are formed rearwardly of forward portion 1710, having a generally C-shaped cross section, in a plane perpendicular to longitudinal axis 1720. Interior facing surfaces of enclosures 1731 together with arms 1724 and 1725 and protrusions 1726 and 1727 guide axial sliding motion of syringe 1050 relative to the main housing element 1010 and to forward housing element 1070. Partially surrounded by each partial enclosure 1731 is an inwardly facing cantilevered engagement element 1732 terminated in a bifurcated tooth element 1733 having an inwardly extending tooth 1734 and a forwardly axially extending tooth 1736.

Forward portion 1710 has an interior facing cylindrical surface 1740 having formed thereon four pairs of inwardly facing, axially extending protrusions 1746. Also formed interior of interior facing cylindrical surface 1740 are a plurality of spring seat defining portions 1750, each of which defines a rearwardly facing shoulder 1752. Spring 1090 sits on shoulders 1752 of spring seat defining portions 1750.

Forward portion 1710 has an outer facing cylindrical surface 1760 having formed thereon a peripheral protrusion 1770 connected with top and bottom axial protrusions 1772. Generally opposite peripheral protrusion 1770, there are formed on inner facing cylindrical surface a pair of inwardly facing protrusions 1774.

Figure 55A:
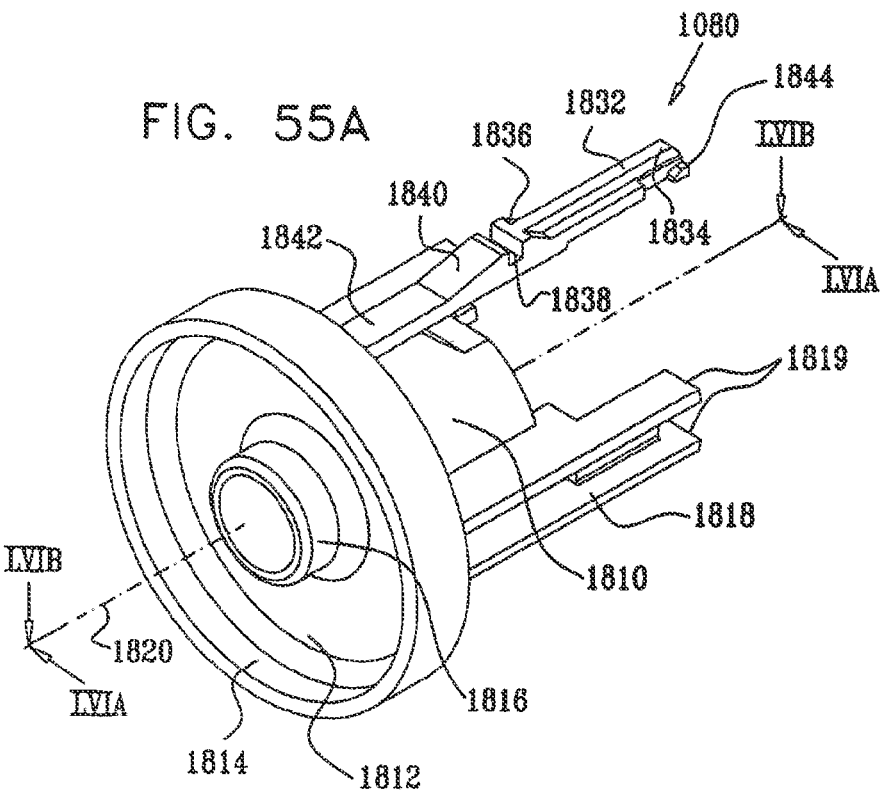
FIGS. 55A and 55B are simplified pictorial illustrations of a needle guard element which forms part of the automatic injection device of FIG. 42.
Figure 55B:
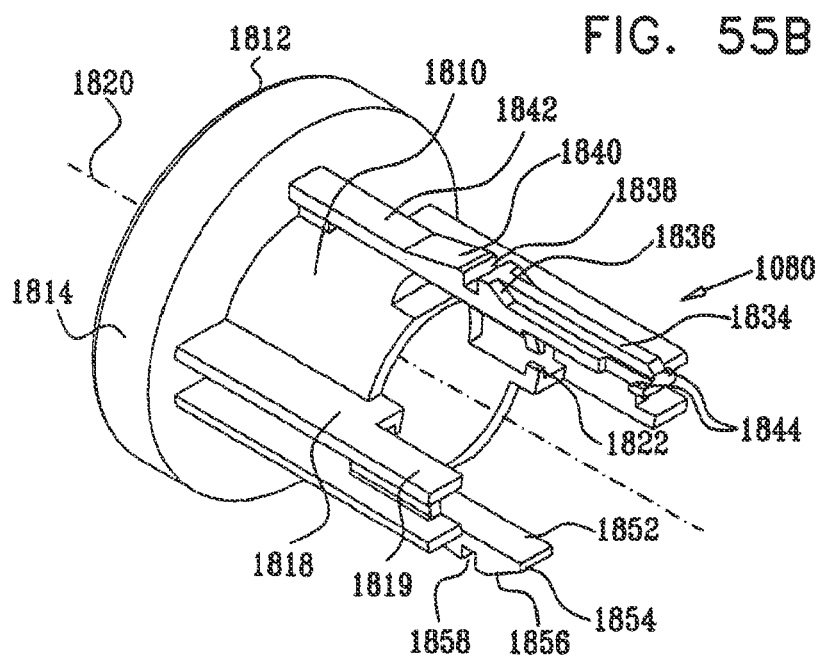
Figure 56A:
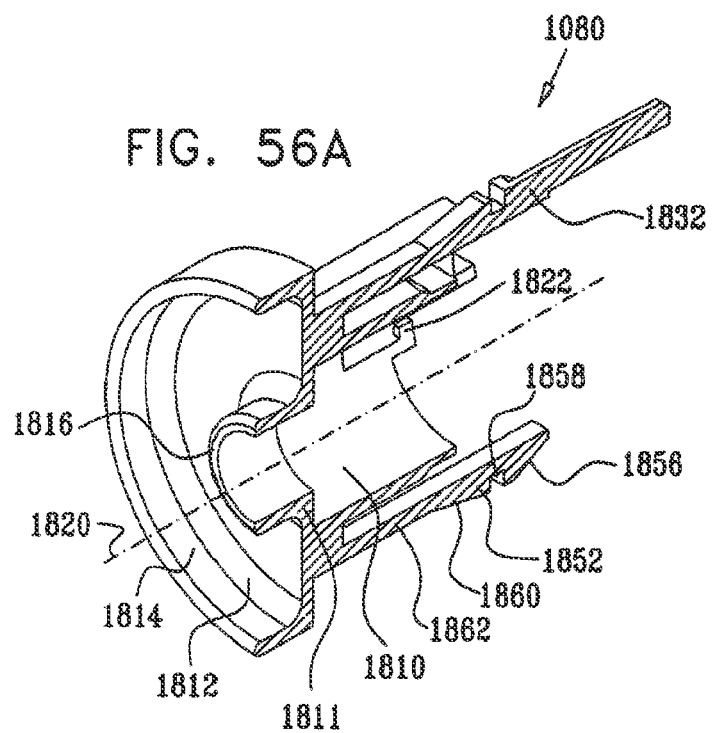
FIGS. 56A and 56B are simplified pictorial sectional illustrations of the needle guard element of FIGS. 55A and 55B, taken along lines LVIA-LVIA and LVIB-LVIB in FIG. 55A.
Figure 56B:
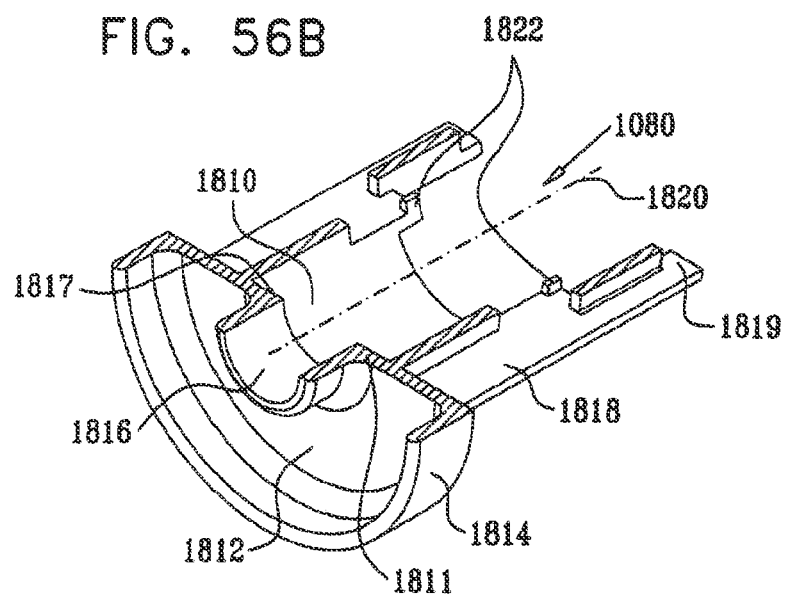
Figure 57A:
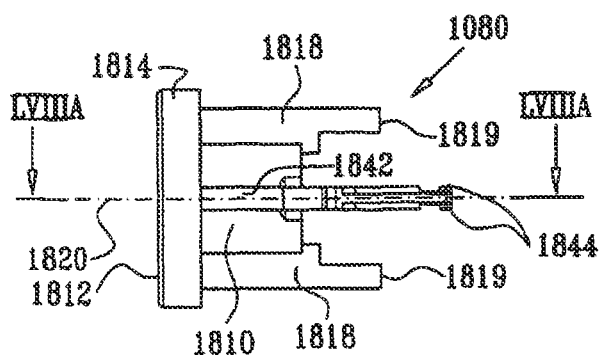
FIGS. 57A and 57B are respective top and side view simplified planar illustrations of the needle guard element of FIGS. 55A and 55B.
Figure 57B:
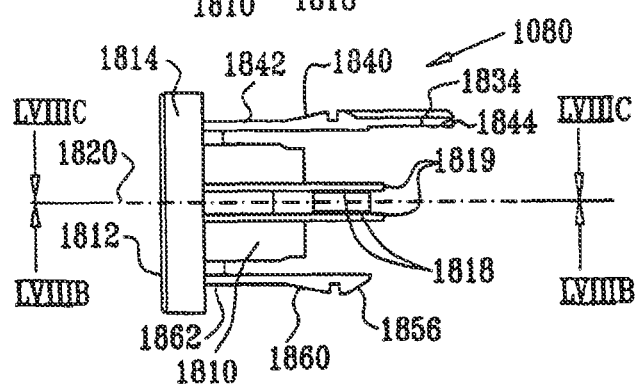
Figure 58A:
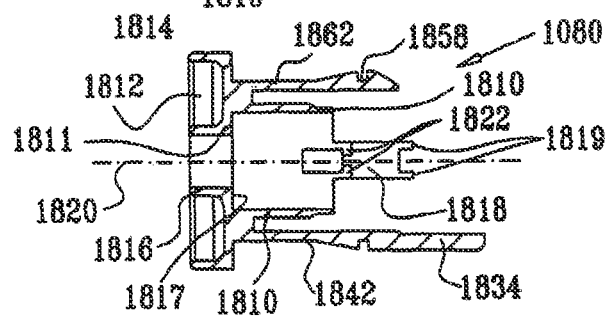
FIGS. 58A, 58B and 58C are sectional illustrations taken along respective section lines and directions LVIIIA-LVIIIA, LVIIIB-LVIIIB and LVIIIC-LVIIIC in FIGS. 57A and 57B.
Figure 58B:
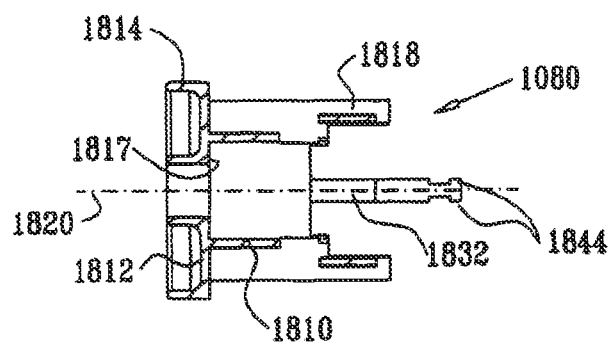
Figure 58C:
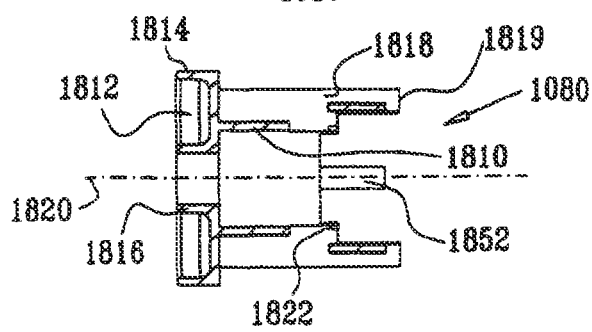

Reference is now made to FIGS. 55A and 55B which are simplified pictorial illustrations of the needle guard element 1080 which forms part of the automatic injection device of FIG. 42, to FIGS. 56A and 56B, which are simplified pictorial sectional illustrations of the needle guard element of FIGS. 55A and 55B, taken along lines LVIA-LVIA and LVIB-LVIB in FIG. 55A, to FIGS. 57A and 57B, which are respective top and side view simplified planar illustrations of the needle guard element of FIGS. 55A and 55B and to FIGS. 58A, 58B and 58C, which are sectional illustrations taken along respective section lines and directions LVIIIA-LVIIIA, LVIIIB-LVIIIB and LVIIIC-LVIIIC in FIGS. 57A and 57B.

As seen in FIGS. 55A-58C, the needle guard element 1080 preferably is an integrally formed element, preferably injection molded of plastic and preferably has a generally cylindrical configuration including a generally tubular portion 1810, having a forward wall 1811 defining forward facing body engaging surface 1812 including a pair of concentric circumferential forward facing rings 1814 and 1816, and a rearward facing spring seat defining surface 1817, which defines a spring seat for spring 1090.

Needle guard element 1080 has a pair of side-to-side symmetric mounting arms 1818 having rearwardmost ends 1819, arranged symmetrically about a longitudinal axis 1820. Arms 1818 extend along and rearwardly of tubular portion 1810 parallel to longitudinal axis 1820, which when the automatic injector device is assembled, is coaxial with longitudinal axes 1120 (FIGS. 43-46C), 1320 (FIGS. 47-50C), 1420 (FIG. 42) and 1720 (FIGS. 51-54C).

Formed interiorly of each of mounting arms 1818 are a pair of spaced mutually facing circumferentially directed teeth 1822, each pair of which is arranged for engagement with a corresponding axially extending tooth 1736 when the automatic injection device is in a pre-use operative orientation, as described hereinbelow with reference to FIGS. 60-62B.

A top engagement arm 1832 also extends rearwardly of tubular portion 1810 and includes a rearwardmost axial portion 1834, an inclined intermediate portion 1836, an axial intermediate portion 1838 and an inclined mounting portion 1840, which extends from a top portion 1842. Formed at an extreme rearward end of top engagement arm 1832 are a pair of oppositely circumferentially directed protrusions 1844.

A bottom engagement arm 1852 also extends rearwardly of tubular portion 1810 and includes an inclined portion 1856, an axial intermediate portion 1858 and an inclined mounting portion 1860, which extends from a bottom portion 1862.

Reference is now made to FIGS. 59A, 59B, 59C, 59D and 59E, which are simplified pictorial illustration of various stages of typical use of the automatic injection device of FIG. 42.

Figure 59A:
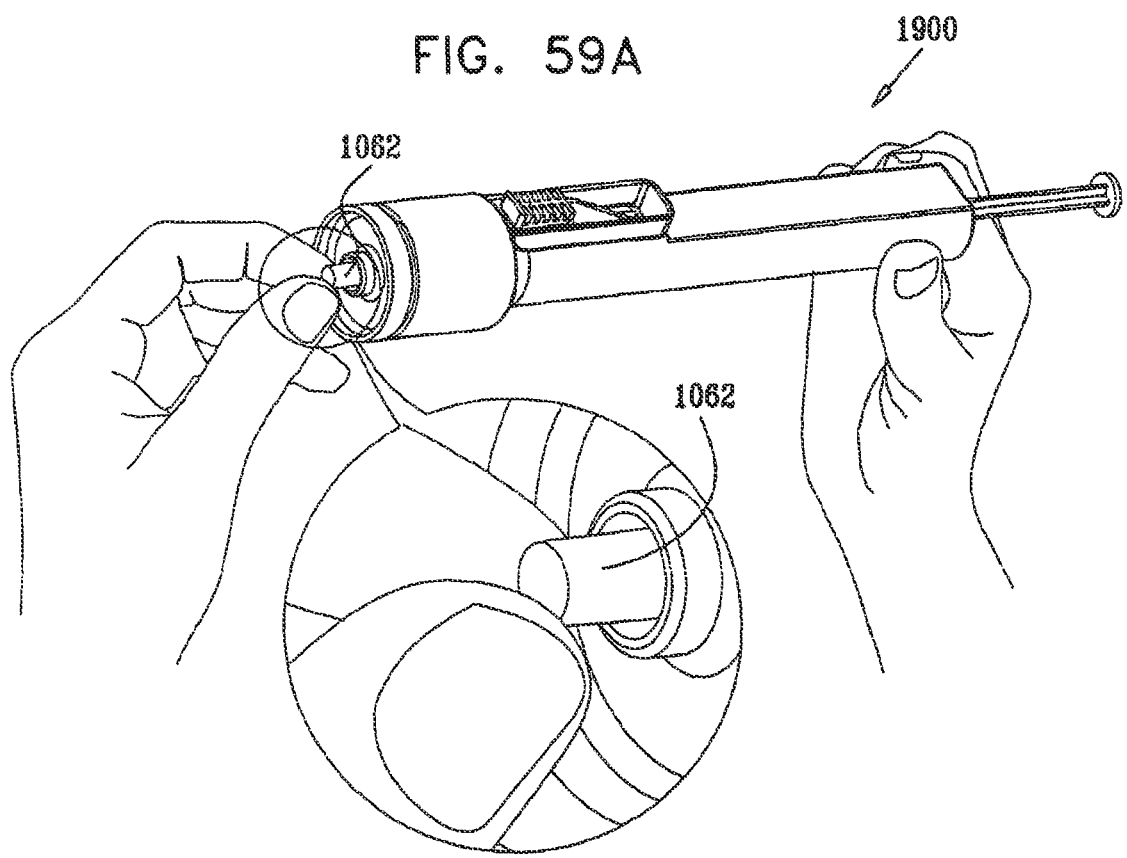

As seen in FIG. 59A, the automatic injection device of FIG. 42 is stored prior to use, as indicated by reference numeral 1900, in a pre-use operative orientation, described hereinbelow with reference to FIGS. 60-62B. While the automatic injection device is stored, it is preferably covered by needle protection cover 1062.

A user enables actuation of the automatic injection device by pushing it against an injection site, as indicated by reference numeral 1902 shown in FIG. 59B and as described hereinbelow with reference to FIGS. 63-65B. Subsequently, in response to the user depressing actuation button 1125 (FIGS. 43A-46C), needle penetration takes place at the injection site, as indicated by reference numeral 1904 shown in FIG. 59C. The operative orientation of the automatic injection device at this stage is described hereinbelow with reference to FIGS. 66-68B.

Figure 59B:
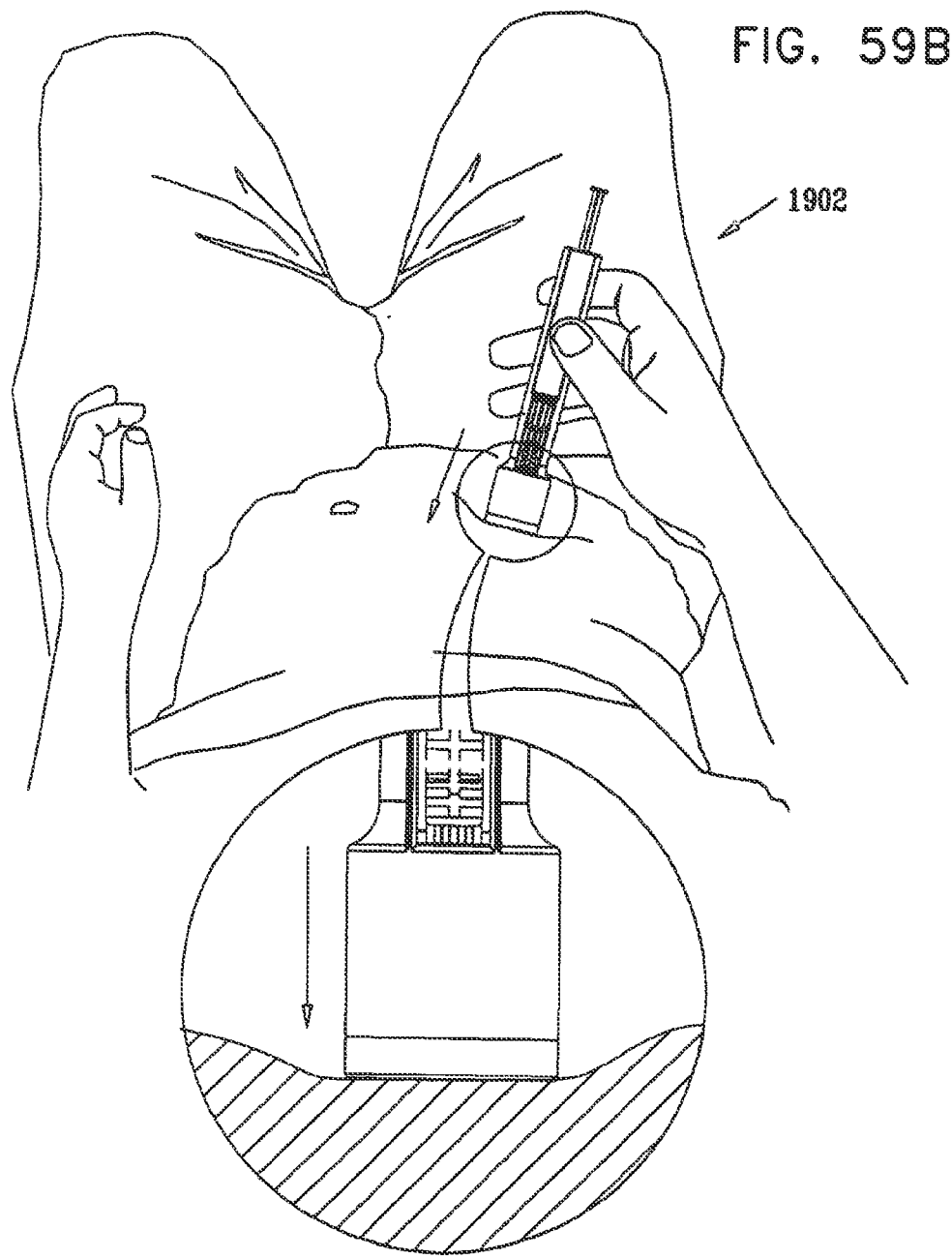
Figure 59D:
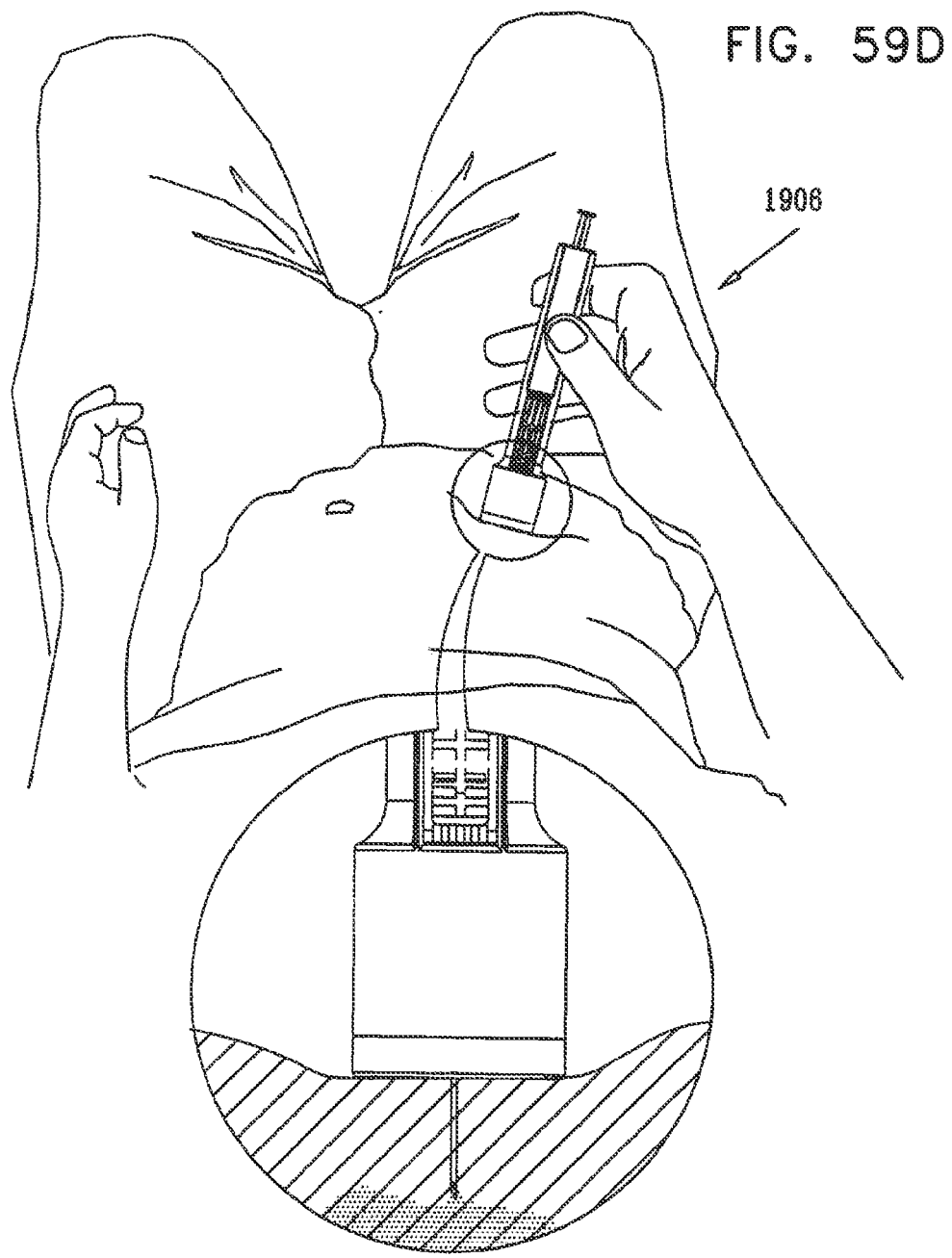

As seen in FIG. 59D, immediately following needle penetration, drug delivery takes place, as indicated by reference numeral 1906. The operative orientation of the automatic injection device at this stage is described hereinbelow with reference to FIGS. 69-71B.

As seen in FIG. 59E, the automatic injection device is then manually disengaged from the injection site, as indicated by reference numeral 1908, during which time the needle guard 1080 is automatically deployed. Immediately upon disengagement, the needle is automatically protected by the needle guard element 1080. The operative orientation of the automatic injection device at this stage is described hereinbelow with reference to FIGS. 72-74B.

Figure 60:
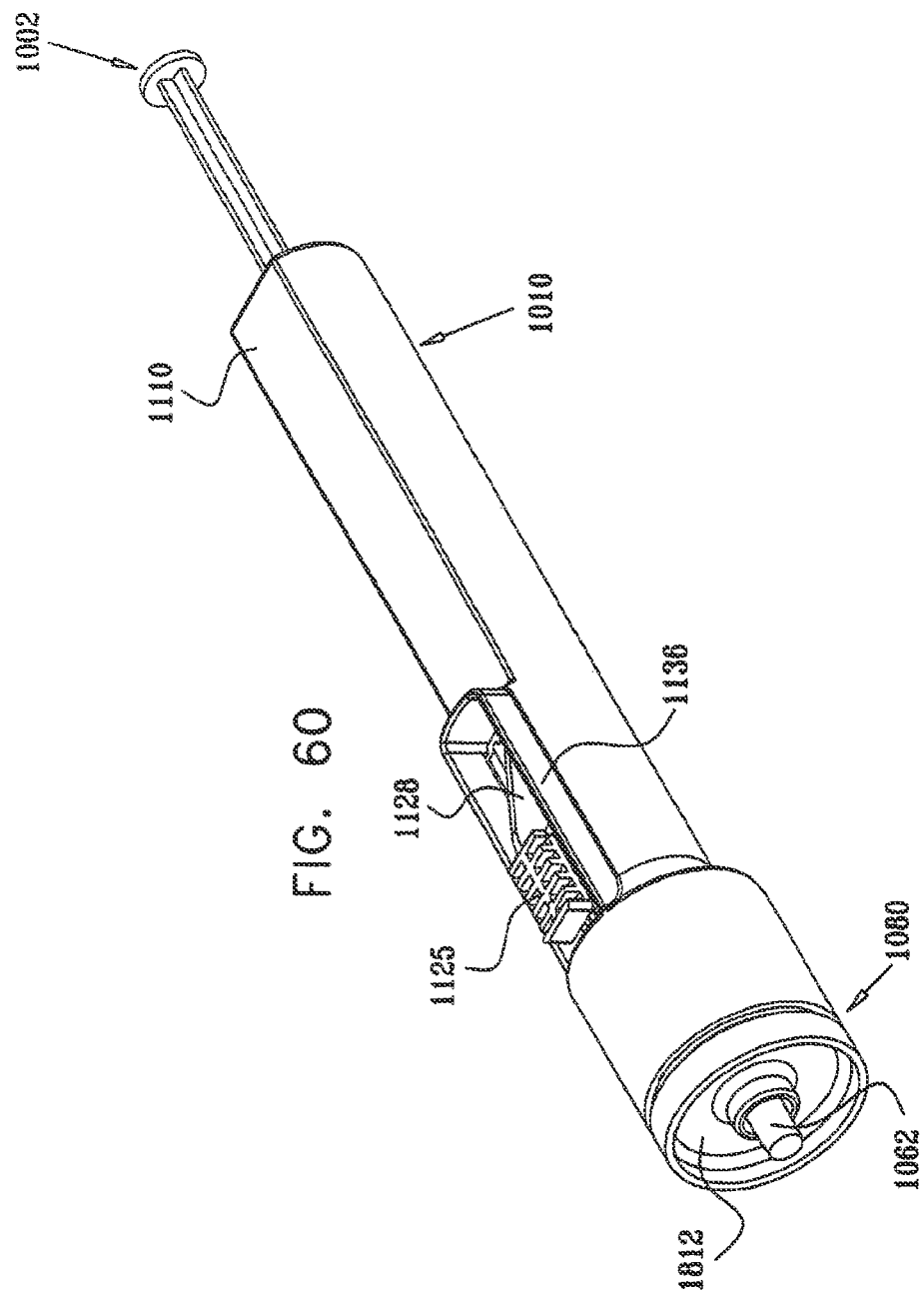
FIG. 60 is a simplified assembled view illustration of the automatic injection device of FIGS. 42 and 59A in a pre-use operative orientation.

Reference is now made to FIG. 60, which is a simplified assembled view illustration of the automatic injection device of FIGS. 42 and 59A in a pre-use operative orientation, to FIGS. 61A and 61B which are respective top and side view simplified planar illustrations of the automatic injection device of FIG. 60 and to FIGS. 62A and 62B which are sectional illustrations taken along respective section lines and directions LXIIA-LXIIA and LXIIB-LXIIB in FIGS. 61A and 61B.

As seen in FIGS. 60-62B, in a pre-use operative orientation of the automatic injection device which is suitable for storage, the main housing portion 1010 is joined to the forward housing portion 1070 by engagement of peripheral protrusion 1770 with peripheral groove 1160, and by engagement of top and bottom axial protrusions 1772 with top and bottom axial grooves 1162 of main housing 1010 (FIGS. 43A-46C and 51A-54B).

Selectable driving element 1030 is retained in a rearward axial position by engagement of forwardly facing surface 1332 (FIGS. 47-50B) with a rearward facing surface of flange 1502 of pre-filled syringe 1050. Pre-filled syringe 1050 is, in turn, retained in its retracted axial position by engagement of a forward facing surface of flange 1502 by rearward facing surface 1130 of selectable syringe engagement portion 1128 of actuation button portion 1124 (FIGS. 43A-46C). Pre-filled syringe 1050 is also retained in its retracted axial position by engagement of inwardly extending teeth 1734 of bifurcated tooth elements 1733 of inwardly facing cantilevered engagement elements 1732 of forward housing element 1070 with a forward facing tapered peripheral surface of the pre-filled syringe 1050.

Inwardly facing cantilevered engagement elements 1732 cannot bend outwards to disengage inwardly extending teeth 1734 from pre-filled syringe 1050 due to engagement of forwardly axially extending teeth 1736 with respective pairs of spaced mutually facing circumferentially directed teeth 1822 formed in arms 1818 of needle guard element 1080. The engagement of forwardly axially extending teeth 1736 with pairs of spaced mutually facing circumferentially directed teeth 1822 formed in arms 1818 of needle guard element 1080 also retains the needle guard element 1080 in its axial position and prevents it from moving outward.

In the pre-use orientation shown in FIGS. 60-62B, the actuation button is retained against inadvertent actuation by the needle guard element 1080 when in its relative forward orientation, as it is maintained in the storage orientation of the automatic injection device. When needle guard element 1080 is in its relative forward orientation, the pair of oppositely circumferentially directed protrusions 1844 of rearwardmost axial portion 1834 of top engagement arm 1832 is retained against radially inward displacement by pair of teeth 1730 of forward housing element 1070 and thus does not allow axial forward movement of selectable syringe engagement portion 1128 and of syringe 1050.

Figure 63:
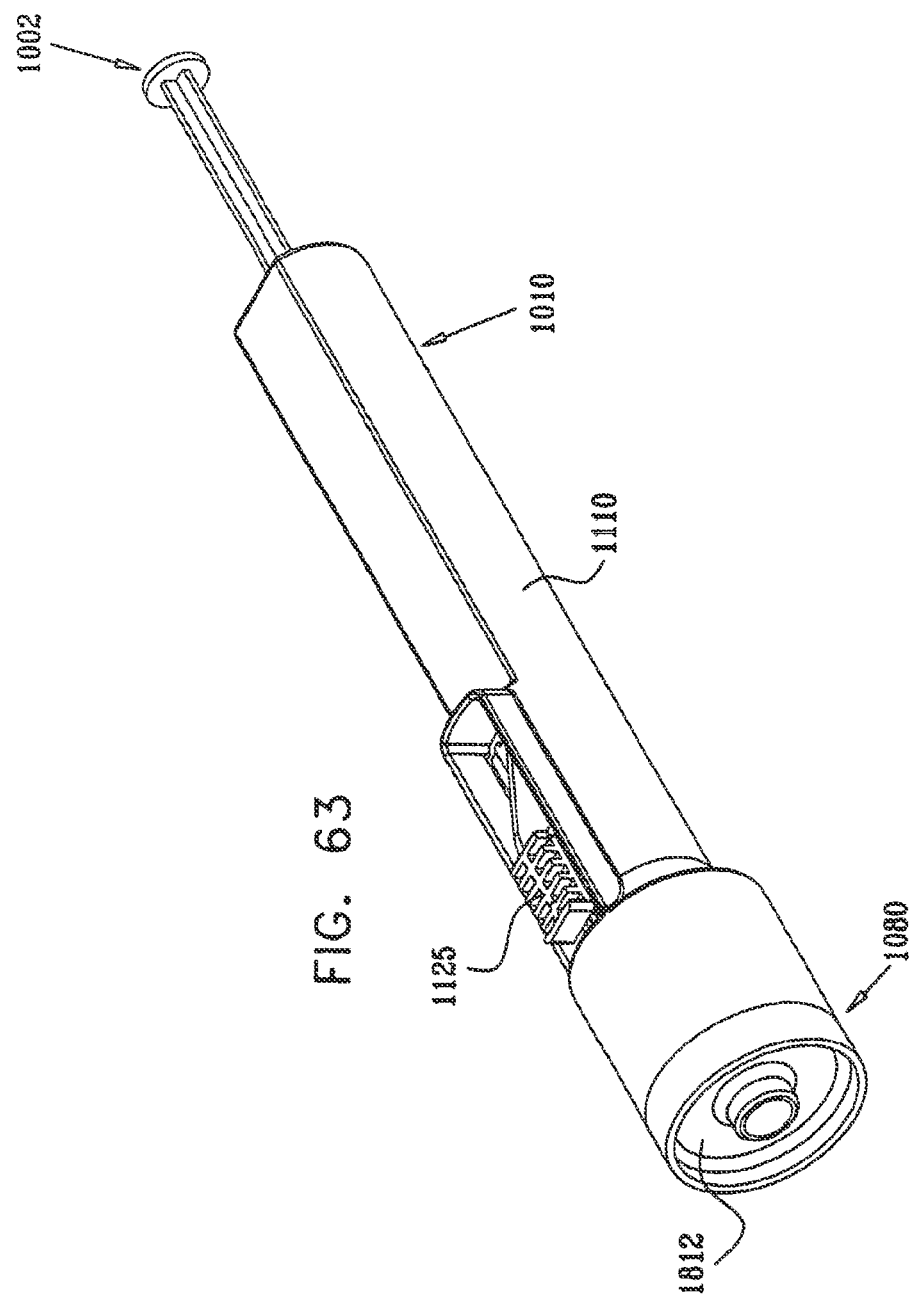
FIG. 63 is a simplified pictorial illustration of the automatic injection device of FIGS. 42 and 59B in an actuatable operative orientation.

Reference is now made to FIG. 63, which is a simplified pictorial illustration of the automatic injection device of FIGS. 42 and 59B in an actuatable operative orientation, to FIGS. 64A and 64B which are respective top and side view simplified planar illustrations thereof and to FIGS. 65A and 65B which are sectional illustrations taken along respective section lines and directions LXVA-LXVA and LXVB-LXVB in FIGS. 64A and 64B.

As seen particularly in the enlarged portion of FIG. 65A, due to engagement of the needle guard element 1080 with an injection site on a body following the removal of needle protection cover 1062, the needle guard element 1080 is forced to move axially in a rearward direction with respect to the remainder of the automatic injection device, thus compressing spring 1090 and causing the rearwardmost axial portion 1834 of the top engagement arm 1832 of the needle guard element 1080 to assume a relatively rearward position, so that the pair of oppositely circumferentially directed protrusions 1844 does not overlie teeth 1730 of forward housing element 1070. This permits inward pressing on the actuation button to cause disengagement of the forward facing surface of flange 1502 from rearward facing surface 1130 of selectable syringe engagement portion 1128 of actuation button portion 1124 (FIGS. 43A-46C), due to outward movement of surface 1130.

Disengagement of the forward facing surface of flange 1502 from rearward facing surface 1130 immediately releases the syringe 1050 to move forward under the urging of selectable driving element 1030, due to engagement of flange 1502 with forwardly facing surface 1332 of selectable driving element 1030. At the same time, rearward movement of the needle guard element 1080 causes the disengagement of the pairs of spaced mutually facing circumferentially directed teeth 1822 formed in arms 1818 of needle guard element 1080 from forwardly axially extending teeth 1736 of inwardly facing cantilevered engagement elements 1732, thus allowing outward bending of inwardly facing cantilevered engagement elements 1732.

Figure 66:
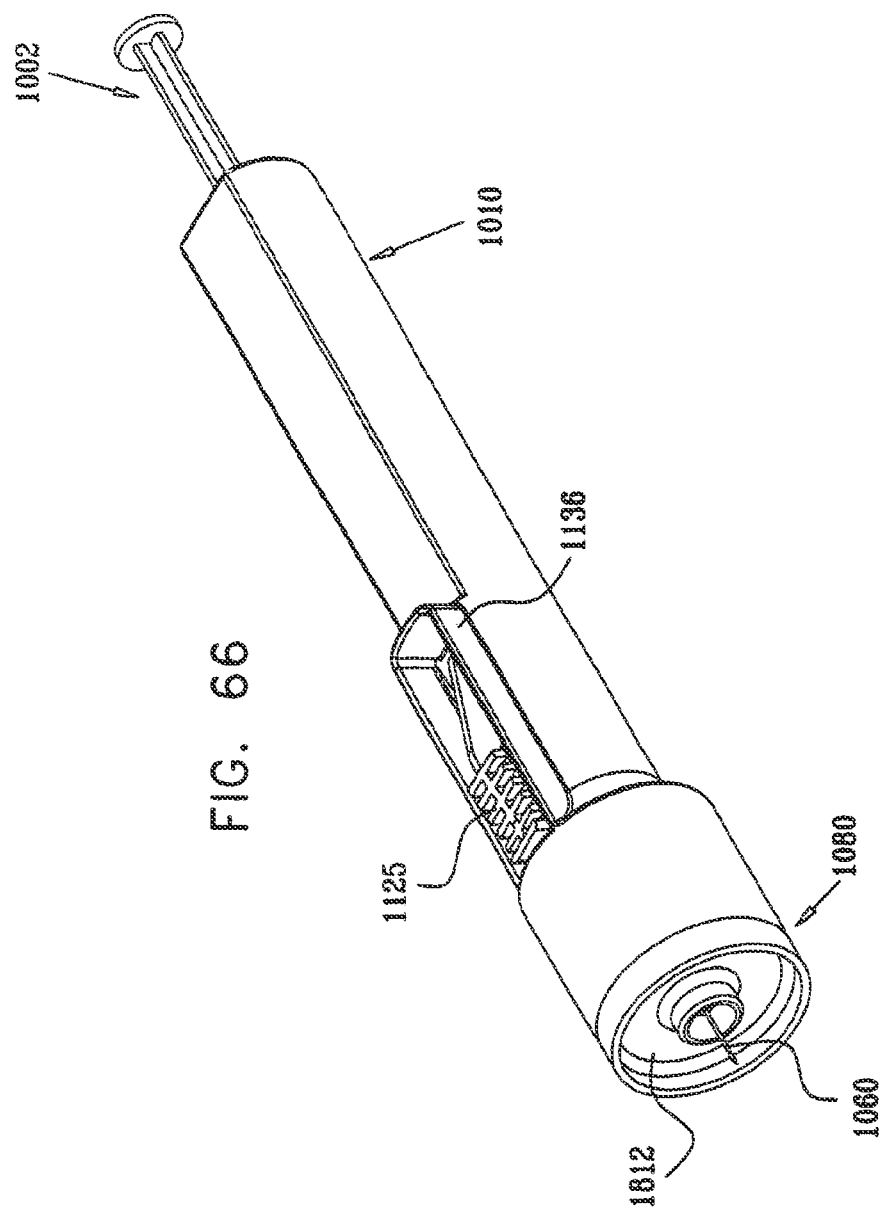
FIG. 66 is a simplified pictorial illustration of the automatic injection device of FIGS. 42 and 59C in an actuated needle penetration operative orientation.

Reference is now made to FIG. 66, which is a simplified pictorial illustration of the automatic injection device of FIGS. 42 and 59C in an actuated needle penetration, pre-drug delivery operative orientation, to FIGS. 67A and 67B which are respective top and side view simplified planar illustrations of the automatic injection device of FIG. 66 and to FIGS. 68A and 68B which are sectional illustrations taken along respective section lines and directions LXVIIIA-LXVIIIA and LXVIIIB-LXVIIIB in FIGS. 67A and 67B. FIGS. 66-68B illustrate an initial stage in the forward motion of the selectable driving element 1030 under the urging of spring 1020 following user actuation of portion 1125 of actuation button portion 1124. It is understood that the axial forward motion of the selectable driving element 1030 produces equivalent axial forward motion of the syringe 1050, due to engagement of flange 1502 by forwardly facing surface 1332 of selectable driving element 1030.

As seen particularly in FIGS. 68A and 68B, as the syringe 1050 approaches its forward needle penetration axial position determined by flange 1502 reaching inwardly facing teeth 1726 and 1727 of forward housing 1070, oppositely directed transversely extending protrusions 1334 at the forward facing surfaces 1332 of the engagement arms 1312 are deflected outwardly by outwardly extending ribs 1135, thus enabling further forward motion of plunger 1002 under the urging of spring 1020.

Forward movement of pre-filled syringe 1050 forces inwardly facing cantilevered engagement elements 1732 to bend outwards and retain their bent state, thus allowing deployment of the needle guard element 1080 upon removal from the injection site as will be described hereinbelow with reference to FIGS. 72-74B.

The forward movement of pre-filled syringe 1050 also ensures that selectable syringe engagement portion 1128 of actuation button portion 1124 is retained in a raised position by engagement therewith of flange 1502, which is located radially inwardly thereof. The raised positioning of selectable syringe engagement portion 1128 maintains the downward displacement of forward actuation button defining portion 1125 of actuation button portion 1124, thus maintaining engagement thereof with rearwardmost axial portion 1834 of the top engagement arm 1832 of needle guard element 1080. The engagement of rearwardmost axial portion 1834 and forward actuation button defining portion 1125 ensures non-interfered deployment of the needle guard element 1080 upon removal of the automatic injection device from the injection site.

Reference is now made to FIG. 69 which is a simplified pictorial illustration of the automatic injection device of FIGS. 42 and 59D in a post-drug delivery operative orientation, to FIGS. 70A and 70B which are respective top and side view simplified planar illustrations of the automatic injection device of FIG. 69 and to FIGS. 71A and 71B which are sectional illustrations taken along respective section lines and directions LXXIA-LXXIA and LXXIB-LXXIB in FIGS. 70A and 70B.

FIGS. 69-71B illustrate a further stage in the forward motion of the selectable driving element 1030 under the urging of spring 1020 following user actuation of forward actuation button portion 1125. As noted above, further axial forward motion of the selectable driving element 1030 does not produce equivalent axial forward motion of the syringe 1050. Continued urging of spring 1020 and consequent forward axial motion of the selectable driving element 1030 causes engagement of forward wall 1340 of selectable driving member 1030 with corresponding protrusions 1404 located along the length of plunger 1002 thus forcing plunger 1002 forward along the interior of pre-filled syringe 1050 which results in drug delivery. Forward axial motion of selectable driving member 1030 and plunger 1002 is stopped when a piston attached to plunger 1002 engages the forward end of syringe 1050 and is prevented from moving further.

Figure 72:
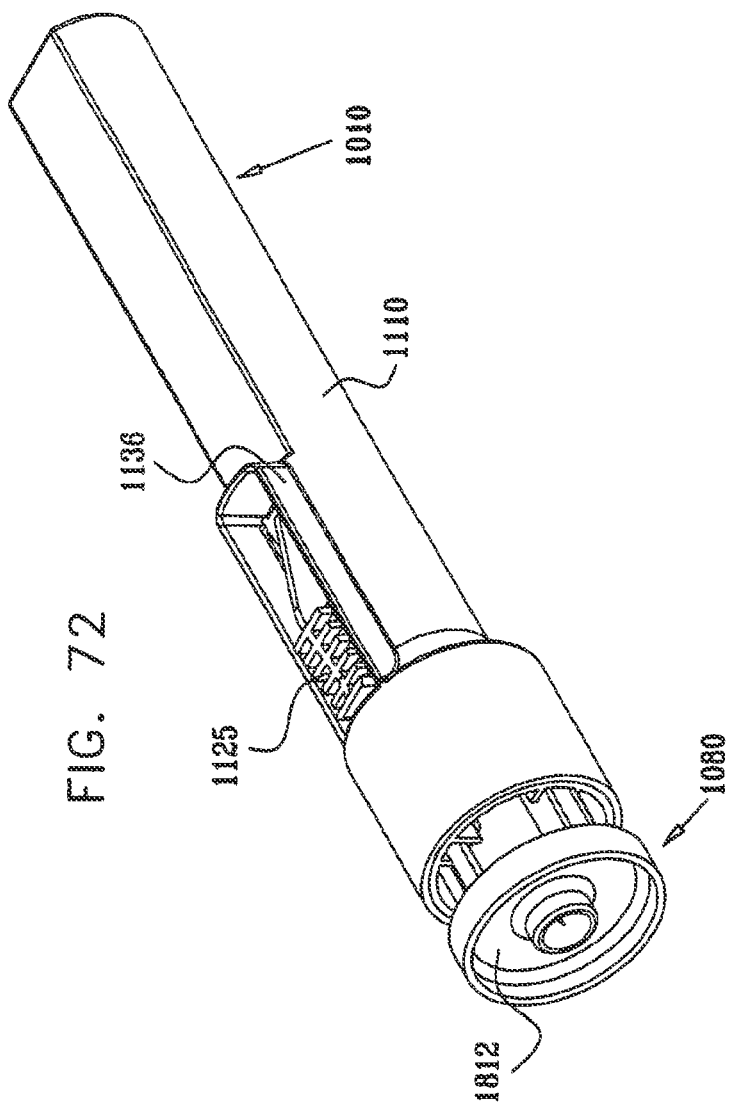
FIG. 72 is a simplified pictorial illustration of the automatic injection device of FIGS. 42 and 59E in post injection site disengagement operational orientation.

Reference is now made to FIG. 72 which is a simplified pictorial illustration of the automatic injection device of FIGS. 41 and 59E in post injection site disengagement operational orientation, to FIGS. 73A and 73B which are respective top and side view simplified planar illustrations of the automatic injection device of FIG. 72 and to FIGS. 74A and 74B which are sectional illustrations taken along respective section lines and directions LXXIVA-LXXIVA and LXXIVB-LXXIVB in FIGS. 73A and 73B.

At this stage, the automatic injection device has been removed from the injection site and the needle guard 1080 has moved axially forward under the urging of spring 1090, so that the exposed portion of the needle 1060 is protected by the needle guard 1080. Due to the forward movement of the needle guard 1080, protrusion 1774 of the forward housing element 1070 engages axial intermediate portions 1838 and 1858 on the needle guard element 1080, thus locking the needle guard 1080 against retraction and further forward movement.

In accordance with an embodiment of the present invention, all or part of any or all of the housing element 1010 and forward housing element 1070 may be transparent, to enable the contents of the syringe 1050 to be viewed by a user from outside the automatic injection device.

In an optional titration step, after the protective needle cover 1062 has been removed and while the needle guard 1080 points upwards a user may push rear wall portion 1402 of plunger 1040 forwardly as the syringe 1050 is retained in place. This forces air bubbles and/or liquid out of the syringe via the needle 1060. It is appreciated that except for the forward movement of the plunger 1040, the remainder of the operative orientation of the automatic injection device remains identical to the pre-use operative orientation. Reference is now made to FIGS. 75-90B, which illustrate automatic injection device constructed and operative in accordance with yet another preferred embodiment of the present invention.

As seen with particular clarity in FIG. 75, the automatic injection device comprises a plunger 2002 which is partially located within a main housing element 2010 into which is seated a main compression spring 2020, which provides selectable forward displacement to a pre-filled syringe 2050 having a hypodermic needle 2060 which is covered by a needle protection cover 2062. Pre-filled syringe 2050 may be a conventional pre-filled syringe, such as a commercially available syringe sold under the catalog designation BD-Hypak™ or may be any other suitable syringe or cartridge.

Plunger 2002 also operatively engages pre-filled syringe 2050 and is selectably operable to inject liquid contents of pre-filled syringe 2050 through hypodermic needle 2060.

The forward portion of main housing element 2010 surrounds and is engaged with a forward housing element 2070. At the forward end of the interior of forward housing element 2070 there is provided a needle guard element 2080, which is positioned by a compression spring 2090.

Reference is now made to FIGS. 43A and 43B, which are simplified pictorial illustrations of a preferred main housing element 1010 which forms part of the automatic injection device of FIG. 42, to FIGS. 44A and 44B which are simplified pictorial sectional illustrations of the main housing element 1010 of FIGS. 43A and 43B, taken along lines XLIVA-XLIVA and XLIVB-XLIVB in FIG. 43A, to FIGS. 45A and 45B, which are respective top and side view simplified planar illustrations of the main housing element of FIGS. 43A-44B and to FIGS. 46A, 46B and 46C which are sectional illustrations taken along respective section lines and directions XLVIA-XLVIA, XLVIB-XLVIB and XLVIC-XLVIC in FIGS. 45A and 45B.

Main housing element 2010 is similar to main housing element 1010 described hereinabove with reference to FIGS. 43A-46C, except in the following respects:

The main housing element 2010 is substantially shorter than main housing element 1010 and does not include various internal structural portions which are required in the embodiment of FIGS. 42-58C but are not required in the embodiment of FIGS. 75-90B.

The main housing element 2010 is formed at a rearward end thereof with side-to-side symmetric outwardly extending finger-engageable retainers 2091.

Plunger 2002, as seen in FIG. 75 is a generally circularly symmetric element, which is preferably formed in an overall ribbed configuration, as shown. Plunger 2002 includes a rear wall portion 2402. At a forward end of plunger 2002 there is provided a peripheral protrusion 2406 forward of which is provided a threaded end 2408. Plunger 2002 is arranged along a longitudinal axis 2420, which when the automatic injector device is assembled, is coaxial with longitudinal axis 1120 (FIGS. 43-46C). As seen in FIG. 75, pre-filled syringe 2050 includes a rear flange 2502 which is engaged by a forward end of main spring 2020.

Reference is now made to FIGS. 51A and 51B, which are simplified pictorial illustrations of a forward housing element 1070 which forms part of the automatic injection device of FIG. 42, to FIGS. 52A and 52B, which are simplified pictorial sectional illustrations of the forward housing element of FIGS. 51A and 51B, taken along lines LIIA-LIIA and LIIB-LIIB in FIG. 51A, to FIGS. 53A and 53B, which are respective top and side view simplified planar illustrations of the forward housing element of FIGS. 51A-52B and to FIGS. 54A and 54B which are sectional illustrations taken along respective section lines and directions LIVA-LIVA and LIVB-LIVB in FIGS. 53A and 53B.

Forward housing element 2070 is identical to forward housing element 1070 described hereinabove with reference to FIGS. 51A-54B.

Reference is now made to FIGS. 55A and 55B which are simplified pictorial illustrations of the needle guard element 1080 which forms part of the automatic injection device of FIG. 42, to FIGS. 56A and 56B, which are simplified pictorial sectional illustrations of the needle guard element of FIGS. 55A and 55B, taken along lines LVIA-LVIA and LVIB-LVIB in FIG. 55A, to FIGS. 57A and 57B, which are respective top and side view simplified planar illustrations of the needle guard element of FIGS. 55A and 55B and to FIGS. 58A, 58B and 58C, which are sectional illustrations taken along respective section lines and directions LVIIIA-LVIIIA, LVIIIB-LVIIIB and LVIIIC-LVIIIC in FIGS. 57A and 57B.

Needle guard element 2080 is identical to needle guard element 1080 described hereinabove with reference to FIGS. 55A-58C.

Figure 76:
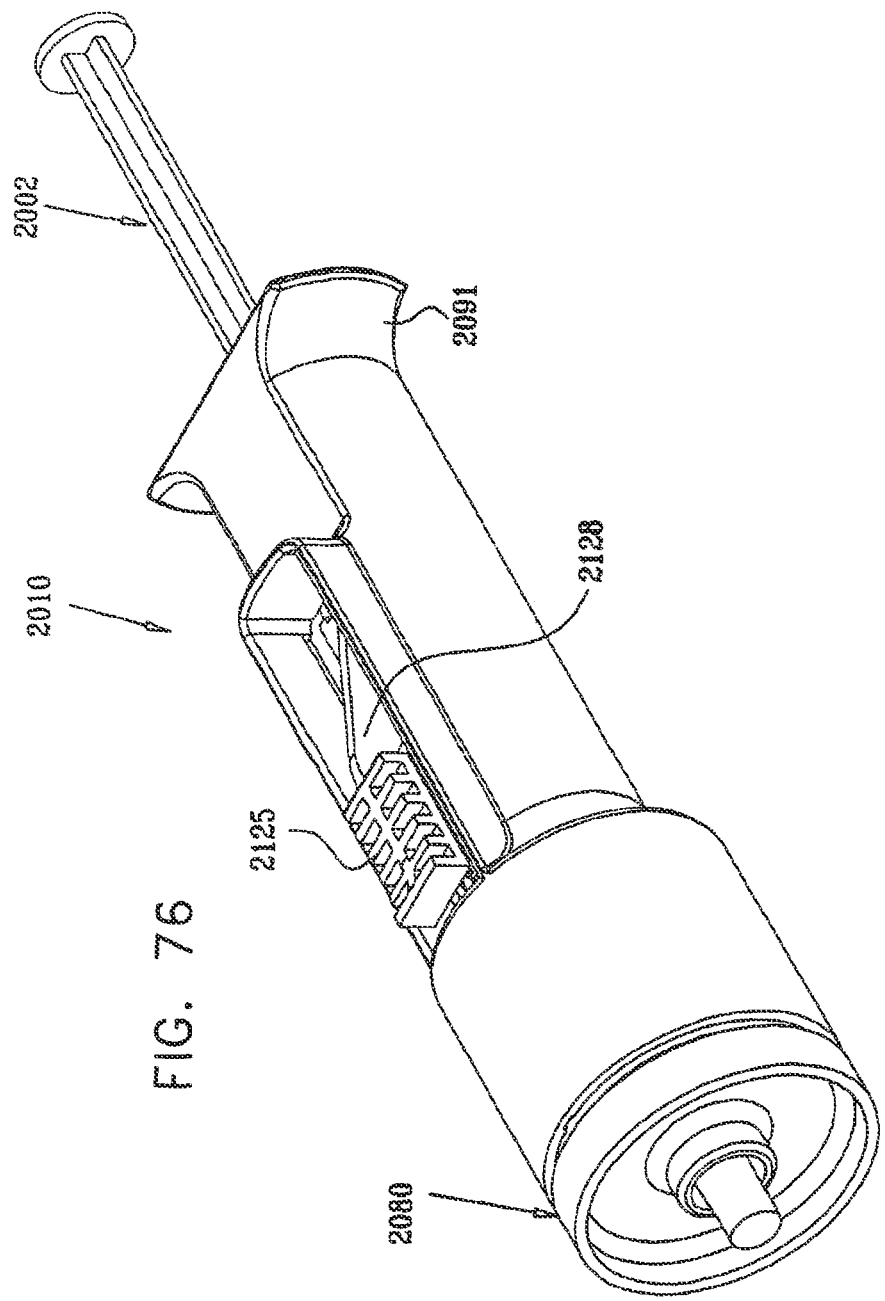
FIG. 76 is a simplified assembled view illustration of the automatic injection device of FIG. 75 in a pre-use operative orientation.

Reference is now made to FIG. 76, which is a simplified assembled view illustration of the automatic injection device of FIG. 75 in a pre-use operative orientation, to FIGS. 77A and 77B which are respective top and side view simplified planar illustrations of the automatic injection device of FIG. 76 and to FIGS. 78A and 78B which are sectional illustrations taken along respective section lines and directions LXXVIIIA-LXXVIIIA and LXXVIIIB-LXXVIIIB in FIGS. 77A and 77B.

As seen in FIGS. 76-78B, in a pre-use operative orientation of the automatic injection device which is suitable for storage, the main housing portion 2010 is joined to the forward housing portion 2070 by engagement of peripheral protrusion 2770 with peripheral groove 2160, and by engagement of top and bottom axial protrusions formed in forward housing element 2070 with top and bottom axial grooves formed in main housing element 2010.

Pre-filled syringe 2050 is retained in its retracted axial position by engagement of a forward facing surface of flange 2502 by a rearward facing surface 2130 of a selectable syringe engagement portion 2128 of an actuation button portion 2124. Pre-filled syringe 2050 is also retained in its retracted axial position by engagement of inwardly extending teeth 2734 of bifurcated tooth elements 2732 of inwardly facing cantilevered engagement elements 2730 of forward housing element 2070 with a forward facing tapered peripheral surface of the pre-filled syringe 2050.

Inwardly facing cantilevered engagement elements 2730 cannot bend outwards to disengage inwardly extending teeth 2734 from pre-filled syringe 2050 due to engagement of forwardly axially extending teeth 2736 with pairs of spaced mutually facing circumferentially directed teeth 2822 formed in arms 2818 of needle guard element 2080. The engagement of forwardly axially extending teeth 2736 with pairs of spaced mutually facing circumferentially directed teeth 2822 formed in arms 2818 of needle guard element 2080 also retains the needle guard element 2080 in its axial position and prevents it from moving outward.

In the pre-use orientation shown in FIGS. 76-78B, the actuation button is retained against inadvertent actuation by the needle guard element 2080 when in its relative forward orientation, as it is maintained in the storage orientation of the automatic injection device. When needle guard element 2080 is in its relative forward orientation, the pair of oppositely circumferentially directed protrusions 2844 of rearwardmost axial portion 2834 of top engagement arm 2832 is retained against radially inward displacement by pair of teeth 2730 of forward housing element 2070 and thus does not allow axial forward movement of selectable syringe engagement portion 2128 and of syringe 2050.

Reference is now made to FIG. 79, which is a simplified pictorial illustration of the automatic injection device of FIG. 75 in an actuatable operative orientation, to FIGS. 80A and 80B which are respective top and side view simplified planar illustrations thereof and to FIGS. 81A and 81B which are sectional illustrations taken along respective section lines and directions LXXXIA-LXXXIA and LXXXIB-LXXXIB in FIGS. 80A and 80B.

As seen particularly in the enlarged portion of FIG. 81A, due to engagement of the needle guard element 2080 with an injection site on a body following the removal of the needle protection cover, the needle guard element 2080 is forced to move axially in a rearward direction with respect to the remainder of the automatic injection device, thus compressing spring 2090 and causing the rearwardmost axial portion 2834 of the top engagement arm 2832 of the needle guard element 2080 to assume a relatively rearward position, so that the pair of oppositely circumferentially directed protrusions 2844 does not overlie teeth 2730 of forward housing element 2070. This permits inward pressing on the actuation button defining portion 2125 to cause disengagement of the forward facing surface of flange 2502 from rearward facing surface 2130 of selectable syringe engagement portion 2128 of actuation button portion 2124, due to outward movement of surface 2130.

Disengagement of the forward facing surface of flange 2502 from rearward facing surface 2130 immediately releases the syringe 2050 to move forward under the urging of main spring 2020. At the same time, rearward movement of the needle guard element 2080 causes the disengagement of the pairs of spaced mutually facing circumferentially directed teeth 2822 formed in arms 2818 of needle guard element 2080 from forwardly axially extending teeth 2736 of inwardly facing cantilevered engagement elements 2730, thus allowing outward bending of inwardly facing cantilevered engagement elements 2730.

Figure 82:
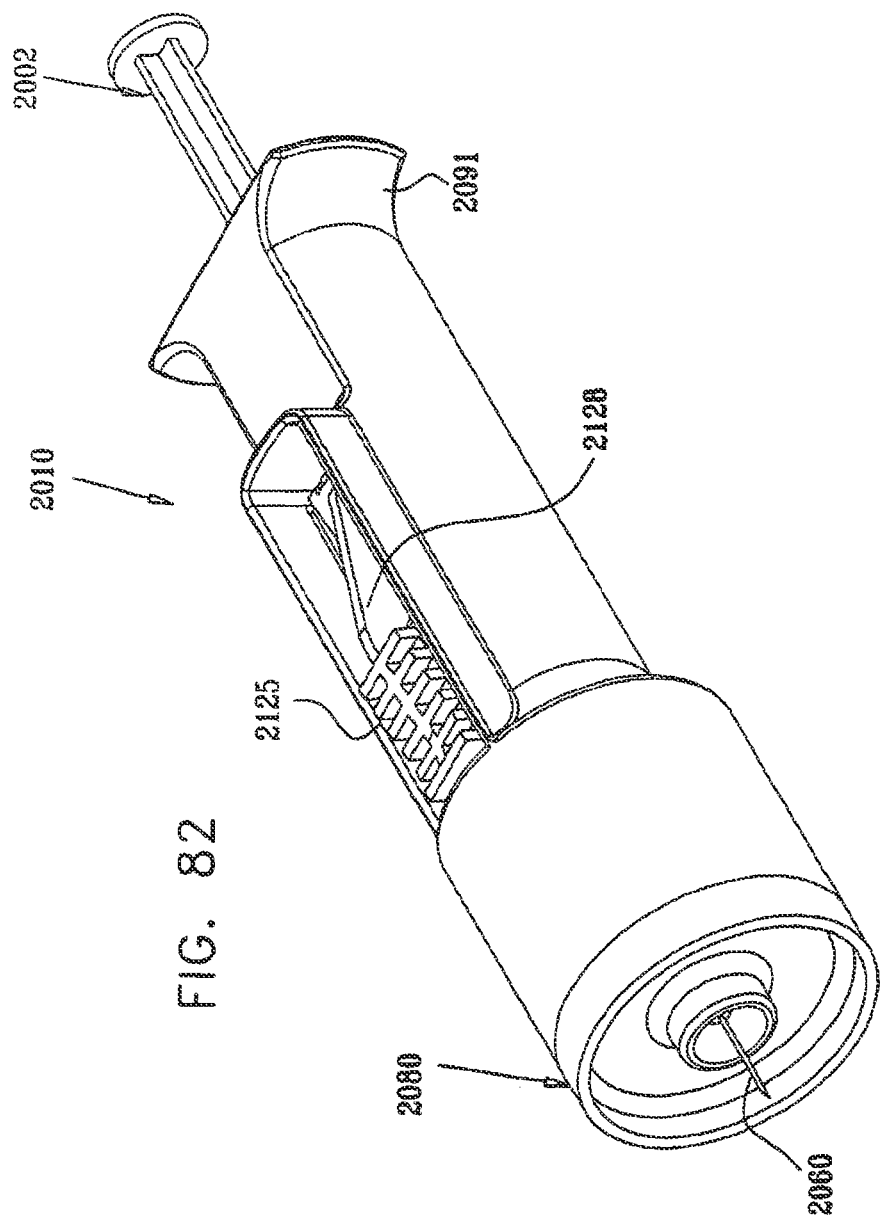
FIG. 82 is a simplified pictorial illustration of the automatic injection device of FIG. 75 in an actuated needle penetration operative orientation.

Reference is now made to FIG. 82, which is a simplified pictorial illustration of the automatic injection device of FIG. 75 in an actuated needle penetration, pre-drug delivery operative orientation, to FIGS. 83A and 83B which are respective top and side view simplified planar illustrations of the automatic injection device of FIG. 82 and to FIGS. 84A and 84B which are sectional illustrations taken along respective section lines and directions LXXXIVA-LXXXIVA and LXXXIVB-LXXXIVB in FIGS. 83A and 83B.

FIGS. 82-84B illustrate a final stage in the forward motion of the syringe 2050 under the urging of spring 2020 following user actuation of button defining portion 2125 of button portion 2124.

As seen particularly in FIG. 84A, as the syringe 2050 approaches its forward, needle penetration axial position determined by flange 2502 reaching inwardly facing teeth 2726 and 2727 of forward housing 2070, the user pushes plunger 2002, thus enabling injection of fluid contained in syringe 2050.

Forward movement of pre-filled syringe 2050 forces inwardly facing cantilevered engagement elements 2730 to bend outwards and retain their bent state, thus allowing deployment of the needle guard element 2080 upon removal from the injection site as will be described hereinbelow with reference to FIGS. 88-90B.

The forward movement of pre-filled syringe 2050 also ensures that selectable syringe engagement portion 2128 of actuation button portion 2124 is retained in a raised position by engagement therewith of flange 2502, which is located radially inwardly thereof. The raised positioning of selectable syringe engagement portion 2128 maintains the downward displacement of forward actuation button defining portion 2125 of actuation button portion 2124, thus maintaining engagement thereof with rearwardmost axial portion 2834 of the top engagement arm 2832 of needle guard element 2080. The engagement of rearwardmost axial portion 2834 and forward actuation button defining portion 2125 ensures non-interfered deployment of the needle guard element 2080 upon removal of the automatic injection device from the injection site.

Figures 86A, 86B:
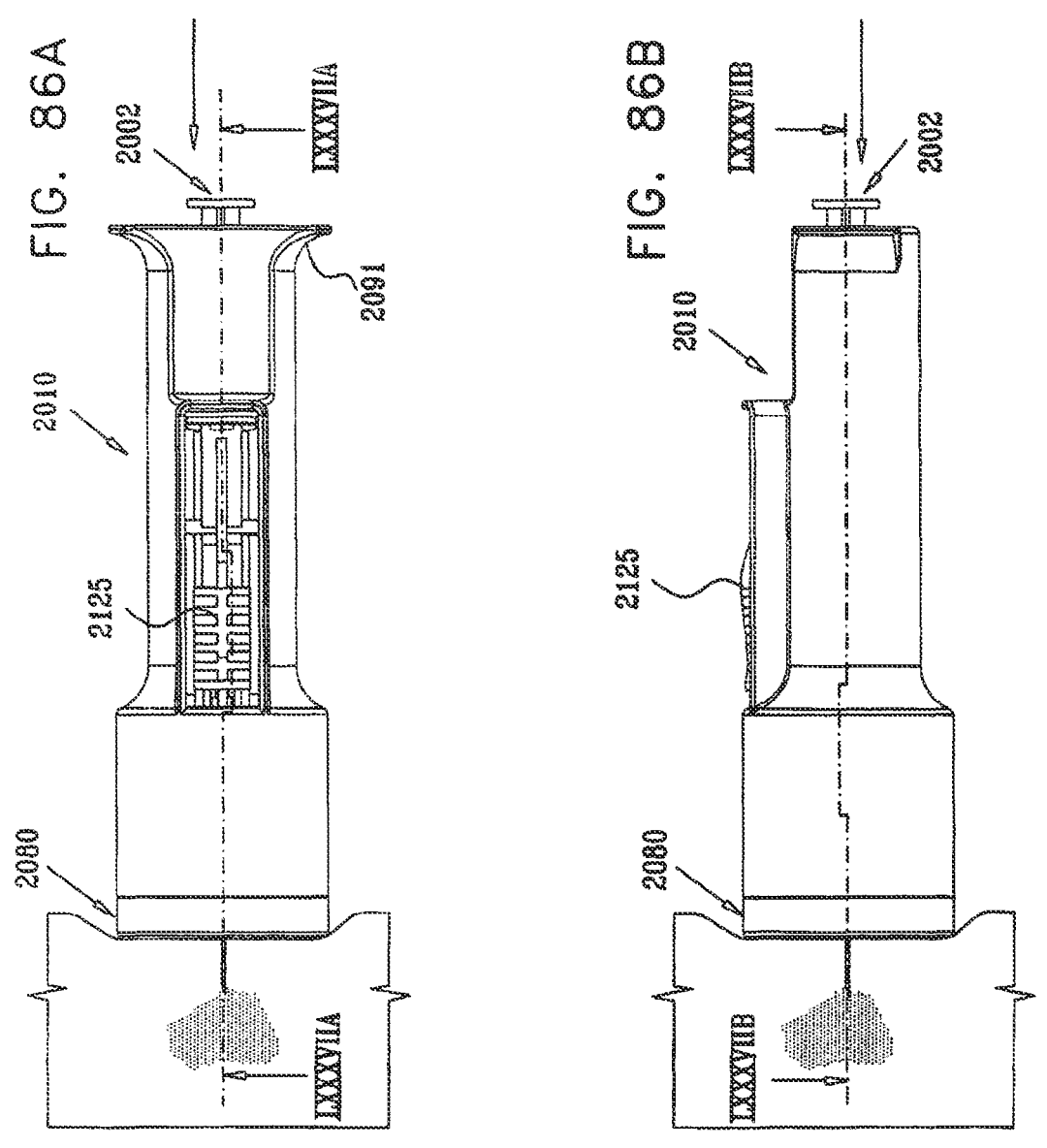

Reference is now made to FIG. 85 which is a simplified pictorial illustration of the automatic injection device of FIG. 75 in a post-drug delivery operative orientation, to FIGS. 86A and 86B which are respective top and side view simplified planar illustrations of the automatic injection device of FIG. 85 and to FIGS. 87A and 87B which are sectional illustrations taken along respective section lines and directions LXXXVIIA-LXXXVIIA and LXXXVIIB-LXXXVIIB in FIGS. 86A and 86B.

FIGS. 85-87B illustrate a further stage following user actuation of forward actuation button portion 2125. The user continues to push plunger 2002 which results in drug delivery. Forward axial motion of plunger 2002 is stopped when a piston attached to plunger 2002 engages the forward end of syringe 2050 and is prevented from moving further.

Reference is now made to FIG. 88 which is a simplified pictorial illustration of the automatic injection device of FIG. 75 in post injection site disengagement operational orientation, to FIGS. 89A and 89B which are respective top and side view simplified planar illustrations of the automatic injection device of FIG. 75 and to FIGS. 90A and 90B which are sectional illustrations taken along respective section lines and directions XCA-XCA and XCB-XCB in FIGS. 89A and 89B.

At this stage, the automatic injection device has been removed from the injection site and the needle guard 2080 has moved axially forward under the urging of spring 2090, so that the exposed portion of the needle 2060 is protected by the needle guard 2080. Due to the forward movement of the needle guard 2080, protrusions 2774 of the forward housing element 2070 engage sockets 2838 and 2858 on the needle guard element 2080, thus locking the needle guard 2080 against retraction and further forward movement.

Reference is now made to FIGS. 91-103C, which illustrate the constituent elements of another automatic injection device constructed and operative in accordance with another preferred embodiment of the present invention.

As seen with particular clarity in FIG. 91, the automatic injection device comprises a rear housing element 4010 in which is seated a main compression spring 4020, which provides selectable forward displacement to a selectable driving assembly 4030, which includes a selectable driving element 4031 and a pair of elastomeric motion damping elements 4032 and 4034, and selectably engages a plunger 4040 and a pre-filled syringe 4050 having a hypodermic needle 4060 which is covered by a needle protection cover 4062. Pre-filled syringe 4050 may be a conventional pre-filled syringe, such as a commercially available syringe sold under the catalog designation BD-Hypak™ or may be any other suitable syringe or cartridge.

Plunger 4040 also operatively engages pre-filled syringe 4050 and is selectably operated by selectable driving assembly 4030 to inject the liquid contents of pre-filled syringe 4050 through hypodermic needle 4060.

The forward portion of rear housing element 4010 as well as spring 4020, selectable driving assembly 4030, plunger 4040 and pre-filled syringe 4050 are located within a forward housing and actuator element 4070. At the forward end of the interior of forward housing and actuator element 4070 there is provided a needle guard element 4080, which is positioned by a compression spring 4090.

Reference is now made to FIG. 92, which is a simplified pictorial illustration of a preferred rear housing element 4010 which forms part of the automatic injection device of FIG. 91, to FIGS. 93A and 93B which are respective top and side view simplified planar illustrations thereof and to FIGS. 94A, 94B and 94C, which are sectional illustrations taken along respective section lines and directions XCIVA-XCIVA, XCIVB-XCIVB and XCIVC-XCIVC in FIGS. 93A and 93B. As seen in FIGS. 92-94C, the rear housing element 4010 preferably is an integrally formed element, preferably injection molded of plastic and preferably has a generally cylindrical configuration including a generally tubular portion 4110, which terminates in a back wall 4112, defining generally symmetric side-facing tabs 4114 in front of which are generally symmetric side facing recesses 4116. Tubular portion 4110 is preferably side-to-side symmetric about a longitudinal axis 4120.

Tubular portion 4110 is formed with a pair of generally symmetric side recesses 4122 at which corresponding generally elongate engagement shaft portions 4124 extend forwardly parallel to longitudinal axis 4120 each terminating in an outward facing protrusion 4126. Above each engagement shaft portion 4124 there is provided a further shaft portion 4127, which extends forwardly of protrusion 4126 and has a somewhat curved cross sectional configuration. Shaft portions 4127 on the two sides of the rear housing element are separated from each other, as shown. A pair of mutually facing ribs 4128 extend from shaft portions 4127 parallel to axis 4120, defining forward facing shoulders 4129. As seen particularly in FIGS. 92 and 94A, a central inward facing protrusion 4130 is provided at a top interior surface of the rear housing, between and rearward of ribs 4128.

A bottom interior surface 4131 of the rear housing element has a generally uniform, slightly concave cross section and includes a plurality of generally radially inwardly directed ribs 4132, which extend generally parallel to longitudinal axis 4120. A bottom exterior surface 4134 of the rear housing element, which is the underside of surface 4131, includes a forward edge 4136 from which a plurality of radially outwardly directed ribs 4138 extend generally parallel to longitudinal axis 4120.

Side interior surfaces 4140 of the rear housing element 4010 each define a forwardly pointed protrusion 4142 which is engaged by an outwardly extending protrusion of a first finger of selectable driving assembly 4030 and by elastomeric motion damping elements 4032 and 4034 forming part of selectable driving assembly 4030, as described hereinbelow. The interior surface of back wall 4112 of the rear housing element 4010 further comprises a rear seat 4160 for the spring 4020.

Figure 95:
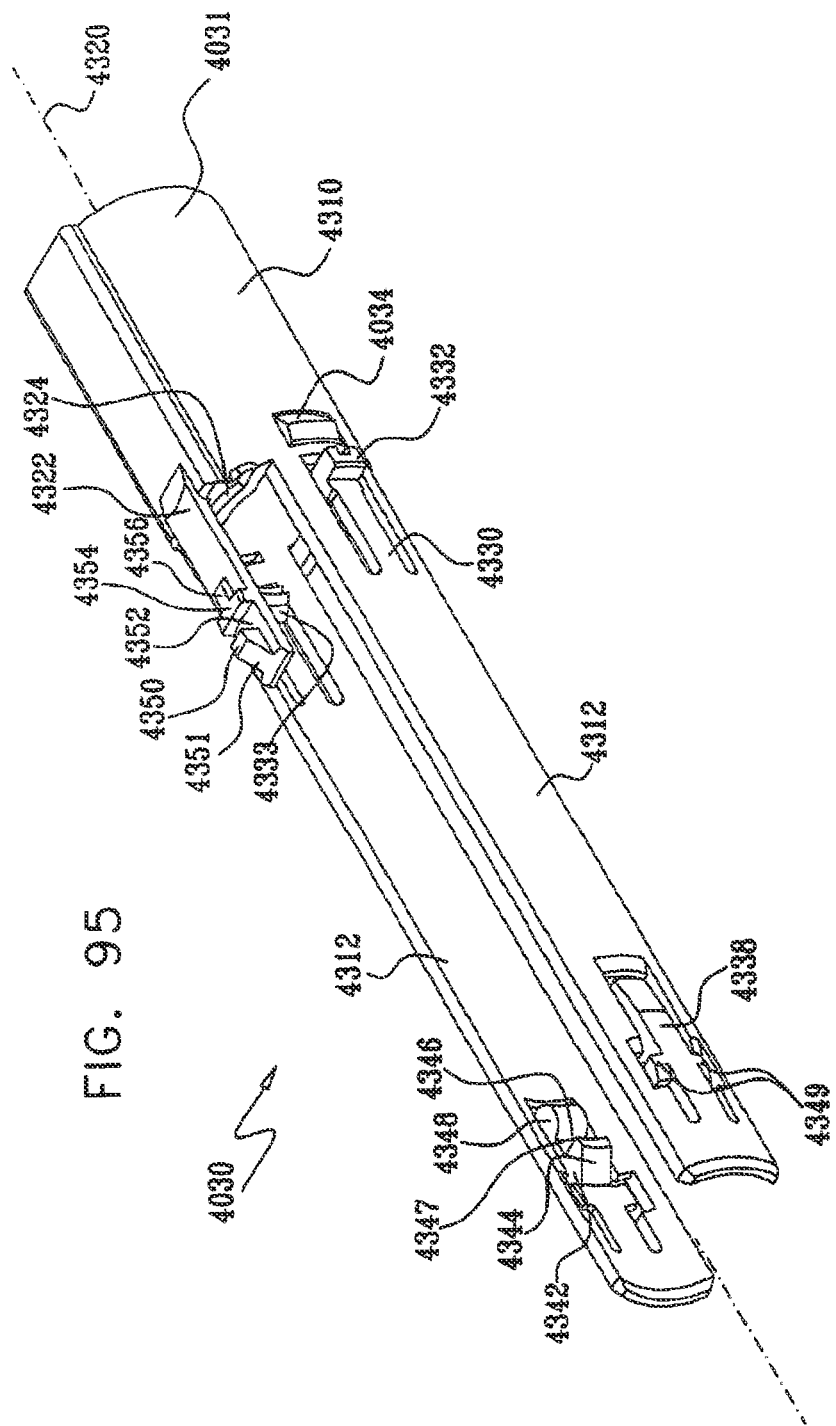
FIG. 95 is a simplified pictorial illustration of a selectable driving assembly which forms part of the automatic injection device of FIG. 91.

Reference is now made to FIG. 95, which is a simplified pictorial illustration of a preferred selectable driving assembly 4030, which forms part of the automatic injection device of FIG. 91, to FIGS. 96A and 96B, which are respective top and side view simplified planar illustrations of the selectable driving assembly and to FIGS. 97A, 97B and 97C, which are sectional illustrations taken along respective section lines and directions XCVIIA-XCVIIA, XCVIIB-XCVIIB and XCVIIC-XCVIIC in FIGS. 96A and 96B.

As seen in FIGS. 95-97C, the selectable driving element 4031 preferably is an integrally formed element, preferably injection molded of plastic and preferably has a generally cylindrical configuration including a generally tubular portion 4310, having an open back and having a pair of side-to-side symmetric actuation arms 4312 which extend forwardly of tubular portion 4310 parallel to a longitudinal axis 4320, which when selectable driving assembly 4030 is assembled with the rear housing element 4010, is coaxial with longitudinal axis 4120 (FIGS. 92-94C). A top engagement arm 4322 also extends forwardly of tubular portion 4310. A narrowed tubular neck portion 4324 is formed forwardly of tubular portion 4310. Elastomeric elements 4032 and 4034, seated in side recesses 4326 and 4328 in the selectable driving element 4031, are located symmetrically at the junction of the tubular portion 4310 and the neck portion 4324.

Each of actuation arms 4312 has a generally curved cross section and includes a rearwardly facing first finger 4330 terminating in an outwardly extending protrusion 4332 and an inwardly extending protrusion 4333 having a serrated edge 4334 and a second rearwardly extending finger 4338 having formed thereon, adjacent an extreme outward end thereof, an inwardly facing generally triangular tooth 4342 having a forwardly facing inclined surface 4344 and a rearwardly facing engagement surface 4346 extending generally perpendicular to longitudinal axis 4320. Separated from tooth 4342 by a notch 4347 is an inwardly facing rounded tooth 4348. Additionally, second finger 4338 has formed thereon top and bottom protrusions 4349.

Top engagement arm 4322 terminates in an outwardly facing protrusion 4350 having an inclined forward facing surface 4351. Rearwardly of protrusion 4350 and separated therefrom by an outwardly facing notch 4352 is an outwardly facing protrusion 4354, having an inclined outwardly facing surface 4356. Plunger 4040, as seen in FIG. 91 is a generally circularly symmetric element, which is preferably formed in an overall ribbed configuration, as shown. Plunger 4040 includes a rear portion 4402 having a relatively large circular cross section which tapers forwardly to a neck portion 4404, having a relatively small circular cross section. Neck portion 4404 has serrated edges herein referenced by numeral 4405. Serrated edges 4405 of plunger 4040 are adapted to engage serrated edge 4334 of inwardly extending protrusion 4333 of first finger 4330. Forwardly of neck portion 4404 is an intermediate portion 4406, whose circular cross section is typically the same as that of rear portion 4402, and a forward portion 4408, whose circular cross section is typically the same as that of neck portion 4404. Plunger 4040 terminates at its forward end in a male threaded protrusion 4410 adapted to fit a corresponding female threaded socket formed in a piston described hereinbelow with reference to FIG. 106A which is movably located in pre-filled syringe 4050. Plunger 4040 is preferably symmetrically disposed about a longitudinal axis 4420, which when assembled together with selectable driving assembly 4030 and rear housing element 4010, is coaxial with longitudinal axes 4120 (FIGS. 92-94C) and 4320 (FIGS. 95-97C).

As seen in FIG. 91, pre-filled syringe 4050 includes a rear flange 4502 which engages notches 4347 formed in respective second fingers 4338 of each of side-to-side symmetric actuation arms 4312 of selectable driving assembly 4030 (FIGS. 95-97C).

Figure 98:
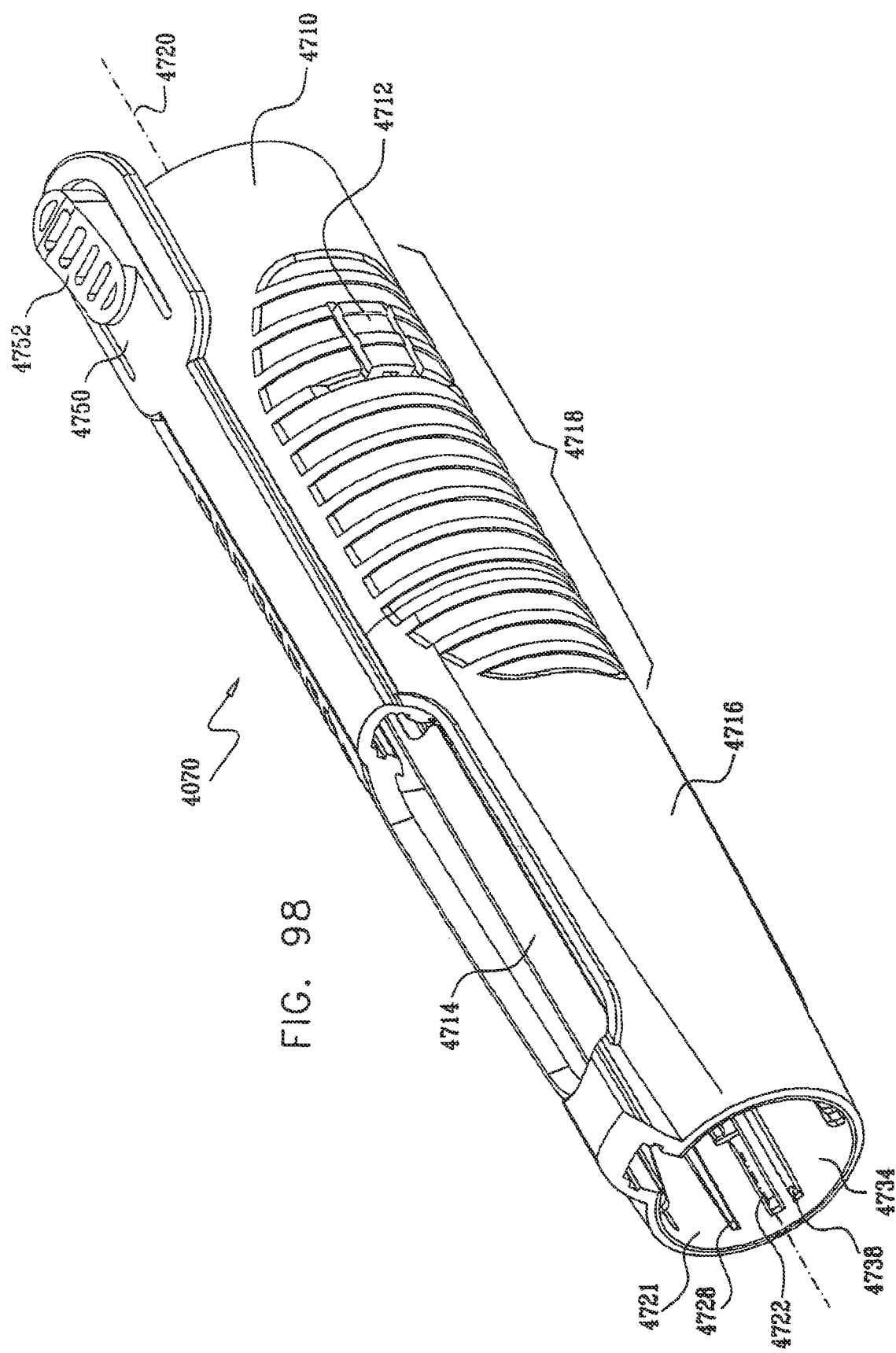
FIG. 98 is a simplified pictorial illustration of a forward housing and actuator element which forms part of the automatic injection device of FIG. 91.
Figure 99A:
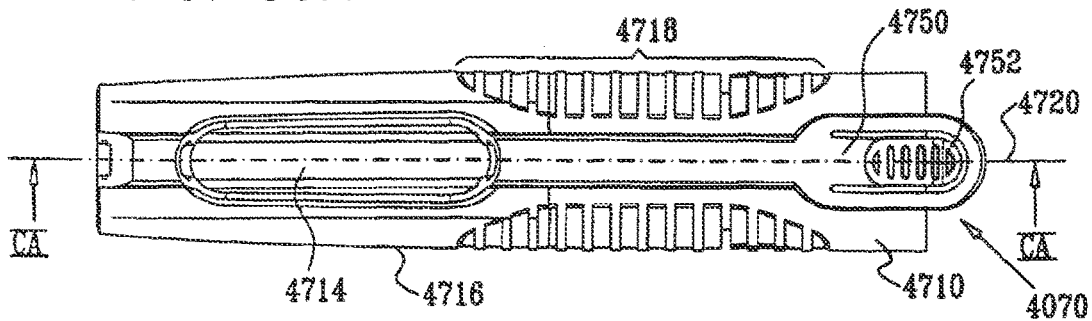
FIGS. 99A and 99B are respective top and side view simplified planar illustrations of the forward housing and actuator element of FIG. 98.
Figure 99B:
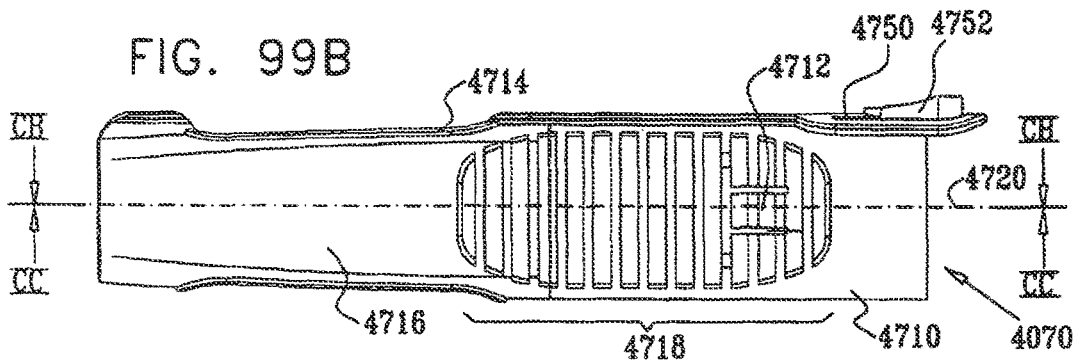
Figure 100A:
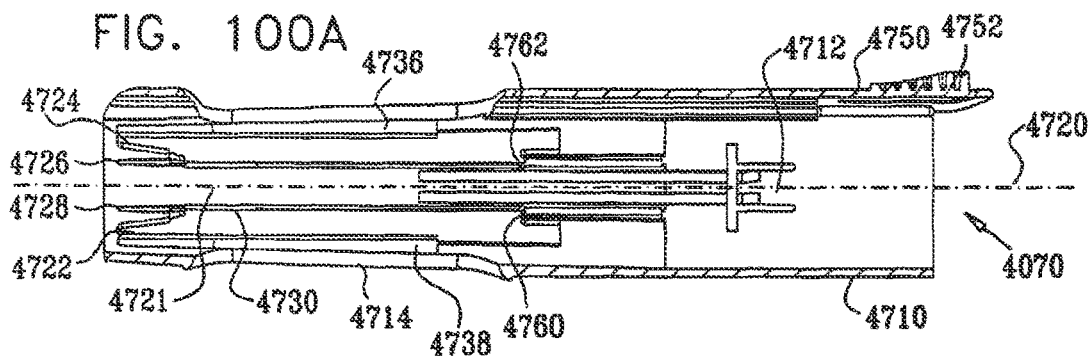
FIGS. 100A, 100B and 100C are sectional illustrations taken along respective section lines and directions CA-CA, CB-CB and CC-CC in FIGS. 99A and 99B.
Figure 100B:
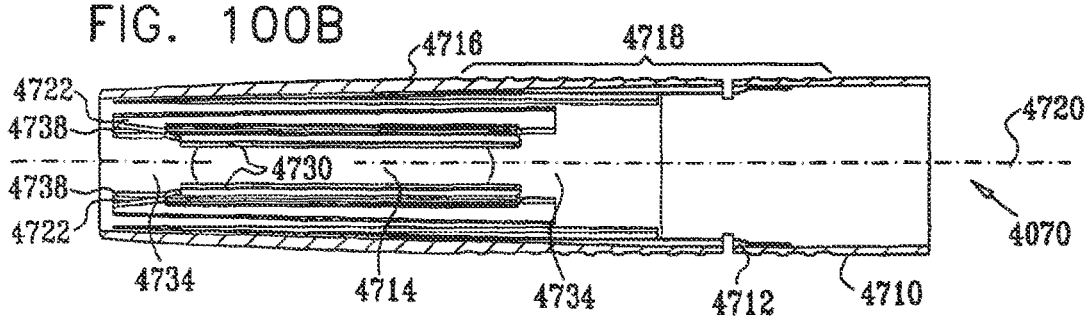
Figure 100C:
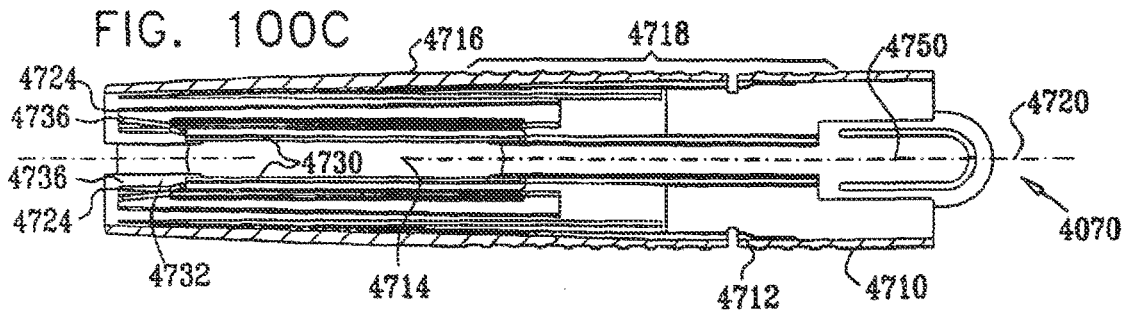

Reference is now made to FIG. 98, which is a simplified pictorial illustration of forward housing and actuator element 4070 which forms part of the automatic injection device of FIG. 91, to FIGS. 99A and 99B, which are respective top and side view simplified planar illustrations thereof and to FIGS. 100A, 100B and 100C, which are sectional illustrations taken along respective section lines and directions CA-CA, CB-CB and CC-CC in FIGS. 99A and 99B.

As seen in FIGS. 98-100C, the forward housing and actuator element 4070 preferably is an integrally formed element, preferably injection molded of plastic and preferably has a generally truncated conical configuration arranged along a longitudinal axis 4720, which when the automatic injection device is assembled, is coaxial with longitudinal axes 4120 (FIGS. 92-94C), 4320 (FIGS. 95-97C) and 4420 (FIG. 91). Forward housing and actuator element 4070 includes a generally tubular rear portion 4710, having an open back and formed with a pair of side-to-side symmetric snap fit engagement sockets 4712 which receive the protrusions 4126 of the rear housing element 4010 during factory assembly of the automatic injection device.

Forward of tubular rear portion 4710 are formed a pair of top-bottom symmetric windows 4714, which allow the pre-filled syringe to be viewed, when the automatic injection device is assembled, including during use thereof.

A pair of outer side surfaces 4716 of forward housing and actuator element 4070 are each formed with ribbed grip regions 4718. Corresponding inner side surfaces 4721 each define a plurality of longitudinally extending ribs 4722, 4724, 4726 and 4728 which are used to slidably guide the needle guard 4080 during axial movement thereof as well as inner facing protrusions 4730, which together with ribs 4722 and 4724 define a forward facing spring seat for spring 4090 (FIG. 91). Inner facing protrusions 4730 are operative to slidably support pre-filled syringe 4050 and to slidably guide actuation arms 4312 of selectable driving assembly 4030.

Inner top and bottom surfaces 4732 and 4734 define respective pairs of ribs 4736 and 4738 which are operative to slidably guide the needle guard 4080 during axial movement thereof. A cantilevered rearwardly extending actuation lever 4750 extends from a location rearward of top window 4714 and defines, at an extreme rearward top facing surface thereof, an actuation button 4752.

As best seen in FIG. 100A, inner facing protrusions 4730 define at rearward facing portions thereof protrusions 4760 and 4762 which form a stopping point for flange 4502, thus limiting the forward movement of the pre-filled syringe 4050.

Figure 101:
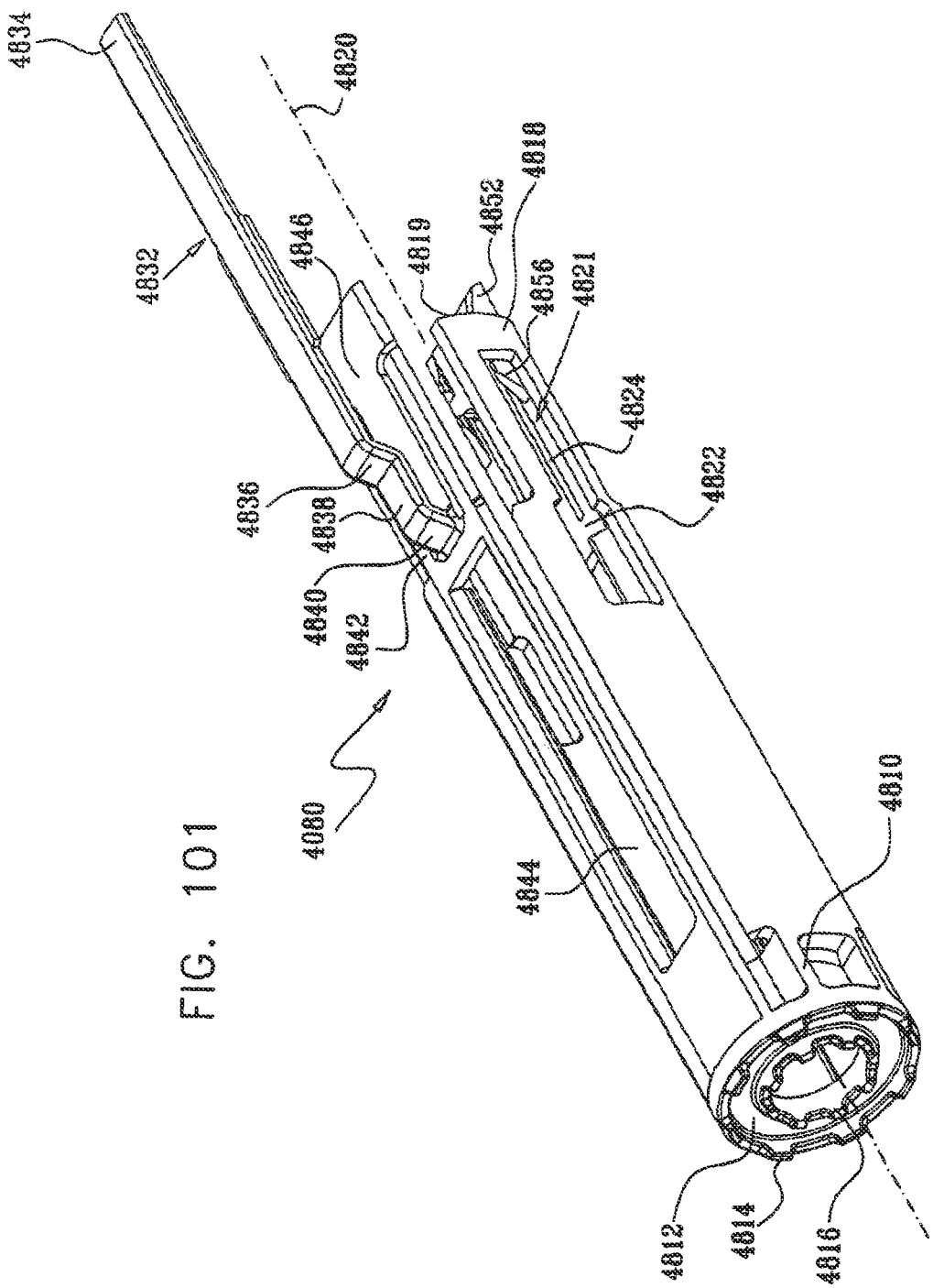
FIG. 101 is a simplified pictorial illustration of a needle guard element which forms part of the automatic injection device of FIG. 91.
Figure 102A:
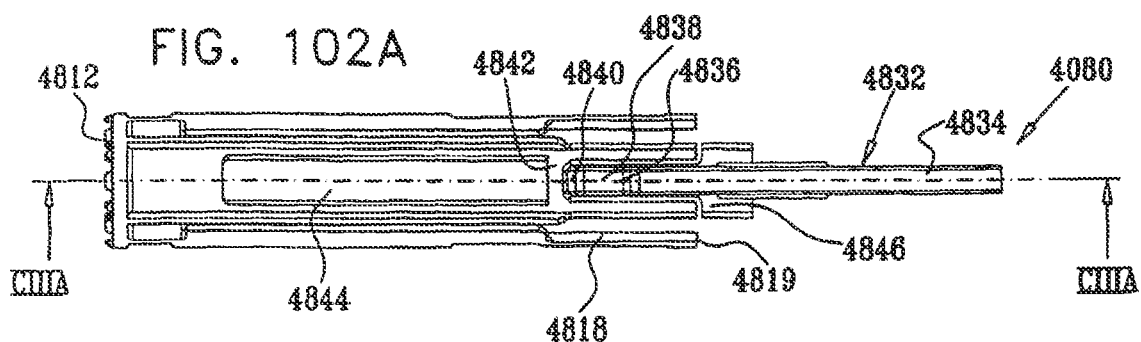
FIGS. 102A and 102B are respective top and side view simplified planar illustrations of the needle guard element of FIG. 101.
Figure 102B:
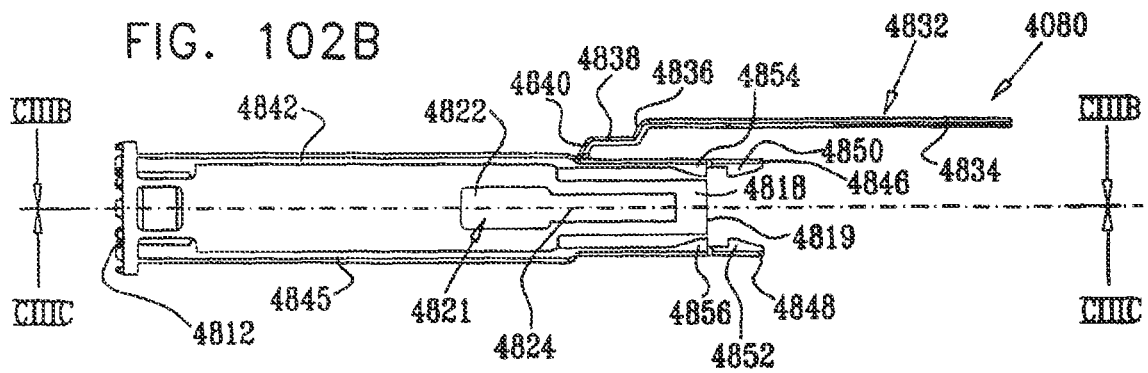
Figure 103A:
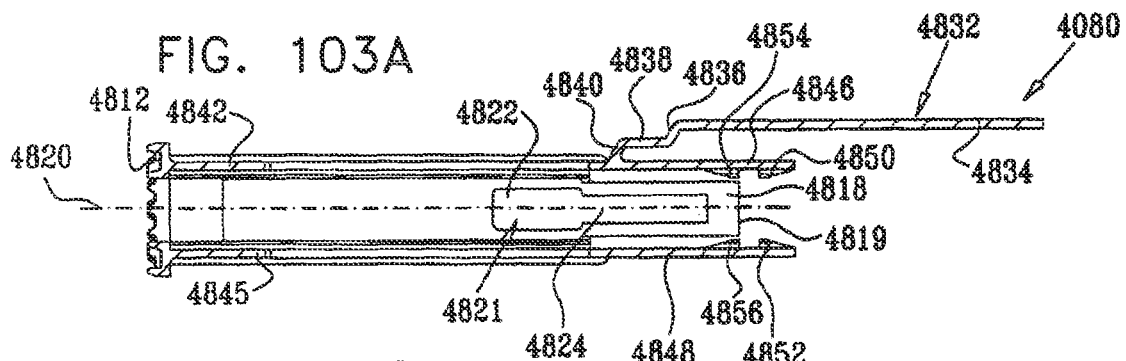
FIGS. 103A, 103B and 103C are sectional illustrations taken along respective section lines and directions CIIIA-CIIIA, CIIIB-CIIIB and CIIIC-CIIIC in FIGS. 102A and 102B.
Figure 103B:
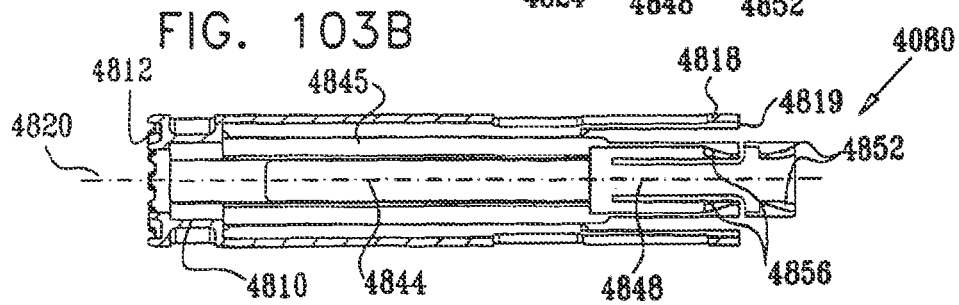
Figure 103C:
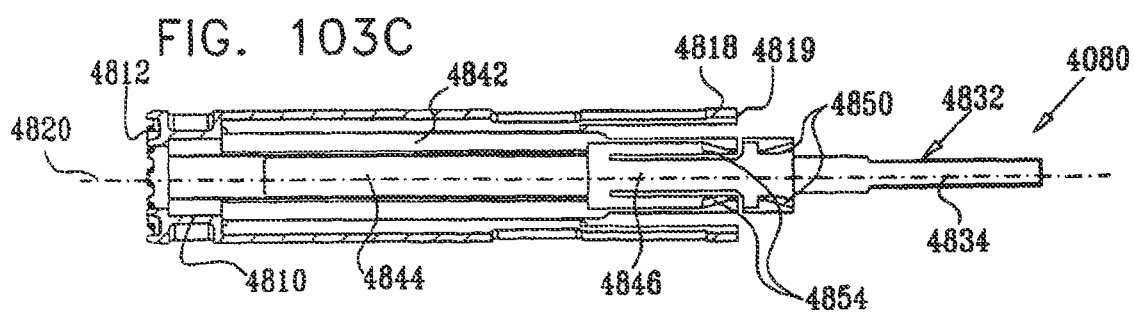

Reference is now made to FIG. 101, which is a simplified pictorial illustration of a needle guard element 4080 which forms part of the automatic injection device of FIG. 91, to FIGS. 102A and 102B, which are respective top and side view simplified planar illustrations thereof and to FIGS. 103A, 103B and 103C, which are sectional illustrations taken along respective section lines and directions CIIIA-CIIIA, CIIIB-CIIIB and CIIIC-CIIIC in FIGS. 102A and 102B.

As seen in FIGS. 101-103C, the needle guard element 4080 preferably is an integrally formed element, preferably injection molded of plastic and preferably has a generally cylindrical configuration including a generally tubular portion 4810, having a forward facing body engaging surface 4812 including a pair of concentric ribbed circumferential forward facing rings 4814 and 4816. The internal surface, located opposite from body engaging surface 4812, forms a spring-seat for spring 4090.

Needle guard element 4080 has a pair of side-to-side symmetric mounting arms 4818 having rearwardmost ends 4819, arranged symmetrically about a longitudinal axis 4820. Each of arms 4818 is formed with a rectangular window 4821 having a relatively wider forward portion 4822 and a relatively narrower rear portion 4824. Arms 4818 extend along and rearwardly of tubular portion 4810 parallel to longitudinal axis 4820, which when the automatic injection device is assembled, is coaxial with longitudinal axes 4120 (FIGS. 92-94C), 4320 (FIGS. 95-97C), 4420 (FIG. 91) and 4720 (FIGS. 98-100C).

A top engagement arm 4832 also extends rearwardly of tubular portion 4810 and includes a rearwardmost axial portion 4834, an inclined intermediate portion 4836, an axial intermediate portion 4838 and an inclined mounting portion 4840, which extends from a top mounting arm 4842, formed with an elongate window 4844. An equivalent elongate window, also referenced by numeral 4844, is formed on a bottom mounting arm 4845. Elongate windows 4844 and top-bottom symmetric windows 4714 of forward housing and actuator element 4070 are positioned in respective parallel locations, such that pre-filled syringe 4050 is visible through the windows.

Top and bottom engagement portions 4846 and 4848 are each formed with backward inwardly directed teeth, here designated by reference numerals 4850 and 4852 respectively, and with forward inwardly directed teeth, here designated by reference numerals 4854 and 4856 respectively.

Reference is now made to FIG. 104, which is a simplified assembled view illustration of the automatic injection device of FIG. 91 in a pre-use operative orientation, to FIGS. 105A and 105B, which are respective top and side view simplified planar illustrations thereof and to FIGS. 106A and 106B, which are sectional illustrations taken along respective section lines and directions CVIA-CVIA and CVIB-CVIB in FIGS. 105A and 105B.

As seen in FIGS. 104-106B, in a pre-use operative orientation of the automatic injection device which is suitable for storage, the rear housing element 4010 is joined to the forward housing and actuator element 4070 by snap fit engagement of protrusions 4126 of rear housing element 4010 in the engagement sockets 4712 formed in the forward housing and actuator element 4070.

Selectable driving assembly 4030 is retained in its axial position by engagement of inward facing protrusion 4130 (FIG. 94A) with outwardly facing notch 4352 of top engagement arm 4322 (FIG. 97A) of selectable driving assembly 4030. In this arrangement, spring 4020 is in a relatively compressed state and is held in that state by pressure from the selectable driving assembly.

The rearwardmost axial portion 4834 of the top engagement arm 4832 of the needle guard 4080 (FIGS. 91-93C) is in a relatively forward position, only partially underlying actuation button 4752 of forward housing and actuator element 4070 (FIGS. 98-100C). Additionally, inward displacement of actuation button 4752 is limited by ribs 4128 (FIGS. 92-94C), thus ensuring that actuation button 4752 does not directly engage protrusion 4350 of engagement arm 4322. Accordingly, in this orientation of the needle guard 4080, inadvertent pressing of button 4752 does not actuate the automatic injection device.

The pre-filled syringe 4050 is retained in a retracted orientation by engagement of flange 4502 thereof with notches 4347 formed in respective second fingers 4338 of each of side-to-side symmetric actuation arms 4312 of selectable driving assembly 4030 (FIGS. 95-97C).

Needle guard 4080 is retained in its axial position, and is prevented from moving forward by engagement of forward inwardly directed teeth 4854 and 4856 with the flange 4502 of the pre-filled syringe 4050. Forward inwardly directed teeth 4854 and 4856 are supported by ribs 4132 formed on surface 4131 and ribs formed on an inner surface of shaft portion 4127 of the rear housing element (FIGS. 92-94C) and thus are prevented from bending outward and disengaging from flange 4502.

Figure 107:
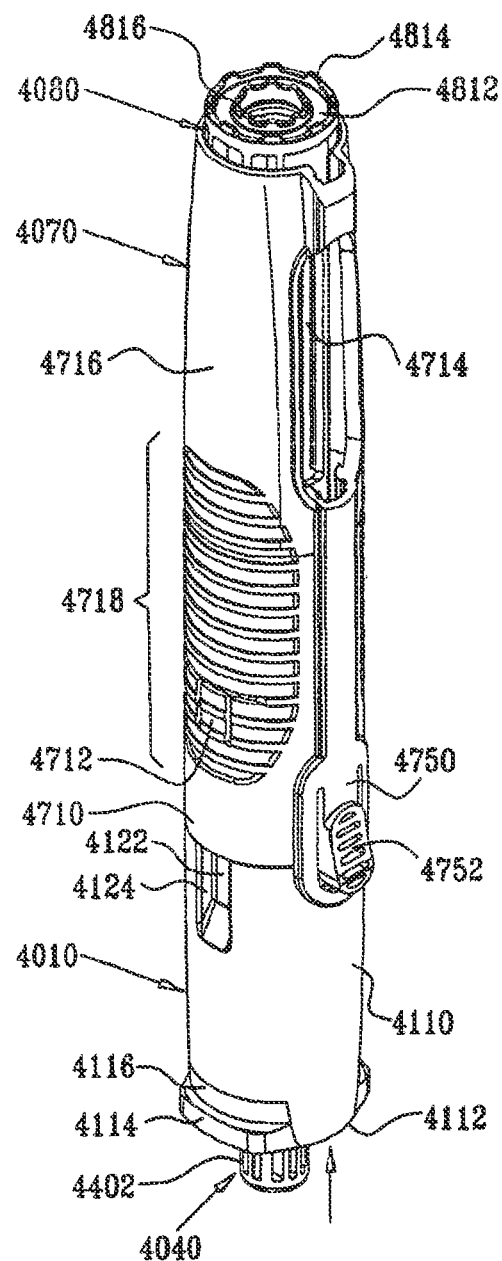
FIG. 107 is a simplified pictorial illustration of the automatic injection device of FIG. 91 in an optional titration operative orientation.

Reference is now made to FIG. 107, which is a simplified pictorial illustration of the automatic injection device of FIG. 91 in an optional titration operative orientation, to FIGS. 108A and 108B, which are respective top and side view simplified planar illustrations thereof and to FIGS. 109A and 109B, which are sectional illustrations taken along respective section lines and directions CIXA-CIXA and CIXB-CIXB in FIGS. 108A and 108B.

In an optional titration step, after the protective needle cover 4062 has been removed and while the needle guard 4080 points upwards a user may push rear portion 4402 of plunger 4040 forwardly as the syringe 4050 is retained in place. This forces air bubbles and/or liquid out of the syringe via the needle 4060. At this stage, protrusions 4349 formed on second fingers 4338 (FIGS. 95-97C) engage the defining walls of narrower rear portion 4824 of rectangular window 4821, thus limiting the third fingers 4338 from bending outward and therefore flange 4502 continues to engage notches 4347 thus inhibiting premature movement of syringe 4050. It is appreciated that except for the forward movement of the plunger 4040, the remainder of the operative orientation of the automatic injection device remains identical to the pre-use operative orientation.

Figure 110:
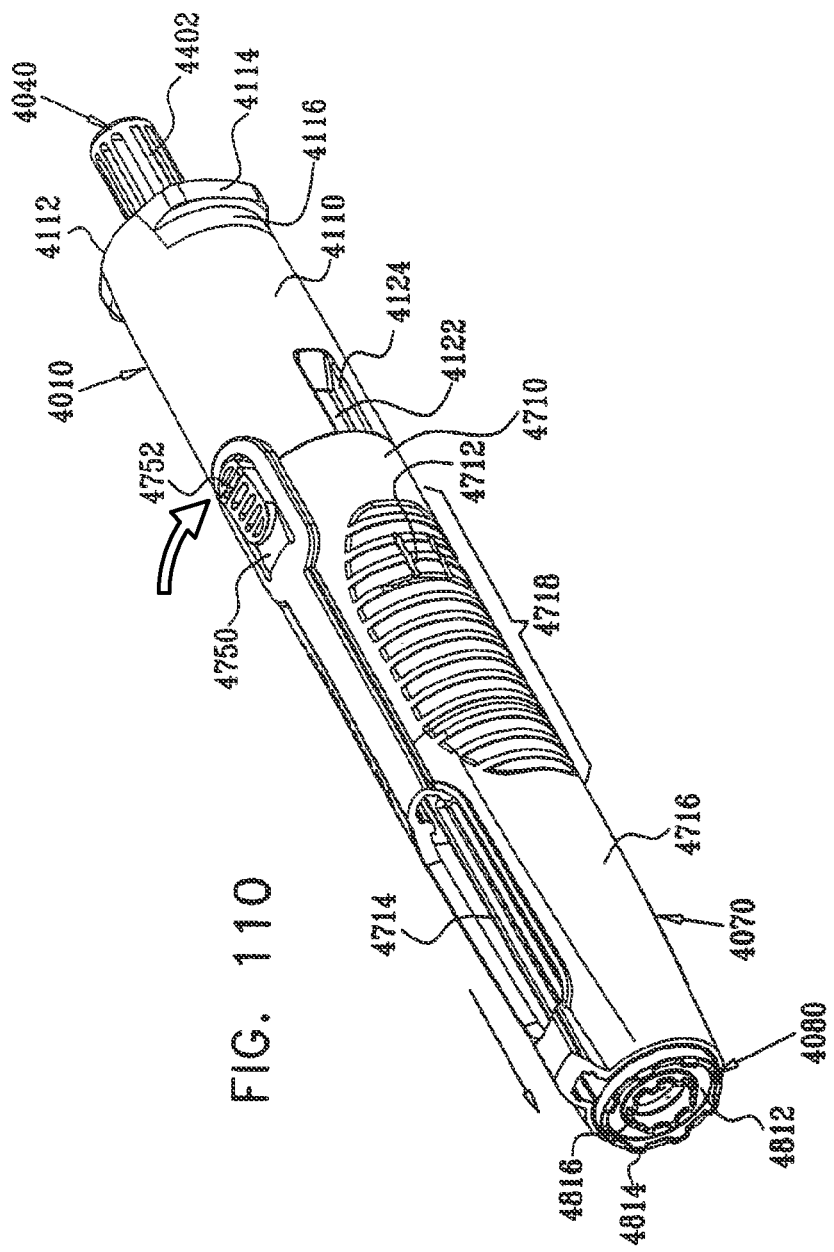
FIG. 110 is a simplified pictorial illustration of the automatic injection device of FIG. 91 in an actuated operative orientation.
Figure 111A:
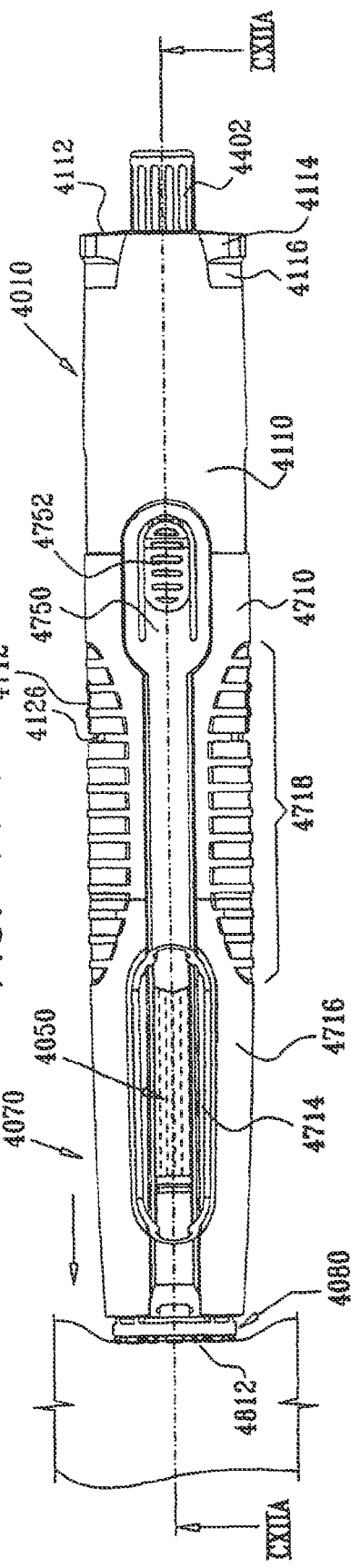
FIGS. 111A and 111B are respective top and side view simplified planar illustrations of the automatic injection device of FIG. 110.
Figure 111B:
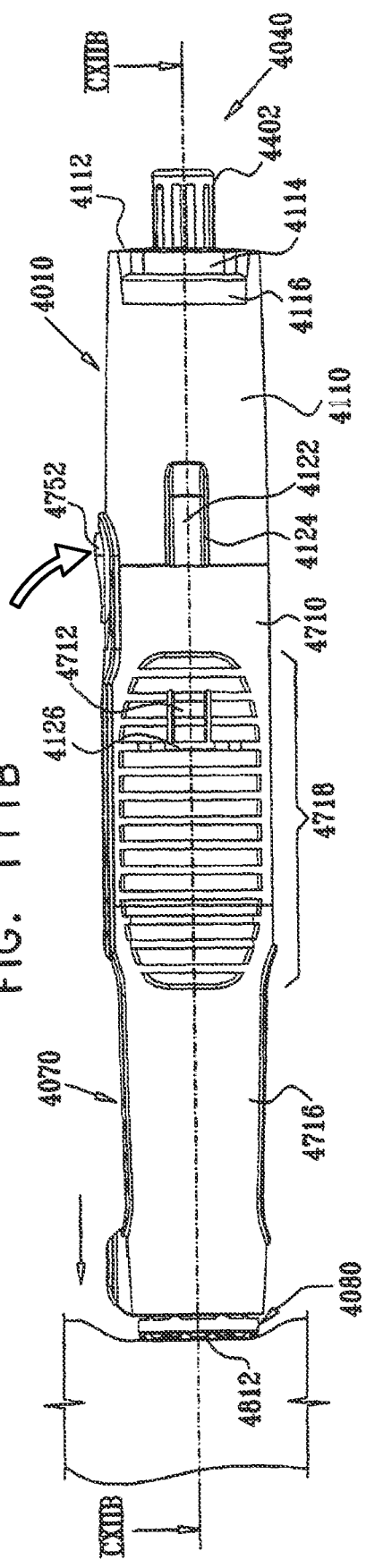

Reference is now made to FIG. 110, which is a simplified pictorial illustration of the automatic injection device of FIG. 91 in an actuated operative orientation, to FIGS. 111A and 111B which are respective top and side view simplified planar illustrations thereof and to FIGS. 112A and 112B which are sectional illustrations taken along respective section lines and directions CXIIA-CXIIA and CXIIB-CXIIB in FIGS. 111A and 111B.

As seen particularly in the enlarged portion of FIG. 112A, due to engagement of the needle guard 4080 with an injection site on a body, the needle guard 4080 is forced to move axially in a rearward direction with respect to the remainder of the automatic injection device, thus compressing spring 4090 and causing the rearwardmost axial portion 4834 of the top engagement arm 4832 of the needle guard 4080 (FIGS. 101-103C) to assume a relatively rearward position, generally underlying actuation button 4752 of forward housing and actuator element 4070 (FIGS. 98-100C). The rearward motion of the needle guard 4080 is limited by engagement of rearwardmost ends 4819 of arms 4818 of the needle guard and the rear edge of the window formed in front of outward facing protrusion 4126 of rear housing element 4010 (FIG. 112B).

In this orientation of the needle guard 4080, pressing of button 4752 does actuate the automatic injection device, by causing portion 4834 to engage protrusion 4350, thus disengaging notch 4352 from protrusion 4130 (FIG. 94A) and thus disengaging engagement arm 4322 from the rear housing element 4010 and permitting forward axial movement of the selectable driving assembly 4030 under the urging of spring 4020.

Figure 113:
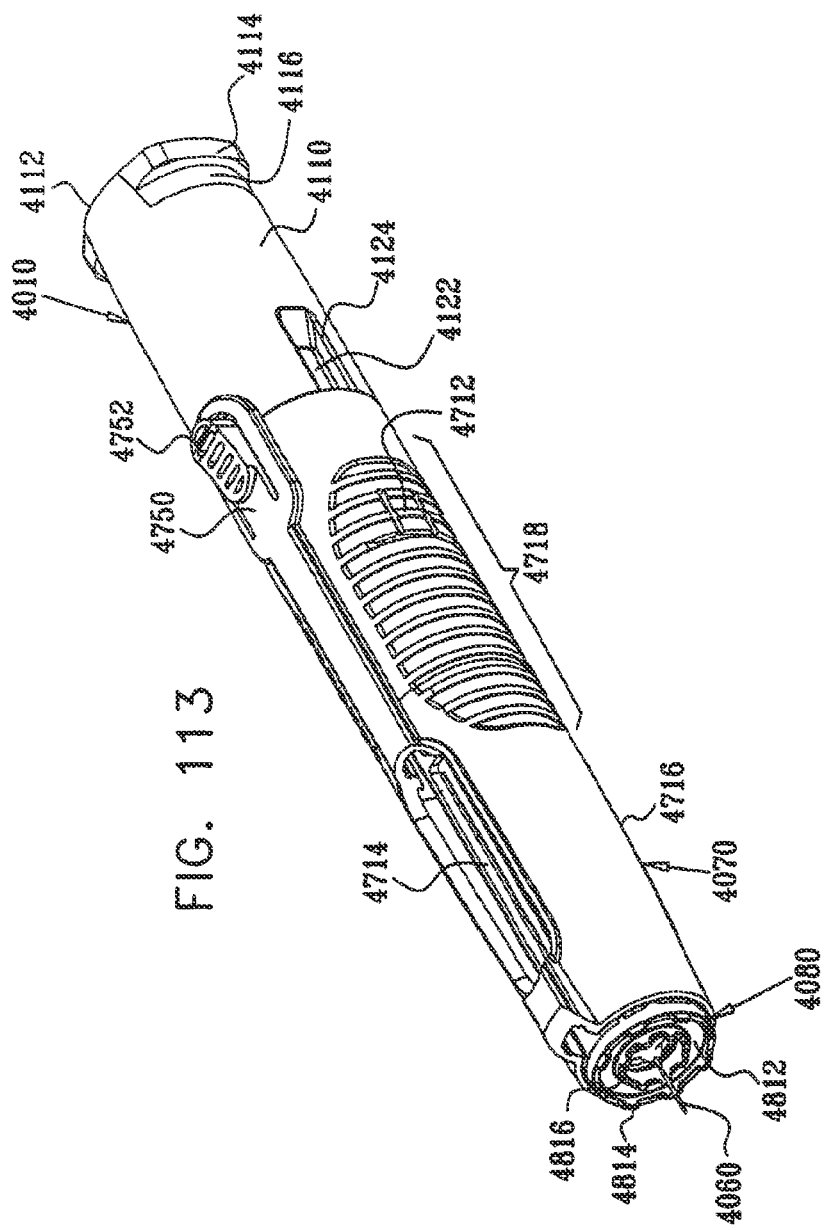
FIG. 113 is a simplified pictorial illustration of the automatic injection device of FIG. 91 in a needle penetration, pre-drug delivery operative orientation.

Reference is now made to FIG. 113, which is a simplified pictorial illustration of the automatic injection device of FIG. 91 in a needle penetration, pre-drug delivery operative orientation, to FIGS. 114A and 114B, which are respective top and side view simplified planar illustrations thereof and to FIGS. 115A and 115B, which are sectional illustrations taken along respective section lines and directions CXVA-CXVA and CXVB-CXVB in FIGS. 114A and 114B.

FIGS. 113-115B illustrate an initial stage in the forward motion of the selectable driving assembly 4030 under the urging of spring 4020 following user actuation of button 4752. Immediately following user actuation of button 4752, serrated edges 4334 of inwardly extending protrusions 4333 of first fingers 4330 engage serrated edges 4405 of plunger 4040. The engagement point of serrated edges 4334 on serrated edges 4405 is dependent on the position of plunger 4040, which in turn is dependent on the possible performance of titration prior to user actuation of the automatic injection device.

The axial forward motion of the selectable driving assembly 4030 produces equivalent axial forward motion of the syringe 4050, due to engagement of flange 4502 in notches 4347 formed in respective second fingers 4338 of each of side-to-side symmetric actuation arms 4312 of selectable driving assembly 4030 (FIGS. 95-97C).

This forward motion results in forward motion of the needle 4060 and needle penetration at the injection site as shown. The forward motion of syringe 4050 and needle penetration stops as flange 4502 reaches protrusions 4760 and 4762 of forward housing and actuator element 4070. The forward motion of the selectable driving assembly 4030 causes the outwardly extending protrusion 4332 to engage forwardly pointed protrusion 4142 of side interior surface 140, thus bending the first finger 4330 inwards. During needle penetration, elastomeric elements 4032 and 4034 engage forwardly pointed protrusion 4142 causing friction therebetween, thus compensating for the force of spring 4020 and resulting in damping of the needle movement and absorbance of the shock applied by protrusions 4760 and 4762 on the flange 4502. As will be described hereinbelow, drug delivery follows needle penetration.

Figure 116:
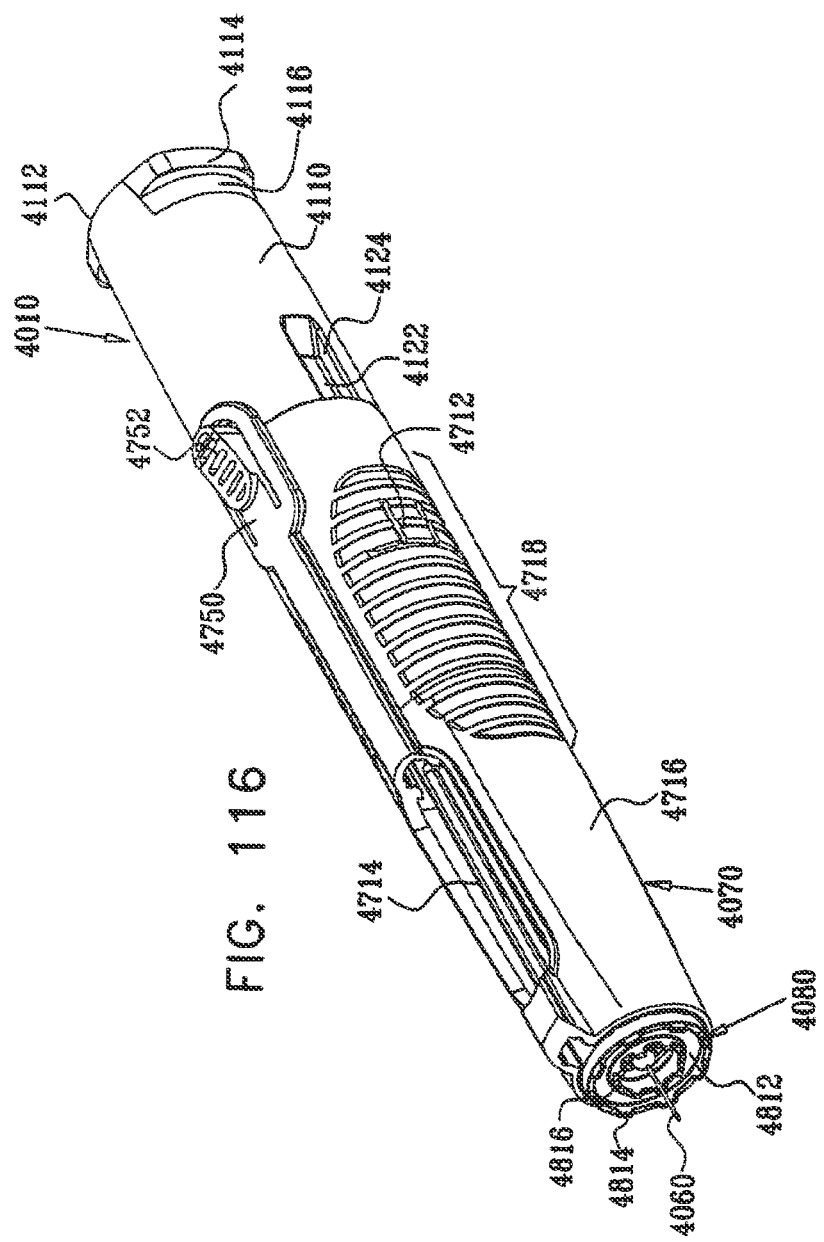
FIG. 116 is a simplified pictorial illustration of the automatic injection device of FIG. 91 in drug delivery operational orientation.

Reference is now made to FIG. 116, which is a simplified pictorial illustration of the automatic injection device of FIG. 91 in drug delivery operational orientation, to FIGS. 117A and 117B which are respective top and side view simplified planar illustrations thereof and to FIGS. 118A and 118B, which are sectional illustrations taken along respective section lines and directions CXVIIIA-CXVIIIA and CXVIIIB-CXVIIIB in FIGS. 117A and 117B.

FIGS. 116-118B illustrate a further stage in the forward motion of the selectable driving assembly under the urging of spring 4020 following user actuation of button 4752. It is seen that the axial forward motion of the selectable driving assembly 4030 does not produce equivalent axial forward motion of the syringe 4050, due to engagement of flange 4502 of syringe 4050 with protrusions 4760 and 4762 of ribs of the forward housing and actuator element 4070 (FIG. 100A).

Continued urging of spring 4020 and the selectable driving assembly 4030 causes protrusions 4349 formed on second fingers 4338 (FIGS. 95-97C) to disengage the defining walls of narrower rear portion 4824 of rectangular window 4821, and bend outward into the space formed by the wider forward portion 4822 of the rectangular window (FIGS. 101-103C), resulting in disengagement of flange 4502 and notches 4347 formed in respective second fingers 4338 of each of side-to-side symmetric actuation arms 4312 of selectable driving assembly 4030 (FIGS. 95-97C).

The disengagement of flange 4502 from notches 4347 and the engagement of serrated edges 4334 of inwardly extending protrusions 4333 and serrated edges 4405 cause plunger 4040 to continue its forward motion together with piston 4501, which is threaded thereto.

Forward motion of piston 4501 forces the drug out of syringe 4050 through needle 4060 into the injection site. During drug delivery, the forward motion of the piston 4501 is governed by friction between elastomeric elements 4032 and 4034 and forwardly pointed protrusion 4142 of side interior surface 140. The amount of friction may be selected by appropriately shaping the forwardly pointed protrusion and the elastomeric elements 4032 and 4034.

The forwardly pointed shape of protrusions 4142 causes a reduction in friction as selectable driving assembly 4030 advances, which compensates for the reduction of the force applied by spring 4020 as it extends. Friction between the protrusion and elastomeric elements 4032 and 4034 also damps shock resulting from movement of the selectable driving element 4030 which is transferred by the engagement of serrated edges 4334 of inwardly extending protrusion 4333 and serrated edges 4405 of plunger 4040, and is then transferred to flange 4502 of the pre-filled syringe 4050, and may help control the drug injection rate.

Figure 119:
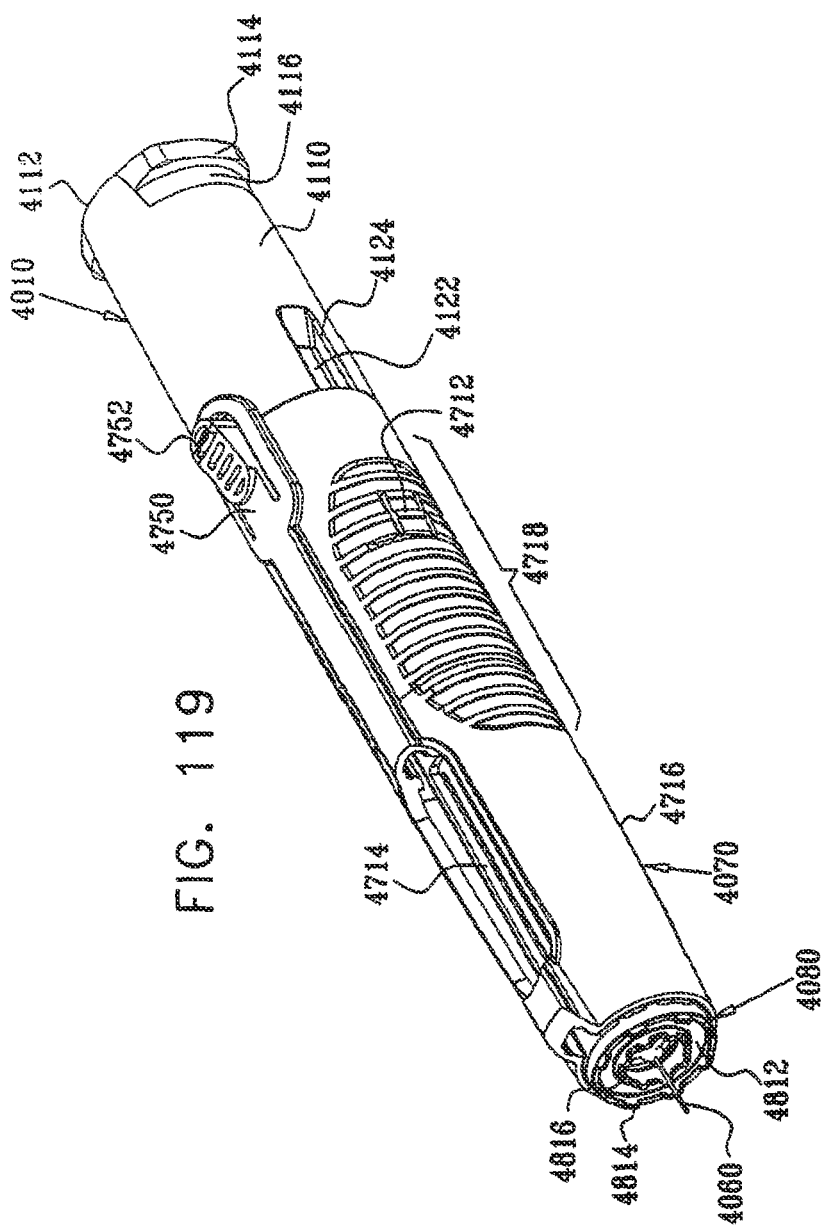
Figure 120A:
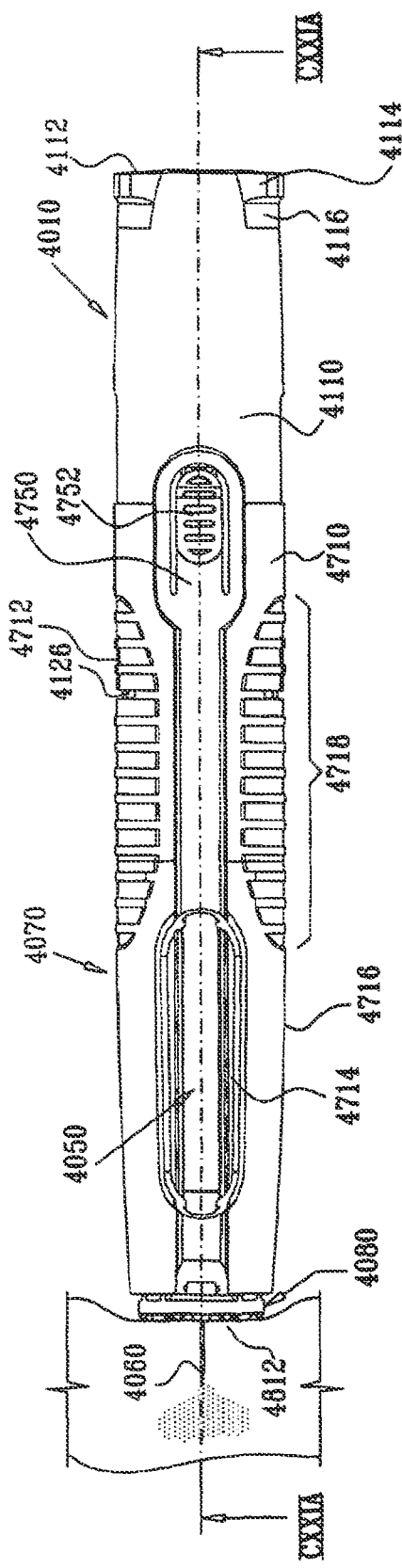
Figure 120B:
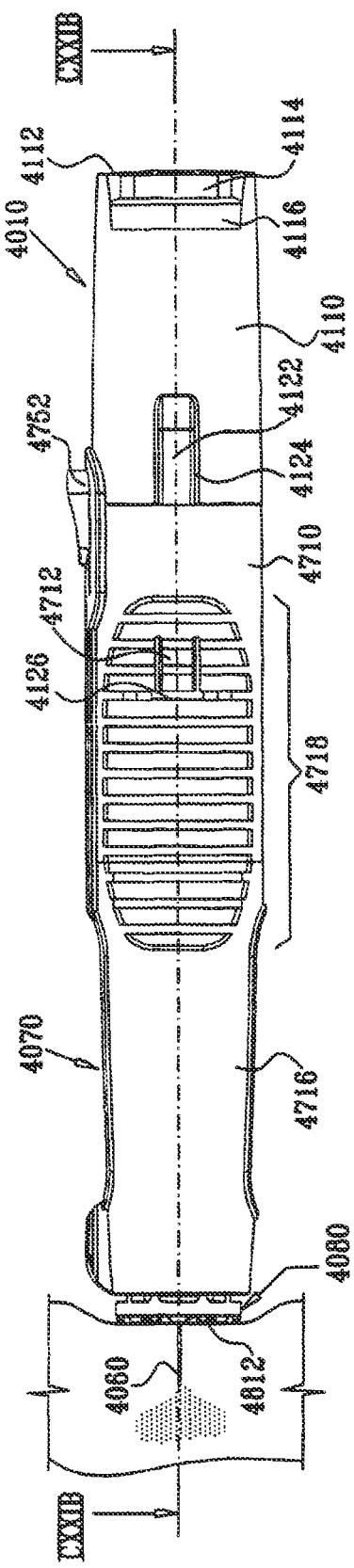

Reference is now made to FIG. 119, which is a simplified pictorial illustration of the automatic injection device of FIG. 91 in an immediate post-drug delivery operational orientation, to FIGS. 120A and 120B, which are respective top and side view simplified planar illustrations thereof and to FIGS. 121A and 121B, which are sectional illustrations taken along respective section lines and directions CXXIA-CXXIA and CXXIB-CXXIB in FIGS. 120A and 120B.

Prior to this stage, forward motion of piston 4501 in the syringe continued until the piston cannot move forward any more, thus terminating drug delivery. Additionally, serrated edges 4334 of inwardly extending protrusions 4333 are maintained in touching engagement with serrated edges 4405 of plunger 4040 by pressure applied from forwardly pointed protrusion 4142.

Figure 122:
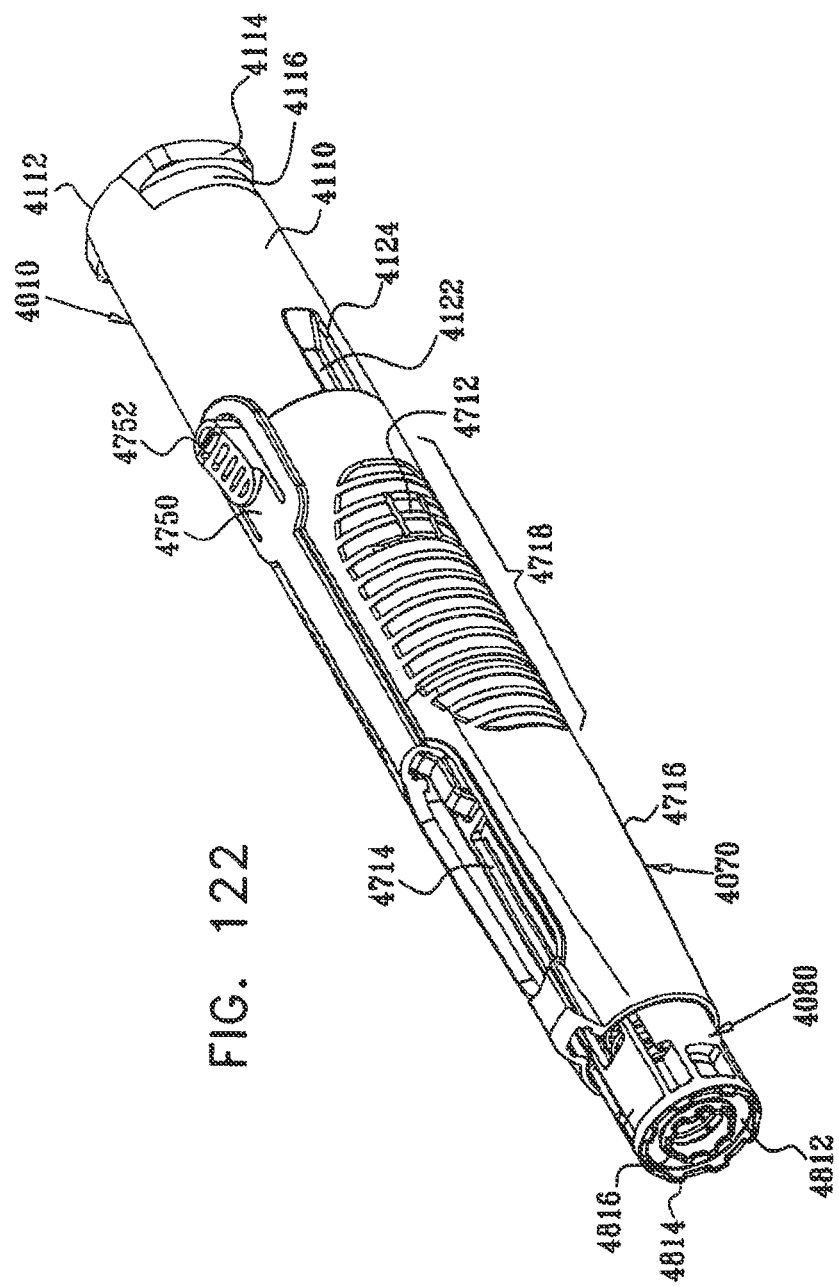
Figures 124A, 124B:
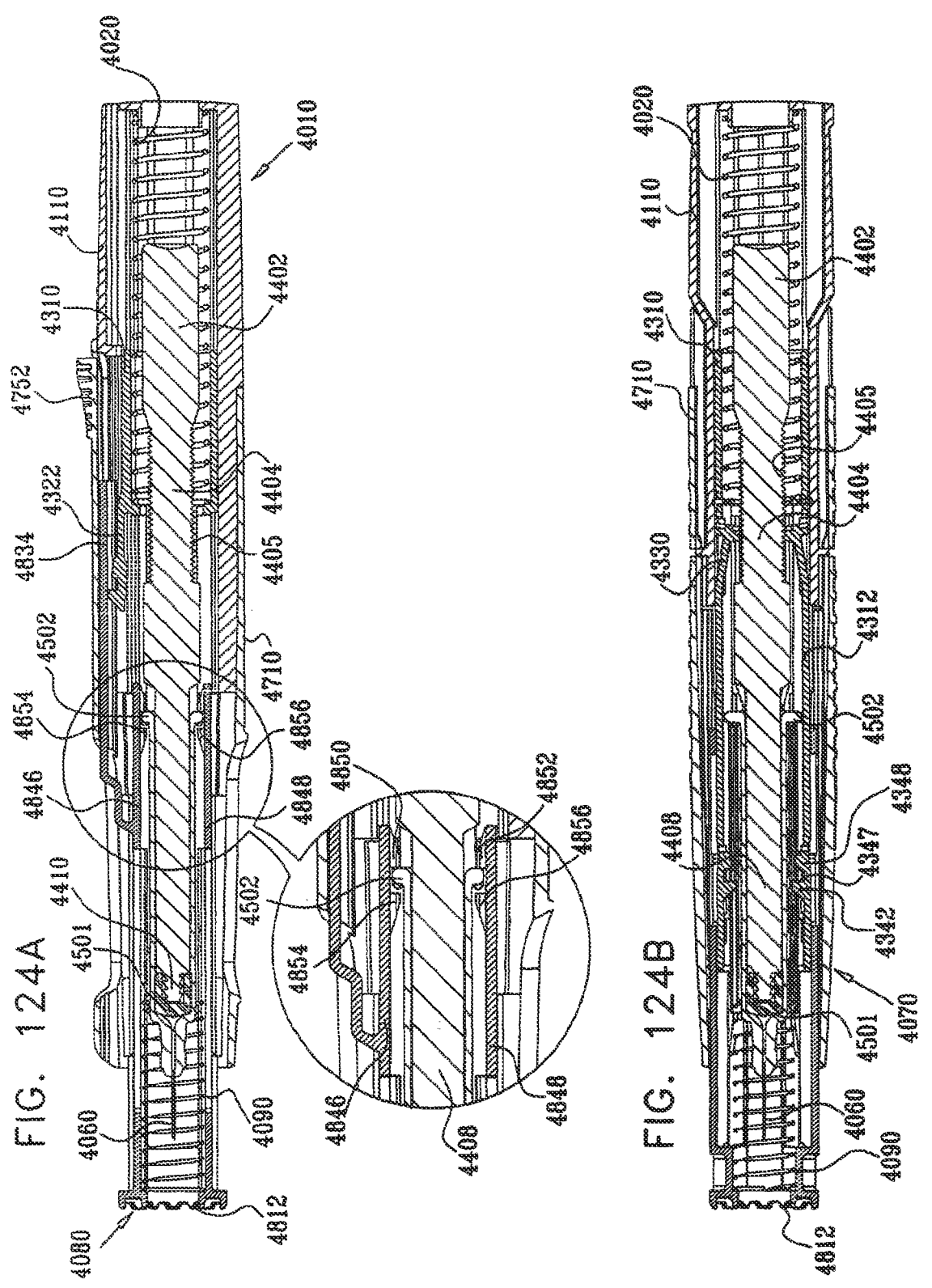

Reference is now made to FIG. 122, which is a simplified pictorial illustration of the automatic injection device of FIG. 91 in a needle protected operational orientation, to FIGS. 123A and 123B which are respective top and side view simplified planar illustrations thereof and to FIGS. 124A and 124B which are sectional illustrations taken along respective section lines and directions CXXIVA-CXXIVA and CXXIVB-CXXIVB in FIGS. 123A and 123B.

At this stage, the automatic injection device is fully disengaged from the injection site and the needle guard 4080 is fully extended to fully enclose the needle 4060, by the force of spring 4090. When the needle guard is fully extended it is locked onto the syringe 4050 by engagement of backward inwardly directed teeth 4850 and 4852 and flange 4502 of the pre-filled syringe 4050, thus inhibiting further movement outwards of the needle guard 4080. In addition, during the forward motion of the needle guard 4080 inwardly directed teeth 4854 and 4856 are released from the support of ribs 4132 formed on surface 4131 and ribs of shaft portions 4127 thus enabling them to bend outwardly and move forward of flange 4502.

Reference is now made to FIG. 125, which is a simplified pictorial illustration of the automatic injection device of FIG. 91 in a needle-guard push back misuse operational orientation, to FIGS. 126A and 126B which are respective top and side view simplified planar illustrations thereof and to FIGS. 127A and 127B which are sectional illustrations taken along respective section lines and directions CXXVIIA-CXXVIIA and CXXVIIB-CXXVIIB in FIGS. 126A and 126B.

FIGS. 125-127B illustrate an important feature of the present invention provided by the locking of forward inwardly directed teeth 4854 and 4856 and the flange 4502 of the pre-filled syringe 4050. Should the needle guard 4080 be pushed rearwardly with respect to the forward housing and actuator element 4070, the forward inwardly directed teeth 4854 and 4856 push against flange 4502 of syringe 4050, thus pushing rearwardly plunger 4040 together with syringe 4050.

Rearward motion of plunger 4040 forces selectable driving assembly 4030 to move rearwardly together with the needle guard, as serrated edges 4334 of inwardly extending protrusions 4333 still engage serrated edges 4405 of neck portion 4404 of plunger 4040. As syringe 4050 and selectable driving assembly 4030 move rearwardly together with needle guard 4080, needle 4060 does not protrude from the needle guard 4080. During this rearward movement, first fingers 4330 cannot bend outward to disengage serrated edges 4334 of inwardly extending protrusions 4333 from serrated edges 4405 of plunger 4040 since the outwardly extending protrusions 4332 of first fingers 4330 are supported by forwardly pointed protrusions 4142 of rear housing element 4010.

Reference is now made to FIGS. 128-140C, which illustrate the constituent elements of yet another automatic injection device constructed and operative in accordance with another preferred embodiment of the present invention.

As seen with particular clarity in FIG. 128, the automatic injection device comprises a rear housing element 5010 in which is seated a main compression spring 5020, which provides selectable forward displacement to a selectable driving assembly 5030, which includes a selectable driving element 5031 and a pair of elastomeric motion damping elements 5032 and 5034, and selectably engages a plunger 5040 and a pre-filled syringe 5050 having a hypodermic needle 5060 which is covered by a needle protection cover 5062. Pre-filled syringe 5050 may be a conventional pre-filled syringe, such as a commercially available syringe sold under the catalog designation BD-Hypak™ or may be any other suitable syringe or cartridge.

Plunger 5040 also operatively engages pre-filled syringe 5050 and is selectably operated by selectable driving assembly 5030 to inject the liquid contents of pre-filled syringe 5050 through hypodermic needle 5060.

The forward portion of rear housing element 5010 as well as spring 5020, selectable driving assembly 5030, plunger 5040 and pre-filled syringe 5050 are located within a forward housing and actuator element 5070. At the forward end of the interior of forward housing and actuator element 5070 there is provided a needle guard element 5080, which is positioned by a compression spring 5090.

Figure 129:
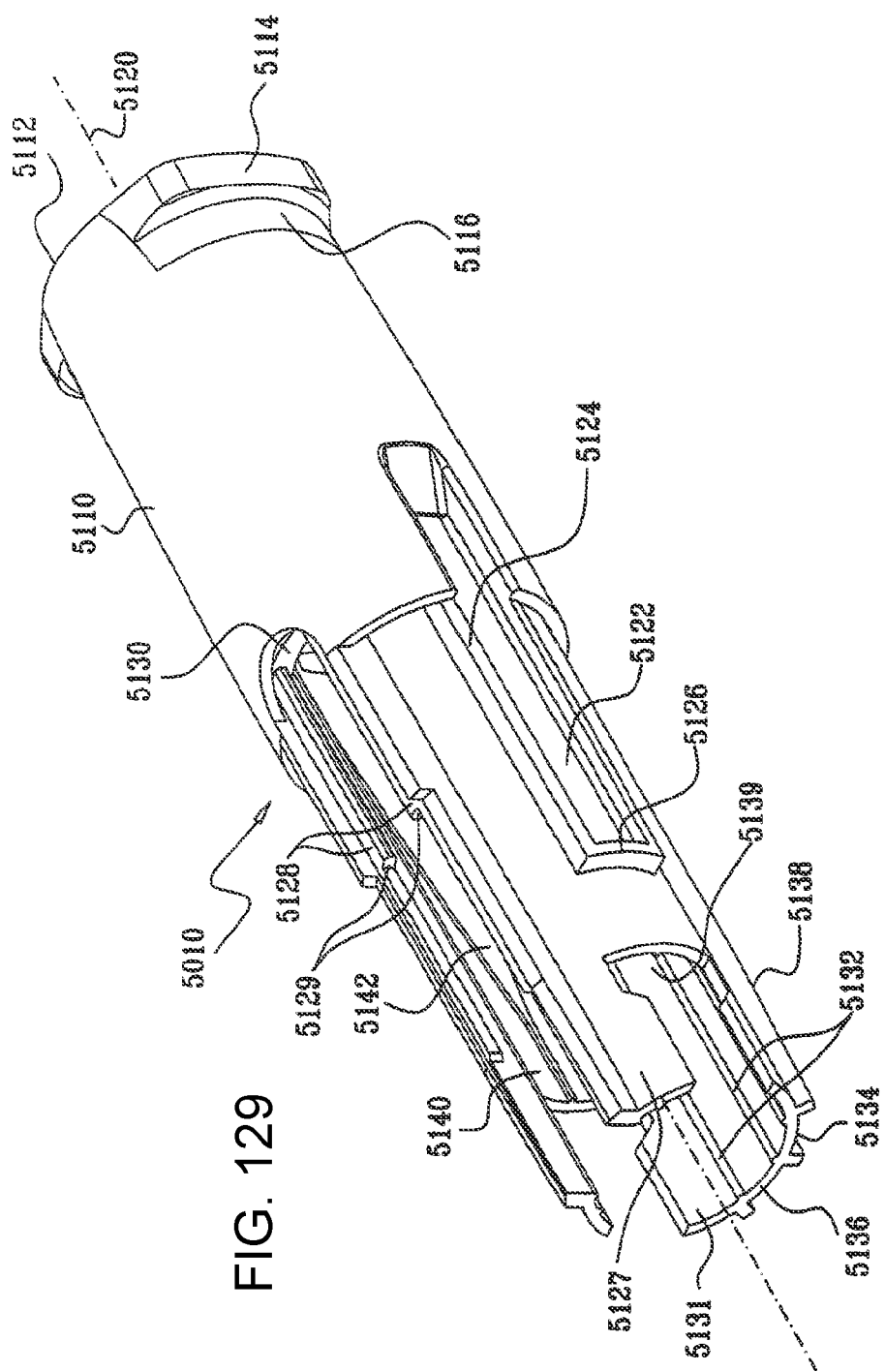

Reference is now made to FIG. 129, which is a simplified pictorial illustration of a preferred rear housing element 5010 which forms part of the automatic injection device of FIG. 128, to FIGS. 130A and 130B which are respective top and side view simplified planar illustrations thereof and to FIGS. 131A, 131B and 131C, which are sectional illustrations taken along respective section lines and directions CXXXIA-CXXXIA, CXXXIB-CXXXIB and CXXXIC-CXXXIC in FIGS. 130A and 130B.

As seen in FIGS. 129-131C, the rear housing element 5010 preferably is an integrally formed element, preferably injection molded of plastic and preferably has a generally cylindrical configuration including a generally tubular portion 5110, which terminates in a back wall 5112, defining generally symmetric side-facing tabs 5114 in front of which are generally symmetric side facing recesses 5116. Tubular portion 5110 is preferably side-to-side symmetric about a longitudinal axis 5120.

Tubular portion 5110 is formed with a pair of generally symmetric side recesses 5122 at which corresponding generally elongate engagement shaft portions 5124 extend forwardly parallel to longitudinal axis 5120 each terminating in an outward facing protrusion 5126. Above each engagement shaft portion 5124 there is provided a further shaft portion 5127, which extends forwardly of protrusion 5126 and has a somewhat curved cross sectional configuration. Shaft portions 5127 on the two sides of the rear housing element are separated from each other, as shown. A pair of mutually facing ribs 5128 extend from shaft portions 5127 parallel to axis 5120, defining forward facing shoulders 5129. As seen particularly in FIGS. 129 and 131A, a central inward facing protrusion 5130 is provided at a top interior surface of the rear housing, between and rearward of ribs 5128.

A bottom interior surface 5131 of the rear housing element has a generally uniform, slightly concave cross section and includes a plurality of generally radially inwardly directed ribs 5132, which extend generally parallel to longitudinal axis 5120. A bottom exterior surface 5134 of the rear housing element, which is the underside of surface 5131, includes a forward edge 5136 from which a plurality of radially outwardly directed ribs 5138 extend generally parallel to longitudinal axis 5120. Side to side parallel windows 5139, having a relatively narrow forward portion and a relatively wide backward portion, are formed below shaft portions 5127 and in front of protrusion 5126.

Side interior surfaces 5140 of the rear housing element 5010 each define a forwardly pointed protrusion 5142 which is engaged by elastomeric motion damping elements 5032 and 5034 forming part of selectable driving assembly 5030, as described hereinbelow. The interior surface of back wall 5112 of the rear housing element 5010 further comprises a rear seat 5160 for the spring 5020.

Reference is now made to FIG. 132, which is a simplified pictorial illustration of a preferred selectable driving assembly 5030, which forms part of the automatic injection device of FIG. 128, to FIGS. 133A and 133B, which are respective top and side view simplified planar illustrations of the selectable driving assembly and to FIGS. 134A, 134B and 134C, which are sectional illustrations taken along respective section lines and directions CXXXIVA-CXXXIVA, CXXXIVB-CXXXIVB and CXXXIVC-CXXXIVC in FIGS. 133A and 133B.

As seen in FIGS. 132-134C, the selectable driving element 5031 preferably is an integrally formed element, preferably injection molded of plastic and preferably has a generally cylindrical configuration including a generally tubular portion 5310, having an open back and having a pair of side-to-side symmetric actuation arms 5312 which extend forwardly of tubular portion 5310 parallel to a longitudinal axis 5320, which when selectable driving assembly 5030 is assembled with the rear housing element 5010, is coaxial with longitudinal axis 5120 (FIGS. 129-131C). A top engagement arm 5322 also extends forwardly of tubular portion 5310. A narrowed tubular neck portion 5324 is formed forwardly of tubular portion 5310. Elastomeric elements 5032 and 5034, seated in side recesses 5326 and 5328 in the selectable driving element 5031, are located symmetrically at the junction of the tubular portion 5310 and the neck portion 5324. Neck portion 5324 is formed with an internal thread 5325.

Each of actuation arms 5312 has a generally curved cross section and includes a rearwardly extending finger 5338 having formed thereon, adjacent an extreme outward end thereof, an inwardly facing generally triangular tooth 5342 having a forwardly facing inclined surface 5344 and a rearwardly facing engagement surface 5346 extending generally perpendicular to longitudinal axis 5320. Separated from tooth 5342 by a notch 5347 is an inwardly facing rounded tooth 5348. Additionally, finger 5338 has formed thereon top and bottom protrusions 5349.

Top engagement arm 5322 terminates in an outwardly facing protrusion 5350 having an inclined forward facing surface 5351. Rearwardly of protrusion 5350 and separated therefrom by an outwardly facing notch 5352 is an outwardly facing protrusion 5354, having an inclined outwardly facing surface 5356.

Plunger 5040, as seen in FIG. 128 is a generally circularly symmetric element, which is preferably formed in a tubular configuration, as shown. Plunger 5040 includes a rear portion 5402 having a relatively large circular cross section which continues forwardly to an externally threaded neck portion 5404 which is adapted to engage the internal thread 5325 of neck portion 5324 for advancing the plunger during titration. Forwardly of externally threaded neck portion 5404 is an intermediate portion 5406 and a forward portion 5408. Plunger 5040 includes a forward end 5410 adapted to engage a piston described hereinbelow with reference to FIG. 144A which is movably located in pre-filled syringe 5050. Plunger 5040 is preferably symmetrically disposed about a longitudinal axis 5420, which when assembled together with selectable driving assembly 5030 and rear housing element 5010, is coaxial with longitudinal axes 5120 (FIGS. 129-131C) and 5320 (FIGS. 132-134C).

As seen in FIG. 128, pre-filled syringe 5050 includes a rear flange 5502 which engages notches 5347 formed in respective fingers 5338 of each of side-to-side symmetric actuation arms 5312 of selectable driving assembly 5030 (FIGS. 132-134C).

Reference is now made to FIG. 135, which is a simplified pictorial illustration of forward housing and actuator element 5070 which forms part of the automatic injection device of FIG. 128, to FIGS. 136A and 136B, which are respective top and side view simplified planar illustrations thereof and to FIGS. 137A, 137B and 137C, which are sectional illustrations taken along respective section lines and directions CXXXVIIA-CXXXVIIA, CXXXVIIB-CXXXVIIB and CXXXVIIC-CXXXVIIC in FIGS. 136A and 136B.

As seen in FIGS. 135-137C, the forward housing and actuator element 5070 preferably is an integrally formed element, preferably injection molded of plastic and preferably has a generally truncated conical configuration arranged along a longitudinal axis 5720, which when the automatic injection device is assembled, is coaxial with longitudinal axes 5120 (FIGS. 129-131C), 5320 (FIGS. 132-134C) and 5420 (FIG. 128). Forward housing and actuator element 5070 includes a generally tubular rear portion 5710, having an open back and formed with a pair of side-to-side symmetric snap fit engagement sockets 5712 which receive the protrusions 5126 of the rear housing element 5010 during factory assembly of the automatic injection device.

Forward of tubular rear portion 5710 are formed a pair of top-bottom symmetric windows 5714, which allow the pre-filled syringe to be viewed, when the automatic injection device is assembled, including during use thereof.

A pair of outer side surfaces 5716 of forward housing and actuator element 5070 are each formed with ribbed grip regions 5718. Corresponding inner side surfaces 5721 each define a plurality of longitudinally extending ribs 5722, 5724, 5726 and 5728 which are used to slidably guide the needle guard 5080 during axial movement thereof as well as inner facing protrusions 5730, which together with ribs 5722 and 5724 define a forward facing spring seat for spring 5090 (FIG. 128). Inner facing protrusions 5730 are operative to slidably support pre-filled syringe 5050 and to slidably guide actuation arms 5312 of selectable driving assembly 5030.

Inner top and bottom surfaces 5732 and 5734 define respective pairs of ribs 5736 and 5738 which are operative to slidably guide the needle guard 5080 during axial movement thereof. A cantilevered rearwardly extending actuation lever 5750 extends from a location rearward of top window 5714 and defines, at an extreme rearward top facing surface thereof, an actuation button 5752.

As best seen in FIG. 137A, inner facing protrusions 5730 define at rearward facing portions thereof protrusions 5760 and 5762 which form a stopping point for flange 5502, thus limiting the forward movement of the pre-filled syringe 5050.

Reference is now made to FIG. 138, which is a simplified pictorial illustration of a needle guard element 5080 which forms part of the automatic injection device of FIG. 128, to FIGS. 139A and 139B, which are respective top and side view simplified planar illustrations thereof and to FIGS. 140A, 140B and 140C, which are sectional illustrations taken along respective section lines and directions CXLA-CXLA, CXLB-CXLB and CXLC-CXLC in FIGS. 139A and 139B.

As seen in FIGS. 138-140C, the needle guard element 5080 preferably is an integrally formed element, preferably injection molded of plastic and preferably has a generally cylindrical configuration including a generally tubular portion 5810, having a forward facing body engaging surface 5812 including a pair of concentric ribbed circumferential forward facing rings 5814 and 5816. The internal surface, located opposite from body engaging surface 5812, forms a spring-seat for spring 5090.

Needle guard element 5080 has a pair of side-to-side symmetric mounting arms 5818 arranged symmetrically about a longitudinal axis 5820. Each of arms 5818 has at a rearwardmost end thereof a pair of top and bottom facing teeth 5819, and is formed with a rectangular window 5821 having a relatively wider forward portion 5822 and a relatively narrower rear portion 5824. Arms 5818 extend along and rearwardly of tubular portion 5810 parallel to longitudinal axis 5820, which when the automatic injection device is assembled, is coaxial with longitudinal axes 5120 (FIGS. 129-131C), 5320 (FIGS. 132-134C), 5420 (FIG. 128) and 5720 (FIGS. 135-137C).

A top engagement arm 5832 also extends rearwardly of tubular portion 5810 and includes a rearwardmost axial portion 5834, an inclined intermediate portion 5836, an axial intermediate portion 5838 and an inclined mounting portion 5840, which extends from a top mounting arm 5842, formed with an elongate window 5844. An equivalent elongate window, also referenced by numeral 5844, is formed on a bottom mounting arm 5845. Elongate windows 5844 and top-bottom symmetric windows 5714 of forward housing and actuator element 5070 are positioned in respective parallel locations, such that pre-filled syringe 5050 is visible through the windows.

Top and bottom engagement portions 5846 and 5848 are each formed with an inwardly directed tooth, here designated by reference numerals 5850 and 5852 respectively.

Reference is now made to FIGS. 141A, 141B, 141C, 141D, 141E, 141F and 141G which are simplified pictorial illustrations of various stages of typical use of the automatic injection device of FIG. 128.

As seen in FIG. 141A, the automatic injection device of FIG. 128 is stored prior to use, as indicated by reference numeral 5900, in a pre-use operative orientation, described hereinbelow with reference to FIGS. 142-144B. While the automatic injection device is stored, it is preferably covered by needle protection cover 5062.

As seen in FIG. 141B, prior to use, after removing the needle protection cover 5062, air bubbles or some of the drug contained in pre-filled syringe 5050 may optionally be manually expelled via the needle, by rotation of rear portion 5402 of plunger 5040, as indicated by reference numeral 5902. The operative orientation of the automatic injection device for this functionality is described hereinbelow with reference to FIGS. 145-147B.

A user actuates the automatic injection device by pushing it against an injection site and depressing actuation button 5752 (FIGS. 135-137C), as indicated by reference numeral 5904 shown in FIG. 141C and as described hereinbelow with reference to FIGS. 148-150B. In response to user actuation, needle penetration takes place at the injection site, as indicated by reference numeral 5906 shown in FIG. 141D. The operative orientation of the automatic injection device at this stage is described hereinbelow with reference to FIGS. 151-153B.

As seen in FIG. 141E, immediately following needle penetration, drug delivery takes place, as indicated by reference numeral 5908. The operative orientation of the automatic injection device at this stage is described hereinbelow with reference to FIGS. 154-156B. The operative orientation of the automatic injection device immediately following completion of drug delivery is indicated by reference numeral 5910 shown in FIG. 141F, as described hereinbelow with reference to FIGS. 157-159B.

As seen in FIG. 141G, the automatic injection device is manually disengaged from the injection site and the needle is automatically protected by the needle guard element 5080, as indicated by reference numeral 5914. The operative orientation of the automatic injection device at this stage is described hereinbelow with reference to FIGS. 160-162B.

Reference is now made to FIG. 142, which is a simplified assembled view illustration of the automatic injection device of FIGS. 128 and 141A in a pre-use operative orientation, to FIGS. 143A and 143B, which are respective top and side view simplified planar illustrations thereof and to FIGS. 144A and 144B, which are sectional illustrations taken along respective section lines and directions CXLIVA-CXLIVA and CXLIVB-CXLIVB in FIGS. 143A and 143B.

As seen in FIGS. 142-144B, in a pre-use operative orientation of the automatic injection device which is suitable for storage, the rear housing element 5010 is joined to the forward housing and actuator element 5070 by snap fit engagement of protrusions 5126 of rear housing element 5010 in the engagement sockets 5712 formed in the forward housing and actuator element 5070.

Selectable driving assembly 5030 is retained in its axial position by engagement of inward facing protrusion 5130 (FIG. 131A) with outwardly facing notch 5352 of top engagement arm 5322 (FIG. 5134) of selectable driving assembly 5030. In this arrangement, spring 5020 is in a relatively compressed state and is held in that state by pressure from the selectable driving assembly.

As seen clearly in the enlarged portion of FIG. 144A, needle guard 5080 is retained in its position by engagement of inwardly directed teeth 5850 and 5852 of top and bottom engagement portions 5846 and 5848 with flange 5502 of pre-filled syringe 5050.

As seen clearly in the enlarged portion of FIG. 144B, plunger 5040 is retained in place by engagement of externally threaded neck portion 5404 and internal thread 5325 of neck portion 5324.

The rearwardmost axial portion 5834 of the top engagement arm 5832 of the needle guard 5080 (FIGS. 138-140C) is in a relatively forward position, only partially underlying actuation button 5752 of forward housing and actuator element 5070 (FIGS. 135-137C). Additionally, downward displacement of actuation button 5752 is limited by ribs 5128 (FIGS. 129-131C), thus ensuring that actuation button 5752 does not directly engage protrusion 5350 of engagement arm 5322. Accordingly, in this orientation of the automatic injection device, inadvertent pressing of button 5752 does not actuate the automatic injection device.

The pre-filled syringe 5050 is retained in a retracted orientation by engagement of flange 5502 thereof with notches 5347 formed in respective fingers 5338 of each of side-to-side symmetric actuation arms 5312 of selectable driving assembly 5030 (FIGS. 132-135C).

Reference is now made to FIG. 145, which is a simplified pictorial illustration of the automatic injection device of FIGS. 128 and 141B in an optional titration operative orientation, to FIGS. 146A and 146B, which are respective top and side view simplified planar illustrations thereof and to FIGS. 147A and 147B, which are sectional illustrations taken along respective section lines and directions CXLVIIA-CXLVIIA and CXLVIIB-CXLVIIB in FIGS. 146A and 146B.

In an optional titration step, after the protective needle cover 5062 has been removed and while the needle guard 5080 points upwards, a user may rotate rear portion 5402 of plunger 5040, causing the externally threaded neck portion 5404 of the plunger to move the plunger forwardly by threading it further in the internal thread 5325 of neck portion 5324. As the plunger moves forwardly, the syringe 5050 is retained in place, thus forcing air bubbles and/or liquid out of the syringe via the needle 5060. At this stage, protrusions 5349 formed on fingers 5338 (FIGS. 132-134C) engage the defining walls of narrower rear portion 5824 of rectangular window 5821, thus limiting the third fingers 5338 from bending outward and therefore flange 5502 continues to engage notches 5347 thus inhibiting premature movement of syringe 5050. It is appreciated that except for the forward movement of the plunger 5040, the remainder of the operative orientation of the automatic injection device remains identical to the pre-use operative orientation.

Reference is now made to FIG. 148, which is a simplified pictorial illustration of the automatic injection device of FIGS. 128 and 141C in an actuated operative orientation, to FIGS. 149A and 149B which are respective top and side view simplified planar illustrations thereof and to FIGS. 150A and 150B which are sectional illustrations taken along respective section lines and directions CLA-CLA and CLB-CLB in FIGS. 149A and 149B.

As seen particularly in the enlarged portion of FIG. 150A, due to engagement of the needle guard 5080 with an injection site on a body, the needle guard 5080 is forced to move axially in a rearward direction with respect to the remainder of the automatic injection device, thus compressing spring 5090 and causing the rearwardmost axial portion 5834 of the top engagement arm 5832 of the needle guard 5080 (FIGS. 138-140C) to assume a relatively rearward position, generally underlying actuation button 5752 of forward housing and actuator element 5070 (FIGS. 135-137C). The rearward motion of the needle guard 5080 is limited by engagement of rearwardmost ends of top and bottom facing teeth 5819 of arms 5818 of the needle guard and the rear edge of window 5139 formed in front of outward facing protrusion 5126 of rear housing element 5010.

In this orientation of the needle guard 5080, pressing of button 5752 does actuate the automatic injection device, by causing portion 5834 to engage protrusion 5350, thus disengaging notch 5352 from protrusion 5130 (FIG. 131A) and thus disengaging engagement arm 5322 from the rear housing element 5010 and permitting forward axial movement of the selectable driving assembly 5030 under the urging of spring 5020.

Reference is now made to FIG. 151, which is a simplified pictorial illustration of the automatic injection device of FIGS. 128 and 141D in a needle penetration, pre-drug delivery operative orientation, to FIGS. 152A and 152B, which are respective top and side view simplified planar illustrations thereof and to FIGS. 153A and 153B, which are sectional illustrations taken along respective section lines and directions CLIIIA-CLIIIA and CLIIIB-CLIIIB in FIGS. 152A and 152B.

FIGS. 151-153B illustrate an initial stage in the forward motion of the selectable driving assembly 5030 under the urging of spring 5020 following user actuation of button 5752. It is seen that the axial forward motion of the selectable driving assembly 5030 produces equivalent axial forward motion of the syringe 5050, due to engagement of flange 5502 in notches 5347 formed in respective fingers 5338 of each of side-to-side symmetric actuation arms 5312 of selectable driving assembly 5030 (FIGS. 132-134C).

This forward motion results in forward motion of the needle 5060 and needle penetration at the injection site as shown. The forward motion of syringe 5050 and needle penetration stops as flange 5502 reaches protrusions 5760 and 5762 of forward housing and actuator element 5070. During needle penetration, elastomeric elements 5032 and 5034 engage forwardly pointed protrusion 5142 of side interior surface 5140 causing friction therebetween, thus compensating for the force of spring 5020 and resulting in damping of the needle movement and absorbance of the shock applied by protrusions 5760 and 5762 on the flange 5502. As will be described hereinbelow, drug delivery follows needle penetration.

Reference is now made to FIG. 154, which is a simplified pictorial illustration of the automatic injection device of FIGS. 128 and 141E in drug delivery operational orientation, to FIGS. 155A and 155B which are respective top and side view simplified planar illustrations thereof and to FIGS. 156A and 156B, which are sectional illustrations taken along respective section lines and directions CLVIA-CLVIA and CLVIB-CLVIB in FIGS. 155A and 155B.

FIGS. 154-156B illustrate a further stage in the forward motion of the selectable driving assembly under the urging of spring 5020 following user actuation of button 5752. It is seen that the axial forward motion of the selectable driving assembly 5030 does not produce equivalent axial forward motion of the syringe 5050, due to engagement of flange 5502 of syringe 5050 with protrusions 5760 and 5762 of ribs of the forward housing and actuator element 5070 (FIG. 137A).

Continued urging of spring 5020 and the selectable driving assembly 5030 causes protrusions 5349 formed on fingers 5338 (FIGS. 132-134C) to disengage the defining walls of narrower rear portion 5824 of rectangular window 5821, and bend outward into the space formed by the wider forward portion 5822 of the rectangular window (FIGS. 138-140C), resulting in disengagement of flange 5502 and notches 5347 formed in respective fingers 5338 of each of side-to-side symmetric actuation arms 5312 of selectable driving assembly 5030 (FIGS. 132-134C).

The urging of spring 5020 causes plunger 5040 to continue its forward motion together with piston 5501 which is engaged thereto.

Forward motion of piston 5501 forces the drug out of syringe 5050 through needle 5060 into the injection site. During drug delivery, the forward motion of the piston 5501 is governed by friction between elastomeric elements 5032 and 5034 and forwardly pointed protrusion 5142 of side interior surfaces 5140. The amount of friction may be selected by appropriately shaping the forwardly pointed protrusion 5142 and the elastomeric elements 5032 and 5034.

The forwardly pointed shape of protrusions 5142 causes a reduction in friction as selectable driving assembly 5030 advances, which compensates for the reduction of the force applied by spring 5020 as it extends. Friction between the protrusion and elastomeric elements 5032 and 5034 also damps shock resulting from engagement of the internal thread 5325 of neck portion 5324 and externally threaded neck portion 5404 of plunger 5040, which is then transferred to flange 5502 of the pre-filled syringe 5050, and may help control the drug injection rate.

Reference is now made to FIG. 157, which is a simplified pictorial illustration of the automatic injection device of FIGS. 128 and 141F in an immediate post-drug delivery operational orientation, to FIGS. 158A and 158B, which are respective top and side view simplified planar illustrations thereof and to FIGS. 159A and 159B, which are sectional illustrations taken along respective section lines and directions CLIXA-CLIXA and CLIXB-CLIXB in FIGS. 158A and 158B.

Prior to this stage, forward motion of piston 5501 in the syringe continued until the piston cannot move forward any more, thus terminating drug delivery.

Reference is now made to FIG. 160, which is a simplified pictorial illustration of the automatic injection device of FIGS. 128 and 141G in a needle protected operational orientation, to FIGS. 161A and 161B which are respective top and side view simplified planar illustrations thereof and to FIGS. 162A and 162B which are sectional illustrations taken along respective section lines and directions CLXIIA-CLXIIA and CLXIIB-CLXIIB in FIGS. 161A and 161B.

At this stage, the automatic injection device is fully disengaged from the injection site and the needle guard 5080 is fully extended to fully enclose the needle 5060. When the needle guard is fully extended it is locked onto the syringe 5050 by engagement of inwardly directed teeth 5850 and 5852 and flange 5502 of the pre-filled syringe 5050, thus inhibiting further movement outwards of the needle guard 5080. As the needle guard disengages from the injection site and moves outwards, top and bottom facing teeth 5819 move along the narrow portion of window 5139, until they engage forward edge 5136, thus inhibiting the needle guard 5080 from moving inwards.

Reference is now made to FIG. 163 which is a simplified exploded view illustration of an automatic injection device constructed and operative in accordance with a still further preferred embodiment of the present invention. The embodiment of FIG. 163 is a modification of the embodiment of FIGS. 1-41. Accordingly, for the sake of conciseness, it is described hereinbelow in somewhat abbreviated form with reference to FIGS. 164-190B.

As seen with particular clarity in FIG. 163, the automatic injection device comprises a rear housing element 6010 in which is seated a main compression spring 6020, which provides selectable forward displacement to a selectable driving assembly 6030, which includes a selectable driving element 6031 and a pair of elastomeric motion damping elements 6032 and 6034, and selectably engages a plunger 6040 and a pre-filled syringe 6050 having a hypodermic needle 6060 which is covered by a needle protection cover 6062. Pre-filled syringe 6050 may be a conventional pre-filled syringe, such as a commercially available syringe sold under the catalog designation BD-Hypak™ or may be any other suitable syringe or cartridge.

Plunger 6040 also operatively engages pre-filled syringe 6050 and is selectably operated by selectable driving assembly 6030 to inject the liquid contents of pre-filled syringe 6050 through hypodermic needle 6060.

The forward portion of rear housing element 6010 as well as spring 6020, selectable driving assembly 6030, plunger 6040 and pre-filled syringe 6050 are located within a forward housing and actuator element 6070. At a forward end of the interior of forward housing and actuator element 6070 there is provided a needle guard element 6080, which is positioned by a compression spring 6090.

Plunger 6040, as seen in FIG. 163, is a generally circularly symmetric element, which is preferably formed in an overall ribbed configuration, as shown. Plunger 6040 includes a rear portion 6402 having a relatively large circular cross section which tapers forwardly to a neck portion 6404, having a relatively small circular cross section. Forwardly of neck portion 6404 is an intermediate portion 6406, whose circular cross section is typically the same as that of rear portion 6402, and a forward portion 6408, whose circular cross section is typically the same as that of neck portion 6404. Plunger 6040 terminates at its forward end in a male threaded protrusion 6410 adapted to fit a corresponding female threaded socket formed in a piston described hereinbelow with reference to FIG. 166A, which is movably located in pre-filled syringe 6050. Plunger 6040 is preferably symmetrically disposed about a longitudinal axis 6420, which when assembled together with selectable driving assembly 6030 and rear housing element 6010, is coaxial with longitudinal axes 6120 and 6320.

Reference is now made to FIG. 2, which is a simplified pictorial illustration of a preferred rear housing element 10 which forms part of the automatic injection device of FIG. 1, to FIGS. 3A and 3B which are respective top and side view simplified planar illustrations thereof and to FIGS. 4A, 4B and 4C, which are sectional illustrations taken along respective section lines and directions IVA-IVA, IVB-IVB and IVC-IVC in FIGS. 3A and 3B.

Rear housing element 6010 is identical to rear housing element 10 described hereinabove with reference to FIGS. 2-4C.

Reference is now made to FIG. 5, which is a simplified pictorial illustration of a preferred selectable driving assembly 30, which forms part of the automatic injection device of FIG. 1, to FIGS. 6A and 6B, which are respective top and side view simplified planar illustrations of the selectable driving assembly and to FIGS. 7A, 7B and 7C, which are sectional illustrations taken along respective section lines and directions VIIA-VIIA, VIIB-VIIB and VIIC-VIIC in FIGS. 6A and 6B.

Selectable driving assembly 6030 is nearly identical to selectable driving assembly 30 described hereinabove with reference to FIGS. 5-7C except for the following differences:

In contrast to the embodiment of FIGS. 1-41, third fingers 6338 including notches 6347 and inwardly facing rounded teeth 6348 are obviated. Teeth 6342 having inclined surface 6344 and a rearward surface 6346 are formed directly on inwardly facing surfaces of side to side symmetric actuation arms 6312.

Reference is now made to FIG. 8, which is a simplified pictorial illustration of forward housing and actuator element 70 which forms part of the automatic injection device of FIG. 1, to FIGS. 9A and 9B, which are respective top and side view simplified planar illustrations thereof and to FIGS. 10A, 10B and 10C, which are sectional illustrations taken along respective section lines and directions XA-XA, XB-XB and XC-XC in FIGS. 9A and 9B.

Forward housing and actuator element 6070 is identical to forward housing and actuator element 70 described hereinabove with reference to FIGS. 8-10B.

Reference is now made to FIG. 11, which is a simplified pictorial illustration of a needle guard element 80 which forms part of the automatic injection device of FIG. 1, to FIGS. 12A and 12B, which are respective top and side view simplified planar illustrations thereof and to FIGS. 13A, 13B and 13C, which are sectional illustrations taken along respective section lines and directions XIIIA-XIIIA, XIIIB-XIIIB and XIIIC-XIIIC in FIGS. 12A and 12B.

Needle guard element 6080 is identical to needle guard element 80 described hereinabove with reference to FIGS. 11A-13C.

Reference is now made to FIG. 164, which is a simplified assembled view illustration of the automatic injection device of FIG. 163 in a pre-use operative orientation, to FIGS. 165A and 165B, which are respective top and side view simplified planar illustrations thereof and to FIGS. 166A and 166B, which are sectional illustrations taken along respective section lines and directions CLXVIA-CLXVIA and CLXVIB-CLXVIB in FIGS. 165A and 165B.

As seen in FIGS. 164-166, in a pre-use operative orientation of the automatic injection device which is suitable for storage, the rear housing element 6010 is joined to the forward housing and actuator element 6070 by snap fit engagement of protrusions 6126 of rear housing element 6010 in the engagement sockets 6712 formed in the forward housing and actuator element 6070.

Selectable driving assembly 6030 is retained in its axial position by engagement of inward facing protrusion 6130 with outwardly facing notch 6352 of top engagement arm 6322 of selectable driving assembly 6030, as shown with particularly in the enlarged portion of FIG. 604A. In this arrangement, spring 6020 is in a relatively compressed state and is held in that state by the selectable driving assembly 6030.

Also seen in the enlarged portion of FIG. 166 is that the rearwardmost axial portion 6834 of the top engagement arm 6832 of the needle guard 6080 is in a relatively forward position, only partially underlying actuation button 6752 of forward housing and actuator element 6070. Additionally, inward displacement of actuation button 6752 is limited by ribs 6128, thus ensuring that actuation button 6752 does not directly engage protrusion 6350 of engagement arm 6322. Accordingly, in this orientation of the needle guard 6080, inadvertent pressing of button 6752 does not actuate the automatic injection device.

The pre-filled syringe 6050 is retained in a retracted orientation by engagement of flange 6502 thereof with rearwardly facing engagement surfaces 6346 of teeth 6342 formed on side-to-side symmetric actuation arms 6312 of selectable driving assembly 6030.

Needle guard 6080 is retained in its axial position, and is prevented from moving forward by engagement of inwardly directed teeth 6850 and 6852 with the flange 6502 of the pre-filled syringe 6050. It is appreciated that in this operative orientation spring 6090 either at rest or in a semi-compressed state.

Reference is now made to FIG. 167 which is a simplified pictorial illustration of the automatic injection device of FIG. 163 in an optional titration operative orientation, to FIGS. 168A and 168B, which are respective top and side view simplified planar illustrations thereof and to FIGS. 169A and 169B, which are sectional illustrations taken along respective section lines and directions CLIXA-CLIXA and CLIXB-CLIXB in FIGS. 168A and 168B.

In an optional titration step, after the protective needle cover has been removed and while the needle guard 6080 points upwards, a user may push rear portion 6402 of plunger 6040 forwardly as the syringe 6050 is retained in place. This forces air bubbles and/or liquid out of the syringe via the needle 6060. At this stage, flange 6502 continues to engage rearwardly facing engagement surfaces 6346 of teeth 6342 thus inhibiting premature movement of syringe 6050. It is appreciated that except for the forward movement of the plunger 6040, the remainder of the operative orientation of the automatic injection device remains identical to the pre-use operative orientation.

Reference is now made to FIG. 170, which is a simplified pictorial illustration of the automatic injection device of FIG. 163 in an actuated operative orientation, to FIGS. 171A and 171B which are respective top and side view simplified planar illustrations thereof and to FIGS. 172A and 172B which are sectional illustrations taken along respective section lines and directions CLXXIIA-CLXXIIA and CLXXIIB-CLXXIIB in FIGS. 609A and 609B.

As seen particularly in the enlarged portion of FIG. 172A, due to engagement of the needle guard 6080 with an injection site on a body, the needle guard 6080 is forced to move axially in a rearward direction with respect to the remainder of the automatic injection device, thus compressing spring 6090 and causing the rearwardmost axial portion 6834 of the top engagement arm 6832 of the needle guard 6080 to assume a relatively rearward position, generally underlying actuation button 6752 of forward housing and actuator element 6070. The rearward motion of the needle guard 6080 is limited by engagement of rearwardmost ends 6819 of arms 6818 of the needle guard with a forward facing edge of outward facing protrusion 6126 rear housing element 6010.

In this orientation of the needle guard 6080, pressing of button 6752 does actuate the automatic injection device, by causing portion 6834 to engage protrusion 6350, thus disengaging notch 6352 from protrusion 6130 and thus disengaging engagement arm 6322 from the rear housing element 6010 and permitting forward axial movement of the selectable driving assembly 6030 under the urging of spring 6020.

Reference is now made to FIG. 173, which is a simplified pictorial illustration of the automatic injection device of FIG. 163 in a needle penetration, pre-drug delivery operative orientation, to FIGS. 174A and 174B, which are respective top and side view simplified planar illustrations thereof and to FIGS. 175A and 175B, which are sectional illustrations taken along respective section lines and directions CLXXVA-CLXXVA and CLXXVB-CLXXVB in FIGS. 174A and 174B.

FIGS. 173-175B illustrate an initial stage in the forward motion of the selectable driving assembly 6030 under the urging of spring 6020 following user actuation of button 6752. It is seen that the axial forward motion of the selectable driving assembly 6030 produces equivalent axial forward motion of the syringe 6050, due to engagement between inwardly extending protrusion 6333 of the bended first finger 6330 of the selectable driving assembly 6030 and intermediate portion 6406 of plunger 6040, which, in turn, forces the syringe to move forward.

This forward motion results in forward motion of the needle 6060 and needle penetration at the injection site as shown. The forward motion of syringe 6050 and needle penetration stops as flange 6502 reaches protrusions 6760 and 6762 of forward housing and actuator element 6070. During needle penetration, elastomeric elements 6032 and 6034 engage forwardly pointed protrusion 6142 causing friction therebetween, thus compensating for the force of spring 6020 and resulting in damping of the needle movement and absorbance of the shock applied by protrusions 6760 and 6762 on the flange 6502. The forward motion of the selectable driving assembly 6030 causes the outwardly extending protrusion 6332 to engage a forwardly pointed protrusion formed on surface 6140, thus bending the first finger 6330 inwards. As will be described hereinbelow, drug delivery follows needle penetration.

Reference is now made to FIG. 176, which is a simplified pictorial illustration of the automatic injection device of FIG. 163 in drug delivery operational orientation, to FIGS. 177A and 177B which are respective top and side view simplified planar illustrations thereof and to FIGS. 178A and 178B, which are sectional illustrations taken along respective section lines and directions CLXXVIIIA-CLXXVIIIA and CLXXVIIIB-CLXXVIIIB in FIGS. 177A and 177B.

FIGS. 176-178B illustrate a further stage in the forward motion of the selectable driving assembly under the urging of spring 6020 following user actuation of button 6752. It is seen that the axial forward motion of the selectable driving assembly 6030 does not produce equivalent axial forward motion of the syringe 6050, due to engagement of flange 6502 of syringe 6050 with protrusions 6760 and 6762 of ribs of the forward housing and actuator element 6070.

Continued urging of spring 6020 and the selectable driving assembly 6030 in addition to the engagement between inwardly extending protrusion 6333 of the bended first finger 6330 of the selectable driving assembly 6030 and intermediate portion 6406 of plunger 6040, cause the plunger 6040 to continue its forward motion together with piston 6501, which is connected thereto.

Forward motion of piston 6501 forces the drug out of syringe 6050 through needle 6060 into the injection site. During drug delivery, the forward motion of the piston 6501 is governed by friction between elastomeric elements 6032 and 6034 and a forwardly pointed protrusion formed on surface 6140. The amount of friction may be selected by appropriately shaping the forwardly pointed protrusion and the elastomeric elements 6032 and 6034.

The forwardly pointed shape of the protrusion causes a reduction in friction as selectable driving assembly 6030 advances, which compensates for the reduction in the force applied by spring 6020 as it extends. Friction between the protrusion and elastomeric elements 6032 and 6034 also damps shock resulting from engagement of inwardly extending protrusion 6333 with intermediate portion 6406 of plunger 6040. may help control the drug injection rate.

Reference is now made to FIG. 179, which is a simplified pictorial illustration of the automatic injection device of FIG. 163 in an immediate post-drug delivery operational orientation, to FIGS. 180A and 180B, which are respective top and side view simplified planar illustrations thereof and to FIGS. 181A and 181B, which are sectional illustrations taken along respective section lines and directions CLXXXIA-CLXXXIA and CLXXXIB-CLXXXIB in FIGS. 180A and 180B.

Prior to this stage, forward motion of piston 6501 in the syringe continued until the piston cannot move forward any more, thus terminating drug delivery. Additionally, outwardly extending protrusions 6332 of first fingers 6330 no longer engage the forwardly pointed protrusion, and are now supported by the internal surfaces of mounting arms 6818.

Reference is now made to FIG. 182, which is a simplified pictorial illustration of the automatic injection device of FIG. 163 in its operation orientation as it is being disengaged from an injection site, to FIGS. 183A and 183B which are respective top and side view simplified planar illustrations thereof and to FIGS. 184A and 184B which are sectional illustrations taken along respective section lines and directions CLXXXIVA-CLXXXIVA and CLXXXIVB-CLXXXIVB in FIGS. 183A and 183B.

At this stage, the automatic injection device is being removed from the injection site and the needle guard 6080 is moving axially forward under the urging of spring 6090, so that the exposed portion of the needle 6060 is protected by the needle guard 6080. Subsequent to the initial forward movement of the needle guard 6080, the first fingers 6330 of each of side-to-side symmetric actuation arms 6312 of the selectable driving assembly 6030 are released and bend outwards to their initial position, thus disengaging from the plunger 6040 and engaging the rearwardmost ends 6819 of arms 6818 of the needle guard 6080.

At this stage the spring 6020 applies more force than does spring 6090 and thus pushes the needle guard 6080 further forward. It is therefore appreciated that even if spring 6090 were to be replaced by a shorter spring, for example a short plastic spring integrated with either forward housing and actuator element 6070 or needle guard 6080, spring 6020 would guarantee that needle guard 6080 would be fully deployed, such that the auto injection device would be maintained in a protected position.

Reference is now made to FIG. 185, which is a simplified pictorial illustration of the automatic injection device of FIG. 163 in a needle protected operational orientation, to FIGS. 186A and 186B which are respective top and side view simplified planar illustrations thereof and to FIGS. 187A and 187B which are sectional illustrations taken along respective section lines and directions CLXXXVIIA-CLXXXVIIA and CLXXXVIIB-CLXXXVIIB in FIGS. 186A and 186B.

At this stage, the automatic injection device is fully disengaged from the injection site and the needle guard 6080 is fully extended to fully enclose the needle 6060. When the needle guard is fully extended it is locked onto the syringe 6050 by engagement of inwardly directed teeth 6850 and 6852 and flange 6502 of the pre-filled syringe 6050, thus inhibiting further movement outwards of the needle guard 6080. During the movement of needle guard 6080 and due to force exerted by spring 6020, inwardly extending protruding portions 6336 of second fingers 6334 snap over flange 6502 within the narrower rear portion 6824 of rectangular window 6821, thus enabling further locking of the needle guard as described hereinbelow.

Reference is now made to FIG. 188, which is a simplified pictorial illustration of the automatic injection device of FIG. 163 in a needle-guard push back misuse operational orientation, to FIGS. 189A and 189B which are respective top and side view simplified planar illustrations thereof and to FIGS. 190A and 190B which are sectional illustrations taken along respective section lines and directions CXCA-CXCA and CXCB-CXCB in FIGS. 189A and 189B.

FIGS. 188-190B illustrate an important feature of the present invention provided by the locking of inwardly extending protruding portion 6336 of second finger 6334 of the selectable driving assembly 6030 and the flange 6502 of the pre-filled syringe 6050. Should the needle guard 6080 be pushed rearwardly with respect to the forward housing and actuator element 6070, the rearwardmost ends 6819 of arms 6818 of the needle guard 6080 push against protrusion 6332 of the selectable driving assembly 6030. Selectable driving assembly 6030 is therefore forced to move rearwardly together with the needle guard. Due to engagement of second fingers 6334 and flange 6502, the selectable driving assembly 6030 forces the needle 6060 and syringe 6050 to move rearwardly together with selectable driving assembly 6030, so that the needle 6060 does not protrude from the needle guard 6080. During this rearward movement, first fingers 6330 cannot bend inwards to cause outwardly extending protrusions 6332 to disengage from rearwardmost ends 6819 of arms 6818, since the inwardly extending protrusions 6333 of first fingers 6330 are supported by intermediate portion 6406 of the plunger 6040.

Reference is now made to FIG. 191 which is a simplified exploded view illustration of an automatic injection device constructed and operative in accordance with a still further preferred embodiment of the present invention. The embodiment of FIG. 191 is a modification of the embodiment of FIGS. 1-41 with the addition of a vial adapter and vial contents mixing functionality. Accordingly, for the sake of conciseness, it is described hereinbelow in somewhat abbreviated form with reference to FIGS. 192-209B.

As seen with particular clarity in FIG. 191, the automatic injection device comprises a rear housing element 7010 into which is seated a main compression spring 7020, which provides selectable forward displacement to a selectable driving assembly 7030, which includes a selectable driving element 7031 and a pair of elastomeric motion damping elements 7032 and 7034, and selectably engages a plunger 7040 and a pre-filled syringe 7050 having a hypodermic needle 7060 which is covered by a needle protection cover 7062. Pre-filled syringe 7050 may be a conventional pre-filled syringe, such as a commercially available syringe sold under the catalog designation BD-Hypak™ or may be any other suitable syringe or cartridge.

Plunger 7040 also operatively engages pre-filled syringe 7050 and is selectably operated by selectable driving assembly 7030 to inject the liquid contents of pre-filled syringe 7050 through hypodermic needle 7060. The forward portion of rear housing element 7010 as well as spring 7020, selectable driving assembly 7030, plunger 7040 and pre-filled syringe 7050 are located within a forward housing and actuator element 7070. At the forward end of the interior of forward housing and actuator element 7070 there is provided a needle guard element 7080, which is positioned by a compression spring 7090.

The above-described apparatus is identical to that described hereinabove with reference to FIGS. 1-13C other than in that plunger 7040 is somewhat longer than plunger 40 in order to provide the vial contents mixing functionality.

As seen, the embodiment of FIG. 191 also includes a vial adaptor 7091 and an associated septum 7092, typically formed of rubber, which are adapted for selectable operative engagement with a conventional drug vial 7093.

The vial adaptor 7091 preferably comprises three concentric cylindrical portions including a needle engagement portion 7094 defining a rearward facing bore 7095 in which is seated septum 7092. Forward of bore 7095 is an intermediate bore 7096 which terminates in a hollow vial puncturing spike 7097. Surrounding vial puncturing spike 7097 is a forward cowl 7098 and partially surrounding needle engagement portion 7094 is a rearward cowl 7099. A radially extending wall 7100 is common to cylindrical portions 7094, 7098 and 7099.

Reference is now made to FIG. 192 which is a simplified assembled view illustration of the automatic injection device of FIG. 191 in a pre-use operative orientation, to FIGS. 193A and 193B, which are respective top and side view simplified planar illustrations thereof and to FIGS. 194A and 194B, which are sectional illustrations taken along respective section lines and directions CXCIVA-CXCIVA and CXCIVB-CXCIVB in FIGS. 193A and 193B.

As seen in FIGS. 192-194B, in a pre-use operative orientation of the automatic injection device which is suitable for storage, the rear housing element 7010 is joined to the forward housing and actuator element 7070 by snap fit engagement of protrusions 7126 of rear housing element 7010 in the engagement sockets 7712 formed in the forward housing and actuator element 7070.

Selectable driving assembly 7030 is retained in its axial position by engagement of inward facing protrusion 7130 with outwardly facing notch 7352 of top engagement arm 7322 of selectable driving assembly 7030. In this arrangement, spring 7020 is in a relatively compressed state and is held in that state by the selectable driving assembly.

As seen in FIG. 194A, the rearwardmost axial portion 7834 of the top engagement arm 7832 of the needle guard 7080 is in a relatively forward position, only partially underlying actuation button 7752 of forward housing and actuator element 7070. Additionally, inward displacement of actuation button 7752 is limited by ribs 7128, thus ensuring that actuation button 7752 does not directly engage protrusion 7350 of engagement arm 7322. Accordingly, in this orientation of the needle guard 7080, inadvertent pressing of button 7752 does not actuate the automatic injection device.

The pre-filled syringe 7050 is retained in a retracted orientation by engagement of flange 7502 thereof with notches 7347 formed in respective third fingers 7338 of each of side-to-side symmetric actuation arms 7312 of selectable driving assembly 7030. At this stage, and in all the further orientations of the automatic injection device, protrusions formed on third fingers 7338 engage the defining walls of a narrower rear portion of a rectangular window formed in needle guard element 7080, thus limiting third fingers 7338 from bending outward and ensuring that flange 7502 will continue to engage notches 7347 resulting in prevention of premature movement of syringe 7050.

Needle guard 7080 is retained in its axial position and is prevented from moving forward by engagement of inwardly directed teeth 7850 and 7852 with the flange 7502 of the pre-filled syringe 7050. It is appreciated that in this operative orientation spring 7090 is either at rest or in a semi-compressed state.

Reference is now made to FIG. 195, which is a simplified pictorial illustration of the automatic injection device of FIGS. 192-194B in an optional vial adaptor mounted operative orientation, to FIGS. 196A and 196B, which are respective top and side view simplified planar illustrations thereof and to FIGS. 197A and 197B, which are sectional illustrations taken along respective section lines and directions CXCVIIA-CXCVIIA and CXCVIIB-CXCVIIB in FIGS. 196A and 196B.

In an optional vial adaptor mounting step, after the protective needle cover 7062 has been removed a user may push vial adaptor 7091 onto needle 7060 so that needle 7060 extends through septum 7092 so that a forward edge of forward housing and actuator element 7070 engages a rearward facing edge of radially extending wall 7100, thus preventing premature actuation by not allowing needle guard element 7080 to be pressed rearwardly as required for firing the needle. It is appreciated that the remainder of the operative orientation of the automatic injection device remains identical to the pre-use operative orientation.

Reference is now made to FIG. 198, which is a simplified pictorial illustration of the automatic injection device of FIGS. 195-197B in a vial communication operative orientation, to FIGS. 199A and 199B which are respective top and side view simplified planar illustrations thereof and to FIGS. 200A and 200B which are sectional illustrations taken along respective section lines and directions CCA-CCA and CCB-CCB in FIGS. 199A and 199B.

As seen in FIGS. 198-200B, the interior of the vial 7093 communicates with the interior of the syringe 7050 via needle 7060, septum 7092, bore 7095, bore 7096 and puncturing spike 7097. It is appreciated that as the plunger moves forwardly, the syringe 5050 is retained in place, thus forcing air bubbles or a portion of the liquid out of the syringe via the needle 5060.

Reference is now made to FIG. 201, which is a simplified pictorial illustration of the automatic injection device of FIGS. 198-200B in a vial injection operative orientation, to FIGS. 202A and 202B which are respective top and side view simplified planar illustrations thereof and to FIGS. 203A and 203B which are sectional illustrations taken along respective section lines and directions CCIIIA-CCIIIA and CCIIIB-CCIIIB in FIGS. 202A and 202B.

As seen in FIGS. 201-203B, the plunger 7040 is forced axially forwardly, thus injecting at least part of the contents of the syringe 7050 into the vial 7093, via needle 7060, septum 7092, bore 7095, bore 7096 and puncturing spike 7097, thus producing mixing in the vial of the contents of the syringe 7050 with the contents of the vial 7093. It is appreciated that as the plunger 7040 moves forwardly, the syringe 7050 is retained in place.

Reference is now made to FIG. 204, which is a simplified pictorial illustration of the automatic injection device of FIGS. 201-203B in a vial aspiration operative orientation, to FIGS. 205A and 205B which are respective top and side view simplified planar illustrations thereof and to FIGS. 206A and 206B which are sectional illustrations taken along respective section lines and directions CCVIA-CCVIA and CCVIB-CCVIB in FIGS. 205A and 205B.

As seen in FIGS. 204-206B, the plunger 7040 is pulled axially rearwardly, preferably to its position shown in FIGS. 198-200B, thus drawing at least part of the mixed contents of the syringe 7050 and the vial 7093 from the vial 7093 into the syringe 7050, via needle 7060, septum 7092, bore 7095, bore 7096 and puncturing spike 7097. It is appreciated that as the plunger 7040 moves rearwardly, the syringe 7050 is retained in place.

Reference is now made to FIG. 207, which is a simplified pictorial illustration of the automatic injection device of FIGS. 204-206B in a vial removed operative orientation, to FIGS. 208A and 208B which are respective top and side view simplified planar illustrations thereof and to FIGS. 209A and 209B which are sectional illustrations taken along respective section lines and directions CCIXA-CCIXA and CCIXB-CCIXB in FIGS. 208A and 208B.

As seen in FIGS. 207-209B, the vial 7093 and the vial adaptor 7091 are separated from the automatic injection device, which is now ready for use as described hereinabove with respect to FIGS. 18-41B.

It is appreciated that in each of the operative orientations in which fluid is transferred between different elements prior to removal of the vial adaptor 7091, the automatic injection device is maintained in a safe orientation, ensuring that the needle guard will not be rearwardly displaced, and there will be no premature actuation of the device, as the vial adaptor covers the needle guard 7080 making it inaccessible.

Reference is now made to FIG. 210 which is a simplified exploded view illustration of an automatic injection device constructed and operative in accordance with a still further preferred embodiment of the present invention. The embodiment of FIG. 210 is a modification of the embodiment of FIGS. 1-41 with the addition of a vial adapter including a luer and vial contents mixing functionality. Accordingly, for the sake of conciseness, it is described hereinbelow in somewhat abbreviated form with reference to FIGS. 211-234B.

As seen with particular clarity in FIG. 210, the automatic injection device comprises a rear housing element 8010 into which is seated a main compression spring 8020, which provides selectable forward displacement to a selectable driving assembly 8030, which includes a selectable driving element 8031 and a pair of elastomeric motion damping elements 8032 and 8034, and selectably engages a plunger 8040 and a needle-less syringe 8050 adapted to have attached thereto a hypodermic needle. Needle-less syringe 8050 may be a conventional needle-less syringe, or may be any other suitable syringe or cartridge.

Plunger 8040 also operatively engages syringe 8050 and is selectably operated by selectable driving assembly 8030 to inject the liquid contents of syringe 8050 through a hypodermic needle (not shown). The forward portion of rear housing element 8010 as well as spring 8020, selectable driving assembly 8030, plunger 8040 and syringe 8050 are located within a forward housing and actuator element 8070.

At the forward end of the interior of forward housing and actuator element 8070 there is provided a needle guard element 8080, which is positioned by a compression spring 8090.

The above-described apparatus is identical to that described hereinabove with reference to FIGS. 1-13C other than in that syringe 8050 is a needle-less syringe and plunger 8040 is somewhat longer than plunger 40 in order to provide the vial contents mixing functionality.

As seen, the embodiment of FIG. 210 also includes a vial adaptor 8091 integrally formed with a vial puncturing spike 8092, which is adapted for selectable operative engagement with a conventional drug vial 8093.

The vial adaptor 8091 preferably comprises three concentric cylindrical portions including a luer engagement portion 8094 defining a rearward facing bore 8095. Forward of bore 8095 is an intermediate bore 8096 which terminates in vial puncturing spike 8092. Surrounding vial puncturing spike 8092 is a forward cowl 8098 and partially surrounding luer engagement portion 8094 is a rearward cowl 8099. A radially extending wall 8100 is common to cylindrical portions 8094, 8098 and 8099.

Reference is now made to FIG. 211 which is a simplified assembled view illustration of the automatic injection device of FIG. 210 in a pre-use operative orientation, to FIGS. 212A and 212B, which are respective top and side view simplified planar illustrations thereof and to FIGS. 213A and 213B, which are sectional illustrations taken along respective section lines and directions CCXIIIA-CCXIIIA and CCXIIIB-CCXIIIB in FIGS. 212A and 212B.

As seen in FIGS. 211-213B, in a pre-use operative orientation of the automatic injection device which is suitable for storage, the rear housing element 8010 is joined to the forward housing and actuator element 8070 by snap fit engagement of protrusions 8126 of rear housing element 8010 in the engagement sockets 8712 formed in the forward housing and actuator element 8070.

Selectable driving assembly 8030 is retained in its axial position by engagement of inward facing protrusion 8130 with outwardly facing notch 8352 of top engagement arm 8322 of selectable driving assembly 8030. In this arrangement, spring 8020 is in a relatively compressed state and is held in that state by the selectable driving assembly.

As seen in FIG. 213A, the rearwardmost axial portion 8834 of the top engagement arm 8832 of the needle guard 8080 is in a relatively forward position, only partially underlying actuation button 8752 of forward housing and actuator element 8070. Additionally, inward displacement of actuation button 8752 is limited by ribs 8128, thus ensuring that actuation button 8752 does not directly engage protrusion 8350 of engagement arm 8322. Accordingly, in this orientation of the needle guard 8080, inadvertent pressing of button 8752 does not actuate the automatic injection device.

The syringe 8050 is retained in a retracted orientation by engagement of flange 8502 thereof with notches 8347 formed in respective third fingers 8338 of each of side-to-side symmetric actuation arms 8312 of selectable driving assembly 8030.

Needle guard 8080 is retained in its axial position and is prevented from moving forward by engagement of inwardly directed teeth 8850 and 8852 with the flange 8502 of the pre-filled syringe 8050. It is appreciated that in this operative orientation spring 8090 is either at rest or in a semi-compressed state.

Reference is now made to FIG. 214, which is a simplified pictorial illustration of the automatic injection device of FIGS. 211-213B in an optional vial adaptor mounted operative orientation, to FIGS. 215A and 215B, which are respective top and side view simplified planar illustrations thereof and to FIGS. 216A and 216B, which are sectional illustrations taken along respective section lines and directions CCXVIA-CCXVIA and CCXVIB-CCXVIB in FIGS. 215A and 215B.

In an optional vial adaptor mounting step, a user may push vial adaptor 8091 onto a forward tapered portion of syringe 8050 so that rearward facing bore 8095 sealingly engages the forward tapered portion of syringe 8050. It is appreciated that the remainder of the operative orientation of the automatic injection device remains identical to the pre-use operative orientation.

Reference is now made to FIG. 217, which is a simplified pictorial illustration of the automatic injection device of FIGS. 214-216B in a vial communication operative orientation, to FIGS. 218A and 218B which are respective top and side view simplified planar illustrations thereof and to FIGS. 219A and 219B which are sectional illustrations taken along respective section lines and directions CCXIXA-CCXIXA and CCXIXB-CCXIXB in FIGS. 218A and 218B.

As seen in FIGS. 217-219B, the interior of the vial 8093 communicates with the interior of the syringe 8050 via spike 8092, bore 8095 and bore 8096 It is appreciated that as the plunger moves forwardly, the syringe 5050 is retained in place.

Reference is now made to FIG. 220, which is a simplified pictorial illustration of the automatic injection device of FIGS. 217-219B in an air injection operative orientation, to FIGS. 221A and 221B which are respective top and side view simplified planar illustrations thereof and to FIGS. 222A and 222B which are sectional illustrations taken along respective section lines and directions CCXXIIA-CCXXIIA and CCXXIIB-CCXXIIB in FIGS. 221A and 221B.

As seen in FIGS. 220-222B, the plunger 8040 is forced axially forwardly, thus injecting air contained in the syringe 8050 into the vial 8093, via spike 8092, bore 8095 and bore 8096. It is appreciated that as the plunger 8040 moves forwardly, the syringe 8050 is retained in place.

Reference is now made to FIG. 223, which is a simplified pictorial illustration of the automatic injection device of FIGS. 220-222B in a vial aspiration operative orientation, to FIGS. 224A and 224B which are respective top and side view simplified planar illustrations thereof and to FIGS. 225A and 225B which are sectional illustrations taken along respective section lines and directions CCXXVA-CCXXVA and CCXXVB-CCXXVB in FIGS. 224A and 224B.

As seen in FIGS. 223-225B, the plunger 8040 is pulled axially rearwardly, preferably to its position shown in FIGS. 217-219B, thus drawing at least part of the content of the vial 8093 into the syringe 8050, via spike 8092, bore 8095 and bore 8096. It is appreciated that as the plunger 8040 moves rearwardly, the syringe 8050 is retained in place.

Reference is now made to FIG. 226, which is a simplified pictorial illustration of the automatic injection device of FIGS. 223-225B in a vial removed operative orientation, to FIGS. 227A and 227B which are respective top and side view simplified planar illustrations thereof and to FIGS. 228A and 228B which are sectional illustrations taken along respective section lines and directions CCXXVIIIA-CCXXVIIIA and CCXXVIIIB-CCXXVIIIB in FIGS. 227A and 227B.

As seen in FIGS. 226-228B, the vial 8093 and the vial adaptor 8091 are separated from the automatic injection device.

Reference is now made to FIGS. 229A and 229B, which are simplified pictorial illustrations of the automatic injection device of FIGS. 226-228B in a needle connection operative orientation, to FIGS. 230A and 230B which are respective top and side view simplified planar illustrations thereof and to FIGS. 231A and 231B which are sectional illustrations taken along respective section lines and directions CCXXXIA-CCXXXIA and CCXXXIB-CCXXXIB in FIGS. 230A and 230B.

As seen in FIGS. 229A-231B, a needle 8902 is attached to the forward tapered portion of syringe 8050, and is covered by a needle protection cover 8104.

Reference is now made to FIG. 232, which is a simplified pictorial illustration of the automatic injection device of FIGS. 229A-231B in a needle cover removed operative orientation, to FIGS. 233A and 233B which are respective top and side view simplified planar illustrations thereof and to FIGS. 234A and 234B which are sectional illustrations taken along respective section lines and directions CCXXXIVA-CCXXXIVA and CCXXXIVB-CCXXXIVB in FIGS. 233A and 233B.

As seen in FIGS. 232-234B, the needle protection cover 8904 is removed from the automatic injection device, which is now ready for use as described hereinabove with respect to FIGS. 18-41B.

It is appreciated that in each of the operative orientations in which fluid is transferred between different elements prior to removal of the vial adaptor 8091, the automatic injection device is maintained in a safe orientation, ensuring that the needle guard will not be rearwardly displaced, and there will be no premature actuation of the device, as the vial adaptor covers the needle guard 8080 making it inaccessible.

It will be appreciated by persons skilled in the art that the present invention is not limited to what has been particularly shown and described hereinabove. Rather the scope of the present invention includes both combinations and subcombinations of various features described hereinabove as well as modifications thereof which would occur to persons skilled in the art upon reading the foregoing specification and which are not in the prior art.

The invention claimed is:

1. An automatic injection device comprising:
    a housing element;
    at least one resilient element arranged to be located within said housing element;
    a syringe; and
    a needle guard adapted for positioning with respect to said syringe and with respect to said housing element in a locked needle guarding orientation in a needle protected operational orientation, whereby displacement of said needle guard in a needle covering direction relative to said housing is prevented by a locking engagement of said needle guard with said syringe and displacement of said needle guard in a needle uncovering direction relative to said housing, opposite to said needle covering direction, is prevented by engagement of said needle guard with said housing element, and said engagement of said needle guard with said housing element does not prevent displacement of said needle guard in said needle covering direction.

2. The automatic injection device according to claim 1 and also comprising a selectable driving element adapted, when actuated, to be driven by said at least one resilient element for initially displacing said syringe relative to said housing element from a non-penetration position to a penetration position.

3. The automatic injection device according to claim 1 and wherein said syringe including at least one syringe piston.

4. The automatic injection device according to claim 3 and also comprising a selectable driving element adapted, when actuated, to be driven by said at least one resilient element for initially displacing said syringe relative to said housing element from a non-penetration position to a penetration position and thereafter displacing said at least one syringe piston in said syringe to effect drug delivery and displacing said needle guard into a needle guarding position.

5. The automatic injection device according to claim 4 and wherein said selectable driving element is also operative for displacing said needle guard into a needle guarding position.

6. The automatic injection device according to claim 4 and wherein said needle guard being operative to permit actuation of said selectable driving element for displacing said syringe relative to said housing element from said non-penetration position to said penetration position.

7. The automatic injection device according to claim 4 and wherein said selectable driving element is also operative when actuated, following suitable displacement of said needle guard relative to said housing element and resulting displacement of said syringe relative to said housing element from said non-penetration position to said penetration position, to be driven by said at least one resilient element for displacing said at least one syringe piston in said syringe to effect drug delivery.

8. The automatic injection device according to claim 4 and also comprising a motion damper operative to limit impact on said syringe produced by motion of said selectable driving element.

9. The automatic injection device according to claim 3 and also comprising a plunger operative for displacing said at least one syringe piston in axial motion relative to said housing element.

10. The automatic injection device according to claim 9 and wherein said selectable driving element adapted, when actuated, to be driven by said at least one resilient element for initially displacing said syringe relative to said housing element from said non-penetration position to said penetration position and at least partially coincidentally therewith engaging said plunger.

11. An automatic injection device comprising:
a housing element;
at least one resilient element arranged to be located within said housing element;
a syringe including at least one syringe piston;
a plunger operative to selectably drive said at least one syringe piston in axial motion relative to said syringe; and
a selectable driving element adapted, when actuated, to be driven by said at least one resilient element for initially displacing said syringe relative to said housing element from a non-penetration position to a penetration position and at least partially coincidentally therewith engaging said plunger for displacing said at least one syringe piston relative to said syringe, wherein said selectably driving element is initially coupled to said syringe and wherein said selectably driving element is decoupled from said syringe to allow displacing said at least one syringe piston relative to said syringe.

12. The automatic injection device according to claim 11 and also comprising a needle guard adapted for selectable positioning with respect to said housing element.

13. The automatic injection device according to claim 12 and wherein said selectable driving element adapted, when actuated, for displacing said syringe relative to said housing element from said non-penetration position to said penetration position, and wherein said needle guard being operative to permit actuation of said selectable driving element for displacing said syringe relative to said housing element from said non-penetration position to said penetration position.

14. The automatic injection device according to claim 12 and wherein said selectable driving element is also operative when actuated, following suitable displacement of said needle guard relative to said housing element and resulting displacement of said syringe relative to said housing element from said non-penetration position to said penetration position, to be driven by said at least one resilient element for displacing said at least one syringe piston in said syringe to effect drug delivery.

15. The automatic injection device according to claim 11 and also comprising a needle guard adapted for selectable positioning with respect to said housing element; and wherein said selectable driving element adapted, when actuated, to be driven for displacing said syringe relative to said housing element from said non-penetration position to said penetration position, said needle guard being operative to permit displacing said syringe relative to said housing element from said non-penetration position to said penetration position.

16. The automatic injection device according to claim 11 and also comprising a needle guard adapted for selectable positioning with respect to said housing element and wherein said selectable driving element is also operative for displacing said needle guard into a needle guarding position.

17. The automatic injection device according to claim 11 and also comprising a motion damper operative to limit impact on said syringe produced by motion of said selectable driving element.

18. The automatic injection device according to claim 17 and wherein said motion damper is operative to limit impact on said at least one syringe piston produced by motion of said selectable driving element.

19. The automatic injection device according to claim 11 and wherein a needle guard is adapted for positioning with respect to said syringe in a locked orientation, whereby displacement of said needle guard relative to said housing requires corresponding displacement of said syringe.

20. The automatic injection device according to claim 11 and also comprising a needle guard adapted for positioning with respect to said syringe and with respect to said housing element in a locked needle guarding orientation in a needle protected operational orientation, whereby displacement of said needle guard in a first direction relative to said housing is prevented by engagement of said needle guard with said syringe and displacement of said needle guard in a second direction relative to said housing, opposite to said first direction, is prevented by engagement of said needle guard with said housing element.

* * * * *